United States Patent
Prockop et al.

(10) Patent No.: US 6,265,157 B1
(45) Date of Patent: Jul. 24, 2001

(54) COMPOSITIONS AND METHODS FOR DETECTING ALTERED COL1A1 GENE SEQUENCES

(75) Inventors: Darwin J. Prockop, Philadelphia, PA (US); Loretta D. Spotila, Haddonfield, NJ (US); Constantinos D. Deltas, Nicosia (CY); Larisa Sereda, Philadelphia, PA (US); Andrea Westerhausen Larson, Forrest Hills, PA (US); Michael Pack; Alain Colige, both of Philadelphia, PA (US); James Early, Upper Darby, PA (US); Jarmo Körkkö, Philadelphia, PA (US); Leena Ala-Kokko, Oulu (FI); Susanna Annunen, Oulu (FI); Tero Pihlajamaa, Oulu (FI); Mirko Vuoristo, Oulu (FI); Petteri Paassilta, Oulu (FI)

(73) Assignees: Allegheny University of the Health Sciences; Thomas Jefferson University, both of Philadelphia, PA (US); University of Oulu, Oulu (FI)

( * ) Notice: Subject to any disclaimer, the term of this patent is extended or adjusted under 35 U.S.C. 154(b) by 0 days.

(21) Appl. No.: 08/943,731

(22) Filed: Oct. 3, 1997

Related U.S. Application Data

(63) Continuation-in-part of application No. 08/212,322, filed on Mar. 13, 1994, now abandoned, which is a continuation of application No. 07/803,628, filed on Dec. 3, 1991, now abandoned.

(51) Int. Cl.[7] .............................. C12Q 1/68; C12P 19/34; C07H 21/04
(52) U.S. Cl. ..................... 435/6; 435/91.2; 536/23.1; 536/23.5; 536/24.31; 536/24.33
(58) Field of Search ..................... 435/6, 91.2; 536/23.1, 536/23.5, 24.3, 24.31, 24.33

(56) References Cited

U.S. PATENT DOCUMENTS

| | | |
|---|---|---|
| 4,683,195 | 7/1987 | Mullis et al. . |
| 4,683,202 | 7/1987 | Mullis . |
| 4,822,731 | 4/1989 | Watson et al. . |

OTHER PUBLICATIONS

Chu et al., Nucleic Acids Res. 10(19), 5925–5934 (1982).*
Ahmad et al., 1995, Arch. Ophthalmol. 113:1454–1457.
Ala–Kokko et al., 1995, Biochem. J. 308:923–929.

(List continued on next page.)

Primary Examiner—Kenneth R. Horlick
(74) Attorney, Agent, or Firm—Morgan, Lewis & Bockius, L.L.P.

(57) ABSTRACT

Compositions and methods useful for determining whether a subject has an alteration in a gene encoding a protein chain of Type I or Type IX collagen are described. Novel intronic sequences of five human genes, COL1A1, COL1A2, COL9A1, COL9A2, and COL9A3 are described. Methods of determining the existence in a subject of a pathological condition associated with an altered gene encoding a Type I or Type IX collagen protein chain are provided, wherein such pathological conditions include diseases and disorders which are known to be associated with an altered gene encoding a Type I or Type IX collagen protein chain. Primers, probes, and methods of detecting a genetic predisposition of a subject for a pathological condition associated with an altered gene encoding a Type I or Type IX collagen protein chain are provided. Diseases and disorders for which the methods and compositions of the invention are useful for diagnostic or prognostic purposes include, but are not limited to osteoporosis, osteoarthritis, chondrodysplasia, multiple epiphyseal dysplasia, osteogenesis imperfecta, shortness of stature, scoliosis, low bone density, and degenerative joint disease.

41 Claims, 307 Drawing Sheets

OTHER PUBLICATIONS

Ausubel et al., 1994, In: Current Protocols in Molecular Biology, Wiley, New York, vol. 1, pp. 2.2.1–2.2.3.
Baldwin et al., 1989, Biochem. J. 262:521–528.
Ballo et al., 1997, Am. J. Med. Genet. 68:396–400.
Barsh et al., 1985 Proc. Natl. Acad. Sci. USA 82:2870–2874.
Bernard et al., 1983, Biochem. 22:1139–1145.
Bernard et al., 1983, Biochemistry 22:5213–5223.
Birnboim et al., 1979, Nucl. Acids Res. 7:1513–1523.
Boedtker et al., 1985, Ann. N.Y. Acad. Sci. 460:85–116.
Bornstein et al., 1980 Ann. Rev. Biochem. 49:957–1003.
Brewton et al., 1995, Genomics 30:329–336.
Brewton et al., 1992, Eur. J. Biochem. 205:443–449.
Briggs et al., 1995, Nature Genet. 10:330–336.
Briggs et al., 1994, Am. J. Hum. Genet. 55:678–684.
Brown et al., 1995, Hum. Molec. Genet. 4:141–142.
Brown et al., 1992, Arch. Ophthalmol. 110:1589–1593.
Bruckner et al., 1985, Proc. Natl. Acad. Sci. USA 82:2608–2612.
Byers, 1993, In: Connective tissue and its heritable disorders, Royce et al., eds., Wiley–Liss, New York, pp. 317–351.
Chipman et al., 1993, Proc. Natl. Acad. Sci. USA 90:1701–1705.
Chu et al., 1993, In: *Connective Tissue and Its Heritable Disorders*, Royce et al., eds., Wiley–Liss, New York, pp. 149–165.
Chu et al., 1985, J. Biol. Chem. 260:2315–2320.
Chu et al., 1984, Nature 310:337–340.
Cohn et al., 1996, Ann. N.Y. Acad. Sci. 785:188–194.
Constantinou et al., 1990, Cytogenet. Cell Genet. 51:979.
D'Alessio et al., 1988, Gene 67:105–115.
de Wet et al., 1987, J. Biol. Chem. 262:16032–16036.
Deere et al., 1995, Am. J. Hum. Genet. 56:698–704.
Diab et al., 1996, Biochem. J. 314:327–332.
Dickson et al., 1984, Proc. Natl. Acad. Sci. USA 81:4524–4528.
Engel et al., 1991, Annu. Rev. Biophys. Biophys. Chem. 20:137–152.
Eyre et al., 1987, FEBS Lett. 220:337–341.
Fässler et al., 1994, Proc. Natl. Acad. Sci. USA 91:5070–5074.
Fertala et al. 1993, Biochem. J. 289:195–199.
Fu et al., 1988, Mol. Cell. Biol. 8:3582–3590.
Ganguly et al., 1995, Electrophoresis 16:1830–1835.
Ganguly et al., 1993, Proc. Natl. Acad. Sci. USA 90:10325–10329.
Ganguly et al., 1991, J. Biol. Chem. 266:12035–12040.
Ganguly et al., 1990, Nucl. Acids Res. 18:3933–3939.
Gordon et al., 1990, Curr. Op. Cell Biol. 2:833–838.
Gubler et al. 1983, Gene 25:263–269.
Haimes et al., 1996, Inflam. Res. 44(Suppl.2):S127–S128.
Hanke et al., 1994, BioTechniques 17:858–860.
Har–El et al., 1992, J. Biol. Chem. 267:10070–10076.
Innis et al., ed., 1990, In: PCR Protocols, Academic Press, Inc., San Diego (too voluminous to submit).
Jacob et al., 1989, Nucl. Acids Res. 17:2159–2180.
Jego et al. 1992, Oncogene 8:209–213.
Kadler et al., 1987, J. Biol. Chem. 262:15696–15701.
Kadler et al., 1990, Biochem. J. 268:339–343.
Körkkö et al., 1997, Hum. Mutat. 9:148–156.
Kuvianiemi et al., 1997, Hum. Mutat. 9:148–156.
Kuivaniemi et al., 1991, FASEB J. 5:2052–2060.
Kuivaniemi et al., 1988 Biochem, J. 252:633–640.
Labhard et al., 1990, Matrix 10:124–130.
Laemmli et al., 1970, Nature 227:680.
Lozano et al., 1985, Proc. Natl. Acad. Sci. USA 82:4050–4054.
Määttä et al., 1991, FEBS Lett. 279:9–13.
Mechling et al., 1996, J. Biol. Chem. 271:13781–13785.
Muragaki et al., 1990, Proc. Natl. Acad. Sci. USA 87:2400–2404.
Muragaki et al., 1990, Eur. J. Biochem. 192:703–708.
Myers et al., 1984, J. Biol. Chem. 259:12941–12944.
Na et al., 1989, Biochem. 28: 7153–7161.
Nakai et al., 1994, Gene 141:171–177.
Nakata et al., 1993, Proc. Natl. Acad. Sci. USA 90:2870–2874.
Nicholls et al., 1984, J. Med. Genet. 21:257–262.
Ninomiya et al., 1990, In: Extracellular Matrix Genes, Sandell et al., eds., Academic press, San Diego, pp. 79–114.
Ninomiya et al, 1985, Biochem. 24:4223–4229.
Ninomiya et al., 1984, Proc. Natl. Acad. Sci. USA 81:3014–3018.
Nishimura et al., 1989, J. Biol. chem. 264:20033–20041.
Nuytincket al., 1996, Human. Genet. 97:324–329.
Perälä et al., 1994, J. Biol. Chem. 269:5064–5071.
Perälä et al., 1993, FEBS Lett. 319:177–180.
Piez, 1984, In: Extracellular Matrix Biochemistry, Piez et al., eds., Elsevier Science pp. Pub. Co. Inc., New York, pp. 1–39.
Pihlajaniemi et al., 1984, J. Biol. Chem. 259:12941–12944.
Prockop et al., 1995, Annu. Rev. Biochem. 64:403–434.
Prockop, 1990 Arth. Rheumat. 31:1–8.
Prockop, 1990, J. Biol. Chem. 265:15349–15352.
Prockop et al., 1989, In: Cytoskeletal and Extracellular Proteins, Aebi et al., eds. Springer Series in Biophysics, vol. 3, pp. 81–89.
Prockop, 1986, Hosp. Pract., Feb. 15, 1986.
Prockop et al., 1989, Biophysics (Eng. Transl. Biofizika) 3:81–89.
Prockop, 1985, J. Clin. Invest. 75:783–787.
Prockop et al., 1984, N. Eng. J. Med. 311:376–386.
Prockop et al., 1979, N. Eng. J. Med. 301:13–23.
Ramirez et al., 1985, Ann. New York Acad. Sci. 460:117–129.
Redford–Badwal et al., 1996, J. Clin. Invest. 97:1035–1040.
Ritvaniemie et al., 1993, Genomics 17:218–221.
Rokos et al., 1994, Matrix Biol. 14:1–8.
Saban et al., 1996, BioTechniques 21:190–192.
Sambrook, et al., 1989, In: Molecular Cloning: A Laboratory Manual, Cold Spring Harbor Laboratory, New York (too voluminous to submit).
Sanger et al., 1977, Proc. Natl. Acad. Sci.USA 74:5463–5467.
Shapiro et al., 1989, Connect Tissue Res. 21:117–123.
Shapiro et al., 1987, Nucl. Acids Res. 15:7155–7174.
Shaw et al., 1991, Trends Biochem. Sci. 16:191–194.
Sherwood et al., 1990, Gene 89:239–244.
Sokolov et al., 1991, Hum. Genet 88: 125–129.
Spotila et al., 1990, Am. J. Hum. Genet. 47:A237.
Sykes et al., 1990, Am. J. Hum. Genet. 46:293–307.
Ting et al., 1993, J. Bone Min. Res. 8:1377–1387.
Tromp et al., 1988, Proc. Natl. Acad. Sci. USA 85:5254–5258.
Tromp et al., 1988, Biochem. J. 253:919–929.
Tsuneyoshi et al., 1991 Biol. Chem. 266: 15608–15613.
van der Rest et al., 1988, J. Biol. Chem. 263:1615–1618.

van der Rest et al., 1987, In *Structure and Function of Collagen Types*, Mayne et al., eds., Academic Press, Orlando, pp. 195–221.
Vasan et al., 1991, Am. J. Hum. Genet. 48:305–31.
Vasios et al., 1988, J. Biol. Chem. 263:2324–2329.
Vaughan et al., 1988, J. Cell. Biol. 106:991–997.
Vuorio et al., 1990, Annu. Rev. Biochem. 59:837–872.
Weil et al., 1990, J Biol. Chem. 265:16007.
Weil et al., 1989, J. Biol. Chem. 264:16804.
Weil et al., 1989, EMBO J. 8:1705.
Weil et al., 1988, J. Biol. Chem. 263:8561.

Werle et al., 1994, Nucl. Acids Res. 22:4354–4355.
Westerhausen et al., 1991, Matrix 11:375–379.
Westerhausen et al., 1990, J. Biol. Chem. 265:13995–14000.
Willing et al. 1996, Am. J. Hum. Genet. 59:799–809.
Willing et al. 1994, Am. J. Hum. Genet. 55:638–647.
Willing et al., 1992, Am. J. Hum. Genet. 51:508–515.
Wood et al., 1960, Biochem. J. 75:588:598.
Wu et al., 1992, J. Biol. Chem. 267: 23007–23014.

* cited by examiner-

FIG. 3A

```
cccacgaaga gctagggaca aacacacccg agctcgaagg agtctttgggc
tctggctca gctgtgccgc gctgtgccgc tgacctgccg tgtggccact cactctcact
ttctggacct cagcctccct atctgtaaaa tgaaagactt ctcggcgggg
cacggtggct catgcctgta atcccagcac tttgggaggc caaggcgggc
agaccatgag gtcaggagtt tgagaccagt cgggccaaca tagtgaaacc
acgtctctac taaaaataca aaagattagc tgggtgtggt ggtgtgcacc
tgtaacccca gctagtcagg aggctgaggc aggagaattg catgaacccg
ggaggtggag gttgcagtga gctgagatca cgccattgca ctccagcctg
ggcaacagtg cgagattcca tctcaaaaaa aaaaaaaaaa agaagaaaga
aagaaagaaa aaatgaaaca cttctccagg ctccatgacc actgctctgt
cctgaaataa gtgtttgttgg tggccctcca cccgacacg tgggatagg
acaggccttt gatatgatag gcacccccag tcttggtgga ttctttgagg
tccaaaagga gatagcagag aagatgaaag ccctttgcag tgcaggccac
agcgggcatc taacagggaa aaggcagagg agcctggaag ggcatcttgg
gaggagtggg ctcagaaagg gcccagcaag aagcacctgc agggcattc
cccgggggcc aaacagtctt ttgaaaagaa agtcccttaa aaagtcccac
tcagagtaaa tgagaggccc caggaggccc tggcttctca cttcagcccc
ctcaaccta actcccttc tccacagGGA... exon 26    ...GTC
```

FIG. 3B

```
gtagtatct cctttccatc cctacctcct tcccattgct gccccggcac
tttctcctcc ctgcaggagg ggtgctagag gccacggtcc tcagctgctc
ggggcctcct aaccctgagt tcccctttgc tctctccctg cagGGT...
    exon 27   ...GCTgt gagtgtccct gatgtggagc tctggggagc
agaaaagggg agacaccctc agccccctcg ctcctcggcc tccccgtgac
tgtagtgttc tctctgtgca gGGT...     ...CAGgtgag
gcctcatggc tgtcaggatg ctgggaggta gggtaggaa acacctcttt
ggtctcttcc agattctaaa cctttcccctcc cttcttcccc catttcccac
ctacagGGT...      exon 29  ...CAG gtaagaggga gcagccggcc
agaggggtgg gagatgcagg gaatccagag ggacaggccc ccgcctccta
gctaatcaga cagccatcaa ctagagggat tgaggttaga caccggaaag
aacttcctcc catgaaggga gcagcacaga gggaagtggg ggctgcatga
ttgctagtct gggtgacttc ttttaagagc tgctggaata tgctgtgact
ttcccctcaac ccttgtattg ataaatcttg gtccatagtt tggggagggg
ggaagccttt gacacatccc taggaggaag agaggggctg tttgggataa
tctcaattca gtgctgagaa gggttcctc tctaatcacg gccagacccc
aggaggaagg accgtgcttt ccagcagagt ggccccaggt aggtttgct
cactgtctgt tcctctctcc ctcccctca gGGT...     exon 30
```

FIG. 3C

```
...AGAgtaa gtaggcctct ctcgctgcat ccgtcaaggt gcgttgtact
tggccctatc tccagagcag ccttcacatg ccctgtcctt cccttctagG
GC...   exon 31   ...AAGgt gagggcagcg tggaaggggc tctggcaagt
ggcccaggga ccaggtctca cccctcctgc agcaggggat ggcgggccat
gaccaaagcc atggagatag ggtgtggggt gggggaaaa gaccagggca
ggggcccaca cacagcctgg agtctgggct gtgagtcttt tcatctttc
tcaaggcttg tcgttggcct tggaaacaag cctgggagat accaagcggg
gcttagggct gtgaccact cttggggccc caggcctcac tccagtcttc
ttggttgtca catagGGT...   exon 32   ...AGAgtaagtt caaccttccc
cctcccctga gccctacatg gctcccatct ctgcctgctt tgaatctctc
agcatctctc cttctctctg ggatctgtcc ctcttctcgc taatcctccc
ctcttcccct ttccccctg gccttttgc tgatgaatcc tctccctgtg
gtccaggccc atctatcccc atgggttacc atggtgatga gaggtggggg
catctccttg gtggaggctc ccttattcat cccgctacac aagtcagggg
cctcttaacc tcagttccac ctgagtctcc aggcaggaac ccttttcct
gaaagaatct ttgagtcctt ggcccaggtg gaggcagggc agagctgcag
agggcctctc aggaaaccca gacacaagca gaacactata ggtcacctcc
ttgccccaca ctggaaatct caagcttatc catgtctttta gGGT...
```

FIG. 3D

```
exon 33/34    ...AAGg tgaggtggcc gcctccccac cttctgccct
aacacatagc ctcctcagca ggcctgggca cggttccgtg gggttgcgtt
gggagagcag gtcctgccaa actgagctgt caacctggga acctggaggg
accagaagga ggggaggctc tcctgggtc  atctactagg agtattcagg
ggaggccctg accctgagcc tcttgtccct tgctctcagG GT...
exon 35    ...CCGtaagta cagaagacct gttaagaccc catacttggc
cctcccctcc cttcacacag cacccctggc cctgtctgtg cctcaccccc
ttgcctctcc cctcaccgca tcccccgctt ccctcctgtc agacgcatct
ctccaatctg actcctttc  ttctagGGA...    exon 36    ...CCT
gtgagtacca agaccccat  cattttcat  caccgactgg gacctgggac
ctcgagggac ggaatgagga caaaggcgtc agccatcctc aggggagaag
ggtggagacg ggattgtttc ccaccaagc  atcttcctgc ctccattact
gctcctcccc caggtagtgg aaactcctgc ctccttccct ccattcaccg
ccctgcttcc tccccagGG  T...   exon 37   ...ATTgtga gtggcttggc
cctctgtgcc cacgaggctg gtgggctggg accaggacg  ggtccaggct
tgatgcgtct gtgctctcct acagGGT...   exon 38    ...CCTgt
gagtatcacc cgcctctctg ttgagcctct cccctctccc caggcagcgg
tggcaggtga gggcagctgg gtcggatgag ttggctgttc tccctctgac
```

FIG. 3E

```
tgttcctatg ttctctcctt ccagGGT...                    exon 39         ...TCTgt
aagtctctgc agcagagtcc actgctctag gttggggtg ctgggtggg
gctgccagaa ggatggtggg gctgactgag gacccaatga tgcaccagag
cccctggag tctgacagcc cctcctatcc tcatccagGG A...
exon 40      ...GCT gtaagtgcca gctcagatct ctgcagctcc
ggaggtgtgc agagctgggg aggggtccct gtgctgctgt ctggcacctc
acccctgttt gcctcccaaa gGGT... exon 41  ...TCTg taagtgcccc
cctcaccttg ggggccctg agaaaaacca tcacaggact tggagtgggg
cggagccaag gagaacagat ttggtagaga tgactccagc ggactcaagg
gtcctcccag accctatctc tggcctgact ctttcttctc ccttagGGT...
     exon 42 ...GAGgtgagc agtcccagc gtacccag
catggccatt gtgccttgc ctaagccctc ttccccggct gactctcact
tctctctctc tctctctgca gGGG...         exon 43       ...AAGgtaag
atggcaacac tccatgacca cagccttgtc tgctgcttcc ctgcccatc
ctggcccttc acccggggct gacccatatt cccctgctct cccgccagG
GT...  exon 44  ...ACTgta agtagctggg ctccagttcc ctgtacctgg
tcaggccagg gactcttcag gcctccttag aggcctgggg atgggtgtcg
gacttcaccc aggcagggg aggaaaggag atcctgcaag atgtcagggc
```

FIG. 3F

```
cttaatccaa aaaactgagt taaagctcag ccctaagtcc cctctcccag
acaggaccgc ctctcccatg agttggcccc agctcccgtg aagattgcag
tggggaggtt tccctgggag ttgggagaga tggccacagt gggaagcagc
tgaggagaga gagatccagc agaggggagg cctcatcctg cagccccagc
ctcagccttc cctgccaag  agctcatgct ttccttgctc tccccagGGT
    exon 45 ...GC Cgtaagtacc ctgctgtgtc ccccatgcct
tcagaactct acagatgcag acagtgcccc actcgatgcc aatgaactt
ccgcctgaca gtttgtccct ttctctcttc tagGGA... exon 46 ...CC
Tgtaagtatg ctcagcccct cccagtcccc catgctgtgc tgtgggatag
gaggggagc ttcgcctcag tttccccctc tggatagtca ttctttcccc
tccctagtgg ggactgggt ctgaagattt gtgggcatgt ccaagtagct
tctgagaggg tgaggggtac acagagaggg attatgggag aggtctctgc
ctatggacac cctcgggcta gattccaga ataatgaagg ggcatgggtt
gcccacactg cccttgtctc tccagccagg cccctcaggct acatttgacg
ctcactgggc ctgaactgcc ttttatct gtccttcagG GC...
exon 47 ...CGAgtaagtc atgccttctc tctccttc ctgagcccca
agccaggct caccctcgggg acccttgcca ggaccaggc acccttgcc
tctctggaga agggttcagg gacaggagt gggcaaagaa aggaagaatc
```

FIG. 3G

```
ctgaacaaac aatctgatct agctttggcc tctctgctcc ccaatccgtc
ctccctggc tcagcggctg ggaggagcta tggcatgtcc tatggaaaga
ggctgaggct ggctctatga gccgtggggc cagagccagc agggagggtg
gtgggcctct cctccagagc tggggttgtt cgggcttctg gcagccttc
tcaaaccatt tcccccactc cagGGT... exon 48 ...GT Tgtatgtagc
ccctcatccc ctctgctcat ggccctccag ccccatagc acttggatgc
cggaatcccc actctcttcc ctctctgtgc agGGT... exon 49
...GTGgtgtg ggcctgccct agcctctccc tccctcctac tcctgccatg
ccagggtccc catgcccata tgtgccccta ccatatggtg ctgctgctc
cctttccctg actccatctt gccctgccct accacagGAG... exon 50
...CAGgt gcgtgagctg gacctcagag ccagtgttag gagatgggct
agcccagtgc tcagaaggga catgaagtcc tggagtaggt ctctgctaag
ggtgatggac agagctgggc tgggaggcag gggtctcagg tccctgctag
tggttcagac acaggctgcc gatgggcagg tggtgccct ctgatataac
ggtgcattgg gcagctctct gaggacccct gacaggaggc cagcaggact
agaggttccc gcatagctca ctcttccctc tctctcctcc ctgcagTTC...
exon 51 ...ACGg tgagtgccca gaatcccag gcagggcccc
acctctccgg ccttgggcat tttggccagg ccatagtgcc ctctcccat
cactcccacg tggtaatgcc ccctcccgtt gtctccgccc cacccccagAG
T... exon 52
```

FIG. 4A-1

|  |  |  |  | Exon # |
|---|---|---|---|---|
| gggcacccc tacccactgg ttagcccacg ccatcctgag gaccagctg caccctacc | 60 | | | |
| acagcacctc ggcctaggc tgggcgggg ctgggggagg cagagctgcg aagagggag | 120 | | | |
| atgtgggtg gactccttc ctcctcctc cccctctcca ttccaactcc CAAATTgggg | 180 | | | |
| gccgggccag gcagtctga ttggctgggg cacgggcggc cggctccccc tctccgaggg | 240 | | | |
| gcagggttcc tccctgctct ccatcaggac agTATAAAAg gggcccgggc cagtcgtcgg | 300 | | | |
| agcagacggg agtttctcct cgggtcgga gcaggaggca cgcggagtgt gaggccacgc | 360 | | | |
| atgagcggac gctaacccc tcccagcca caaagagtct acatgtctag ggtctagacA | 420 | | | |
| TGTTCAGCTT TGTGGACCTC CGGCTCCTGC TCCTCTTAGC GGCCACCGCC CTCCTGACGC | 480 | | | 1 |
| ACGGCCAAGA GGAAGGCCAA GTCGAGGGCC AAGACGAAGA CAgtaagtcc caaacttttg | 540 | | | |
| ggagtgcaag gatactctat atcgcgcctt gcgcttggtc ccggggccg cggcttaaaa | 600 | | | |
| cgagacgtgg atgatccgga gactcgggaa tggaagggag atgatgaggg ctcttcctcg | 660 | | | |
| gcgccctgag acaggaggga gctcaccctg ggcgaggtt gggttgaac gcgccccggg | 720 | | | |
| agcgggaggt gagggtggag cgccccgtga gttggtgcaa gagagaatcc cgagagcgca | 780 | | | |
| accgggaaag tgggatcag ggtgcagagt gggaaagta cgtcgaagat gggatgggg | 840 | | | |
| cgccgagcgg ggcatttgaa gcccaagatg tagaagcaat caggaaggcc gtgggatgat | 900 | | | |
| tcataaggaa agattgccct ctctgcgggc tagagtgttg ctgggccgtg ggggtgctgg | 960 | | | |
| gcagccgcgg gaaggggtg cgggagcgtgg gcgggtggag gatgagaaac tttggcgcgg | 1020 | | | |
| actcggcggg gcgggtcct tgccgccct gctgaccgat gctgaccact cgtctcccg | 1080 | | | |
| gtccaacgct tactgggca ggaccggag cgggaagacc cggttattg ctgggtgcgg | 1140 | | | |
| accccacct ctagatctgg aaagtaaagc caggatggg gcagcccaag cctcttaaag | 1200 | | | |
| aggtagtcgg gccggtgagg tcggccccgc cccggcccca ttgcttagcg ttgcccgaca | 1260 | | | |

FIG. 4A-2

| Sequence | Position | Exon # |
|---|---|---|
| cctagtggcc gtctggggag ccgctagcgc ggtgggagtg gttagctaac ttctgacta | 1320 | |
| tttgcggact ttttggttct ttggctaaaa gtgacctgga ggcattggct ggctttgggg | 1380 | |
| gactggggat ggcccgaga gcgggctttt aagatgtcta ggtgctgag gttagggtgt | 1440 | |
| ctcctaattt tgagtacat ttcaagtctt gggggggcgt cccttccaat cagccgctcc | 1500 | |
| cattcttta gccccgcccc cgccaccca catgcccagg gaatgggggc gggatgaggg | 1560 | |
| atggacctcc cttctctcct ccctcgccct cctcctgtct ctaccacgca agccactccc | 1620 | |
| cacgagcctg ccctccgat gggccctc ctattctccc cccgccctcc ccctctcacc | 1680 | |
| ctgtgttttt atttcacttg gcttcagcgc caatgggctg aggttggagt tggaagccac | 1740 | |
| cgcggactaa agctttgttt aaattcctga gaactggaaa gagttacagc ctccctggcc | 1800 | |
| aggcgcctcg gcgctgtcac ccgcgctgat gaggagcagg cgagcttta aggatttgag | 1860 | |
| gaaagaagaa cggggggagg ggcgggaagt gaaaaatcca agtgtgcctc ttagacccgg | 1920 | |
| gggaaaggtg gttaagctgg gggttgcagt cactactgac aacgcccctc ttccgcctgt | 1980 | |
| cccagTCCCA CCAATCACCT GGTACAGAA CGGCCTCAGG TACCATGACC GAGACGTGTG | 2040 | |
| GAAACCCGAG CCCTGCCGGA TCTGCCGGA GATCCCCCGG CGCCGAAGTC CCCGAGGGCG AGTGCTGTCC | 2100 | 2 |
| GATCTGTGAC GAGACCAAGA ACTGCCCCGG CGCCGAAGTC CCCGAGGGCG AGTGCTGTCC | 2160 | |
| CGTCTGCCCC GACGGCTCAG gtgcggctgc gctcggggcc tggggcctgg ggctggggct | 2220 | |
| ggggtggtc ggcgctcgct ggccctccgt gctggaggcc tctgccgacg ggagcagcat | 2280 | |
| tagcaaacct tggctctaac gggcgtctct tcgtcccta gAGTCACCCA CCGACCAAGA | 2340 | 3 |
| AACCACCGGC GTCGAAgtaa tctcctgccc tcgaattttg ccctcgcgcg gccgtgact | 2400 | |
| cctcacagtc ctcccttctc taacctggcc tcttgttct tctcccccaa tcccacagGG | 2460 | |
| ACCCAAGGGA GACACTGGCC CCCGAGGCCC AAGgtaagc gttgcactct gggctgtggg | 2520 | 4 |

FIG. 4A-3

```
                                                                                       Exon #
gggctgcagg tgggcatggc tctcggccgc acgctcaccc cggcccccgcc ctctcccct   2580
gcagGGACCC GCAGGCCCCC CTGGCCGAGA TGGCATCCCT GGACAGCCTG GACTTCCCGG   2640    5
ACCCCCGGA CCCCCGGAC CTCCCGGACC CCCTGGCCTC GGAGGAgtaa gtgagaggc      2700
cttgtgtgtc cactctcccc tgttttgttt ttgtttttg gcagatgaca taattttata   2760
ctttgaaata atttcaaact tacagaaaag ttgcaagaat cctacaggaa actctcacat  2820
acccttcaca gtttgtgaca tgtgctttat tagtctctgt ttatgtatat gtatctttt   2880
ttttctgaac tgtttgagca agttgctaac atcaggctct tttgcgccta aatacttagg  2940
tgtgtttttc ctaaaaacaa gagcattctc ttaactgacc tacacaatga ttaaattcac  3000
tctctaatgt gcagtccgta ctcaaagttc accgatgtcc cgataatgtc ctttatagat  3060
tccaccccc accacccaa tctggatcc agtccaggat tatgtattgc atttaatcat    3120
catgtctcta gttccacaa atgtagaacg ttcctcagac tttctttgtc tttagtggca   3180
ctgggagttt tgatgagtcc agttgttttg cagactgtcc ctcaatttgg gattgtctca  3240
ttagattaga tgcagggatg catctttggc aggaatgtct taaaagcaat gttattcttc  3300
tcagcacatc acaccaggaa gtgcatgatg tcagttcttt ccatcctcag tgccgtcttc  3360
tgcctttcaa ttcactgtcc tcactctgac ttctcttgtt tgttctagAA CTTTGCTCCC  3420    6
CAGCTGTCTT ATGGCTATGA TGAGAAATCA ACCGGAGGAA TTTCCGTGCC TGGCCCCATG  3480
gtgagccagc agggggagca tggatgacag aagagagaat gggtatccag aggatgtggg  3540
catacgcggc tggtatacac agcttgggag gtccatatca cctttgggac ctcagagtcc  3600
agaaaggatg caagacgact gggtggtccc aacaggcatg aatgactaca tccacatgct  3660
ttcctacaga gggatcacca tgacccccct ttcttctccc tctatagGGT CCCTCTGGTC  3720    7
CTCGGGTCT CCCTGGCCCC CCTGGTGCAC CTgtgagtat ccaggacgtc ttcatatgcc   3780
```

FIG. 4A-4

| | | Exon # |
|---|---|---|
| tcctggct tggtctttt ggagggaaga ctggatgag ggcaggagag atgctcagag | 3840 | |
| atctcttgt aagattggag aaggttgaca ggacttgtc ttctaaccca tctttttcct | 3900 | |
| tcttctcaag GTTCCCAAGG GCTTCCAAGG TCCCCCTGGT GAGCCTGGCG AGCCTGGAGC | 3960 | 8 |
| TTCAgtaagc actctctata cagattcata ctccttctac aaacacacag actctcctat | 4020 | |
| agaagaactc ccaggcctgg ggtcttcctt acctcttccc ttcaatccca gccttcccct | 4080 | |
| tcttttttc ttatccatat tctaaccacc tctttctatct tttctagGGT CCCATGGGTC | 4140 | 9 |
| CCCGAGGTCC CCAGGTCCC CCTGGAAAGA ATGGAGATGA Tgtaagtatc cccagcaaga | 4200 | |
| agataccatc tgacccatg gcctccatgg gttggtcct gcaatttcca ctccaccaca | 4260 | |
| tttgggaacg atactcagag gaaggagggc aagtcctctc tgatgcacgg actgccctgg | 4320 | |
| aacaatgatc ttttcgctta gtgagatgat tccatgtccc caacaaagtg actgttctcc | 4380 | |
| tcaccccagc cacttagag caatcccca cccatccct ttggggaaat tggtgcgcag | 4440 | |
| atggtgaaat taaaatgctg gtgacagaag tagacagaaa ttcctttaga ggcactcaga | 4500 | |
| tttcaccaaa cgaaggtttc actgtagatt taaactgagc tctagattca aagataagat | 4560 | |
| tctgggcccc caaacctgac ctgcaacaat ccaaagaaga ctgagacctt ctccacttt | 4620 | |
| ccagccccta ggcggtggtg gggaggcaga ggcatgatgg tcttttctct ccctctcagG | 4680 | 10 |
| GGGAAGCTGG AAAACCTGGT CGTCCTGGTG AGCCTGGGCC TCCTGGCCT CAGgtgagca | 4740 | |
| gggctgtg gctgaacctg gcttcactg gcttcactgg ctcttggct tcatttagga gctggtcca | 4800 | |
| cagtgatgtg ttctaatgc cctccttgt cttcttcatc tctctccagG GTGCTGAGG | 4860 | 11 |
| ATTGCCCGGA ACAGCTGGCC TCCCTGGAAT GAAGGGACAC AGAgtgagtc acctttgagt | 4920 | |
| catttaagct cccaagtcc ctagcatacc cccagcctct tccccaaaag ccaagggcca | 4980 | |
| atcctgagtt gcatcatggt gggtggcagc tacagaagtc ccaaggtcca ggagagtggac | 5040 | |

FIG. 4A-5

| Sequence | Position | Exon # |
|---|---|---|
| atccaaaagc actcctcatg gaatcccgat taccgattgg gtgagatctt agagccattt | 5100 | |
| ggggtttagt ctagctcaga aacaaaggga tggcggtgat gacctcccaa ggctcttcct | 5160 | |
| cagatctagg tggatgtcaa ggctgttcca cccctccac agttcttac cttctacctc | 5220 | |
| tttcctgctt tagGGTTTCA GTGGTTTGGA TGGTGCCAAG GGAGATGCTG GTCCTGCTGG | 5280 | 12 |
| TCCTAAGgta agaggctgtc tgaacatcat gtcctccac atcccagag tcccaccatg | 5340 | |
| aatgaatttc tcactcatta ttctctgatc tacagGGTGA GCCTGGCAGC CCTGGTGAAA | 5400 | 13 |
| ATGGAGCTCC TGGTCAGATG gtgagtgtgc ccagttccag agggcagga tggggcagga | 5460 | |
| ggcaggggca agatggaggc ctgggggaac aaggctgtct cccatctcat ctgacttctc | 5520 | |
| ttggtttggt tgtcagGGCC CCCGTGGCCT GCCTGGTGAG AGAGGTCGCC CTGGAGCCCC | 5580 | 14 |
| TGGCCCTGCT gtaagtactc ctgcccccctt gggggatccc tgagctctgg aagggctcc | 5640 | |
| ccaggaactc tagggactgg ccagtgctca gtggacttaa cgggcttcc cctctctcct | 5700 | |
| gcagGGTGCT CGTGGAAATG ATGGTGCTAC TGGTGCTGCC TGGTGCTGCC GGCCCCCTg tgagtgtggc | 5760 | 15 |
| ctgtaggcct cagggcctgg gagtgggag ggtctcagt gtctgctctt ggggctgaca | 5820 | |
| atggggcag gttatgttgg tctgaacccc aggacttcct ctgtcccagg gtgtgacttg | 5880 | |
| cagctgccat ctctccttc tcgctgacat ctccattca ttcacagGGT CCCACCGGCC | 5940 | 16 |
| CCGCTGGTCC TCCTGGCTTC CCTGGTGCTG TTGGTGCTAA Ggtgagaccc cccactctcc | 6000 | |
| tctaagcatg accctcatgg gccaagggt tcatgtctcc ctgttcccca aaccaaaggg | 6060 | |
| acccagagtg gcaagagagc agcccgttca ctaacacctt tgtcctgggg tctccgtctc | 6120 | |
| tgatcttaga gtcctgatca ttgctctcct gtctctcctc cccttcctc ctgccatccc | 6180 | |
| gagaggcaag gttgggtttc ccaggggtggc ttctgatatg tccttcttc tgattcagGG | 6240 | |
| TGAAGCTGGT CCCCAAGGGC CCCGAGGCTC TGAAGGTCCC CAGGGTGTGC GTGGTGAGCC | 6300 | 17 |

FIG. 4A-6

| Exon # | | |
|---|---|---|
| | | |

```
TGGCCCCCT GGCCTGCTG GTGCTGCTGG CCCTGCTgta agtgtcccg actcagtgtc      6360
ccctttgcca ctttctaacc tcagagtcct tgcctgttgc tgacactcct ttctctgtgc   6420
cacagGGAAA CCCTGGTGCT GATGGACAGC CTGGTGCTAA AGGTGCCAAT gtaagtatcc   6480   18
tgccaggctt cagtcccact cctgccgcct gcagcctgcc tgccccttc cctctgctcc    6540
taggctcacg ccctgctgt ctgcctccca cagGGTGCTC CTGGTATTGC TGGTGCTCCT    6600
GGCTTCCCTG GTGCCCGAGG CCCCTCTGA CCCCAGGCC CCGGCGGCCC TCCTGGTCCC     6660   19
AAGGGTAACA GCgtgagtac caaactctcc cttctgccca cccatgcac tggctccagt    6720
gcggctctca tctggggagc aggaagacgc aggccaactg agcgccccg actctcagct    6780
catcctcttc tccccccttg cagGGTGCTCC TGGCAGCAAA GGAGACACTG              6840   20
GTGCTAAGGG AGAGCCTgta agtctccccg ccatcctct tgcagcccag cccaccctgc    6900
cctagagcc cctgaggga aatccagaaa ggaagaggag ccctagtct tctggggag       6960
tccctgccac accccagga acccctgaca ctggaggccc agcctcagcc ggctctgagg    7020
ctggcacagg atggccctc accacaggcc gcctcctcct ctcggccctc tccagGGCCC    7080
TGTTGGTGTT CAAGGACCCC CTGGCCCTGC TGGAGAGGAA GGAAAGGCGAG GAGCTCGAGG  7140   21
TGAACCCGGA CCCACTGGCC TGCCCGGACC CCCTGGCGAG CGTgtaagtg tccctgcccg   7200
ccccctccca ctccaccctc attgcctggc tggtgcctgt gtgtcgcgga gttcactggc   7260
ctcctctcct cctgcagGGT GGACCTGGTA GCCGTGGTT CCCTGGCGCA GATGGTGTTG    7320   22
CTGGTCCCAA Ggtaacctct ccttgcggcc gggggctga ccctgccgct ccctggcat    7380
cttcttcctc ttttggcccg tggcaaagag ccacaaactt gagacctaa ctgttcctgt   7440
gacttccccc aaccagGGTC CGCTGGTGA ACGTGGTTCT CCTGGCCCG CTGGCCCCAA     7500   23
AGGATCTCCT GGTGAAGCTG GTCGTCCCGG TGAAGCTGGT CTGCCTGGTG CCAAGgtgag  7560
```

FIG. 4A-7

| | Exon # |
|---|---|
| gcccaggct ttcagcctgg cttggccagg ccctgaccat cccgtgtagg gtctgggatg 7620 | |
| aggcgttctg gatcaggccc aagggtctgc cctctggagt cctccccac ctccatcatg 7680 | |
| cttctcccca agtcccactc atacctctct gcctccctag GTCTGACTG GAAGCCCTGG 7740 | 24 |
| CAGCCCTGGT CCTGATGGCA AAACTGGCCC CCCTgtaagt atcactcccc ctgaacccc 7800 | |
| tgccattgtc ctgtctgcct ccctgctgtc ctcactgctg ctttcgtgcc tcccatcctt 7860 | |
| agGGTCCCGC CGGTCAAGAT GGTGCGCCCG GACCCCCAGG CCCACCTGGT GCCCGTGGTC 7920 | 25 |
| AGGCTGGTGT GATGGGATTC CCTGACCTA AAGGTGCTGC Tgtgagtatt aagtgaggat 7980 | |
| ccatgaagag ccaggacaa acacacctga gacttgaagg agtcctgggc tctggctca 8040 | |
| gctgtgccgc tgacctgccg tgtggccact cactctcact ttctgacct cagcctccct 8100 | |
| atctgtaaaa tgaaagactt ctcggcgggg cacggtggct catgcctgta atcccagcac 8160 | |
| tttgggaggc caaggcgggc agaccatgag gtcaggagtt tgagaccagt cgggccaaca 8220 | |
| tagtgaaacc acgtctctac taaaaatcaa aaagattagc tgggtgtggt ggtgtgcacc 8280 | |
| tgtaacccca gctagtcagg aggctgaggc aggagaattg catgaaccg ggaggtggag 8340 | |
| gttgcagtga gctgagatca cgccattgca ctccagcctg ggcaacagtg cgagattcca 8400 | |
| tctcaaaaaa aaaaaaaaaa agaagaaaga aagaaagaaa aaatgaaaca cttctccagg 8460 | |
| ctccatgacc actgctctgt cctgaaataa gtgttgttgg tgccctcca cccgacacg 8520 | |
| tggggatagg acaggccttt gatatgatag aagatgaaag cccttttgcag ttcttttgagg 8580 | |
| tccaaaagga gatagcagag aagatgaaag cccttttgcag tgcaggccac agcgggcatc 8640 | |
| taacagggaa aaggcagagg agcctggaag ggcatcttgg gaggagtggg ctcagaaagg 8700 | |
| gcccagcaag aagcacctgc agggcattc ccgggggcc aaacagtctt ttgaaaagaa 8760 | |
| agtcccttaa aaagtcccac tcagagtaaa tgagaggccc caggaggccc tggcttctca 8820 | |

FIG. 4A-8

| Sequence | Position | Exon # |
|---|---|---|
| cttcagcccc ctcaaccta actcccttc tccacagGGA GAGCCCGGCA AGGCTGGAGA | 8880 | 26 |
| GCGAGGTGTT CCCGGACCCC CTGGCGCTGT Cgtaagtatc tcctttccat ccctacctcc | 8940 | |
| ttcccattgc tgccccggca ctttctcctc cctgcaggag gggtgctaga ggccacggtc | 9000 | |
| ctcagctgct cgggcctcc taaccctgag ttcccctttg ctctctccct gcagGTCCT | 9060 | 27 |
| GCTGGCAAAG ATGGAGAGGC TGGAGCTCAG GGACCCCCTG GCCCTGCTgt gagtgtccct | 9120 | |
| gatggggaga tctggggagc agaaaagggg agacaccctc agccctcgt ctcctcggcc | 9180 | |
| tccccgtgac tgtagtgttc tctctgtgca gGGTCCCGCT GGCGAGAGAG GTGAACAAGG | 9240 | 28 |
| CCCTGCTGGC TCCCCGGAT TCCAGgtgag gcctcatggc tgtcaggatg ctgggagta | 9300 | |
| gggtaggaa acacctcttt gtctcttcc agattctaaa ccttccctcc cttcttcccc | 9360 | |
| catttcccac ctacagGGTC TCCCTGGTCC TGCTGGTCCT CAGGTGAAG CAGGCAAACC | 9420 | 29 |
| TGGTGAACAG gtaagaggga gcagccggcc agagggtgg gagatgcagg gaatccagag | 9480 | |
| ggacaggccc ccgcctccta gctaatcaga cagccatcaa ctagagggat tgaggttaga | 9540 | |
| caccggaaag aacttcctcc catgaaggga gcagcacaga gggaagtggg ggctgcatga | 9600 | |
| ttgctagtct gggtgacttc ttttaagagc tgctggaata tgctgtgact ttccctcaac | 9660 | |
| ccttgtatt ataatcttg gtccatagtt tggggagggg ggaagcctt gacacatccc | 9720 | |
| taggagaag agaggggctg ttttgggataa tctcaattca gtgctgagaa ggggttcctc | 9780 | |
| tctaatcacg gccagaccc aggaggaagg accgtgcttt ccagcagagt ggccccaggt | 9840 | |
| aggttttgct cactgtctgt tcctctctca gGGTGTTCCT GGAGACCTTG | 9900 | 30 |
| GCGCCCTGG CCCCTCTGGA GCAAAGAgta gtaggcctct ctcgctgcat ccgtcaaggt | 9960 | |
| gcgttgtact tggccctatc tccagagcag ccttcacatg ccctgtcctt cccttctagG | 10020 | |
| GCGAGAGAGG TTTCCCTGGC GAGCGTGGTG TGCAAGGTCC CCCTGGTCCT GCTGGTCCCC | 10080 | 31 |

FIG. 4A-9

| Sequence | Position | Exon # |
|---|---|---|
| GAGGGGCCAA CGGTGCTCCC GGCAACGATG GTGCTAAGgt gaggcagcg tggaagggc | 10140 | |
| tctggcaagt ggcccaggga ccagtctca cccctcctgc agcagggat ggcggccat | 10200 | |
| gaccaaagcc atggagatag ggtgtggggt gtgagtcttt tcatcttttc tcaagcttg tcgttgcct | 10260 | |
| cacagcctgg agtctgggct gtgagtcttt tcatcttttc tcaagcttg tcgttgcct | 10320 | |
| tggaaacaag cctgggagat gcttagggct gtgaccact cttggggcc | 10380 | |
| caggcctcac tccagtcttc ttggttgtca catagGGTGA TGCTGGTGCC CCTGGAGCTC | 10440 | |
| CCGTAGCCA GGGCGCCCCT GGCCTTCAGG GAATGCCTGG TGAACGTGGT GCAGCTGGTC | 10500 | 32 |
| TTCCAGGGCC TAAGGGTGAC AGAgtaagtt caaccttccc cctccctga gccctacatg | 10560 | |
| gctccatct ctgcctgctt tgaatctctc agcatctctc cttctctctg ggatctgtcc | 10620 | |
| ctcttctcgc taatcctccc ctcttccct ttccccctg gcctttttgc tgatgaatcc | 10680 | |
| tctccctgtg gtccaggccc atctatcccc atgggttacc atggtgatga gaggtgggg | 10740 | |
| catctccttg gtggagctc ccttattcat ccgctacac aagtcagggg cctcttaacc | 10800 | |
| tcagttccac ctgagtctcc agcaggctc ccttttttcct gaaagaatct ttgagtcctt | 10860 | |
| ggcccaggtg gaggcaggc agagctgcag agggcctctc aggaaaccca gacacagca | 10920 | |
| gaacactata ggtcacctcc ttgcccaca ctggaaatct caagcttatc catgtcttta | 10980 | |
| gGGTGATGCT GGTCCCAAAG GTGCTGATGG CTCTCCTGGC AAAGATGGCG TCCGTGGTCT | 11040 | 33 |
| GACCGGCCCC ATTGGTCCTC CTGGCCCCGC TGGTGCCCCT GGTGACAAGg tgaggtggcc | 11100 | 34 |
| gcctcccac cttctgccct aacacatagc ctcctcagca ggcctgggca cggttccgtg | 11160 | |
| gggttgcgtt gggagagcag gtcctgccaa actgagctgt caacctggga acctggaggg | 11220 | |
| accagaagga ggggaggctc tcctggggtc atctactagg agtattcagg ggaggccctg | 11280 | |
| acccctgagcc tcttgtccct tgctctcagG GTGAAAGTGG TCCCAGGGGC CCTGCTGGTC | 11340 | 35 |

FIG. 4A-10

```
                                                                            Exon #
CCACTGGAGC TCGTGGTGCC CCCgtaagta cagaagacct gttaagaccc catacttggc    11400
ccttccctcc cttcacacag cacccctggc cctgtctgtg ccttcacccc ttgcctctcc    11460
cctcaccgca tcccgcctt cctcctgtc agacgcatct ctccaatctg actcctttc      11520
ttctagGGAG ACCGTGGTGA GCCTGGTCCC CCCGGCCCTG CTGGCTTTGC TGGCCCCCT    11580  36
gtgagtacca agaccccat cattttcat caccgactgg gacctgggac ctcgagggac     11640
ggaatgagga caaggcgtc agccatcctc aggggagaag ggtggagacg ggattgtttc    11700
ccacccaagc atcttcctgc ctccattact gctcctcccc caggtagtgg aaactcctgc   11760
ctccttccct ccattcaccg ccctgcttcc tccccagGG TGCTGACGGC CAACCTGGTG    11820
CTAAAGGCGA ACCTGGTGAT GCTGGTGCTA AAGGCGATGC TGGTCCCCCT GGCCCTGCCG   11880  37
GACCCGCTGG ACCCCCTGGC CCCATGtgtga gtggcttggc cctctgtgcc cacgaggctg  11940
gtgggctggg accaggacg ggtccaggct tgatgcgtct gtgctctcct acagGGTAAT   12000  38
GTTGGTGCTC CTGGAGCCAA AGGTGCTCGC GGCAGCGCTG GTCCCCCTGt gagtatcacc   12060
cgcctctctg ttgagcctct cccctctccc caggcagcgg tggcaggtga gggcagctgg   12120
gtcggatgag ttggctgttc tggctgtttc ttctctcctt ccagGGTGCT                12180  39
ACTGGTTTCC CTGGTGCTGC TGGCCGAGTC GGTCCTCCTG GCCCCTCTg aagtctctgc    12240
agcagagtcc actgctctag gttgggggtg ctgggtgggg gctgccagaa ggatggtggg   12300
gctgactgag gaccaatga tgcaccagag cccctggag tctgacagcc cctcctatcc     12360
tcatccagGG AAATGCTGGA CCCCCGGCC CTCCTGGTCC TGCTGGCAAA GAAGGCGGCA    12420
AAGGTCCCCG TGGTGAGACT GGCCCTGCTG GACGTCCTGG TGAAGTTGGT CCCCCTGGTC   12480  40
CCCCTGGCCC TGCTGGCGAG AAAGGATCCC CTGGTGCTGA TGGTCCTGCT gtaagtgcca   12540
gctcagatct ctgcagctcc ggaggtgtgc agagctgggg agggtccct gtgtgctgt    12600
```

FIG. 4A-11

| | | | | | Exon # |
|---|---|---|---|---|---|
| ctggcacctc | accctgttt | gcctcccaaa | gGGTGCTCCT | GGTACTCCCG | GGCCTCAAGG | 12660 |
| TATTGCTGGA | CAGCGTGGTG | TGTCGGCCT | GCCTGGTCAG | AGAGGAGAGA | GAGGCTTCCC | 12720 | 41 |
| TGGTCTTCCT | GGCCCCTCTg | taagtgcccc | cctcaccttg | ggggccctg | agaaaacca | 12780 |
| tcacaggact | tggagtgggg | cggagccaag | gagaacagat | ttggtagaga | tgactccagc | 12840 |
| ggactcaagg | gtcctcccag | acctatctc | tggcctgact | ctttcttctc | ccttagGGTG | 12900 |
| AACCTGGCAA | ACAAGTCCC | TCTGGAGCAA | GTGGTGAACG | TGGTCCCCCT | GGTCCCATGG | 12960 | 42 |
| GCCCCCCTGG | ATTGGCTGGA | CCCCCTGGTG | AATCTGGACG | TGAGgtgagc | agtcccagc | 13020 |
| cccatgcca | gtaccctcag | catgcctt | gtggccttgc | ctaagccctc | ttccccggct | 13080 |
| gactctcact | tctctctctc | tctctctgca | gGGGGCTCCT | GGTGCCGAAG | GTTCCCCTGG | 13140 | 43 |
| ACGAGACGGT | TCTCCTGGCG | CCAAGgtaag | atgcaaacac | tccatgacca | cagccttgtc | 13200 |
| tgctgctctc | ctgcccatc | acccgggct | gaccatatt | cccctgctct | 13260 |
| ccccgccagG | GTGACCGTGG | TGAGACCGGC | CCCGCTGGAC | CCCCTGGTGC | TCCTGGTGCT | 13320 | 44 |
| CCTGTTGCCC | CTGGCCCCGT | TGGCCCTGCT | GGCAAGAGTG | GTGATCGTGG | TGAGACTgta | 13380 |
| agtagctggg | ctccagttcc | ctgtacctgg | tcaggccagg | gactccttcag | gcctccttag | 13440 |
| aggcctgggg | atgggtgtcg | gacttcaccc | aggcaggggg | aggaaaggag | atcctgcaag | 13500 |
| atgtcaggggc | cttaatccaa | aaaactgagt | taaagctcag | ccctaagtcc | cctctcccag | 13560 |
| acaggaccgc | ctctcccatg | agttggcccc | agctcccgtg | aagattgcag | tggggaggtt | 13620 |
| tccctgggag | ttgggagaga | tggccacagt | gggaagcagc | tgaggagaga | gagatccagc | 13680 |
| agaggggagg | cctcatcctg | cagcccagc | ctcagccttc | cctggccaag | agctcatgct | 13740 |
| ttccttgctc | tccccagGGT | CCTGCTGGTC | CCGCCGGTCC | TGTCGGCCCT | GTTGGCGCCC | 13800 | 45 |
| GTGGCCCCGC | Cgtaagtacc | ctgctgtgtc | cccatgcct | tcagaactct | acagatgcag | 13860 |

FIG. 4A-12

```
                                                                           Exon #
acagtgcccc actcgatgcc aatggaactt ccgcctgaca gtttgtccct ttctctcttc 13920
tagGGACCCC AAGGCCCCG TGGTGACAAG GGTGAGACAG GCGAACAGGG CGACAGAGGC 13980    46
ATAAAGGTC ACCGTGGCTT CTCTGGCCTC CAGGGTCCCC CTGGCCCTCC Tgtaagtatg 14040
ctcagcccct cccagtccc catgctgtgc tgtgggatag gagggggagc ttcgcctcag 14100
tttcccctc tggatagtca ttctttcccc tccctagtgg ggactggggt ctgaagattt 14160
gtgggcatgt ccaagtagct tctgagaggg tgaggggtac acagagaggg attatgggag 14220
aggtctctgc ctatggacac cctcgggcta gatttccaga ataatgaagg ggcatgggtt 14280
gcccacactg cccttgtctc tccagccagg ccctcaggct acattgacg ctcactgggc 14340
ctgaactgcc tttttatct gtccttcagG GCTCTCCTGG TGAACAAGT CCCTCTGGAG 14400    47
CCTCTGGTCC TGCTGGTCCC CGAgtaagtc atgccttctc tctccctcttc ctgagcccca 14460
agcccaggct cacctcgggg acccttgcca ggaccaggc accctttgcc tctctggaga 14520
agggttcagg gacagggagt gggcaaagaa aggaagaatc ctgaacaaac aatctgatct 14580
agctttggcc tctctgctcc ccaatccgtc ctcccctggc tcagcggctg ggaggagcta 14640
tggcatgtcc tatggaaaga ggctgaggct ggctctatga gccgtggggc cagagccagc 14700
agggaggtg gtgggcctct cctccagagc tggggttgtt cgggcttctg gcagcctttc 14760
tcaaaccatt tccccactc cagGGTCCCC CTGGCTCTGC TGGTGCTCCT GGCAAAGATG 14820    48
GACTCAACGG TCTCCCTGGC CCCATTGGGC CCCCTGGTCC TCGCGGTCGC ACTGGTGATG 14880
CTGGTCCTGT Tgtatgtagc ccctcatccc actctcttcc ctctctgtgc agGTCCCCC CGGCCCTCCT 14940
acttggatgc cggaatcccc gtcccccTGG TCCTCCCAGC GCTGGTTTCG ACTTCAGCTT CCTGCCCCAG 15000
GGACTCCTG GTCCCCCTGG TCCTCCCAGC GCTGGTTTCG ACTTCAGCTT CCTGCCCCAG 15060
CCACCTCAAG AGAAGGCTCA CGATGGTGGC CGCTACTACC GGGCTGATGA TGCCAATGTG 15120    49
```

FIG. 4A-13

```
                                                                              Exon #
GTTCGTGACC GTGACCTCGA GGTGGACACC ACCCTCAAGA GCCTGAGCCA GCAGATCGAG  15180
AACATCCGGA GCCCAGAGGG AAGCCGCAAG AACCCCGCCC GCACCTGCCG TGACCTCAAG  15240
ATGTGCCACT CTGACTGGAA GAGTGgtgtg ggcctgccct agcctctccc tccctcctac  15300
tcctgccatg ccagggtccc catgcccata tgtgccccta ccatatggtg ctggctgctc  15360
cctttccctg actccatctt gccctgccct accacagGAG AGTACTGGAT TGACCCCAAC  15420
CAAGGCTGCA ACCTGGATGC CATCAAAGTC TTCTGCAACA TGGAGACTGG TGAGACCTGC  15480    50
GTGTACCCCA CTCAGCCCAG TGTGGCCCAG AAGAACTGGT ACATCAGCAA GAACCCCAAG  15540
GACAAGAGGC ATGTCTGGTT CGGCGAGAGC ATGACCGATG GATTCCAGgt gcgtgagctg  15600
gacctcagag ccagtgttag gagatgggct agcccagtgc tcagaaggga catgaagtcc  15660
tggagtaggt ctctgctaag ggtgatggac agagctgggc tgggaggcag gggtctcagg  15720
tccctgctag tggttcagac acaggctgcc gatgggcagg tggtgccct ctgatataac  15780
ggtgcattgg gcagctctct gaggacccctg gacaggagc cagcaggact agaggttccc  15840
gcatagctca ctcttccctc tctctcctcc ctgcagTTCG AGTATGGCGG CCAGGCTCC  15900
GACCCTGCCG ATGGGCCCAT CCAGCTGACC TTCCTGCGCC TTGCTGTCCAC CGAGGCCTCC  15960    51
CAGAACATCA CCTACCACTG CAAGAACAGC GTGGCCTACA TGGACCAGCA GACTGGCAAC  16020
CTCAAGAAGG CCCTGCTCCT CAAGGGCTCC AACGAGATCG AGATCCGCGC CGAGGGCAAC  16080
AGCCGCTTCA CCTACAGCGT CACTGTCGAT GGCTGCACGG tgagtgccca gaatcccag  16140
gcagggcccc acctctccgg ccttgggcat tttggccagg ccatagtgcc ctctctccat  16200
cactcccacg tggtaatgcc ccctcccgtt gtctccgccc caccccagAG TCACACGGA  16260
GCCTGGGGCA AGACAGTGAT TGAATACAAA ACCACCAAGA CCTCCCGCCT GCCCATCATC  16320    52
GATGTGGCCC CCTTGGACGT TGGTGCCCCA GACCAGGAAT TCGGCTTCGA CGTTGGCCCT  16380
```

FIG. 4A-14

| | | | | Exon # |
|---|---|---|---|---|
| GTCTGCTTCC TGTAAactcc | ctccatccca acctggctcc | ctccaccca | accaactttc | 16440 |
| ccccaaccc ggaaacagac | aagcaaccca aactgaaccc | cccaaaagc | caaaaaatgg | 16500 |
| gagacaattt cacatggact | ttggaaaata ttttttcct | ttgcattcat | ctctcaaact | 16560 |
| tagttttat ctttgaccaa | ccgaacatga ccaaaaacca | aaagtgcatt | caaccttacc | 16620 |
| aaaaaaaaaa aaaaaaaaaa | aagAATAAAT AAATAActtt | ttaaaaaagg | aagcttggtc | 16680 |
| cacttgcttg aagaccatg | cggggtaag tccctttctg | cccgttgggt | tatgaaaccc | 16740 |
| caatgctgcc ctttctgctc | ctttctccac accccccttg | gcctccctc | cactccttcc | 16800 |
| caaatctgtc tccccagaag | acacaggaaa caatgtattg | tctgcccagc | aatcaaaggc | 16860 |
| aatgctcaaa cacccaagtg | gcccccaccc tcagcccgct | cctgcccgcc | cagcaccccc | 16920 |
| aggccctggg gacctggggt | tctcagactg ccaaagaagc | cttgccatct | ggcgctccca | 16980 |
| tggctcttgc aacatctccc | cttcgttttt gagggggtca | tgccggggga | gccaccagcc | 17040 |
| cctcactggg ttcggaggag | agtcaggaag ggccacgaca | aagcagaaac | atcggatttg | 17100 |
| gggaacgcgt gtcatccctt | gtgccgcagg ctgggcggga | gagactgttc | tgttctgttc | 17160 |
| cttgtgtaac tgtgttgctg | aaagactacc tcgttcttgt | cttgatgtgt | caccggggca | 17220 |
| actgcctggg ggcggggatg | ggggcaggt tggggtgggg | agggaatcac | ataccaaagg | 17280 |
| tgctacatct atgtgatggg | ggccagcaaa tgttccttt | tgttcaaagt | gaaattgaga | 17340 |
| tgccccccca ggccagcaaa | tgttccttt tgttcaaagt | ctattttat | tccttgatat | 17400 |
| ttttccttc ttttttttt | ttttgtgga tggggacttg | tgaattttc | taaggtgct | 17460 |
| atttaacatg ggaggagagc | gtgtgcgctc cagccagcc | cgctgctcac | tttccaccct | 17520 |
| ctctccacct gcctctgct | tctcaggcct ctgctctccg | acctctctcc | tctgaaaccc | 17580 |
| tcctccacag ctgcagccca | tcctcccggc tccctcctag | tctgtcctgc | gtcctctgtc | 17640 |

FIG. 4A-15

| | Exon # |
|---|---|
| ccgggtttc agagacaact tcccaaagca caaagcagtt tttccctagg ggtgggagga | 17700 |
| agcaaaagac tctgtaccta tttgtatgt gtataataat ttgagatgtt tttaattatt | 17760 |
| ttgattgctg gAATAAagca tgtggaaatg accaaacat aatccgcagt ggcctcctaa | 17820 |
| tttccttctt tggagttggg ggaggggtag acatggggaa ggggccttgg ggtgatgggc | 17880 |
| ttgccttcca ttcctgccct ttccctcacc ttcttatacc tctagatccc tccataaccc | 17940 |
| cactcccctt tctctcaccc ttcttatacc gcaaacctt ctacttcctc tttcattttc | 18000 |
| tattcttgca atttccttgc acctttcca aatcctcttc tcccctgcaa taccatacag | 18060 |
| gcaatccacg tgcacaacac acacacacac tcttcacatc tggggttgtc caaacctcat | 18120 |
| accactccc cttcaagccc atccagccc atcccccctgg atgccctgca cttgtgtgcg | 18180 |
| gtgggatgct catggatact gggaggtga gggagtgga acccgtgagg aggacctggg | 18240 |
| ggcctctcct tgaactgaca tgaaggtca tctgccctct gctcccttct cacccacgct | 18300 |
| gacctcctgc cgaaggagca acgcaacagg agagggtct gctgagcctg gcgagggtct | 18360 |
| gggaggggacc aggaggaagg cgtgctccct ctgtctcc ctggcccctgg gggagtgagg | 18420 |
| gagacagaca cctgggagag ctgtggggaa ggcactcgca ccgtgctctt ggaaggaag | 18480 |
| gagacctggc cctgctcacc acggactggg tgcctcgacc tcctgaatcc ccagaacaca | 18540 |
| acccccctgg gctggggtgg tctggggaac catcgtgccc ccgcctcccg cctactcctt | 18600 |
| tttaagctt | |

FIG. 4B-1 gggcacccc tacccactgg ttagcccacg ccatcctgag gaccagctg caccctacc
acagcacctc gggcctagge tggcggggg gctgggagg cagagctgcg aagaggag
atgtggggtg gactccctte cctcctcctc cccctctcca ttccaactcc CAAATTgggg
gccggccag gcagctctga ttgctgggg cacgggcggc cgctccccc tctccgaggg
gcaggttcc tccctgctct ccatcaggac agTATAAAAg gggcccggc cagtcgtcgg
agcagacggg agtttctcct cgggtcgga gcaggagca cgcggagtgt gaggccacgc
atgagcggac gctaacccc tcccagcca caaagagtct acatgtctag ggtctagac

FIG. 4B-2 gtaagtcc caaactttg
ggagtgcaag gatactctat atcgcgcctt gcgcttggtc ccggggccg cggcttaaaa
cgagacgtgg atgatccgga gactcggaa tggaagggag atgatgaggg ctcttcctcg
gcgccctgag acaggaggga gctcaccctg gggcgaggtt gggttgaac gcgccccggg
agcggaggt gagggtggag cgccccgtga gttggtgcaa gagagaatcc cgagagcgca
accggggaag tggggatcag ggtgcagagt gaggaaagta cgtcgaagat gggatgggg
cgccgagcgg ggcatttgaa gcccaagatg tagaagcaat caggaaggcc gtggatgat
tcataaggaa agattgccct cctgcgggc tagagtgttg ctggccgtg ggggtgctgg
gcagccgcgg gaaggggtg cgagcgtgg gcgggtggag gatgagaaac tttggcgcgg
actcgcgggg gcgggtcct tgcgcccct gctgaccgat gctgagcact gcgtctcccg
gtccaacgct tactgggca ggaccggag cgggaagacc cgggttattg ctgggtgcgg
acccacct ctagatctgg aaagtaaagc caggatggg gcagcccaag cctcttaaag

FIG. 4B-3 aggtagtcgg gccggtgagg tcgccccgc cccgccccca ttgcttagcg ttgcccgaca
cctagtggcc gtctggggag ccgctagcgc ggtgggagtg gttagctaac ttctggacta
tttgcggact ttttggttct ttggctaaaa gtgacctgga ggcattggct ggctttgggg
gactgggat ggccccgaga gcgggcttt aagatgtcta ggtgctggag gttaggtgt
ctcctaattt tgagtacat ttcaagtctt gggggggcgt cccttccaat cagccgctcc
cattcttta gccccgccc cgccacccca catgccccagg gaatggggggc gggatgaggg
atggacctcc cttctctcct ccctcgccct cctcctgtct ctaccacgca agccactccc
cacgagcctg ccctccccgat ggggccccctc ctattctccc cccgccctcc ccctctcacc
ctgtggtttt atttcacttg gcttcagcgc caatgggctg aggttggagt tggaagccac
cgcggactaa agctttgttt aaattcctga gaactggaaa gagttacagc ctccctgcc
aggcgcctcg gcgctgtcac ccgcgctgat gaggagcagg cgagcttta aggatttgag
gaaagaagaa cgggggggagg ggcgggaagt gaaaaatcca agtgtgcctc ttagacccgg
gggaaaggtg gttaagctgg gggttgcagt cactactgac aacgcccctc ttccgcctgt
cccag

FIG. 4B-4 gtgcggctgc gctcgggcgc tgggccctgg ggctgggggct
ggggtggtc ggcgctcgct ggccctccgt gctggaggcc tctgccgaccc ggagcagcat
tagcaaacct tggctcctaac gggcgtctct tcgtcccccta g

FIG. 4B-5

```
              gtaa tctcctgccc tcgaattttg ccctgcgcg gcccgtgact
cctcacagtc ctcccttctc taacctggcc tcttgtttct tctccccaa tcccacag
```

FIG. 4B-6

```
                           gtaagc gttgcactct gggctgtggg
gggctgcagg tgggcatggc tctcggcccc acgctcaccc cggcccgcc ctctcccct
gcag
```

FIG. 4B-7

```
                                     gtaa gtggagaggc
cttgtgtgtc cactctcccc tgttttgttt ttgttttttg gcagatgaca taattttata
ctttgaaata atttcaaact tacagaaaag ttgcaagaat cctacaggaa actctcacat
acccttcaca gttgtgaca tgtgctttat tagtctctgt ttatgtatat gtatctttt
tttctgaac tgttgagca agttgctaac atcaggctct tttgcgctct aatacttagg
tgtgttttc ctaaaaacaa gagcattctc ttaactgacc tacacaatga ttaaattcac
tctctaatgt gcagtccgta ctcaaagttc accgatgtcc cgataatgtc ctttatagat
tccaccccc accaccccaa tctggatcc agtccaggat tatgtattgc attaatcat
catgtctcta gtttccacaa atgtagaacg ttcctcagac tttctttgtc tttagtggca
ctgggagttt tgatgagtcc agttgttttg cagactgtcc ctcaatttgg gattgtctca
ttagattaga tgcagggatg catctttggc aggaatgtct taaagcaat gttattcttc
tcagcacatc acaccaggaa gtgcatgatg tcagtttctt catcctcag tgccgtcttc
tgcctttcaa ttcactgtcc tcactctgac ttctcttgtt tgttctag
```

FIG. 4B-8 gtgagccagc aggggagca tggatgacag aagagagaat gggtatccag aggatgtggg
catacgcggc tggtatacac agcttgggag gtccatatca ccttgggac ctcagagtcc
agaaaggatg caagacgact gggtggtccc aacaggcatg aatgactaca tccacatgct
ttcctacaga gggatcacca tgaccccct ttcttctccc tctatag

FIG. 4B-9 gtgagtat ccaggacgtc ttcatatgcc
tccttgggct ttggtctttt ggagggaaga ctgggatgag ggcaggagag atgctcagag
atctcttggt aagattggag aaggttgaca gggacttgtc ttctaaccca tcttttcct
tcttctcaag

FIG. 4B-10 gtaagc actctcctata cagattcata ctccttctac aaacacacag actctcctat
agaagaactc ccaggcctgg ggtcttcctt acctcttccc ttcaatccca gccttccct
tctttttttc ttatccatat tctaaccacc tcttctatct tttctag

FIG. 4B-11 agataccatc tgacccatg gcctccatgg gttgggtcct gcaatttcca ctccaccaca gtaagtatc cccagcaaga
tttggaacg atactcagag gaaggagggc aagtcctctc tgatgcacgg actgccctgg
aacaatgatc ttttcgctta gtgagatgat tccatgtccc caacaaagtg actgttctcc
tcacccagc caccttagag caatccccaa ccccatccct ttgggaaat tggtgcgcag
atggtgaaat taaaatgctg gtgacagaag tagacagaaa ttcctttaga ggcactcaga
tttcaccaaa cgaaggtttc actgtagatt taaactgagc tctagattca aagataagat
tctggccccc caaacctgac ctgcaacaat ccaaagaaga ctgagacctt ctccactttt
ccagcccta ggcggtggtg gggaggcaga ggcatgatgg tcttttctct ccctctcag

FIG. 4B-12 gggggctgtg gctgaacctg ggcttcactg ggcttcactg cacttgggct tcatttagga gctgggtcca gtgagca
cagtgatgtg ttctaatggc ccttccttgt cttcttcatc tctctccag

FIG. 4B-13

```
                                                       gtgagtc acctttgagt
catttaagct cccaagtcc ctagcatacc cccatccagt ccagcctct tcccaaaag
atcctgagtt gcatcatggt gggtggcagc tacagaagtc ccaagggca gagagtggac
atccaaaagc actcctcatg aatcccgat taccgattgg gtgagtctt agagccattt
ggggtttagt ctagctcaga aacaaaggga tggcggtgat gacctcccaa ggctcttct
cagatctagg tggatgtcaa ggctgttcca cccctccac agttcttac cttctacctc
tttcctgctt tag
```

FIG. 4B-14

```
            gta agaggctgtc tgaacatcat ggtcctccac atcccagag tcccaccatg
aatgaattc tcactcatta ttctctgatc tacag
```

FIG. 4B-15

```
                gtgagtgtgc ccagttccag agggcaggga tggggcagga
ggcagggca agatggaggc ctgggaaac aaggctgtct ccatctcat ctgacttctc
ttggtttggt tgtcag
```

FIG. 4B-16

```
           gtaagtactc ctgcccctt gggggatccc tgagctctgg aagggctcc
ccaggaactc taggactgg ccagtgctca gtggacttaa cgggcttcc cctctccct
gcag
```

FIG. 4B-17 ctgtaggcct caggcctgg gagtggggag gggtctcagt gtctgctctt ggggctgaca g tgagtgtggc
atgggggcag gttatgttgg tctgaacccc aggacttcct ctgtcccagg gtgtgacttg
cagctgccat ctcttccttc tcgctgacat ctccatttca ttcacag

FIG. 4B-18 gtgagaccc cccactctcc
tctaagcatg accctcatgg gccaagggt tcatgtctcc ctgttcccca aaccaaaggg
accagagtg gcaagagc agcccgttca ctaacacctt tgtcctgggg tctccgtctc
tgatcttaga gtcctgatca ttgctctcct gtccctgtct ccccttcctc ctgccatccc
gagaggcaag gttgggtttc ccagggtggc ttctgatatg tccttcttc tgattcag

FIG. 4B-19 gta agtgtccccg actcagtgtc
cccttttgcca ctttctaacc tcagagtcct tgcctgttgc tgacactcct ttctctgtgc
cacag

FIG. 4B-20 gtaagtatcc
tgccaggctt cagtcccact cctgccgcct gcagcctgcc tgcccttc cctctgctcc
taggctcacg ccctggctgt ctgcctccca cag

FIG. 4B-21 gtgagtac caaactctcc cttctgccca cccatgcac tggctccagt
gcggctctca tctggggagc aggaagacgc aggccaactg agcgccccg actctcagct
catcctcttc tcccccttg cag

FIG. 4B-22 gta agtctccccg ccatccttct tgcagcccag cccaccctgc
cctaggagcc ccctgaggga aatccagaaa ggaagaggag ccctagtct tctgggggag
tccctgccac acccccagga acccctgaca ctggaggccc agcctcagcc ggctctgagg
ctgcacagg atgcccctc accacaggcc gcctcctcct ctggccctc tccag

FIG. 4B-23 gtaagtg tccctgcccg
cccctccca ctccaccctc attgcctggc tggtgcctgt gtgtcgcgga gttcactggc
ctcctctcct cctgcag

FIG. 4B-24 gtaacctct ccttgcggcc gggggggctga cctgccgct cctgggcat
cttctcctc tttggcccg tggcaaagag ccacaaactt gagaccctaa ctgttcctgt
gacttccccc aaccag

FIG. 4B-25 gccccaggct ttcagcctgg cttggccagg ccctgaccat cccgtgtagg gtctgggatg gtgag
aggcgttctg gatcaggccc aagggtctgc cctctggagt cctcccccac ctccatcatg
cttctcccca agtcccactc atacctctct gcctccctag

FIG. 4B-26 gtaagt atcactcccc ctgaaccccc
tgccattgtc ctgtctgcct ccctgctgtc ctcactgctg ctttcgtgcc tcccatcctt
ag

FIG. 4B-27

```
                                                          gtgagtatt aagtgaggat
ccatgaagag ccaggacaa acacacctga gacttgaagg agtcctgggc tctggctca
gctgtgccgc tgacctgccg tgtggccact cactctcact ttctgacct cagcctccct
atctgtaaaa tgaaagactt ctcggcgggg cacggtggct catgcctgta atcccagcac
tttgggaggc caaggcgggc agaccatgag gtcaggagtt tgagaccagt cggccaaca
tagtgaaacc acgtctctac taaaaataca aaagattagc tgggtgtggt ggtgtgcacc
tgtaacccca gctagtcagg aggctgaggc aggagaattg catgaacccg ggaggtggag
gttgcagtga gctgagatca cgccattgca ctccagcctg ggcaacagtg cgagattcca
tctcaaaaaa aaaaaaaaaa agaagaaaga aagaaaagaaa aaatgaaaaca cttctccagg
ctccatgacc actgctctgt cctgaaataa gtgttgttgg tgccctcca cccgacacg
tggggatagg acaggccttt gatatgatag gcaccccag tcttgtgga ttctttgagg
tccaaaagga gatagcagag aagatgaaag ccctttgcag tgcaggccac agcgggcatc
taacagggaa aaggcagagg agcctggaag ggcatcttgg gaggagtggg ctcagaaagg
gcccagcaag aagcacctgc aggggctc ccgggggcc aaacagtctt ttgaaaagaa
agtcccttaa aaagtcccac tcagagtaaa tgagaggccc caggagccc tggcttctca
cttcagccc ctcaaccta actcccttc tccacag
```

FIG. 4B-28

```
                                     gtaagtatc tcctttccat ccctacctcc
ttcccattgc tgccccggca ctttctcctc cctgcaggag gggtgctaga ggccacggtc
ctcagctgct cgggcctcc taaccctgag ttcccctttg ctctctccct gcag
```

FIG. 4B-29

```
                                                   gt gagtgtccct
gatggggaga tctggggagc agaaaagggg agacaccctc agccctcgt ctcctcggcc
tcccgtgac tgtagtgttc tctctgtgca g
```

FIG. 4B-30

```
                        gtgag gcctcatggc tgtcaggatg ctgggaggta
ggggtaggaa acacctcttt ggtcctcc agattctaaa cctccctcc cttcttcccc
catttcccac ctacag
```

FIG. 4B-31

```
             gtaagaggga gcagccggcc agagggtgg gagatgcagg gaatccagag
ggacaggccc ccgcctccta gctaatcaga cagccatcaa ctagagggat tgaggttaga
caccggaaag aacttcctcc catgaaggga gcagcacaga gggaagtggg ggctgcatga
ttgctagtct gggtgacttc ttttaagagc tgctggaata tgctgtgact ttccctcaac
ccttgtattg ataaatcttg gtccatagtt tggggagggg ggaagccttt gacacatccc
taggaggaag agaggggctg tttgggataa tctcaattca gtgctgagaa ggggttcctc
tctaatcacg gccagacccc aggaggaagg accgtgcttt ccagcagagt ggcccaggt
aggttttgct cactgtctgt tcctctctcc ctccccctca g
```

FIG. 4B-32 gtaa gtaggcctct ctcgctgcat ccgtcaagt
gcgttgtact tggccctatc tccagagcag cctcacatg cctgtcctt ccctctag

FIG. 4B-33 gt gagggcagcg tggaaggggc
tctggcaagt ggcccaggga ccagtctcca cccctcctgc agcagggat gcgggccat
gaccaaagcc atggagatag ggtgtgggt gtgagtcttt tcatcttttc tcaaggcttg tcgttgcct
cacagcctgg agtctgggct gtgagtcttt tcatcttttc tcaaggcttg tcgttgcct
tggaaacaag cctgggagat accaagcggg gcttaggct gtgaccact cttggggccc
caggcctcac tccagtcttc ttggttgtca catag

FIG. 4B-34 gtaagtt caaccttccc cctccctga gccctacatg
gctcccatct ctgcctgctt tgaatctctc agcatctctc cttctctg ggatctgtcc
ctcttctgc taatcctcc ctcttccct ttcccctg gcttttgc tgatgaatcc
tctccctgtg gtccaggccc atctatcccc atgggttacc ccgctacac aagtcagggg cctcttaacc
catctccttg gtgaggctc cctattcat cccgctacac aagtcagggg cctcttaacc
tcagttccac ctgagtctcc aggcaggaac cctttttcct gaaagaatct ttgagtcctt
ggcccaggtg gaggcagggc agagctgcag agggcctctc aggaaccca gacacaagca
gaacactata ggtcacttca ttgcccaca ctggaaatct caagcttatc catgtctttta
g

FIG. 4B-35 gcctccccac cttctgccct aacacatagc ctcctcagca ggcctgggca cggttccgtg
gggttgcgtt gggagagcag gtcctgccaa actgagctgt caacctggga acctggaggg
accagaagga ggggaggctc tcctgggtc atctactagg agtattcagg ggagccctg
accctgagcc tcttgtccct tgctctcag                                    g tgaggtggcc

FIG. 4B-36 gtaagta cagaagacct gttaagaccc catacttggc
ccttccctcc cttcacacag caccctggc cctgtctgtg ccttcacccc ttgcctctcc
cctcaccgca tccccgcctt ccctcctgtc agacgcatct ctccaatctg actccttttc
ttctag

FIG. 4B-37 gtgagtacca agaccccat catttttcat caccgactgg gacctgggac ctcgagggac
ggaatgagga caaggcgtc agccatcctc aggggagaag ggtggagacg ggattgtttc
ccaccaagc atcttcctgc ctccattact gctcctcccc caggtagtgg aaactcctgc
ctccttccct ccattcaccg ccctgcttcc tcccccag

FIG. 4B-38 gtga gtggcttggc cctctgtgcc cacgaggctg
gtgggctggg accaggacg ggtccaggct tgatgcgtct gtgctctcct acag

FIG. 4B-39 cgcctctctg ttgagcctct ccctctccc caggcagcgg tggcaggtga gggcagctgg
gtcggatgag ttggctgttc tccctgac tgttcctatg ttctctcctt ccag gt gagtatcacc

FIG. 4B-40 agcagagtcc actgctctag gttggggtg ctgggtgggg ctgccagaa ggatggtggg
gctgactgag gacccaatga tgcaccagag cccctggag tctgacagcc cctccctatcc
tcatccag gt aagtctctgc

FIG. 4B-41 gctcagatct ctgcagctcc ggaggtgtgc agagctgggg aggggtccct gtgctgctgt
ctggcacctc accctgttt gcctcccaaa g gtaagtgcca

FIG. 4B-42 tcacaggact tggagtgggg cggagccaag gagaacagat ttggtagaga tgactccagc
ggactcaagg gtcccag accctatctc tggcctgact ctttcttctc ccttag g taagtgcccc cctcaccttg ggggccctg agaaaacca

FIG. 4B-43 cccatgcca gtaccctcag catggccatt gtggccttgc ctaagccctc ttcccggct gtgagc agtccccagc
gactctcact tctctctctc tctctctgca g

FIG. 4B-44 gtaag atggcaacac tccatgacca cagccttgtc
tgctgcttcc ctgccccatc ctggcccttc accggggct gacccatatt ccctgctct
ccccgccag

FIG. 4B-45 gta
agtagctggg ctccagttcc ctgtacctgg tcaggccagg gactcttcag gcctcttag
aggcctgggg atgggtgtcg gacttcaccc aggcaggggg aggaaaggag atcctgcaag
atgtcagggc cttaatccaa aaaactgagt taaagctcag ccctaagtcc cctctcccag
acaggaccgc ctctcccatg agttggcccc agtccccgtg aagattgcag tgggaggtt
tccctgggag ttgggagaga tggccacagt gggaagcagc tgaggagaga gagatccagc
agaggggagg cctcatcctg cagcccccagc ctcagccttc cctggccaag agctcatgct
ttccttgctc tccccag

FIG. 4B-46

```
         gtaagtacc ctgctgtgtc cccatgcct tcagaactct acagatgcag
acagtgcccc actcgatgcc aatgaactt ccgcctgaca gtttgtccct ttctctcttc
tag
```

FIG. 4B-47

```
                                                        gtaagtatg
ctcagcccct cccagtccc catgctgtgc tgtgggatag gaggggagc ttcgcctcag
tttcccctc tggatagtca ttctttcccc tccctagtgg ggactgggt ctgaagattt
gtgggcatgt ccaagtagct tctgagaggg tgagggtac acagagagg attatgggag
aggtctctgc ctatggacac cctcggcta gatttccaga ataatgaagg ggcatgggtt
gcccacactg ccctgtctc tccagccagg ccctcaggct acatttgacg ctcactgggc
ctgaactgcc tttttatct gtccttcag
```

FIG. 4B-48

```
         gtaagtc atgccttctc tctcctcttc ctgagcccca
agcccaggct cacctggggg acccttgcca ggaccaggc acccttgcc tctctggaga
agggttcagg gacaggagt gggcaaagaa aggaagaatc ctgaacaaac aatctgatct
agctttggcc tctctgctcc ccaatccgtc ctccctggc tcagcggctg ggaggagcta
tggcatgtcc tatggaaaga ggctgaggct ggctccatga gccgtgggc cagagccagc
agggagggtg gtgggcctct cctccagagc tggggttgtt cgggcttctg gcagcctttc
tcaaaccatt tccccactc cag
```

FIG. 4B-49 gtatgtagc ccctcatccc ctctgctcat ggccctccag ccccatagc
acttggatgc cggaatcccc actctcttcc ctctctgtgc ag

FIG. 4B-50 gtgtg ggcctgccct agcctctccc tccctcctac
tcctgccatg ccaggtccc catgccccata tgtgcccta ccatatggtg ctggctgctc
cctttccctg actccatctt gccctgccct accacag

FIG. 4B-51 gt gcgtgagctg
gacctcagag ccagtgttag gagatgggct agcccagtgc tcagaaggga catgaagtcc
tggagtaggt ctctgctaag ggtgctgac agagctgggc tgggaggcag gggtctcagg
tccctgctag tggttcagac acaggctgcc gatgggcagg tggtgcccct ctgatataac
ggtgcattgg gcagctctct gaggacctg gacaggaggc cagcaggact agaggttccc
gcatagctca ctcttccctc tctccctcc ctgcag

FIG. 4B-52 g tgagtgccca gaatcccag
gcaggcccc acctctccgg ccttgggcat tttggccagg ccatagtgcc ctctctccat
cactcccacg tggtaatgcc ccctcccgtt gtctccgccc cacccag

FIG. 4B-53

```
          actcc ctccatccca acctggctcc ctcccaccca accaactttc
cccccaccc ggaaacagac aagcaaccca aactgaaccc cccaaaagc caaaaatgg
gagacaattt cacatggact ttggaaaata tttttttcct ttgcattcat ctctcaaact
tagttttat cttgaccaa ccgaacatga ccaaaaacca aaagtgcatt caaccttacc
aaaaaaaaa aaaaaaaaaa aagAATAAAT AAATAACttt ttaaaaagg aagcttggtc
cacttgcttg aagaccatg cggggtaag tcccttctg ccgttgggt tatgaaaccc
caatgctgcc ctttctgctc cttctccac accccccttg gcctccctc cactccttcc
caaatctgtc tcccagaag acacaggaaa caatgtattg tctgcccagc aatcaaagc
aatgctcaaa cacccagtg gcccccaccc tcagccccgct cctgcccgcc cagcaccccc
aggccctggg gacctgggt tctcagactg ccaaagaagc cttgccatct ggcgctccca
tggctcttgc aacatctccc cttcgttttt gaggggtca tgccggggga gccaccagcc
cctcactggg ttcggaggag agtcaggaag ggccacgaca aagcagaaac atcgatttg
gggaacgcgt gtcatccctt gtgccgcagg ctgggcggga gagactgttc tgttctgttc
cttgtgtaac tgtgttgctg aaagactacc tcgtttcttgt cttgatgtgt caccggggca
actgcctggg ggcggggatg ggggcagggt ggaagcggct ccccattttt ataccaaagg
tgctacatct atgtgatggg tggggtgggg agggaatcac tggtgctata gaaattgaga
tgccccccca ggccagcaaa tgttcctttt tgttcaaagt ctattttat tccttgatat
tttttctttc tttttttttt ttttgtgga tggggacttg tgaatttttc taaggtgct
atttaacatg ggaggagagc gtgtgcgctc cagcccagcc cgctgctcac tttccaccct
ctctccacct gcctctggct tctcaggcct ctgctctccg acctctctcc tctgaaacc
tcctccacag ctgcagccca tcctcccggc tccctcctag tctgtcctgc gtcctctgtc
```

FIG. 4B-54

```
ccggtttc agacaact tccaaagca caaagcagtt tttccctagg ggtgggagga
agcaaaagac tctgtaccta ttttgtatgt gtataataat ttgagatgtt tttaattatt
ttgattgctg gAATAAagca tgtggaaatg acccaaacat aatccgcagt ggcctcctaa
tttccttctt tggagttggg ggaggggtag acatggggaa gggcctttgg ggtgatgggc
ttgccttcca ttcctgccct ttccctcccc actattctct tctagatccc tccataaccc
cactcccctt tctctcaccc ttcttatacc ttctctcctt ctacttcctc tttcattttc
tattcttgca atttccttgc accttttcca aatcctcttc tcccctgcaa taccatacag
gcaatccacg tgcacaacac acacacacac tcttcacatc tggggttgtc caaacctcat
accactccc cttcaagccc atccactctc caccccctgg atgccctgca cttgtggcg
gtgggatgct catggatact gggaggtgta gggagtgga accgtgagg aggacctggg
ggcctctcct tgaactgaca tgaagggtca tctgcctct gctccttct caccacgct
gacctcctgc cgaaggagca acgcaacagg agaggggtct gctgagcctg gcgagggtct
gggagggacc aggaggaagg cgtgctccct gctcgctgtc ctggccctgg gggagtgagg
gagacagaca cctgggagag ctgtggggaa ggcactcgca ccgtgctctt gggaaggaag
gagacctggc cctgctcacc acggactggg tgcctcgacc tcctgaatcc ccagaacaca
accccctgg gctggggtgg tctggggaac catcgtgccc ccgcctcccg cctactcctt
tttaagctt
```

FIG. 5A-1

| | | | | Exon # |
|---|---|---|---|---|
| cattaccacc | ctgagtcatt | ttgctcagaa | ttagtctctg actctcagca acacaggaca | 60 |
| aatacacaca | tatgccctgc | aaggtaatt | cagcacagtg gtaacaatga ttcttagaaa | 120 |
| tcattctca | ctcttctgat | atgcagaaaa | aaatttgtta tgatgtagta ttgaagtttt | 180 |
| tctttcctga | taaaaatgat | ttccacttta | aaagttttt gttagttctg taacggtgat | 240 |
| atttcaggga | aatgttaaaa | atgttcttgg | aatatacaat tcaacctcag gtcttttgtt | 300 |
| gttgtgttc | ctagaaccta | gaaaacttca | acattgttg cctagttaga aaaaatttg | 360 |
| aatgtggatt | gctccctgta | aacccccttc | taggaatgac cagtaaccct ttcaaattct | 420 |
| ttcactccca | gttacttcaa | aaaatcatcc | aaagtggtct cccaagtgag tgcctttaat | 480 |
| tagaataaaa | caagagttta | ttatagtttt | tggttatcca cttttacttg cattaacctt | 540 |
| tttttcttct | tttacattta | gaaagagtaa | cctgctttag aatagtccct tttatttaca | 600 |
| gaagctgctg | atggagttaa | cttctgcaga | aattcttcct taaggcaaag caaaaaaagc | 660 |
| ggggaggggg | tgggggggaag | gaagggaaaa | agattctcag ggaactacag cccacttgct | 720 |
| tctgtttctt | agagacagaa | ctgacctaaa | gatgccccct ttgcgatgac ttctggata | 780 |
| gagcagcact | ctaactaggc | ccccgctgcc | tcatgggggac cttaggcaag tagaggagag | 840 |
| gcctgacaca | cacacacaca | cacacacaca | cacgcgcgcg cgcgcgcaca | 900 |
| cacacacaca | cagccttca | aacctagggc | ctggaatgcc atcccaagag gctttagaaa | 960 |
| aaggcacagg | acctttggcc | tcccacctca | ggtcaaagt accagttcct cctctcccta | 1020 |
| gtagggagtg | gagggttgga | tggaggcggc | cagagaagag ggaagttggg tgctggggag | 1080 |
| agagttaaca | tccacgttgg | tgggcgcact | gcttggggtg ttaccagcga agattacgaa | 1140 |
| gacccaagc | tcgaatcaga | agggcctctg | gatgtgctag gggaggtgct tgggtgtaac | 1200 |
| tgtaagagat | gggacagaga | gtaagcagca | aggtcaagag ggaccggggg gctcacggga | 1260 |

FIG. 5A-2

| | | | | | Exon # |
|---|---|---|---|---|---|
| gggttgaagg | gtccaggctc | aggtagaac | tggtaaatcc | agacaaggag | cccatggaga | 1320 |
| aggggagggg | agactggaaa | ccatgaaaga | tcccccaccg | cagcctcaga | aaggagagac | 1380 |
| tgagaaataa | gttctcggtc | tccagtcgg | ttggagtcgt | gtcggagtgc | cagaccatcc | 1440 |
| cccaaaagac | cctctttga | atgagcctca | gcaaaggcaa | gctaggaggt | cgaaggactt | 1500 |
| ccccaggtga | ctcggtctag | tctagagttc | gcaaagccta | tcctccctgt | agccgggtgc | 1560 |
| caagcagcct | cgagcctgct | cccagccca | cctgccaaca | aaaggcgccc | tccgactgca | 1620 |
| accagccct | ccacagacag | gacccgccct | ttcccgaagt | cataagacaa | agagagtgca | 1680 |
| tcactgctga | aacagtgggc | gcacacgagc | cccaaagcta | gagaaaagct | ggaaggggct | 1740 |
| ggggcgggg | tgcagggtg | gagggggtg | gaggcgggct | ccggctgcgc | acgctatcg | 1800 |
| agtcttccct | ccctccttct | ctgccccctc | cgctcccgct | ggagccctcc | accctacaag | 1860 |
| tggcctacag | ggcacaggtg | aggcgggact | ggacagctcc | tgctttgatc | gccggagatc | 1920 |
| tgcaaattct | gccatgtcg | gggctgcaga | gcactccgac | gtgtcccata | gtgtttccaa | 1980 |
| acttggaaag | ggcggggag | ggcggggaga | tgcggaggg | tgaggtatgc | agacaacgag | 2040 |
| tcagagtttc | cccttgaaag | cctcaaaagt | gtccacgtcc | tcaaaaagaa | tggaaccaat | 2100 |
| ttaagaagcc | agcccgtgg | ccagcccgtg | tcccccattc | gctccctcct | ctgcgccccc | 2160 |
| gcaggctcct | cccaggctgtg | gctgccctgg | cccccagccc | cagcccctcc | attggtggag | 2220 |
| gcccttttgg | agcaccta | ggccaggga | aactttttgcc | gtataaatag | ggcagatccg | 2280 |
| ggctttatta | ttttagcacc | acggcagcag | gaggtttcgg | ctaagttgga | gtactggcc | 2340 |
| acgactgcat | gcccgcgccc | gccaggtgat | acctccgccg | gtgaccagg | ggctctgcga | 2400 |
| cacaaggagt | ctgcatgtct | aagtgctaga | CATGCTCAGC | TTTGTGGATA | CGGGACTTT | 2460 | 1 |
| GTTGCTGCTT | GCAGTAACCT | TATGCCTAGC | AACATGCCAA | Tgtaagtgcc | ttcagcttgt | 2520 |

FIG. 5A-3

```
                                                                              Exon #
ttgggggaga ctgggtagag aggttagatg ggaggcacc ctgccctgaa aaggaaaacc    2580
tgtaacctga attccaggta cacttggagg gcagactctc agcatgtgg gaaaacgccg    2640
gaattgataa gaaacatgga aattacttta aaaaatgaaa acataaaagc cttgccaaaa    2700
gttagggaac ttttcctcta agttcagagt gagacagtta actcggtctg gctcctcagc    2760
ttagtaaccc ccaaagggag cggaaggtct ttttccctaa ggatgagata ttaacgacca    2820
atgtggtgga ggaagtcaag ggcctgcacc ccacaggccc cataaccgca ctgatgtcca    2880
ccttgtaaaa cttgaggcct gcgttagaaa gcccttcaac tgagtaatgt aaaactcacc    2940
tcctaagagc ttttatcttc tgggcattgt aaggcttgtc cggaggagga ggatgacgat    3000
gctgatatga tgatggttat aaggcgccct ctggaggaag gaaaatgaaa gtacaggga    3060
cagggcctta agcagatgga atcccaatta aagcttctac ggattatac agattaatga    3120
tcagcatttc tggttggagc ctttcccagt ggctagtcag tgaaccctgg aaagaagaat    3180
ggatgctact tggagtgggt acattctgaa aagtaatata agtgtctcaa ttcactttct    3240
agtcatggaa atggtaacat tttttaactc aaatctgtc taaattttgt ttgagcctga    3300
gaattacccc tttgacatgt tcccagtgat aagcaaacat tatgaacgca gcaagttgag    3360
aaatatcaac attgagatga gactcaagag accggggttt ttcccatgag tctgacacca    3420
atttgctgcg tgactttggg caagtcaaac ggccttttct aaaatgtgag acagagatta    3480
aagggacccc aaggccactt tccagctcta ggttccatgg ccagactttc atgtcaacag    3540
agaatgaaga agatcagtcc gttttcatct tgaaaatggc tgccaaagtg ctagacaaag    3600
atattgacta gatggggat ggtattgtct gaccacaccc agtactccaa aaagttgttc    3660
cacccacaca gcacggtgtc taccactgca taatttctaa tgcatttgtg tgcttgtgtg    3720
tgtgtgtgtg tgtgtgtgtc tgtgtgtctg tgtgtctctt cccctttcat tcactttag    3780
```

FIG. 5A-4

```
                                                                              Exon #
tatacatact gtggatacta aggagtaatt gcagtgaaca aattcacatt accgagttca  3840
tattttaat gagatcttga gagtgggagg aaagagtcgg ctcctagaga ataaaatgaa   3900
ggcagactta gggaaatttg aaggtacaaa ggcaacttac cttctgatca acagccaacc  3960
acagtctgga ataaatgtta tcaaacacac attcttcaaa atggtccgtg tctgagtaat  4020
taaaaggcaa atttccaaaa tcataaggac ttccgttaat caagtcaggc ataattattc  4080
ttcctactga tgacacaatg aagtaaacat atcattcttg taatttaaca gtaattctcg  4140
taaattgccc ttaaatgtca gtgctggatg tggtccaccc tcctaaattg tgactgttgc  4200
aacagatgtt ctcacttcaa ataacgcact tcttggccac ctaattaaag caatttttgg  4260
ggtgattcat cctactgcaa gcttggccac acttgtatcc tgtattaacc tataatttt   4320
gtaccgtagg agaagaattc actctttaag gacttataac aattatggca aaaggggga   4380
tagtactttt gtttattttt tctattattt ttcaagatct ttaatccggt ttttccattt  4440
atacaaaact ctttcctccga gacaaaaatg atacatattg gtaaaatgat cttacctaat  4500
ttaagtgaac taatttaaag caaaattcag atgtctgaat taatccattt tcatagttaa  4560
taatgtgcaa attagaacct ttggaaaaaa gatattaaga gtaagtcagc ttcaatgaag  4620
tactaggtaa cttcaatgtt ttataaaaaa gtaacacata gtaagtcagc ttcaatgttt cataaaaaac  4680
aaattcaata tagaatttta agtaacata ctttcctaaa tttaccttt tttcgatatt  4740
taggtattaa aaatgatcaa aatcataaat tatttcctca tcaatttact agtcttacat  4800
tcagcgattc atctgtgcac tttaccagct taattgctaa gcattcaaaa tatccttcag  4860
acacattaat atttcacaac agttataaaa tagtaaataa ttaataattt aattcaaaat  4920
acattacat attaatatg caaacaaatc acctgctga tccctgccat actttgacc    4980
tgcataattt ctaggtcatt aaaaatattct taaaaaaata taattggtcc ttaattaggt  5040
```

FIG. 5A-5

```
aattcaattc tataaacttg tttctctatt tgttaattat tgctattgat ccatgaagtg    5100
atactaataa ttgtttccta ctttttcttt tttttttcta cagCTTTACA AGAGgtgagt    5160    2
aaacttttt ttagaatttt taaaaatact ttgattccct tggctacagt gatgtcttct    5220
cttggaaggg aagaagttac attatattg accatcctag attaaaacct ttctgctgc    5280
cttagaaagt acccacccaa ttttccaaaa taggcggggc tactgaataa gactagttt    5340
ataaatatt cataagaaat atagagtaaa taatccaata gaagtttgag tttaggatc    5400
agcttctatg aagcagaaga tttcactgag ctagagaatc tttcactcc tttgaatta    5460
tttgcaaaag cacttattgt taacacattc ttagctcatg agttgaattt gaggcataag    5520
tacaggtacg tattgctatg tattttttgtt ctgtaggtac atatttttat ttgacatgtt    5580
ggtaaatttt taaattgtag tttgaaatat taaactgaga taatagtaaa tgcataatgt    5640
aatgaattgt gaagtatat ttgtatacta caccaaaatg gaagctgttt ttaaatatat    5700
atatacaatt ttcttcataa taatctttga tttattcttt tctagGAAAC TGTAAGAAAG    5760    3
gtaagagtac actactctc cataaattatc aggataaca taatttaact aatttaact    5820
aaatttatag tagactatag aaggaaaata ctttatcaaa attttgttca tatgaatata    5880
cattagctaa agcataaaat aaagtagctt tgatgttaa gataacaaag tttaattatc    5940
ttctggaatc atctgtaatt acattatgt gatacaaact ggtgatttac atacaaaagg    6000
aaaaaaaag acttgttttt attctggaga tggaaggcat attatgttaa ttataggag    6060
taaaaaagt ttatttttaaa gggtttgact atataaatgt gctgttaaaa atgtaacaaa    6120
atgatcattt aatctacagt tatcatctta ttcaaaatgc tatgcatagt attgtcctaa    6180
tagctgaaga ctatagcagc ttccaatcct ccagctgaaa aaaaattacg tataattaca    6240
attaaaatat atactttatc tattgcattg tgtcaatttt ttatatgcta tctaataaca    6300
```

Exon #

FIG. 5A-6

```
                                                                                    Exon #
ttgtagttac atcagtctta ccaactaatt attatcaaga atgatttgtt tgttcactgg 6360
aaattacttc ttaggcattt attattgtcc tgtttgtatc tttcctgtag GGCCAGCCG  6420      4
GAGATAGAGG ACCACGTGGA GAAAGGgtgt gtaattttg aactataaag ggcttcgtcc 6480
cgtatttgaa taactatatg ttagaaacta caggaactgg caatttataa gaatattatg 6540
tatccagata attgtacacc cctttaaaca ggtaatgcac tgcagaagaa gcgaatgagc 6600
attattatat atgatcaata tttgttttag gtcaaaatta ccgttaaaaa agaaaaactg 6660
ttacagtcat attctttgca tgtctactt tctttatttg taattgaccc atccaacaca 6720
tgcataatgg aaatatatct acctaccacc acagtcctct tttaacaca tttcatttgc 6780
ttttgaacta agatcccta ggtagcttgg aaataataqt gaattagtag tcagtaacat 6840
gtttcctgc tcaaattcat gcatgtacaa gtcaggctta cattttattt gtggcattct 6900
taaatctccc tgctatgctt atttgacatt tataactatg tggttttgca ttgtataaca 6960
cttttgccaa tatatgaata cctatatctt atatctatta ggaagaggag acttacatgt 7020
atttcactca atttattaga aatagaatta aatcagttaa ttatttttaac aatacaagta 7080
gttaatgata gtaaatctgc aggattttct ctcctatgat aaagtgacct tattaactgt 7140
cacatcagtt aattcattca catgtaacat accaaaacaa ttgaatcagt ttgtcacagt 7200
cagagatcgg caataaaaat acgatgtaag tccttgtgca ctgttaaaca tatgaagcac 7260
gtggaaccat acattttggc tataattttt atatttgaat actggagctt cagtatgaat 7320
taatattcaa tggccgagat agttcttag gaaaactacc ctgtgatatc ttaagagtta 7380
ttaaccctct ttctaaaata gactcataag tgaatttcaa tcaatgacaa atatagtata 7440
ttaaatttcc accctacttg cacatagaaa ggtctgaaca actgatctta ccacatataa 7500
ttcttagtt tctacaggc ctgtctaacc tgacctact cacttttac ataacagGGT  7560
```

FIG. 5A-7

| | Exon # |
|---|---|
| | 5 |

```
CCACCAGGCC CCCCAGGCAG AGATGGTGAA GATGGTCCCA CAGGCCCTCC TGGTCCACCT  7620
GGTCCTCCTG GCCCCCTGG TCTCGGTGGG gtaaggtgtc ttacgtattg ctaactttta  7680
gctaacttca gttgaaagaa ggttattgt ggaattatt tttagcagtt aaggataat   7740
tcttccattt gaaaattagt atattttatt tcatttattt gttttttca ctcaagattc  7800
tgctttaccc attctctttg tgagccctty tcaattacag gactggtctt tgtgtgcact  7860
gaagttagct gtggccatca ttaccattat ttaatttgga gatttaatat cttttattag  7920
taaggcacaa ataagaggtg ttgcattatt aaggattttg attagattga actgtgtaag  7980
tgaaatccct gatcttaagc aatttacaa acatcctacg cttttattc tccttgactt   8040
gaagtctgct gaaccaacat tcaaagcggt tttaggttta atttgcttga aactaatttg  8100
agaaagtac atttcccttt ttcattaata tcttcttta gcttcatgtc tttaacaatg   8160
gtatgagtgc caaatgacct cactgcagga aggaaaacat atttgcttaa ttggttagca  8220
ctatgaatca gaagcctgat tctaataccc aactgtatgt cagtaaaata agacctttct  8280
ccccaaaga tcttattatg attgcttatc tatgaattgc attaaaaagc agcttcttta   8340
atagagctac cactataaga gagatcttta acagtaaagt tattactgtg aactagtttt  8400
tagaagtttt atcttccaag gggtatttta atttaattt cctctaaact tgaaaactct   8460
ttatgccctt cctgaaactc cagcaagaaa aagatctctt agtcatttg tgtagctccg   8520
gtggggaagg gcaacaggtg aaaatgtgaa gatgtcctct tgagctctgt ctaatttgtc   8580
aggagccctt agtaacatta aaagtttaga aagcttccct tcctcagagt agaggtaaaa  8640
ggtgggagtg gagacaccga gttaaggcag aggaagggct caaaaagtaa agtagggaag  8700
ttctccattt caaagaggtg tcggccaagt ttttgacgta cagctctcat aactttttag  8760
gaatttagtt caatatagaa ttttaaacta ataattatat caaaaacatt gccctctttt   8820
```

FIG. 5A-8

| | Exon # |
|---|---|
| aataacaac agaaaaaatat ttacaagtag aatgagaaaa tgaactacat gactagtaac | 8880 |
| taaaaatatt ttatatatat atataatttt tttttttac ttctctagAA CTTTGCTGCT | 8940   6 |
| CAGTATGATG GAAAAGGAGT TGGACTTGGC CCTGGACCAA TGgtatgctt atctgtttat | 9000 |
| cttagccaaa aaaattgcta aataaatcat tcatttatg tcacatttta ccacgccatt | 9060 |
| tatttagcta cctaagttaa cactcaatac ttagattata taaaaacaac tctttttgtt | 9120 |
| ttcaaattta tgaaaacata agttaaggag ttcactttc tttacaaaag aaagattaat | 9180 |
| tgatcttttta tgattatatg atcttttga ttatatgatc ctcattaaga tagatcatat | 9240 |
| acttatgtcc aagaaataat ctttgacat agtaaccata acttgggcaa atcaatttaa | 9300 |
| tttaaaacag taatcactct gattaatttt ttaatattct ttaacattgc ttagaatttt | 9360 |
| aagcaacact tagaggcata gaactattta ttaagttctc tgaacttgtt ggaaaggatc | 9420 |
| aacaagttct atctagtcca gctaactcat tttaaaatgg gagagtttaa gcccttttct | 9480 |
| caaagtcatc caggtaacta atgacataac tagaactaga tgccaggcaa gatgtctaat | 9540 |
| atttgcttac atcatggttt atgtacctag tccttgaata aaccactcat ttagtcaaca | 9600 |
| gatattaatc agatgccttc aatggcccct aaactgtatt aggaactggg gaaattacaa | 9660 |
| ggaatatgac agattctgat cctttcctcaa ggagttaaca atataggaaa tgtttcttt | 9720 |
| tctgaattt gaccaaaaaa atcctttttt agtctattga ttgtaaatct atatagaaga | 9780 |
| gagtatgagt aaaaatctag catttatgtc actcagtaca aatattcagc accatacct | 9840 |
| atcagtggag caccgcttag aaacattccc tatatgatga tgatgatgat gatgactatt | 9900 |
| aacaaatgaa gcttctaaca agcattagag agaagtttga agggaaaaat gctaatacga | 9960 |
| gcatgcaaaa tgtatactag catatatgaa ataagagggga aaactgccag aagtcaaagt | 10020 |
| gttaggttga ttaagcacta cagaatttaa tgtatacaca cacacgcaat ttagtgattt | 10080 |

FIG. 5A-9

| | | | | Exon # |
|---|---|---|---|---|
| taattaattg | tttcaaaaca | aaggtattta | tctgcccaaa | gtcaacaagg tctttaaaat 10140 |
| gtaaatttta | cctgagcagt | gcacttagtg | ctctatcttc | aaaagaagat gttctgctgg 10200 |
| agctaatggc | ccacagtaag | ctaatatact | ctaagggtga | gataatattt tctgtaaatt 10260 |
| aaaactccca | cttgagaaat | aatgtacctt | taattgacga | cttctaattc cctaattttt 10320 |
| tctggtagtt | taaaatgttc | atatctgaaa | tgaaaaagta | gagtgtttct tttggctttg 10380 |
| tttatattgg | atttttgaaa | ttagctgttt | cagctaatgc | tggacattag tcagttttaa 10440 |
| agcagtacct | acatctcaag | aagaagcaag | ggggcggaaa | gtaaagagct actaaatgtc 10500 |
| atttttaaaa | agcccactaa | gctgggaaaa | ttaatatgga | tttcagatac cctgttttc 10560 |
| ggaacatctg | tcttggcata | aagcagagta | tttactttg | aaatatcagt gaaatataat 10620 |
| ttaagcttgc | acatccacac | acatgcacag | acatatgtaa | tcaacagata tctgtttcac 10680 |
| aaataggaa | gataggcagc | aataaagtat | taaaataatt | tccatgttgg aaaatcaata 10740 |
| actataaaac | cccacaggt | tcttctctga | attaatgagt | aatcacagcc tccatgaaat 10800 |
| acactacatt | ttatgtaaat | gaaattgttg | caaatacatg | aaaaaataaa tataattaga 10860 |
| aattcatgat | gtcaaagaaa | attattttt | aatgtatgcc | taaaaagcta ttgtgatgga 10920 |
| aaagtgacag | tttctttaa | tgtcagagca | atttctaaaa | ccaaatgaat aattcttata 10980 |
| attaaaatga | cgtacatttt | agataaaatc | catgttattt | cactctaggc attaatacag 11040 |
| taaggtaggt | ttgactgcag | agtcccaca | gctgatgtca | cgaacaaatt acttgagact 11100 |
| ggtacatgaa | atattttcag | cattatgagg | aacagaccct | acggatgagc ttacacaggc 11160 |
| attgattact | gcaaagagga | gtcaagaaag | tgtatttagc | ttaacaacta ttaacagccc 11220 |
| tgttttaccc | tactttgtg | ctatggaaac | aacaaagggg | aaaacaatct tccatcattt 11280 |
| gggccatatt | ttcaacaata | atatcatata | atagactctt | ccagaaggct gtttcaataa 11340 |

FIG. 5A-10

| Sequence | Position | Exon # |
|---|---|---|
| tgttttattt ttccttcacc cctcattaca tccacttttg tttgacattt tcatcagtca | 11400 | |
| ccaataaccc ttagaggagc gataaggtta taacaaactt ctctctaatc attaagaagg | 11460 | |
| acttttgatt cttttcaatt tatgtccttt gtggcaataa aaataccaat ttcttagcta | 11520 | |
| aatatgacat aggaagatga catatgatca aagatatcca aatggacatg cttcatctgc | 11580 | |
| tgtatagaag acaattgtat attctgcact tctgcaaaga ctgattcact tcattgcatc | 11640 | |
| agaacaatct caatatgccc aattgtgcac aacttaagg aacctatctg cccgtctaa | 11700 | |
| ttctcattga tttctgttga tatggattgg gagaaaagga aaagcaaagg gagagaacta | 11760 | |
| gtgcaggaag tttgagtcct taaattcttc cttgggagga ataaaaacta tggaatcaaa | 11820 | |
| ccacaacaat ggcactgcta agttggtcat gtctgacccc agccacacc atgacaactt | 11880 | |
| atcagtgcta actgttgata tatctgcttt ctttacagGG CTTAATGGGA CCTAGAGGCC | 11940 | 7 |
| CACCTGGTGC AGCTGGAGCC CCAgtaagta ctgaaagctt gtaatgcctc ttatgtaaaa | 12000 | |
| agacagagaa ttaagaaata aaggcttgga gtatgacatt ctttttct tttagGGCCC | 12060 | 8 |
| TCAAGGTTTC CAAGGACCTG CTGGTGAGCC TGGTGAACCT GGTCAAACTg tgagtacatt | 12120 | |
| tttccaccttt tgtgataagt ttttttccag gaagtttatg aatataacct tagtgaaatg | 12180 | |
| atgggtctcc cattttctta gGGTCCTGCA GGTGCTCGTG GTCCAGCTGG CCCTCCTGGC | 12240 | 9 |
| AAGGCTGGTG AAGATgtaag tatttactct taagcacttt caaaatgcta tttaaatact | 12300 | |
| cttgcctcaa caagattttc tagattcaaa ttaagtattc tgccaaaagc tgaatatgcc | 12360 | |
| tgacagaact cttaatgtat gggaaatatt atttaatga aatattaact aacctacttg | 12420 | |
| tattaaggga aagattaaat atatatctgg atccatattt ttatgtgata actttctccc | 12480 | |
| ctttgtaaa aaccagatt ccccatttt gtctgatagt ttaccaagaa gaagttgact | 12540 | |
| ctacaatgtt ttcatgttta gGGTCACCCT GGAAAACCCG GACGACCTGG TGAGAGAGGA | 12600 | 10 |

FIG. 5A-11

| | | | | | Exon # |
|---|---|---|---|---|---|
| GTTGTTGGAC CACAGgtgag | acttttttaca | ttggtagata | gcacaaacat | cataggccta | 12660 |
| taagatagtt gctaaaacta | gcatcaatct | aaatgacaac | atagatgtca | cccaaactca | 12720 |
| taacatgaat cgaagcatc | taataaagaa | aaaagcctag | ttaaaaaaaa | atgcatatac | 12780 |
| attttattca tgcaaataat | ggaatataaa | tgacagcaag | cataccataa | gcaactaaat | 12840 |
| tgtgttttct acaaataccg | tattattagt | tactcacatt | agagcaagtt | aatttgtcgc | 12900 |
| tctgtgctta gaggtatact | gactttggt | tcaaagcttg | aactttgatg | agaataaata | 12960 |
| ctttggaggg aagaagtcac | tgtctttta | tttatggtaa | aacattattc | accatcttct | 13020 |
| gtattctttt ctaagGGTGC | TCGTGGTTTC | CCTGGAACTC | CTGGACTTCC | TGGCTTCAAA | 13080 11 |
| GGCATTAGGg tgagcacatt | ctttactcag | aagagagaaa | atgcctatta | atttttggaa | 13140 |
| aaaactcaag tatgtttaaa | atcttgggtg | acatactc | actttcaaat | ccctggagtt | 13200 |
| tgccaaaggg aagaaagagt | taaagaagtca | gatttcttga | aagtaaagtg | gggtgcaatt | 13260 |
| ttttcagtct gttcatagct | accaaaaaac | aggctcacta | cagagaaaat | tatatagaac | 13320 |
| atgtattact tattgagtat | ttacaaccgt | ctgaaaatca | taaaattatt | aaggatgaa | 13380 |
| aagatgtgag agaacaccta | gtcctccatc | ctctctctc | aatgcaaga | aagtaagtg | 13440 |
| acctatctag ggcaatagac | tgagtttgct | gggacctgga | acactggact | tctttctact | 13500 |
| gcagcagaca agacttaccc | aagagagatt | aatggcaaag | atatacaata | caattttat | 13560 |
| ttgaccaaac actatcatgg | aacagcattt | tataataagg | cttcctttc | agGGACACAA | 13620 |
| TGGTCTGGAT GGATTGAAGG | GACAGCCCGG | TGCTCCCTGT | GTGAAGgtaa | atattaaatt | 13680 12 |
| agaagcactg tttttaagca | cttgattgaa | attcccatg | acctccaaaa | aagtatatta | 13740 |
| tactgaagac taccatatt | acaaaaagta | tttttatttt | tttctttcc | tgtacttcaa | 13800 |
| atccctcaag gatgggact | atgagagtct | gtgaaaaaag | gtcaattatt | aatatttatt | 13860 |

FIG. 5A-12

| Sequence | Position | Exon # |
|---|---|---|
| aaattcaat atctattaaa caattgagat aaaaataata ttaatagttt cttgttccat | 13920 | |
| ttcctttcct ccctctataa ttccagtgta tctctgcagc caaaataaaa gtaaataaac | 13980 | |
| atataatcag agattacgac actctgtatt attttaaact gtaaattctc ctttgccaca | 14040 | |
| cactaattag ataggtacat tcatgtcgct atacactttt caacctcttt cctgtgattt | 14100 | |
| atctgtgcac actcaaaaaa attttaatta ggtaattaaa gtctcagaag tgtgttatct | 14160 | |
| cttggctagg ctcttctctg acagcgtttt caactataaa atgttctctt tcctattaag | 14220 | |
| gagataatgt gatattaaag tgaataccaa cgtaattaca aattaatgag taacgaatac | 14280 | |
| tagcgggacc agaaatgaac atgaatatgg agaatctatt ctaacttcc agctgccaca | 14340 | |
| caaatggata aggtcaaact cattctccca agagcccgat ataacagctc agactactaa | 14400 | |
| tcactgtatc cataaaatgt tagagctgca aggagctttg gagacccct catttgcag | 14460 | |
| aggtgggaaa ctgaggcttc gtgagagcaa ttgacttgcc caaagtcaca catctagagg | 14520 | |
| ttagaaagtc ataggctaga aatgatcccc ccttgccact tcaatgctta ttcccaaaga | 14580 | |
| atagacttca catagaatcc tggaaattaa gggtccttat gaggtctctt aaaccatatt | 14640 | |
| tcccctatat ctaaatcaga ttatctttaa aaaagttct tttacatgtg ccatagtatt | 14700 | |
| aaatcccact actactacta ctactactac taccctgtt ttttactcagg ataagaatat | 14760 | |
| agattggaaa taaatatgat ggctctaaaa aataccatga agcttcaatt tttcatgcac | 14820 | |
| attttatgaa agtgataaca ctgagtgttc aaaataactt taaaaaggat aaatatggtt | 14880 | |
| acattgaaag caaatttatc ctttgccatc tctttttatg atattgtttc tagtatataa | 14940 | |
| ttgatatcct gaatctaagg gagaaattgg gggaggta cactcaaata accacatctc | 15000 | |
| cttagaacct ggatgtgtgg tactatctga ataaaaactc atgttagcac attttaaaat | 15060 | |
| ctgtgtgtct ggcataattg aaaaacaatc tatatgtgta agaatatta tgaagtatat | 15120 | |

FIG. 5A-13

| | Exon # |
|---|---|
| gaatggttca aagtaaaaaa aatagagtaa aattgcacta tcaggaaaaa taattgttat 15180 | |
| atttaatgaa caaaaactca atccttctcc atgtagGGTG AACCTGGTGC CCCTGGTGAA 15240 | 13 |
| AATGGAACTC CAGGTCAAAC Agtaagtatt gactacttca ttgtaaattt aaatgtgtac 15300 | |
| actctttatg agatggaact tctttaatgt tttgctaat cactgtatcc ttcagcattg 15360 | |
| tattctttga tgtttttcta atagccttct gatacttaat tgaaatccac tactgtttag 15420 | |
| ttggaattag aaggcaactt atttatttt agtgtattct tgtacaggtt ggaaactgaa 15480 | |
| caaagcaaat gatgcctgtg actttttta aattgcatt ctggatttta ttgaaaatat 15540 | |
| ttctgcttct agGGAGCCCG TGGGCTTCCT GGTGAGAGAG GACGTGTTGG TGCCCCTGGC 15600 | 14 |
| CCAGCTgtaa gtgcttccat ttttgttcag tttcatcctt ttaaaaaatc ttctaatggc 15660 | |
| tgtcatttaa gtttccacct gatcttccct ttattttctt cttagGGTGC CCGTGGCAGT 15720 | 15 |
| GATGGAAGTG TGGGTCCCGT GGGTCCTGCT gtaagttttg acactgggga gtttgaaagg 15780 | |
| agttgagaat gtggggtggg tgctgtcttc ttcattaatc tcttacgaaa tagcatcatt 15840 | |
| tcagacactt taccaaatgt tctgtgaggt cttttgaagg ctccatttat aagtagtgta 15900 | |
| agccatttat aacttttgatt gatgtataaa gcaaaatatc cccaccctgg 15960 | |
| ataccatgaa tgtcttgcct ttgatgagat cctaacgaca acagactggt tgtcagtttt 16020 | |
| tttctttact aatataaaca gtgtcatgcc actgtaagca acttcaatct tctgccattg 16080 | |
| ttattgtttt cttaatttac ttggaggaaa tttcttacca ccttctgctt tgatttcagG 16140 | 16 |
| GTCCCATTGG GTCTGCTGGC CCTCCAGGCT TCCCAGGTGC CCTGGCCCC AAGtaaaaa 16200 | |
| cactggtgac cattgtcact actttgataa actttttact gtgatgtgaa agattggaac 16260 | |
| tgtgtttgca gataaagaga taattacgaa acagttacct taattattcc ttcccttcaa 16320 | |
| aatggacata gaatgaccag tttctcact ctacatttga aatagatcat ttctctgcac 16380 | |

FIG. 5A-14

| | | | | | | Exon # |
|---|---|---|---|---|---|---|
| tgtgcactgt | gccatcgat | atagatgaca | acatggaaat | tgtctctagg | actagttagt | 16440 |
| taggactgac | tgagaaccag | agtcaaccac | agagagacag | aaggagaggg | aaggtagtaa | 16500 |
| cagtagccaa | gatggcagaa | tcaagcaagg | aaaataggaa | accaaactca | aatccttgtaa | 16560 |
| taaaacggat | aagaaaaata | attgcaattt | tgaagtttta | tgaagacatt | tcataaaact | 16620 |
| tggcatctta | aaaacagata | tgctgtttca | ttattgctg | gttaattcct | tggtttaatt | 16680 |
| tcctctttta | gGGTGAAATT | GGAGCTATTG | GTAACGCTGG | TCCTGCTGT | CCCGCCGGTC | 16740 | 17 |
| CCCGTGGTGA | AGTGGGTCTT | CCAGGCCTCT | CCGGCCCCGT | TGGACCTCCT | gtaagtagcc | 16800 |
| actgtcttta | aactttattg | agtaaaagaa | aacaaaggtg | gagtatgggg | aagaagaaga | 16860 |
| atgaagatgg | ggtcaaagaa | gaaccgaaat | attccaatta | actgatatcc | ttctcctttc | 16920 |
| cttttcctca | tagGGTAAATC | CTGGAGCAAA | CGGCCTTACT | GGTGCCAAGG | GTGCTGCTgt | 16980 | 18 |
| gagtatacct | gtgtagctaa | aatgtgctgc | tatgattta | aaggcattta | atgtgtgctg | 17040 |
| cctctacagc | ccatcacctc | cctaatgagc | cacactgcat | tttccttcat | agGGCCTTCC | 17100 |
| CGGCGTTGCT | GGGGCTCCCG | GCCTCCCTGG | ACCCCGCGT | ATTCCTGGCC | CTGTTGGTGC | 17160 | 19 |
| TGCCGGTGCT | ACTGGTGCCA | GAGGACTTGT | Tgtaagtggt | catgactgtg | gttctcatca | 17220 |
| tcctgaaata | ccacctctgc | catcatttca | tcactatcta | gacttccact | tgtagttta | 17280 |
| ttattcctat | tttctcttc | cttagcattt | ttagtttata | tttcttatat | atatatgtac | 17340 |
| actcccgtct | gctatatgca | cacagacatg | ccctttcctgt | tatcttaaat | cattacctca | 17400 |
| aggtaaatga | ggcaaagttc | tacaatatca | gttttgtccc | ttcgaccaat | aataccattc | 17460 |
| ccctgtactc | aatttaaata | tgaacagggt | acatttccta | gagaacttga | gcttctctt | 17520 |
| acccttgaccc | acaaatattc | taagagatt | gtctgcaaga | gagtttcaac | aaatgtttgt | 17580 |
| cctttgacca | ctgttctgta | ttgaaccccta | gGGTGAGCCT | GGTCCAGCTG | GCTCCAAAGG | 17640 | 20 |

FIG. 5A-15

|  |  | Exon # |
|---|---|---|
| AGAGAGCGGT AACAAGGGTG AGCCCgtaag tagctctatc atcacacttt tataaagtta | 17700 | |
| attgttttc tcattccagt ttctccagct ggacatagta ttaaaattat tttttttact | 17760 | |
| ccctcttctt ttgttctttt cattaaacag GGCTCTGCTG GCCCCAAGG TCCTCCTGGT | 17820 | |
| CCAGTGGTG AAGAAGGAAA GAGAGCCCT AATGGGGAAG CTGGATCTGC CGGCCCTCCA | 17880 | 21 |
| GGACCTCCTG GGCTGAGAgt aggtttcaaa tgctcccaac accctaacac accagaggca | 17940 | |
| gattatgata cccctcatt gggaattggt caaaattact gactgtgttt tcttaggcaa | 18000 | |
| aaaaagcatc tgctttccat ctgcctttatt aaatcagtga ctctcaattt aaatatgttat | 18060 | |
| aaaattggcc tggaaacaat gttgacctac ttttgcagga tgctcatcta tgaattcctc | 18120 | |
| tagggttgg gtgaagtgtt ttggcttggt ttgtgtctgt atctcccctg taagagatca | 18180 | |
| tgctatttt aacaaactct accttatcaa agccaagaga tttctttaat tctctctatt | 18240 | |
| tcatgtactt tcttgcagGG TAGTCCTGT TCTCGTGGTC TTCCTGGAGC TGATGGCAGA | 18300 | 22 |
| GCTGGCGTCA TGgtaagctg tctatcactt acttcctaga aagggcttg ctgcttctgg | 18360 | |
| tggtgggtgt gtcattagct ttagcatcct cctccctctat ctgttttttt tttttttttg | 18420 | |
| aatagGGCCC TCCTGGTAGT CGTGGTGCAA GTGCCCCTGC TGGAGTCCGA GGACCTAATG | 18480 | 23 |
| GAGATGCTGG TCGCCCTGGG GAGCCTGGTC TCATGGGACC CAGAgtaagt ttcaaactga | 18540 | |
| ttctgagcaa atcacacctg gcattacttc cttctttaaa gggttggtta atattgaaga | 18600 | |
| taacaataaa aacatcaaaa gtaaatttgt tagtagtctt gctgacagtt gcattttga | 18660 | |
| ctttatcaaa gctcagtaga tattttcatg cattaatta gttcataaat tttctattta | 18720 | |
| ttacttgata caatggctat gaggttttg gaagaataga tctattttaa tatatccaaa | 18780 | |
| ttagattggt cctcctatca gcatgaatct tttatcttaa tttgtgagtt ttatataagg | 18840 | |
| tgttcatgaa atatattagg actatacatt tttcgtttat tagattcata agtgaagtct | 18900 | |

FIG. 5A-16

| Sequence | Position | Exon # |
|---|---|---|
| tttcctagc aatcacaaag tgctgtaatg tattcagcat cacactagct atgagaaat | 18960 | |
| aacctctagg tccatagaca cactaatcca tagcaataga gtaatttttt tgcctccatt | 19020 | |
| acctcttatg ggtgaatatc aactgtaatt gtaccacaaa caagtaatag ggacaccaaa | 19080 | |
| tatagcaata agaaatccac tttggaaatt gtttactaaa agtattagtt tttctattat | 19140 | |
| gaggtaaata acgtgataca ttttgccat atacatgttg cttaacagtt tcttgagata | 19200 | |
| tctataaaag gatgagttgc actaaatttc aataaaagga aagccacaaa aaaatagaag | 19260 | |
| aaaaatttca gaactctttt cacacttccc agctagtggc taatattcct aatgatttac | 19320 | |
| cctaggcaac aacaaaaag tcggggaaa aggtgccttt gttagacttc agttaatcta | 19380 | |
| aggcttgagt atgtaagtta aagtgccaat ataaaaacat cctcattatt tatagGGTCT | 19440 | 24 |
| TCCTGGTTCC CTGGAAATA TCGGCCCCGC TGGAAAAGAA GGTCCTGTCg taagtattgc | 19500 | |
| tcattttccc attatatttt caaggacact tattgcaccc ttatcaagtc tatttttgtgg | 19560 | |
| cttatttata catgaacaca ttgaaaataa atatcagaca catacatcat ctgggaatgc | 19620 | |
| agagtaatag attgtaatta tggagtccaa atgaatacag gactgaaagc agagcagggg | 19680 | |
| agagaaaaac atggcaggga aaattgaagc aggtgacaag gggatgcaag agaagggaat | 19740 | |
| gagggaaatt gcatacatac gagattgaat tggctatgtg tgtactgaca tcctagttag | 19800 | |
| aaaaggaaaa tggattcata atttattaac gctttataca agaagctcta tgcattcaga | 19860 | |
| aaactattct gtttcatccg tggcagcatc ataagcttga ggttgtgaga atatgttgac | 19920 | |
| actgagtaaa cttgaaataa ctctgctttc agGGCCTCCC TGGCATCGAC GGCAGGCCTG | 19980 | |
| GCCCAATTGG CCCCGTTGGA GCAAGAGGAG AGCCTGGCAA CATTGGATTC CCTGACCCA | 20040 | 25 |
| AAGGCCCCAC Tgtaagaatc accacaactt tcttaccctc agcactttct gtagccaaat | 20100 | |
| tttaccaaac tctagtattt atctcctgcg aatcagtcca gtctcaggga gtttccttc | 20160 | |

FIG. 5A-17

| | | | | | Exon # |
|---|---|---|---|---|---|
| acacaggaa | aactgcaggc | cacttatcac | attaaagtt | tacctctagt | gtatccttat | 20220 |
| atccctgcta | aaaatccatc | tcctgagccc | catgcttcca | cagacacagg | gacatcttac | 20280 |
| tgtacatgga | gctgcatggt | gatgatcat | cctagataa | cagaaccac | agactaggga | 20340 |
| tctcaaaaga | acacaaaaac | aagcaggatt | caacattgca | aaatcaccgt | ggttaatttg | 20400 |
| acattaaatg | tgcaaagctg | ttctttgttt | tgtttttcat | tttactcta | gGGTGACCCT | 20460 | 26 |
| GGCAAAAACG | GTGATAAAGG | TCATGCTGGT | CTTGCTGGT | CTTGCTGGT | CTCGGgtagg | tgctaacttg | 20520 |
| tgtacagatc | tattcacata | gcattcatct | aagaaccaca | ctttttttt | tacaccatct | 20580 |
| gatatcattt | tgtcactttc | ttttcaagat | ggcatcccca | gggtcctt | tactatcata | 20640 |
| aaatgccttt | ttaaaaacca | aacttataaa | acagtgagca | aaaacaaatc | agaatataca | 20700 |
| ttaggtcaaa | aaatacagaa | gcacttggct | tttattttat | tcatttgta | attaaaaggg | 20760 |
| tatgaatatg | tagtagcatt | ctctggcctt | tataaattgc | cttgtgtcgc | atacttcgct | 20820 |
| tgagtcatat | caaaagttag | taggcaaacc | cataaatata | tatacctact | atgtaccac | 20880 |
| acaaattaaa | aatttaaaaa | gttagtaggc | agtatttggg | ctttcgtggg | aacccacaat | 20940 |
| gagttaatt | catgctaaaa | tgacaaactt | gtttaagga | agtaatacct | gaggctttga | 21000 |
| gacatcttaa | actacctgct | tgcagctaac | catcagcctt | tctgttaaat | attttagGG | 21060 | 27 |
| TGCTCCAGGT | CCTGATGGAA | ACAATGGTGC | TCAGGGACCT | CCTGGACCAC | AGgtgagtat | 21120 |
| ttctcccact | cttgtgctct | tctgcactag | aatgtatata | gtcctcaaac | tggccatctc | 21180 |
| catttcagt | ccaaaagtta | tacagctaga | caacagtggt | gacatacgtt | gctatttatg | 21240 |
| ctctctttcc | tgtcctttc | agGGTGTTCA | AGGTGGAAAA | GGTGAACAGG | GTCCCGCTGG | 21300 | 28 |
| TCCTCCAGGC | TTCCAGgtaa | gtcaactcaa | gcatatacaa | tactgccttt | ggtcagccta | 21360 |
| ttgagctgta | aatcaccata | ccgtacctct | cttctccacc | acaataacat | gatttcagga | 21420 |

FIG. 5A-18

| | | | | Exon # |
|---|---|---|---|---|
| ctgaagcaaa gaaggtgca ttttttcaa acaaactttt gtgtaatgct taataacata | 21480 | |
| caatcgtgct catgttgata tttggtagcc accaccccca aactcaatta ttagcaaatc | 21540 | |
| tcctgaacgt agccatggga ttgagatttg tatttctttt cattttagG GTCTGCCTGG | 21600 | 29 |
| CCCCTCAGGT CCCGCTGGTG AAGTTGGCAA ACCAGGAGAA AGGgtgagta aaacaagtaa | 21660 | |
| tagtaagtag taactactaa acttgagaat ttcccctgt ttaatacccc actgctatgc | 21720 | |
| aattataata tgtaaaagaa aatttcgtat ttcatatgtt aatgatagtg ttttacatac | 21780 | |
| tttggtgctg atggagagaa tgagccaaat tactttagtt ctgattactt tgttttacag | 21840 | |
| atttaatgaa acatcacctt atgaaagtaa aatctatcaa tgaatatttt atttaatagc | 21900 | |
| cttactttt gtattgttct tgataacgtt aagatacaaa ttatttcctt cccatagtg | 21960 | |
| aaaaagtaaa tgcacaattt tcaatcaaac tagatcccga aaaattcctt ttgtgttttt | 22020 | |
| cttggcattc agacatgaca ctactataca caatcagggc atgagttctg agtcattttc | 22080 | |
| tctctaattg tgatgaatgt gcccctattt agttacattc tgtggcctgg tctcctttgt | 22140 | |
| caacagtagg acatattaag gagacagctg gtcagtaata aaaagagata cacttgggta | 22200 | |
| tacaattaac taggcaatgt acagaatatg ataatttctc ttaagaagac gatctgttat | 22260 | |
| acagctaaaa ataggcaacg tctaatattc attattatt atcttattat tgaaggaaat | 22320 | |
| agtctgtcac ttttaaaaa gcaataaaact aaataatgg aaacaaattt tttgatacca | 22380 | |
| agttctggga tggatacatt tttgtcgacc aataaaattc tctctttctg tatctttcca | 22440 | |
| tactaaaagt tgttcttatt agcctgtgta cttatgcact catgtagata ctgccaggtt | 22500 | |
| tatttcactc tttccaaatt tttcaaatat tttaatcata agtgaattta cagatcacac | 22560 | |
| acagatttca tgctttattc tcatgttttg tctagGGTCT CCATGGTGAG TTTGGTCTCC | 22620 | 30 |
| CTGGTCCTGC TGGTCCAAGA gtaagtgtta cttcattaac tttcataaac tctggcaatg | 22680 | |

FIG. 5A-19

| Sequence | Position | Exon # |
|---|---|---|
| tgttttaaa agtagtagtg ctttctcctt aaagccactg atgacctgc aacaagtctc | 22740 | |
| tgatgctctt ctatagtcaa atgtaatctg tagaaagcat tagatttcta agttgataga | 22800 | |
| gaatttttg tttcatggct catattcct attcaataat tacatagtta taagaaacac | 22860 | |
| ataaatcaat atatattata gtcagtgatt tatatagaca actatgctac atttgtgaca | 22920 | |
| gtggctcaac ttgagctagg aaaaataata tgttactaag atataaagtt aattttggcc | 22980 | |
| atgtgtgttg atgttcaaag cctaaagccg aacttatgag tagtcatata agaaaaaaaa | 23040 | |
| aacttagttt ctctatgggt attagcatca ctgaaatgat taatttgccc tgaaagtatt | 23100 | |
| ccatcatgtc actagttaac acatatgtag gaagctcaaa gaacccaact tataacaagg | 23160 | |
| tcctttgaaa cagttacaac gtggacctat gtgataaata tttggcta tagaatgcta | 23220 | |
| tgctctagtg atatttagat gtaaattgga tagacagaca tatatatata | 23280 | |
| tacacaaata catatcaa atatacatat gaatattgta actgttatat cattattaca | 23340 | |
| cagggttata aaaggggggc atagatagga gaatatctaa tgttatctac acctgccatt | 23400 | |
| gctattcaac taaaatgaca caatcttttc tttgaatact acacataact ggcatctgtt | 23460 | |
| tttacctatg gattatcac agaaaagact cctcaaagaa ggggaatgaa ttgcaaaaat | 23520 | |
| tgaatattat actctagaag caacgaattc tggagtcgta gtcatggaac attagcta | 23580 | |
| agtgacactt tagagaatat ctcatcaatc tcttcatttt actagtggag aaattaggaa | 23640 | |
| caaagaaat tttaatttgc taataaatgc aaaccagggc tcggaagcta cacaaatgta | 23700 | |
| aactctcata tgtaaaacag tatcactgaa agtgatgaat ggtgcaacac ttcttctaat | 23760 | |
| cacttttttc agGGGGAACG CGGTCCCCCA GGTGAGAGTG GTGCTGCCGG TCCTACTGGT | 23820 | 31 |
| CCTATTGGAA GCCGAGGTCC TTCTGGACCC CCAGGGCCTG ATGGAAACAA Gtaaaatct | 23880 | |
| tatgttttct atattgctgg tttggcccag tctgcctgga ataagtagac cctttacaat | 23940 | |

FIG. 5A-20

| Sequence | Position | Exon # |
|---|---|---|
| agaaagataa ttgtttttca gatttttatt tatttccagt tctgtgatga cttccctctc | 24000 | |
| agtaaacagc aatccgattc cagtggacct gaattattct aaacaaacaa acaatagcaa | 24060 | |
| caactgtgg gggaaaattc agagttccca aaacataaat gaattagtat gggttgtcac | 24120 | |
| tcttttctcc tcacgctgtt tatgctttg tttaatcta gaaacattgt attcattgga | 24180 | |
| cattattttc agagaaaata actttttatc ttaacatctc atcccataga gtaaaatttc | 24240 | |
| aacaagtagt ctgactttta ataataagag tttatgatga tgaaaattca ttgggcaata | 24300 | |
| cattcacccc caaaaatttg tctggaaact tgtgttccaa aatagaatct gtggtttaga | 24360 | |
| ttttaaaata gatttaatat acattcctga aaaagagatt accttaacca caataaaaag | 24420 | |
| aagacaacac atattatttt cattcttaac tctagggaaa aaatgtaaac attagttgca | 24480 | |
| aaaagctatt ttagtgtatg gaaggatgtt cttgggaaaa aaataaaaac ataaaaggga | 24540 | |
| gagaggaaat aaagaaaacca cggttttgtg agtagtact ttcaaaggga tctatgtatc | 24600 | |
| tcagaagcta gtcaacaggt tttaagtatg tggaattgta ggtttttata taaaaatgaa | 24660 | |
| gatacagtct ctactcttaa ggagattaaa acacaaacat ctccctcaatt gacaaggtct | 24720 | |
| ctttccatgc tttctatctg ggctaagaga cttatcctg aaaaatgttt gtgggtaaac | 24780 | |
| attttttact ctctgcttcc cattgtccta tcctctctc catgcctgcc atccttaaga | 24840 | |
| ggactgaagc aggttataga ggaatcgcag ctgtgcactc ccactaccct catctcttca | 24900 | |
| gtcaccatgt cattaacagc atctctctct gctatattct ccctccttc aatagcccag | 24960 | |
| ccttctttgt gtttcaaagc aggcaagaag cctgtctagc tagctgttta aattggaatt | 25020 | |
| cttctagagt ttgattcttc atttctttct ttctccacta aaattgattt cacatgtgtt | 25080 | |
| tgactcaagG GTGAACCTGG TGTGGTTGGT GCTGTGGGCA CTGCTGGTCC ATCTGGTCCT | 25140 | |
| AGTGGACTCC CAGGAGAGAG GGGTGCTGCT GGCATACCTG GAGGCAAGGG AGAAAAGgta | 25200 | 32 |

FIG. 5A-21

| | | | | Exon # |
|---|---|---|---|---|
| cgtgttgacc | cctattacat | attgttgatg | aactctagta aagaaggctg cacaagatg | 25260 |
| cccagtttt | cacaattctt | ggcaggtggt | ctggtagcat tttcatatct atctatatac | 25320 |
| attccctct | accacctagc | acctacacat | ttctaaactc actaatctgg caagaagttc | 25380 |
| cttgctacca | tgaatttca | cacaaacaga | tggtgttgag taatacatga ggctcatttt | 25440 |
| aatgccacta | acaataatgc | ctcatcctgt | cctaattaat gggaagaagc tacattgaac | 25500 |
| agctgtcaac | catgctgctg | cattagttat | gccgtaagag tgatcaggcg ctgcagccca | 25560 |
| ttgtgatgtt | gccttacaat | tctgtccaca | tgaatctgta ccttgcttga ttatgcttca | 25620 |
| ggagagtgta | cggaaattag | aaaagattgt | ttaacaataa tctggaaatg gccttgaatt | 25680 |
| attttttcct | cattattttt | ctcgattaac | attctacaga atggtaagga atcgagacat | 25740 |
| tgctaaaaat | cttaaatgac | tgaaggtatc | atagcatctt ctgtaaaaaa gaaaaaaact | 25800 |
| tcatattaat | ttcgattcaa | aattttggtc | agaaaacaaa aagttgctct tgctttatac | 25860 |
| tttcagGGTG | AACCTGGTCT | CAGAGGTGAA | ATTGGTAACC CTGGCAGAGA TGGTGCTCGT | 25920 | 33 |
| gtgagtagaa | tttttgtttgt | atgttcctc | gtacttggat ttttttttat gttgaattga | 25980 |
| gaattttcca | aattcgaact | acacacactt | tattatcaa gttaataaa ataatattcc | 26040 |
| ttctctcctg | ggctatgaca | ataatatcat | tttacagttc caaaggaaaa attaaaggga | 26100 |
| tttaacctct | ttgaaaataa | tatccgaatt | ttctaacttc ctagtgtcaa tgatccaact | 26160 |
| acaaactat | agaccaaaag | ctttaggttt | aatagaatat taaatgatgc ttcaagtgat | 26220 |
| aacagagatt | aaaataaaata | aatataaata | tctccctatgc tttaggaagc cgggacctct | 26280 |
| aacaagattc | tatagttatt | caaacctact | cctagaaat ttatcaccca aagagcagcc | 26340 |
| ccaaagatta | gctgttaatg | ccatgaagat | gccaaagata atcccatgac agtctaatta | 26400 |

FIG. 5A-22

| | | | | | Exon # |
|---|---|---|---|---|---|
| ccttatctcg | tatgtcagcc | tcatgggtct | tctaggccac | agtcggcctg gattcctta | 26460 |
| ttcacctctc | cttcagagct | gaaaactgac | tgtagcacat | ctgtaatagt ctttctttg | 26520 |
| aatcacatag | ttctaacagt | ttcaaacagt | gctactcatt | tgctgctctc caggaattt | 26580 |
| tacaatagcg | gaaagttcag | atctcccaaa | tttctgacct | gctatgactt acacattcc | 26640 |
| ataaccttta | ttactggagt | accctccttc | tgagagtggc | ttctaatagt cttgttaatt | 26700 |
| agaaccaaaa | tacatcagag | gccttctaga | tatccaacca | gagtgcagtg aaagtgttca | 26760 |
| gtcactgtat | aagcacagaa | aaaaagaatg | acaaggttca | cttttgatga tacggggtgt | 26820 |
| tattaataag | acatgtttcc | tttttggtac | tagGGTGCTC | ATGGTGCTGT AGGTGCCCCT | 26880 34 |
| GGTCCTGCTG | GAGCCACAGG | TGACCGGgta | agcatgcatt | ttcactaagc caacagcaat | 26940 |
| atctaaaatt | tcccgccttc | cctagtccca | aagagcccca | gcaattcatt tttatgctt | 27000 |
| ggtataaagc | ctacttattt | aaaaacctag | ctattgtgat | agagcagcag gaaacaaatg | 27060 |
| ctgtgtgttt | aaaattactt | ttccccttcct | atagatttgc | cagctatatctg atctatactc | 27120 |
| taatccctag | catttgtttt | aaagtctctc | catgttgcgc | attaacaata tcctaatgca | 27180 |
| ctgaggcttc | tcaaagcctt | caattattac | caaaaaatca | ataaaataca tagtgtgccc | 27240 |
| atttcacatt | gaactctcca | cttaaaatag | atcttattta | ttgtattgca aagattgcca | 27300 |
| caaatagatc | agcccgtgt | ccatctaaaa | attaaaatgt | ctcctcctg gtattgtagg | 27360 |
| cactgattta | tagtgtttc | tcaagtgtat | aacccatacc | acttaaccccc caaaatgaat | 27420 |
| atagcattaa | gtaaaaatcc | acttcattt | actctgtgag | atgtgcgtca gttatctctt | 27480 |
| ccaaggcaac | taagactctg | tctgtccacc | actgtctct | ctcccctccca gttctttgag | 27540 |
| catctatgtc | aggcacatta | acagattcat | ctttggtccc | attataGGC GAAGCTGGGG | 27600 35 |
| CTGCTGGTCC | TGCTGGTCCT | GCTGGTCCTC | GGGAAGCCC | Tgtaagtaag aacctgggtc | 27660 |

FIG. 5A-23

| Sequence | Position | Exon # |
|---|---|---|
| atttgtata ctcacacctc acaatgttta gacattgatg aacctaggat tgataacaca | 27720 | |
| tttttaaatc ccttctccca cctagGGTGA ACGTGGCGAG GTCGGTCCTG CTGGCCCCAA | 27780 | 36 |
| CGGATTTGCT GGTCCGGCTg tgagtatcac ataatgaaga ttaatctgaa aacatcctaa | 27840 | |
| gttggggagt agagtgggtc ggaataccag agctgtaact gtttatttcc aacagGGTGC | 27900 | |
| TGCTGGTCAA CCGGGTGCTA AAGGAGAAAG AGGAGGCAAA GGGCCTAAGG GTGAAAACGG | 27960 | 37 |
| TGTTGTTGGT CCCACAGGCC CCGTTGGAGC TGCTGGCCCA GCTgtaagtt gaattcactg | 28020 | |
| gtggtccaca cagcagctac ccattagatc ttccaattaa atatatatcc gtcaagtgcc | 28080 | |
| tgctatgcaa caggaatat accagataga agatggaaaa taacgaaagg attaacattt | 28140 | |
| gcacactgct ttacaaagta taaaagtttc atgaatattg tttattta attctctgat | 28200 | |
| aacctcataa gggtggtaat attgaagaac attctgacac agatagtcat tttttattc | 28260 | |
| tatatttct tctaagagat gcgggaatga tccacttgaa gaaaagagta gcatttacaa | 28320 | |
| gggttgttt gtgattgac tccatctttt ttgtttgcat ttagGGTCCA AATGGTCCCC | 28380 | 38 |
| CCGGTCCTGC TGGAAGTCGT GGTGATGGAG GCCCCCTgt gagtattaca atggacctct | 28440 | |
| cgccgctttt ctttttcag aatctattaa ggacacttga aagtttgaa attttggta | 28500 | |
| aatttggact accatgagga aactttgaa attcaagttc attctattca gagcaattcc | 28560 | |
| gatattgatg ttaacttgaa ctcagctgga actcagtgta tgttgctatc agctcacttg | 28620 | |
| aggtaataac caaggtgggc cctaggcagt ttaattgtaa agtcggaaaa aatattcctt | 28680 | |
| ttgcgttta ttaatatgcc cctttctctg cctgaccatg tccttctcct ttgcaggcaa | 28740 | |
| tgctatcaca acaattctct agagacccag agctcccccaa aaatgaactt tactgacttc | 28800 | |
| ttctctcact ggacagtgct gaattatcta ggtcatttgt tattctttg tccatgaaca | 28860 | |
| ccattaccta ttaagtgtcc cactcagcca ggtggtaaag atagttatta | 28920 | |

FIG. 5A-24

```
                                                                         Exon #
atgtatacac attaatgtgt aataatgaca tagtgtctta tcttcatacc tttacaacca        28980
taagataata tgtcagcatt tcagaaagga ccatccaaac cttaacgcaa aatatggca         29040
ttgcaactgg taatatgctg gtaaggaaga tgtgtggaga aggagggcct tcagggtcct        29100
ggctaaataa tgccctatat gaagctgcct gatttccaa aacaaagaaa ttcccatctt         29160
acccaaattc ttggagttga tgttgactgt ggaattctaa tgtgcttggc tcttagGGTA       29220  39
TGACTGGTTT CCCTGGTGCT GCTGGACGGA CTGGTCCCCC AGGACCCTCT gtaagtaaat        29280
cactgtaaac gtgtcttcat ttactctagc caaaggcct ggcttctgat aggaaactgg        29340
taagaaactc ttcatgaaaa cacatcacta ttactctcct ggtctgaagt                   29400
cagcttttct gaaccattaa ggtatttcat cacaagttat atttataat atcagtttaa        29460
gaggcttta ttcatgtgaa caccagtccc ctttcagggg catgtctttt ttgaaaaaaa         29520
aaaacaaaaa aacgaacagt tttagccaca tatcagatat ttctatatct aattatcctt      29580
tatggctaac attctgcctc cattgttaag gtataattgt tcctgaattt aaggtggtt       29640
tggcctctaa tttaattctg attcagactc tcctgtcagg actcaagaaa atttaattaa     29700
ttaccaagga ttaagtcttc tggttaaggt ttctgggaaa aaaaaatagc aaagatgttg       29760
atttcttgga atccttttac aggttcataa cagaaaaatc ttcattccct gtaggcattt      29820
aattaaacct agttgagaag tgtgtgggat tcctcaatta tgaacaaaac acgtatattg      29880
gctttcttta aaaaaaaaaa aaagaagaaa aaagaaaagg caaagtcctt cgaaactcag        29940
agtcccattc atttatcatt aactcctatc attctacata gttctgattc caatatgcca       30000
gggtaccagt ggcatgacat tgtttttcct cataaaattt tgccatagtc tctccccat        30060
tatttggttg gttacagcct cataaaggaa gacaggagtt gcttctttct gcaagaaaga       30120
aggttaaaaa ctataatat ttcccccaaa tggccaggt attattttat tgcatcacat        30180
```

FIG. 5A-25

| | Exon # |
|---|---|
| tgtttgcatc ttaagatcta gaatctttgc tgctctcttc caggcccttg gtgattaaca | 30240 |
| gaaaggaaat gaccttgtac atttgctcat agGGTATTTC TGGCCCTCCT GGTCCCCCTG | 30300 |
| GTCCTGCTGG GAAAGAAGG CTTCGTGGTC CTCGTGGTGA CCAAGGTCA GTTGGCCGAA | 30360 | 40
| CTGGAGAAGT AGGTGCAGTT GGTCCCCCTG GCTTCGCTGG TGAGAAGGGT CCCTCTGGAG | 30420 |
| AGGCTGGTAC TGCTgtaagt gatttccaac tcctctttct taatacctta tgctgaatta | 30480 |
| aaataaagcc cctacacaga tcttcaagtg gcatctattt gttgatgagt attgcaggct | 30540 |
| ctcaagtaga gctcagttga gccaggaaat ctgtccagca cacactgagg ggctgtggct | 30600 |
| tccaagatgc tcagaaagca caaatcggga agacaataaa tgagggaact cagttttatc | 30660 |
| acaaaccct taaagctatt gaaggcacct tactggtacc aggattagaa cagagtccca | 30720 |
| ttgctgtggc catcctacta catattaatc aatctcagta ggctaccaat ttcttaaaca | 30780 |
| tacactgtcc agtattagtg ctactctgaa aggtgcccct attagacctt agaggccaaa | 30840 |
| gtcaaattt gcttccttt gatatactga tttactgat ttccttttg tttttgtttt | 30900 |
| ttgttttgt tttgttttt ttgtttttgg atggagttcc cctcgttgc ccaggctgga | 30960 |
| gtgcagtggc acgatctcag ctcactgcga cttccgctcc cagttcaagt aattatcttg | 31020 |
| tctcagcctc cgagtagctg ggactacagg cacacaccat catgcctagc taattttgt | 31080 |
| atttagtaa agacggggtt tcaccatatt gtcaggctg gtctcgatct cctgacctca | 31140 |
| ggtgatccac ccaccttgac ctccaaagt gctgggatta cacatgtgag ccacccacc | 31200 |
| cagcctgatt tcctttcctt tgtgtatata ccagcagtg tgattgctgg atcttatggt | 31260 |
| agttctattt ttagttttt gaggaacccc tcctactatg tacaactatt atgtatccat | 31320 |
| aacaatttaa attttttat ttgtttccct gcctagaggc tataaaaact ctatttcacc | 31380 |
| acccagtg tctttataaa tctcaaccac atattttaa atgttgtgcc attgtctca | 31440 |

FIG. 5A-26

```
                                                                                       Exon #
aggatgaatc agatacaaaa gtattcatgc caagatgtaa actcaccgtc atcactagag 31500
aaaagatatc caaggatatg tcctagtaat aggaggtcat tagcctttt ctaagctgaa 31560
gacagtttat tctcacaatc ttcaagccaa cctgtgttat cacctaggt cttaccata  31620
atactcagta ttttttctct atttagGGAC CTCCTGGCAC TCCAGGTCCT CAGGGTCTTC 31680
TTGGTGCTCC TGGTATTCTG GGTCTCCCTG GCTCGAGAGG TGAACGTGGT CTACCTGGTG 31740  41
TTGCTGGTGC TGTGgtgagt gcttgacagt attctgactc cattaacata agaaaagatt 31800
ttaaaagctg ccacttcaaa tgtgacagat tgatcactga ataacttcac ttaagatttt 31860
tattcatggc atttttcttta tacagatcac atgtcactta tctaagaagc tttaatacca 31920
ccttacttag acacacacta taaagacaca gcttaattat gcagaatgat ttttgttct   31980
ttcccacgcac ttaggaacga tacaatctct aattgcgttt actcctctgc aatatgaaat 32040
gctgcatca tttatcctgt aggaagaatg aaactctgga agttctgaat cgttccatta 32100
aaccttatac gtgacaacaa ctagaaaacca tctcatctcc ataaaatata tcaactttt 32160
gaattcattt catttgggat actgaatgac acgaggctca cttttacag agcaacatcc 32220
cgtgattaca taaagctggc catctacatg tggagaagga gggcagagat gatactaatg 32280
atacttctta ccatgtgtg accattcac attcaattta cctctctct tcaaactaga 32340
atctccctgag tagggttgtt ttggaggga aggttagcat tccatcgaat aaggggaatg 32400
tcatttatc ttctctgcct gttagGGTG AACCTGGTCC TCTTGGCATT GCCGCCCTC  32460
CTGGGCCCG TGGTCCTCCT GGTAGTCCTG GTAGTCCTGG AGTCAACGGT GCTCCTGGTG 32520  42
AAGCTGGTCG TGATgtgagt ccaacacttg gtttgtaaaa taaaactgag caggatttca 32580
ttgtgtgaaa ctttatgtcc tgagctgagg ttctcttctt ccaaatttct gaacaagatg 32640
```

FIG. 5A-27

| | | | | | Exon # |
|---|---|---|---|---|---|
| gtcaagcttc | tccatagtat | ctacacctag | tactgaaaat | atgaaaattg cttaggccaa | 32700 |
| agaatgggct | tttcaatagc | acactgcaaa | actggcccaa | gtattaaaa catctctaaa | 32760 |
| aaatatctag | gttggcaggt | ttttatccct | agtttaaca | gtctgaaaga gggttcgtta | 32820 |
| ctgagcactg | gaagtgatga | agacagagta | gctacaacat | agggctggt aggcagcaga | 32880 |
| gcctcaccaa | cagccttaat | ttgtgtggtg | tcttcacagG | GCAACCCTGG GAACGATGGT | 32940 | 43 |
| CCCCAGGTC | GCGATGGTCA | ACCCGACAC | AAGgtcagta | cactttcat ctttctctaa | 33000 |
| ttcaaaagtg | attaaaatgc | aacccagatt | gatgctaagc | ttcattttgc ctttggtagG | 33060 |
| GAGAGCGCGG | TTACCCTGGC | AATATTGGTC | CCGTTGGTGC | TGCAGGTGCA CCTGGTCCTC | 33120 | 44 |
| ATGGCCCCGT | GGGTCCTGCT | GGCAAACATG | GAAACCGTGG | TGAAACTgta agtttgtgaa | 33180 |
| taccagtccc | tcagtgcagc | attctcgtgg | gcttcacttc | tgacttcccc acactgggg | 33240 |
| atggtggagg | agtgggggagg | ggtatcttgg | gcctagctaa | gttgtgtttt tctttttcat | 33300 |
| ttcacagGGT | CCTTCTGGTC | CTGTTGGTCC | TGCTGGTGCT | GTTGGCCCAA GAGGTCCTAG | 33360 | 45 |
| Tgtatgtaca | tgctgaagat | ttctttgcaa | cactaacatt | tagagagaat cagtccaaaa | 33420 |
| catctgttaa | gaaaataaac | aatatatcag | ctagacttaa | tattttttaa aaatttcagt | 33480 |
| ccatgctgag | aattgataca | aattgatct | agccactta | cagatagcac aactaaagca gattaccagc | 33540 |
| ttaaacaatt | acaaggatct | agccactta | cagatagcac | aactaaagca gattaccagc | 33600 |
| agaggtgaga | gcctagctaa | accattacat | gtcctgagtt | acctttgtaa acgaattaag | 33660 |
| cagtatttgt | ggtgaagtga | gtgccattt | tttaaaacgg | taagtcttat ccatcctct | 33720 |
| gtttctttat | agGCCCACA | AGGCATTCGT | GGCGATAAGG | GAGAGCCCGG TGAAAAGGGG | 33780 | 46 |
| CCCAGAGGTC | TTCCTGGCTT | CAAGGGACAC | AATGGATTGC | AAGGTCTGCC TGGTATCGCT | 33840 |
| gtaagtaaac | tgtagccatc | tcgcacataa | actgatcctg | aaggccttca gctcagaagg | 33900 |

FIG. 5A-28

| Sequence | Position | Exon # |
|---|---|---|
| atttcatat tttcactgct attgttccag tatagcctat ataatatcca tttccattc | 33960 | |
| tctggctaac tccatctcac tcttggaggt aatgctattt catgccaaca tgaaaggtga | 34020 | |
| ggattaaggg agatagaaat atacaatata ataaatctc ctggtaacaa tgtccttcaa | 34080 | |
| ccccacttaa aataaacata attagaggaa tgactaatat tgcactgctg aaataggttg | 34140 | |
| tgaaaaaaaa ttgaatataa tagacataat gggagaaaag agccccactt tacatttca | 34200 | |
| attttctcaa tccggagtcc attaactaa agtttcccat tgaatttgga aaaaaaaaa | 34260 | |
| atatgtctct tgacatgtgc tctgaaagtg tgattttcct cttctgtctt taaagGGTCA | 34320 | 47 |
| CCATGTGAT CAAGGTGCTC CTGCTCCGT GGGTCCTGCT GGTCCTAGGg taggtggact | 34380 | |
| caagagaaga cagttcatct ctgaaataga ggctaaagcg agcagtgagc cccaggctgc | 34440 | |
| tgctccctg gtgggattca ccagctcaca tgtacctggt gtctgtcttc cttagGGCCC | 34500 | 48 |
| TGCTGGTCCT TCTGCCCCTG CTGGAAAAGA TGGTCGCACT GGACATCCTG GTACGGTTGG | 34560 | |
| ACCTGCTGGC ATTCGAGGCC CTCAGGGTCA CCAAGGCCCT GCTgtaagta tgatttgggg | 34620 | |
| aaataataaa gaagatcacg gacctaagga atgttttctt cagactaaac caagacaact | 34680 | |
| ttgacaaccc attaaagtta gccccatttc aatatatcct ctaaaatatc tggaaattgt | 34740 | |
| ctatatgcaa tgggcttgtt aagtccatcc catgcaagtg tgcctggggg ctcgttattt | 34800 | |
| atttatgtga acttgattat tttttactga gtctctcact ataaagcctc tcctatctaa | 34860 | |
| gaaaatctgc tgccatggat gtctctcact gtaaaaaaat ataaagcctc tcctatctaa | 34920 | |
| ctttcaccttt tgcagGGCCC CCCTGGTCCC CCTGGCCCTC CTGGACCTCC AGGTGTAAGC | 34980 | |
| GGTGGTGGTT ATGACTTTGG TTACGATGGA GACTTCTACA GGGCTGACCA GCCTGCTCA | 35040 | |
| GCACCTTCTC TCAGACCCAA GGACTATGAA GTTGATGCTA CTCTGAAGTC TCTCAACAAC | 35100 | 49 |
| CAGATTGAGA CCCTTCTTAC TCCTGAAGGC TCTAGAAAGA ACCCAGCTCG CACATGCCGT | 35160 | |

FIG. 5A-29

| | Exon # |
|---|---|
| GACTTGAGAC TCAGCCACCC AGAGTGGAGC Agtggtaggt caagatgtcc agaccagact | 35220 |
| gacccttctc acaagttgag ctttcaaaa ttagtttcca ttgacattta gagtgaaaat | 35280 |
| gcattgggt aaagattaca ttatgtgaaa tcacacccaa ttaatggagc gtcatctttct | 35340 |
| cccaaccagc accaacctc atttcccta aatgtattt ttgcactttt catagtaata | 35400 |
| agtaccctga tttgattttt catggaggag gggagggaag gaactgtcta atcttaaaaa | 35460 |
| tagccaccct cttcctctta aatatggggt agacaatcaa aaatgttact tatgagagtc | 35520 |
| agtatctttc attagttatt attagaatct gtgttctgct caatgagaag tttcatgatc | 35580 |
| tgaatgttat tttcttaaaa gGTTACTACT GGATTGACCC CAACCAAGGA TGCACTATGG | 35640 |
| AAGCCATCAA AGTATACTGT GATTTCCCTA CCGGCGAAAC CTGTATCCGG GCCCAACCTG | 35700 | 50 |
| AAAACATCCC AGCCAAGAAC TGGTATAGGA GCTCCAAGGA CAAGAAACAC GTCTGGCTAG | 35760 |
| GAGAAACTAT CAATGCTGGC AGCCAGgtga ggaatcccac aaacacctct ccttctgcta | 35820 |
| aataatattt tggtaggact gtttgttaat tatctgcatt ttaatctctg acaaaaatgg | 35880 |
| gcttattaaa aaaagacctg ttcctttcct ggttccaat tttgtgccta aattgcacat | 35940 |
| tagaagatgg attgattgga cacatccatg taattcaaag ttattattca aatttgactt | 36000 |
| aattggtaat cattgaaaaa actgactaat gtcatttagt gtgaaggagc actggccagc | 36060 |
| tatatgccac actcatacat atgcatttc agaatgtgag cagctttct gaatttttaa | 36120 |
| tcaaacctt tcaccaactt tactgaatgc ctactggaat tccataaatt acaaaatgac | 36180 |
| agaaaagaa aaatgtcaga atttctacct cctcattctc ttattctaaa gaagaacgat | 36240 |
| atgcaaaaag gattaattga aacagataac tttttagat gaccttgcct cagtctagta | 36300 |
| ggtctttatgt tcatctaggt aactgatact tcaaagacaa gtgaattaag tttctttaa | 36360 |
| aagtacccttt ttcctaagct tggatctgag tctactcttc ctgagatctt tttttttctt | 36420 |

FIG. 5A-30

| Sequence | Position | Exon # |
|---|---|---|
| tttttttttt ttcatgtttg actcttagta tctgagtcct tctccactta actgaattt | 36480 | |
| catcctattt tctgtagTTT GAATATAATG TTGAAGGAGT GACTTCCAAG GAAATGGCTA | 36540 | |
| CCCAACTTGC CTTCATGCGC CTGCTGGCCA ACTATGCCTC TCAGAACATC ACCTACCACT | 36600 | 51 |
| GCAAGAACAG CATTGCATAC ATGGATGAGG AGACTGGCAA CCTGAAAAAG GCTGTCATTC | 36660 | |
| TACAGGGCTC TAATGATGTT GAACTTGTTG CTGAGGGCAA CAGCAGGTTC ACTTACACTG | 36720 | |
| TTCTTGTAGA TGGCTGCTCT gtaagtaata gtgaaatatg ggaatagctt tgggaagtgg | 36780 | |
| gatggagggg gttctaactt agactgcccc caagggggt ctaaaggggg gttaaaagaa | 36840 | |
| cagagaatg agagaactaa cttatttcat aagtaaattc agtttttgta tgtattttat | 36900 | |
| atttatttat ttatacgtat taatttcgta cttaaattca gatgataaat tcagagtatt | 36960 | |
| cttatcagat agtgccttct gaaatgctga aatgtatact atgtccatgc attgttttt | 37020 | |
| cttagcatg tttttaaat ggtaatgtgt gcccagaact taaaatttct tgagcttcag | 37080 | |
| tggcctaaac tataatttat agttatgtgt attttatttt actattagt atggctacat | 37140 | |
| ttaactttta atgcttttc tacaatatgc tataaatata agaaaaatta aaattcacta | 37200 | |
| acagcaagac tacataccca cccagttccc gctcccaaag acacacatag agggacatac | 37260 | |
| acacaacaat cctaaaaatg actttgtaga dataggtcac ttggaatgtg tgttgaaatg | 37320 | |
| ttgttgggttt tttgttgg tttgttttgtt tgtttttgt tagactgata gggagcccct | 37380 | |
| cccactaaaag acacccttga tactgttatt tcaaggatga acttatttat ctgggacaga | 37440 | |
| catcttcaga atgacacatg ccaaacagtg gttcttatta aatcaaggt tcagatatta | 37500 | |
| tcagattcag aaatagtgat gctttgtgta tctattttct tctctttaaa cagAAAAAGA | 37560 | |
| CAATGAATG GGGAAAGACA ATCATTGAAT ACAAAACAAA TAAGCCATCA CGCCTGCCCT | 37620 | |
| TCCTTGATAT TGCACCTTTG GACATCGGTG GTGCTGACCA TGAATTCTTT GTGGACATTG | 37680 | 52 |

FIG. 5A-31

```
                                                                         Exon #
GCCCAGTCTG TTTCAAATAA atgaactcaa tctaaattaa aaaagaaaga aatttgaaaa         37740
aactttctct ttgccatttc ttctctctct tttttaactg aaagctgaat ccttccattt        37800
cttctgcaca tctacttgct taaattgtgg gcaaaagaga aaaagaagga ttgatcagag        37860
cattgtgcaa tacagtttca ttaactcctt ccccgctcc cccaaaatt tgaatttttt          37920
tttcaacact cttacacctg ttatgaaaa tgtcaacctt tgtaagaaaa ccaaaataaa         37980
aattgaaaaa taaaaaccat aaacatttgc accacttgtg gcttttgaat atcttccaca        38040
gagggaagtt taaaacccaa acttccaaag gtttaaacta cctcaaaaca ctttcccatg        38100
agtgtgatcc acattgttag gtgctgacct agacagagat gaactgaggt ccttgttttg       38160
tttgttcat aatacaaagg tgctaattaa tagtatttca gatacttgaa gaatgttgat        38220
ggtgctagaa gaatttgaga agaaatactc ctgtattgag ttgtatcgtg tggtgtattt       38280
tttaaaaaat ttgatttagc attcatatttt tccatcttat tcccaattaa aagtatgcag     38340
attatttgcc caaagttgtc ctcttcttca gattcagcat ttgttctttg ccagtctcat       38400
tttcatcttc ttccatggtt ccacagaagc tttgttcctt gggcaagcag aaaaattaaa       38460
ttgtacctat tttgtatatg tgagatgttt aataaattg tgaaaaaaat gaaataaagc       38520
atgtttggtt ttccaaaaga acatatttgag taaaattcct tgcttcaatg ctctttgcaa     38580
tataaatatg catctctacc agccattaga ccaagtgcct ctgattagat agaaattatg       38640
caaaagggc agtttggtgt ggtagaagag cagagaacga gg                          38682
```

FIG. 5B-1

```
cattaccacc ctgagtcatt ttgctcagaa ttagtctctg actctcagca acacaggaca
aatacacaca tatgccctgc aaaggtaatt cagcacagtg gtaacaatga ttcttagaaa
tcatttctca ctcttctgat atgcagaaaa aaatttgtta tgatgtagta ttgaagtttt
tctttcctga taaaaatgat ttccacttta aaagttttt gttagttctg taacggtgat
atttcaggga aatgttaaaa atgttcttgg aatatacaat tcaacctcag gtctttttgtt
gttgttgttc ctagaaccta gaaaacttca acattgttg cctagttaga aaaaaatttg
aatgtggatt gctccctgta aaccccttc taggaatgac cagtaaccct ttcaaattct
ttcactccca gttacttcaa aaaatcatcc aaagtggtct cccaagtgag tgcctttaat
tagaataaaa caagagttta ttatagtttt tggttatcca cttttacttg cattaaccctt
tttttcttct tttacattta gaaagagtaa cctgctttag aatagtccct tttatttaca
gaagctgctg atggagttaa cttctgcaga aattcttcct taagcaaag caaaaaaagc
gggagggg tggggggaag gaaggaaaa agattctcag ggaactacag cccacttgct
tctgtttctt agagacagaa ctgacctaaa gatgccccct ttgcgatgac ttctggata
gagcagcact ctaactaggc ccccgctgcc tcatgggac cttaggcaag tagaggagag
gcctgacaca cacacacaca cacacacaca cacgcgcgcg cgcgcgcaca
cacacacaca cagcctttca aacctaggc ctggaatgcc atcccaagag gctttagaaa
aaggcacagg acctttggcc tcccacctca gggtcaaagt accagttcct cctctcccta
gtagggagtg gaggttgga tggaggcggc cagagaagag ggaagttggg tgctggggag
agagttaaca tccacgttgg tgggcgcact gcttgggtg ttaccagcga agattacgaa
gacccaagc tcgaatcaga agggcctctg gatgtgctag ggaggtgct tgggtgtaac
tgtaagagat gggacagaga gtaagcagca aggtcaagag ggaccgggg gctcacggga
```

FIG. 5B-2

```
gggttgaagg gtccaggctc aggtagaac tggtaaatcc agacaaggag cccatggaga
aggggagggg agactggaaa ccatgaaaga tccccaccg cagcctcaga aaggagagac
tgagaaataa gttctcggtc tccaggtcgg ttggagtcgt gtcggagtgc cagaccatcc
cccaaagac cctctttgga atgagcctca gcaaaggcaa gctaggaggt cgaaggactt
cccaggtga ctcggtctag tctagagttc gcaaagccta tcctccctgt agccgggtgc
caagcagcct cgagcctgct cccagccca cctgccaaca aaaggcgccc tccgactgca
acccagccct ccacagacag gacccgccct ttcccgaagt cataagacaa agagagtgca
tcactgctga aacagtgggc gcacacgagc cccaaagcta gagaaaagct ggaagggct
gggggcgggg tgcagggggtg gagggcggg gaggcgggct ccggctgcgc acgctatcg
agtcttccct ccctccttct ctgccccctc cgctcccgct ggagccctcc accctacaag
tggcctacag ggcacaggtg aggcgggact ggacagctcc tgctttgatc gccggagatc
tgcaaattct gcccatgtcg gggctgcaga gcactccgac gtgtcccata gtgtttccaa
acttggaaag ggcgggggag ggcgggagga tgcggagggc ggaggtatgc agacaacgag
tcagagtttc cccttgaaag cctcaaaagt gtccacgtcc tcaaaaagaa tggaaccaat
ttaagaagcc agcccgtgg ccactccct gctccctcct ctgcgcccc
gcaggctcct cccagctgtg gctgccggg cccccagccc cagccctccc attggtggag
gcccttttgg aggcaccta ggccaggga aacttttgcc gtataaatag ggcagatccg
gcctttatta ttagcacc acggcagcag gaggtttcgg ctaagttgga ggtactggcc
acgactgcat gcccgcgccc gccaggtgat acctccgccg gtgaccagg ggctctgcga
cacaaggagt ctgcatgtct aagtgctaga c
```

FIG. 5B-3

```
                                                         gtaagtgcc ttcagcttgt
ttgggggaga ctgggtagag aggttagatg ggagggcacc ctgccctgaa aaggaaaacc
tgtaacctga attccaggta cacttggagg gcagactctc agcatgtgg gaaaacgccg
gaattgataa gaaacatgaa aattacttta aaaaatgaaa acataaaagc cttgccaaaa
gttagggaac tttcctcta agtcagagt gagacagtta actcggtctg gctcctcagc
ttagtaaccc ccaaagggag cggaaggtct ttttccctaa ggatgagata ttaacgacca
atgtggtgga ggaagtcaag ggcctgcacc ccacaggccc cataaccgca ctgatgtcca
ccttgtaaaa cttgaggcct gcgttagaaa gcccttcaac tgagtaatgt aaaactcacc
tcctaagagc ttttatcttc tgggcattgt aaggcttgtc cggaggagga ggatgacgat
gctgatatga tgatggttat aaggcgccct ctggaggaag gaaaatgaaa gtacagggga
cagggcctta agcagatgga atcccaatta aagcttctac ggatttatac agattaatga
tcagcatttc tggttggagc ctttcccagt ggctagtcag tgaaccctgg aaagaagaat
ggatgctact tggagtgggt acattctgaa aagtaatata agtgtctcaa ttcactttct
agtcatgaaa atggtaacat tttttaactc aaatctgctc taaattttgt ttgagcctga
gaattacccc tttgacatgt tcccagtgat aagcaaacat tatgaacgca gcaagttgag
aaatatcaac attgagatga gactcaagag accgggtttt ttcccatgag tctgacacca
atttgctgcg tgactttggg caagtcaaac ggccttttct aaaatgtgag acagagatta
aaggacccc aagccactt tccagctcta ggttccatgg ccagactttc atgtcaacag
agaatgaaga agatcagtcc gttttcatct tgaaaatggc tgccaaagtg ctagacaaag
atattgacta gatgggggat ggtattgtct gaccacaccc agtactccaa aaagttgttc
cacccacaca gcacggtgtc taccactgca taatttctaa tgcatttgtg tgcttgtgtg
```

FIG. 5B-4

```
tgtgtgtgtg tgtgtgtgtc tgtgtgtctg tgtgtctctt cccccttcat tcacttttag
tatacatact gtggatacta aggagtaatt gcagtgaaca aattcacatt accgagttca
tattttaat gagatcttga gagtgggagg aaagagtcgg ctcctagaga ataaaatgaa
ggcagactta gggaaatttg aaggtacaaa ggcaacttac cttctgatca acagccaacc
acagtctgga ataaatgtta tcaaacacac attcttcaaa atggtccgtg tctgagtaat
taaaaggcaa atttccaaaa tcataaggac ttccgttaat caagtcaggc ataattattc
ttcctactga tgacacaatg aagtaaacat atcattcttg taatttaaca gtaattctcg
taaattgccc ttaaatgtca gtgctggatg tggtccaccc tcctaaattg tgactgttgc
aacagatgtt ctcacttcaa ataacgcact tcttggccac ctaattaaag caatttttgg
ggtgattcat cctactgcaa gcttggccac acttgtatcc tgtattaacc tataattttt
gtaccgtagg agaagaattc actctttaag gacttataac aattatggca aaaggggga
tagtactttt gtttatttt tctattattt ttcaagatct ttaatccggt ttttccattt
atacaaaact ctttctccga gacaaaaatg atacatattg gtaaaatgat cttacctaat
ttaagtgaac taatttaaag caaaattcag atgtctgaat taatccattt tcatagttaa
taatgtgcaa attagacctt ttggaaaaag gatattaaga atgtacaaa ctcaatgaag
tactagtaa cttcaatgtt ttataaaaaa gtaagtcagc ttcaatgttt cataaaaaac
aaattcaata tagaattta agtaacata cttcctaaa tttacctt tttcgatatt
taggtattaa aaatgatcaa aatcataaat tatttcctca tcaattact agtcttacat
tcagcgattc atctgtgcac tttaccagct taattgctaa gcattcaaaa tatccttcag
acacattaat atttcacaac agttataaaa tagtaaataa ttaataattt aattcaaaat
acatttacat attaatattg caaacaaatc acctgctga tccctgccat actttgacc
```

FIG. 5B-5 tgcatatttt ctaggtcatt aaaatattct taaaaaaata taattggtcc ttaattaggt
aattcattc tataacttg tttctctatt tgttaattat tgctattgat ccatgaagtg
atactaataa ttgtttccta ctttctttt tttttttcta cag

FIG. 5B-6 gtgagt
aaaacttttt ttagaatttt taaaaatact ttgattccct tggctacagt gatgtcttct
cttggaaggg aagaagttac attaatattg accatcctag attaaaacct ttctggctgc
cttagaaagt accaccccaa tttccaaaa taggcggggc tactgaataa gactaggttt
ataaaatatt cataagaaat atagagtaaa taatccaata gaagtttgag ttttaggatc
agcttctatg aagcagaaga tttcactgag ctagagaatc tttcactcc tttggaatta
tttgcaaaag cacttattgt taacacattg tattttttgtt gttgaattt gaggcataag
tacaggtacg tattgctatg tttgctatg ctgtaggtac atatttttat ttgacatgtt
ggtaaattt taaattgtag tttgaaatat taaactgaga taatagtaaa tgcataatgt
aatgaattgt gaaggtatat ttgtatacta caccaaaatg gaagctgttt ttaaatatat
atatacaatt ttcttcataa taatctttga tttattcttt tctag

FIG. 5B-7

```
gtaagagtac actacttctc cataaatatc taaaattatc aggataaca taatttaact
aaatttatag tagactatag aaggaaaata ctttatcaaa atttgttca tatgaatata
cattagctaa agcataaaat aaagtagctt tgatgtttaa gataacaaag tttaattatc
ttctggaatc atctgtaatt acatttatgt gatacaaact ggtgattac atacaaaagg
aaaaaaaag acttgttttt attctggaga tggaaggcat attatgttaa ttataggag
taaaaaagt ttattttaaa gggtttgact atataaatgt gctgttaaaa atgtaacaaa
atgatcattt aatctacagt tatcatctta ttcaaaatgc tatgcatagt attgtcctaa
tagctgaaga ctatagcagc ttccaatcct ccagctgaaa aaaaattacg tataattaca
attaaaatat atactttatc tattgcattg tgtcaatttt ttatatgcta tctaataaca
ttgtagttac atcagtctta ccaactaatt attatcaaga atgatttgtt tgttcactgg
aaattacttc ttaggcattt attattgtcc tgtttgtatc tttcctgtag
```

FIG. 5B-8

```
                   gtgt gtaattttttg aactataaag ggcttcgtcc
cgtatttgaa taactatatg ttagaaacta caggaactgg caattataa gaatattatg
tatccagata attgtacacc cctttaaaca ggtaatgcac tgcagaagaa gcgaatgagc
attattatat atgatcaata tttgtttag gtcaaaatta ccgttaaaaa agaaaaactg
ttacagtcat attcttttgca tggtctactt tctttatttg taattgaccc atccaacaca
tgcataatgg aaatatatct acctaccacc acagtcctct tttaacaca tttcatttgc
tttgaacta agatcccta ggtagcttgg aaataatagt gaattagtag tcagtaacat
gtttctgc tcaaattcat gcatgtacaa gtcaggctta catttatt gtggcattct
taaatctccc tgctatgctt atttgacatt tataactatg tggtttttgca ttgtataaca
cttttgccaa tatatgaata cctatatctt atatctatta ggaagaggag acttacatgt
atttcactca attattaga aatagaatta aatcagttaa ttatttttaac aatacaagta
gttaatgata gtaaatctgc aggatttct ctcctatgat aaagtgacct tattaactgt
cacatcagtt aattcattca catgtaacat accaaaaacaa ttgaatcagt ttgtcacagt
cagagatcgg caataaaaat acgatgtaag tccttgtgca ctgttaaaca tatgaagcac
gtggaaccat acattttggc tataattttt atatttgaat actggagctt cagtatgaat
taatattcaa tggccgagat agttcctttag gaaaactacc ctgtgatatc ttaagagtta
ttaaccctct ttctaaaata gactcataag tgaatttcaa tcaatgacaa atatagtata
ttaaatttcc acctacttg cacatagaaa ggtctgaaca actgatctta ccacataa
ttcttaggtt tctacaggc ctgtcctaacc tgacccttact cactttttac ataacag
```

FIG. 5B-9

```
                                        gtaaggtgtc ttacgtattg ctaactttta
gctaacttca gttgaaagaa ggtttattgt ggaatttatt tttagcagtt aagggataat
tcttccattt gaaaattagt atatttatt tcattattt gttttttca ctcaagattc
tgcttaccc attctctttg tgagcccttg tcaattacag gactggtctt tgtgtgcact
gaagttagct gtggccatca ttaccattat ttaatttgga gatttaatat cttttattag
taaggcacaa ataagaggtg ttgcattatt aaggattttg attagattga actgtgtaag
tgaaatcccct gatcttaagc aatttacaa acatcctacg ctttttattc tccttgactt
gaagtctgct gaaccaacat tcaaagcggt tttaggttta atttgcttga aactaatttg
agaaaagtac atttccctt tccattaata tcttcttta gcttcatgtc tttaacaatg
gtatgagtgc caaatgtgacct cactgcagga aggaaaacat atttgcttaa ttggttagca
ctatgaatca gaagcctgat tctaataccc aactgtatgt cagtaaaata agaccttct
ccccaaaga tcttattatg attgcttatc tatgaattgc attaaaaagc agcttcttta
atagagctac cactataaga gagatcttta acagtaaagt tattactgtg aactagtttt
tagaagtttt atcttccaag gggtatttta atttaatttt cctctaaact tgaaaactct
ttatgcccctt cctgaaactc cagcaagaaa aagatctctt agtcattttg tgtagctccg
gtgggggaagg gcaacagtg aaaatgtgaa gatgtcctct tgagctctgt ctaatttgtc
aggagccctt agtaacatta aagtttaga aagcttccct tcctcagagt agaggtaaaa
ggtgggagtg gagacaccga gttaaggcag aggaagggct caaaaagtaa agtagggaag
ttctccattt caaagaggtg tcggccaagt tttgacgta cagctctcat aactttttag
gaatttagtt caatatagaa ttttaaacta ataattatat caaaaacatt gccctctttt
aaataacaac agaaaaatat ttacaagtag aatgagaaaa tgaactacat gactagtaac
taaaatatt ttatatatat atataattt tttttttac ttctctag
```

FIG. 5B-10

```
                                                         gtatgctt atctgtttat
cttagccaaa aaaattgcta aataaatcat tcatttatg tcacatttta ccacgccatt
tatttagcta cctaagttaa cactcaatac ttagattata taaaaacaac tctttttgtt
ttcaaattta tgaaaacata agttaaggag ttcacttttc tttacaaaag aaagattaat
tgatctttta tgattatatg atcttttga ttatatgatc ctcattaaga tagatcatat
acttatgtcc aagaaataat ctttggacat agtaaccata acttggcaa atcaatttaa
tttaaaacag taatcactct gattaatttt ttaatattct ttaacattgc ttagaatttt
aagcaacact tagaggcata gaactattta ttaagttctc tgaacttgtt ggaaaggatc
aacagttct atctagtcca gctaactcat tttaaaatgg gagagtttaa gccctttct
caaagtcatc caggtaacta atgacataac tagaactaga tgccaggcaa gatgtctaat
atttgcttac atcatggttt atgtacctag tccttgaata aaccactcat ttagtcaaca
gatattaatc agatgccttc aatggccct aaactgtatt aggaactggg gaaattacaa
ggaatatgac agattctgat cctcctcaa ggagttaaca atataggaaa tgtttctttt
tctgaatttt gaccaaaaaa atcctttttt agtctattga ttgtaaatct atatagaaga
gagtatgagt aaaaatctag catttatgtc actcagtaca aatattcagc accataccct
atcagtggag caccgcttag aaacattccc tatatgatga tgatgatgat gctaatacga
aacaaatgaa gcttctaaca agcattagag agaagtttga agggaaaaat gctaatacga
gcatgcaaaa tgtatactag catatatgaa atagagggga aaactgccag aagtcaaagt
gttaggttga ttaagcacta cagaatttaa tgtatacaca cacacgcaat ttagtgattt
taattaattg tttcaaaaca aaggtattta tctgcccaaa gtcaacaagg tctttaaaat
gtaaatttta cctgagcagt gcacttagtg ctctatcttc aaaagaagat gttctgctgg
agctaatgc ccacagtaag ctaatatact ctaagggtga gatatatttt tctgtaaatt
aaaactccca cttgagaaat aatgtacctt taattgacga cttctaattc cctaattttt
tctggtagtt taaaatgttc atatctgaaa tgaaaaagta gagtgtttct tttggctttg
tttatattgg attttgaaa ttagctgttt cagctaatgc tggacattag tcagttttaa
```

FIG. 5B-11

```
agcagtacct acatctcaag aagaagcaag gggcggaaa gtaaagagct actaaatgtc
atttttaaaa agcccactaa gctgggaaaa ttaatatgga tttcagatac cctgtttc
ggaacatctg tcttggcata agcagagta tttactttg aaatatcagt gaaatataat
ttaagcttgc acatccacac acatgcacag acatatgtaa tcaacagata tctgtttcac
aaataggaa gataggcagc aataaagtat taaaataatt tccatgttgg aaaatcaata
actataaaac cccacaggt tcttctctga attaatgagt aatcacagcc tccatgaaat
acactacatt ttatgtaat gaaattgttg caaatacatg aaaaaataaa tataattaga
aattcatgat gtcaaagaaa attattttt aatgtatgcc taaaaagcta ttgtgatgga
aaagtgacag tttcttttaa tgtcagagca atttctaaaa ccaatgaat aattcttata
attaaaatga cgtacatttt agataaaatc catgttattt cactctagc attaatacag
taaggtaggt ttgactgcag agtcccaca gctgatgtca cgaacaaatt acttgagact
ggtacatgaa atattttcag cattatgagg aacagaccct acggatgagc ttacacagc
attgattact gcaaagagga gtcaagagga tgtatttagc ttacaacta ttaacagccc
tgtttaccc tactttgtg ctatgaaac aacaaaggg aaaacaatct tccatcattt
gggccatatt ttcaacaata atatcatata atagactctt ccagaaggct gtttcaataa
tgttttattt ttccttcacc cctcattaca tccacttg tttgacattt tcatcagtca
ccaataaccc ttagaggagc gataaggtta taacaaactt ctctctaatc attaagaagg
actttttgatt cttttcaatt tatgtccttt gtgcaataa aaataccaat ttcttagcta
aatatgacat aggaagatga catatgatca aagatatcca aatgacatg cttcatctgc
tgtatagaag acaattgtat attctgcact tctgcaaaga ctgattcact tcattgcatc
agaacaatct caatatgccc aattgtgcac aactttaagg aacctatctg ccccgtctaa
ttctcattga tttctgttga tatggattgg gagaaaagga aaagcaaagg gagagaacta
gtgcaggaag tttgagtcct taaattcttc cttgggagga ataaaaacta tggaatcaaa
ccacaacaat ggcactgcta agttggtcat gtctgacccc agccaacacc atgacaactt
atcagtgcta actgttgata tatctgcttt ctttacag
```

FIG. 5B-12

```
                                    gtaagta ctgaaagctt gtaatgcctc ttatgtaaaa
agacagagaa ttaagaaata aaggcttgga gtatgacatt cttttttct tttag
```

FIG. 5B-13

```
                                                            g tgagtacatt
tttccaccttt tgtgataagt tttttccag gaagtttatg aatataacct tagtgaaatg
atgggtctcc catttctta g
```

FIG. 5B-14

```
            gtaag tatttactct taagcacttt caaaatgcta tttaaatact
cttgcctcaa caagattttc tagattcaaa ttaagtattc tgccaaaagc tgaatatgcc
tgacagaact cttaatgtat gggaaatatt attttaatga aatattaact aacctacttg
tattaaggga aagattaaat atatatctgg atccatattt ttatgtgata actttctccc
cttttgtaaa aaccaagatt ccccatttt gtctgatagt ttaccaagaa gaagttgact
ctacaatgtt ttcatgttta g
```

FIG. 5B-15

```
                gtgag acttttaca ttggtagata gcacaaacat cataggccta
taagatagtt gctaaaacta gcatcaatct aatgacaac atagatgtca cccaaactca
taacatgaat cgaaggcatc taataaagaa aaaagcctag ttaaaaaaaa atgcatatac
attttattca tgcaaataat ggaatataaa tgacagcaag cataccataa gcaactaaat
tgtgttttct acaaataccg tattattagt tactcacatt agagcaagtt aattgtcgc
tctgtgctta gaggtatact agactttggt tcaaagcttg aactttgatg agaataaata
ctttggaggg aagagtcac tgtcttttta tttatggtaa aacattattc accatcttct
gtatttcttt ctaag
```

FIG. 5B-16

```
      g tgagcacatt ctttactcag aagagagaaa atgcctatta attttggaa
aaaactcaag tatgttaaa atcttgggtg acatatactc actttcaaat ccctgagtt
tgccaaggg aagaaagagt taaagagtca gatttcttga aagtaaagtg gggtgcaatt
ttttcagtct gttcatagct accaaaaaac aggctcacta cagagaaaat tatatagaac
atgtattact tattgagtat ttacaaccgt ctgaaaatca taaattatt aaggatggaa
aagatgtgag agaacaccta gtcctccatc cttctctctc aatggcaaga aagttaagtg
acctatctag ggcatagac tgagtttgct gggacctgga acactgact tctttctact
gcagcagaca agacttaccc aagagagatt aatgcaaag atatacaata caatttttat
ttgaccaaac actatcatgg aacagcattt tataataagg ctttcctttc ag
```

FIG. 5B-17

```
                                                         gtaa atattaaatt
agaagcactg ttttaagca cttgattgaa attcccatg acctccaaaa aagtatatta
tactgaagac taccatatt acaaaaagta ttttatttt tttctttcc tgtacttcaa
atccctcaag gatgggact atgagagtct gtgaaaaag gtcaattatt aatatttatt
aaattcaat atctattaaa caattgagat aaaaataata ttaatagttt cttgttccat
ttcctttcct ccctctataa ttccagtgta tctctgcagc caaaataaaa gtaaataaac
atataatcag agattacgac actctgtatt attttaaact gtaaattctc ctttgccaca
cactaattag ataggtacat tcatgtcgct atacactttt caacctcttt cctgtgattt
atctgtgcac actcaaaaaa attttaatta ggtaattaaa gtctcagaag tgtgttatct
cttggctagg ctcttctctg acagcgtttt caactataaa atgttctctt tcctattaag
gagataatgt gatattaaag tgaataccaa cgtaattaca aattaatgag taacgaatac
tagcgggacc agaaatgaac atgaatatgg agaatctatt ctaactttcc agctgccaca
caaatggata aggtcaaact cattctccca agagcccgat ataacagctc agactactaa
tcactgtatc cataaaatgt tagagctgca aggagcttg gagaccccct cattttgcag
aggtgggaaa ctgaggcttc gtgagagcaa ttgacttgcc caaagtcaca catccagagg
ttagaaagtc ataggctaga aatgatcccc ccttgccact tcaatgctta ttcccaaaga
atagacttca catagaatcc tggaaattaa gggtccttat gaggtctctt aaaccatatt
tcccctatat ctaaatcaga ttatcttttaa aaaagttct tttacatgtg ccatagtatt
aaatcccact actactacta ctactactac taccctggtt tttactcagg ataagaatat
agattggaaa taaatatgat ggctctaaaa aataccatga agcttcaatt tttcatgcac
attttatgaa agtgataaca ctgagtgttc aaaataactt taaaaaggat aaatatggtt
```

FIG. 5B-18 acattgaaag caaatttatc ctttgccatc tcttttatg atattgtttc tagtatataa
ttgatatcct gaatctaagg gagaaattgg ggaggaggta cactcaaata accacatctc
cttagaacct ggatatgtgg tactatctga ataaaaactc atgttagcac atttaaaat
ctgtgtgtct ggcataattg aaaacaatc tatatgtgta agaaatatta tgaagtatat
gaatggttca aagtaaaaaa aatagagtaa aattgcacta tcaggaaaaa taattgttat
atttaatgaa caaaaactca atccttctcc atgtag

FIG. 5B-19 gtaagtatt gactacttca ttgtaaattt aaatgtgtac
actctttatg agatggaact tctttaatgt ttttgctaat cactgtatcc ttcagcattg
tattcttga tgttttcta atagccttct gatacttaat tgaaatccac tactgtttag
ttggaattag aaggcaactt atttattttt agtgtattct tgtacaggtt ggaaactgaa
caaagcaaat gatgccctgtg actttttta aattagcatt ctggatttta ttgaaaatat
ttctgcttct ag

FIG. 5B-20 gtaa gtgcttccat tttgttcag tttcatcctt ttaaaaatc ttctaatggc
tgtcatttaa gttccacct gatcttccct ttatttctt cttag

FIG. 5B-21

```
                                          gtaagttttg acactgggga gtttgaaagg
agttgagaat gtgggtggg tgctgtcttc ttcattaatc tcttacgaaa tagcatcatt
tcagacactt taccaaatgt tctgtgaggt cttttgaagg ctccatttat aagtagtgta
agccatttat aagtacctga actttttgatt gatgtataaa gcaaaatatc cccaccctgg
ataccatgaa tgtccttgcct ttgatgagat cctaacgaca acagactggt tgtcagtttt
tttctttact aatataaaca gtgtcatgcc actgtaagca acttcaatct tctgccattg
ttattgtttt cttaatttac ttgaggaaa tttcttacca cctttctgctt tgattttcag
```

FIG. 5B-22

```
                                          gtaaaaaa
cactggtgac cattgtcact actttgataa acttttact gtgatgtgaa agattgaac
tgtgtttgca gataaagaga taattacgaa acagttacct taattattcc ttcccttcaa
aatggacata gaatgaccag tttctccact ctacatttga aatagatcat ttctctgcac
tgtgcactgt gccatcgat atagatgaca acatgaaat tgtctctagg actagttagt
taggactgac tgagaaccag agtcaaccac agagagacag aaggagaggg aaggtagtaa
cagtagccaa gatgcagaa tcaagcaagg aaaataggaa accaaactca aatcttgtaa
taaaacggat aagaaaaata attgcaattt tgaagtttta tgaagacatt tcataaaact
tggcatctta aaaacagata tgctgtttca ttatttgctg gttaattcct tggtttaatt
tcctctttta g
```

FIG. 5B-23

```
actgtcttta aacttattg agtaaaagaa aacaaggtg gagtatgggg aagagaaga
atgaagatgg ggtcaaagaa gaaccgaaat attccaatta actgatatcc ttctcctttc
cttcctca tag
                                                           gtaagtagcc
```

FIG. 5B-24

```
gagtatacct gtgtagctaa aatgtgctgc tatgatttta aaggcattta atgtgtgctg
cctctacagc ccatcacctc cctaatggac cacactgcat tttccttcat ag
                                                           gt
```

FIG. 5B-25

```
tcctgaaata ccacctctgc catcatttca tcactatcta gacttccact tgtagtttta
ttattcctat tttctccttc cttagcattt ttagtttata tttcttatat atatatgtac
actccgtct gctatatgca cacagacatg ccctccctgt tatcttaaat cattacctca
aggtaaatga ggcaagttc tacaatatca gttttgtccc ttgaccaat aataccattc
ccctgtactc aatttaaata tgaacagggt acatttccta gagaacttga gctctcttt
acctgaccc acaaatattc taagagattt gtctgcaaga gagtttcaac aaatgtttgt
cctttgacca ctgttctgta ttgaaccctg
                                 gtaagtggt catgactgtg gttctcatca
```

FIG. 5B-26 attgttttc tcattccagt ttctccagct ggacatagta ttaaattat tttttact
ccctctctt ttgttctttt cattaaacag gtaag tagctctatc atcacacttt tataagtta

FIG. 5B-27 gt aggtttcaaa tgctcccaac acctaacac accagaggca
gattatgata cccctcatt gggaattggt caaaattact gactgtgttt tcttagcaa
aaaagcatc tgctttccat ctgccttatt aaatcagtga ctctcaattt aatatgttat
aaaattggcc tggaaacaat gttgacctac tttttgcagga tgctcatcta tgaattcctc
taggggttgg gtgaagtgtt ttggcttggt ttgtgtctgt atctcccctg taagagatca
tgctattttt aacaaactct accttatcaa agccaagaga tttctttaat tctctctatt
tcatgtactt tcttgcag

FIG. 5B-28 gtaagctg tctatcactt acttcctaga aagggcttg ctgcttctgg
tggtgggtgt gtcattagct ttagcatcct cctcctctat ctgttttttt tttttttttg
aatag

FIG. 5B-29

```
ttctgagcaa atcacacctg gcattacttc cttctttaaa gggttggtta atattgaaga
taacaataaa aacatcaaaa gtaaatttgt tagtagtctt gctgacagtt gcattttga
ctttatcaaa gctcagtaga tattttcatg catttaatta gttcataaat tttctattta
ttacttgata caatggctat gaggttttg gaagaataga tctattttaa tatatccaaa
ttagattggt cctcctatca gcatgaatct tttatcttaa tttgtgagtt ttatataagg
tgttcatgaa atatattagg actatacatt tttcgtttat tagattcata agtgaagtct
ttttcctagc aatcacaaag tgctgtaatg tattcagcat cacactagct atggagaaat
aacctctagg tccatagaca cactaatcca tagcaataga gtaatttttt tgcctccatt
acctcttatg ggtgaatatc aactgtaatt gtaccacaaa caagtaatag ggacaccaaa
tatagcaata agaaatccac tttgaaaatt gtttactaaa agtattagtt tttctattat
gaggtaaata acgtgataca tttttgcccat atacatgttg cttaacagtt tcttgagata
tctataaaag gatgagttgc actaaatttc aataaaagga aagccacaaa aaaatagaag
aaaaatttca gaactctttt cacacttccc agctagtggc taatattcct aatgatttac
cctaggcaac aaacaaaaag tcgggggaaa aggtgccttt gttagacttc agttaatcta
aggcttgagt atgtaagtta aagtgccaat ataaaaacat cctcattatt tatag
```

FIG. 5B-30

```
                                                        g taagtattgc
tcatttccc attatatttt caaggacact tattgcaccc ttatcaagtc tatttgtgg
cttattata catgaacaca ttgaaaataa atatcagaca catacatcat ctgggaatgc
agagtaatag attgtaatta tggagtccaa atgaatacag gactgaaagc agagcagggg
agagaaaaac atgcaggga aaattgaagc aggtgacaag gggatgcaag agaagggaat
gagggaatt gcatacatac gagattgaat tggctatgtg tgtactgaca tcctagttag
aaaggaaaa tggattcata atttattaac gctttataca agaagctcta tgcattcaga
aaactattct gtttcatccg tggcagcatc ataagcttga ggttgtgaga atatgttgac
actgagtaaa cttgaaataa ctctgctttc ag
```

FIG. 5B-31

```
         gtaagaatc accacaactt tcttaccctc agcactttct gtagccaaat
tttaccaaac tctagtattt atctcctgcg aatcagtcca gtctcaggga gtttcctttc
aacacaggaa aactgcaggc cacttatcac attaaaagtt tacctctagt gtatccttat
atccctgcta aaaatccatc tcctgagccc catgcttcca cagacacagg gacatcttac
tgtacatgga gctgcatggt gatggatcat ccttagataa cagaaaccac agactaggga
tctcaaaaga acacaaaaac aagcaggatt caacattgca aatcaccgt ggttaatttg
acattaaatg tgcaaagctg ttctttgttt tgttttcat tttttactcta g
```

FIG. 5B-32

```
                                              gtagg tgctaacttg
tgtacagatc tattcacata gcattcatct aagaaccaca ctttttttt tacaccatct
gatatcattt tgtcactttc tttcaagat ggcatcccca gggtccttt tactatcata
aatgccttt ttaaaaacca aacttataaa acagtgagca aaaacaaatc agaatataca
ttaggtcaaa aaatacagaa gcacttggct tttattttat tcattttgta attaaaaggg
tatgaatatg tagtagcatt cctgcctt tataaattgc cttgtgtcgc atacttcgct
tgagtcatat caaagttag taggcaaacc cataaatata tatacctact atgtacccac
acaaattaaa aatttaaaaa gttagtaggc agtatttggg ctttcgtggg aacccacaat
gagtttaatt catgctaaaa tgacaaactt gttttaagga agtaatacct gaggctttga
gacatcttaa actacctgct tgcagctaac catcagcctt tctgttaaat attttag
```

FIG. 5B-33

```
                                                       gtgagtat
ttctcccact cttgtgctct tctgcactag aatgtatata gtcctcaaac tggccatctc
catttcagt ccaaagtta tacagctaga caacagtggt gacatacgtt gctatttatg
ctctctttcc tgtcactttc ag
```

FIG. 5B-34

```
              gtaa gtcaactcaa gcatatacaa tactgccttt ggtcagccta
ttgagctgta aatcaccata ccgtacctct cttccacc acataacat gatttcagga
ctgaagcaaa gaaaggtgca tttttttcaa acaaacttt gtgtaatgct taataacata
caatcgtgct catgttgata tttggtagcc accaccccca aactcaatta ttagcaaatc
tcctgaacgt agccatggga ttgagatttg tatttctttt cattttag
```

FIG. 5B-35

```
                                            gtgagta aaacaagtaa
tagtaagtag taactactaa acttgagaat ttccccctgt ttaatacccc actgctatgc
aattataata tgtaaaagaa aatttcgtat ttcatatgtt aatgatagtg tttacatac
tttggtgctg atggagagaa tgagccaaat tactttagtt ctgattactt tgttttacag
atttaatgaa acatcacctt atgaaagtaa aatctatcaa tgaatatttt attaatagc
cttactttt gtattgttct tgataacgtt aagataacaaa ttattttcctt cccatagtg
aaaaagtaa tgcacaattt tcaatcaaac tagatcccga aaaattcctt ttgtgttttt
cttggcattc agacatgaca ctactataca caatcaggc atgagttctg agtcatttc
tctctaattg tgatgaatgt gcccctattt agttacattc tgtggcctgg tctcctttgt
caacagtagg acatattaag gagacagctg gtcagtaata aaaagagata cacttgggta
tacaattaac taggcaatgt acagaatatg ataatttctc ttaagaagac gatctgttat
acagctaaaa ataggcaacg tctaatattc attattattt atcttattat tgaaggaaat
agtctgtcac tttttaaaaa gcaataaact aaataatggg aaacaaattt tttgatacca
agttctggga tggatacatt tttgtcgacc aataaaattc tctcttctg tatcttcca
tactaaaagt tgttcttatt agcctgtgta cttatgcact catgtagata ctgccaggtt
tatttcactc tttcaaatt tttcaaatat tttaatcata agtaattta cagatcacac
acagatttca tgcttttattc tcatgttttg tctag
```

FIG. 5B-36

```
                  gtaagtgtta cttcattaac tttcataaac tctgcaatg
tgtttttaaa agtagtagtg ctttctcctt aaagccactg atgaccctgc aacaagtctc
tgatgctctt ctatagtcaa atgtaatctg tagaaagcat tagatttcta agttgataga
gaatttttg tttcatgct catattcct attcaataat tacatagtta taagaaacac
ataaatcaat atatattata gtcagtgatt tatatagaca actatgctac atttgtgaca
gtggctcaac ttgagctagg aaaaataata tgttactaag atataaagtt aattttggcc
atgtgtgttg atgttcaaag cctaaagccg aacttatgag tagtcatata aagaaaaaaa
aacttagttt ctctatgggt attagcatca ctgaaatgat taatttgccc tgaaagtatt
ccatcatgtc actagttaac acatatgtag gaagctcaaa gaaccaact tataacaagg
tcctttgaaa cagttacaac gtggacctat gtgataaata tttttggcta tagaatgcta
tgctcctagtg atatttagat gtaaattgga gatatttaga tagacagaca tatatatata
tacacaaata catatatcaa atatacatat gaatatttgta actgttatat cattattaca
caggggttata aaaggggc atagatagga gaatatctaa tgttatctac acctgccatt
gctattcaac taaaatgaca caatcttttc tttgaatact acacataact ggcatctgtt
tttacctatg gatttatcac agaaaagact cctcaagaa gggaatgaa ttgcaaaaat
tgaatattat actctagaag caacgaattc tggagtcgta gtcatggaac attagagcta
agtgacactt tagagaatat ctcatcaatc tcttcatttt actagtggag aaattaggaa
caaagaaat tttaatttgc taataaatgc aaaccagggc tcggaagcta cacaaatgta
aactctcata tgtaaaacag tatcactgaa agtgatgaat ggtgcaacac ttcttctaat
cacttttttc ag
```

FIG. 5B-37

```
                                                                     gtaaatct
tatgttttct atattgctgg tttgcccag tctgcctgga ataagtagac cctttacaat
agaaagataa ttgtttttca gatttttatt tatttccagt tctgtgatga cttccctctc
agtaaacagc aatccgattc cagtggacct gaattattct aaacaaacaa acaatagcaa
caaactgtgg gggaaaattc agagttccca aaacataaat gaattagtat gggttgtcac
tcttttctcc tcacgctgtt tatgcttttg tttaatcta gaaacattgt attcattga
cattattttc agagaaaata acttttatc ttaacatctc atcccataga gtaaaatttc
aacagtagt ctgactttta ataataagag tttatgatga tgaaaattca ttgggcaata
cattcacccc caaaaatttg tctgaaact tgtgttccaa aatagaatct gtggtttaga
ttttaaaata gatttaatat acattcctga aaaagagatt accttaacca caataaaaag
aagacaacac atattatttt cattcttaac tctaggaaa aaatgtaaac attagttgca
aaaagctatt ttagtgtatg gaaggatgtt cttgggaaaa aaataaaaac ataaaaggga
gagaggaaat aaagaaacca cggttttgtg aggtagtact ttcaaaggga tctatgtatc
tcagaagcta gtcaacagt tttaagtatg tggaattgta gggtttata taaaaatgaa
gatacagtct ctactcttaa ggagattaaa acacaaacat ctcctcaatt gacaagtct
cttccatgc tttctatctg ggctaagaga cttatccttg aaaaatgttt gtgggtaaac
atttttact ctctgcttcc cattgtccta tcctctctc catgctgcc atcctcttca
ggactgaagc aggttataga ggaatcgcag ctgtgcactc cctccttc aatagccag
gtcaccatgt cattaacagc atctctctct gctatattct ccctccttc catctcttca
ccttctttgt gtttcaaagc aggcaagaag cctgtctagc tagctgttta aattgaatt
cttctagagt ttgattcttc atttctct ttctccacta aaattgattt cacatgtgtt
tgactcaag
```

FIG. 5B-38

```
cgtgttgacc cctattacat attgttgatg aactctagta aagaaggctg cacaaggatg gta
cccagtttt cacaattctt ggcaggtggt ctggtagcat tttcatatct atctatatac
atttccctct accacctagc acctacacat ttctaaactc actaatctgg caagaagttc
cttgctacca tggaatttca cacaaacaga tggtgttgag taatacatga ggctcatttt
aatgccacta acaataatgc ctcatccctgt cctaattaat gggaagaagc tacattgaac
agctgtcaac catgctgctg cattagttat gccgtaagag tgatcaggcg ctgcagccca
ttgtgatgtt gccttacaat tctgtccaca tgaatctgta ccttgcttga ttatgcttca
ggagagtgta cggaaattag aaaagattgt ttaacaataa tctggaaatg gccttgaatt
attttttcct cattattttt ctcgattaac attctacaga atggtaagga atcgagacat
tgctaaaaat cttaaatgac tgaagtatc atagcatctt ctgtaaaaaa gaaaaaact
tcatattaat ttcgattcaa aatttggtc agaaacaaa aagttgctct tgctttatac
tttcag
```

FIG. 5B-39

```
gtgagtagaa tttgtttgt atgtttcttc gtacttggat ttttttttat gttgaattga
gaatttcca aattcgaact acacacactt tattatcaa gttaataaa ataatattcc
ttctctcctg ggctatgaca ataatatcat tttacagttc caaaggaaaa attaaaggga
tttaacctct ttgaaaataa tatccgaatt ttctaacttc ctagtgtcaa tgatccaact
acaaaactat agaccaaaag ctttaggttt aatagaatat taaatgatgc ttcaagtgat
aacagagatt aaaataaata aataaataag tctcctatgc tttaggaagc cgggacctct
aacaagattc tatagttatt caaacctact ttatcaccca ttatcaccca aagagcagcc
ccaagatta gctgttaatg ccatgaagat gccaaagata atcccatgac agtctaatta
ccttatctcg tatgtcagcc tctggtct tctaggccac agtcggcctg gattcctta
ttcacctctc cttcagagct gaaaactgac tgtagcacat ctgtaatagt ctttcttttg
aatcacatag ttctaacagt ttcaaacaag gctactcatt tgctgctctc cagggaattt
tacaatagcg gaaagttcag atctcccaaa tttctgacct gctatgactt acacatttcc
ataaccttta ttactggagt accctccttc tgagagtggc ttctaatagt cttgttaatt
agaaccaaaa tacatcagag gccttctaga tatccaacca gagtgcagtg aaagtgttca
gtcactgtat aagcacagaa aaaagaatg acaaggttca ctttgatga tacggggtgt
tattaataag acatgtttcc ttttggtac tag
```

FIG. 5B-40 atctaaaatt tcccgccttc cctagtccca aagagcccca gcaattcatt tttatgctt
ggtataaagc ctacttattt aaaaacctag ctattgtgat agagcagcag gaaacaaatg
ctgtgtgttt aaaattactt ttcccttcct atagatttgc cagctatctg atctatactc
taatccctag cattgttttt aaagtctctc catgttgcgc attaacaata tcctaatgca
ctgagcttc tcaaagcctt caattattac caaaaaatca ataaaataca tagtgtgccc
attcacatt gaactctcca cttaaaatag atcttattta ttgtattgca aagattgcca
caaatagatc agcccgtgt ccatctaaaa attaaaatgt cctcctcctg gtattgtagg
cactgattta tagtgttttc tcaagtgtat aacccatacc acttaaccc caaaatgaat
atagcattaa gtaaaaatcc acttcatttt actctgtgag atgtgcgtca gttatctctt
ccaaggcaac taagactctg tctgtccacc actgttctct ctccctccca gttctttgag
catctatgtc aggcacatta acagattcat ctttggtccc attatag gta agcatgcatt ttcactaagc caacagcaat

FIG. 5B-41 gtaagtaag aacctgggtc
attttgtata ctcacacctc acaatgttta gacattgatg aacctaggat tgataacaca
tttttaaatc cctcctccca cctag

FIG. 5B-42 g tgagtatcac ataatgaaga ttaatctgaa aacatcctaa
gttggggagt agagtgggtc ggaataccag agctgtaact gtttatttcc aacag

FIG. 5B-43

```
                                                   gtaagtt gaattcactg
gtggtccaca cagcagctac ccattagatc ttccaattaa atatatatcc gtcaagtgcc
tgctatgcaa cagggaatat accagataga agatggaaaa taacggaagg attaacattt
gcacactgct ttacaagta taaaagtttc atgaatattg tttatttta attctctgat
aacctcataa gggtggtaat attgaagaac attctgacac agatagtcat tttttattc
tatatttct tctaagagat gcgggaatga tccacttgaa gaaaagagta gcattacaa
gggttgttt gtgattgac tccatcttt ttgtttgcat ttag
```

FIG. 5B-44

```
                                            gt gagtattaca atggacctct
cgccgctttt ctttttcag aatctattaa ggacacttga aagttttgaa attttggta
aatttgact accatgagga aacttttgag attcaagttc attctattca gagcaattcc
gatattgatg ttaacttgaa ctcagctgga actcagtgta tgttgctatc agctcacttg
agtaataac caaggtgggc cctaggcagt ttaattgtaa agtcggaaaa aatattcctt
ttggcgttta ttaatatgcc cctttctctg cctgaccatg tccttctcct ttgcaggcaa
tgctatcaca acaattctct agagacccag agctcccaa aaatgaactt tactgacttc
ttctctcact ggacagtgct gaattatcta ggtcatttgt tattctttg tccatgaaca
ccattaccta ttaagtgtcc atttccttac cactcagcca ggtggtaaag atagttatta
atgtatacac attaatgtgt aataatgaca tagtgtctta tcttcatacc tttacaacca
taagataata tgtcagcatt tcagaaagga ccatccaaac cttaacgcaa aatatgggca
ttgcaactgg taatatgctg gtaaggaaga tgtgtggaga aggaggccct tcaggtcct
ggctaataa tgccctatat gaagctgcct gattttccaa aacaaagaaa ttcccatctt
acccaattc ttggagttga tgttgactgt ggaattctaa tgtgcttggc tcttag
```

FIG. 5B-45

```
                                                                        gtaagtaaat
cactgtaaac gtgtcttcat ttactctagc caaaaggcct ggcttctgat aggaaactgg
taagaaactc ttcatgaaaa cacatcacta atattcgcta ttactctcct ggtctgaagt
cagcttttct gaaccattaa ggtatttcat cacaagttat atttataat atcagtttaa
gaggctttta ttcatgtgaa caccagtccc ctttcagggg catggtcttt ttgaaaaaaa
aaacaaaaa acgaacagt tttagccaca tatcagatat ttctatatct aattatcctt
tatggctaac attctgcctc cattgttaag gtataattgt tcctgaattt aaggtggtt
tggcctctaa tttaattctg attcagactc tcctgtcagg actcaagaaa attaattaa
ttaccaagga ttaagtcttc tggttaaggt ttctggaaa aaaaaatagc aaagatgttg
atttcttgga atccttttac aggttcataa cagaaaaatc ttcattccct gtaggcattt
aattaaacct agtgagaag tgtgtgggat tcctcaatta tgaacaaaac acgtatattg
gcttcttta aaaaaaaaaa aaagaagaaa aaagaaaagg caaagtcctt cgaaactcag
agtccattc atttatcatt aactcctatc attctacata gttctgattc caatatgcca
gggtaccagt ggcatgacat tgttttttcct catagaaatt tgccatagtc tctcctccat
tatttggttg gttacagcct cataaaggaa gacaggagtt gcttcttcct gcaagaaaga
aggttaaaaa ctataaatat ttcccccaaa tggccagggt attatttat tgcatcacat
tgtttgcatc ttaagatcta gaatctttgc tgctctcttc caggcccttg gtgattaaca
gaaaggaaat gaccttgtac atttgctcat ag
```

FIG. 5B-46

```
          gtaagt gatttccaac tcctcttct taataccta tgctgaatta
aaataaagcc cctacacaga tcttcaagtg gcatctattt gttgatgagt attgcaggct
ctcagtaga gctcagttga gccaggaaat ctgtccagca cacactgagg ggctgtggct
tccaagatga tcagaaagca caaatcggga agacaataaa tgagggaact cagttttatc
acaaaccct taaagctatt gaaggcacct tactggtacc aggattagaa cagagtccca
ttgctgtggc catcctacta catattaatc aatctcagta ggctaccaat ttcttaaaca
tacactgtcc agtattagtg ctactctgaa agtgcccct attagaccct agaggccaaa
gtcaaattt gcttccttt gatatactga tttactgat ttccttttg ttttgttt
ttgttttgt tttgtttt ttgttttggg atggagttcc cctctgttgc ccaggctgga
gtgcagtggc acgatctcag ctcactgcga cttccgctcc cagttcaagt aattatcttg
tctcagcctc cgagtagctg ggactacagg cacacaccat catgcctagc taatttttgt
attttagtaa agacgggggtt tcaccatatt ggtcaggctg gtctcgatct cctgacctca
ggtgatccac ccaccttgac ctccaaagt gctggatta cacatgtgag ccaccccacc
cagcctgatt tccttccctt tgtgtatata cccagcagtg tgattgctgg atcttatggt
agttctattt ttagtttt gaggaacccc tcctactatg tacaactatt atgtatccat
aacaattaa attttta ttgtttccct gcctagaggc tataaaaact ctattcacc
accccaagtg tctttataaa tctcaaccac atatttaa atgttgtgcc attggtctca
aggatgaatc agatacaaaa gtattcatgc caagatgtaa actcaccgtc atcactagag
aaaagatatc caaggatatg tcctagtaat aggaggtcat tagccttttt ctaagctgaa
gacagtttat tctcacaatc ttcaagccaa cctgtgttat cacctaggt cttacccata
atactcagta ttttctct atttag
```

FIG. 5B-47

```
         gtgagt gcttgacagt attctgactc cattaacata agaaaagatt
ttaaagctg ccacttcaaa tgtgacagat tgatcactga ataacttcac ttaagatttt
tattcatggc atttctttta tacagatcac atgtcactta tctaagaagc tttaatacca
ccttacttag acacacacta taaagacaca gcttaattat gcagaatgat ttttggttct
ttccacgcac ttaggaacga tacaatctct aattgcgttt actcctctgc aatatgaaat
gctggcatca tttatcctgt aggaagaatg aaactctgga agttctgaat cgttccatta
aaccttatac gtgacaacaa ctagaaacca tctcatctcc ataaaatata tcaacttttt
gaattcattt cattgggat actgaatgac acgaggctca cttttacag agcaacatcc
cgtgattaca taaagctggc catctgtgtg accattcac attcaattta cctcttcct tcaaactaga
atacttctta ccattgtgtg accattcac attcaattta cctcttcct tcaaactaga
atctcctgag tagggttgtt ttggaggga aggttagcat tccatcgaat aagggaatg
tcatttatc ttctctgcct gtttag
```

FIG. 5B-48

```
         gtgagt ccaacacttg gtttgtaaaa taaaactgag caggatttca
ttgtgtgaaa ctttatgtcc tgagctgagg ttctctctt ccaaatttct gaacaagatg
gtcagcttc tccatagtat ctacacctag tactgaaaat atgaaaattg cttaggccaa
agaatgggct tttcaatagc acactgcaaa actggcccaa gtatttaaaa catctctaaa
aaatatctag gttggcaggt ttttatccct agttttaaca gtctgaaaga gggttcgtta
ctgagcactg gaagtgatga agacagagta gctacaacat agggctggt aggcagcaga
gcctcaccaa cagccttaat ttgtgtggtg tcttcacag
```

FIG. 5B-49 gtcagtac actttcatc tttctctaa
ttcaaagtg attaaaatgc aacccagatt gatgctaagc ttcatttgc cttggtag

FIG. 5B-50 gta agtttgtgaa
taccagtccc tcagtgcagc attctcgtgg gcttcacttc tgacttcccc acacttgggg
atggtggagg agtgggagg agtatcttgg gcctagctaa gttgtgtttt tctttttcat
ttcacag

FIG. 5B-51 gtatgtaca tgctgaagat ttctttgcaa cactaacatt tagagagaat cagtccaaaa
catctgttaa gaaaataaac aatatatcag ctagacttaa tattttttaa aaatttcagt
ccatgctgag aattgataca aataacttga gctattttaa atctcttatg ctgtttgta
ttaaacaatt acaaggatct agccacttta cagatagcac aactaaagca gattaccagc
agaggtgaga gcctagctaa accattacat gtcctgagtt accttgtaa acgaattaag
cagtatttgt ggtgaagtga gtgccatttt tttaaaacgg taagtcttat ccatcctct
gttcttat ag

FIG. 5B-52

```
gtaagtaaac tgtagccatc tcgcacataa actgatcctg aaggccttca gctcagaagg
attttcatat tttcactgct attgttccag tatagcctat ataatatcca tttccattc
tctgctaac tccatctcac tcttggaggt aatgctattt catgccaaca tgaaaggtga
ggattaaggg agatagaaat atacaataca ataaaatctc ctggtaacaa tgtccttcaa
ccccacttaa aataaacata attagaggaa tgactaatat tgcactgctg aaataggttg
tgaaaaaaaa ttgaatataa tagacataat gggagaaaag agcccactt tacatttca
attttctcaa tccggagtcc attaactaa agtttcccat tgaatttgga aaaaaaaaa
atatgtctct tgacatgtgc tctgaaagtg tgatttcct cttctgtctt taaag
```

FIG. 5B-53

```
                                                              g taggtggact
caagagaaga cagttcatct ctgaaataga ggctaaagcg agcagtgagc cccaggctgc
tgctccctg gtgggattca ccagctcaca tgtacctggt gtctgtcttc cttag
```

FIG. 5B-54

```
                                                  gtaagta tgatttgggg
aaataataaa gaagatcacg gacctaagga atgttttctt cagactaaac caagacaact
ttgacaaccc attaaagtta gcccattc aatatatcct ctaaaatatc tggaaattgt
ctatatgcaa tgggcttgtt aagtccatcc catgcaagtg tgcctgggg ctcgttattt
atttatgtga acttgattat tttttactga tgagaacatg cttccgtgtg aagctcaact
gaaatctgc tgccatggat gtctctcact gtaaaaaat ataaagcctc tcctatctaa
ctttcacctt tgcag
```

FIG. 5B-55

```
                                        gtggtaggt caagatgtcc agaccagact
gacccttctc acaagttgag ctttcaaaa ttagtttcca ttgacattta gagtgaaaat
gcattgggt aaagattaca ttatgtgaaa tcacacccaa ttaatggagc gtcatcttct
cccaaccagc accaacctc atttccctta aatgtattt ttgcacttt catagtaata
agtaccctga tttgatttt catggaggag ggaggag gaactgtcta atcttaaaaa
tagccaccct cttcctctta aatatgggt agacaatcaa aaatgttact tatgagagtc
agtatctttc attagttatt attagaatct gtgttctgct caatgagaag tttcatgatc
tgaatgttat tttcttaaaa g
```

FIG. 5B-56

```
         gtga ggaatcccac aaacacctct ccttctgcta
aataatattt tggtaggact gtttgttaat tatctgcatt ttaatctctg acaaaaatgg
gcttattaaa aaaagacctg ttccttcct gggttccaat tttgtgccta aattgcacat
tagaagatgg attgattgga cacatccatg taattcaaag ttattattca aattgactt
aattggtaat cattgaaaaa actgactaat gtcatttagt gtgaaggagc actggccagc
tatatgccac actcatacat atgcattttc agaatgtgag cagcttttct gaattttaa
tcaaaccttt tcaccaactt tactgaatgc ctactggaat tccataaatt acaaaatgac
agaaaaagaa aaatgtcaga atttctacct cctcattctc ttattctaaa gaagaacgat
atgcaaaaag gattaattga aacagataac tttttagat gacccttgcct cagtctagta
ggtcttatgt tcatctaggt aactgatact tcaaagacaa gtgaattaag tttctttaa
aagtaccctt ttcctaagct ttcctaagct tggatctgag tctactcttc ctgagatctt tttttttctt
tttttttt tcatgtttg actcttagta tctgagtcct tctccactta actggaattt
catcctattt tctgtag
```

FIG. 5B-57

```
gatggagggg gttctaactt agactgcccc caagggggt ctaagggggg gtaaaagaa
                                                              gtaagtaata gtgaaatatg ggaatagctt tgggaagtgg
cagaagaatg agagaactaa cttatttcat aagtaaattc agttttgta tgtattttat
atttatttat ttatacgtat taatttcgta cttaaattca gatgataaat tcagagtatt
cttatcagat agtgccttct gaaatgctga aatgtatact atgtccatgc attgtttttt
ctttagcatg ttttttaaat ggtaatgtgt gcccagaact taaaatttct tgagcttcag
tggcctaaac tataatttat agttatgtgt atttttattt actattagt atggctacat
ttaactttta atgctttttc tacaatatgc tataaatata agaaaaatta aaattcacta
acagcaagac tacataccca cccagtccc gctcccaaag acacacatag aggacatac
acacaacaat cctaaaaatg actttgtaga gataggtcac ttggaatgtg tgttgaaatg
ttgttggttt ttttggttgg tttgtttgtt tgtttttgt tagactgata gggagcccct
cccactaaag acaccctga tactgttatt tcaaggatga acttatttat ctggacaga
catcttcaga atgacacatg ccaaacagtg gttcttatta aatcaaaggt tcagatatta
tcagattcag aaatagtgat gctttgtgta tctatttct tctctttaaa cag
```

FIG. 5B-58

```
                                                    atgaactcaa tctaaattaa aaaagaaaga aatttgaaaa
aactttctct ttgccatttc ttcttcttct tttttaactg aagctgaat ccttccattt
cttctgcaca tctactgct taaattgtgg gcaaagaga aaaagaagga ttgatcagag
cattgtgcaa tacagtttca ttaactccct ccccgctcc cccaaaatt tgaattttt
tttcaacact cttacacctg ttatggaaaa tgtcaacctt gtaagaaaa ccaaataaa
aattgaaaa taaaaaccat aaacatttgc accactgtg gcttttgaat atcttccaca
gagggaagtt taaaaccaa acttccaaag gttaaacta cctcaaaaca ctttcccatg
agtgtgatcc acattgttag gtgctgacct agacagagat gaactgaggt ccttgtttg
ttttgttcat aatacaaagg tgctaattaa tagtatttca gatacttgaa gaatgttgat
ggtgctagaa gaatttgaga agaaatactc ctgtattgag ttgtatcgtg tggtgtattt
tttaaaaat ttgatttagc attcatattt tccatcttat tcccaattaa aagtatgcag
attatttgcc caaagttgtc ctcttcttca gattcagcat ttgttctttg ccagtctcat
tttcatcttc ttccatggtt tttgtatatg tttgttttctt gggcaagcag aaaaattaaa
ttgtacctat tttgtatatg tgagatgttt aaataaattg tgaaaaaat gaaataaagc
atgtttggtt ttccaaaaga acatattgag taaaattcct tgcttcaatg ctctttgcaa
tataaatatg catctctacc agccattaga ccaagtgcct ctgattagat agaaattatg
caaaagggc agtttggtgt ggtagaagag cagagaacga gg
```

FIG. 10A-1

Exon #

```
   1 tctgctcaac tctggtagtc tcagagttta agaataaaca acaagtaggg
  51 ggcttgatgt tacattttat caggatttct atccatgagg tagagagagg
 101 gaatgtgtat ttagtaatag gcatggcact ttgaaaaagt tacttcattt
 151 tctgcttcct caacttttctt atttggagaa taagggtaac ttcagtctta
 201 ccttataatg ttgttgtgag aattaaatgg cattaagctt tgagcatttt
 251 caacagacgg aggtgcataa tgaagcgtta gctatgaaga cgatgacaaa
 301 taatgattgt tgggtgttag accctctgcc tttgatacct cattaattc
 351 tcaaaaccat tgttttaatg taagcatttt caatctgttt tacagttagg
 401 gcatctagtt acagaaaggt gaagtaactc tctcaaggac acacagctag
 451 taagcttcag aataaacagg gattgaaact taggttgatc gggcaccaag
 501 gctcccacga gtttccacac ctctgcctcc cagtggcac attttactg
 551 gaacctcagc cctctgaaag cttccactgt attcctatag cagttctgaa
 601 agctgccatt gtactcctat agcagatcta aaagcatcta ctgtgttcct
 651 atagcacctt gcctggatct ttctggtgaa tttcccaca tcctgatttt
 701 attttttttct tttcagcaaa cttcccctg taaatccctc cttcagtata
 751 acccttgttag ctttgaggac acaccctag gcctgggctc agagcgctgc
 801 ttctcccaca cccttttcctt tgcttcagtt taaagtgtca cgagatgcct
 851 ctggttctct cccttgctt ttagccctca ccggggcag gaggaccaa
 901 ggctgggcca gaacacatag tcctaggta acagtgaagg ggtcgtgagg
 951 ggacagtgac tcccttccaa cccctttctc ataggactg ttggcaaaca
1001 aagaaaatca actgggaaaA TGAAGACCTG CTGgtaagac aataaccctg
```

FIG. 10A-2

| | | | | Exon # |
|---|---|---|---|---|
| | | | | 1 |

```
1051 gaaagagtgg tgggagatg gagctggggg tcctcagaac caaggtctg
1101 tattttttgc agcagtggta agatgagagt aggtgagcct caaggtgaga
1151 gacagaaaga gagacggatg agagagtaag acaagagggc aagcgtgaga
1201 aaccgaagac agacacaaaa aaccgaagac agacagagga agggagagaa
1251 agtgacggcc acagaaaaag agaggaagga aatcaaaggt gaaagaaacc
1301 agagacaaag aaataggtac caaaacagtg agataggtag ataccgagaa
1351 ggtgagatca ataaaacaac aacgacagtn ngtctgaaaa catgagttcc
1401 ttacatctct cagtagggtt tcaaagtaaa aatgaaggct gggtgcggtg
1451 gcttatgctt gtaatcccag cactttggga ggccgaggcg ggcgaatcac
1501 gaggtcagga gttcaagacc agactgacca ccatggtgaa accctgtctc
1551 cactaaaaat agaaaaagta actggtgtg gtggcacgtg cctgtaatcc
1601 cagttactca ggaggctgag gcaggagagt cgtttgagcc caggaggtgg
1651 aggttgcaaa gagccgagat cgcgccattg cactccagcc tgggtgacag
1701 agcgagactc cgtctcaaaa aaaaaaaaaa aaaaaaagaa atgaaaaaaa
1751 aactatactg tgatttgatc accttacatt aattaggttt actaggtttg
1801 aaaatatgga agtattttcc atctgcgggg actcctgttt cagtcattt
1851 tcttctctct tcttcagGAA AATTCCAGTT TTCTTCTTTG TGTGCAGTTT
1901 CCTGGAACCC TGGGCATCTG CAGCTGTCAA GCGTCGCCCC Agtaagggcc
1951 atagtttcta gactttcaaa gatcacttat tcccagaaat gatcaggcag
2001 ggctgtggct gactgaagac tgagtgaggc attcatagtc cttcacaccc
2051 tcactcttca atccagcttt ggggcacagg gatacattag gttctggttt
```

FIG. 10A-3

```
                                                                          Exon #
2101 tccatggtca atcgtgggta tggaaagtNN NNcctcttca aaacgaacat
2151 tttcccagcc agattattag agcaactttg tgccttgcat ccacccttc
2201 caggatgagt tgcaggtgga cagattataa tcgtagaggc atggaggtaa
2251 agccaaacac tttacctcta agcaagctgg tataatattg aattttaaat
2301 atttattatt attgatacat cctgaaatct ttttttgtg gtcaattgct
2351 attttctgt tctaaatttt attattatta ttattatttt attttatttt
2401 attattatta tactttaagt tagagtggat gaagtagaat gacatgctat
2451 ctcttttgca gGATTCCCTG TCAATTCCAA TTCTAATGGT GGAAATGAAC   2
2501 TCTGTCCAAA GATCAGGATT GGCCAAGATG ACTTACCAGg tgagtagcaa
2551 tgtacctat tgctttctat aaacctgatt tttttttta
2601 tttggaaag ttgtggaaag aaataaaacc aatctcattt tagacttttc
2651 atttgtatt cccattctat agGGTTTGAT CTGATCTCTC AGTTCCAGGT   3
2701 AGATAAAGCA GCATCTAGAA GAGCTATCCA GAGAGTAGTG GGATCAGCTA
2751 CATTGCAGGT GGCTTACAAG TTGGGAAATA ATGTAGACTT CAGGATTCCA
2801 ACTAGgtaat ctatcaaaaa tatttaatc taattatctg actcaaatgc
2851 attaaaaatg gatagctatc caatgttaga gttttcttat gancaatgtt
2901 tcttggatt ataattgtat ttaaagatga agaaatttat ttacctgcct
2951 atcttcagta ccttaatact gcattcgat gttttcNNNN aagcacggac
3001 catgaatgta caggaatgat tgnacttctg taaggtctt tatgaacagt
3051 catgaaagaa caaacggtac ataggttttt acactgtagc ttttctatag
3101 gtctggcatc taaaatggcc tcaaaaggga atgtggtaaa tacatatggg
```

FIG. 10A-4

Exon # 4

```
3151 tacaggaaac aagatgcatg tttactattt aaaaatttta ctcagGAATT
3201 TATATCCCAG TGGACTGCCT GAAGAATACT CCTTCTTGAC GACGTTTCGA
3251 ATGACTGGAA GCACTCTCAA AAAGAACTGG AACATTGGC AGATTCAGGA
3301 TTCCTCTGGG AAGGAGCAAG TTGGCATAAA GATTAATGGC CAAACACAAT
3351 CTGTTGTATT TTCATACAAG GGACTGGATG GAAGTCTCCA AACAGCAGCC
3401 TTTTCGAATT TGTCCTCCTT GTTTGATTCC CAGTGGCATA AGATCATGAT
3451 TGGCGTGGAG AGGAGTAGTG CTACTCTTTT TGTTGACTGC AACAGGATTG
3501 AATCTTTACC TATAAAGCCA AGAGGCCCAA TTGACATTGA TGGCTTTGCT
3551 GTGCTGGGAA AACTTGCAGA TAATCCTCAA GTTTCTGTTC CAgtaagtat
3601 aaaaccacac actatggcag attaaagcaa aactagattg gtaaaaatga
3651 acatctcaag catctttgat aatcagctga gtgcagcatg tcccagatgg
3701 aatttggaat cagaggaagt taagtagata gcttctggtc ttgaggagct
3751 taaagttgga aagtgttaca tgcccaccta gtgcaccag agtcttctg
3801 aggcaactta gaaagaNNNN gtccttctga ttgccacttt ttttttctgt
3851 ctctaatctc ccatctaaaa tcttacagca tatattccct gtagagttca
3901 atagccctgg gtttcaaccc agactctgac acttattggt ttgtgacttg
3951 gaccgttctc gttctctctg aacctcatct agtaggatc tacatcttga
4001 gattgtcatc agaacagaaa tagaaagtca gtgctggtgg tctgtttcca
4051 ggctaggggt atgctgaaat aattcaaagc taaagacatc tatacctaat
4101 aatcagagaa acttgtgaaa gcttccaacc catttccatt agaaaacttg
4151 tattcaagga aaagccaaga gtcctggtcc agtgtgctca accagttcaa
```

FIG. 10A-5

| | | Exon # |
|---|---|---|
| 4201 | gttgattcc aattatttaa caattagacg caactcatct ctctcttgaa | |
| 4251 | tgaccagctt cagtcgtcca aaaaaccta cctgactgtc tactaccttt | |
| 4301 | ctccagTTTG AACTTCAATG GATGCTGATC CATTGTGACC CCTGCGGCC | 5 |
| 4351 | CAGGAGAGAA ACTTGCCATG AGCTGCCAGC CAGAATAACG gtgagtcccc | |
| 4401 | tgactacctg caaaggccac ttctacccag ctcaaccctc tccacctcac | |
| 4451 | cactttccca tcttgccacc tccccagcac ccctcctccc cactctcttt | |
| 4501 | cgctaagaga gcctgtgctt tgctgtactg actagagaaa tattagggaa | |
| 4551 | gtacacttca tactttcgac ctggcgggta gaaaccacct gcagcctggc | |
| 4601 | aggtagaaac cacctgcggg tgtgtggttg tcccttttggt agcttatgga | |
| 4651 | ccctcctccc ttactctcaa acatgtccaa gaacacttga gttctactgg | |
| 4701 | ccagcactgg cacaggccac ccggaaggt ctccgaggac agccagaagc | |
| 4751 | tgcactgggg tggatgggat ggaggcagag ctgcgtgctc agtcctcgcc | |
| 4801 | tgtgcgcgg cagggaaggg gttaagggcg actgttgtca ttctatccgt | |
| 4851 | cctccccttc cccctagctc tcctccaatc ccaggaccct ctccggggcc | |
| 4901 | attcataaac aggggnaac gcgcccctcc cgggcctgga cgctttggca | |
| 4951 | accgctactc ccggggtgc ttttctgca gggacgaagt gccacctatg | |
| 5001 | ctagtggcgg gtctggaagc ctagagggga accaggctgc agagcgggc | |
| 5051 | caagggatta gcggcggggcg gcgggcATGG CCTGGACTGC GCGGACCGC | 6 |
| 5101 | GGGGCCCTGG GGCTGCTGCT GTTGGGGCTC TGCTTGTGCG CGGCTCAAgt | |
| 5151 | aagttgcgat cgagtttgag gggtgctttt ctcactttct cccatcttt | |
| 5201 | tctttctccag CCCAGCCAGA CCACCGACGA Ggtaagttgg gggcagggag | 7 |

FIG. 10A-6

| | | | | | Exon # |
|---|---|---|---|---|---|
| 5251 | tgtttgcatt | tttcaagcgc | acacgaggac | aggtcggggc | gcacgggtcg |
| 5301 | agggagctgt | gagaaaggcg | cgganatccc | caggctctc | agacccgcgc |
| 5351 | ttcctccagc | ctcgagcacc | tgccgcgagt | cctatcgaag | tccagaccg |
| 5401 | tagatgaccc | cttggtgacc | gaaggggggc | tcctcccaa | tctggtcct |
| 5451 | ccctactgca | NNNNaatgca | ctctgcagag | gtgagaacca | gtgaagcctc |
| 5501 | cccaaccttt | gggggcgtca | atcctgctct | agcccacag | tttagctcat |
| 5551 | tagaatatgg | cggagaccaa | agctgcgctt | gcttggaggt | ctgagacatt |
| 5601 | tttgcgttgg | gttgcaaaac | ccggcctcct | ctggaagta | actttaccc |
| 5651 | cacggaggcg | ggggcttcag | ggcaccggc | tcagttgctc | cctgttgccc |
| 5701 | gatgtgctcc | actaacctat | gtctgctatt | tttgccagAG | AGGTCCCCCG | 8 |
| 5751 | GGTGAGCAGG | GTCCTCCCGG | GCCTCCGGGC | CCCCCTGGAG | TTCCAGGCAT |
| 5801 | CGATGGCATC | GACgtaagtt | tctatctcca | ggccacctct | gttcccagt |
| 5851 | cctgcccttt | cctattcttt | tcccagggct | cctgtgggt | tttttttt |
| 5901 | tcagagagga | ccaggtctc | cccttcctgc | caccccactt | aaaggcagga |
| 5951 | tcagacatgg | gcgagagttg | ggggtaggat | cctaggaacc | cgggatttt |
| 6001 | tggagggaga | ggtgtctctg | ttgtccttgt | tggtcatgaa | cctccacgtt |
| 6051 | tgaccctac | accatcccca | tctgtgaagt | gagctctcct | ggattgtcc |
| 6101 | cagtgggggtc | ctcagcctat | ctcgctcata | gactgctctc | tcttttctc |
| 6151 | ctaccctcc | agGGTGACCG | AGGTCCTAAG | GGCCCCCGG | GCCCCCGgt | 9 |
| 6201 | aagttgattg | gagcatatgg | cgctccactt | ccttccttta | gacgtgttt |
| 6251 | gcagcccct | gtttctgaag | ggtctcaact | ttgcaccttt | ttctctcctg |

FIG. 10A-7

| | Exon # |
|---|---|
| 6301 ccccgcacc cttctgcccc tgctcagGGT CCTGCAGGTG AACCGGAAA | 10 |
| 6351 GCCAGGAGCT CCAGGCAAGC CTGGCACACC TGGCGCTGAT gtgagtaggc | |
| 6401 gagtgctggg agggcgccca gcctggggtg tgtggtgggt acgagtaagt | |
| 6451 gtgtgttttg tgggggggg agggagagag agaaagagag agagagaacg | |
| 6501 cgctgtggct ctaaacttgg cctcctgcca gcgcctgatt gatccgtgga | |
| 6551 actggcagct tttgcaaaNN NNccaaagca gagacaaaaa acactgaatt | |
| 6601 attgaaccct gtgataaaca atgcagttag caggaagtta ggagtatgat | |
| 6651 acaacttatc aagaagaaat aatcacaaca gcagatcttt ctgttaatct | |
| 6701 tttgagtaag actatagtaa ggtattctt tataaatatt tgcatcatac | |
| 6751 ttatgtaacc atcctgtaga caattaataa ataaaatgaa agttttctac | |
| 6801 ttagtgtgttt gcctaaggat gttatgatag ttctaacatc attgtcttgc | |
| 6851 tctattagGG ATTAACAGGA CCTGATGGAT CCCCTGGCTC CATTGGGTCA | 11 |
| 6901 AAGGGACAAA AAgtaagtta gccatctgc attaattgct agtacgaaaa | |
| 6951 tgctgaagta taattttatt gcagtgtttg caagccaaact aacattaagt | |
| 7001 tatgaagtat ctaaaatgca ctcgttcaac taaaattgtg tttaaaaaca | |
| 7051 ccatgatgtg gaatactatg cagccatatg aaggaacaag atcatgtcct | |
| 7101 ttgcaggac gtgatggag ctggaagcca cctgaactta aaataaaagt tggaaattta | |
| 7151 gcaccnnctg cacatgtacc ctgaactta aatgctttt aatgctntca atatttatgc | |
| 7201 aaaaaaaaa acaccatatt gggtgttt aatgctntca atatttatgc | |
| 7251 agtttcaca tttacatatt catgatatga aggtcagta caatgaaact | |
| 7301 attttatt ttagGGAGAA CCTGGTGTGC CTGGATCGCG TGGATTTCCA | 12 |

FIG. 10A-8

| | | | | | Exon # |
|---|---|---|---|---|---|
7351 gtaagtaaat gtaaagctac agaattgaaa atttcctatc tttaggtaaa
7401 attctgccat tgtgaaatct tttatttat tttattattt attattat
7451 ttattattat actttgggtt ttagggtaca tgtgcagttt tctgcataat
7501 atacatgaga nataagttga tgacatctgg tatggtaagc atttctacta
7551 tgagtggaaa aattttagag aagtttgaat gtacagtaga aaatatatat
7601 nctatttgca ggtgtattt cccagcagac aattcccctct ttacctgcca
7651 tgatagaNNN NagcagagCc gtgtttgctt ttctttattc agtgctttct
7701 ttagaatgag catcatttt agtaatagag tttatggttt attttagctg
7751 agttatgtct acattcatat ttatactaag tataaacctc aagctataac
7801 cattttatt gtactctttt agGGCCGTGG TATTCCTGGA CCCCCTgtaa   13
7851 gtatcacttc atcatttatt tttatgcagt ctataaaaat gtcctatttc
7901 tcaaatcccc accttattct cctactaacg gtctactcag tggtgtttac
7951 agtgttctac ctgcaagntc ttaggtggct actaaggata acacccttat
8001 tctgctanac nnnatattta ttaatttagg aaatttctgc tgtatcttaa
8051 gtaattaaag tttggtcaaa tgagttattg tgtcattgga aaccaaagct
8101 aatacagaaa tgtaaatcta atatttatca tatttgatat aatgtatgat
8151 agattgtaaa aatattcata aatgaccatt tgctttgatt tgttgacttc
8201 agGGTCCTCC TGGGACAGCA GGACTCCCTG GAGAGCTTGG CCGTGTAGGA   14
8251 CCTGTTgtga gtaccacagt gcactttgat agacgtttgc tgatttaata
8301 gaagatgtta tttgggaaag caaattaccc taactgtaca tttccacttg
8351 caaaccaaaa catggcagat gaattcatt ccagtttata atattgatgt

FIG. 10A-9

Exon #

```
8401 gaaccaggaa taataataat ttttgcagag tgattttaat ttttcctaa
8451 attttcagc taaactttc ttcccaactt ccagattgtc aagtaagaga
8501 gtgtcgtcct cattttacag actctcagcc aggactggag tctagtggct
8551 tttgtattag gctccctgca tganataaaa gtgaatagcc taaaattatt
8601 accatgtgta tttatgttag gntcattaaa ttataattNN NNaatgcac
8651 tagcagtata ggttgctcta ggtcctctgt aaatcaacca aaaaaataag
8701 tagtgtttcc aatttgctnt cagagtagat aaaatgtttg tctgatagag
8751 aagaattggc tttgcnnttt ccctagctt ctctctgact tgttttatta
8801 cctcggtgag actgaatgc ctttattact ctcattttgt agaactaatt      15
8851 ggataacggg ccaccatcg attttgtgtgg caggtctatg catggctgag
8901 ctcggtgggg nnnnccagta ataccattct cttatgcctc actggtntta
8951 tgtactgtgt tttgacacat gtataaccac tgtgtcgcaa ttttcaaata
9001 acttagGGTG ACCCTGGGAG AAGAGGACCA CCTGGCCCCC CTGGTCCCCC
9051 AGGACCAGA gtaagttatt tgcagcttga atttctgttt gtgtctgaga
9101 gtcagggttg aaaaaaatct aagaatccaa aatggaagtt cctattaatt
9151 gagtcattgt cccaaatttn caaaacggct atcaattttt ccatgcactc
9201 aagggcatgg ttctgtttag ggcaagaagt agaagaatca caataattta
9251 aaaggtggtt tttataggt atatcttact cattactttt gaagtctttt
9301 gacagttgtg atgtctcaaa tgctcaaaac ttagatatat aaatgaagca
9351 ttttcaaatg aactagtttt tacaaaggtt ttcatagtaa gaaaaattta
9401 aagaatatga gttaaatga aggtaattc atattttat ttgtaattca
```

FIG. 10A-10

| | Exon # |
|---|---|
| 9451 gagttccca cattttctat tttgcctctt attcgtttc ccttcaatgt | |
| 9501 ctcccaaaa taatctactg caattcatg ctctccaaag agaacatgcc | |
| 9551 catgagtcag gattntagaa tattagcata ttatctggtt tcttatattt | |
| 9601 tattaaacaa atatatttta tactttttgcc tgatgagctt tctagtatta | |
| 9651 gtatgtttga attcattatt taattgtatt ctgaacctta atattttgtt | |
| 9701 tactttagGG AACAATTGGC TTTCATGATG GAGATCCATT Ggtaagatgc | 16 |
| 9751 tttcctttga acaaaatata gttttaattc aaagaccata tagcctgcag | |
| 9801 atgagttttc tttaaaagat ttccctggaa tattctatgt gtctgtgttt | |
| 9851 tcctttcact caaatggcag agcagtctgt aacactagtg gactagtggc | |
| 9901 ttgcatctac tcagactaat aattttcat tatagatgta tctttgttct | |
| 9951 tctatgatct ttttacttta tgactaagac atgcttttNN NNctggcttt | |
| 10001 aaatgtgaaa taataataat aaaaagaaa ggggtgttta gaattattca | |
| 10051 atgaatatta ttgcaatgga gttctgtaac tggaatccct taaaaagata | |
| 10101 ctgtcacaaa gcgggagtcc tagtttatgc actctgtctg tctttcttc | |
| 10151 tcttttgttcc ctctctccct ggcagTGTCC CAATGCCCTGT CCACCAGTC | |
| 10201 GCTCAGGATA TCCAGGCCTA CCAGGCATGA GGgtaagaga ataacttcca | 17 |
| 10251 gtattttaag agtattatcc acagataaaa tggagccttt actttaagca | |
| 10301 ttagccttcc tggtgcagag accccactg gatgatcagg cgagtagtgc | |
| 10351 ttattcagtc ctagcaattc cagttgccct tgacatgtat tcctgtattc | |
| 10401 ctaccaagac atggaggttt aatcatagga tggctttcta gttcaggaa | |
| 10451 gaaataccaa taaaatacat tggattgaga gactttNNNN ccttcctcca | |

FIG. 10A-11

| | | Exon # |
|---|---|---|
10501 ccatcaggaa ggaggtggga atggaggagg ccgaagggtt ttcagagcag
10551 ccttcagagg gcagggata gccagctgag cttggtcaag gctgtcactt
10601 ctgaaaggtt aagttactgg aactagagaa gacttaatgc tcctaacccg
10651 tgtgaggaag ttggagaaat agggaatagg gatctaggaa atagcaggca
10701 agtatcaatg aatcacattg ctgaactagg taatgaagtg tattattcta
10751 gagcagtgtt tttctattaa gtaacactga tattaattat atatggcagt
10801 catggtgctg ttaaggtcat ttaagcatt aatttctctt gtgacataac
10851 tcattctta gtaatacatt ggcactgatt tagggaagca ggatcacttt
10901 atgagccttc tgatcactt ctgtaccaaa ctcaagacaa ttacttattt
10951 tgcatttgtt agGGTCATAA AGGGGCTAAA GGAGAAATTG GTGAACCAGG    18
11001 AAGACAAGGA CACAAGgtaa ggaaaatggg tatttagtgg ataaattgtg
11051 attaggagtt attggtcact ttcattataa gaaattagga attataggaa
11101 ataatgaacc tcgatatttt accattcttt ttaaataat gattgataag
11151 ttctaagcag atgcatcaat atttgactaa atatcatatt ctgaagttgt
11201 tcatttacaa taaaacactt acaaataagg caccagacat tttcattttt
11251 ttctgtcact acctttctt ttctttcaa atcaatcaca ctcagctttt
11301 ttccttgatg ctatgatagc caacattatt cagcagttgt tccacttcac
11351 cagcaaNNNN tttccttgata tctttgtctc tcttcctctt tcccccactt
11401 tagaaaaact ttgaaagaat aacatctaaa tgttactggt atttatagt
11451 taaatggtgg tattttggtg acattttata tgtaggcttc tctgtatttt
11501 ctgaatgttc tacaattaat ttggactacc catataaata atttaagaaa

FIG. 10A-12

```
                                                                              Exon #
1551 gtagaataat tcaggagtca ccaagttaac ttaaaacata atgagttaga
1601 ccaagcctat ttctatgttc gttgctaga ataacattg gtgtgctttt
1651 ctttttctt tttttctt agGGTGAAGA AGGTGACCAG GGAGAACTCG       19
1701 GAGAAGTTGG AGCTCAAGGA CCTCCAgtaa agtatttttt aaaaatatt
1751 taactaggat atgtaaatat tctttttttt catgactgtt ggaatatttt
1801 ctatttagca gttgatgaa tagcattaca tgaacttggt gtcctctatt
1851 ttccaccacg ccagcactgg gggataacta cttcttcaaa ataggagagg
1901 gtcttcatta tatattctag cacttttta acagaaaaat tctacctata
1951 atttacatac attcgtttac cagatttcag ggccaggcaa ttgaaaagca
2001 aatactaagc acaaaaggat gatactcatc ttttatgttc tatcgtatta
2051 tcacatgata taatgagaaa attttgtgtg ttctaaatat gcagtaggta
2101 tatcatttat tggattaatg tagcttattc cagtatgcaa tcattataat
2151 taattaaaac attcttaatt gctcatatca tgtcttttaa taaaaaattg
2201 gtccctcgtg ctttagcaga tttctgccaa taatattcaN NNNacatgcc
2251 atgaaggaag tgggaatgat agtgtaagtt ctacatacaa gttaaaaggt
2301 aagtcaaaaca tattatcaca atttctctta tgctggtatt tacttttttt
2351 gtcataagtg atttgtcaa ctccagtttt gtgtaagact tcagaatttt
2401 ataaaaaggt ttaccatcag aagaattctc cttggactt ctaaactaga
2451 aatgtttgtc tatatatata tagttactat ttcttggtat taccttggt
2501 tatgataata cccattgtct agatcagctt ttgtgatgag atttttaaaa
2551 atctttgctt caactaaaat aattcacttc tcttttcac atttccagGG
```

FIG. 10A-13

| | | | Exon # |
|---|---|---|---|
| 12601 | AGCCCAGGGT TGCGAGGCA TCACCGGCAT AGTTGGGGAC AAAGGGAAA | | 20 |
| 12651 | AAgtaagatg gtgatgacaa taatataata ccaaaatgtg ttaaatattt | | |
| 12701 | aaaattttgg ccatttaaac ataacttttt atcttcaaca acttttttt | | |
| 12751 | tttttttttt gagatggagt ttcactcttg ttgcccaggc tggagtgcaa | | |
| 12801 | tggcgcgatc ttggctcact gcaacctctg cctcctgggt tcaagcgatt | | |
| 12851 | ctcctgtctc agcatcacga gtagagcagc tgggattaca ggcgcctgcc | | |
| 12901 | accacgccNN NNttacctga ggtgcctgag naattactcc tcaggatca | | |
| 12951 | ctgtgtgtat nacaggcaca aaacctcctt ttcatctggc tattaaattt | | |
| 13001 | ctttagaaag atggatgctt cctttaacat acatgactga tctcagtttt | | |
| 13051 | tttccattgt cttgttttt tgcagGGTGC TCGGGCTTA GATGGTGAAC | | 21 |
| 13101 | CTGGGCCTCA GGGTCTTCCT GGTGCACCTg taagtgattt tccttccaca | | |
| 13151 | aaacccaatg atagattttt tttttttgc tatgtatgca tgtgtgtgca | | |
| 13201 | gtattgttta tgtgtgaata attaaagtgg aaaagtggac aatttatata | | |
| 13251 | tatatgttta aatttaaatt taattaagac aggtatcttt ctcggtaca | | |
| 13301 | tagaaatgtt cttctgactt gacatgattt tttcttcat agattaagcc | | |
| 13351 | aaattattaa gtatttatgt ttgcgtgttt tccttttctt tggttattag | | |
| 13401 | gacgcctga gtctcagtaa ctatctcgtt tctNNNNaca gaggcatagt | | |
| 13451 | gcatttaagg ggaaaacaaa agaccatcaa gtgtcagtta tctctatggc | | |
| 13501 | aatatccatt tttaagacaa ttccgttttt ataaaaagac ttcttcatct | | |
| 13551 | aggcttcctt gatagagcaa agccattgtg gtggaagact aatagtttgg | | |
| 13601 | tgacgtggat gatactttct aatttttaaa agttgattaa taagtaactt | | |
| 13651 | ttgcttgtat taacaaaatt ttattttcat acagGGTGAT CAAGGACAGC | | 22 |

FIG. 10A-14

```
                                                                                    Exon #
13701 GAGGACCTCC AGGAGAAGCA GGTCCCAAAG GAGATAGAgt gagtttaaat
13751 tcagtcactc caagcctcct gcttttcagt gtcatctgct gattatgctg
13801 atctctttga caagtcctaa tattatgtta actgaacatg tcttgtctat       23
13851 tctttctctt cctccctgca gGGGGCTGAA GGTGCTAGAG GAATTCCTGG
13901 TCTCCCTGGG CCCAAAGGAG ACACGgtatg tcctgagctg tagtcatcaa
13951 gcacattttt cagtgatcat tgacttgcaa tgaaactttta gaaataatg
14001 aagggaaaaa gaatgtgact gtgtgtaaga gacagtatgt ttctttgtgt       24
14051 gtgtttagGG TTTGCCAGGT GTGGATGGCC GTGATGGGAT CCCTGGAATG
14101 CCTGGAACAA AGgtaggctg tgtaatttac tccaagagtg agtgggctg
14151 tctctgccct ggccaactga gtgtggcatt tccattacta aatcaccaaa
14201 agatttattt agctagcttt ggcttttctcc cttcctttaa tttttgaatc
14251 aagtgtcaaa tatgaaatac ttactagaat agtataatta tttgcttggt
14301 ttcaggaact cagtagcatt gccctgttga tgaaagtaag ttgagagaga
14351 ctgtgcattt tggtttgaatt atgtcctatt tcccaccta ctcccccacc        25
14401 ctaaattaag tcactttata aaagtgcatg taaagtcagc tgttgggaca
14451 atccttttac ttaaaacgtc tgtgctcctc cgttttcttaa aagaaataca
14501 gcagctcata caggtcaat catgtgataa aagcttttt tgcagGGTGA
14551 ACCAGGAAAA CCTGGGCCTC CTGGTGATGC AGGATTGCAT GGGTTACCAg
14601 taagtatttg attctttaca tgttaattgg tttatataca tgttttaaag
14651 atatacattt tggggagaga catgctacct aatctgataa gttctgggga
14701 agatatgatg tttttactttt acattttac aattacatt tgtatttat
14751 attttatact ttttctctga atagctattt gtgtaataact tgtaataat
```

FIG. 10A-15

| | | | Exon # |
|---|---|---|---|
| 14801 | aggctttaat tttatgctttt ggattccttt tctctcttta gttactcag | | |
| 14851 | tcttttttta catattttt aactaaccct aagctgtagg ccagtgtgat | | |
| 14901 | atatttcatt ccactttaaa ccggttctaa agctccttgtt agtaggatta | | |
| 14951 | agcaacaaga gtgctgagag tatactcagg tgacccctta gattatgtac | | |
| 15001 | tatttttNNN Ncctagtaga gctcctcttg acctgaaagt ggtactgat | | |
| 15051 | tctaatttgg gaagtttgtc cttgaaaagt aactttagtt taaagacaag | | |
| 15101 | atttgcttta agggtactta gctttaacaa gccagatata gtaaagtcat | | |
| 15151 | gccctctaaa ctgtgggtaa ttctataaat gactgtgcag agtttgggaa | | |
| 15201 | ctaggaagca tcttccttac attaaagctt tgaggttacc atgattccct | | |
| 15251 | cagcctcect gcagtgtgca gtgggcttgg catctcagag attctcagag | | |
| 15301 | gaggtgatta aactcggatt gtgtatgtat tcttttagGG TGTACCTGGA | | 26 |
| 15351 | ATTCCTGGTG CAAAGGGTGT TGCTGGTGAA AAGgtaaaat attttaaaat | | |
| 15401 | ttaagttaat atctttctta atttctttat tatttactaa cgtatttgta | | |
| 15451 | atttttaata ttttcagcat gtgttttatt ttatatttgg ccctagggag | | |
| 15501 | aaataaaaag gtaaatgtgt taaggcttca aatactaatc tttttcctag | | |
| 15551 | ctacagaaag catactttga caaatgctg ctaattagat ttccttaatg | | |
| 15601 | NNNNtgacat ttgacctta atatatttct cagactcaca gacaatatct | | |
| 15651 | tgaatctaaa ggatttcgat gtatctaaca agaaagagat tctgcacatt | | |
| 15701 | cccagatnct cagtgtgaaa gcagggaatt aatgctattc aaatgtaaga | | |
| 15751 | gatcccagtc tgggtaaggc agattgatga ttatgcttac ttcagcatga | | |
| 15801 | gttactttga atgttgcatt ttaccctag GGTAGCACAG GTGCTCCAGG | | 27 |
| 15851 | GAAGCCTGGT CAGATGGGAA ATTCAGGCAA ACCGgtaaga caccatttta | | |

FIG. 10A-16

```
                                                                                        Exon #
15901 cctctcctga agttctaacc tgttgtaatc agtaggtgtt aactttttt
15951 ctaccttcct tcctgataac agGGCCAACA GGGCCTCCA GGAGAGGTGG      28
16001 GACCCGAGG ACCCCGGGG CTTCCTgtga gtattccttg ctgttctttc
16051 ctaaagcacc ttctcaggac tttgctggat gttcttccat tcattcatcc
16101 atccatccat gaatgctgtc tgatgttttga gcccatgcta gtccaagaca
16151 cacaaggaga tgaaatgcta tttagatgca cagcatgcct tttcagaaaa
16201 tggaaacaaa aataaagtgc ttcaaaaaNN NNcttcagaa acttcagaaa
16251 tttttaccat ctgtgtcttt ttgaagttgc aatagtaatt taaggcaaa
16301 catatctatt atgtgttcct tttttcactc tgttgaggtt taagatcatt
16351 tgccagatgt tgctttgaaa tgttctgtag acctgagaat ttattctgtg
16401 ttctaggcac tgtgcagaat tccaaattaa tatttaacaa tacttaaga
16451 acacataatc taagtgaggg cttaaaacat ggacacaaat aaccataata
16501 aaagttagga tgtgatttag atgttgaaag tgactaattg ccatttcata
16551 tacatgcata gctatcattt ctaaacgtct gtaatcacag taaacagcat
16601 tcgaatcatt caatgcaaga tgaacacagg atgctgtagg cactatgtag
16651 gatgcctat gcctttagct gaaggaaaaa aacctagta ggatgttatt
16701 ttatttacat agtaacaag catttgaatt ttggcaaaat atccaattga
16751 caatgtttgt gtttttacag GGCAGTAGAG GAGAATTAGG ACCAGTGGGA     29
16801 TCCCCAGGCC TACCAGGTAA ACTGgtaagt agaaaagttt cgtttatttg
16851 ccttctacga aacacaatgc attttaaaa ataagcaaga ggagaaaaca
16901 atttacaatt gaattacctg tacttgattt ctcttgttat gtgaatatga
16951 gaacaatgta aagggaaat ttcaaattat gggtaggata ccctcagagg
```

FIG. 10A-17

```
                                                                              Exon #
17001 gtattttaat ctgcgtggtt tgtagcatcc attttaaac ctggtgaaat
17051 gtgaagtgct gcattggcc tctggttgtt cttggaatgg cagaaaacag
17101 agtgaatggt gcctttact tcctgtgcag tgcttgttta catagctaga
17151 ggagcagcag cgccattgca ggcagtgcgn nggtgnngng ggcttgactg
17201 aaaaagccta ctgttgccaa ggagtgcaag gggaactgag gacctaggg
17251 tggagtgaag gctgggagaa cattggcccc gccctcttct cctgagaata
17301 tgaaagagag gcaaacccaa gaagcagagt tcaaccaacc acagcacgtt
17351 tattttagac acaagtcaac acacccaagg ttgtttctgc cttccgtgct
17401 ttcagtgttg cagtgacagt aactccgggg acttttgtttt tgctttccag
17451 GGTTCTCTGG GTAGCCCTGG CCTCCCCTGG TTGCCTGGGC CCCCTGACT      30
17501 TCCTGGAATG AAAGGTGACA GGgtaagagc tccagcactc cagaaggttc
17551 tttatttgga agggtgattt ctaccatgtt gagaaacaaa gcttgctttt
17601 ggccctgtgg agaattttct agaatttatc ataaacagct atcaagaaag
17651 atattttaaa ttactcagag ttgagattaa gaagcaaaaa gtctattaat
17701 ataatttaac agaaggaaaa aaagctgaga aaagtaaaaa ctgtccgttg
17751 taatcacact ttctacttag ccctcaattt acatttctac tagtcaaatt
17801 ttatgaggat gtgactcaga gaatgcccca agttccagag cctcttggaa
17851 aattgtgacc taatgtggaa acttatgttt tggtcctgat tcttgttggg
17901 tggtgaggag tgggaacgtc ctctcccatc acattatccg tacttgtgct
17951 tatccaccca cccaataagg ttcacttgaa attatataaa cagttgaaaa
18001 tactgaaaaa gtattatatt ttatttatta cagGGTGTAG TCGGTGAACC       31
18051 GGTCCAAAG GGTGAACAGg tcagtcttat tatttaattg gtataaaatg
```

FIG. 10A-18

Exon #

```
18101 caatgtttga tatgcaccat ttcacaagca aggggaatg gctgtttat
18151 ggggttaat aaaaccatga aggctaacag ttttctcaa tgtgttcata
18201 gtgagtgaaa cctggtgttg agtttggtcc gcagcattgt ttactatttt
18251 aacaagctgg agctaaagat ggctctgctc caggactgca cactgtcttt
18301 cctttgaaga gcgtggctct gtctctggtt cacggaattg gtttattcat
18351 atccaatgag ccttccacag ccacattaga atgtcttagg tttttcttga
18401 tcaagacctc agcaaataaa ctgtttatat gaattagact cagtcctttc
18451 cctggttcc tttttctact gtagattccc tatttcaagg gccaattata
18501 aaattgttga atatggtcat ttatccttca ttctagctga aactcagcct
18551 caccttctgg ctttcctctc cgctattttc tgattgggac taaccactga
18601 cagctagatt ggaaagccgc tgagagcatt ttgtatttct gcatgattct
18651 gggaacactg tgggcactta tgaatgctta tcaatgttta ctggttaaaa
18701 ttgggcaatg ggactaagaa ttttaaaatg taaccttta tcttaattt
18751 tagGGTGCCT CTGGTGAAGA AGGTGAAGCA GGAGAAAGGG GGGAACTTgt
18801 aagattttt ttttctggtt aatgatgaag ctttaccaat tttgaactgt
18851 tagaagtata tatatatact tctaacacag ttcaaaattg gtatatatat
18901 atatgtggtt atttctgga cactgttatc ctcactgcct tctttaaagg
18951 ttatgatgtt tctcctatca gctaacaaaa gtctcccaag attgcagcca
19001 aNNNNaattc ttgacaccta gcatttgaga tctggatgaa accctggaaa
19051 gctctgattc aaccctntta nttaacagan naattagcca aaggctggga
19101 ggctacatag cttacagagg gtcacagagt taagtagaac tgagattaga
19151 atccaaaatt ggagtctaat attttttgc agtgccagag ttaatctgtt
```

| | Exon # |
|---|---|
| 19201 catggttttc cgtattttag tagcacaata acttttaaag tgttttcagg | |
| 19251 aaattatcaa atgtgaatac attgttctaa cataaatttc tttattgat | |
| 19301 ttagGGAGAT ATAGGATTAC CTGGCCCAAA GGGATCTgta agtaggtga | 33 |
| 19351 atagtaatgg tataaaaaaa ttaaaaacat taataaagct gtagaatata | |
| 19401 taatattctg ctttatgaaa tcattatgta acattcaatt cttttttttt | |
| 19451 tttgagatgg agtctcactc tgtcgcccag gcgtgaatgc agtggtgcaa | |
| 19501 tcttggctca ctgcaacctc tgcctcctgg gttcaagcaa ttctcctgcc | |
| 19551 ttagcctccc aagtagctgg gattacaggc atgcaccacc atgcccggct | |
| 19601 aatttttgta tttttagtag agatgggggtt tcaccatgtt ggtcagactg | |
| 19651 gtctcgaatt ccttacctca ggtgatctgg cccacctcag cctcccaaag | |
| 19701 tgctgggttt acaggNNNNa gatgggtaag ttgtgtagca ttatgtgtct | |
| 19751 tcacccttgca gtgaaggttt tgtaacctct gaaagaacac ctgttaggat | |
| 19801 gcagagtgca ggaaaccgca aatttcatat aagtgtttat atgagtatga | |
| 19851 agcaggcaca ttctttatgc ttagccctgg tttgatagtg tgcaattgtg | |

FIG. 10A-20

| | | | | | Exon # |
|---|---|---|---|---|---|
| 19901 | ttccagGCAG | GTAATCCTGG | GGAACCTGGC | TTGAGAGGGC | CTGAGGAAG 34 |
| 19951 | TCGGGGGCTT | CCTGGAGTGG | AAGGACCAAG | AGGACCACCT | GGACCCCGGG |
| 20001 | GTGTGCAGGG | AGAACAGGGT | GCCACCGGCC | TGCCTGGTGT | CCAGGCCCT |
| 20051 | CCGgtgagtg | gtgggcagct | tctgtgttt | ccctctggag | actccatccc |
| 20101 | acagcaggag | ggctgttcta | ggcatcagct | tctcaacaag | ttctcttgta |
| 20151 | aatccagcca | cctggctcct | tgcagagtct | gtcagtttac | aacttaacaa |
| 20201 | tgttctcttt | atggtttcat | gcataaactg | cctttttttc | ttttctgtcc |
| 20251 | cagGGTAGAG | CACCGACAGA | TCAGCACATT | AAGCAGGTTT | GCATGAGAGT 35 |
| 20301 | CATACAAGgt | aaataaatca | caatgtttg | acttttccaa | ccatcaactc |
| 20351 | ttgtttctta | agatttatt | cttgtagata | cacaagggta | aacaagagtg |
| 20401 | acttttgtg | tgccttaaag | ataggacatt | tagggtaata | ttaatgccaa |
| 20451 | ttctgtttt | ccaactattg | gcatccacaa | tagtatacag | cccgtagcct |
| 20501 | caatgtaaaa | tattacttt | ctggttatcc | tgccttttt | tttttttt |
| 20551 | ttgtttgtt | ttttttgtt | tttgccat | ggggctaat | ttataacaaa | gtgcacacac |
| 20601 | acacacacac | acacttttt | cctttggaac | acaagattct | tagttgtctc |
| 20651 | tccccgtcct | taagaccta | gccacttagt | gtgtacctag | cactgaccta |
| 20701 | ggctttctct | acattttgtg | agaagtaaat | gacagactcc | atgccataa |
| 20751 | gaagcataag | gacattatcg | ccattcatgt | acacatatgt | aaaaacaatc |
| 20801 | aataaccagc | attaccaaa | attatgacac | atttcatac | ttgttaaccc |
| 20851 | ttatcaaaat | ttatctgtag | ctatggcaat | tgttatttgt | ttcagaattg |
| 20901 | gtctagttat | aaaaacacac | agaaaatgaa | gatgtgcaaa | agcaccctat |

FIG. 10A-21

Exon #

```
20951 agctgaggag ttctgtaaca ctgaagccta cagctagtta cagtattctg
21001 gtgtagctaa ctttgtcatg aagagatact cttttgtatg ttcactaggc
21051 agtctagttt gtctaggaga cttgagaagt tttccagaac caaataggaa
21101 tgaaacattc acttctatat ttgaaaagca atataggcct cttcattgca
21151 gacattttgt cctgaaagtc tattttagtt ttaaacatat ctaaaaaatt
21201 attattccat gcaaactctt acttatataa gcaaatttaa aatactcaca
21251 tttaaacaat ttaaaaatgt tgggtagaaa tttgtttcca tttcatattc
21301 tcctttaccc tctaagttta aaaaatatta catgagaata tttcccttag
21351 aatgttttca tggggatatt ttgttgtagg ccatgccttt agtggtgat
21401 tctgaatcta tttaatggtt cctgaaaaag cccacacagt tattattttt
21451 taagactaac tctgaccatt cccagaaaac aagttattt taatgtttgt
21501 tgtctatttc aagcatggaa aaaacttctg agaaggaggg tttataagaa
21551 gctgtgactc ctggggatat ttcagtttat ataatatctt caaactaaga
21601 atgtgaggcg aggtctcaaa tggtgctgaa tattaattct ggacaatgtt
21651 cttggctttt aaaaactgtc tggacatctg cttcacatat gttaagaaac
21701 tcttttttctt cccatcctgg gttttcagat accagcagg gattcaggtg
21751 acatccttcc agaacatcat tcaccccaaa gcctgtagtt taagattttt
21801 gtgaatccca cccctgcta cctccctccc cgtgccctga ctctgtctca
21851 gaacaacagg accaaatata tccaggaga gctgcatcaa acagcaccag
21901 cgaagctntc tggcagaaag cccacagaga aattatccaa ctttattcat
21951 ttcttactac caattttgaa gatctggtga cacatttaga aaaaaggca
```

FIG. 10A-22

| | Exon # |
|---|---|
| 22001 tttggaatac ctctcttttc attagaataa cttttatgtt tctgcactt | |
| 22051 ctgggttgtt ttgtttattc tcttttagAA CATTTGCTG AGATGGCTGC | 36 |
| 22101 CAGTCTTAAG CGTCCAGACT CAGGTGCCAC TGGGCTTCCT GGAAGGCTG | |
| 22151 GCCCTCCTGG TCCCCCGGC CCTCCTGGAG AGAATGGTTT CCCAGGCCAG | |
| 22201 ATGGGAATTC GTGGCCTTCC GGGCATTAAG GGTCCCCCTG GTGCTCTTGG | |
| 22251 TTTGAGGGGA CCTAAAGgta agtcatcttg cccatgtgga accaaagaac | |
| 22301 acaacctttt tcagatgtat aatctgtatc aagctcgagg aatttatgtt | |
| 22351 ttaccaattt ctgaatatcc agtgagataa gatgtattat tctctttca | |
| 22401 atagtgacgg tgaagattca aaaactgtta tatatattc ccttgaccct | |
| 22451 gctctaccac aacagtagac caaatactag aaNNNNcatt ccagtatcta | |
| 22501 tgaatataat aatttgattt tccccccta gatctattaa tagatgaact | |
| 22551 tgattttgc cttgctacat actcactaca atctagttta tggcaatttc | |
| 22601 atgacctttt ggtttctgaa ttttagattt gctgaaagtt taaagatgcg | |
| 22651 gaagtttatt tttatagata tgtagaaaaa taacatttct ttaatgtaat | |
| 22701 gcagGTGACT TGGGAGAAAA GGGGGAGCGT GGCCCTCCAG GAAGAGGTCC | 37 |
| 22751 CAACGGTTTG CCAGGAGCTA TAGGTCTCCC AGtaagtgt gttgtatagc | |
| 22801 tgagagagg aggtagcgaa attggtagca agtacacagc ctgaattgaa | |
| 22851 taaaatttta aaataattgt tatttgatca cttaagcata ttaattattc | |
| 22901 agaatggcta gcatagattt ttcaagacca gctttagtaa agaattaaat | |
| 22951 gatctgtaaa tcaaatcaga aaataggtat caggacttga aatactaatt | |
| 23001 tccttaaata gatgcttcaa gaaaatagt gtcaaggtcc aggcacaatg | |
| 23051 cacttgttat aaaattctga ataaattgga tcctatctat ttctaaagca | |

FIG. 10A-23

| | Exon # |
|---|---|
| 23101 ggtgatagtt tcctgttttt ttttaatcta aaatgccaga gcagtaggaa | |
| 23151 gattagcctg tttttaatct cttgcacaag gagtaactga aatttattt | |
| 23201 ttaaagctcc ctttcaaac accagaNNN Ngaactattt acatttttt | |
| 23251 catatgaagt ctttaaaatc caggggtgtt tgatccttag ttcatctcca | |
| 23301 ttgggcctca tcacatttca gctctcaata ggcacctgtg gctggaggct | |
| 23351 accatggtgc acggtgcagc tctactgatg gaaatggggg ttagagacac | |
| 23401 tgaggtctct ttctgctttt aatttccatg aaaacccaag tccaaggaag | |
| 23451 ggatcttatt atcatcatca tcatcatcat caccagtcat caccagtcat | |
| 23501 catccatcgt ttccaaaagc gtttgttaaa cccctatct gagcgctgct | |
| 23551 gagccatgcc ctctgccagt ttgcatcaat gaggattctc ctgttcacat | |
| 23601 gtgcaatctt ctgtgtgttt cagGTGACCC AGCCCCTGCC AGCTATGGGA | 38 |
| 23651 AAAATGGCCG AGACGGTGAG CGAGGCCCCC CAGGGCTGGC AGGAATTCCT | |
| 23701 GGAGTGCCTG GACCCCCGGG ACCTCCTGGG CTTCCCGGTT TCTGTGAGCC | |
| 23751 AGCCTCCTGC ACCATGCAGG CTGGTCAGCG AGCATTTAAC AAAGGGCCTG | |
| 23801 ACCCTTgaaa ggcttactgc tgggctg tctgcatgaa ccacgcctgg | |
| 23851 tgaaggagcc tgggtgagaa acaccatcca aagctggggc aaagatgatt | |
| 23901 accttcagca tgattacaat gtattacctt cagtatgatt acagaagtcc | |
| 23951 tacttgacaa tcacatatag aagaacggtg ctattcagta agttctcttt | |
| 24001 cctttcccct ggagggaaga cagcagagtc atcagttaaa aaaaaaaaa | |
| 24051 aagaaaacca aacacctccc ttgaacaaat ttatactcct gttcccagga | |
| 24101 tcttgagctt tagtgtgcta tacctatgtg tcttatcgtg ggccactgtg | |
| 24151 ccaataaaca aaaacaactg tttggtttac ctc | |

FIG. 10B-1

```
tctgctcaac tctggtagtc tcagagttta agaataaaca acaagtaggg
ggcttgatgt tacatttat caggatttct atccatgagg tagagagagg
gaatgtgtat ttagtaatag gcatggcact ttgaaaaagt tacttcattt
tctgcttcct caacttctt atttggagaa taagggtaac ttcagtctta
ccttataatg ttgttgtgag aattaaatgg cattaagctt tgagcatttt
caacagacgg aggtgcataa tgaagcgtta gctatgaaga cgatgacaaa
taatgattgt tgggtgttag accctctgcc tttgatacct cattaattc
tcaaaaccat tgtttaaatg taagcatttt caatctgttt tacagttagg
gcatctagtt acagaaaagt gaagtaactc tctcaaggac acacagctag
taagcttcag aataaacagg gattgaaact taggttgatc gggcaccaag
gctcccacga gtttccacac ctctgcctcc cagtgggcac attttactg
gaacctcagc cctctgaaag cttccactgt attcctatag cagttctgaa
agctgccatt gtactcctat agcagatcta aaagcatcta ctgtgttcct
atagcaccct gcctgatct ttctggtgaa tttccccctg taaatcccctc cttgattt
attttttct tttcagcaaa ctttcccctg taaatccctc cttcagtata
accttgttag ctttgaggac acacccctag gcctgggctc agagcgctgc
ttctcccccac ccctttcctt tgcttcagtt taaagtgtca cgagatgcct
ctggttctct ccctttgct ttagccctca ccggggcag gagggaccaa
ggctgggcca gaacacatag tcctaggta acagtgaagg ggtcgtgagg
ggacagtgac tcccttccaa ccccttcttc ataggactg ttggcaaaca
aagaaaatca actgggaaaA TGAAGACCTG CTGgtaagac aataaccctg
gaaagagtgg tgggagatg gagctggggg tcctcagaac caagggtctg
```

FIG. 10B-2

```
tatttttgc agcagtggta agatgagagt aggtgagcct caaggtgaga
gacagaaaga gagacggatg agagagtaag acaagagggc aagcgtgaga
aaccgaagac agacacaaaa aaccgaagac agacagagga agggagagaa
agtgacggcc acagaaaaag agaggaagga aatcaaaggt gaaagaaacc
agagacaaag aaataggtac caaaacagtg agataggtag ataccgagaa
ggtgagatca ataaacaac aacgacagtN Ngtctggaaa catgagttcc
ttacatctct cagtagggtt tcaaagtaaa aatgaaggct gggtgcggtg
gcttatgctt gtaatcccag cactttggga ggccgaggcg ggcgaatcac
gaggtcagga gttcaagacc agactgacca ccatggtgaa accctgtctc
cactaaaaat agaaaaagta actgggtgtg gtggcacgtg cctgtaatcc
cagttactca ggaggctgag gcaggagagt cgtttgagcc caggaggtgg
aggttgcaaa gagccgagat cgcgccattg cactccagcc tgggtgacag
agcgagactc cgtctcaaaa aaaaaaaaaa aaaaaaagaa atgaaaaaaa
aactatactg tgatttgatc acctacatt aattaggttt actaggtttg
aaaatatgga agtattttcc atctgcgggg actcctgttt cagtcatttt
tcttctctct tcttcag
```

FIG. 10B-3

```
                                                           gtaagggcc
atagtttcta gactttcaaa gatcacttat tcccagaaat gatcaggcag
ggctgtggct gactgaagac tgagtgaggc attcatagtc cttcacaccc
tcactcttca atccagcttt gggcacagg gatacattag gttctggttt
tccatggtca atcgtgggta tggaaagtNN NNcctcttca aaacgaacat
tttccagcc agattattag agcaactttg tgccttgcat ccaccccttc
caggatgagt tgcaggtgga cagattataa tcgtagaggc atggaggtaa
agccaaacac tttacctcta agcaagctgg tataatattg aatttaaat
attattatt attgatacat cctgaatct ttttttgtg tcaattgct
attttctggt tctaaatttt attattatta ttattattt atttattttt
attattatta tactttaagt tagagtggat gaagtagaat gacatgctat
ctcttttgca g
```

FIG. 10B-4

```
                                                         g tgagtagcaa
tgtaccctat tgaaaatgca tgctttctat aaacctgatt ttttttta
tttggaaag ttgtggaaag aaataaaacc aatctcattt tagactttc
attttgtatt cccattctat ag
```

FIG. 10B-5

```
gtaat ctatcaaaaa tattttaatc taattatctg actcaaatgc
attaaaatg gatagctatc caatgttaga gttcttat gaNcaatgtt
tcttgggatt ataattgtat ttaaagatga agaaatttat ttacctgcct
atcttcagta ccttaatact gcatttcgat gttttcNNNN aagcacggac
catgaatgta caggaatgat tgNacttctg taaggtctt tatgaacagt
catgaaagaa caaacggtac ataggttttt acactgtagc ttttctatag
gtctggcatc taaatggcc tcaaaaggga atgtggtaaa tacatatggg
tacaggaaac aagatgcatg tttactattt aaaattttta ctcag
```

FIG. 10B-6

```
                                                                          gtaagtat
aaaccacac actatggcag attaaagcaa aactagattg gtaaaatga
acatctcaag catctttgat aatcagctga gtgcagcatg tcccagatgg
aatttggaat cagaggaagt taagtagata gcttctggtc ttgaggagct
taagttgga aagtgttaca tgcccaccta gtgcaccag agtctttctg
aggcaactta gaaagaNNNN gtccttctga ttgccactt tttttctgt
ctctaatctc ccatctaaaa tcttacagca tatattccct gtagagttca
atagccctgg gtttcaaccc agactctgac acttattggt ttgtgacttg
gaccgtttct gttctctctg aacctcatct tagtaggatc tacatcttga
gattgtcatc agaacagaaa tagaaagtca gtgctggtgg tctgtttcca
ggctaggggt atgctgaaat aattcaaagc taaagacatc tatacctaat
aatcagagaa acttgtgaaa gcttccaacc catttccatt agaaaacttg
tattcaagga aagcaagga gtcctggtcc agtgtctca accagttcaa
gttgatttcc aattatttaa caattagacg caactcatct ctctcttgaa
tgaccagctt cagtcgtcca aaaaaccta cctgactgtc tactacctt
ctccag
```

FIG. 10B-7

```
                                                        gtgagtcccc
tgactacctg caaggccac ttctacccag ctcaaccctc tccacctcac
cactttccca tcttgccacc tcccagcac ccctcctccc cactctcttt
cgctaagaga gcctgtgctt tgctgtactg actagagaaa tattagggaa
gtacacttca tactttcgac ctgcgggta gaaccacct gcagcctggc
aggtagaaac cacctgcggg tgtgtggttg tcccttTggt agcttatgga
ccctcctccc ttactctcaa acatgtccaa gaacacttga gttctactgg
ccagcactgg cacaggccac ccggaaggt ctccgaggac agccagaagc
tgcactgggg tggatgggat ggaggcagag ctgcgtgctc agtcctcgcc
tgtgcggcgg cagggaaggg gttaagggcg actgttgtca ttctatccgt
cctccccttc ccctagctc tcctccaatc ccagaccct ctccggggcc
attcataaac aggggNaac gcgcccctcc cggcctgga cgctttggca
accgctactc ccggggtgc tttttctgca gggacgaagt gccacctatg
ctagtgcgg gtctggaagc ctagagggga accaggctgc agagccgggc
caagggatta gcggcgggcg gcgggc
```

FIG. 10B-8

```
                                                        gt
aagttgcgat cgagtttgag gggtgctttt ctcactttct ccccatcttt
tcttctcag
```

FIG. 10B-9

```
                                              gtaagttgg gggcagggag
tgtttgcatt tttcaagcgc acacgaggac agtcggggc gcacggtcg
agggagctgt gagaaaggcg cggaNatccc caggctctc agaccgcgc
ttcctccagc ctcgagcacc tgccgcgagt cctatcgaag tccagagccg
tagatgaccc cttggtctag gaaggggggc tcctcccaa tctggtcct
ccctactgca NNNNaatgca ctctgcagag gtgagaacca gtgaagcctc
cccaacctt gggggcgtca atcctgctct agcccacag tttagctcat
tagaatatgg cggagaccaa agctgcgctt gcttggaggt ctgagacatt
tttgcgttgg gttgcaaaac ccggcctcct ctggaaggta actttaccc
cacggaggcg ggggcttcag ggcaccgcgc tcagttgctc cctgttgccc
gatgtgctcc actaacctat gtctgctatt tttgccag
```

FIG. 10B-10

```
           gtaagtt tctatctcca ggccacctct gttcccagt
cctgccctt cctattcttt tcccagggct cctgtgggt ttttttttt
tcagagagga ccaggtctc cccttcctgc cacccactt aaaggcagga
tcagacatgg gcgagagttg gggtaggat cctaggaacc cgggatttt
tggagggaga ggtgtctctg ttgtccttgt tggtcatgaa cctccacgtt
tgaccttac accatcccca tctgtgaagt gagctctcct ggattgtcc
cagtggggtc ctcagcctat cccgctcata gactgctctc tcttttctc
ctacccctcc ag
```

FIG. 10B-11 aagttgattg gagcatatgg cgctccactt ccttcctta gacgtgtttt gt
gcagccct gtttctgaag ggtctcaact ttgcacctt ttctctcctg
ccccgcacc ctctgcccc tgctcag

FIG. 10B-12 gtgagtaggc
gagtgctggg agggcgccca gcctggggtg tgtggtgggt acgagtaagt
gtgtgttttg tggggggggg agggagagag agaagagag agagagaacg
cgctgtgct ctaaacttgg cctcctgcca gcgcctgatt gatccgtgga
actggcagct tttgcaaaNN NNccaaagca gagacaaaaa acactgaatt
attgaccct gtgataaaca atgcagttag caggaagtta ggagtatgat
acaacttatc aagagaaat aatcacaaca ggcagatctt ctgttaatct
tttgagtaag actagtaa ggtatttctt tataaatatt tgcatcatac
ttatgtaacc atcctgtaga caattaataa ataaaatgaa agttttctac
ttagtggttt gcctaaggat gttatgatag ttctaacatc attgtcttgc
tctattag

FIG. 10B-13

```
           gtaagtta gccatctggc attaattgct agtacgaaaa
tgctgaagta taattttatt gcagtgtttg caagccaact aacattaagt
tatgaagtat ctaaaatgca ctcgttcaac taaaattgtg tttaaaaaca
ccatgatgtg aatactatg cagccataaa aaggaacaag atcatgtcct
ttgcagggac gtggatggag ctggaagcca ttaNNNNcta tgtaaNNNNt
gcaccNNctg cacatgtacc cctgaactta aaataaaagt tggaaattta
aaaaaaaaa acaccataat ggggtgtttt aatgctNtca atatttatgc
agtttcaca tttacatatt catgatatga aggtcagta caatgaaact
attttatttt ttag
```

FIG. 10B-14

```
gtaagtaaat gtaaagctac agaattgaaa atttcctatc tttaggtaaa
attctgccat tgtgaaatct tttatttat ttattattt attattat
ttattattat actttgggtt ttaggtaca tgtgcagttt tctgcataat
atacatgaga Nataagttga tgacatctgg tatggtaagc atttctacta
tgagtggaaa aattttagag aagtttgaat gtacagtaga aaatatatat
Nctatttgca ggtggtattt cccagcagac aattccctct ttacctgcca
tgataganNN Nagcagagcc gtgtttgctt ttctttattc agtgctttct
ttagaatgag catcattttt agtaatagag tttatggttt atttagctg
agttatgtct acattcatat ttatactaag tataaacctc aagctataac
catttttatt gtactctttt ag
```

FIG. 10B-15

```
gtatcacttc atcatttatt tttatgcagt ctataaaaat gtcctatttc
tcaatcccc acccttattct cctactaacg gtctactcag tggtgttac
agtgttctac ctgcaagNtc ttaggtggct actaaggata acacccttat
tctgctaNac NNNatattta ttaatttagg aaatttctgc tgtatcttaa
gtaattaaag tttggtcaaa tgagttattg tgtcattgga aaccaaagct
aatacagaaa tgtaaatcta atatttatca tatttgatat aatgtatgat
agattgtaaa aatattcata aatgaccatt tgctttgatt tgttgacttc
ag
                                                    gtaa
```

FIG. 10B-16

```
      gtga gtaccacagt gcactttgat agacgtttgc tgatttaata
gaagatgtta tttgggaaag caaattaccc taactgtaca tttccacttg
caaaccaaaa catggcagat gaatttcatt ccagtttata atattgatgt
gaaccaggaa taataataat ttttgcagag tgattttaat tttttcctaa
attttcagc taaacttttc ttcccaactt ccagattgtc aagtaagaga
gtgtcgtcct cattttacag actctcagcc aggactggag tctagtggct
tttgtattag gctccctgca tgaNataaaa gtgaatagcc taaaattatt
accatgtgta tttatgttag gNtcattaaa ttataattNN NNaatggcac
tagcagtata ggttgctcta ggtcctctgt aaatcaacca aaaaaataag
tagtgtttcc aatttgctNt cagagtagat aaaatgtttg tctgatagag
aagaattggc tttgcNNttt ccctagctt ctctctgact tgttttatta
cctcggtgag actggaatgc ctttattact ctcatttgt agaactaatt
ggataacggg ccaccatcg atttggtgg caggtctatg catggctgag
ctcggtgggg NNNNccagta ataccattct cttatgcctc actggtNtta
tgtactgtgt tttgacacat gtataaccac tgtgtcgcaa ttttcaaata
acttag
```

FIG. 10B-17

```
              gtaagttatt tgcagcttga atttctgttt gtgtctgaga
gtcaggggttg aaaaaatct aagaatccaa aatggaagtt cctattaatt
gagtcattgt cccaatttN caaaacggct atcaattttt ccatgcactc
aagggcatgg ttctgtttag ggcaagaagt agaagaatca caataattta
aaaggtgggtt tttataggt atatcttact cattactttt gaagtctttt
gacagttgtg atgtctcaaa tgctcaaaac ttagatatat aaatgaagca
ttttcaaatg aactagtttt tacaaaggtt ttcatagtaa gaaaaattta
aagaatatga gtttaaatgg aaggtaattc atatttttat ttgtaattca
gagttcccca catttctat tttgcctctt atttcgtttc ccttcaatgt
cttcccaaaa taatctactg caattcatgg ctctccaaag agaacatgcc
catgagtcag gattNagaa tattagcata ttatctggtt tcttatattt
tattaaacaa atatatttta tactttgcc tgatgagctt tctagtatta
gtatgtttga attcattatt taattgtatt ctgaacctta atatttgtt
tactttag
```

FIG. 10B-18

```
                                                  gtaagatgc
tttcctttga acaaatata gttttaattc aaagaccata tagcctgcag
atgagttttc tttaaagat ttccctggaa tattctatgt gtctgtgttt
tcctttcact caaatggcag agcagtctgt aacactagtg gactagtggc
ttgcatctac tcagactaat aatttttcat tatagatgta tctttgttct
tctatgatct ttttactta tgactaagac atgcttttNN NNctggcttt
aaatgtgaaa taataataat aaaaggaaa ggggtgttta gaattattca
atgaatatta ttgcaatgga gttctgtaac tggaatccct taaaaagata
ctgtcacaaa gcgggagtcc tagtttatgc actctgtctg tctttctttc
tctttgttcc ctctctccct ggcag
```

FIG. 10B-19

```
                                     gtaagaga ataacttcca
gtatttaag agtattatcc acagataaaa tggagccttt actttaagca
ttagccttcc tggtgcagag acccacttg gatgatcagg cgagtagtgc
ttattcagtc ctagcaattc cagttgccct tgacatgtat tcctgtattc
ctaccaagac atggaggttt aatcatagga tggctttcta gttcaggaa
gaataccaa taaatacat tggattgaga gactttNNNN cctcctcca
ccatcaggaa ggaggtggga atggaggagg ccgaaggtt ttcagagcag
ccttcagagg gcagggata gccagctgag cttggtcaag gctgtcactt
ctgaaaggtt aagttactgg aactagagaa gacttaatgc tcctaacccg
tgtgaggaag ttggagaaat agggaatagg gatctaggaa atagcaggca
agtatcaatg aatcacattg ctgaactagg taatgaagtg tattattcta
gagcagtgtt tttctattaa gtaacactga tattaattat atatggcagt
catggtgctg ttaaggtcat ttaaggcatt aattcttt gtgacataac
tcattctta gtaatacatt ggcactgatt tagggaagca ggatcacttt
atgagccttc tgatcacttt ctgtaccaaa ctcaagacaa ttacttattt
tgcatttgtt ag
```

FIG. 10B-20

```
                    gtaa ggaaatggg tatttagtgg ataaattgtg
attaggagtt attggtcact ttcattataa gaaattagga attataggaa
ataatgaacc tcgatatttt accattcttt ttaaataat gattgataag
ttctaagcag atgcatcaat atttgactaa atatcatatt ctgaagttgt
tcatttacaa taaaacactt acaaataagg caccagacat tttcattttt
ttctgtcact accttttctt ttcttttctt caa atcaatcaca ctcagctttt
ttccttgatg ctatgatagc caacattatt cagcagttgt tccacttcac
cagcaaNNNN tttcttgata tctttgtctc tcttcctctt tcccccactt
tagaaaaact ttgaaagaat aacatctaaa tgttactggt atttttatagt
taaatggtgg tatttggtg acatttata tgtaggcttc tctgtatttt
ctgaatgttc tacaattaat ttggactacc catataaata atttaagaaa
gtagaataat tcaggagtca ccaagttaac ttaaaacata atgagttaga
ccaagcctat ttctatgttc gttgctaga ataacatttg gtgtgctttt
cttttttctt ttttcttt ag
```

FIG. 10B-21

```
                gtaa agtatttttt aaaaatatt
taactaggat atgtaaatat tctttttt catgactgtt ggaatattt
ctattagca gttggatgaa tagcattaca tgaacttggt gtcctctatt
ttccaccacg ccagcactgg gggataacta cttcttcaaa ataggagagg
gtcttcatta tatattctag cactttttta acagaaaaat tctacctata
atttacatac attcgtttac cagatttcag ggccaggcaa ttgaaaagca
aatactaagc acaaaaggat gatactcatc ttttatgttc tatcgtatta
tcacatgata taatgagaaa attttgtgtg ttctaaatat gcagtaggta
tatcatttat tggattaatg tagcttattc cagtatgcaa tcattataat
taattaaaac attcttaatt gctcatatca tgtcttttaa taaaaattg
gtccctcgtg ctttagcaga tttctgccaa taatattcaN NNNacatgcc
atgaaggaag tgggaatgat agtgtaagtt ctacatacaa gttaaaaggt
aagtcaaaca tattatcaca atttctctta tgctggtatt tacttttttt
gtcataagtg attttgtcaa ctccagtttt gtgtaagact tcagaatttt
ataaaaaggt ttaccatcag aagaattctc cttggactt ctaaactaga
aatgtttgtc tatatatata tagttactat ttcttggtat taccttggt
tatgataata cccattgtct agatcagctt ttgtgatgag attttaaaa
atctttgctt caactaaaat aattcacttc tctttttcac atttccag
```

FIG. 10B-22

```
gtaagatg gtgatgacaa taatatata ccaaatgtg ttaaatattt
aaaattttgg ccatttaaac ataactttt atcttcaaca acttttttt
ttttttttt gagatggagt ttcactcttg ttgcccaggc tggagtgcaa
tggcgcgatc ttggctcact gcaacctctg cctcctgggt tcaagcgatt
ctcctgtctc agcatcacga gtagagcagc tgggattaca ggcgcctgcc
accacgccNN NNttacctga ggtgcctgag Naattactcc tcaggatca
ctgtgtgtat Nacaggcaca aaacctcctt ttcatctggc tattaaattt
ctttagaaag atggatgctt cctttaacat acatgactga tctcagtttt
tttccattgt cttgtttttt tgcag
```

FIG. 10B-23

```
                                           g taagtgatttt tccttccaca
aacccaatg atagattttt ttttttttgc tatgtatgca tgtgtgtgca
gtattgttta tgtgtgaata attaaagtgg aaaagtggac aatttatata
tatgtttta aattaaaatt taattaagac aggtatcttt ctcggtaca
tagaaatgtt cttctgactt gacatgattt tttttcttcat agattaagcc
aattattaa gtatttatgt ttgcgtgttt tccttttctt tggttattag
gacgccttga gtctcagtaa ctatctcgtt tctNNNNaca gaggcatagt
gcatttaagg ggaaacaaa agaccatcaa gtgtcagtta tctctatggc
aatatccatt tttaagacaa ttccgttttt ataaaaagac ttccttcatct
aggcttcctt gatagagcaa agccattgtg gtggaagact aatagtttgg
tgacgtggat gatactttct aattttaaa agttgattaa taagtaactt
ttgcttgtat taacaaaatt ttattttcat acag
```

FIG. 10B-24

```
                                 gt gagtttaaat
tcagtcactc caagcctcct gctttcagt gtcatctgct gattatgctg
atctctttga caagtctaag tattatgtta actgaacatg tcttgtctat
tctttctctt cctccctgca g
```

FIG. 10B-25

```
                                          gtatg tcctgagctg tagtcatcaa
gcacattttt cagtgatcat tgacttgcaa tgaaactta gaaataatg
aaggaaaaa gaatgtgact gtgtgtaaga gacagtatgt ttctttgtgt
gtgtttag
```

FIG. 10B-26

```
           gtaggctg tgtaatttac tccaagagtg agtggggctg
tctctgccct ggccaactga gtgtggcatt tccattacta aatcaccaaa
agattattt agctagcttt ggctttttcc cttcctttaa tttttgaatc
aagtgcaaa tatgaaatac ttactagaat agtataatta tttgcttggt
ttcaggaact cagtaaaatt gccctgttga tgaaagtaag ttgagagaga
ctgtgcattt tggttgaatt atgtcctatt tcccaccta ctccccacc
ctaaattaag tcactttata aagtgcatg taagtcagc tgttgggaca
atccttttac ttaaacgtc tgtgctcctc cgttcttaa aagaaataca
gcagctcata caggttcaat catgtgataa aagcttttt tgcag
```

FIG. 10B-27

```
taagtatttg attctttaca tgttaattgg tttatataca tgttttaaag g
atatacattt tggggagaga catgctacct aatctgataa gttctgggga
agatatgatg tttactttt acatttttac aattacatt tgtattttat
atttatact tttctctga atagctattt gtaataac tgtaaataat
aggctttaat tttatgcttt ggattccttt tctctcttta gttactcag
tctttttta catttttt aactaaccct aagctgtagg ccagtgtgat
atatttcatt ccacttaaa ccggttctaa agctcttgtt agtaggatta
agcaacaaga gtgctgagag tatactcagg tgaccctta gattatgtac
tatttttNNN Ncctagtaga gctcctcttg acctgaaagt ggtactggat
tctaatttgg gaagtttgtc cttgaaaagt aactttagtt taaagacaag
atttgcttta agggtactta gctttaacaa gccagatata gtaaagtcat
gccctctaaa ctgtgggtaa ttctataaat gactgtgcag agtttgggaa
ctaggaagca tcttccttac attaaagctt tgaggttacc atgattccct
cagcctccct gcagtgtgca gtgggcttgg catctcatgg attctcagag
gaggtgatta aactcggatt gtgtatgtat tcttttag
```

FIG. 10B-28

```
                                                        gtaaat attttaaaat
ttaagttaat atctttctta atttctttat tatttactaa cgtatttgta
attttaata ttttcagcat gtgttttatt ttatatttgg ccctagggag
aaataaaaag gtaaatgtgt taaggcttca aatactaatc tttttcctag
ctacagaaag catactttga caaaatgctg ctaattagat ttccttaatg
NNNNtgacat ttgaccttta atatatttct cagactcaca gacaatatct
tgaatctaaa ggatttcgat gtatctaaca agaaagagat tctgcacatt
cccagaNct cagtgtgaaa gcaggaatt aatgctattc aatgtaaga
gatcccagtc tgggtaaggc agattgatga ttatgcttac ttcagcatga
gttactttga atgttgcatt ttaccctag
```

FIG. 10B-29

```
                                                        gtaaga caccatttta
cctctcctga agttctaacc tgttgtaatc agtaggtgtt aactttttt
ctaccttcct tcctgataac ag
```

FIG. 10B-30

```
                   gtga gtattccttg ctgttctttc
ctaagcacc ttctcaggac tttgctggat gttcttccat tcattcatcc
atccatccat gaatgctgtc tgatgtttga gcccatgcta gtccagaca
cacaaggaga tgaaatgcta tttagatgca cagcatgcct tttcagaaaa
tggaaacaaa aataaagtgc ttcaaaaaNN NNcttcagaa acttcagaaa
tttttaccat ctgtgtcttt ttgaagttgc aatagtaatt taaagcaaa
catatctatt atgtgtttct tttttcactc tgttgaggtt taagatcatt
tgccagatgt tgctttgaaa tgttctgtag acctgagaat ttattctgtg
ttctaggcac tgtgcagaat tccaaattaa tatttaacaa tacctaaga
acacataatc taagtgaggg cttaaaacat ggacacaaat aaccataata
aagttagga tgtgatttag atgttgaaag tgactaattg ccatttcata
tacatgcata gctatcattt ctaacgtct gtaatcacag taaacagcat
tcgaatcatt caatgcaaga tgaacacagg atgctgtagg cactatgtag
gatggcctat gcctttagct gaaggaaaaa aacctaggta ggatgttatt
ttatttacat agtaactaag catttgaatt ttgcaaaat atccaattga
caatgtttgt gttttacag
```

FIG. 10B-31

```
                                       gtaagt agaaagttt cgtttatttg
ccttctacga aacacaatgc attttaaaa ataagcaaga ggagaaaaca
attacaatt gaattacctg tactttgattt ctctgttat gtaatatga
gaacaatgta aagggaaat ttcaaattat gggtaggata ccctcagagg
gtattttaat ctgcgtggtt tgtagcatcc attttaaac ctggtgaaat
gtgaagtgct gcatttggcc tctggttgtt cttggaatgg cagaaaacag
agtgaatggt gcctttact tcctgtgcag tgcttgttta catagctaga
ggagcagcag cgccattgca ggcagtgcgN NggtgNNgNg ggcttgactg
aaaagccta ctgttgccaa ggagtgcaag gggactgag gacctaggg
tggagtgaag gctgggagaa cattgccccc gccctcttct cctgagaata
tgaaagagag gcaaacccaa gaagcagagt tcaaccaacc acagcacgtt
tatttagac acaagtcaac acacccaagg ttgtttctgc cttccgtgct
ttcagtgttg cagtgacagt aactccgggg actttgtttt tgctttccag
```

FIG. 10B-32

```
                      gtaagagc tccagcactc cagaaggttc
tttatttgga agggtgattt ctaccatgtt gagaaacaaa gcttgctttt
ggccctgtgg agaattttct agaatttatc ataaacagct atcaagaaag
atattaaa ttactcagag ttgagattaa gaagcaaaaa gtctattaat
ataatttaac agaaggaaaa aaagctgaga aagtaaaaa ctgtccgttg
taatcacact ttctacttag ccctcaattt acatttctac tagtcaaatt
ttatgaggat gtgactcaga gaatgcccca agttccagag cctcttgaa
aattgtgacc taatgtggaa acttatgttt tggtcctgat tcttgtgg
tggtgaggag tggaacgtc ctctcccatc acattatccg tacttgtgct
tatccaccca cccaataagg ttcacttgaa attatataaa cagttgaaaa
tactgaaaaa gtattatatt ttatttatta cag
```

FIG. 10B-33

```
                                g tcagtcttat tatttaattg gtataaatg
caatgtttga tatgcaccat ttcacaagca aggggaatg gctgtttat
ggggttaat aaaaccatga agctaacag ttttctcaa tgtgttcata
gtgagtgaaa cctggtgttg agtttggtcc gcagcattgt ttactatttt
aacaagctgg agctaaagat ggctctgctc caggactgca cactgtcttt
cctttgaaga gcgtggctct gtctctggtt cacggaattg gtttattcat
atccaatgag cctttccacag ccacattaga atgtcttagg tttttcttga
tcaagacctc agcaaataaa ctgtttatat gaattagact cagtcctttc
cctgggtcc tttctctact gtagattccc tatttcaagg gccaattata
aaattgttga atatggtcat ttatccttca ttctagctga aactcagcct
caccttctgg cttcctctc cgctatttc tgattgggac taaccactga
cagctagatt ggaaagccgc tgagagcatt ttgtatttct gcatgattct
gggaacactg tgggcactta tgaatgctta tcaatgttta ctggttaaaa
ttgggcaatg ggactaagaa ttttaaaatg taacctttta tcttaatttt
tag
```

FIG. 10B-34

```
aagattttt ttttctggtt aatgatgaag cttaccaat tttgactgt gt
tagaagtata tatatatact tctaacacag ttcaaattg gtatatat
atatgtggtt attttctgga cactgttatc ctcactgcct tctttaaagg
ttatgatgtt tctcctatca gctaacaaaa gtctcccaag attgcagcca
aNNNaattc ttgacaccta gcattgaga tctggatgaa accctgaaa
gctctgattc aaccctNtta NttaacagaN Naattagcca aaggctggga
ggctacatag cttacagagg gtcacagagt taagtagaac tgagattaga
atccaaaatt ggagtctaat atttttttgc agtgccagag ttaatctgtt
catggttttc cgtattttag tagcacaata actttaaag tgttttcagg
aaattatcaa atgtgaatac attgttctaa cataaattc ttttattgat
ttag
```

FIG. 10B-35

```
                                                 gta agtatggtga
atagtaatgg tataaaaaaa ttaaaaacat taataaagct gtagaatata
taatattctg ctttatgaaa tcattatgta acattcaatt ctttttttt
tttgagatgg agtctcactc tgtcgcccag gcgtgaatgc agtggtgcaa
tcttggctca ctgcaacctc tgcctcctgg gttcaagcaa ttctcctgcc
ttagcctccc aagtagctgg gattacaggc atgcaccacc atgcccggct
aattttgta ttttagtag agatggggtt tcaccatgtt ggtcagactg
gtctcgaatt cctttacctca ggtgatctgg cccacctcag cctcccaaag
tgctggttt acaggNNNNa gatgggtaag ttgtgtagca ttatgtgtct
tcaccttgca gtgaaggttt tgtaacctct gaaagaacac ctgttaggat
gcagagtgca ggaaaccgca aatttcatat aagtgtttat atgagtatga
agcaggcaca ttctttatgc ttagccctgg tttgatagtg tgcaattgtg
ttccag
```

FIG. 10B-36

```
        gtgagtg gtgggcagct tctgtggttt ccctctggag actccatccc
acagcaggag ggctgttcta ggcatcagct tctcaacaag ttctctttgta
aatccagcca cctgctcct tgcagagtct gtcagtttac aacttaacaa
tgttctcttt atggtttcat gcataaactg cctttttttc ttttctgtcc
cag
```

FIG. 10B-37

```
gt aaataaatca caatggtttg acttttcca ccatcaactc
ttgttcctta agattatt cttgtagata cacagggta aacagagtg
acttttgtg tgcttaaag ataggacatt tagggtaata ttaatgccaa
ttctgttttt ccaactattg gcatccacaa tagtatacag ccgtagcct
caatgtaaaa tattacttt ctggttatcc tgcctttt ttttttt
ttgttttgtt ttttgccat ggggctaat ttataacaaa gtgcacacac
acacacacac acactttt cctttggaac acaagattct tagttgtctc
tccccgtcct taagaccca gccacttagt gtgtacctag cactgaccta
ggcttctct acattttgtg agaagtaaat gacagactcc atgccataa
gaagcataag gacattatcg ccattcatgt acacatgt aaaaacaatc
aataaccagc atttaccaaa attatgacac attttcatac ttgttaaccc
ttatcaaaat ttatctgtag ctatgggcaat tgttatttgt ttcagaattg
gtctagttat aaaaacacac agaaaatgaa gatgtgcaaa agcaccctat
agctgaggag ttctgtaaca ctgaagccta cagctagtta cagtattctg
gtgtagctaa cttttgtcatg aagagatact cttttgtatg ttcactaggc
agtctagttt gtctaggaga cttgagaagt tttccagaac caaataggaa
tgaaacattc acttctatat ttgaaaagca atataggcct cttcattgca
gacattttgt cctgaaagtc tattttagtt ttaaacatat ctaaaaaatt
attattccat gcaaactctt acttatataa gcaaattaa aatactcaca
tttaaacaat ttaaaaatgt tgggtagaaa tttgtttcca tttcatattc
tcctttaccc tctaagttta aaaaatatta catgagaata tttcccttag
aatgttttca tggggatatt ttgtttgtagg ccatgccttt agtgggtgat
```

FIG. 10B-38

```
tctgaatcta tttaatggtt cctgaaaaag cccacacagt tattaatttt
taagactaac tctgaccatt cccaagaaac aagttatttt taatgtttgt
tgtctatttc aagcatggaa aaaacttctg agaaggaggg tttataagaa
gctgtgactc ctgggatat ttcagtttat ataatatctt caaactaaga
atgtgaggcg aggtctcaaa tggtgctgaa tattaattct ggacaatgtt
cttggctttt aaaactgtc tggacatctg cttcacatat gttaagaaac
tcttttctt cccatcctgg gttttcagat accagcagg gattcaggtg
acatccttcc agaacatcat tcaccccaaa gcctgtagtt taagattttt
gtaatccca cccccgcta cctccctccc cgtgccctga ctctgtctca
gaacaacagg accaaatata tccagggaga gctgcatcaa acagcaccag
cgaagctNtc tggcagaaag cccacagaga aattatccaa ctttattcat
ttcttactac caatttgaa gatctggtga cacatttaga aaaaaggca
tttggaatac ctctctttc attagaataa cttttatgtt tctgacactt
ctgggttgtt ttgtttattc tcttttag
```

FIG. 10B-39

```
          gta agtcatcttg cccatgtgga accaagaac
acaacctttt tcagatgtat aatctgtatc aagctcgagg aatttatgtt
ttaccaattt ctgaatatcc agtgagataa gatgtattat tctctttca
atagtgacgg tgaagattca aaaactgtta tataatattc ccttgaccct
gctctaccac aacagtagac caaatactag aaNNNNcatt ccagtatcta
tgaatataat aatttgattt tcccccctta gatctattaa tagatgaact
tgattttttgc cttgctacat actcactaca atctagttta tggcaatttc
atgacctttt ggtttctgaa ttttagattt gctgaaagtt taaagatgcg
gaagtttatt tttatagata tgtagaaaaa taacatttct ttaatgtaat
gcag
```

FIG. 10B-40

```
                                                          gtaagtgt gttgtatagc
tgagaggagg aggtagcgaa attggtagca agtacacagc ctgaattgaa
taaatttta aaataattgt tatttgatca cttaagcata ttaattattc
agaatggcta gcatagattt ttcaagacca gctttagtaa agaattaaat
gatctgtaaa tcaaatcaga aaataggtat caggacttga aatactaatt
tccttaaata gatgcttcaa gaaaaatagt gtcaaggtcc aggcacaatg
cacttgttat aaaattctga ataaattgga tcctatctat ttctaaagca
ggtgatagtt tcctgttttt tttaatcta aatgccaga gcagtaggaa
gattagcctg tttttaatct cttgcacaag gagtaactga aattttattt
ttaaagctcc cctttcaaac acccagaNNN Ngaactattt aacattttt
catatgaagt cttaaaatc caggggtgtt tgatccttag ttcatctcca
ttgggcctca tcacatttca gctctcaata ggcacctgtg gctggaggct
accatggtgc acggtgcagc tctactgatg gaaatggggg ttagagacac
tgaggtctct ttctgctttt aatttccatg aaaaccaag tccaaggaag
ggatcttatt atcatcatca tcatcatcat caccatcat caccagtcat
catccatcgt ttccaaaagc gtttgttaaa cccttatct gagcgctgct
gagccatgcc cctgccagt ttgcatcaat gaggattctc ctgttcacat
gtgcaatctt ctgtgtttt cag
```

FIG. 10B-41

```
      tgaaa ggcttactgc tgcatggctg tctgcatgaa ccacgcctgg
tgaggagcc tgggtgagaa acaccatcca aagctggggc aaagatgatt
accttcagca tgattacaat gtattacctt cagtatgatt acagaagtcc
tacttgacaa tcacatatag aagaacggtg ctattcagta agttctcttt
cctttccctt ggagggaaga cagcagagtc atcagttaaa aaaaaaaaaa
aagaaaacca aacacctccc ttgaacaaat ttatactcct gttcccagga
tctttgagctt tagtgtgcta tacctatgtg tcttatcgtg ggccactgtg
ccaataaaca aaaacaactg tttggtttac ctc
```

FIG. 11A-1

Exon #

```
  1 atatatatat atatatggac tattagtatc ccatttac agatgagaa
 51 aatgagactt catagagttn gggtgcctg tggtcatatc tataattgtg
101 aaaagtcag attccaaagc atttaccaa tattgcctaa gtgagtggga
151 gggaagggaa ggctctctgg agtcgggcta tgctggacag cggggttcgg
201 aaactctggt gaataaagtg gtagttgttt ctatgaacat ggagtgagaa
251 ggcccaatcc taaacacacc agtgcttaag gcagctgcag agaattaaag
301 gcaatagaaa aaggggagct ggatgcagg agcttggatg gggaagactt
351 caagggcagg tgaagatgcc aacagcttcc tgcctggagg accgaagaag
401 ggttgggctt cactgcagac ctccaggaga cagatttgct tcttggaca
451 gagtagggag gtgaaagcga ggtgaggaag ttcggggtgg gggaggtgca
501 cacagttcca ctaaagagtt ggaagaggcc gatgagtat tcatgagacg
551 gctgatccag gaaggactgt ggcatattaa tatgaaaaag gcctgtttgt
601 ttgtgcttgg agaggaagga gccagaggag aggggagcaa ggtgggcggg
651 agctggggag agcctgcagc aagatctgca gagcccgagg tgctctcggc
701 atgggccctg gagggacgt agggtaagtg atggggcaca ggcngtgcgt
751 caggggaag gtgctggggc ctgaaggtcc cgagggaac ntcagacggc
801 cttatgcctt ctcacaaaga aactgacca tcatttccga cccgcacccc
851 ggtcgcccct cgaggacaga gggtgggcgc aggagctgg accgagcggg
901 gcggagctgg atgcctggcg ccggcatccc tcccggcaac cccccggtc
```

FIG. 11A-2

| | | Exon # |
|---|---|---|

```
 951 ctctcaggtg acagtcacgc ccggcccccg cccgcccccc cgcatattca
1001 aggagcccca gccaccctg cccgcaaca gccagcgctg gaggagcgcc
1051 gggagactct gccgtcggtg cgtgcgcgga cacgcaccg tcccccttgg
1101 tctcgccgcc agccATGGCC GCCGTACGG CCTCCCCCG CAGCCTCTT
1151 GTTCTCCTCC AGTTGGTAGT GCTCGCTCTG GCGCAGATTg taagtttcgc
1201 agccctccg ctgccaggt ccaggtgcg gggtctggag tccgggatgg
1251 aggagctctg cctgtcccc gcgcctactg acacccctag cccgagaggc
1301 cacctgagga cagcgccgcg cgagtcccc tcgtgggtg catacatggt
1351 gccatcgcg gcacgtgaat ggaggtggct gagcggagag tcaaacggga
1401 ccgtcccca gacgcgcggc ccgcccggg acaggcagcg tggggcagga
1451 gctgcgcc gtcctgca gccgggag cccaggtgc gggcatacaa
1501 tggtgctcat tcaccgatg cgcagcatcc gccccgccg cttccaggg
1551 ggccgcggct ccaaccagac gccgctgtcg cccgaggcg gcttntcggc
1601 cctgccgcc tacccacgtc tcccttccga gggccgccgg gggctgcggg
1651 cgcgcgggta gggcagagac tgggcccggt cgggtgctgg gtgtggtttc
1701 gagctcgcat gcggggcgcc agcctggcac ttcgcggcct ggggaggtcg
1751 tgggcaccgg gaccctgca tgggtccgag ctggcttctt aaaagggccg
1801 cctttaaga tctctgatct gttcagagat gggcagcagg atggagactc
1851 tccagctgtg agctcgcctc atcttgatat gacttgtgac ctccctgaaa
```

FIG. 11A-3

| | | | | | | Exon # |
|---|---|---|---|---|---|---|
| 1901 | cctcacaccc | accaggggc | attgaattgc | aggcaaacgg | gatccagaga | |
| 1951 | gagggtctgc | tttctgggag | gtgccggctc | ctcctgctcc | cctgcagcag | |
| 2001 | tcaggcttca | gcagaggag | gaccgggcag | ctgtgctgcc | gaaggggcgc | |
| 2051 | tccgagtggg | aagatagtac | ccgcttcacc | tccctacacc | tcctttctct | |
| 2101 | gcgcctcccc | cactttccgt | cgggtttttcc | cgcaccatgg | ggagaggagg | |
| 2151 | aggcgctgtc | tctgcctgtc | gttcacgtaa | gaacaacaac | ccgagccacc | |
| 2201 | gctcactgag | ggcggcagc | ctgctaggca | caaccttaca | ttccatctgt | |
| 2251 | gatttatttg | agctgtccac | gtctccatct | attcccacg | cgaccgcgca | |
| 2301 | agggcaaact | ggcacagtgg | aaggagtcgg | gcagatccag | ggcggactcc | |
| 2351 | tgcgccgccg | cccactctca | gtgaccatgg | acccttcacg | ttctgagcca | |
| 2401 | gtttcttcga | ctgcaaactg | gggcccgtaa | tagggcccgc | tcccggttct | |
| 2451 | gagtattctg | taagataatg | aatgcatacgt | gggagttcgc | ggaagagctg | tgcctgctat |
| 2501 | acagaagatt | ctcaatacgt | gggagttcgc | ggaagagctg | cgcccctagg | |
| 2551 | annctcccag | ggtgnntgca | gccccgggga | cgcccagctt | cctgcactgt | |
| 2601 | ctgaggactg | cccaccccg | tgtgtgtttt | tcagAGAGGT | CCACCGGGAG | |
| 2651 | AGCGGGGCC | CCCGGTCCC | CCGGGACCGC | CGGGAGTGCC | TGGATCCGAC | 2 |
| 2701 | GGCATCGACg | taagtctcta | acctgagacc | agggcgggag | ggaggcggca | |
| 2751 | gacaaggag | aactttgtga | gcgctgtggt | ggggtgggg | acttcggggt | |
| 2801 | gcccgagat | gtagtgcccc | tcgtcgccaa | tagnncccgc | ccnnaccaca | |

FIG. 11A-4

Exon #

```
2851 aggacgccgt tgttctgca aaaacctcaa accagccctg acatncggag
2901 cccgttatag ccgcgacag acaaggagct gctgttcagt ccgccggccg
2951 cagctcacag cgangnnnn tccccctcct ctccttccc ctccttgtgg
3001 ggtaggaggc gactcaaccc ctcaccctgc tctggcaca tctggacgct
3051 tcttcaggtt cgcttgggag ccttggccag accacgacc agcttgggcc
3101 agactcctgt ctcttccctt cggtttctc tcccgattt agaatcagct
3151 gggcttgttc ctgcagggtg agggttaaat acctcattct gaaagctccc
3201 gcaggagggc cgcttgatgt ttaccagtct ggacagactt ctattcaacc
3251 tgtgccccca cccccaaac acaggatgct ggccccccgc caggccctgg
3301 ctgctgaggg ctctgaaatg cctgaggcc tctgggc tgaatcgcac
3351 tctaccggcc ctgcctgccc accaagg gtccttggc actggaagga
3401 ggtccttccc tcctgggaa cactgaattt cccccttgca gtcccccttg
3451 gtccttgcca ctggctcagc ttcccgttct cctgccctgc agtctgaat
3501 agagctgctg cccaactcgc tcatcccct tcacgtttct ctaaaagccc
3551 caacctttcct cccacacgtg cccaaatcca agaggcatna gcttggagcc
3601 cccagccctg gtagtgggtc tcacagctgg cacctcaccc tctccagccc ggccaggcatg
3651 tctgtacctt cttgcatgtt gctgtcaccc tgtgtcaccc ggccaggtt
3701 attctcatgc tcctgtgatt tgttttggt tttattttt gaggaaaagg
3751 gggctcttt cccaagatt gcaaggctta gggacctgg acagaagaga
```

FIG. 11A-5

```
                                                                                    Exon #
3801 ggagagtgag gagagccttt gggagcggcc tgccagggcc tgtgtgtgcc
3851 cacttggggt agtgtgagcc gtagtgtgct gtctcaccaa cttgtatctt
3901 gcagGGTGAC AATGGGCCCC CTGGAAAAGC TGGCCCTCCG gtgagtgctt    3
3951 tatcctcttt ggcctttgac cctcctgct cttgccctcc tctgctcat
4001 gtttgttcca tctctgtttt caagGGACCC AAGGGCGAGC CTGGCAAAGC    4
4051 TGGGCCAGAT GGGCCAGACG GGAAGCCCGG GATTGATgtg agtagctgag
4101 tgtcgggtgg ggcagggtag gctctgccaa ttgacctcca gggcctggct
4151 ctggcatctt cactgatctg ttcagagatg ggcagcagga tggagattct
4201 ccagctgtga gccccctca ccttgatatg acttgtgacc ttcctgaac
4251 ctcactctca cccaggtca ttgatttgca ggcaaccggg gtccagagag
4301 agggtctgct ttctgggagg tgcaggttcc tcctgctacc cctcagcagt
4351 caggacttag tctcacattt ctggcctcca aggatcaggc tgaatatgtt
4401 gggtggggct gtcctgtgt gccctgtcct ttcctccgct cttccctga
4451 ccctaccca cagcccagg catgactcag gagagaaaca tcattagct
4401 gataccacag agctcccagg gggaccccca agtcacagg ctcttgaaca
4551 cagccagccc caggggcatg aggacaacat ctgatggggg ttacactggg
4601 tcagtcactg aaagatggga gaaggagaa accccatga cttgcctctg
4651 ccctgctggc tcatgaggtg tgaccagggc tgggacagtc accagaccc
4701 cttcaaactc atccacaccc tgcaacgatt acaaggcata ttgcctctca
```

FIG. 11A-6

| | | Exon # |
|---|---|---|
| 4751 | tgttgcatca gttctcacat ccacccagag aggcacccag atgagaact | |
| 4801 | aaggctcaga aaaagttgcc aatggcctgg cgtggtggct tatgcctgta | |
| 4851 | atcccagcac tttgggaggc cgagtgggc agattacttg aggtcaggag | |
| 4901 | ctcaagacca gcctggccaa catggcgaaa cccatctct actaaaaata | |
| 4951 | caaaaattac ccaagcgtgg tggcgcatgc ccctggtcct agctacttgg | |
| 5001 | gaggctgggg cacaagaatc atttgaaccc aggaagcggg ggttgcagtg | |
| 5051 | agctgagact gtgccactgc actccagcct gagcaacaga gtgagactgt | |
| 5101 | gtctcaattg aaaaaaaaaa gaaagaaaaa gaaaagagaa aggaaagaaa | |
| 5151 | agaaaagaaa atgaaaaagt tgtcaaggta ggacatcaag caaatgacca | |
| 5201 | atcttgaccc atggctaggt cttctagact cctgaaccg gaggcatgaa | |
| 5251 | gcctgggtct ggcataaagc caaatctttg ggctttggtt tctcatcttt | |
| 5301 | caaagaagg gaattgttct gcctgcctcc tagggttact atgggaactg | |
| 5351 | gggaaaagga aagaaaggtg tggaggttcc taggccttca tgaggtgtgg | |
| 5401 | caaaaaggag cctcggccca cccaggaggg acccttgaac ctgccctgct | |
| 5451 | ctgtgggtca gggagcaggt tggccctcat tgatctacat tttcattctt | |
| 5501 | ccccagGGTT TAACTGGAGC CAAGGGGAG CCTGGCCCCA TGGGATCCC | 5 |
| 5551 | TGGAGTCAAG gtaaggggcc tgctgggcc tcagcgtggg caatctaggg | |
| 5601 | ccagcgtttg ggagtggctg tagagaggaa gtaggagccg gggaacccc | |
| 5651 | agcctctgag cctttctcgt tgcttctctgca gGGCCAGCCC GGGCTTCCTG | 6 |

FIG. 11A-7

```
                                                                        Exon #
5700 GTCCTCCTGG CCTTCCGgtg agtacaacct gcaaggcttc gaggactct                 7
5751 tggggagag gggacctgca gagggagcca tgaagccaat tttcttcttt
5801 tctgttccag GGCCCTGGTT TTGCTGGACC TCCTgtaagt cctcaggat
5851 ggggcaggat cccagaact cccaggaag gagggacaa cagaaaggct
5901 tcgagggnat ggccaccatg ggaaggagcc agcttgctgt gatagtgtca
5951 ggaataagtg gacctgccag agaccaggg ccagcccact ctggcctgt                  8
6001 ccactggctc tgnaattctc tggtccttaa agcctcagtc tgtcagtctc
6051 tctggggttg gcaaaaaaa aaaaaaagta aaagtggaga aacggcttt
6101 gggtgcctgt ctctaccttt gtgccaggg tatctgaccc tctgaggcat
6151 cctgaccatc aactctctgc tcccagGGG CCTCCTGGAC CTGTTGGCCT
6201 CCCTGGTGAG ATTGGAATCC GAGGCCCAA Ggtgagcctc agccacctc
6251 tgttcactgc ctctgcctt ctatctccaa gctgcaagc tgggtggtct
6301 ttctggaagt tcctgggcct gctcctggcc actgggaaac tcctccagt
6351 ctggggcaga aacccctcct atgagcccac ccggcactag gtctttagg
6401 gacngctggc cccatcccct gtcaatcagg ccttcatctc ccaagatggt
6451 ggatctcaca aagtgaccgg gaagacaggg tggagagggc agaggcagga
6501 cctggaggag ggcactaggg taagctggta agggctggtc agggtatga                  9
6551 tttggcttc ttttgcttcc agGGGACCC TGACCAGAT GGACCATCGG
6601 GGCCCCAGG ACCCCCTGGG AAACCTgtaa gtgtccccag accccgaca
```

FIG. 11A-8

| Position | Sequence | | | Exon # |
|---|---|---|---|---|
| 6651 | tgcaaagtg caggggaagg agaagggtct | ttgagcaagc | ctgcggcggg | |
| 6701 | aaagggtcag gccaagctcc atcttcatgt | ctcctctcag | GGTCGCCCGG | 10 |
| 6751 | GAACCATCCA GGTCTGGAA GGCAGTGCGG | ATTCCTGgt | gagagacgag | |
| 6801 | gtctggggcg gggctaacac aggggggcgg | ggccacagag | atgggaggc | |
| 6851 | ggggccacgg agatgggggt gtctggagag | atggggaggg | gctgcagtgc | |
| 6901 | aggggttcca ccaggtgagg cggaggagag | cacggggctt | ggagagatgg | |
| 6951 | gggcgcactg cccagctgat cacaggaccc | tgtggatt | tctgtttcca | |
| 7001 | gTGTCCAACC AACTGTCCAC CCGGAATGAA | AGTCCCCA | GGGCTGCAGG | 11 |
| 7051 | GAGTGAAGgt gagagctcct ggcctgaatc | ttgggaggggt | ggtgcaggtg | |
| 7101 | acaggagggg acctcgtatt gagctctctc | cttcccttca | gGGGCATGCG | 12 |
| 7151 | GCAAACGCG GGATTCTGGG TGATCCTGGC | CACCAGGGGA | AGCCGtgag | |
| 7201 | tgcaagggct gagggctgtg ggtcaggat | acgtggagat | ggtcctacag | |
| 7251 | ggctctgtcc ccttcttcgt cccctccccct | tcccctgtgg | gttctgggga | |
| 7301 | cagagccttg agccggnggc tggaggcctg | tgctccaggt | cggcatgtct | |
| 7351 | ctggtcatgt ctccttgct ggcttttctc | tatctgtaac | acaggactgt | |
| 7401 | agggttcgta gtagtccctc cgtctgctt | gtgctgggga | aaagaggtgg | |
| 7451 | tatctttgct tgtctgtata tgtctcttc | catctgcctg | cctgtctgac | |
| 7501 | agctcatccc tgcccttag GGTCCCAAGG | GAGATGTGGG | TGCCTCTGGA | 13 |
| 7551 | GAGCAAGGCA TCCCTGGACC ACCGgtaagg | aacaccttgc | ctcagtggcc | |

FIG. 11A-9

```
                                                                              Exon #
7601  ctcttctccc tcacccagg agcccttcat ggagtcattc cctgctcag
7651  gcctctagct tgtaaaagag acacctgtgt ctagctggga gcatctctgg
7701  atggggagat ggaggctgaa attgtcagga atgagggaca ggaaccaaag
7751  ctgtcagcaa gaagcccagg ctgaggtcca ggtctgccac tgtccctttg
7801  agtaatgcag tgagtccctc ctcatctctg aacctccatg tccatccat
7851  gagacagaga ctctgctgcc tacctcaaaa gggcactgta agattgaagg
7901  tgggcatcag acaagtatc atgaagtggg ccttgcaatt gccattgctg
7951  tcatttttct ttctcaacag GGTCCCCAGG GCATCAGGGG CTACCCAGGC   14
8001  ATGGCAGGGC CCAAGGGAGA GACGgtaagt gaatcttggg gtgttctaca
8051  agagcttcca ggagctgcct tctggcccct ggagttcagc caggactgac
8101  ctgcaaccct ttcctctccc cagGCCCCTC ATGGATATAA AGGCATGGTG   15
8151  GGGCGCTATCG GTGCCACTGG GCCACCGgta agccctctttt tgctcccta
8201  cccctgaggc tggagctcct acagctacag ccacagagtg ggcatggctc
8251  cccctgagcc tgtgtgacct ggattcctgc ttgtcttttct tgccagGGTG   16
8301  AGGAAGGTCC TAGGGGACCG CCAGGCCGAG CTGGGGAGAA GGGTGACGAG
8351  gtgagtcctc aggcaccat tgttcagtca ggncccctgg ggagtactgg
8401  gcaggacaag gcacccccta aggctgtgtg tgtgagagtg catgagtgtg
8451  tgcgtgagtg tgaatgtgta gtgtgtgtga gtgtagtg tgtgtgtg
8501  tagactgtgt gtatgtgagt gtatgtgtac agtgtgtatg tgtgaggctg
```

FIG. 11A-10

Exon #

```
8551 tctgtgagtg tgtgtagtat gtgtatgtga gtgtgtgagg atatctctga
8601 gtgtgtgtgt gtgactgtga gtgtatgtat gtgtgtgtga gtgagtgtgt
8651 gtgtgtctgc ccaagtgggt gacctgctgg ggaggaccat ctgtgccaag
8701 agcccagtca gcccaaattc agactttagg cgannntggg atccagtccc
8751 atggtcactg gggccagaca atgagattcc agcaaatcag ccatgggct
8801 aatggggattt ggtctcgatc ccagttctct taactctttt tttttttt
8851 tcccaattaa tagacctgtt ggggaagcg gttttaagtt tacagaaaaa
8901 tggagcagaa aacacagtta actgttatta ttattttagtt tttaaatta
8951 tttctttttc ttttaaaaa ttaaaaaatt cttatactt tatttttcta
9001 ttagacagca gagatcatct agttgttttg ttttgttttg ttttgagat
9051 ggagttttat tcttgttgcc caggctggag tgcatggtgc gatctcggct
9101 cactgcaacc tccgcctccc tggttcaaga gattctcctg cctcagccac
9151 ccaagtggct gggattacag gcatgcgcca ccatgctcag ctaatttttgt
9201 atttttagta gagacagggt ttcaccatgt taggctggtc tcgaactcct
9251 gacntcaggt ganccacctg cctcggcctc ccaaagtgct gggattacag
9301 gtgtgagcca acacgcccag caatatctag tttttaatg caattttta
9351 actatacaga aaaccagtga gagtgatata aagaatcccc atgtacctat
9401 cacaggttcc aantcagtta ttaacatttt gtcagtcttg tgtcctctat
9451 cccccagacc cctccttcct ttgatttttgt tattgctttg ctctgatgtt
```

FIG. 11A-11

| | | | | Exon # |
|---|---|---|---|---|
| 9501 | ttcaagtaaa tccttaacat cctatcatct cagccctaga tactttgta | | | |
| 9551 | catatctcta aacataagc actcattctc acatatctc attatcacaa | | | |
| 9601 | ctgacaaaat aaacaagtac tccctaacat catctaatgg ccagtctctg | | | |
| 9651 | ttcagttttt cccaattatc tcaaaaatgt cttttcctgg ttcttgttca | | | |
| 9701 | aatcaagact cacacacagcat ccacacactg cattcggttg ttgtgttcct | | | |
| 9751 | ttggctgagt ggattgtggg gccttggcca aggtctcagt ggattctggc | | | |
| 9801 | tcccacccct gctctggctc agcccagcct ggcctcctgg cactgacttc | | | |
| 9851 | tcctccctcc tgctgtgcc agggcaggaa gggtactccc aaggctctct | | | |
| 9901 | cctcggccc ctgcatggtg tggcctgtgc cagaggaact ctgggaccta | | | |
| 9951 | gaggcactg ttctcagtgg ttccctctc tgcacagcca gacagggcc | | | |
| 10001 | caacatcctg agggtgacct gatctctctc cgctttgcag GGCAGCCCAG | | | 17 |
| 10051 | GTATTCGTGG ACCCCAGGGG ATCACAGGCC CGAAAGGAGC AACGgtaggt | | | |
| 10101 | gccagaggcc taggcccacc aggacagagg ccagggccca gctgctttgt | | | |
| 10151 | ccaaccccca agaagagaag cctgggatgc tagtctgaac tctgcaactg | | | |
| 10201 | gtgggctggc tccataacct caggaaatgc ctccctttct gtgcctcagt | | | |
| 10251 | ttcttcacct gtaaacaggg gtgatgacat acggaggtc atggggagct | | | |
| 10301 | tgcagcagtc ggggacacca ccctccacac taggaagga ctgtgttccg | | | |
| 10351 | tgaccctcat cccttccca cttcaactcc cctccccag ttggccagtg | | | |
| 10401 | gggcttcctg ggatgaccag agccactccc tccctgcaca ctgcagctgt | | | |

FIG.11A-12

|  |  | Exon # |
|---|---|---|
| 10451 | ctcagaggaa caggggtggg tggccagacc ccagacatct ccgcattatc | |
| 10501 | actctcccct gaactttcct cctgggtagG GCCCCCAGG CATCAACGGC | 18 |
| 10551 | AAGGATGGGA CCCCAGGCAC GCCTGCCATG AAGgtaggag tggggctgct | |
| 10601 | gatgggactg gggcaggggc aggaccttga gtcctggatt ctagacacca | |
| 10651 | agagcctggg gccctcaggt catgacatg cccttcttg cctctgatc | |
| 10701 | tcagtttccc tacctgcatc tgggtagaag ccatgccct ctggctggag | |
| 10751 | ctttaattg tatctttggt tatctgtcta tcccagGGCA GTGCAGGACA | 19 |
| 10801 | GGCGGGACAG CCCGAAGTC CAGGCCACCA GGGCCTAGCG gtaagtgtca | |
| 10851 | ggtggagcca caggggctgg ccagggcta gtggctgatg aggttagaat | |
| 10901 | ccacacacac ccgggctct tgctcaatca ccacctcttg ccttgttacc | |
| 10951 | aactctgtgg ccctggnct ggcgaaggct tcattacttg gacaattact | |
| 11001 | ctagccttct ctttgccat tccagtcctc catgttggct aaatgggatc | |
| 11051 | tgaccatttc tgcactatag caccttccat ggctcccccac cgctccccagg | |
| 11101 | aaaaagtcat tcagtccagt ccttcaataa gtagttattg aggtcgggtg | |
| 11151 | cagtggctca tgcctataat cccagcactt caggaggctc agctgagtgg | |
| 11201 | atcacttgag gtcaggagtt caaaaccagc ctggccaatg tggtgacacc | |
| 11251 | ccgtctctac taaaaataca aaaattagct gggcgtggcg gctcatgcct | |
| 11301 | gtaatctcag ctactcagga ggctgaggca ggagaattgc ttgagccag | |
| 11351 | gaggcgaggt tgcactgagc caagattaca ccactgcact ccagcctggg | |

FIG. 11A-13

| | | Exon # |
|---|---|---|
| 11401 | taacagagca agactccatc tcaaaaaaa aaaaaaaaa aatagttatt | |
| 11451 | gagtatctga ggtatactaa gtgcaggta acaattata aatagacag | |
| 11501 | atgcaatctt tgtctttcat ggctcatctt accattcaat gaccaccata | |
| 11551 | atctgacccc aacctgcccc tcctgccata tcagcaatgg cccctctctg | |
| 11601 | tcctttccct tctcaacagg ccttggcttt tctgcctca caccttagg | |
| 11651 | cctttgctgg tccctctgtt tgaaatgccc tttctggtct ctttgtgcct | |
| 11701 | tcttatcgtt caggccatc tccattccat acctcctga gtccagtcca | |
| 11751 | tgggagcctg ccctccctcc ctgtggggt actgagtggc caaacctgtt | |
| 11801 | tctgtgcaca catgcagact tgtgttcctg cgtgcactca catggctca | |
| 11851 | ggcacctgag agcacatatc catctcttcc acgtagaccc caggtcctgg | |
| 11901 | aanacaggcc attctctgtg cccactcct ctgncaccac tgtgggaatg | |
| 11951 | tacagtnaag ttcatcatgc cgtggctgga ccttctgttg ttcagctccc | |
| 12001 | acaggtgggg gaaatctgga ttggggatgg gaagcaaagc agcaggtgca | |
| 12051 | tgggctccc tcatgccagg gcagaaactg acttcaactt cttcctgcag | |
| 12101 | GGTGTGCCAG GCCAGCCTGG GACAAAAGGA GGCCCTGGAG ACCAGgtgag | 20 |
| 12151 | gcgatcccaa gctgggaca gaattgagca aggaagtctg gggccaggaa | |
| 12201 | gacagcaagg cccaggcctc agccaagtct cagaggctca gccagaacat | |
| 12251 | aagcccttg ggcctaacca cctcctcct gccacctccc accatcatg | |
| 12301 | cactcctcag cctgcctcag tgcagatagg atggcatggc ttaaaatcca | |

FIG. 11A-14

```
                                                                              Exon #
12351  gaggagaaac aaacaggaaa atcaggagcc aaggagattg accaagaat
12401  accctcttcc ccgtcccagc tcatctggtt ccaggtctg tttaggcttc
12451  gttgggtttc cctgaggcca agggctgact ggccaccca gactgacctg
12501  agaactgttt tcctgcagGG TGAGCCGGGC CGCAGGGCC TTCCTGGATT
12551  CTCTGGTCCC CCTGGGAAAG AGgtaaatgc ccctgcact gacacaagg        21
12601  ttcctgcttt agggtgaggc catggggtgg agcctaacct agggagagct
12651  ccgagttagt ctggctctgc ctgaccaat gattcaggga agctctttct
12701  cctccctggg cctgtttccc tatgtacatt gcaggaggg tgggactgg
12751  ctctgttctg gagtgtgact ttcctagatg gccaagttga tgggctggga
12801  atccaacagg cagagttgtt cgttcattta ttcattgcat aaacattcac
12851  taaacacttg caactatgag tctcctcttc atatggaggg tatagtttaa
12901  tggaagaaat agacatgaaa taaatgatca cgccggggc nnnnncacgc
12951  ctgtaatccc agcatttttgg gaggctgagg cgggtggatc acgaggtcag
13001  gagatccaga ccgcggtgaa acccgtctc tactaaaaat acaaaaaatt
13051  agcctggggc ggtggcaggc acctgtagtc ccagctactc tggaggctga
13101  ggcaggagaa tggcatgaac ccgggaggcg gagcttgcag tgagcggaga
13151  tcgcgccact gcattccagc ctgggtgaca gagcaagact ccctctcaaa
13201  aaaaaaaaaa aaaaaaaaaa agaaagaaaag aaatgatcac atgataagta
13251  attcaaattg tgttgggtcc tttgaaagaa aactacaggg acccaaaacc
```

FIG. 11A-15

| | | Exon # |
|---|---|---|
| 13301 | atggaacagg tggtctggga aaccttccct gatgaagcaa attagctgag | |
| 13351 | acccagggta gggaggggct ggccaggtgt ggaagggtgg gttccaccag | |
| 13401 | gtcaaacgct tagcccccaat ttctccttcc tccagGGAGA GCCAGGGCCT | 22 |
| 13451 | CGAGGAGAAA TTGGTCCCCA GGGCATCATG GGACAGAAGg taagtgcctg | |
| 13501 | gcacaatgcc cctccccgg gggcctctgc ggcagctggc actgctggat | |
| 13551 | acagcatctg ctccgtgcag cccgtgagat gcctccccag gcaggccta | |
| 13601 | ggtttgcttt gctgtctgc caagtggaga aggaccccc tgccagtgac | |
| 13651 | agcaggaatg gagggcaccc tgaccatgcg gtgccaggcc tcgtgcggg | |
| 13701 | aggctacccc tgctgagagc tgctgaggtt gtgaccttct ctttccattt | |
| 13751 | cagGGTGACC AAGGCGAGAG GGGTCCAGTG GGGCAACCAG GCCCTCAGGG | 23 |
| 13801 | AAGGCAGgtg agtgcaggcc agctaaggtg ggcagggcgt catatccagg | |
| 13851 | cccctcattc catttattcc tttggtttct tttctcctca gGGCCCTAAG | 24 |
| 13901 | GGGGAGCAGG GCCCCCGG AATTCCAGGG CCCAAGGCT TGCCAGGGGT | |
| 13951 | CAAAGGAGAC AAGgtgagac ggggagtggg gtcgcagga ctcagancct ggaaaggggc | |
| 14001 | cctataacag ggggagtggg gtcgcagga ctcagancct tccggagcct | |
| 14051 | ccaaacctgc ggntctcagg gttctggtct ggtcggcgag gcggagttgg | |
| 14101 | aaagaggggt gtggccgaaa gttaggtggg ggacccgtg gagggggag | |
| 14151 | ctcgccaaac ccctcactgc cgctttctc cagGGCTCCC CAGGAAGAC | 25 |
| 14201 | CGGGCCCGC GGCAAAGTGg tgagttccag cacccctgtt cccagcgacc | |

FIG. 11A-16

| Position | Sequence | | | Exon # |
|---|---|---|---|---|
| 14251 | cccaaccctg ctctgcgtcc | ccgcgccac cgcgcgtctg | acccgtgtt | |
| 14301 | ctctctgcag GGTGACCCAG | GGTGGCCGG CCTCCCCGGA | GAGAAAGGCG | 26 |
| 14351 | AGAAGtgag cgcgcgccta | gggaagggcg gctgcccttg | gctgcccgg | |
| 14401 | ggtccnnggc ttcgtgaccg | ctgctccttg tgcctgcagG | GCGAGTCCGG | 27 |
| 14451 | CGAGCCGGGG CCCAAGGGAC | AGtgagtcc tccctcccg | gcgttctccg | |
| 14501 | actttcctgg gcggccactc | ccttcctcga cccccaccc | ccactctgc | |
| 14551 | ccacccgggc gccttctcac | ccggctctgc tccacccc | atcccccgc | |
| 14601 | agCAAGGAGT ACGTGGAGAA | CCCGGCTACC CTGGCCCCAG | CGGGGATGCG | 28 |
| 14651 | GGGCCCCCAG GGGTTCAGGG | CTACCCTGGT CCCCCCGCC | CTCGAGGACT | |
| 14701 | GGCCGGGAAC CGAGGCGTGC | CAGGACAGCC CGGAGACAG | GGCGTGGAGg | |
| 14751 | tgagtcgggc cccggggtag | gaggtgcttc tttctaggtag | atctgttctg | |
| 14801 | gggtgcggct taccccgcca | aggctaggga ttcccagaga | ctcaccgact | |
| 14851 | tccccgagac tggttccaag | ccccagagca gacaggaagg | ctgtgagtgc | |
| 14901 | agcctgaggg attaccccgc | gaccttccca agtaagcct | tggccctgcc | |
| 14951 | caggtacaat ctgttcctca | gcttgggaat taatgactca | acaccagagt | |
| 15001 | ctcctccatg gcggcctcac | gctcagccag gtgggatagg | agcggtgggc | |
| 15051 | ccttgtagcc aggggcttct | tcctgaaagc ctctgctttc | agGGCCGGGA | 29 |
| 15101 | TGCCACTGAC CAGCACATCG | TGGATGTGGC GCTGAAGATG | CTGCAAGtg | |
| 15151 | agggcagca accccctccct | acagtcagtt cgagggcatc | gccgccccct | |

FIG.11A-17

| | | Exon # |
|---|---|---|
| 15201 | caccccctcc cggagcctcc acgtgttcac ttgtctgaaa atctggagtc | |
| 15251 | ctggggctc cttccagtcc agtctctgaa gggttttggg acctttgaata | |
| 15301 | agtcactctg ggcctttgac ttccgcaaaa cagagcccac ggaaggtggt | |
| 15351 | gcttttctgt ctgcaaacct aggggcagg gccatcgga atgtctgcc | |
| 15401 | tcccctagtg ttactgctga cacccatctc atagacttcc ctctccctcc | |
| 15451 | tnctcnctcc ctccagAGCA ACTGGCAGAG GTCGCCGTGA GTGCCAAGCG | 30 |
| 15501 | GGAAGCCCTG GGTGCGGTGG GCATGATGGG TCCTCCAGGA CCTCCTGGGC | |
| 15551 | CCCCTGGGTA CCCAGGCAAG CAGGGCCCCC ATGGGCACCC TGGCCCTCGG | |
| 15601 | GGGGTTCCTG GCATCGTGGG AGCCGTGGGT CAGATCGGCA ACACGGGGCC | |
| 15651 | CAAGgtgag tgctcctctg cggtgggcat ggggccagg cagtgaggat | |
| 15701 | ttgtccaggc cggccctttc cccattccct tctcaggatg acatacagac | |
| 15751 | ccttcccccgg ttcctcagcc acatggtcca ggagacactc ctgnctcttt | |
| 15801 | tcctagtagc aaacgatgg caatgaatgt actatgttat cactcggggt | |
| 15851 | ttctggggtt tgtttttgaa tgtgcttagt ggtacccccat aagcatctttt | |
| 15901 | ccatgtcaat agatgnggg cggcagacca gcagagcagt aaagcaggca | |
| 15951 | ggctggagcc acacacgggt gtgaatccag actccccttt ctcatcgtgg | |
| 16001 | ctctcagacg agttacctgc taatttccct ggccttagg tttactatct | |
| 16051 | gtaaaatggg gncactgaaa gtaccaacct catcatgtgg cagtgaggac | |
| 16101 | tatccttaga gtagtttaca tagagtttgt cttagttcac tgagacacag | |

FIG. 11A-18

| | | Exon # |
|---|---|---|
| 16151 | taaatgctag atattgttat gcttgctttc ctgtaataaa ctttattggt | |
| 16201 | tacataatct tccatccttt gtctgcacct tcctttattt aacagccct | |
| 16251 | gcgtgaccat ttccaacttt cctctattac aaactagcac aaaacaggaa | |
| 16301 | taatttcttt gcgtgaaaca tagcaaaaaa tagaggaaaa gcattttcca | |
| 16351 | attctgaaaa atgaagattt cctttttgt ctacagGAAA ACGTGGAGAG | 31 |
| 16401 | AAGGGTGATC CAGGAGAAGT GGGACGGGGG CACCCCGGGA TGCCTGGGCC | |
| 16451 | CCCAGGGATC CCAGgtaagc cattggccct gccagctgc agtgtgttcc | |
| 16501 | tcagcttggg aattaatgac gtgtggacac tgcggtctcc tccatggcgg | |
| 16551 | cctcacgctc agccagctca gtccttgata cccagcttct gcacccttt | |
| 16601 | ggagcaccc ggagtctctg ggtggttcca gctctggaag ctgggcctct | |
| 16651 | caggacttcc caggatccac caccatcact tcacagaggt gatggaaggg | |
| 16701 | atgtttgctc ccaagctca ctgattggga gctggggta ggggacaatc | |
| 16751 | acagaatctc tgcctctggg gcagagtcct ttctcctatg gtgtttggc | |
| 16801 | ctcatttct ccatctgaaa agtttcccca ccttcaaaat tctggcctg | |
| 16851 | agacaagagg tgcccctaat gtcttgactt tctcctgttc acagGACTCC | 32 |
| 16901 | CTGGCCGGCC TGGCCAGGCA ATCAACGGCA AGGATGGAGA TCGAGGTCC | |
| 16951 | CCAGGGCTC CAGGAGAGGC AGTGGACCT GGCCTGCCAG GCCCGTGGG | |
| 17001 | GCTGCCGGGC TTCTGTGAAC CTGCCGCCTG CCTTGGAGCT TCGGCCTATG | |
| 17051 | CCTCTGCCCG CCTTACAGAG CCTGGATCCA TCAAGGGGCC Ttgagcatca | |

FIG. 11A-19

Exon #

```
17101 ggcccagaca gagcctggag gcatcctggc gggaaggacc aggtcccctc
17151 tggtggacat gcacccatcc ccagtccagg aaaccatctc cccagacc
17201 ttctgtctgg gactcaggag tcctaaggaa aaggaattct aaaacatggg
17251 ggaaggggag gtagagcact gatgggtgaa aaagtgaggc caacacacag
17301 ggcaagtggt gtcgatggag tcgaagcgct gaaggaatag ggcggctttc
17351 cttccagcga gcatcattcg gctgttacca aaacaaacat cttaatctgc
17401 accttcctcc actggccatc ttgtccttgg gtcagtggga catggcacc
17451 tcgggaggcc cgggccctgc ccagctacag ttccaccct cagcttgagg
17501 accaatactg aggtctatgc cagttcctga tcccatctca ctctctggac
17551 ctactaggtg actgctgctg gggtgactcc cctgaggcgg ctatacccct
17601 aagcca
```

FIG. 11B-1

```
atatatat atatggac tattagtatc ccatttac agatgaggaa
aatgagactt catagagttn gggtgcctg tggtcatatc tataattgtg
aaaagtcag attccaaagc attttaccaa tattgcctaa gtgagtggga
gggaaggaa ggctctctgg agtcgggcta tgctgacag cggggttcgg
aaactctggt gaataaagtg gtagttgttt ctatgaacat ggagtgagaa
ggcccaatcc taaacacacc agtgcttaag gcagctgcag agaattaaag
gcaatagaaa aaggggagct ggatggcagg agcttggatg gggaagactt
caagggcagg tgaagatgcc aacagcttcc tgcctggagg accgaagaag
ggttgggctt cactgcagac ctccaggaga cagatttgct tcttggaca
gagtagggag gtgaaagcga ggtgaggaag ttcgggtgg gggaggtgca
cacagttcca ctaaagagtt ggaagaggcc gatgagtat tcatgagacg
gctgatccag gaaggactgt ggcatattaa tatgaaaaag gcctgtttgt
ttgtgcttgg agaggaagga gccagagga agggagcaa ggtggcggg
agctggggag agcctgcagc aagatctgca gagcccgagg tgctctcggc
atgggccctg gagaggacgt agggtaagtg ctgaaggtcc cgagggaac ntcagacggc
caggggaag gtgctggggc ctgaaggtcc cgagggaac tcagacggc
cttatgcctt ctcacaaaga aactgacca tcatttccga cccgcaccc
ggtcgcccct cgaggacaga gggtgggcgc aggaggctgg accgagcggg
gcggagctgg atgcctggcg ccggcatccc tcccggcaac cccccggtc
ctctcaggtg acagtcacgc ccgccccccg cccccccc cgcatattca
aggagcccca gcccaccctg cccgcgaaca gccagcgctg gaggagcgcc
gggagactct gccgtcggtg cgtgcgcgga cacgcacccg tccccttgg
tctcgcgcc agcc
```

FIG. 11B-2

```
agccctccg ctgccaggt ccagggtgcg gggtctggag tccgggatgg gtaagtttcgc
aggagctctg cctgtgtccc ggcctactg acacccctag cccgagaggc
cacctgagga cagcgccgcg cgagtcccc tcggtgggtg catacatggt
gcccatcgcg gcacgtgaat ggaggtggct gagcggagag tcaaacggga
ccgtcccca gacgcgcggc ccggcccggg acaggcagcg tggggcagga
gctggcgccc ggtcctgca gccggggag ccaggtggc gggcatacaa
tggtgctcat tcaccgatg cgcagcatcc gccccgccg cttcccaggg
ggcgccggct ccaaccagac gccgctgtcg ccccgaggcg gcttntcggc
cctgcccgcc tacccacgtc tcccttccga ggccgccgg gggctgcggg
cgcgcgggta gggcagagac tgggcccgt cgggtgctgg gtgtggtttc
gagctcgcat gcggggcgcc agcctggcac ttcgcgcct ggggaggtcg
tgggcaccgg gacccctgca tgggtccgag ctggcttctt aaaaggccg
cctttaaga tctctgatct gttcagagat gggcagcagg atggagactc
tccagctgtg agctcgcctc atcttgatat gacttgtgac ctccctgaaa
cctcacaccc accagggc attgaattgc agcaaacgg gatccagaga
gagggtctgc tttctgggag gtgccggctc ctcctgctcc cctgcagcag
tcagggctta gcagagggag gaccgggcag ctgtgctgcc gaagggcgc
tccgagtggg aagatagtac ccgcttcacc tccctacacc tcctttctct
gcgcctcccc cactttccgt cgggtttcc cgcaccatgg ggagaggagg
aggcgctgtc tctgcctgtc gttcacgtaa gaacaacaac ccgagccacc
```

FIG. 11B-3

```
gctcactgag ggccggcagc ctgctaggca caaccttaca ttccatctgt
gatttatttg agctgtccac gtctccatct attcccacg cgaccgcgca
agggcaaact ggcacagtgg aaggagtcgg gcagatccag ggcggactcc
tgcgccgccg cccactctca gtgaccatgg acccttcacg ttctgagcca
gtttcttcga ctgcaaactg gggcccgtaa tagggcccgc tcccggttct
gagtattctg taagataatg aatgcatgta atgcacacag tgcctgctat
acagaagatt ctcaatacgt gggagttcgc ggaagagctg cgcccctagg
annctcccag ggtgnntgca gccccgggga cgcccagctt cctgcactgt
ctgaggactg cccacccccg tgtgtgtttt tcag
```

FIG. 11B-4

```
gtaagtctcta acctgagacc agggcgggag ggagcggca
gacaaggag aactttgtga gcgctgtggt ggggtgggg acttcgggt
gccggagat gtagtgcccc tcgtcgccaa tagnncccgc ccnaccaca
aggacgccgt ttgttctgca aaaacctcaa accagccctg acatncggag
cccgttatag ccgccgacag acaaggagct gctgttcagt ccgccggccg
cagctcacag cgangnnnn tccccctcct ctcctttccc ctccttgtgg
ggtaggagc gactcaaccc ctcaccctgc tctgcaca tctggacgct
tcttcaggtt cgcttgggag ccttggccag accaccgacc agcttggcc
agactcctgt ctcttccctt cggttttctc tcccgattt agaatcagct
gggcttgttc ctgcaggtg agggttaaat acctcattct gaaagctccc
gcaggaggc cgcttgatgt ttaccagtct ggacagactt ctattcaacc
tgtgcccca cccccaaac acaggatgct gcccccgc caggccctgg
ctgctgaggg ctctgaaatg cctggaggcc tctctggggc tgaatcgcac
tctacggcc ctgcctgccc accaccaagg gtccttggc actggaagga
ggtcctcc tccttgggaa cactgaattt cccccttgca gtcccttg
gtccttgcca ctggctcagc ttccgttct cctgccctgc agtctgaat
agagctgctg cccaactcgc tcatcccct tcacgtttct ctaaagccc
caaccttcct cccacacgtg cccaaatcca agagcatna gcttggagcc
cccagcctg gtagtgggtc tcacagctgg cacctcatga catcagcatg
tctgtacctt cttgcatgtt gctgtcaccc tctccagccc ggccagggtt
attctcatgc tcctgtgatt tgttttggt tttatttt gaggaaaagg
```

FIG. 11B-5 gggctctttt cccaagatt gcaaggctta gggacctgg acagaagaga
ggagagtgag gagagcattt gggagcggcc tgccaggcc tgtgtgcc
cacttggggt agtgtgagcc gtagtgtgct gtctcaccaa cttgtatctt
gcag

FIG. 11B-6 gtgagtgctt
tatcctcttt ggccttttgac ccttcctgct cttgccctcc tctgctcat
gtttgttcca tctctgtttt caag

FIG. 11B-7 gtg agtagctgag
tgtcgggtgg ggcagggtag gctctgccaa ttgacctcca gggcctggct
ctggcatctt cactgatctg ttcagagatg ggcagcagga tggagattct
ccagctgtga gcccccctca ccttgatatg acttgtgacc ttcctggaac
ctcactctca cccaggtca ttgatttgca ggcaaccggg gtccagagag
agggtctgct ttcctgggagg tgcaggttcc tcctgctacc cctcagcagt
caggacttag tctcacattt ctggccctcca agatcaggc tgaatatgtt
gggtggggct gtccttgtgt gccctgtcct ttcctccgct cttcccctga
ccctaccca cagcccagg catgactcag gagagaaaca tcattagct
gataccacag agctcccagg gggaccccca agtcacagg ctcttgaaca

FIG. 11B-8

```
cagccagccc cagggcatg aggacaacat ctgatggggg ttacactggg
tcagtcactg aaagatggga gaaaggagaa accccatga cttgcctctg
ccctgctggc tcatgaggtg tgaccagggc tggacagtc accaggaccc
cttcaaactc atccacaccc tgcaacgatt acaaggcata ttgcctttcta
tgttgcatca gttctcacat ccacccagag aggcacccag atgagaaact
aaggctcaga aaagttgcc aatggcctgg cgtggtggct tatgcctgta
atcccagcac tttgggaggc cgagtgggc agattacttg aggtcaggag
ctcaagacca gcctggccaa catgcgcgaaa cccatctct actaaaaata
caaaattac ccaagcgtgg tggcgcatgc ccctggtcct agctacttgg
gaggctgggg cacaagaatc atttgaaccc aggaagcggg ggttgcagtg
agctgagact gtgccactgc actccagcct gagcaacaga gtgagactgt
gtctcaattg aaaaaaaaa gaaagaaaaa gaaaagagaa aggaaagaaa
agaaagaaa atgaaaaagt tgtcaaggta ggacatcaag caaatgacca
atcttgaccc atggctaggt cttctagact cctgaaccccg gaggcatgaa
gcctggtct ggcataaagc caatctttg ggctttggtt tctcatcttt
caaagaagg gaattgttct gcctgctcc taggvttact atggaactg
ggaaaagga aagaaaggtg tggaggttcc taggcctca tgaggtgtgg
caaaaggag cctcggccca cccagaggg accctgaac ctgccctgct
ctgtgggtca gggagcaggt tggccctcat tgatctacat tttcattctt
ccccag
```

FIG. 11B-9

```
                    gtaaggggcc tgctggggcc tcagcgtggg caatctaggg
ccagcgtttg ggagtggctg tagagaggaa gtaggagccg ggaaccccc
agcctctgag cctttctcgt tgcttctgca g
```

FIG. 11B-10

```
           gtg agtacaacct gcaaggcttc gaggactct
tgggggagag gggacctgca gagggagcca tgaagccaat tttcttttctt
tctgttccag
```

FIG. 11B-11

```
                                   gtaagt cctcagggat
ggggcaggat cccagaact cccagggaag gagggacaa cagaaaggct
tcgagggnat ggccaccatg ggaaggagcc agcttgctgt gatagtgtca
ggaataagtg gacctgccag agaccaggg ccagcccact ctggcctgt
ccactggctc tgnaattctc tggtccttaa agcctcagtc tgtcagtctc
tctgggttg gcaaaaaaa aaaaaagta aaagtggaga aacgggcttt
gggtgcctgt ctctaccttt gtgccaggg tatctgaccc tctgaggcat
cctgaccatc aactctctgc tccccag
```

FIG. 11B-12 tgttcactgc ctcctgcctt ctatctccaa gctggcctc gtgagcctc agccaccctc
ttctgaagt tcctggcct gtcctgcc actggaaac tcctccagt tggtggtct
ctgggcaga aacccctcct atgagcccac cggcactag gtctttagg tcctccagt
gacngctggc cccatcccct gtcaatcagg ccttcatctc ccaagatggt
ggatctcaca aagtgaccgg gaagacagg tgagagggc agaggcagga
cctggaggag ggcactaggg taagctggta agggctggtc agggtatga
tttgggcttc tttgcttcc ag

FIG. 11B-13 gtaa gtgtccccag accccgaca
tggcaaagtg caggggaagg agaagggtct ttgagcaagc ctgcgcggg
aaaggtcag gccaagctcc atcttcatgt ctcctctcag

FIG. 11B-14 gt gagagacgag
gtctggggcg gggctaacac aggggggcg ggccacagag atggggaggc
ggggccacgg agatgggggt gtctggagag atggggaggg gctgcagtgc
aggggttcca ccaggtgagg cggagagag cacgggct ggagagatgg
gggcgcactg cccagctgat cacaggaccc tgtgggattt tctgtttcca
g

FIG. 11B-15

```
   gt gagagctcct ggcctgaatc ttgggagggt ggtgcaggtg
acaggagggg acctcgtatt gagctctctc cttcccttca g
```

FIG. 11B-16

```
                                              gtgag
tgcaagggct gagggctgtg ggtcaggat acgtggagat ggtcctacag
ggctctgtcc cctcttcgt cccttcccct tccctgtgg gttctgggga
cagagccttg agccggnggc tggagcctg tgctccaggt cggcatgtct
ctggtcatgt ctccttgctt ggcttttctc tatctgtaac acaggactgt
agggttcgta gtagtccctc ccgtctgctt gtgctgggga aaagaggtgg
tatctttgct tgtctgtata tgtgtctttc catctgcctg cctgtctgac
agctcatccc tgcccttag
```

FIG. 11B-17

```
                                    gtaagg aacaccttgc ctcagtggcc
ctcttctccc tcacccagg agcccttcat ggagtcattc ccctgctcag
gcctctagct tgtaaaagag acacctgtgt ctagctggga gcatctctgg
atggggagat ggaggctgaa attgtcagga atgagggaca ggaaccaaag
ctgtcagcaa gaagcccagg ctgaggtcca ggtctgccac tgtcctttg
agtaatgcag tgagtccctc ctcatctctg aacctccatg tccatccat
gagacagaga ctctgctgcc tacctcaaaa gggcactgta agattgaagg
tgggcatcag acaaggtatc atgaagtggg ccttgcaatt gccattgctg
tcatttttct ttctcaacag
```

FIG. 11B-18

```
                                gtaagt gaatcttggg gtgttctaca
agagcttcca ggagctgcct tctgccccct ggagttcagc caggactgac
ctgcaaccct ttcctctccc cag
```

FIG. 11B-19

```
                                   gta agcctctttt tgctcccta
cccctgaggc tggagctcct acagctacag ccacagagtg ggcatggctc
cccctgagcc tgtgtgacct ggattcctgc ttgtctttct tgccag
```

FIG. 11B-20

```
gtgagtcctc aggcaccat tgttcagtca ggncccctgg ggagtactgg
gcaggacaag gcacccta aggctgtgtg tgtgagagtg catgagtgtg
tgcgtgagtg tgaatgtgta gtgtgtgtga gtgtgtagtg tgtgtgtgtg
tagactgtgt gtatatgagt gtatgtgtac agtgtgtatg tgtgaggctg
tctgtgagtg tgtgtagtgt gtgtatgtga gtgtgtgagg atatctctga
gtgtgtgtgt gtgactgtga gtgtatgtat gtgtgtgtga gtgagtgtgt
gtgtgtctgc ccaagtgggt gacctgctgg ggaggaccat ctgtgccaag
agcccagtca gcccaattc agactttagg cganntggg atccagtccc
atggtcactg gggccagaca atgagattcc agcaaatcag ccatgggct
aatggattt ggtctcgatc ccagttctct taactctttt tttttttt
tcccaattaa tagacctgtt gggggaagcg gttttaagtt tacagaaaaa
tggagcagaa aacacagtta actgttatta ttgttagtt ttaatta
tttctttc tttaaaaa ttaaaaaatt cttatacttt tatttctta
ttagacagca gagatcatct agttgttttg ttttgtttg tttttgagat
ggagttat tcttgttgcc caggctggag tgcatggtgc gatctggct
cactgcaacc tccgcctccc tggttcaaga gattctcttg cctcagccac
ccaagtggct gggattacag gcatgcgcca ccatgctcag ctaattgt
atttagta gagacaggt ttcaccatgt taggctggtc tcgaactcct
gacntcaggt ganccactg cctcggcctc ccaagtgct gggattacag
gtgtgagcca acacgcccag caatatctag tttttaatg caattttta
actatacaga aaccagtga gagtgatata aagaatcccc atgtacctat
```

FIG. 11B-21

```
cacaggttcc aantcagtta ttaacatttt gtcagtcttg tgtcctctat
ccccagacc cctccttcct ttgattttgt tattgctttg ctctgatgtt
ttcaagtaaa tccttaacat cctatcatct cagccctaga tactttgta
catatctcta aacataagc actcattctc acataatcac attatcacaa
ctgacaaaat aaacaagtac tccctaacat catctaatgg ccagtctctg
ttcagttttt cccaattatc tcaaaaatgt cttttcctgg ttcttgttca
aatcaagact cacacagcat ccacacactg cattcggttg ttgtgttcct
ttggctgagt ggattgtggg gccttggcca aggtctcagt ggattctggc
tcccacccct gctcctggctc agcccagcct ggcctcctgg cactgacttc
tcctccctcc tgctggtgcc agggcaggaa gggtactccc aaggctctct
cctccggccc ctgcatggtg tggcctgtgc cagaggaact ctggaccta
gaggccactg ttctcagtgg ttcccctctc tgcacagcca gacagggcc
caacatcctg agggtgacct gatctctctc cgctttgcag
```

FIG. 11B-22 gccagaggcc taggcccacc aggacagagg ccagggccca gctgctttgt gtaggt
ccaaccccc agaagagaag cctgggatgc tagtctgaac tctgcaactg
gtgggctgc tccataacct caggaaatgc ctcctttct gtgcctcagt
ttcttcacct gtaaacaggg gtgatgacat acgggaggtc atggggagct
tgcagcagtc gggacacca ccctccacac tagggaagga ctgtgttccg
tgaccctcat cccctccca cttcaactcc cctccccag ttgccagtg
gggcttcctg ggatgaccag agccactccc tccctgcaca ctgcagctgt
ctcagaggaa caggggtggg tggccagacc ccagacatct ccgcattatc
actctccct gaacttcct cctgggtag

FIG. 11B-23 gatgggactg gggcagggc aggacctga gtcctggatt ctagacacca gtaggag tggggctgct
agagcctggg gccctcagt catggacatg cccttcttg cctctggatc
tcagtttccc tacctgcatc tgggtagaag ccatggccct ctggctggag
ctttaatttg tatctttggt tatctgtcta tcccag

FIG. 11B-24

```
ggtggagcca cagggctgg ccagggcta gtggctgatg aggttagaat gtaagtgtca
ccacacac ccgggctct tgctcaatca ccacctcttg cctgttacc
aactctgtgg ccctggnct ggcgaaggct tcattacttg gacaattact
ctagccttct ctttggccat tccagtcctc catgttggct aaatgggatc
tgaccatttc tgcactatag cacctttccat ggctcccac cgctcccagg
aaaagtcat tcagtccagt ccttcaataa gtagttattg aggtcgggtg
cagtggctca tgcctataat cccagcactt caggaggctc agctgagtgg
atcacttgag gtcaggagtt caaaaccagc ctggccaatg tggtgacacc
ccgtctctac taaaaataca aaaattagct gggcgtggcg gctcatgcct
gtaatctcag ctactcagga ggctgaggca ggagaattgc ttgagcccag
gaggcgaggt tgcactgagc caagattaca ccactgcact ccagcctggg
taacagagca agactccatc tcaaaaaaaa aaaaaaaa aatagttatt
gagtatctga ggtatactaa gtggcaggta aacaattata aataggacag
atgcaatctt tgtctttcat ggctcatctt accattcaat gaccaccata
atctgacccc aacctgccc tcctgccata tcagcaatgg cccctctctg
tcctttccct tctcaacagg ccttggcttt tctgcctcca cacctttagg
cctttgctgg tccctctgtt tgaaatgccc tttctgtcct ctttgcct
tcttatcgtt cagggccatc tccattccat acctcctgga gtccagtcca
tgggagcctg ccctccctcc ctgtgggggt actgagtggc caaacctgtt
tctgtgcaca catgcagact tgtgttcctg cgtgcactca catggctca
```

FIG. 11B-25

```
ggcacctgag agcacatatc catctcttcc acgtagaccc caggtcctgg
aanacaggcc attctctgtg cccactcct ctgncaccac tgtgggaatg
tacagtnaag ttcatcatgc cgtggctgga ccttctgttg ttcagctccc
acaggtgggg gaaatctgga ttggggatgg gaagcaaagc agcaggtgca
tggggctccc tcatgccagg gcagaaactg acttcaactt ctttctgcag
```

FIG. 11B-26

```
                                                    gtgag
gcgatcccaa gctggggaca gaattgagca aggaagtctg gggccaggaa
gacagcaagg cccaggcctc agccaagtct cagaggctca gccagaacat
aagcccctg ggcctaacca cctccctcct gccacctccc accatcatg
cactcctcag cctgcctcag tgcagatagg atggcatggc ttaaaatcca
gaggagaaac aaacaggaaa atcaggagcc aagaggattg aaccaagaat
acccttcc ccgtcccagc tcatctggtt ccaggctctg tttaggcttc
gttgggtttc cctgaggcca agggctgact ggccaccca gactgacctg
agaactgttt tcctgcag
```

FIG. 11B-27

```
                                          gtaaatgc cccctgcact gacacaaggg
ttcctgcttt agggtgaggc catggggtgg agcctaacct agggagagct
ccgagttagt ctggcctctgc ctgacccaat gattcaggga agctcttct
cctccctggg cctgttcccc tatgtacatt gcagggaggg tgggactgg
ctctgttctg gagtgtgact ttcctagatg gccaagttga tgggctggga
atccaacagg cagagttgtt cgttcattta ttcattgcat aaacattcac
taaacacttg caactatgag tctcctcttc atatgaaggg tatagtttaa
tggaagaaat agacatgaaa cgccggggc nnnnncacgc
ctgtaatccc agcattttgg gaggctgagg cggtggatc acgaggtcag
gagatccaga ccgcggtgaa accccgtctc tactaaaaat acaaaaaatt
agcctgggc ggtggcaggc acctgtagtc ccagctactc tggaggctga
ggcaggagaa tggcatgaac ccgggaggcg gagcttgcag tgagccgaga
tcgcgccact gcattccagc ctgggtgaca gagcaagact ccctctcaaa
aaaaaaaaaa aaaaaaaaaa agaaagaaag aaatgatcac atgataagta
attcaaattg tgttgggtcc tttgaaagaa aactacaggg accaaaacc
atgaacagg tggtctggga aaccttccct gatgaagcaa attagctgag
acccagggta gggaggggct ggccaggtgt ggaagggtgg gttccaccag
gtcaaacgct tagccccaat ttctccttcc tccag
```

FIG. 11B-28

```
                                                           g taagtgcctg
gcacaatggc cctccccgg gggcctctgc ggcagctggc actgctggat
acagcatctg ctccgtgcag cccgtgagat gcctccccag gcagggccta
ggtttgcttt gctggtctgc caagtggaga aaggacccc tgccagtgac
agcaggaatg gagggcaccc tgaccatgcg gtgccaggcc tcggtgcggg
aggctacccc tgctgagagc tgctgaggtt gtgacttct ctttccattt
cag
```

FIG. 11B-29

```
         gtg agtgcaggcc agctaaggtg ggcagggcgt catatccagg
cccctcattc cattattcc tttggtttct tttcctca g
```

FIG. 11B-30

```
           gtgccag atggggctgg gaaacncctg ggaaaggggc
cctataacag ggggagtggg gtcggcagga ctcagancct tccggagcct
ccaaacctgc ggntctcagg gttctggtct ggtcggcgag gcggagttgg
aaagaggggt gtggccgaaa gttaggtggg ggaccccgtg gagggggag
ctcgccaaac ccctcactgc ccgctttctc cag
```

FIG. 11B-31 g tgagttccag caccctgtt cccagcgacc
cccaaccctg ctctgcgtcc ccgccgccac cgcgcgtctg acccgtggtt
ctctctgcag

FIG. 11B-32 gtgag cgcgcgccta gggaagggcg gggagcgggcg gctggcccgg
ggtccnnggc ttcgtgagg ctgctccttg tgcctgcag

FIG. 11B-33 gtgagtcc tcccctcccg gcgttctccg
actttcctgg gcggccactc cttcctcga cccccaccccc ccactctcgc
ccaccccggc gccttctcac ccggctctgc tccacccca tccccccgc
ag

FIG. 11B-34

```
                                                          g
tgagtcgggc ccggggtag gaggtgcttc ttctaggtag atctgttctg
gggtgcggct tacccgccaa aggctaggga ttcccagaga ctcaccgact
tccccgagac tggttccaag cccagagca gacaggaagg ctgtgagtgc
agcctgaggg attacccgc gaccttccca agtaagccct tggccctgcc
caggtacaat ctgttcctca gcttgggaat taatgactca acaccagagt
ctcctccatg gcggcctcac gctcagccag gtgggatagg agcggtgggc
ccttgtagcc aggggcttct tcctgaaagc ctctgctttc ag
```

FIG. 11B-35

```
                                                  gtg
aggggcagca accccctcctc acagtcagtt cgagggcatc gccgccccct
caccccctcc cggagcctcc acgtgttcac ttgtctgaaa atctggagtc
ctggggctc cttccagtcc agtctctgaa gggttttggg accttgaata
agtcactctg gcctttgac ttccgcaaaa cagagcccac ggaaggtggt
gcttttctgt ctgcaaacct agggccagg gccatcgga atgctctgcc
tccctagtg ttactgctga caccatctc atagacttcc ctctccctcc
tnctcnctcc ctccag
```

FIG. 11B-36

```
gtgag tgctccctg cggtgggcat gggggccagg cagtgaggat
ttgtccaggc cggccctttc ccattccct tctcaggatg acatacagac
ccttcccgg ttcctcagcc acatggtcca ggagacactc ctgnctctt
tcctagtagc aaacggatgg caatgaatgt actatgttat cactcgggt
ttctgggtt tgttttgaa tgtgcttagt ggtacccat aagcatcttt
ccatgtcaat agagatnggg cggcagacca gcagagcagt aaagcaggca
ggctggagcc acacacgggt gtgaatccag actcccttt ctcatcgtgg
ctctcagacg agttacctgc taatttccct ggccttagg tttactatct
gtaaatgggg gncactgaaa gtaccaacct catcatgtgg cagtgaggac
tatccttaga gtagtttaca tagagtttgt cttagttcac tgagacacag
taaatgctag atattgttat gcttgctttc ctgtaataaa ctttattggt
tacataatct tccatccttt ccaacttt gtctgcacct tcctttattt aacaagccct
gcgtgaccat ttccaactt gcgtgaaaca tagcaaaaa tagaggaaaa gcatttcca
taattttcctt gcgtgaaaca tagcaaaaa tagaggaaaa gcatttcca
attctgaaaa atgaagattt cctttttgt ctacag
```

FIG. 11B-37

```
                                  gtaagc cattggccct gcccagctgc agtgtgttcc
tcagcttggg aattaatgac gtgtggacac tgcggtctcc tccatggcgg
cctcacgctc agccagctca gtccttgata cccagcttct gcacccttt
ggagcacccc ggagtctctg gtggttcca gctctggaag ctgggcctct
caggacttcc caggatccac caccatcact tcacagaggt gatggaaggg
atgtttgctc ccaaagctca ctgattggga gctgggggta ggggacaatc
acagaatctc tgccctgggg gcagagtcct ttctcctatg gtgttttggc
ctcattttct ccatctgaaa agtttcccca ccttcaaaat tctggcctg
agacaagagg tgccctaat gtcttgactt tctcctgttc acag
```

FIG. 11B-38

```
                                                     tgagcatca
ggcccagaca gagcctggag gcatcctggc gggaaggacc agtgccctc
tggtggacat gcaccatcg cccaggc aaaccatctc cccaggacc
ttctgtctgg gactcaggag tcctaaggaa aaggaattct aaaacatggg
ggaagggag gtagagcact gatgggtgaa aaagtgaggc caacacacag
ggcaagtggt gtcgatggag tcgaagcgct gaaggaatag ggcggctttc
cttccagcga gcatcattcg gctgttacca aaacaaacat cttaatctgc
accttcctcc actgccatc ttgtccttgg gtcagtggga catggcacc
tcggaggcc cggggccc ccagctacag ttccacccct cagcttgagg
accaatactg agttctatgc cagttcctga tccatctca ctctctgac
ctactaggtg actgctgctg gggtgactcc cctgaggcgg ctataccctt
aagcca
```

FIG. 12A-1

```
                                                                      Exon #
gctctcccct gcgcccctgt ctttgtaaat tgacccttct ggagtggggg gcggcgggca       60
gggctgcttt tcttagtctg ataccaagca aggcctttc tgaataaatt catttgactt      120
tgagtctttg gtatggaccg gggtcctgtt gggtgctgg tagggctggt gtcacagctg      180
atgtccctcc agctccagt gctggcctg gccggctac cgcctcacat tgctccacca       240
ggtgcctgtg gggcagagt ggtggccag cccctcccac acaccactt ggccacacag       300
tcccaggca tgaacaggtg ggcaggctgc agcctcccag agcctctgaa ggtggaaccg      360
aggtccctca gcaggctttt gccacctagt tgaagatgag tctgggctt cccttgggt      420
tggccggggc agtgcttgtg catggtgggg tctggaccag gccttcttgc ctgctgtgat     480
ctgggatgcg ctgctgtgcc tcgggcaggc ttggcagtac tctctggcgg gcccttggc    540
tccctcaggt ctggtggaga ccaggtgtgc cccaggca gtcccctcct gcagtctgcc     600
cttgtcaccc tgggccagga ccccccgctt cccgttccc ctacatttct acatcagcag    660
ggtaagggc tttttgtggg gcctcagagg aggggccaga cacttgtctt tgctcagtga    720
aggacagggc agaccctgggg caccccctgg tgggaggtt aaagctgtag accctggtac    780
cacttcagat aaaatgccca gctccatct gtccaccg gatacacgag ccggaagtca     840
ctggggagag acacccgagg ttcaataatc cccagagct gcgtggggaa gctgtgggac     900
ccctgtgcc tcaagtgtgg ctcaggggat tcctgccatg gaggaaact gaggcagtga     960
gctggacata ggctagaag tgcagtcact gggcagcgc ccggcagatc cagcgtcccc    1020
agtccaggcc gttgtgggc tggagtcggt gaaatcagc gcctgaagtg aggagcctgt    1080
tggagcagcc ctggggccg atgcctggcg gtgggcacct ggggccagca ggcagtgctg    1140
gccagccaac ccgggcttca gggagagttg accccacaaca ggcgggcagc aggagctct    1200
gcccactcaa aagtgagccg ggggaggctg agctctgaca gtcccacc gtgccacccc    1260
```

FIG. 12A-2

| | | | | | Exon # |
|---|---|---|---|---|---|
| atctgcctgg | agctgggggt | ggtttttga | gggcttgaa | ggtgttcgg | gggggacacc | 1320 |
| aagcaggtgt | cccaggcatg | aggtggctcc | cctggcctga | ggtgaaggcc | agctgtgttt | 1380 |
| tgtctgattt | gggtcagata | gcagtccttg | ctgactgcat | gctgggcatc | atggggatag | 1440 |
| gcaaagtggg | gtgtggggcc | agggaccagg | ggagagccac | tgaggagggg | gctgccaca | 1500 |
| gggtcatctt | gccagtgga | actggtaggg | aggacttatc | ctgtccccca | gaccctgggc | 1560 |
| ttggggtggg | gctggtgctg | ggagcccta | aggccccctg | ctgtctgggc | tgacctgctc | 1620 |
| cactcacctc | tcccgtaat | caaagtcct | ctgttaggaa | gctctgtgcc | aggatgactt | 1680 |
| ggactcctca | ggagggtggg | cctttcagc | tcctcccacc | tcgcctgatg | gaattcgcac | 1740 |
| acacccctcc | cagcccagcc | accgcgctca | cccagcagtg | aaggagaat | ctccctccac | 1800 |
| tcacttcacc | gcgggagaga | ttagagcgac | actattattt | tgagacagg | tctcactctc | 1860 |
| ttgcccaggc | aggagtgcag | tggcgcctc | ttggctcact | gcagcccga | ccttacaggc | 1920 |
| tcaagcgatc | ctcttgcctc | agcctcccgt | gtagctgga | ctacaggcga | gcaccaccat | 1980 |
| gcccagccga | tgttttaatt | tttggtagac | atgaggcctc | cctctgtctc | caagctggcc | 2040 |
| acgcccggcc | gatgtttcaa | tttttggtag | agatgaggcc | tcccctctgtc | gccaggctga | 2100 |
| ctgcgccgg | ccagagtgcg | gtgctcctgc | tgagcagttt | tgcccact | cccctctcat | 2160 |
| cccctcccgc | ccttgctaac | tcacagcatt | gcaacagtca | tgagtccca | cctgccgaaa | 2220 |
| ggaagctcct | gcagcccct | acaacccca | gggcagcctt | tctcgggaat | tttcaagatt | 2280 |
| cctggggag | gggctggcat | ctgcgccttc | actgagccta | caggcaactg | gaagctttga | 2340 |
| gtccctagg | gcagcgactg | ccctggcctg | ctgaggcaga | caggcagcta | gcttggccgg | acctgcgac | 2400 |
| ccctgagctt | ctgggaaatg | gacatgcca | cctggcagc | gcaccgcctt | caggttcctg | cccaggcac | 2460 |
| ggttccttca | ggccggggat | cccgggggagg | ggttcttccc | ctcggccagg | gtcatcgttt | 2520 |

FIG. 12A-3

| | | | | | | Exon # |
|---|---|---|---|---|---|---|
| tgcgatctct | cctgggagtc | tgggtttgga | gtctggtctt | agccggtagc | aactgacgtg | 2580 |
| gcctgaccac | cggcccgtc | caggtccacg | ggtgaggggc | cgcggtgggg | gtgctcccag | 2640 |
| cccagcaggc | agcgctggac | agtgacccg | gagcgggaac | cagggctgcg | ctggcactg | 2700 |
| accgggccct | ggtaccgggg | attcaccctc | cccggggtgt | ccctgggcct | tgggtcgcct | 2760 |
| gggtccgctc | cgcgcctgg | ggaggatct | gcgcttcgg | aaactcgcgg | gtctcccctg | 2820 |
| cccctccctg | aaggcggccc | ttcagcgccc | ggccgttccg | ccccacact | cgggttgagg | 2880 |
| agcaaggaga | gaaaagagcg | tctttctctc | ttgctcaaag | ctgcgtgtgc | gcaacgcgcc | 2940 |
| agtcccagga | taattttaac | tcgcggccgg | agagaacgcg | cgcccgccc | ggcgtctttt | 3000 |
| ttgttttcgc | ccaggcgggc | tggacgggcg | cgcgggggcgg | gtggaaccc | ccacgcaggt | 3060 |
| gggcccggct | gaatgggggg | cttgtgcagg | cggggcggg | aagggaagg | ggaaggggcc | 3120 |
| gcccacctcc | cgcccgccc | gccccgcgcc | cgcccgcgc | cgccgccgcag | ctcagactcc | 3180 |
| gctcagccAT | GGCCGGGCCG | CGCGCGGTGCG | CGCCGGTGCG | CGCCGCTCCT | CTCCTCGGGC | 3240 |
| AGCTTCTGGC | GGCCGCCGGG | GCGCAGgtga | gcgcagatc | cgggctctga | ggctgacgt | 3300 |
| ggagccgcga | cctcccagc | cccgaacccg | ccactccggg | gtgcccgcgc | agtcacgacg | 3360 |
| cccccagccc | gtgtcgccgt | cggggagagg | agtcgccagc | gcctcgggat | gagccccgtc | 3420 |
| cggccgcgtc | ctcgatgggt | cctcgctggc | ccggcggcc | gccgcccgcc | cctctgggag | 3480 |
| cacaaggggg | cctttgttcc | cgccgccgga | gggaggcgg | ggacacactc | ggcggggcg | 3540 |
| cctgcctcga | ggctttgggt | ctcaccgagg | agagcggcgg | tcgtcgcagg | ccccggagcc | 3600 |
| gctcggggacc | cgggaggagg | ggacgccggg | tcaggccacg | gggcacctg | cgctccttaa | 3660 |
| tgagttttct | ccgtttcagA | GAGTGGGACT | CCCCGGCCCC | CCCGGCCCC | CAGGGCCGCC | 3720 |
| CGGGAAGCCC | GGCCAGGACG | GCATTGACGt | gagtttgggg | gtggggaggg | ccccgagcgc | 3780 |

FIG. 12A-4

```
                                                                    Exon #
tctggggttc tggctctggc cccacctcc  ctgagctccc cggcctgatg gagagaaaac   3840
caggcccac  ctcccagagc cggggtgaca tcaggggaca gccagtgcct tcacggatg    3900
ggggtggccc tgcgggactg ctgtgggta  ggggtggagg gtgtcatgtg gtggtcctcc   3960
accagaatt  ccggcactga ggtgtgtgtc tctgggtccc tgaggggccc gtgccctgt    4020
gttcggggtt ctggcctctg gctgaagtgg gagaggcacg tcctttgggt ggttggggc    4080
cggggtcttg ttggaggctg ctgggctctg gagccagcca tggagggct  taggagccga   4140
ctcagtcctg agatgatgtc ccctatgggt atctcaggac tggtgtgggc caagcagcag   4200
gaggaggcgg ctgaaattct acaattgtgc ctccctcgga gggaccgtct ggggtgaacc   4260
tcccatgtg  accaccacca gggcaggagt cccctcaggg cctgtccacg ctgtgtggtc   4320
cccgtggagg gctgtgtgagg gctgcaccaa gagccccca  tgaccaccc  tctgccccc   4380
tgcccagctc ggcctcaatg gccatagcct ccttccagtc tgtccagttc acccctttgc   4440
ccagtgctgc cccacacatg ggaggtgcc  ctctaggtag ggatcggggg ctcaggggcc   4500
cctttgtct  gctggggctg ggggctctgg gctgatttgg agccagcgc  tgctctttc    4560
ccgaggcggg gttcttgagg gaccccctgat tttcagggtt acatgtgggt gtctttcctc   4620
acagGGAGAA GCTGGTCCTC CAGGTCTGCC TGGGCCCCG  gtgagtgtcc ctggctgggg   4680
agacagcctt tttcagtct  ggagagaaag ggggaactca gaacagaggg gtcattgata   4740
tcctgtctca tcctgccgga gcccggttg  cctgagggga ggcctcagag ggcttggagc   4800
aggcctggc  ccagcggggc ggagggagt  gtgggctcag cctctgcaca tgttcagggc   4860
agggcctggc tttgaagctt tcttggacc  agccaggc   aggcgggacc aggcggctgata  4920
cagcttcagg tcccccaggc ctgaggtcac ctgagccct  cccaccttct tcagttcctg   4980
ggggttgaggg tcctgggggct cagagccctg tctgggccca ctgggcccct gacagagatg   5040
```

Exon # 3 (at row 4620)

FIG. 12A-5

| | | | | | Exon # |
|---|---|---|---|---|---|
| ctgctggcc | cttagccagg | gaggccgagg | tgaccagacg | aaggtgttac | agatgccact | 5100 |
| gagggatggg | gcgggcagcc | ttcctgggcc | agcaaggtgt | gggcaagcag | gacacacgag | 5160 |
| cccagctga | gccggtctg | ccagacagta | gggggaccc | aggagagggg | cccatcccgt | 5220 |
| atgttgggct | gggggaagtg | gaaagcattt | tgcttcattg | ctgaagcctg | ggctccaggc | 5280 |
| cagaccccgc | cttcacatct | ctgcccttc | ctcctgcaca | gGACCAAAG | GGGGCCCAG | 5340 |
| GAAAGCCGGG | GAAACCAGA | GAGGCTGGGC | TGCCGGGACT | GCCGGGTGTG | GATgtgagtg | 5400 | 4 |
| cgcctgcccc | tcccgccat | gcccactcc | ccgctccggg | tccctggagg | agtccggccc | 5460 |
| taattgctgt | tgtccagctg | ggcctgctca | ggcgggaagc | ccagtcctga | gagaagtctc | 5520 |
| cagaagtccc | ccaacagggg | tccttggcc | ttcatcccag | acgccaccag | catctggcag | 5580 |
| gggacagagc | cagcccagtg | gagtcggaag | tcccgccca | ctccttgct | tgtccaggaa | 5640 |
| tgagtgccca | ttgtcaggac | cttctgccca | ctgctggcct | cacttagtca | tctttgggctc | 5700 |
| caggccagcc | ccaggccacg | gagtttgttc | ggaggaagcc | gggcctgaga | agtgagctgt | 5760 |
| ccagtcctgc | tgggttggtc | cccgtggcct | gactacagca | ggtgcctccg | ttgctgctt | 5820 |
| ccgctgggct | gcccctccc | tcctccagc | ctctgctac | agcaggcaga | cagtggacag | 5880 |
| ggccaagaga | ggaggctgcc | accctaaggg | tctttctatgc | ctctctggac | tcaccaaggg | 5940 |
| aagggtccgt | gcttccattt | ttgcctcatt | ggtggcatgt | gcttccatg | tggcccctcg | 6000 |
| agctcgcccct | ctgcctctcc | ccagGTCTG | ACTGGACGAG | TGGACCCC | TGGACCCAAG | 6060 | 5 |
| GGTGCCCCTG | GGGAACGGGt | aagtgcctgc | gccgaaccca | gtggcttggg | ttcagaggtg | 6120 |
| aggtccctg | gccacctctg | gctgctctgt | gtccacaagg | ccaaggagct | ggtagttcca | 6180 |
| aggacagctg | ccctgcccgt | gcctgggtg | gaggggcaga | aggggcaggt | gccaagtgc | 6240 |
| cagtcccctg | tgcctgcctc | cctgcctcac | ctccacgtat | ggtcagagtt | gtcctggtat | 6300 |

FIG. 12A-6

| | | | | | Exon # |
|---|---|---|---|---|---|
| ccagaccatg | gcagggagaa | ggggatggt | ttggggaac | ccaccccagg | tgcctcctca | 6360 |
| gaatgtccct | gaagccccca | agccctggc | agaccaccac | caggaccc | cgggcacgca | 6420 |
| gcctgcagag | tccctgtgc | ctgcctgttg | gacactgaat | cctttaccct | gacgagcgg | 6480 |
| caccacacc | caaggtgcc | tttctcccct | tgtgcttct | gagtacaaac | ccgaagccag | 6540 |
| caatccctct | ttggcttcat | aagacgtggc | tgtcagcagc | ccggtgcca | ctgccccag | 6600 |
| gcgcaaagca | tcacagaggg | caggaaggct | gggctgggga | cacgaggaca | cagccctgcc | 6660 |
| cttgggacc | cttgggagct | cgtcaggca | tgaggcggat | tctgagctga | aaacaggagg | 6720 |
| gaaacagtag | ctgctggcca | gcgagtccgt | ggtgccag | ggtgtgggt | ggctggtcc | 6780 |
| caggctttca | ggaggggcct | ccagcctcag | cacagggccc | gtgcgtgccg | tccaggaat | 6840 |
| gaggcattc | aggcagcagg | ggccagacag | ggccagaggg | tgtggaggc | agacagggcc | 6900 |
| tggctgccaa | ggctctgggg | ctcgctgacg | tgggcggggg | ctgaggactc | agcaggctcc | 6960 |
| gtgggtgggt | tatcgggagg | gcttcctggt | ggagacaggc | accccgggtc | acttcggtgc | 7020 |
| ctctcagccc | tgcctcagtt | tgcaccttct | tgcagcgagc | gctggactc | tggtgccatc | 7080 |
| tgtctccagc | agctcccag | gacggcaaag | accctccagg | tcaagagggc | tcagaggcct | 7140 |
| gccctctgt | gaagtgggga | cttgaccct | gttgtcctgg | gagttggagt | tgtgacgtca | 7200 |
| cacttcagag | ggaggggatt | gggtttgcaa | atagaggccc | agccaaccta | gacgcctgct | 7260 |
| ttcctcccac | agGAAGTCT | GGACCCCCG | GGGCCGCCG | GGCTGGGGgt | gagtatgag | 7320 | 6 |
| tgtggtcctc | tcctctccat | gggagtttgg | ggagctggag | agtctggtct | aaatgggtg | 7380 |
| gcctccagga | atcccagga | ccatcctcatc | ccctctctg | tgcagcctct | ccggagctgg | 7440 |
| tgcctggatg | gggtcctggt | gccctctctg | ggctgggacc | agacaccat | cctggaacc | 7500 |
| gcccttccc | caggaccac | ctgagccatc | ttaggaggg | gtgagcgcag | cccttcttgt | 7560 |

FIG. 12A-7

|  |  |  |  |  | Exon # |
|---|---|---|---|---|---|
| gcctggcagg | ctctgacccc | atgtttggct | ttgcagGGCA | AAGGCTCCC | TGGACCCCC | 7620 | 7 |
| gtgagtactg | acaacccttg | gggccctgag | caagcacgca | agtcccgaga | gcctgccagg | 7680 |
| ctggatgtc | ccaaaccgtg | cctggggtg | gggcttctca | gggcagcca | tctgaccacc | 7740 |
| ccatacttgg | agccctctc | cttcggaggc | ggcacaggcc | acctgggtg | gggatcctcg | 7800 |
| gggcttccgg | gtgcagacct | cccacctct | cttacttcc | ctccagGGAG | AGGCAGGAGT | 7860 | 8 |
| GAGGGGCCCC | CCAGGTGGGA | TCGGCCTCCG | CGGCCCCCG | GGCCCCCCG | gtcccagagc | 7920 |
| ccctcagagt | gtgctcacct | gtggcctcca | ccccagact | cccagccag | gggtccctc | 7980 |
| ccctctccct | tttccttc | tccccaacc | ccaccttggg | ttgttggtag | aagccctggc | 8040 |
| caatgatcca | gacccgacct | caggacgcac | acaccagcag | agtccgtggg | agtggggct | 8100 |
| ggtgggagct | gggcgtgtcc | acctccctgg | gagaagccgg | gcacctcact | caggtgggg | 8160 | 9 |
| ctgtcccac | tctgtctaag | tcataccccc | tccccagGGA | CCTTCTGGAC | TCCCGGCCT | 8220 |
| CCCTGGTCCC | CCAGGACCTC | CCGGACCCC | Tgtaagtact | gggcagaggc | tctaagaagt | 8280 |
| gctgggcatg | gactaggaca | ctgggttggc | cccctcccat | tccccctcc | caggctccat | 8340 |
| gccctccga | gatctcctaa | ccctaacttg | gccactcccc | aggaacagtc | aatggtgggg | 8400 |
| gcagtgggct | gtgctaggcc | agccaacttg | ggatggtcag | gactcaggtc | cccatgccat | 8460 |
| cctgcccaa | ggacacttgg | agccacttgg | attctgtcgt | tgtcacatac | cctgtgggtg | ggccagcagc | 8520 |
| tcccagcact | ggccacttgg | gggacaggat | gaagggtctc | caagtccct | ggtgatggg | 8580 |
| gaaggtgtg | gtccgtcaga | gagtgggtgg | gtgggttggg | tggctgcagg | tggctggga | 8640 |
| ggcgggaga | atgtcagctg | tctcttttg | tcttagGGAC | ACCCAGGAGT | CCTCCCTGAA | 8700 | 10 |
| GGGCTACTG | ACCTTCAGgt | aggcactga | agcatttgt | taagggtgct | ggggtgcc | 8760 |
| tacctgggg | ggaggggttc | ggcctggag | ccatactgg | ccatactggc | aagaaggcag | 8820 |

FIG. 12A-8

```
                                                                              Exon #
gccgagccc tccctggga caggagctca gagcagacag ctcggcaca acctgcaga    8880
gaggctggct ggacctccc ctcccctt cccaccctcc tcaccacgt ctagacctgc    8940
actgtccctc atgaagccac caggcgcatg gagctgtaca aatgtaatga atcacaatca 9000
tgtcacagag ccatccagct ccctgcgtc atccgcagag ggcgccctg gccacagatg   9060
gcgacagaac tggagtctga gacccacctt tatcttgatc tttgagcctt gtcatttgcc 9120
tgaaagaaa acaggctcag gtcaggcgca gtggctcagg cctgtaatcc cagcactttg  9180
ggaggccag acaggaggat cgcttaagct caggagtttg agaccagcct gggcaacata  9240
gtgagatctt tgtctctaca aaaaattgtt aaagtagcca gacgtggtgg cgtgcctgtt 9300
gtcctagcta cttggatggc tgtggtggga ggatcacttg agcccaggag gcagtggttg 9360
cagggtgctg tgatcaagcc actgcactcc agcgtgacga gccaagctaa gcctgtctca  9420
aaaaaatgaa gaggaaagaa aatgggcttc ggaggccacg gatccatctc tcctctctgt  9480
ttggccgtcc gtggtggcag tcagcgcctt gtttccatag agaggtttga tagttttgaa  9540
gggaaaagct cggccactc tgacctgacc accgacgctg tctaccagcc tctctcctca   9600
ccccaccccg gggcctaggt gcctggccag cctgtgtccc agaaggagg ctttagggaa   9660
ccttccagaa tgtggtgcgt ggttgggccc ccgatcgtgg gctgagtggg gcagggcta   9720
aagatacggg tctgcaccct tggcctggcc tgcccattgc agctgtagga tcatctagaa  9780
gcagccctgg gtttcctgag catcagacct gttgcctggg ctcacagtgc ccctcctaaa  9840
agcccatgc cgagcacatt cctgctgctga ggatggccc gacctgaggc tgctgaaggc    9900
ccctgcagt gccggccggg actgtgctga atggctgctt tgatagccag tgtctgccgt   9960
gggccggctg ctccatgcag ccctgctga cttggccagt gctgaaggag accctgtctg  10020
tgtcctgtcc cagtgccatc tcctgtacga gtgcctcct gggtcccgt cactgtgtgg  10080
```

FIG. 12A-9

```
                                                                          Exon #
agtggcctcc tggggtcccg tcactgtgtg gagtggcctc ctgggtcct gtcacccaga    10140
gtgtcccgac accgcgccg gagtggcctc ccggggcccg tcacccacgc ggagtggcct    10200
cctggggtcc cgtcactgtg tggagtggcc tcctgggggtc ccgtcactgt gtggagtggc  10260
ctcctggggt cctgtcacca tgaggagtgg cctcccgggg tcccgtcacc gtgcagagtg   10320
gcctcctggg gtccatcat ctgtgcggag tggcctcctg gtgcctcctg actgatgcgg    10380
agtggcctcc tggggtcctg tcaccgtgag gagtggcctc ccggggtccc gtcaccgtgc   10440
agagtggcct cctgggtcc cgcgggcgct gacccctgcg tgacgtcct gctctgtttg     10500
gctgggaggg gtctgactgc tctgttttcc gacagTGCCC AAGTATCTGC CCGCCAGGTC   10560   11
CCCCAGGGCC CCCTGGAATG CCAGGGTTCA AGgtgagtca cggtgactg ggaccaagc     10620
accacctgt gctgggcagg aggcagctgg gctcccatgg ggctgtgag gtgcgggtc      10680
cagaaagctg gaccctggtt ccacgttgc cccaggaaga aagctaggcc agcctcctg     10740
tccgccttc agcacccag tgacacgctg atgtggccag gctgggactg gccataggca    10800
tcagagactg cggggagag ctagcctcaa gctcccaccc cagcccagcc ctgcccgct    10860
cctgaccgca gagcgcctc atgtggggtc ctagcgcctc tcaggcctca gtttcccat   10920
gagggcccag acccgcggtc ctgtgcgctg cgtgtgcgg ggcctgggc tgactgaccc   10980
tgcaggcct acttcagtgt tgccaggag gggtgtcgg gggtctggg tgggcagtg       11040
accccacatt tgcttgcagG GACCCACTGG CTACAAAGGC GAGCAGGGG TGGGCAGTG     11100   12
GGACGGGCAG AAGgtgaagc AAgtgaagc cagcgggga ggagctgggga actgaggct    11160
gggctccggc gggaggagg ggctgggctc cggggtgggctc cggcgtgggctc ttcatgggtg 11220
cacctgcact ggcaccttct gtgctgtctt ccagataggg cctggctggt cagagctggg   11280
tgatttaggc tgggtcctgg acagaccccg tcctgcctgg cctcgctgtg gaagctccct   11340
```

FIG. 12A-10

| | | | | | Exon # |
|---|---|---|---|---|---|
| ggtttgtgtc | tgtggccggg | gcgaggggca | tctgtgagga | tggctggctt | tagcctgtag | 11400 |
| cctccctca | cctgtggtcg | ctgtccgtgg | agggtgtctg | tccatggtca | cctgcaggcc | 11460 |
| ggggaccag | gtctggatg | cccttagcg | tggctggagt | gatcagatga | ggagaccca | 11520 |
| ggtgcacatc | agaggggtcc | ctgcttggcc | acgaggaggg | gcctggacag | ggctgaaggg | 11580 |
| ccttgtggga | acagtgacca | cggaccccgg | cccgcaggg | cgaggccacc | cgagactcgcg | 11640 |
| ggactgctct | ggaactgtgg | gcaagtgtcc | ccttcacaga | gcctccaagg | cccagctgtg | 11700 |
| aagcgggcaa | cacccccagc | tgcttgggct | tgagtaggt | gactggaggc | accgaaaggt | 11760 |
| gcaaggagag | ccagactggg | ccgctgacca | ccctatcccc | tctgttttcag | GGTGACCCTG | 11820 13 |
| GCCCCCCTGG | GCCCGCCGGC | CTCCCGGGCA | GCGTGGGGCT | GCAGgtgagg | ctaggaaggg | 11880 |
| gtaaggatgg | tgggatggga | actcagccca | cagagtgatc | aagccctgca | catatctacc | 11940 |
| cccgagggggg | ccagctccgg | ctgggggtg | tttggccaac | accaggcac | aggagcgcga | 12000 |
| cctggctggg | ggtcccacct | ctgccaagc | tgctgacctc | aaggctgtg | ccccctccct | 12060 |
| ctggggacc | tgagctgagg | ctgagggctc | atggaagaca | ccaggctcc | caggggtacc | 12120 |
| ccgagggcct | tggcctgggg | tgatccccgg | ggtggaggtg | cagcccagc | ctctgcatct | 12180 |
| gtgcctctct | ctcgcagGGC | CCCGGGGAT | TACGAGGACT | GCCAGGGCCA | CTCGGGCCCC | 12240 14 |
| CTGGGACCG | Ggtaagtcct | gcagcccta | gtggggccg | gccagtggc | tgggggcctg | 12300 |
| gttgtctgca | cctccagact | tcagatggc | cccgtgagtg | acactctgaa | gcagccggca | 12360 |
| ccctgctct | ggccatcgcc | actgtggcgc | aggccttgct | ctgggcccct | gttctcgcat | 12420 |
| gtgcctgggc | gagagctgac | agtcggcgac | ctgatgcc | cactgatgcc | cccaggctgc | 12480 |
| gtgcctggct | gttcacgcgt | gtgcccgggc | gaggctgat | gaactctgct | cgctgacacc | 12540 |
| cacacacacg | gtcccaggct | gctgtgaggg | ctgttgtggc | ttaggccaga | gcaggagggg | 12600 |

FIG. 12A-11

```
                                                                            Exon #
aagcagggat ttggagacta ctaggtggca tcttgggga acttgctggg gagcctaga      12660
ggaagggctg cttgtgtctg ggccgcccct gaggagcac tggggatg ccagccagc       12720
ctcagacaag aggacccgg atccctctc tcctctgcag GGTCCCATTG GGTTCCGAGG     12780  15
GCCGCCTGGG ATCCCAGGAG CGCCTGGGAA AGCGgtacgt gtgtcagtgg acgtgggcg    12840
ccatgccacg tgacctctct ccctttccc tctgctcctc tcagacgccc ccagcccac     12900
tggggcccct cttctctggc tgagctgttc cctgacacc ctgggaggc ttgtggcatg     12960
ggtacggggg tgcttaccaa tggaatccat tctttgtgag acattcgcct cctttctgt    13020
tctggacgtg gaatgagggg tcaccatcgt cctctgca cctccagcca tctctgacca    13080
ctcctggagg gtccaggcct ggaggccc ccatcccact ctctgaccac tcctggaggg    13140
ctgtcccccg cccgggcctg gagggccc ctcatcctactc tccgaccatc tccatggtgt   13200
taactctgtc cctgccccac ctcatccttt ccagGTGAC CGAGGCGAGA GGGGCCCAGA    13260  16
AGGGTTCCGC GGCCCCAAGG GTGACCTCgt aagtgagagg gaagttggtt ccctggtcc    13320
ttatgtgaa gaaccaatt tccctcctga ctcgtgctgg ggaggggac acacttggga      13380
gtgagactgc aagggctgc ctgggtggc ctgggtgc gtgggggtga gcctgaccct       13440
ggagggccccg agatctctcc ctgcccag ccgttctccc agagccacat gggagctctg    13500
tggcccctg cagagcggcc cacgggcc gagggaccag gctccagggc ttggatcctg     13560
cccccagaga aaacgctct cgggttgagc aagtgaacat aaggaaagtc cagaggcagc    13620
caagcgttcc aggagtgaa ctgaagtgac cgtcagcc ctggtcagcc tccacacctc     13680
cctcgactga gccctggcag ccggagtgca gggagccgcc gtgccgtcct gcagcatctg   13740
tggatccaaa cacagttttc tccacgcacc cacaggcccc agggtggttg gtcgggggtg   13800
gccccctgccg ctgcccacca tagctccttg gtgtcccga gcagctggcc ggagaatgcg   13860
```

FIG. 12A-12

| | | | | | Exon # | |
|---|---|---|---|---|---|---|
| tgaggccgtc | tgggaagaga | ctgccactgc | ttctgtcact | tgtgtgtcct | ctagGCAGA | 13920 17 |
| CCTGGTCCCA | AGGAACCCC | CGGAGTGGCC | GGGCCAAGCG | GAGAGCCGgt | gagtgcacgt | 13980 |
| ggctgctcat | ggaatgctcc | tccccgggt | cctgggtatg | tacaggtga | gatgcattc | 14040 |
| agaaggctg | gagctcagtg | ccctctgctg | tggccatctt | gaaatctggg | ttaacggtgg | 14100 |
| aacagccccg | cagcccaca | catttctctc | ttgcccagag | cctcacgagt | gtgcaggagt | 14160 |
| agggcctca | ggctgggttt | acctgcacag | aggacacggg | aagtaaggt | gggtgggtag | 14220 |
| caccactggg | cagaggtggg | cactcccagg | gtcccgggca | cccgtgcggg | caccttcctt | 14280 |
| cctgctgggt | gcccaccctc | agcccagacc | tgagctccct | tctagccct | cgtgttgcct | 14340 |
| ctgccccgga | gtagtgccct | gtcttgggac | acccagcagt | tggctgtgtc | ctgattccaa | 14400 |
| aaccagtcca | ccaaacttcc | ttagggacc | agcaggcc | atgatgtgcc | caccgtaaaa | 14460 |
| tgggccagaa | gggtgaccg | agcaggcct | gcctaaggcc | tggtggacga | ggcctcgggc | 14520 |
| gtcagcactg | catcagcacc | gcctctgcca | cccacccgca | ccctgacct | gtgcggtcac | 14580 |
| cgaggtagca | ctggttgcca | cacggccacc | ttggtcatga | accagataa | ctgccagggt | 14640 |
| gtggggcag | acacagtttt | aggttgatgg | ggaaggaggc | tgccccagg | gcgggactgt | 14700 |
| agagggaggg | aggggggcca | ctgcccgacg | ggccttactc | atccctttgtc | cccagGGCAT | 14760 18 |
| GCCAGGCAAG | GACGGCCAGA | ATGGGCCACA | AGGACTCGAT | GGCCAGAAGg | ttggcatggg | 14820 |
| gctcagggtg | tgacgggag | gaggggctg | gagggagtt | cggcctcccg | agcctcagc | 14880 |
| ctccccttcc | gcaccccaat | ctctgtcctc | acagGGAGAG | GCTGGTCGCA | ACGGTGCTCC | 14940 19 |
| GGGAGAGAAG | GGCCCCAACG | GCTGCCGgt | gagtgcccgg | cgggtggggc | cagcctgggg | 15000 |
| cgccacagct | tctgcctgct | cagtggcca | tgttgggctg | ggtgggttgg | tcactgtagg | 15060 |
| gccgactccc | tgtgagggt | tctggggcct | gtgtccatca | gtgtccatca | caaccccctgg | 15120 |

FIG. 12A-13

| | | | | | Exon # |
|---|---|---|---|---|---|
| tgcccagtgg | tgctgtggac | ggttgcctgt | atgtttgcat | gtgtgtgctt | attcgtgtgt | 15180 |
| acatgggaca | tgtgtgaaca | tgttgatggc | catccctgga | tgccgtgcgg | tcatcacccc | 15240 |
| catgggctct | gagtaggggc | tcctgcatcc | aaggccaggg | aggctgtcaa | atcctcacct | 15300 |
| caggtccaca | aggctgggag | aagttgccc | tgccttttggg | tgcactcact | ctgccccgg | 15360 |
| cgccctgcct | gcgtgcacgc | ccctgggtgc | tgctgccggc | gtgcaatgta | actgcagcc | 15420 |
| ctgaccgcaa | gctctctcct | ggcagGGCT | CCCTGGACGA | GCGGGTCCA | AAGGCGAGAA | 15480 20 |
| GGGAGAACGG | gtatgtggct | gcagcgcttt | ctctctggga | ggggaggcga | ggggccggga | 15540 |
| ggcaagggc | tgggcagcga | gtgcaggtgt | aggcaggcac | tcacagctct | ccttcctcta | 15600 |
| cagGGCAGAG | CTGGGGAGCT | GGGTGAGGCC | GCCCCTCTG | GAGAGCCAGG | CGTCCCTgtg | 15660 21 |
| agtatctgcg | gcgccccaga | ccctcccca | tccagcctgt | gtgcagaccc | tgcctgaca | 15720 |
| ccctccttcc | tttccctgta | gGGAGATGCT | GGCATGCCTG | GGGAGCGCGG | TGAGGCTGC | 15780 22 |
| CACCGGGGCT | CAGCGtgag | tgcagggaca | tggcccgggg | tcggggtta | gcactgagcc | 15840 |
| attggcacat | ggcccagtt | tctgagcagg | atgccaggag | atttggttgc | cttgatgggc | 15900 |
| caggcccaca | aaagcctagg | atgcctagg | gtgtggggcc | ccatcttctt | gtccctcacc | 15960 |
| cgctgggaga | cggtcgggc | caggccggag | ctgccctgtt | ttcaagcctt | ctatgctgag | 16020 |
| cccagcctg | tgccccata | gactgagata | atgacagcac | cagccacagg | gccctggtgg | 16080 |
| gggagccag | ggcatgggt | gcctgcccc | gagtctgggc | tgacaaattg | ggtccaggtt | 16140 |
| atgccgagtt | ctgagacccc | ctaaactgcc | ctgggaggta | gccctgcctt | tgtcccagc | 16200 |
| aacccagcca | ggtggcttag | aaccggctcc | tgtgtccacc | cactctgggg | gaaggctgag | 16260 |
| ccaggctccc | tgggcctct | tgggggagtcc | tcgaaccctg | agacatccgc | tcacacctca | 16320 |
| cctttgtctt | ccagGGGGCC | CTCGGCCCAC | AAGGCCCTCC | CGGAGCCCCT | GGTGTCCGAG | 16380 23 |

FIG. 12A-14

| | | | | | Exon # |
|---|---|---|---|---|---|
| GCTTCCAGgt | gggtgaggtt | gggcaaggg | cctggcatgg | cacccagacg | 16440 |
| ggccagaccc | gacagtatgg | gcactgacga | gccaggacct | GGCCAGAAGG | 16500  24 |
| GCAGCATGGG | AGACCCCGGC | CTTCCAGGCC | CCCAGGGCCT | CCGAGTGAC | 16560 |
| GGtaagtgg | ccctctcagc | aggaagctcc | ctctacccat | gtaccacagt | 16620 |
| ccccacccc | ccaccacagt | ccctgggac | gcagacaggg | agaggccctt | 16680 |
| gtgggaaatc | tggccatggg | ccctgggac | ctgcgtggcg | gaggcagtgg | 16740 |
| ccgactgtgg | cccctttgc | ccctcctgacc | ttccacgtgg | tgttccttgt | 16800 |
| ctgcgggagc | ctgggcgctc | tgcctcctgc | cctgcgtaga | cgcctggcgg | 16860 |
| cggtcagtgt | tcattcctca | agatcgtgga | ggctgaggct | caagaccac | 16920 |
| gcctagcggg | tgtctgtgga | ggcgcggttg | acagaggatc | acgttgctat | 16980 |
| tgaacaccat | gtcccaagtg | actgtaacgg | tcacagcttc | tacctcgtca | 17040 |
| ctgctggtct | tgcagcagct | gcagcattag | ctccttggg | gtccgggcag | 17100 |
| cggcctaccc | agggcccag | ctcactggaa | ggagcctgtg | gtctgtct | 17160 |
| catgctccac | caggtccttg | gggacctcgt | gtgcctgctg | tggccacctc | 17220 |
| acagacccct | ttagatgt | caatcccgag | aagcctccag | gacacggctg | 17280 |
| gtcattccag | ggtgatggtc | attccagggt | gatggccgg | gctgtgaca | 17340 |
| taggggata | gcgggctgtt | tgttgcctc | caggcaggac | attccagagg | 17400 |
| gccagcaacc | tcagggcctc | cgagagatgg | tagggctggc | acccctgcg | 17460 |
| ctgtcccagg | tgtggtggg | gcctggtggc | tgaatttccc | tttcactta | 17520 |
| aagtctcct | gcttttctgc | cctttgggcc | agttctcact | tatgtggcca | 17580 |
| tggacatttt | ttaaagggat | tcatagcaac | tcccagacat | gtcctcattt | 17640 |

FIG. 12A-15

| | | | | | Exon # |
|---|---|---|---|---|---|
| ggggaaggtg | attagatgag | cttttgcatc | tttgactcta | ctgtgatgga | attatcctgc | 17700 |
| aattgtgcag | aaacacccgc | acgaattcac | gggtgttaca | aacagtgcaa | acctaacggg | 17760 |
| acttcactac | ccacaagggg | aggctggaca | gagccatcgg | gcccagaggc | tgtgaacgtg | 17820 |
| agcttgcct | ttgggcctgt | gtctgggagc | cgtgttcac | agaagcccct | tgtgcagcac | 17880 |
| agatggagat | gtggggaggt | gtttaccatt | cctggccca | gggcaggctc | actttaggga | 17940 |
| ttcctgccat | tcctctaatc | cagagccttc | tctccacacc | cagGGTCCGG | GAGGTGCCGC | 18000 |
| AGGCCCTAAG | GGAGACCAGg | tgagctgggc | acaggctggg | gcaaaaggaa | tgaaggcaaa | 18060 | 25 |
| gctgcacagc | ttctcccagg | ctcctcctgt | cccggctctg | gccctggctg | tgttttcggg | 18120 |
| acactgagcc | tcctttctcc | tcttgccgtg | tctgtcagtc | gcccttttctg | gctcctgccc | 18180 |
| ctcctgctta | gcacagcgaa | agcagctctg | ggcaccccagc | cccaggcac | gccccggcat | 18240 |
| ccgccgctgc | cttcctgggt | gcaaacagct | ggccatgagt | gtccctgcat | ggctctgggt | 18300 |
| gcacagaagc | tgcttctagt | ccaggaggca | ccaatgggaa | ctctcaaagg | gacagaggtg | 18360 |
| tgtcctgcca | tccttccgga | gaactgacag | agggcagggg | ctaggctctg | cgtgtgtgtt | 18420 |
| ttgcaggcag | attcgaaatg | catttctgct | gttcgaagca | ctcttctttt | tggaaaagtg | 18480 |
| tcagggtggg | tggggccatg | gccgtggctg | ccccgcccctc | ctgcagtgcc | tgctctgggt | 18540 |
| gggccccgtg | gtctggctgc | cccgcccctc | tgctgagcct | gctctcactt | ctaggcacaa | 18600 |
| ggcctttcca | taccgcgctg | gaggcctgca | gccatcgaac | cccaccgca | ggttctgctt | 18660 |
| ggcagaaaaa | cctcattatg | caaacaaatg | tcttccgttt | tttggccccg | cccctgcctg | 18720 |
| caggtctccc | aagggctgtg | tttggagcgg | gttaaaaggc | agccctgggg | cctggcttt | 18780 |
| tggcctcgac | cttaagatga | acattacacc | tacggaggct | tgagagcagg | gactttaagg | 18840 |
| catgaagtcc | ctactcatgc | atgaacagct | cttttaactt | tggggtgtat | cgtttttcagG | 18900 | 26 |

FIG. 12A-16

| | | | | | Exon # |
|---|---|---|---|---|---|
| GTATTGCAGG | TTCCGACGGT | CTTCCTGGGG | ATAAAGGAGA | ACTGgtgagt | aattaggtaa | 18960 |
| cctcactgtt | accaacagct | gggagcgagg | tcgccactgt | ggctggggaa | cagtcctggg | 19020 |
| gacaggtca | aaatctgcag | ctcccgtgg | aagatcggca | gctctgctgg | gcagcgtggg | 19080 |
| gatggagcag | ggtcgggcag | aggccttgc | cactggccat | ccctagcaa | gtgggctggg | 19140 |
| cctggcaggg | aaactcagcg | gctctggagt | ctgacctgac | ccggtgctca | gacgtgtggg | 19200 |
| ctcccgcact | ctgcccgtg | gagtggcacc | tgcatgaagc | agtcacagct | gcattttgt | 19260 |
| ttttttgttt | ttggttttt | gggtttctt | gtttttgtt | ttgagacgag | tctcactctg | 19320 |
| tcacccaggc | tggagtgcag | tggcgcgatc | tcggctcgct | gcaagctccg | cctcccggt | 19380 |
| tcacgccatt | ctcctgcctc | agcctcccaa | gtacctggga | ctacaggcgc | ccgccaccat | 19440 |
| gccccagctaa | tttttttgtat | ttttagtaga | gacggggttt | caccgtgtta | ggccaggatg | 19500 |
| gtctccatct | cctgacctcg | tgatcatccc | gccttgtct | ctcaaagtgc | tgggattaca | 19560 |
| ggcgtgacga | ccgggcccgg | ccgggttt | ttttgagacg | aagttttgct | ctgttgccca | 19620 |
| ggctggagca | cagtggcgcg | atctcggttc | actgcagcct | ctgcctcctg | ggtcaagcga | 19680 |
| ttttcagcct | cagcctcctg | agtagccagg | attataggcc | ctcccacagt | cgactaattt | 19740 |
| tttgtgtttt | ggggggtttt | gtttgtttgt | ttgtttttga | gatggagtct | cgctcttcg | 19800 |
| ccaggctgga | gcgcagtgac | gccatctcgg | ctcactgcaa | ccttcccagt | tcaagcgatt | 19860 |
| ctcctgcctc | agcttcctga | atagctggga | ttacaggcgc | ccgccaccac | gcccagctaa | 19920 |
| tgtttgtatt | tttagtagag | acaaggttc | accatgctgg | ccaggctggt | ctcgaattcc | 19980 |
| cgacctcagg | caatctgcc | gcctcggcct | ccaaagtgct | gggattacag | gtacgagcca | 20040 |
| ccgccctgg | cctaatttt | gtatttttag | tagagacggg | tttc | | 20084 |

FIG. 12B-1

```
                                                                                    Exon #
ctcccaagt gctgggatta caggcgtgag ccacctcgcc cagccattt agtgaattct     60
tagacaacac tgacaaatgg accctggaaa tcccagaagc tgccctacgt ggccactgtt  120
gctggtgggg tgagcagagc cccttgcagg cggaaaacct aaggctttgc tctcagctac  180
tcgcacggtc gggctgtgtg agtgaccc ctaccctcct ggcctccgcg gagcatgctg    240
tctgggcccg gtcggtccct ctgctgtcg gttagactgt gtcagtctgt attctgcagc   300
tgtaacagaa caccgcagct tgggtagttt acaagggaaa gagatccatg tggctcctag  360
ttctggaggc tgggaagccc aagaccgagg ggtgcatcca tcgagggcct cccactgcg   420
tcattccatg gtggaaggca gaagggccaa gaggaggtgc cagagagaga aagggccca   480
acccatcctt ttcatgagga acccactgcg gagacaacgg tgttagttta ctccggagag  540
ccgagctctc aaacctaatc acctcttaat agcattgcag tgcagtggcc gttcaattgc  600
agcatgtgtt ttggaggaga cattaacccg gctgactgtg tgttgacgca cctgggccca  660
gtcattcctg aggaccagc tggaggggt tccagggttt tagggcagag aggttcagcc   720
cagcattagg cgtgttagta agaaaaagga atggaagcaa agtaagcgtg tgtaagagac  780
agcaccgtgc agctaacaaa gtcactcttc ccaggaaagt aagttttaa aaactcaatc   840
aatcagtgca atcacagaaa tataaaaaat gtatatagaa gaacggaagg aaccactgtc  900
aatatttgga tgtagtctaa tagcaggtgt gtggatgatt tgatttattt tatcctcaac  960
tggctacttc ccaccaccc aacaatacac ttagttcaaa cacacaactt ttctctttcac 1020
agGGTCCCAG CGGCCTGGTC GGACCCAAAG GAGAGgtgag tgccggcga ctgttccgat  1080   27
gacaccatcc atgggccctg ctggcttcct gccacctct gggcaaccag gcaccctgca  1140
ggcactgccc agatccgaga tgtaaaaaag cttgctctgg tcaaggctgg gcaagacggc  1200
tcgtgccggc tgggaaagag cacgtcgggg ctcctgggct tggctctgga ggccctgac  1260
```

FIG. 12B-2

```
ccacttcct ctgttcctct gcagTCTGGC AGTCGAGGGG AGCTGGCCCC CAAAGGCACC   1320
CAGGTCCCA ACGGCACCAG CGTGTTCAG GGTGTCCCCG GGCCCCCCGG TCCTCTGGGC   1380
CTGCAGGGCG TCCCGGGTGT TCCTGGCATC ACGGGGAAGC CGGGAGTTCC Ggtacgtcgc   1440
ttttccggct tttccagctt tcacaggt gagatcgtgt tttttccgga aggaagttac   1500                        28
tttgcgggct gacggtggga atgcctcacc gaggctgccg ccccatgct gacgaatgtg   1560
tggggtgaat tccagGGGAA GGAGGCCAGC GAGCAGCGCA TCAGGGAGCT GTGTGGGGG   1620
ATGATCAGCG gtaagtcagc cacctgcacc ggctgcagcg gggcccatcc ccgcctgggg   1680
gtcccgtgcc tggggctaca cagaagccaa cgtgccactg ctttccagcc aaagtgagcc   1740                        29
cctagcactc acccgcctg ttagcccctg gggtccacg tccgccttgg gtctgctgtc   1800
ctctgcacta gaggatggcc cacgctcccg cccgattc aaccagattc ccagcacgca   1860
gcagacgccc taaagcctgc tgaatgcaat gggtacaaga acagcggagt gtgccctgt   1920
ggctggcagg gcaggtcct aagggcactt cctttcacctt agcattcatc acccaaagc   1980
cttctcaggc tccaaggggt tgggggtcct ttctagctcc ctggaagaca gcaccgagta   2040
agttaaacca ttttccatca atcagaagga aaacttgctt ctgaagaca gcaccgagta   2100
gatatttat gctttacgta acaatacttc tgatgatcct ctctcgagta aacgcctgca   2160
ccctgttttt cccaaagAAC AAATTGCACA GTTAGCCGCG CACCTAAGGA AGCCTTTGC   2220                        30
ACCGGGTCC ATTGGTCGGC CCGGTCCAGC TGGCCCCCT GGGCCCCCAG GACCCCCAGG   2280
CTCCATTGGT CACCCTGGCG CTCGAGGACC CCCGGATAC CCGGGTCCA CTGGGGAGCT   2340
GGGAGACCCC GGGCCCAGAG gtgagtgttt gacccatga cacggtcacc ctgctgtaaa   2400
aatccctgag actgacttgt tagtaggcgc tgcttctggt gcctgccatg cgccctcagg   2460
ggtacccct ggaacgtggg ggcctctcat gttgggc ctagcgcatg ttaactcctt     2520
```

FIG. 12B-3

```
ggtaatcctg tgggaactgg aacattttta acatgtgatg ttttttctcaa ataccattag 2580
aacaatattt ggcagggagg gattgattta aaatgtgacg aaggctgggc gccgtggctc 2640
acgcctgtaa tcccaacact ttgggggct gaggtgggca gatcacgagg tcgggagttc 2700
aagaccagcc tgaccaacat ggtgaaaccc tgtctctact aaaaatacaa aaattagctg 2760
ggcatggtgg cacacgcctg taatcccagc tactcaggag gctgaggcag gagaatctct 2820
tgaaccctga agcagaggt tgcagcgagc tgagatcgca ggattgcact ccagcttggg 2880
cgacagagcg agactccgtc tccataaaag aaaaaaaaaa tgtgaggaat ggccgggtgc 2940
ggtggctcat gcctgtaatc ccagcacgtt gggaggacga ggcaggtgga ttactggaag 3000
tcaggagttc aagaccagcc tggtcaacat ggtgaaaccc cgcctctact aaaaatacaa 3060
aattagccag gcaaaacaca gatgtaagat ttgaatgacg caattagagg gatgtgaaaa 3120
tgcccttagg tgaaggatgg gtggaaaatc atttaaaaca tgattacaaa atattaataa 3180
atactcaact gcttaatagg cataaatatt ctaaaatccc atttaaattg 3240
gctgccagag gtcagggagg tggttcagcc gtgcacggct cagcagcagg cataggttct 3300
gacggctgtg ccactgggcg gtttcactgt ggaacatctg agttcactta cgcaagcccg 3360
gcctcctgca ccctgggcc gtgtgccaga gcctggggtt tatgctgca gacctgcaca 3420
gcctgttact gggctgggtc ttgtgggcgg ttctaacctg gtggtgggta tctgtgttaa 3480
atacatccaa acacgggaaa ggaatggtaa aaattgggta tgataatctt aagggaccac 3540
tgtcacctat gcggtgcgtc gtccacctgc agccgtcctg cagtctaaga ctgtgtacag 3600
gtgggtccct ctcgtcgggc cccgtcaagc cctacgcgc tgacatctgt actttttctaa 3660
atgttttccac ttcagtgaaa agctgcacc ctgttttgtta caaggttga tcagacaccg 3720
ctgtggtgtg gctgcaacag atactctaac catatgtctg tgtccacacc tggtgacagG 3780
```

```
AAACCAGGGT GACAGAGGAG ACAAAGGCGC GGCAGGAGCA GGGCTGGACG GGCCTGAAGG   3840
AGACCAGGGG CCCCAAGgta cgagtccacg gccagcaagg cttcactggg tgacatctct   3900
tccgccatct tgtagcttta tgtggggcgt gcttgggtta tgaatgggtc tcttttcctc   3960
ttctcttggc aaagcagtct tagagacaag attaggaatt gtctcaataa ccactttaat   4020
acataaaagt ttaatcgggg ctgggcgcgg tggcttacac ctgtaatccc agcactttgg   4080
gaggctgagg cagacggata acctgaggtc agcagtttga gaccagcctg gccaacacag   4140
tgaaacccca tctgtattaa aaatacaaaa atgagccggg cgtggtggcg ggcgctgtaa   4200
tcccagatac ttgggaggct gagacaagag aatcgcttga acccgggagc ggaggttgca   4260
ggttgcagtg agccaagatg gcgccactgc cttccagcct ggcgacagag cgagactcca   4320
tctcaaaaaa aaaaagttta atcagtaagc agatcctcct ggatctattt tagctaagtc   4380
aatttggtta gattctgttt aagctactca gtatctattt cagttaaagt ataacagaat   4440
tttctcttaa ttgacctgtg catacgttga atatttccat ttccaatgtc aaaaataaat   4500
gctttgcacg gagggaggca cgcgaggatc cttggcaaag gccatcccct gcccgcccct   4560
gtcttagcct ggtgccttct caaaaccagg agccttaga ctccaaggat gtgtgtgtcc   4620
agatgagaag gatcccgaac agtcttcgag aaggcacccg ctccacctc tgcctgggtg   4680
ccctggagcc ttctcctctc ctctcctcca cgcactcaca ctgctcctg gatgccctgg   4740
agccctctcc tcctcctcac ccacccacc tcccctggg cccctgggag ccctcctc   4800
tcctccaccc acccacctc cctggggtg cctggagcc ctcctccct ctccaccac   4860
cccacctctc cctggtgcc ctggagccct gtcctcccct ccatgcacgc acgctgctct   4920
ctgggtgccc tggagccctc tcccctctc cctccacgc acacactg ctctctgggt   4980
gccccatgct cctgactct cctttgctga cctagctct cctacctg cctctacctg gtgtccaaac   5040
```

FIG. 12B-5

```
gcacaggggt cccagccccc agccacgtct ctcgcctgtg gtctctgaaca gcatctgtgt    5100
tgcacttgct ggtggacagc agcctcccgg ccgcaccat cccacacca                 5160
tgcccgcacc attctgact ttgtcacctc atctcagtga agggtctga cacccccac      5220
ttaggcggct gactccctct tccctcacac ccaggcctcc catgtttcca ctgtcatcac   5280
tcaccaaagc caccccacaa ccccccactc cgggcccct gctcactcca aatccactcc   5340
ttactcacac agcccccacc aaacccgcgt aagtcagagt gcgggtgtcc tcaggacggc   5400
tctgcacccc tgcctggggc tggccgcgcc tggccttccc cgacactcc cgaccgccag   5460
cccgcggag agcctttgtg tgccgttccc tgcctctcc cacccgctgt ggctctcccc    5520
caagtgaaga gtgagcagat ggaagagcag ggcttgccca cagctggatg tcaagtcccc  5580
ctgctttcag tccgggctgc agctgaactc acctttctgc tctgccaag GACCCCAAGG  5640
CGTGCCCGGC ACCAGCAAGG ACGGCCAGA CGGTGCTCCC GGCGAGCCTG GGCCTCCCGG  5700
AGATCCTGGG CTTCCAGGTG CCATTGGGGC CCGGGGACA CCGGGGATCT GCGACACCTC  5760
AGCCTGCCAA GGAGCCGTGT TAGGAGGGT CGGGGAGAAA TCAGCTCTC GAAGCTCATA   5820
AAATTCAACG TGAGGAAGCA AGTGACAAGG ACGCCCGAAG CACAGTGGAC GGTCATGAAG  5880
GAGCGGGGT GTGGCAGGCG GGTGACGTCC AGGAGAGGGA GCGCCCCTGG CTGCCCCTCG  5940
GCCGCGACT GGACGCCTGG GCCTTGCCAG CGAGCACCCT CATTGGGCTG TCGCCTGACA  6000
GCATACCTCA AAAGGCCCTA GCTAATAAAC CTGTAAGCCC AGCATTTGAG AGAAGGTAGG  6060
GTGTGTATAT ATAAAAGGTT GTGTACAACT CCACGAGGTG AAAAATATTC AGTAACTTGT  6120
TTGCATAGCA TTTGTGTAAA GACTATGATC TCATCCCAAT AAAATGATAT ATTAAATCTT  6180
CAGATTAATG ACTGGCTACA GAGTAACACA AAATAAACAA TTTAATGTAC AGTAAATTCT  6240
CTCCCA
```

FIG. 12C-1

```
gctctcccct gcgcccctgt ctttgtaaat tgacccttct ggagtggggg gcggcgggca
gggctgcttt tcttagtctg ataccaagca agcctttttc tgaataaatt catttgactt
tgagtctttg gtatggaccg gggtcctgtt gggtgctgg tagggctggt gtcacagctg
atgtccctcc agctccagt ggctggcctg gccggctac cgcctcacat tgctccacca
ggtgcctgtg gggcagagt ggtggcccag cccctcccac acaccactt ggccacacag
tccccaggca tgaacaggtg ggcaggctgc agcctcccag agcctctgaa ggtggaaccg
aggtccctca gcaggctttt gccacctagt tgaagatgag tctgggctt ccctggggt
tggccggggc agtgcttgtg catgttgtgc tcgggcaggc ttggcagtac tctctggcgg gccccttggc
ctgggatgcg ctgctgtgcc tcgggcaggc ttggcagtac tctctggcgg gccccttgcc
tccctcaggt ctggtggaga ccaggtgtgc cccaggca gtccctccct gcagtctgcc
cttgtcaccc tgggccagga ccccccgctt cccggttccc ctacatttct acatcagcag
ggtaagggc tttttgtggg gcctcagagg aggggccaga cactgtctt tgctcagtga
aggacagggc agacctgggg cacccctggg tgggagggtt aaagctgtag acctggtac
cacttcagat aaaatgccca gctcccatct gtggcaccg gatacagag ccgaagtca
ctgggaggag acacccgagg ttcaataatc cccagagct gcgtgggaa gctgtgggac
ccctggtgcc tcaagtgtgg ctcagggat tcctgccatg gaggaaact gaggcagtga
gctggacata gggctagaag tgcagtcact gggcagcgc ccggcagatc cagcgtcccc
agtccaggcc gttgtgggc tggagtcggt gaaaatcagc gcctgaagtg aggagcctgt
tggagcagcc ctgggggccg atgcctggcg gtgggcacct gggccagca ggcagtgctg
gccagccaac ccgggcttca ggagagttg accacacaaca ggcgcagc aggagctct
gccactcaa aagtgagccg gggaggctg agctctgaca gtgccaccc tctgcctagg
atctgcctgg agctgggggt ggttttttga gggcttgaa ggtgttcgg ggggacacc
```

FIG. 12C-2

```
aagcaggtgt cccaggcatg aggtggctcc cctggcctga ggtgaaggcc agctgtgttt
tgtctgattt ggtcagata gcagtccttg ctgactgcat gctggcatc atgggatag
gcaaagtggg gtgtgggcc agggaccagg ggagccac tgaggaggg gctggccaca
gggtcatctt gccagtgtga actgtaggg aggacttatc ctgtccccca gaccctgggc
ttggggtggg gctggtgctg ggagcccta aggcccctg ctgtctgggc tgacctgctc
cactcacctc tccccgtaat caaaagtcct ctgttaggaa gctctgtgcc aggatgactt
ggactcctca ggagggtggg ccttttcagc tcctcccacc tcgcctgatg gaattcgcac
acaccctcc cagccagcc accgcgctca cccagcagtg aaggagaat ctccctccac
tcacttcacc gcggagaga ttagagcgac actattattt tgagacaggg tctcactctc
ttgccagge aggagtgcag tggcgccgtc ttggctcact gcagccccga ccttacaggc
tcaagcgatc ctcttgcctc agcctcccgt gtagcgtgga ctacaggcga gcaccaccat
gcccagccga tgtgttaatt ttttggtagac atgaggcctc cctctgtctc caagctgcc
acgcccggcc gatgtttcaa tttttggtag agatgaggcc tccctgtc gccaggctga
ctgcgcccgg ccagagtgcg gtgctcctgc tgagcagttt tgcccaact cccctctcat
cccctcccgc ccttgctaac tcacagcatt gcaacagtca tgagtcccca cctgccgaaa
ggaagctcct gcagccccct acaaccccca gggcagcctt tctcgggaat tttcaagatt
cctggggag gggctggcat ctgcgcctc actgagccta caggcaactg gaagctttga
gtccccctagg gcagcgactg ccctggcagc ctgaggcaga gcttgccgg acctggcgac
ccctgagctt ctgggaaatg gacatggcca gcaccgcctt caggttcctg ccagggcac
ggttccttca ggccggggat ccggggagg ggttcttccc ctcggccagg gtcatcgttt
tgcgatctct cctgggagtc tgggtttgga gtctggtctt agccggtagc aactgacgtg
gcctgaccac ccggccgtc caggtccacg ggtgaggg cgcggtgggg gtgctcccag
```

FIG. 12C-3 cccagcaggc agcgctggac agtgaccccg gagcgggaac caggctgcg ctgggcactg
acgggccct ggtaccgggg attcaccctc ccggggtgt cctgggcct tgggtcgcct
ggtccgctc cggcgcctgg ggaggatct gcggcttcgg aaactcgcgg gtctccctg
cccctccctg aaggcggccc ttcagcgccc ggccgttccg ccccacact cgggttgagg
agcaaggaga gaaaagagcg tctttctctc ttgctcaaag ctgcgtgtgc gcaacgcgcc
agtcccagga taattttaac tcgcggccgg agagaacgcg ccgcccgccc ggcgtctttt
ttgtttttcgc ccaggcgggc tggacgcggc tggtgcagg cggggcggg gtgaacccc ccacgcaggt
gggccggct gaatggggg cttgtgcagg cggggcggg aagggaagg ggaaggggcc
gcccactcc cgcccgccc gcccgcgcc cgcccgccc gacgccgcag ctcagactcc
gctcagcc

FIG. 12C-4 gtga gcgcgagatc cggctctga ggctggacgt
ggagccgcga cctcccagc cccgaaccg ccactccggg gtgccgcgc agtcacgacg
cccccagcc gtgtccgt cgggagagg agtcgccagc gcctcgggat gagcccgtc
cggccgcgtc ctcgatggt cctcgctggc ccgggcggcc gccgccgcct cctctgggag
cacaagggg cctttgttcc cgccgcgga gggaggcggg ggacacactc ggcgggggcg
cctgcctcga ggctttggt ctaccgagg agagcggcgg tcgtcgcagg ccccggagcc
gctcggggacc cggggaggg ggacgccggg tcaggccacg gggccacctg cgtccttaa
tgagtttct ccgtttcag

FIG. 12C-5

```
                                   gt gagtttgggg gtggggaggg cccgagcgc
tctggggttc tggctctggc cccacctcc ctgagctccc cgcctgatg gagagaaaac
caggcccac ctcccagagc cggggtgaca tcaggggaca gccagtgcct tcacggatg
ggggtggccc tgcggactg ctggtgggta ggggtggagg gtgtcatgtg gtggtcctcc
acccagaatt ccggcactga ggtgtgtc tctgggtccc tgaggggccc gtgccctgt
gttcggggtt ctgcctctg gctgaagtgg gagaggcacg tcctttgggt ggttggggc
cggggtcttg ttggaggctg ctggctctg gagcctctg gagccagcca tggagggct taggagccga
ctcagtcctg agatgatgtc ccctatgggt atctcaggac tggtgtgggc caagcagcag
gaggaggcgg ctgaaattct acaattgtgc ctccctcgga gggaccgtct gggtgaacc
tcccccatgtg accaccacca gggcaggagt cccctcaggg cctgtccacg ctgtgtggtc
cccgtggagg gctgtggagg gctgcaccaa gagcccca tgaccaccc tctgcccccc
tgcccagctc ggcctcaatg gccatagcct ccttccagtc tgtccagttc acccctttgc
ccagtgctgc cccacacatg ggagggtgcc ctctaggtag ggatcgggg ctcagggcc
cctttgtct gctgggctg gggctctggg gctgatttgg aggccagcgc tgctcttttc
ccgaggcggg gttcttgagg gaccctgat tttcagggtt acatgtgggt gtctttcctc
acag
```

FIG. 12C-6

```
agacagcctt tttccagtct ggagagaaag ggggaactca gaacagaggg gtcattgata gtgagtgtcc ctggctgggg
tcctgtctca tcctgccgga gcccggttg cctgagggga ggcctcagag ggcttggagc
aggcctggag ccagcggggc ggaggggagt gtgggctcag cctctgcaca tgttcagggc
agggcctggc tttgaagctt tctttggacc agcgccaggc aggcgggacc ggggctgata
cagcttcagg tccccagg ctgaggtcac ctggagccct cccaccttct tcagttcctg
gggttgaggg tcctgggct cagagccctg tctgggccca ctggggtcc gacagagatg
cctgctggcc cttagccagg gaggccgagg tgaccagacg aaggtgttac agatgccact
gagggatggg gcgggcagcc ttcctgggcc agcaaggtgt gggcaagcag gacacacgag
cccagctga gccgggtctg ccagacagta gggggaccc aggagagggg cccatcccgt
atgttgggct ggggaagtg gaaagcattt tgcttcattg ctgaagcctg ggctccaggc
cagacccgc cttcacatct ctgccctttc ctcctgcaca g
```

FIG. 12C-7

```
cgcctgcccc tcccgccat gccccactcc ccgctccggg tccctggagg agtccggccc gtgagtg
taattgctgt tgtccagctg ggcctgctca ggcgggaagc ccagtcctga gagaagtctc
cagaagtccc ccaacagggg tcctttggcc ttcatcccag acgccaccag catctggcag
gggacagagc cagcccagtg gagtcggaag tcccgccagc cctccttgct tgtccaggaa
tgagtgccca ttgtcaggac cttctgccca ctgctggcct cacttagtca tctttgggctc
caggccagcc ccaggccacg gagtttgttc ggaggaagcc gggcctgaga agtgagctgt
ccagtcctgc tgggttggtc ccgtggcct gactacagca gtgcctccg ttgctggctt
cccgctggct gccccctccc tcctcccag ctctggctac agcaggcaga cagtggacag
ggccaagaga ggaggctgcc accctaaggg tcttctatgc ctctctggac tcaccaaggg
aagggtccgt gcttccattt ttgcctgggg ggtggcatgt gcttcccatg tggccctcg
agctcgccct ctgcctctcc ccag
```

FIG. 12C-8

```
                         gt aagtgcctgc gccgaaccca gtggcttggg ttcagaggtg
aggtcccctg gccacctctg gctgctctgt gtccacaagg ccaaggagct ggtagttcca
aggacagctg ccctgcccgt gcctggggtg gagggcaga aggcagggt gccaagtggc
cagtcccctg tgcctgcctc cctgcctcac ctccacgtat ggtcagagtt gtcctgtat
ccagaccatg gcaggagaa gggatggt ttgggaac ccacccagg tgcctcctca
gaatgtccct gaagccccca agccctggc agaccaccac caggaccc cgggcacgca
gcctgcgag tcccctgtgc ctgcctgttg gacactgaat cctttaccct gacggagcgg
caccaccacc caaggtgcc tttctcccct tgtgcttct gagtacaaac ccgaagccag
caatcccctct ttggcttcat aagacgtggc tgtcagccaa ccgggtgcca ctggccccag
gcgcaaagca tcacagaggg caggaaggct gggctgggga cacgaggaca cagccctgcc
cttggggacc cttgggagct cgtcagggca tgaggcgat tctgagctga aaacaggagg
gaaacagtag ctgctggcca gcgagtccgt ggtgccagg ggtgtggggt gggctggtcc
caggcttca ggagggcct ccagcctcag cacagggccc gtgcgtccg tccagggaat
gaggcatttc aggcagcagg ggccagacag ggccagaggg tgtggaggc agacagggcc
tggctgccaa ggctctgggg ctcgctgacg tgggcggggg ctgaggactc agcaggctcc
gtgggtgggt tatcgggagg gcttcctggt ggagacaggc accccgggtc acttcggtgc
ctctcagccc tgcctcagc ctcacctct tgcagcgagc gctggactc tggtgccatc
tgtctccagc agtccccag acggcaaag accctccagg tcaagagggc tcagaggcct
gcccctctgt gaagtgggga cttgaccct gttgtcctgg gagttggagt tgtgacgtca
cacttcagag ggaggggatt gggtttgcaa atagaggccc agccaaccta gacgcctgct
ttcctcccac ag
```

FIG. 12C-9

```
tgtggtcctc tcctctccat gggagtttgg ggagctggag agtctggtct aaatggggtg
gcctccagga atcccaggga ccatccctgg ccctctcatc tgcagcctct ccggagctgg
tgcctggatg gggtcctggt gccctctctg gctgggacc agacaccat ccctggaacc
gcccttccc caggaccac ctgagccatc ttagggaggg gtgagcgcag cccttcttgt
gcctggcagg ctctgacccc atgtttggct ttgcag
```

FIG. 12C-10

```
gtgagtactg acaaccccttg gggccctgag caagcacgca agtcccgaga gcctgccagg
ctgggatgtc ccaaaccgtg cctggggtg ggcttctca gggcagcca tctgaccacc
ccatacttgg agcccctctc cttcggaggc ggcacaggcc accctgggtg gggatccctcg
gggcttccgg gtgcagacct ccccacctct cttacttcc ctccag
```

FIG. 12C-11

```
                                                      gtgagtggct gtcccagagc
ccctcagagt gtgctctcacct gtggcctcca cccccagact caacagccag gggtcccttc
ccctctccct tttcctttc tccccaacc ccaccttggg ttgttggtag aagccctgc
caatgatcca gaccgacct caggacgcag acaccagcac agtccgtggg agtggggct
ggtgggagct gggcgtgtcc acctccctgg gagaagccgg gcacctcact caggtgggg
ctggtcccac tctgtctaag tcatacccc tccccag
```

FIG. 12C-12

```
                    gtaagtact gggcagaggc tctaagaagt
gctgggcatg gactaggaca ctgggttggc ccctcccat tcccctccc caggctccat
gcccctccga gatctcctaa ccctaacttg gccactcccc aggaacagtc aatgtgggg
gcagtgggct gtgctaggcc agccaacttg gatggtcag gactcaggtc ccatgccat
cctgcccaa ggacgcaggtgg attctgtcgt tgtcacatac cctgtgggtg ggccagcagc
tcccagcact ggccacttgg gggacaggat gaagggtctc caagtcccct ggtggatggg
gaaggttgtg gtccgtcaga gagtgggtgg gtgggttggg tggctgcagg tggctggga
gggcggggaga atgtcagctg tctcttttg tcttag
```

FIG. 12C-13

```
           gt aggcacttga agccatttgt taagggtgct gggggtgcc
tacctggggg ggaggggttc tggcctggag aggggcttgt ccatactggc aagaaggcag
gcccgagccc tccctgggga caggagctca gagcagacag ctcgggcaca acctggcaga
gaggctggct gggacctccc cctcccctt cccaccctcc tcaccacgt ctagacctgc
actgtccctc atgaagccac caggcgcatg gagctgtaca aatgtaatga atcacaatca
tgtcacagag ccatccagct ccctgcgtc atccgcagag ggcgccctg gccacagatg
gcgacagaac tggagtctga gacccacctt tatcttgatc tttgagcctt gtcattgcc
tgaaaagaaa acaggctcag gtcaggcgca gtgctcagg cctgtaatcc cagcactttg
ggaggcccag acaggaggat cgcttaagct caggagtttg agaccagcct gggcaacata
gtgagatctt tgtctctaca aaaaattgtt aaagtagcca gacgtggtgg cgtgcctgtt
gtcctagcta cttggatggc tgtgtggga ggatcacttg agcccaggag gcagtggttg
cagggtgctg tgatcaagcc actgcactcc agcgtgacga gccaagctaa gcctgtctca
aaaaaatgaa gaggaaagaa aatgggcttc ggaggccacg gatccatctc tcctctctgt
ttggccgtcc gtggtgcag tcagcgcctt gtttccatag agaggtttga tagtttttgaa
gggaaaagct cggcccactc tgacctgacc accgacgctg tctaccagcc tctctcctca
ccccaccccg gggcctaggt gcctggccag cctgtgtccc agaagggagg cttagggaa
ccttccagaa tgtggtgcgt ggttgggccc ccgatcgtgg gctgagtggg gcagggcta
aagatacggg tctgcaccct tgcccattgc agctgtagga tcatctagaa
```

FIG. 12C-14

```
gcagccctgg gtttcctgag catcagacct gttgcctggg ctcacagtgc ccctcctaaa
agcccatgc cgagcacatt cctgtgctga ggatgggccc gacctgaggc tgctgaagc
ccctgcagt gccgcccggg actgtgctga atggctgctt tgatagccag tgtctgccgt
gggccggctg ctccatgcag cccctgctga cttggccagt gctgaaggag accctgtctg
tgtcctgtcc cagtgccatc tcctgtacga gtggcctcct gggtccctgt cactgtgtgg
agtggcctcc tggggtcccg tcactgtgtg gagtgcctc ctgggtcct gtcaccaga
gtgtcccgac accggccg gagtggcctc ccgggccg tcaccacgc ggagtggcct
cctggggtcc cgtcactgtg tggagtggcc cgtcactgt gtggagtggc
ctcctgggt cctgtcacca tgaggagtgg cctcccgggg tcccgtcacc gtgcagagtg
gcctcctggg gtccatcat ctgtgcgag tggcctcctg gggtccctc actgatgcgg
agtggcctcc tggggtcctg tcaccgtgtc gagtggcctc ccgggtcct gtcaccgtgc
agagtggcct cctgggcgg cgcggcgct gacccctgcg tcgacgtcct gctctgtttg
gctgggaggg gtctgactgc tctgttttcc gacag
```

FIG. 12C-15

```
                  gtgagtca cgggtgactg ggacccaagc
accaccctgt gctggcagg aggcagctgg gctcccatgg ggctgtggag gtggcgggtc
cagaaagctg gacccctggtt ccacggttgc cccaggaaga aagctaggcc agcctccttg
tcccgccttc agcacccag tgacacgctg atgtggccag gctggactg gccataggca
tcagagactg cggggagag ctagcctcaa gctcccaccc cagcccagcc ctggcccgct
cctgaccgca gagccctc atgtggggtc ctagccctc tcaggcctca gtttcccat
gagggccag accggcggtc ctgtgcgctg cccgtgtgcg ggccctggc tgactgaccc
tgcaggcctc acttcagtgt tgccagggag gggtgtcgg gggtctggg tgggcagtg
accccacatt tgcttgcag
```

FIG. 12C-16

```
           gtgaagc tgccgcacag cagctgggga ggagctgggg actgaggct
gggctccggc ggggggagg ggctgggctc cggcggtggg gagggaccgt ttcatgggtg
cacctgcact ggcaccttct gtgctgtctt ccagataggg cctggctggt cagagctggg
tgatttaggc tgggtcctgg acagaccccg tcctgcctgg cctgctgtg gaagctccct
ggtttgtgtc tgtgccggg gcgagggca tctgtgagga tggctgctt tagcctgtag
cctccctca cctgtggtcg ctgtccgtgg agggtgtctg tccatggtca cctgcaggcc
gggggaccag gtctgggatg ccctttagcg tggctggagt gatcagatga ggagaccca
ggtgcacatc agaggggtcc ctgcttggcc acgaggaggg gctgaacag ggctgaaggg
ccttgtggga acagtgacca cggaccccgg cccgcaggg cgaggccacc gagactgcg
ggactgctct ggaactgtgg gcaagtgtcc ccttcacaga gcctccaagg cccagctgtg
aagcgggcaa cacccccagc tgcttggct tgagtaggt gactgaggc accgaaaggt
gcaaggagag ccagactggg ccgctgacca ccctatcccc tctgtttcag
```

FIG. 12C-17

```
                                     gtgagg ctaggaaggg
gtaaggatgg tgggatggga actcagccca cagagtgatc aagccctgca catatctacc
cccgagggg ccagctccgg ctggggggtg tttgccaac accaggcac aggagcgcga
cctggctggg ggtcccacct ctgccaaggc tgctgacctc aaggctggtg cccctcccct
ctgggggacc tgagctgagg ctgagggctc atggaagaca ccaggctcc cagggtacc
ccgagggcct tggccctggg tgatccccgg ggtggaggtg cagcccagc ctctgcatct
gtgcctctct ctcgcag
```

FIG. 12C-18

```
           gtaagtcct gcagcccta gtggggccg gccaggtggc tggggcctg
gttgtctgca cctccagact tcagatgggc cccgtgagtg acactctgaa gcagccggca
ccctgctct ggccatcgcc actgtggcgc aggccttgct ctggccct gttctcgcat
gtgcctgggc gagagctgac agtcggcgct cactgatgcc cgcacgcggt cccaggctgc
tgtgagggct gttcacgcgt gtgcccgggc gagggctgat gaactctgct cgctgacacc
cacacacg gtccaggct gctgtgaggg ctgttgtggc ttaggccaga gcaggagggg
aagcagggat ttggagacta ctaggtggca tcttggggga acttgctggg gagccctaga
ggaagggctg cttgtgtctg ggccgcccct gagggagcac tgggggatg ccagccaggc
ctcagacaag aggacccgg atcccctc tcctctgcag
```

FIG. 12C-19

```
           gtacgt gtgtcagtgg acggtggggcg
ccatgccacg tgacctctct cccctttccc tctgctcctc cctgacacc ctgggagggc ccagcccac
tggggcccct cttcctggc tgagctgttc cctgacacc tctttgtgag acattcgcct cctttctggt
ggtacgggg tgcttaccaa tggaatccat tctttgtgag acattcgcct cctttctggt
tctggacgtg gaatgagggg tcaccatcgt ccttctggca cctccagcca tctctgacca
ctcctgagg gtccaggcct ggagggccct ggaggggccc ccatcccact ctctgaccac tcctgaggg
ctgtccccg cccgggcctg gagggcccc cgtcctactc tccgaccatc tccatggtgt
taacctctgtc cctgccccac ctcatccttt ccag
```

FIG. 12C-20

```
                                                         gt aagtgagagg gaagttggtt cctgggtcc
ttatgtggaa gaaccaatt tccctcctga ctcgtgctgg ggaggggac acacttggga
gtgagactgc aagggctgc ctgggtgggc ctggggtgc gtggggtga gcctgaccct
ggagggcccg agatctctcc ctggccccag ccgttctccc agagccacat gggagctctg
tggccccctg cagagcggcc cacgggcctg gaggaccag gctccagggc ttggatcctg
ccccagaga aaacggctct cggttgagc aagtgaacat aaggaaagtc cagaggcagc
caagcgttcc aggagtggaa ctgaagtgac cgtccccaga ctggtcagcc tccacacctc
cctcgactga gccctggcag ccggagtgca gggagccgcc gtgccgtcct gcagcatctg
tggatccaaa cacagttttc tccacgcacc cacaggcccc agggtggttg gtcggggtg
gcccctgccg ctgccacca tagctccttg gtgtcccga gcagctggcc ggagaatgcg
tgaggccgtc tgggaagaga ctgccactgc ttctgtcact tgtgtgtcct ctag
```

FIG. 12C-21

```
ggctgctcat ggaatgctcc tccccgggt cctgggtatg gt gagtgcacgt
agaagggctg gagctcagtg ccctctgctg tggccatctt tacaggtgga gatggcattc
acagccccg cagcccaca catttctctc ttgcccagag gaaatctggg ttaacgtgtgg
agggcctca ggctgggttt acctgcacag aggacacggg aagtaagggt gtgcaggagt
caccactggg cagaggtggg cactcccagg gtcccgggca cccgtgcggg cacttcctt
cctgctgggt gcccacccctc agcccagacc tgagctcccct tctagccccct cgtgttgcct
ctgccccgga gtagtgccct gtcttgggac accagcagt tggctgtgtc ctgattccaa
aaccagtcca gggtgaccg aggcaggcct gcctaaggcc tcagtttccc caccgtaaaa
tgggccagaa ccaaacttcc ttagggcacc atgatgtgcc tggtggacga ggcctcgggc
gtcagcactg catcagcacc gcctctgcca cccacccgca cccctgacct gtgcggtcac
cgaggtagca ctggttgcca cacggccacc ttggtcatga aaccagataa ctgccaggggt
gtggggggcag acacagtttt aggttgatgg ggaaggaggc tgcccccagg gcggactgt
agagggaggg aggggggcca ctgcccgacg ggccttactc atcccttgtc cccag
```

FIG. 12C-22

```
                                              g ttggcatggg
gctcagggtg tgacgggagg gaggggctg gagggagtt cggcctcccg aggcctcagc
ctcccttcc gcacccaat ctctgtcctc acag
```

FIG. 12C-23

```
                     gt gagtgcccgg cgggtgggc cagcctgggg
cgccacagct tctgcctgct cagtggccca tgttggctg gtgggttgg tcactgtagg
gccgactccc tgtgagggt tctgggcct tgtccatca ggcctggca caaccctgg
tgcccagtgg tgctgtggac ggttgcctgt atgtttgcat gtgtgtctt attcgtgtgt
acatgggaca tgtgtgaaca tgttgatggc tcctgcatcc catccctgga tgccgtgcgg tcatcacccc
catgggctct gagtaggggc tcctgcatcc aaggccaggg aggctgtcaa atcctcacct
caggtccaca aggctgggag aagttggccc tgcctttggg tgcactcact ctggcccgg
cgccctgcct gcgtgcacgc cctgggtgc tgctgccggc tgctgccggc gtgcaatgta actggcagcc
ctgaccgcaa gctctctcct ggcag
```

FIG. 12C-24

```
         gtatgtggct gcagcgcttt ctctctggga ggggaggcga ggggccggga
ggcaaggggc tgggcagcga gtgcaggtgt aggcaggcac tcacagctct ccttcctcta
cag
```

FIG. 12C-25 agtatctgcg gcgccccaga cccctccccca tccagcctgt gtgcagaccc tgccctgaca
cctcttcc tttccctgta g

FIG. 12C-26 gtgag tgcagggaca tgcccggg tcggggtta gcactgagcc
attggcacat ggccccagtt tctgagcagg ccgggtggc atttggttgc cttgatgggc
caggcccaca aaagcctagg atgccaggag gtgtggggcc ccatcttctt gtccctcacc
cgctgggaga cggtcggggc caggccgag ctgccctgtt ttcaagcctt ctatgctgag
cccagccttg tgccccata gactgagata atgacagcac cagccacagg gccctggtgg
ggggagccag gggcatgggt gcctgcccc gagtctgcc tgacaaattg ggtccagggt
atgccgagtt ctgagacccc ctaaactgcc ctggaggta gccctgcctt tgtcccagc
aaccagcca ggtggcttag aaccggctcc tgtgtccacc cactctgggg gaaggctgag
ccaggctccc tggggcctct tggggagtcc tcgaacctg agacatccgc tcacacctca
cctttgtctt ccag

FIG. 12C-27 gt gggtgaggtt ggggcaaggg cctggcatgg ggggcggca cacccagacg
ggccagaccc gacagtatgg gcactgacga gccaggacct cctcccag gtg
gtgcagaccc tgccctgaca

FIG. 12C-28

```
gtaagtgg ccctctcagc aggaagctcc cctgcacccc ctctaccat gtaccacagt
cccccacccc ccaccacagt ccctgggac gcagacaggg agaggccctt gcagctccca
gtgggaaatc tggccatggg cagtgtctcc ctgcgtggcg gaggcagtgg catcagggcc
ccgactgtgtg cccttttgc ccctctgacc ttccacgtgg tgttccttgt gggtgggagg
ctgcgggagc ctgggcgctc tgcctcctgc cctgcgtaga cgcctggcgg gacctgcaca
cggtcagtgt tcattcctca agatcgtgga ggctgaggct caagagccac gcctgctccc
gcctagcggg tgtctgtgga ggcgcggttg acagaggatc acgttgctat aaaataggtt
tgaacaccat gtcccaagtg actgtaacgg tcacagcttc tacctcgtca agactttttc
ctgctggtct tgcagcagct gcagcattag ctccttgggg gtccgggcag aagcggggca
cggcctaccc agggccccag ctcactggaa cctgcctgtg ggctgttg ggcccagc
catgctccac caggtccttg gggacctcgt gtgcctgctg tggccacctc tgctggcag
acagaccct tttagatgt caatcccgag aagcctccag gacacggctg cagatgcccc
gtcattccag ggtgatggtc attccaggt gatgccggg gctgtgaca ccaccacccc
taggggata gcgggcctc tgttggcctc caggcaggac attccagagg tggggccat
gccagcaacc tcaggcctg tgtgggtggg gcctggtggc tgaatttccc tttcacttta aactcacggg
ctgtcccagg tgtgggtggg gcctggtggc tgaatttccc tttcacttta aactcacggg
aagtctcct gcttttctgc cctttgggcc agttcctcact tatgtggcca tgtgagcaaa
tggacatttt tttaaggat tcatagcaac tcccagacat gtcctcattt cacaatgccg
ggaaggtg attagatgag ctttttgcatc tttgactcta ctgtgatgaa attatcctgc
aattgcag aaacacccgc acgaattcac gggtgttaca aacagtgcaa acctaacggg
acttcactac ccaaggggg aggctggaca gagccatcgg gccagagc acctaacggg
agcttggcct ttgggcctgt gtctgggagc cggtgttcac agaagccctt tgtgcagcac
agatggagat gtgggaggt gtttaccatt cctgggccca gggcaggctc actttaggga
ttcctgccat tccctctaatc cagagccttc tctccacacc cag
```

FIG. 12C-29

```
           g tgagctgggc acaggctggg gcaaaaggaa tgaaggcaaa
gctgcacagc ttctcccagg ctcctcctgt cccggctctg gccctgctg tgttttcggg
acactgagcc tcctttctcc tcttgccgtg tctgtcagtc gcccttcctg gctcctgccc
ctcctgctta gcacagcgaa agcagctctg ggcacccagc cccaggcac gccccggcat
ccgccgctgc cttcctgggt gcaaacagct ggccatgagt gtccctgcat ggctctgggt
gcacagaagc tgcttctagt ccaggaggca ccaatgggaa ctctcaaagg gacagaggtg
tgtcctgcca tccttccgga gaactgacag agggcagggg ctaggctctg cgtgtgtgtt
ttgcaggcag attcgaaatg catttctgct gttcgaagca ctcttctttt tggaaaagtg
tcagggtggg tggggccatg gccgtggctg cccgccctc tgctgagcct gctctcactt
ggggcccgtg gtctgctgc cccgccctcc tgctgagcct gctctcactt ctaggcacaa
ggcctttcca tacgcgctg gaggcctgca gccatcgaac cccaccgca ggttctgctt
ggcagaaaaa cctcattatg caaacaaatg tcttccgttt tttggccccg cccctgcctg
caggtctccc aagggctgtg tttggagcgg gttaaaaggc agccctgggg cctggcttt
tggcctcgac cttaagatga acattacacc tacgaggct tgagagcagg gactttaagg
catgaagtcc ctactcatgc atgaacagct cttttaactt tggggtgtat cgtttcag
```

FIG. 12C-30

```
cctcactgtt accaacagct gggagcgagg tcgccactgt ggctgggaa cagtcctggg
gacagggtca aaatctgcag ctcccgtgg aagatcggca gctctgctgg gcagcgtggg
gatggagcag ggtcgggcag aggccttggc cactggccat cccttagcaa gtgggctggg
cctggcaggg aaactcagcg gctctggagt ctgacctgac ccggtgctca gacgtgtggg
ctcccgcact ctgccccgtg gagtggcacc tgcatgaagc agtcacagct gcattttgt
tttttgtttt ttggttttt gggtttctt gttttttgtt ttgagacgag tctcactctg
tcacccaggc tggagtgcag tggcgcgatc tcggctcgct gcaagctccg cctcccgggt
tcacgccatt ctcctgcctc agcctcccaa gtacctggga ctacaggcgc ccgccaccat
gcccagctaa tttttttgtat ttttagtaga cacggggttt caccgtgtta ggccaggatg
gtctccatct cctgacctcg tgatcatccc gccttggtct ctcaaagtgc tggattaca
ggcgtgacga ccgggcccgg ccggggtttt ttttgagacg aagttttgct ctgttgccca
ggctggagca cagtggcgcg atctcggttc actgcagcct ctgcctcctg ggtcaagcga
ttttcagcct cagcctccctg agtagccagg attataggcc ctcccacagt cgactaattt
tttgtgtttt gggggttttt gttttgttgt ttgtttttga gatgagtct cgctctttcg
ccaggctgga gcgcagtgac gccatctcgg ctcactgcaa ccttcccagt tcaagcgatt
ctcctgcctc agcttcctga atagctggga ttacaggcgc ccgccaccac gcccagctaa
tgtttgtatt tttagtagag acaaggtttc accatgctgg ccaggctggt ctcgaattcc
cgacctcagg caatctgccc gcctcggcct ccaaagtgct ggattacagg tacgagcca
ccgcccctgg cctaattttt gtattttag tagagacggg tttc
                                               gtgagt aattaggtaa
```

FIG. 12C-31

```
ctcccaagt gctgggatta caggcgtgag ccacctcgcc cagcccattt agtgaattct
tagacaacac tgacaaatgg accctgaaa tcccagaagc tgccctacgt ggccactgtt
gctggtgggg tgagcagagc cccttgcagg cggaaaacct aaggctttgc tctcagctac
tcgcacggtc gggctgtgtg aggtgaccc ctaccctcct ggcctccgcg gagcatgctg
tctgggcccg gtcggtccct ctgctgtgcg gttagactgt gtcagtctgt attctgcagc
tgtaacagaa caccgcagct tgggtagttt acaagggaaa gagatccatg tggctcctag
ttctggaggc tgggaagccc aagaccgagg ggtgcatcca tcgagggcct cccactgcg
tcattccatg gtggaaggca gaaggccaa gaggaggtgc cagagagaga aagggccca
acccatcctt ttcatgagga acccactgcg gagacaacgg tgttagttta ctccggagag
ccgagctctc aaacctaatc acctcttaat agcattgcag tgcagtggcc gttcaattgc
agcatgtgtt ttggaggaga cattaacccg gctgactgtg tgttgacgca cctggggcca
gtcattcctg aggaccagc tggaggggt tccagggttt tagggcagag aggttcagcc
cagcattagg cgtgttagta agaaaaagga atggaagcaa agtaagcgtg tgtaagagac
agcaccgtgc agctaacaaa gtcactcttc ccagaaagt aagttttaa aaactcaatc
aatcagtgca atcacagaaa tataaaaat gtatatagaa gaacggaagg aaccactgtc
aatatttgga tgtagtctaa tagcaggtgt gtggatgatt tgatttattt tatcctcaac
tggctacttc ccaccaccc aacaatacac ttagttcaaa cacacaactt ttctcttcac
ag
```

FIG. 12C-32 gacaccatcc atggccctg ctggcttcct gccacctct gtgagtgcccggcgactgttccgat
ggcactgccc agatccgaga tgtaaaaaag cttgctctgg ggcaaccag gcaccctgca
tcgtgccggc tgggaaagag cacgtcgggg tggctctggg tcaaggctgg gcagacggc
ccaccttcct ctgttcctct gcag ctcctgggct ggcccctgac

FIG. 12C-33 gtacgtcgc
ttttccggct tttccagctt tcacagggtt gagatcgtgt ttttccgga aggaagttac
tttgcgggt gacggtggga atgcctcacc gaggctgccg cccatgct gacgaatgtg
tggggtgaat tccag

FIG. 12C-34 gtaagtcagc cacctgcacc ggctgcagcg ggccatcc ccgcctgggg
gtcccgtgcc tggggctaca cagaagccaa cgtgccactg cttccagcc aaagtgagcc
cctagcactc accccgcctg ttagcccttg gggtccacg tccgcctgg gtctgctgtc
ctctgcacta gaggatggcc cacgctcccg ccccggattc aaccagatt ccagcacgca
gcagagccc taaagcctgc tgaatgcaat gggtacaaga acagcggagt gtgccctgt
ggctggcagg gcaggtcct aaacaccccc aagggcactt ccttcacctt cccactcagg
cttctcaggc tccaaggggt tggggtcct ttctagctcc agcattcatc acccaaagc
agttaaacca tttttcatca atcagaagga aaacttgctt ctggaagaca gcaccgagta
gatattttat gcttacgta acaatacttc tgatgatcct ctctcgagta aacgcctgca
ccctgttttt cccaaag

FIG. 12C-35

```
aatccctgag actgacttgt gtgagtgttt gaccccatga cacggtcacc ctgctgtaaa
ggtaaccct ggaacgtggg tagtaggcgc tgcttctgt gcctgccatg cgccctcagg
ggtaatcctg tggaactgg ggcctcat gttgggc ctagcgcatg ttaactcctt
aacaatattt ggcaggagg aacattta acatgtgatg tttctcaa ataccattag
acgcctgtaa tcccaacact ttggggct gaggtgggca gatcacgagg tcggagttc
aagaccagcc tgaccaacat ggtgaaaccc tgtctctact aaaaatacaa aaattagctg
ggcatggtgg cacgcgcctg taatcccagc tactcaggag gctgaggcag gagaatctct
tgaaccctga aggcagaggt tgcagcgagc tgagatcgca ggattgcact ccagcttggg
cgacagagcg agactccgtc tccataaaag aaaaaaaaaa tgtgaggaat ggccgggtgc
ggtggctcat gcctgtaatc ccagcacgtt gggaggacga ggcaggtgga ttactggaag
tcaggagttc aagaccagcc tggtcaacat ggtgaaaccc cgcctctact aaaaatacaa
aattagccag gcaaaacaca gatgtaagat ttgaatgacg caattagagg gatgtgaaaa
tgcccttagg tgaaggatgg gtggaaaatc atttaaaaca tgattacaaa atattaataa
atactcaact gcttaatagg cataaatatt ttgaacaaaa ctaaatccc atttaaattg
gctgccagag gtcaggagg tggttcagcc gtgcacggct cagcagcagg cataggttct
gacggctgtg ccactgggcg cccctgggcc gtgtgccaga gcctggggtt tatgctgca gacctgcaca
gcctcctgca cccctgggcc gtgtgccaga gcctggggtt tatgctgca gacctgcaca
gcctgttact ggctgggtc ttgtgggcgg ttctaacctg gtgtgggta tctgtgttaa
atacatccaa acacgggaaa ggaatggtaa aaattgggta tgataatctt aaggaccac
tgtcacctat gcggtgcgtc gtccactgc agccgtcctg cagccgcgtg cagtctaaga ctgtacag
gtgggtccct ctcgtcgggc cccgtcaagc cctacgcgtg tgacatctgt actttctaa
atgttccac ttcagtgaaa agctggcacc ctgttgtta caaggttga tcagacaccg
ctgtggtgtg gctgcaacag atactctaac catatgtctg tgtccacacc tggtgacag
```

FIG. 12C-36

```
             gta cgagtccacg gccagcaagg cttcactggg tgacatctct
tccgccatct tgtagcttta tgtgggcgt gcttgggtta tgaatgggtc tcttttcctc
ttctcttgc aaagcagtct tagagacaag attaggaatt gtctcaataa ccactttaat
acataaaagt ttaatcgggg ctggcgcgg tggcttacac ctgtaatccc agcactttgg
gaggctgagg cagacggata acctgaggtc agcagtttga gaccagcctg gccaacacag
tgaaacccca tctgtattaa aaatacaaaa atgagccggg cgtggtggcg ggcgctgtaa
tcccagatac ttgggaggct gagacaagag aatcgcttga acccgggagc ggaggttgca
ggttgcagtg agccagatg gcgccactgc cttccagcct ggcgacagag cgagactcca
tctcaaaaaa aaaaagttta atcagtaagc agatcctcct ggatctattt tagctaagtc
aatttggtta gattctgttt aagctactca gtatctattt cagttaaagt ataacagaat
tttctcttaa ttgacctgtg catacgttga atatttccat ttccaatgtc aaaaataaat
gctttgcacg gaggaggca cgcgaggatc cttgcaaag gccatcccct gcccgcccct
gtcttagcct ggtgccttct caaaaccagg aggccttaga ctccaaggat gtgtgtgtcc
agatgagaag gatcccgaac agtcttcgag aaggcaccg ctcccaccto tgccctgggtg
ccctggagcc ttctctctc ctctcctcca cgcactcaca ctgctctctg gatgccctgg
agccctctcc tctcctccac ccaccacc tcccctggg tgccctggag ccctcctc ctcacccac
tcctccacc accccactc tccctggtg cctggagccc ctcctcccct ccatgcacgc acgctgctct
cccacctctc cctggtgccc ctggagccctc tccccttctc ccctccacgc acacactg tctctgggt
ctgggtgccc tggagccctc tccccttctc cctttgctga cctagctctg cctctacctg gtgtccaaac
gccccatgct cctggactct cctggcccc agccacgccc agccacgccc agccacgtct ctgcctgtg gctctgaaca gcatctgtgt
gcacagggt cccaggcccc agccacgccc agccacgtct ctgcctgtg gctctgaaca gcatctgtgt
tgcacttgct ggtggacagc agcctcccgg ccgcaccat gccaccacca
```

FIG. 12C-37

```
tgcccgcacc attctggact ttgtcacctc atctcagtga agggctctga cacccccac
ttaggcggct gactccctct tccctcacac ccaggcctcc catgtttcca ctgtcatcac
tcaccaaagc cacccacaa cccccactc cggcccct gctcactcca aatccactcc
ttactcacac agccccacc aaacccgcgt aagtcagagt gcgggtgtcc tcaggacggc
tctgcacccc tgcctggggc tggccgcgcc tggccttccc cggacactcc cgaccgccag
cccgcggag agccttttgtg tgccgttccc tcggcctccc cacccgctgt ggcctctccc
caagtgaaga gtgagcagat ggaagagcag ggcttgccca cagctggatg tcaagtcccc
ctgctttcag tccgggctgc agctgaactc acctttctgc tctgcccaag
```

FIG. 13

```
gtgcaatctt ctgtgtgttt cagGTGACCC AGGCCCTGCC AGCTATGGGA
AAAATGGCCG AGACGGTGAG CGAGGCCCCC CAGGGCTGGC AGGAATTCCT
      2
GGAGTGCCTG GACCCCCGGG ACCTCCTGGG CTTCCCGGTT TCTGTGAGCC
AGCCTCCTGC ACCATGCAGG CTGGTCAGCG AGCATTTAAC AAAGGGCCTG
ACCCTtgaaa ggcttactgc tgcatggctg tctgcatgaa ccacgcctgg
tgaaggagcc tgggtgagaa acaccatcca aagctggggc aaagatgatt
accttcagca tgattacaat gtattacctt cagtatgatt acagaagtcc
tacttgacaa tcacatatag aagaacggtg ctattcagta agttctcttt
                              3
cctttcccctt ggaggaaga cagcagagtc atcagttaaa aaaaaaaaa
aagaaaacca aacacctccc ttgaacaaat ttatactcct gttcccagga
tcttgagctt tagtgtgcta tacctatgtg tcttatcgtg ggccactgtg
ccaataaaca aaaacaactg tttggtttac ctc
```

```
H  +300   agttctactg  gccagcactg  gcacaggcca  cccgggaagg  tctccgagga
M  +242   g.g...c..c  c..t.t.--   .....:...   ...tt.gca.  a....t.g...
C  +261   ctg...c..t  .-...-...   --c.t..g..  a..t.--...  -----....g cagccagaag  ctgcactggg  gtggatggga  tggaggcaga  gctgcgtgct
          ....nn....  n.ag...aa.  aaatg....C  ....a....   a...t.cat.
          a.a..-----  ..tgc...--  --...g.t..  .......---  -----....C cagtcctcgc  ctgtgcggcg  gcaggg-aag  gggttaaggg  cgactgttgt
          t..g..t.-   --....a.at  ..ca..-..a  .......ct.  g........
          a.aa.aa.-   ---a...--a  ---a...C.a  ........    -t...C...

cattctatcc  gtcctcccct  tccc--cct-  -agctctcct  [ccaatcc-a]
          .g...t....  c......ag   g..t--gt.-  -........   ..........
          ....a....   -..t...---  ....ag...t  C.........  -.........

ggaccctctc  cggggccatt  [cataaacagg]  gggnaacgcg  cccctcccgg  ←
          .......t    .a....g..   .g.-......   aa.a...C.a  ggt.C..tt..
          .......C    .Ca...ag.   .----.a...   -...a.ct.t  ---aggg.t
```

| CONTROL | GGTCCAGCT | GGCCCCCT | GGGCCCCCA | GGACCCCCA | GGCTCCATT |
| --- | --- | --- | --- | --- | --- |
| DEL A1 | GGTCCAGCT | GGCCCCCT | GGG | CCCCCA | GGCTCCATT |
| DEL A2 | GGTCCAGCT | GGGCCCCT | GGGCCCCCA | GG | CTCCATT |

FIG. 21A

| GENE REGION | 5' PRIMER<br>3' PRIMER | SEQ ID NO | POS. | TRANSCRIPT LENGTH |
|---|---|---|---|---|
| PROMOTER | ATCCTGAGGACCCAGCTGCAC<br>GTTAGCCGTCCGCTCATGCGTG | 216<br>217 | -387<br>-44 | 344 |
| EXON 1 | GACGGGAGTTTCTCCTCGGGGTC<br>GAGTCTCCGGATCATCCACGTC | 218<br>219 | -115<br>103 | 321 |
| EXON 2 | GCTGATGAGGAGCAGGCGAG<br>ATCCAAGTGTGCCTCTTAGAC<br>GTTTGCTAATGCTGCTCCCGTC | 220<br>221<br>222 | -161<br>-90<br>108 | 404<br>333 |
| EXON 3 | GTGCTGGAGGCCTCTGCCCGACGGGGAGCAGC<br>GGCCTCGGGGGCCAGTGTCTC | 223<br>224 | -73<br>133 | 242 |

FIG. 21B

| GENE REGION | 5' PRIMER<br>3' PRIMER | SEQ ID NO | POS. | TRANSCRIPT LENGTH |
|---|---|---|---|---|
| EXON 4 | GCCTCTGCCGACGGGAGCAGC<br>AGGCTGTCCAGGGATGCCATC | 225<br>226 | -201<br>135 | 372 |
| EXON 5 | ACCTGGCCTCTTGTTTCTTCTC<br>CTGTAGGATTCTTGCAACTTTTCT | 227<br>228 | -162<br>122 | 386 |
| EXON 6 | CACACCAGGAAGTGCATGATGTCAG<br>CTCCCAAGCTGTCTATACCAGCCGC | 229<br>230 | -91<br>90 | 261 |
| EXON 7 | ATAGGCGGCTGGTATAGACAG<br>TCTCTGAGCATCTCTCCCTGCCCCTCA | 231<br>232 | -173<br>89 | 307 |
| EXON 8 | CGTCTTCATATGCCTCCTTG<br>AAGACCCAGGCCTGGGAGTTCTTCT | 233<br>234 | -127<br>82 | 280 |

FIG. 21C

| GENE REGION | 5' PRIMER<br>3' PRIMER | SEQ ID NO | POS. | TRANSCRIPT LENGTH |
|---|---|---|---|---|
| EXON 9 | CCCCTGGTGAGCCTGGCGAG<br>CTGAGTATCGTTCCCAAATGTG | 235<br>236 | -194<br>97 | 347 |
| EXON 10 | CTGGGGCCCCCAAACCTGACCTGC<br>GGCCATTAGAACACACTCACTG | 237<br>238 | -108<br>88 | 260 |
| EXON 11 | CTGAACCTGGGCTTCACTGCAC<br>GATGTCCACTCTCTGGCCCTTG | 239<br>240 | -90<br>140 | 292 |
| EXON 12 | CAAAGGGATGGCGGTGATGAC<br>CTGTAGATCAGAGAATAATGAG | 241<br>242 | -111<br>88 | 253 |
| EXON 13 | GTAAGAGGCTGTCTGAACATC<br>GTCAGATGAGATGGGAGACAGC | 243<br>244 | -88<br>95 | 228 |

FIG. 21D

| GENE REGION | 5' PRIMER<br>3' PRIMER | SEQ ID NO | POS. | TRANSCRIPT LENGTH |
|---|---|---|---|---|
| EXON 14 | GGTGAGTGTGCCCAGTTCCAG<br>CGTTAAGTCCACTGAGCACTG | 245<br>246 | -117<br>92 | 263 |
| EXON 15 | GATCCCTGAGCTCTGGAAGGGGCTC<br>GAGATGGCAGCTGCAAGTCAC | 247<br>248 | -83<br>145 | 279 |
| EXON 16 | GGGCGAGGTTATGTGTTGGTCTG<br>TTTGGGGAACAGGGAGACATGAACC | 249<br>250 | -102<br>73 | 229 |
| EXON 17 | CTGATCATTGCTCTCTCCCTGTCCCCTGT<br>ACCAGGCTGTCCATCAGCAC | 251<br>252 | -102<br>118 | 320 |
| EXON 18 | TAAGTGTCCCCGACTCAGTGTC<br>AGCCAGGGGCGTGACGTAGGAG | 253<br>254 | -88<br>87 | 220 |

FIG. 21E

| GENE REGION | 5' PRIMER<br>3' PRIMER | SEQ ID NO | POS. | TRANSCRIPT LENGTH |
|---|---|---|---|---|
| EXON 19 | AAGTATCCTGCCAGGCTTCAG<br>GAAGAGGATGAGCTGAGAGTC | 255<br>256 | -100 | 307 |
| EXON 20 | CAAGGGTAACAGCGTGAGTAC<br>TGAGGCTGGGCCTCCAGTGTC | 257<br>258 | -135 | 342 |
| EXON 21 | GGCTCTGAGGCTGGCACAGGATG<br>GGAAACCACGGCTACCAGGTC | 259<br>260 | -75 | 309 |
| EXON 22 | CCGGACCCCCTGGCGAGCGTG<br>CACAGGAACAGTTAGGGTCTC | 261<br>262 | -116 | 279 |
| EXON 23 | CCCAAGGTAACCTCTCCTTGC<br>GATCCGGAACGCCCTCATCCCCAAGAC | 263<br>264 | -123 | 304 |

Note: POS. values shown: EXON 19: -100, 112; EXON 20: -135, 199; EXON 21: -75, 121; EXON 22: -116, 109; EXON 23: -123, 75

FIG. 21F

| GENE REGION | 5' PRIMER<br>3' PRIMER | SEQ ID NO | POS. | TRANSCRIPT LENGTH |
|---|---|---|---|---|
| EXON 24 | GTCTTGGGATGAGGCGTTCCGGATC<br>GTCCGGGGCGACCATCTTGAC | 265<br>266 | -104<br>119 | 284 |
| EXON 25 | GCCCTGGCCAGCCCCTGGTCCTG<br>TAGGGAGGCTGAGGTCCAGAAAGTG | 267<br>268 | -129<br>139 | 367 |
| EXON 26 | AGGGCCCAGCAAGAAGCACCTGC<br>GCTGAGGACCGTGGCCCTCTAGC | 269<br>270 | -157<br>94 | 307 |
| EXON 27 | CCTGCAGGAGGGGTGCTAGAG<br>CACAGAGAGAACACTACAGTCAC | 271<br>272 | -85<br>100 | 239 |
| EXON 28 | CTGCTGTGAGTGTCCCTGATG<br>GGAGGGAAGGTTTAGAATCTG | 273<br>274 | -108<br>85 | 247 |

FIG. 21G

| GENE REGION | 5' PRIMER<br>3' PRIMER | SEQ ID NO | POS. | TRANSCRIPT LENGTH |
|---|---|---|---|---|
| EXON 29 | GGTGAGGCCTCATGGCTGTC<br>TGGCTGTCTGATTAGCTAGGAGGCGG | 275<br>276 | -113<br>85 | 251 |
| EXON 30 | GGGTTCCTCTCTAATCACGGCCAGAC<br>AGAAGGGAAGGACACAGGGCATGTGAAG | 277<br>278 | -110<br>90 | 246 |
| EXON 31 | CCTCTGGAGCAAGAGTAAGTAG<br>ACCCCACACCCCTATCTCCATG | 279<br>280 | -107<br>112 | 308 |
| EXON 32 | TTTCTCAAGGCTTGTCGTTGGCCTTG<br>GATTCAAAGGAGGCAGAGATGGGAGC | 281<br>282 | -116<br>63 | 287 |

FIG. 21H

| GENE REGION | 5' PRIMER<br>3' PRIMER | SEQ ID NO | POS. | TRANSCRIPT LENGTH |
|---|---|---|---|---|
| EXON 33-4 | CCTCTCAGGAAACCCAGACACAAGCA<br>GTTCCCAGGTTGACAGCTCAG | 283<br>284 | -87<br>124 | 319 |
| EXON 35 | GTCCTGCCAAACTGAGCTGTC<br>ATTGGAGAGATGCGTCTGACAGGAGG | 285<br>286 | -129<br>144 | 326 |
| EXON 36 | CCCTGTCTGTGCCTTCACCCCTTGC<br>CTTCTCCCCTGAGGATGGCTGAC | 287<br>288 | -97<br>98 | 249 |
| EXON 37 | TGCCTCCATTACTGCTCCTCC<br>TGTAGGAGAGCACAGACGCATCAAGC | 289<br>290 | -78<br>96 | 274 |

FIG. 21I

| GENE REGION | 5' PRIMER<br>3' PRIMER | SEQ ID NO | POS. | TRANSCRIPT LENGTH |
|---|---|---|---|---|
| EXON 38 | TGAGTGGCTTGGCCCTCTGTG<br>AGAGGGAGAACAGCCAACTCATCCG | 291<br>292 | -96<br>99 | 240 |
| EXON 39 | GAGTATCACCCGCCCTCTCTGTTGAGC<br>TCAGTCAGCCCCCACCATCCTTCTG | 293<br>294 | -124<br>81 | 259 |
| EXON 40 | GTGGGGGCTGCCAGAAGGATG<br>TGAGGTGCCAGACAGCAGCACAG | 295<br>296 | -94<br>81 | 337 |
| EXON 41 | AGTGCCAGCTCAGATCTCTGCAGCTC<br>GTCCGCTGGAGTCATCTCTAC | 297<br>298 | -98<br>103 | 309 |
| EXON 42 | GAGAACAGATTTGGTAGAGATGAC<br>CAGGGGAACCTTCGGCACCAG | 299<br>300 | -84<br>135 | 327 |

FIG. 21J

| GENE REGION | 5' PRIMER<br>3' PRIMER | SEQ ID NO | POS. | TRANSCRIPT LENGTH |
|---|---|---|---|---|
| EXON 43 | CCCATGCCAGTACCCTCAGCATGGC<br>GGGAGAGCAGGGGAATATGGGTCAG | 301<br>302 | -90<br>98 | 242 |
| EXON 44 | GCAACACTCCATGACCACAGC<br>CCTGCCCTGGGTGAAGTCCGAC | 303<br>304 | -96<br>100 | 304 |
| EXON 45 | GGAGAGAGAGATCCAGCAGAGGGGA<br>GGGACAAACTGTCAGGCGGAAGTTC | 305<br>306 | -94<br>98 | 246 |
| EXON 46 | CATGCCCTTCAGAACTCTACAG<br>GGGGAAAGAATGACTATCCAG | 307<br>308 | -90<br>99 | 297 |
| EXON 47 | GTTGCCCACACTGCCCTTGTC<br>AACCCTTCTCCAGAGAGGCAAAGGG | 309<br>310 | -92<br>103 | 249 |

FIG. 21K

| GENE REGION | 5' PRIMER<br>3' PRIMER | SEQ ID NO | POS. | TRANSCRIPT LENGTH |
|---|---|---|---|---|
| EXON 48 | CCGTGGGGCCAGAGCCAGCAG<br>GCACAGAGAGGGAAGAGAGTGGGGA | 311<br>312 | -102<br>89 | 299 |
| EXON 49 | GCTGGTCCTGTTGTATGTAGC<br>CCAGCACCATATGGTAGGGGCACAT | 313<br>314 | -103<br>89 | 475 |
| EXON 50 | CCAGGGTCCCCATGCCCATATGTGC<br>CATGTCCCCTTCTGAGCACTGGGCTA | 315<br>316 | -87<br>66 | 344 |
| EXON 51 | GGACCCTGGACAGAGGGAAGGCCAGCAGG<br>GATGGAGAGAGGGCACTATGGC | 317<br>318 | -74<br>82 | 410 |
| EXON 52 | GGGCTTTTTGGCCAGGCCATAGTGCC<br>GAGGGGGGTTCAGTTTGGGTTTGCTTGTCTG | 319<br>320 | -84<br>93 | 321 |

FIG. 21L

| GENE REGION | 5' PRIMER<br>3' PRIMER | SEQ ID NO | POS. | TRANSCRIPT LENGTH |
|---|---|---|---|---|
| PA1 REGION | TTTTTCCTTTGCATTCATCTCTC<br>CATTGTTTCCTGTGTCTTCTGG | 321<br>322 | 141<br>443 | 303 |
| PA2 REGION | AGAGACAACTTCCCAAAGCAC<br>AGGCCCCTTCCCCATGTCTAC | 323<br>324 | 1279<br>1475 | 217 |

FIG. 22A

| GENE REGION | 5' PRIMER / 3' PRIMER | SEQ ID NO | POS. | TRANSCRIPT LENGTH |
|---|---|---|---|---|
| PROMOTER | AAGTCCGCGTATCCACAAAGCTGAGCAT | 325 | -310 | 338 |
|  | GCCACGTCCCTTCCCCCATTC | 326 | 28 (EXON 1) |  |
| EXON 1 | AGTTGGAGGTACTGGCCACGACTG | 327 | -108 | 315 |
|  | GCGTTTCCCACATGCCTGAG | 328 | 137 |  |
| EXON 2 | TGCTGATCCCTGCCATACTTTTGAC | 329 | -189 | 280 |
|  | CTCTCCCTTCCAAGAGAAGACATC | 330 | 80 |  |
| EXON 3 | GTGAAGGTATATTTGTATACTACAC | 331 | -97 | 279 |
|  | TGTTATCTTAAACATCAAAGCTAC | 332 | 167 |  |
| EXON 4 | CATTGTAGTTACATCAGTCTTACC | 333 | -112 | 294 |
|  | GCTTCTTCTGCAGTGCATTACCTG | 334 | 146 |  |

FIG. 22B

| GENE REGION | 5' PRIMER<br>3' PRIMER | SEQ ID NO | POS. | TRANSCRIPT LENGTH |
|---|---|---|---|---|
| EXON 5 | TCCACCCTACTTGCACATAGAAAGG<br>GACAAGGGCTCACAAAGAGAATGGG | 335<br>336 | -110<br>182 | 385 |
| EXON 6 | TCGGCCAAGTTTTTGACGTACAGCT<br>TGGCGTGGTAAAATGTGACATAAAA | 337<br>338 | -261<br>76 | 338 |
| EXON 7 | GGGAGGAATAAAAACTATGGAATC<br>GACCAGCTTCACCAGGCTCAC | 339<br>340 | -125<br>141 | 311 |
| EXON 8 | GTACTGAAAGCTTGTAATGCCTC<br>GGAGACCCATCATTTCACTAAGG | 341<br>342 | -88<br>81 | 223 |
| EXON 9 | TGAACCTGGTCAAACTGTGAGTAC<br>TGTCAGGCATATTCAGCTTTTGGCA | 343<br>344 | -108<br>110 | 272 |

FIG. 22C

| GENE REGION | 5' PRIMER<br>3' PRIMER | SEQ ID NO | POS. | TRANSCRIPT LENGTH |
|---|---|---|---|---|
| EXON 10 | ACCAAGATTCCCCCATTTGTGCTGA<br>GTTGCTTATGGTATGCTTGCTGTC | 345<br>346 | -70<br>220 | 345 |
| EXON 11 | TTTGTCGCTCTGTGCTTAGAGG<br>CTTCCCTTTGGCAAACTCCAGGGAT | 347<br>348 | -143<br>124 | 321 |
| EXON 12 | GCTGGGACCTGGAACACTGGACTTC<br>TGGAGGTCATGGGGAATTTCAATCA | 349<br>350 | -145<br>61 | 260 |
| EXON 13 | GAACCTGGATATGTGGTACTATCTG<br>GAATACAATGCTGAAGGATACAGTG | 351<br>352 | -212<br>104 | 361 |
| EXON 14 | CTTGTACAGGTTGGAAACTGAAC<br>CCACGGGCACCCTAAGAAGA | 353<br>354 | -94<br>110 | 258 |

FIG. 22D

| GENE REGION | 5' PRIMER<br>3' PRIMER | SEQ ID NO | POS. | TRANSCRIPT LENGTH |
|---|---|---|---|---|
| EXON 15 | CCGTGGGCTTCCTGGTGAGAG<br>TGGTAAAGTGTCTGAAATGATGC | 355<br>356 | -148<br>105 | 298 |
| EXON 16 | CACCCTGGATACCATGAATGTC<br>CTGCAAACACAGTTCCAATCTTTCA | 357<br>358 | -187<br>77 | 318 |
| EXON 17 | CAGTAGCCAAGATGGCAGAATC<br>CCAGTAAGGCCGTTTGCTCCAG | 359<br>360 | -191<br>172 | 462 |
| EXON 18 | CGTTGGACCTCCTGTAAGTAG<br>AAAATGCAGTGTGGTCCATTAGG | 361<br>362 | -156<br>105 | 306 |
| EXON 19 | TAATGTGTGCTGCCTCTACAGC<br>CATATAGCAGACGGGAGTGTAC | 363<br>364 | -64<br>167 | 330 |

FIG. 22E

| GENE REGION | 5' PRIMER<br>3' PRIMER | SEQ ID NO | POS. | TRANSCRIPT LENGTH |
|---|---|---|---|---|
| EXON 20 | CTTGAGCTTCTCTTTACCTTGAC<br>CACCACTGGGACCAGGAGGAC | 365<br>366 | -106<br>128 | 288 |
| EXON 21 | CGTAAGTAGCTCTATCATCAC<br>AAGGCAGATGGAAAAGCAGATG | 367<br>368 | -126<br>129 | 311 |
| EXON 22 | GGGTTGGGTGAAGTGTTTTGGCTTG<br>GAGGATGCTAAAGCTAATGACAC | 369<br>370 | -135<br>79 | 268 |
| EXON 23 | GCTGTCTATCACTTACTTCCTAG<br>TCAAAAATGCAACTGTCAGCAAGAC | 371<br>372 | -109<br>136 | 344 |
| EXON 24 | AAAAAGTCGGGGAAAAGGTGCCTT<br>TCTCCCCTGCTCTGCTTTCAGTCCT | 373<br>374 | -101<br>194 | 349 |

FIG. 22F

| GENE REGION | 5' PRIMER<br>3' PRIMER | SEQ ID NO | POS. | TRANSCRIPT LENGTH |
|---|---|---|---|---|
| EXON 25 | TTTCATCCGTGGCAGCATCATAAGC<br>CTGAGACTGGACTGATTCGCAG | 375<br>376 | -81<br>96 | 276 |
| EXON 26 | TGGAGCTGCATGGTGATGGATC<br>TATCAGATGGTGTAAAAAAAAGT-<br>GTGGTTCTTAGATG | 377<br>378 | -165<br>79 | 298 |
| EXON 27 | GCTTTCGTGGGAACCCACAATGAGT<br>TAGCAACGTATGTCACCACTG | 379<br>380 | -139<br>95 | 288 |
| EXON 28 | TGGCCATCTCCATTTTCAGTC<br>TGCTTCAGTCCCTGAAATCATGT | 381<br>382 | -92<br>111 | 257 |
| EXON 29 | GAGCTGTAAATCACCATACCGTAC<br>TGGCTCATTCTCTCCATCAGCAC | 383<br>384 | -227<br>164 | 445 |

FIG. 22G

| GENE REGION | 5' PRIMER<br>3' PRIMER | SEQ ID NO | POS. | TRANSCRIPT LENGTH |
|---|---|---|---|---|
| EXON 30 | TGCACTCATGTAGATACTGCCAGGT<br>GACTTGTTGCAGGGTCATCAGTGGC | 385<br>386 | -121<br>100 | 264 |
| EXON 31 | AAACCAGGGGCTCGGAAGCTACACAA<br>GGTCCACTGGGAATCGGATTGCTGTT | 387<br>388 | -102<br>158 | 359 |
| EXON 32 | TCTCCCTCCTTTCAATAGCCCAGCC<br>GTGAAAACTTGGGCATCCTTGTGCA | 389<br>390 | -152<br>75 | 336 |
| EXON 33 | GAATGGTAAGGAATCGAGACATTGC-<br>AATTTGGAAATTCTCAATTCAACA-<br>TAAAAAAAATCCAAGTACGAAG | 391<br>392 | -148<br>74 | 276 |
| EXON 34 | GGAGTACCCTCCTTCTGAGAGTGGC<br>ATTGCTGGGGCTCTTTGGGACTAGG | 393<br>394 | -198<br>78 | 330 |

FIG. 22H

| GENE REGION | 5' PRIMER<br>3' PRIMER | SEQ ID NO | POS. | TRANSCRIPT LENGTH |
|---|---|---|---|---|
| EXON 35 | ACTCTGTGAGATGTGCGTCAG<br>GTTGGGGCCAGCAGGACCGAC | 395<br>396 | -137<br>140 | 320 |
| EXON 36 | GAAGCCCTGTAAGTAAGAACCTG<br>GTTACAGCTCTGGTATTCCGAC | 397<br>398 | -112<br>80 | 246 |
| EXON 37 | GATTTGCTGGTCCGGCTGTGAG<br>CTTCCGTTATTTCCATCTTCTATC | 399<br>400 | -113<br>127 | 348 |
| EXON 38 | TGCGGGAATGATCCACTTGAAGAAA<br>TCGGAATTGCTCTGAATAGAATGAA | 401<br>402 | -85<br>144 | 283 |
| EXON 39 | GAAATTCCCATCTTACCCAAATTCTTG<br>GAAAAGCTGACTTCAGACCAGGAG | 403<br>404 | -70<br>139 | 263 |

FIG. 22I

| GENE REGION | 5' PRIMER<br>3' PRIMER | SEQ ID NO | POS. | TRANSCRIPT LENGTH |
|---|---|---|---|---|
| EXON 40 | CATAAAGGAAGACAGGAGTTGC<br>GTGTGTGCTGGACAGATTTCCTGGC | 405<br>406 | -192<br>150 | 504 |
| EXON 41 | CTCACACAATCTTCAAGCCAACCTGTG<br>TCTGTCACATTTGAAGTGGCAGCTT | 407<br>408 | -75<br>75 | 258 |
| EXON 42 | GGAGGGGAAGGTTAGCATTCCATCG<br>AAAGCCCATTCTTTGGCCTAAGCAA | 409<br>410 | -64<br>119 | 291 |
| EXON 43 | AGGGTTCGTTACTGAGCACTG<br>CCACGGGGCCATGAGGACCAG | 411<br>412 | -110<br>159 | 323 |
| EXON 44 | ATGGTCAACCCGGACACAAG<br>CAACTTAGCTAGGCCCAAGATAC | 413<br>414 | -106<br>117 | 331 |

FIG. 22J

| GENE REGION | 5' PRIMER<br>3' PRIMER | SEQ ID NO | POS. | TRANSCRIPT LENGTH |
|---|---|---|---|---|
| EXON 45 | CAACCCAGATTGATGCTAAGCTTC<br>GTATCAATTCTCAGCATGGACTG | 415<br>416 | -288<br>138 | 480 |
| EXON 46 | GCAGATTACCAGCAGAGGTGAGAGC<br>TGAAAATCCTTCTGAGCTGAAGGCC | 417<br>418 | -145<br>67 | 320 |
| EXON 47 | TCCCATTGAATTTGGAAAAAAAATATGTCTCTTGAC<br>GACACCAGGTACATGTGAGCTG | 419<br>420 | -81<br>114 | 257 |
| EXON 48 | CAAGAGAAGACAGTTCATCTCTG<br>TGGGGCTAACTTTAATGGGTTGTC | 421<br>422 | -115<br>103 | 326 |
| EXON 49 | GAACATGCTTCCGTGTGAAGCTC<br>AGGGAAATGAGGTTGGGTGCTGGTT | 423<br>424 | -102<br>177 | 535 |

FIG. 22K

| GENE REGION | 5' PRIMER<br>3' PRIMER | SEQ ID NO | POS. | TRANSCRIPT LENGTH |
|---|---|---|---|---|
| EXON 50 | TGTTACTTATGAGAGTCAGTATCTTTC<br>GTCCAATCAATCCATCTTCTAATGTG | 425<br>426 | -98<br>176 | 459 |
| EXON 51 | CCCTTTCCTAAGCTTGGATCTGAG<br>TTAACCCCCTTTAGACCCCCTTG | 427<br>428 | -132<br>96 | 471 |
| EXON 52 | GGACAGACATCTTCAGAATGAC<br>TTGCCCACAATTTAAGCAAGTAG | 429<br>430 | -120<br>134 | 401 |
| PA1 REGION | CCTTCCATTTCTTCTGCACATCTAC<br>TGTGGATCACACTCATGGGAAAGTG | 431<br>432 | 91<br>413 | 323 |
| PA2 REGION | GTTCATAATACAAAGGTGCTAAT<br>GAAACAAAGCTTCTGTGGAACC | 433<br>434 | 525<br>737 | 273 |

FIG. 23A

| GENE REGION | 5' PRIMER<br>3' PRIMER | SEQ ID NO | POS. | TRANSCRIPT LENGTH |
|---|---|---|---|---|
| PROMOTER & EXON 1 | CCTATAGCACCTTGCCTGGATC<br>CACTGTTACCCTAGGACTATG | 435<br>436 | -249<br>40 (EXON 1) | 290 |
| EXON 1 | CTGGGCTCAGAGCGCTGC<br>ACAGACCCTGGTTCTGAGGAC | 437<br>438 | -114<br>68 | 320 |
| EXON 2 | TTGAAAATATGGAAGTATTTTCCATCTGCGG<br>TGAAGGACTATGAATGCCCTC | 439<br>440 | -70<br>104 | 248 |
| EXON 3 | TTATTTGGGAAAGTTGTGGAAAG<br>ATTAAGGTACTGAAGATAGGCAGG | 441<br>442 | -75<br>162 | 370 |
| EXON 4 | GTAGCTTTTCTATAGGTCTGGCATC<br>ACTGGGAATCAAACAAGGAGGAC | 443<br>444 | -110<br>239 (EXON 4) | 349 |

FIG. 23B

| GENE REGION | 5' PRIMER<br>3' PRIMER | SEQ ID NO | POS. | TRANSCRIPT LENGTH |
|---|---|---|---|---|
| EXON 4 | CTGGGAAGGAGCAAGTTGGC<br>CATCTGGGACATGCTGCACTCAGC | 445<br>446 | 111(EXON 4)<br>107 | 394 |
| EXON 5 | CAGTGTGCTCAACCAGTTCAAG<br>GCAAAGCACAGGCTCTCTTAGCG | 447<br>448 | -127<br>133 | 344 |
| EXON 6,7 | GACGAAGTGCCACCTATGCTAG<br>CCTTTCTCACAGCTCCCTCGAC | 449<br>450 | -93(INTRON 5)<br>87(INTRON 7) | 335 |
| EXON 1* | GACGAAGTGCCACCTATGCTAG<br>CCTTTCTCACAGCTCCCTCGAC | 451<br>452 | -93(INTRON 5)<br>87(INTRON 7) | 335 |
| EXON 8 | CTGGAAGGTAACTTTTACCCCAC<br>GGAGCCCTGGGAAAAGAATAGG | 453<br>454 | -108<br>69 | 252 |

FIG. 23C

| GENE REGION | 5' PRIMER<br>3' PRIMER | SEQ ID NO | POS. | TRANSCRIPT LENGTH |
|---|---|---|---|---|
| EXON 9,10 | CCCCATCTGTGAAGTGAGCTC<br>CACAAAACACACACTTACTCGTAC | 455<br>456 | −97 (INTRON 8)<br>71 (INTRON 10) | 396 |
| EXON 11 | ATACTTATGTAACCATCCTGTAGAC<br>TATGGCTGCATAGTATTCCACATC | 457<br>458 | −112<br>166 | 332 |
| EXON 12 | CACCATAAATGGGGTGTTTAATGC<br>ATAAAAGATTTCACAATGGCAG | 459<br>460 | −103<br>76 | 215 |
| EXON 13 | CAGTGCTTTCTTTAGAATGAGCATC<br>AACACCACTGAGTAGACCGTTAG | 461<br>462 | −133<br>101 | 258 |

FIG. 23D

| GENE REGION | 5' PRIMER<br>3' PRIMER | SEQ ID NO | POS. | TRANSCRIPT LENGTH |
|---|---|---|---|---|
| EXON 14 | GGTCAAATGAGTTATTGTGTCATTGG<br>TGCAAGTGGAAATGTACAGTTAGG | 463<br>464 | -139<br>96 | 289 |
| EXON 15 | CTATGCATGGCTGAGCTCGGTG<br>ACTTCTTGCCCTAAACAGAACC | 465<br>466 | -121<br>170 | 345 |
| EXON 16 | GAGAACATGCCCATGAGTCAGG<br>CTGAGTAGATGCAAGCCACTAG | 467<br>468 | -119<br>123 | 375 |
| EXON 17 | TCACAAAGCGGGAGTCCTAG<br>GGACTGAATAAGCACTACTCG | 469<br>470 | -72<br>129 | 258 |
| EXON 18 | CTGATTTAGGGAAGCAGGATCAC<br>TGATGCATCTGCTTAGAACTTATC | 471<br>472 | -88<br>152 | 293 |

FIG. 23E

| GENE REGION | 5' PRIMER<br>3' PRIMER | SEQ ID NO | POS. | TRANSCRIPT LENGTH |
|---|---|---|---|---|
| EXON 19 | GCTTCTCTGTATTTCTGAATGTTC<br>AGGACACCAAGTTCATGTAATGC | 473<br>474 | -187<br>119 | 360 |
| EXON 20 | CCATCAGAAGAATTCTCCTTGGAC<br>GCAACAAGAGTGAAACTCCATC<br>GATAAAAGTTATGTTTAAATGGC | 475<br>476<br>477 | -185<br>132<br>81 | 320<br>371 |
| EXON 21 | | | | |
| EXON 22 | TTGGTGACGTGGATGATACTTTC<br>GACCAGGAATTCCCTCTAGCAC | 480<br>481 | -88<br>31 (EXON 23) | 306 |
| EXON 23 | CAGTCACTCCAAGCCTCCTG<br>CCATCCACACCTGGCAAACC | 482<br>483 | -120<br>20 (EXON 24) | 327 |

FIG. 23F

| GENE REGION | 5' PRIMER<br>3' PRIMER | SEQ ID NO | POS. | TRANSCRIPT LENGTH |
|---|---|---|---|---|
| EXON 24 | TATGTCCTGAGCTGTAGTCATC<br>GGAAATGCCACACTCAGTTGGC | 484<br>485 | -132<br>71 | 257 |
| EXON 25 | AGTCAGCTGTGTTGGGACAATCC<br>GAACTTATCAGATTAGGTAGCATGTC | 486<br>487 | -112<br>95 | 261 |
| EXON 26 | GGGAACTAGGAAGCATCTTCCTTAC<br>CAAAGTATGCTTTTCTGTAGCTAGG | 488<br>489 | -143<br>186 | 374 |
| EXON 27 | CAAATGTAAGAGATCCCAGTC<br>AAGTTAACACCTACTGATTACAACAGGTTAGAACTTCAGGAG | 490<br>491 | -91<br>61 | 206 |
| EXON 28 | TTCAGGCAAACCGGTAAGACAC<br>GATGAATGAATGGAAGAACATCC | 492<br>493 | 41 (EXON 27)<br>73 | 228 |

FIG. 23G

| GENE REGION | 5' PRIMER<br>3' PRIMER | SEQ ID NO | POS. | TRANSCRIPT LENGTH |
|---|---|---|---|---|
| EXON 29 | GCACTATGTAGGATGGCCTATG<br>ATGGATGCTACAAACCACGCAG | 494<br>495 | -131<br>208 | 393 |
| EXON 30 | GGTGTTTCTGCCTTCCGTGC<br>TTTGCTTCTTAATCTCAACTCTGAG | 496<br>497 | -72<br>166 | 310 |
| EXON 31 | CATTATCCGTACTTGTGCTTATCC<br>CACTCACTATGAACACATTGAG | 498<br>499 | -102<br>138 | 248 |
| EXON 32 | | | | |
| EXON 33 | GTGCCAGAGTTAATCTGTTCATGG<br>GTTACATAATGATTTCATAAAGCAG | 502<br>503 | -123<br>95 | 251 |

FIG. 23H

| GENE REGION | 5' PRIMER<br>3' PRIMER | SEQ ID NO | POS. | TRANSCRIPT LENGTH |
|---|---|---|---|---|
| EXON 34 | TTTATATGAGTATGAAGCAGGCAC<br>GAGAAGCTGATGCCTAGAACAG | 504<br>505 | -71<br>81 | 249 |
| EXON 35 | CACCTGGCTCCTTGCAGAGTC<br>TCTTGTTTACCCCTTGTGTATCTAC | 506<br>507 | -95<br>89 | 239 |
| EXON 36 | CCAATTTGAAGATCTGGTGACAC<br>CATCTTATCTCACTGGATATTCAG | 508<br>509 | -119<br>117 | 425 |
| EXON 37 | CTCACTACAATCTAGTTTATGGC<br>TCAATTCAGGCTGTGTACTTGC | 510<br>511 | -133<br>67 | 278 |
| EXON 38 | TGAGCCATGCCCTCTGCCAG<br>GTGTTTCTCACCCAGGCTCC | 512<br>513 | -74 | 325 |

FIG. 24A

| GENE REGION | 5' PRIMER<br>3' PRIMER | SEQ ID NO | POS. | TRANSCRIPT LENGTH |
|---|---|---|---|---|
| EXON 1 | AGGAGCGCCGGGAGACTCTG<br>GGGCTAGGGGTGTCAGTAGG | 514<br>515 | -73<br>104 | 253 |
| EXON 2 | CACAGTGCCTGCTATACAGAAG<br>CCACAGCGCTCACAAAGTTCTC | 516<br>517 | -149<br>70 | 294 |
| EXON 3 | ATTGCACGGCTTAGGGGACC<br>ACAGAGATGGAACAAACATGAGCC | 518<br>519 | -137<br>77 | 250 |
| EXON 4 | GGTGAGTGCTTTATCCTCTCTTTGGC<br>CAGTGAAGATGCCAGAGCCAGG | 520<br>521 | -85<br>80 | 226 |
| EXON 5 | TGGAGGTTCCTAGGCCTTCATG<br>TTTCCCGGCTCCCTACTTCC | 522<br>523 | -137<br>86 | 277 |

FIG. 24B

| GENE REGION | 5' PRIMER<br>3' PRIMER | SEQ ID NO | POS. | TRANSCRIPT LENGTH |
|---|---|---|---|---|
| EXON 6 | GCGTTTGGGAGTGGCTGTAG<br>GAGGTCCAGCAAAACCAGGG | 524<br>525 | -78<br>22 (EXON 7) | 229 |
| EXON 7 | GCCCGGGCTTCCTGGTCCTC<br>GGCTGGCCCTGGGTCTCTGG | 526<br>527 | 6 (EXON6)<br>152 | 300 |
| EXON 8 | GTGCCTGTCTCTACCTTTGTGC<br>ACCACCCAGCTTGCCAGCTTG | 528<br>529 | -75<br>67 | 196 |
| EXON 9 | GGCACTAGGGTAAGCTGGTAAG<br>CTGAGAGGAGACATGAAGATGG | 530<br>531 | -62<br>104 | 228 |
| EXON 10 | GACCCCCGACATGGCAAAGTG<br>CAGACACCCCCATCTCCGTG | 532<br>533 | -101<br>87 | 236 |

FIG. 24C

| GENE REGION | 5' PRIMER<br>3' PRIMER | SEQ ID NO | POS. | TRANSCRIPT LENGTH |
|---|---|---|---|---|
| EXON 11 | CACGGAGATGGGGGTGTCTG<br>GGAGAGAGCTCAATACGAGGTC | 534<br>535 | -146<br>73 | 275 |
| EXON 12 | CCAGTGTCCAACCAACTGTCC<br>ATGACCAGAGACATGCCGACCTG | 536<br>537 | -4<br>163 | 360 |
| EXON 13 | ATCTGTAACACAGGACTGTAGG<br>ACAAGCTAGAGGCCTGAGCAGG | 538<br>539 | -139<br>89 | 282 |
| EXON 14 | GGGCATCAGACAAGGTATCATG<br>TCAGTCCTGGCTGAACTCCAG | 540<br>541 | -69<br>75 | 198 |
| EXON 15 | CTTCCAGGAGCTGCCTTCTG<br>ATCCAGGTCACACAGGCTCAG | 542<br>543 | -69<br>97 | 220 |

FIG. 24D

| GENE REGION | 5' PRIMER<br>3' PRIMER | SEQ ID NO | POS. | TRANSCRIPT LENGTH |
|---|---|---|---|---|
| EXON 16 | CCTACAGCTACAGCCACAGAG<br>GTGCCTTGTCCTGCCCAGTAC | 544<br>545 | -79<br>64 | 197 |
| EXON 17 | CTCTGGGACCTAGAGGCCAC<br>CATTTCCTGAGGTTATGGAGC | 546<br>547 | -102<br>135 | 291 |
| EXON 18 | CTGCAGCTGTCTCAGAGAACAG<br>CCCCAGGCTCTTGGAGTCTAG | 548<br>549 | -89<br>78 | 221 |
| EXON 19 | TGGATCTCAGTTTCCCTACCTG<br>CAAGAGGTGGTGATTGAGCAAGAGC | 550<br>551 | -92<br>99 | 245 |
| EXON 20 | GTTCATCATGCCGTGGCTGGAC<br>CAGGCTGAGGAGTGCATGATGG | 552<br>553 | -141<br>169 | 355 |

FIG. 24E

| GENE REGION | 5' PRIMER<br>3' PRIMER | SEQ ID NO | POS. | TRANSCRIPT LENGTH |
|---|---|---|---|---|
| EXON 21 | GCTCATCTGGTTCCAGGCTCTG<br>GAGCCAGACTAACTCGGAGCTC | 554<br>555 | -100<br>95 | 249 |
| EXON 22 | ACCATGGAACAGGTGGTCTGG<br>GCAGATGCTGTATCCAGCAGTG | 556<br>557 | -138<br>72 | 264 |
| EXON 23 | CTTTGCTGGTCTGCCAAGTGG<br>CTTGTCTCCTTTGACGCCTGG | 558<br>559 | -147<br>72 (EXON 24) | 357 |
| EXON 24 | GAGGTTGTGACCTTCTCTTTCC<br>GACCAGACCAGAACCCCTGAG | 560<br>561 | -29 (INT.22)<br>122 | 361 |
| EXONS 25 AND 26 | GGGGTGTGGCCGAAAGTTAGG<br>CAAGGAGCAGCGGTCACGAAG | 562<br>563 | -78 (INTRON 24)<br>76 (INTRON 26) | |

FIG. 24F

| GENE REGION | 5' PRIMER<br>3' PRIMER | SEQ ID NO | POS. | TRANSCRIPT LENGTH |
|---|---|---|---|---|
| EXON 27 | | | | |
| EXON 28 | | | | |
| EXON 29 | AACACCAGAGTCTCCTCCATG<br>CAGATTTTCAGACAAGTGAACACG | 568<br>569 | -103<br>98 | 256 |
| EXON 30 | AGGTGGTGCTTTTCTGTCTGC<br>CCGGGGAAGGGTCTGTATGTCA | 570<br>571 | -123<br>105 | 417 |
| EXON 31 | TTTAACAAGCCCCTGCGTGACC<br>CCACACGTCATTAATTCCCAAGC | 572<br>573 | -149<br>60 | 291 |
| EXON 32 | TCTCCTATGGTGTTTTGGCCTC<br>TAGGACTCCCTGAGTCCCAGAC | 574<br>575 | -113<br>333 (EXON 32) | 446 |

FIG. 25A

| GENE REGION | 5' PRIMER<br>3' PRIMER | SEQ ID NO | POS. | TRANSCRIPT LENGTH |
|---|---|---|---|---|
| EXON 1 | AGGTGGGCCCGGCTGAATGG<br>GGCGCTGGCGACTCCTCTCC | 576<br>577 | | |
| EXON 2 | CCGAGGAGAGCGGGCGGTCGTC<br>CTCTCCATCAGGCCGGGGAGC | 578<br>579 | | |
| EXON 3 | CTGATTTGGAGGCCAGCGCTGC<br>CAGGCCTGCTCCAAGCCCCTCTG | 580<br>581 | | |
| EXON 4 | TGAGCCGGGTCTGCCAGACAG<br>TGAGCAGGCCCAGCTGGACAAC | 582<br>583 | | |
| EXON 5 | CACCAAGGGAAGGGTCCGTGC<br>CTACCAGCTCCTTGGCCTTGTGG | 584<br>585 | | |

FIG. 25B

| GENE REGION | 5' PRIMER<br>3' PRIMER | SEQ ID NO | POS. | TRANSCRIPT LENGTH |
|---|---|---|---|---|
| EXON 6 | GACCCTGTGTCCTGGGAGTTGG<br>GCTCCGGAGAGAGGCTGCAGATG | 586<br>587 | | |
| EXON 7 | CTCTCCCGGAGCTGTGGTGCCTGG<br>CAAGTATGGGGGTGGTCAGATGGC | 588<br>589 | | |
| EXON 8 | TGGGGGGTGGGGCTTCTCAGG<br>GGATCATTGGCCAGGGCTTCTACC | 590<br>591 | | |
| EXON 9 | CCAGACCCCGACCCTCAGGACGC<br>GGCCAAGTTAGGGTTAGGAGATC | 592<br>593 | | |
| EXON 10 | GGAAGGTTGTGGTCCGTCAGAG<br>CTGTCTGCTCTGAGCTCCTGTC | 594<br>595 | | |
| EXON 11 | GACCCCTGCGTCGACGTCC<br>CTGGCCCTAGCTTTCTTCCTG | 596<br>597 | | |

FIG. 25C

| GENE REGION | 5' PRIMER<br>3' PRIMER | SEQ ID NO | POS. | TRANSCRIPT LENGTH |
|---|---|---|---|---|
| EXON 12 | GACCCTGCAGGCCTCACTTCA<br>CTCGCCCCGGCCCACAGACACAA | 598<br>599 | | |
| EXON 13 | GCTGCTTGGGCTTGAGTAGGGTG<br>CTTGAGGTCAGCAGCCTTGGCAG | 600<br>601 | | |
| EXON 14 | CTGCCAAGGCTGCTGACCTCAAG<br>GGCTGAGGGCTCATGGAAGAC | 602<br>603 | | |
| EXON 15 | GGAGACTACTAGGTGGCATCT<br>CCAGGGAACAGCTCAGCCAGAG | 604<br>605 | | |
| EXON 16 | CCTCCAGCCATCTCTGACCAC<br>GCAGTCTCACTCCCAAGTGTG | 606<br>607 | | |
| EXON 17 | GCCGCTGCCCACCATAGCTCC<br>CTGAATGCCATCTCCACCTGTAC | 608<br>609 | | |

FIG. 25D

| GENE REGION | 5' PRIMER<br>3' PRIMER | SEQ ID NO | POS. | TRANSCRIPT LENGTH |
|---|---|---|---|---|
| EXON 18 | CACCGAGGTAGCACTGGTTGCC<br>GCGACCAGCCCTCTCCCTGTGAG | 610<br>611 | | |
| EXON 19 | CCCGACGGGCCTTACTCAT<br>CCAACATGGGCCACTGAGC | 612<br>613 | | |
| EXON 20 | CCTCACCCTCAGGTCCACAAGGC<br>GTCTGGGGCGCCCGCAGATACTC | 614<br>615 | | |
| EXON 21 | GTATGTGGCTGCAGCGCTTTCT<br>GGCCCCATCAAGGCAACCAAAT | 616<br>617 | | |
| EXON 22 | GTATGTGGCTGCAGCGCTTTCT<br>GGCCCCATCAAGGCAACCAAAT | 618<br>619 | | |

FIG. 25E

| GENE REGION | 5' PRIMER<br>3' PRIMER | SEQ ID NO | POS. | TRANSCRIPT LENGTH |
|---|---|---|---|---|
| EXON 23 | GAACCGGCTCCTGTGTCCA<br>GGTCCTGGCTCGTCAGTGC | 620<br>621 | | |
| EXON 24 | GTATGGGCACTGACGAGCCAGGAC<br>GGGGGTGGGGGACTGTGGTA | 622<br>623 | | |
| EXON 25 | GCCGGTGTTCACAGAAGCCC<br>CTGACAGACACGGCAAGAGGAGA | 624<br>625 | | |
| EXON 26 | GGCCTCGACCTTAAGATGAAC<br>GCCGATCTTCCACCGGGAGCT | 626<br>627 | | |
| EXON 27 | CCTCAACTGGCTACTTCCCACC<br>CATCTCGGATCTGGGCAGTGCC | 628<br>629 | | |

FIG. 25F

| GENE REGION | 5' PRIMER<br>3' PRIMER | SEQ ID NO | POS. | TRANSCRIPT LENGTH |
|---|---|---|---|---|
| EXON 28 | GCTCTGGTCAAGGCTGGGCAAG<br>CGTCACCCCGCAAAGTAACTTCC | 630<br>631 | | |
| EXON 29 | GGAAGTTACTTTGCGGGGTGACG<br>CTAGTGCAGAGGACAGCAGAC | 632<br>633 | | |
| EXON 30 | CTGGAAGACAGCACCGAGTAGA<br>GCGCCTACTAACAAGTCAGTCTC | 634<br>635 | | |
| EXON 31 | CCTACGCGTGTGACATCTGTAC<br>GACCCCATTCATAACCCAAGCAC | 636<br>637 | | |
| EXON 32 | GAGCAGATGGAAGAGCAGGCTTG<br>GTGCTTCGGGCGTCCTTGTCAC | 638<br>639 | | |

COMPOSITIONS AND METHODS FOR DETECTING ALTERED COL1A1 GENE SEQUENCES

CROSS-REFERENCE TO RELATED APPLICATIONS

The present application is a continuation-in-part of U.S. application Ser. No. 08/212,322, filed Mar. 13, 1994 (now abandoned), which is a file wrapper continuation of U.S. application Ser. No. 07/803,628, filed Dec. 3, 1991 (now abandoned).

GOVERNMENT SUPPORT

Portions of this invention were supported in part by the U.S. Government (National Institutes of Health Grant AR-38188), and the U.S. Government may therefore have certain rights in the invention.

FIELD OF THE INVENTION

The field of the invention is detecting altered collagen gene sequences.

BACKGROUND OF THE INVENTION

The collagen genes are an important family of genes, the products of which provide the extracellular framework for virtually all multicellular organisms (Bornstein et al., 1980 Ann. Rev. Biochem. 49:957–1003). More than nineteen distinct types of collagen have been described (Ramirez et al., 1985, Ann. New York Acad. Sci. 460:117–129; Vuorio et al., 1990, Annu. Rev. Biochem. 59:837–872; Chu et al., 1993, In: *Connective Tissue and Its Heritable Disorders*, Royce et al., eds., Wiley-Liss, New York, pp.149–165; Prockop et al., 1995, Annu. Rev. Biochem. 64:403–434). The biosynthesis of collagen has been described (Prockop et al., 1979, N. Eng. J. Med. 301:13–23).

Large collagen structures form by nucleated growth of collagen chains into triple helical collagen subunits. Collagen fibrils form by nucleated growth of collagen subunits, a fibril comprising a quarter-staggered array of subunits (Gross et al., 1958, Annu. Rev. Cell Biol. 2:421–457; Wood et al., 1960, Biochem. J. 75:588:598; Prockop et al., 1984, N. Eng. J. Med. 311:376–386; Kadler et al., 1987, J. Biol. Chem. 262:15696–15701; Na et al., 1989, Biochem. 28: 7153–7161; Kadler et al., 1990, Biochem. J. 268:339–343; Prockop et al., 1989, Biophysics (Eng. Transl. Biofizika) 3:81–89). During nucleated growth, the collagen protein chains fold into the triple helical conformation that is a unique and characteristic feature of all collagens (Engel, 1987, Adv. Meat. Res. 4:145–158; Engel et al., 1991, Annu. Rev. Biophys. Biophys. Chem. 20:137–152; Piez, 1984, In: *Extracellular Matrix Biochemistry*, Piez et al., eds., Elsevier Science Pub. Co. Inc., New York, pp. 1–40).

Each of the three α chains in a collagen subunit comprises a repeating tripeptide sequence having the general amino acid sequence Gly-X-Y. The presence of glycine, the smallest amino acid, in every third position is critical, since the amino acid in this position fits into a restricted space in which the three chains come together in the center of the triple helix. The X- and Y-amino acid residues are frequently proline and 4-hydroxyproline, respectively. Because the highly flexible glycine bonds flank the relatively inflexible peptide bonds of proline and 4-hydroxyproline (Hyp), individual α chains do not independently fold into any defined three-dimensional structure. Instead, the chains fold into a defined structure only by forming hydrogen bonds and water bridges that link the Gly-X-Y sequences in one α chain to equivalent Gly-X-Y sequences in the two other α chains.

It is essential to proper collagen molecule conformation that the three a chains are in register, in the sense that the Gly-X-Y tripeptide units in one chain are hydrogen-bonded to the corresponding tripeptide units in the other two α chains. Otherwise, the chains have exposed ends or internal loops of non-triple-helical tripeptide units. Substitution of one or more amino acids of the Gly-X-Y tripeptide sequence with other amino acids, particularly substitution of Gly with an amino acid having a relatively bulky side chain, can produce a structurally abnormal but partially functional collagen subunit. A large number of mutations comprising said substitutions have been described (e.g. Kuivaniemi et al., 1991, FASEB J. 5:2052–2060). Numerous diseases and disorders are associated with mutations in one or more of the Type I or Type IX collagen genes including, but not limited to, osteoporosis, osteoarthritis, chondrodysplasia, multiple epiphyseal dysplasia, osteogenesis imperfecta, shortness of stature, scoliosis, low bone density, and degenerative joint disease.

Type 1 Collagen

Type I collagen accounts for about 80 to 90% of the protein found in bone. It is also found in large amounts in tissues such as skin, ligaments, and tendons. In many tissues, the Type I collagen fibrils are associated with other types of collagen and with other components of the extracellular matrix.

Type I collagen is synthesized as a precursor denoted Type I procollagen, which comprises two proα1(I) chains and one proα2(I) chain. Each proα chain comprises three separate domains, namely an N-propeptide domain, a central domain, and a C-propeptide domain.

The N-propeptide domain located at the amino-terminal end of each proα chain comprises a globular subdomain, a short triple-helical subdomain, and another short subdomain that forms part of the cleavage site at which the N-propeptide is separated from the mature collagen molecule.

The central domain of each proα chain is denoted the α-chain domain, which comprises about several hundred amino acid residues and, with the exception of a short sequence at the end of the domain, every third amino acid is glycine. The α-chain largely comprises the Gly-X-Y tripeptide repeating unit.

The globular C-propeptide domain located at the carboxyl-terminal end of each proα chain is responsible for association of the proα chains during biosynthesis of collagen. Hydrophobic and electrostatic interactions among the C-propeptide domains of the three proα chains direct inclusion of two proα1(I) chains and one proα2(I) chain into the procollagen molecule. Formation of interchain disulfide bonds among the proα subunits further stabilizes the structure of the procollagen molecule, provides the correct registration of the Gly-X-Y tripeptide units of the three chains, and forms a triple helical nucleus of Gly-X-Y units of the three chains. After formation of the triple helical nucleus, triple helical association of the Gly-X-Y units of the three chains proceeds in a zipper-like fashion from the carboxyl-toward the amino-terminal portions of the three chains.

Biosynthesis of the procollagen molecule involves a large number of post-translational modifications, requiring at least eight procollagen-specific enzymes and several non-specific enzymes. Over a hundred amino acids in each a chain are modified post-translationally. After procollagen is assembled, it is secreted from cells. Extracellularly, the N-propeptide is cleaved from the procollagen molecule by one enzyme and the C-propeptide is cleaved from the procollagen molecule by a second enzyme, yielding an individual mature collagen subunit. The solubility of the collagen subunit is about two thousand times lower than the solubility of the corresponding procollagen subunit. Low collagen solubility drives spontaneous polymerization of collagen subunits into collagen fibrils. Indeed, in vitro assembly of collagen subunits formed by enzymatic cleavage of procollagen subunits has been demonstrated (Prockop et al., 1989, In: *Cytoskeletal and Extracellular Proteins*, Aebi et al., eds., Springer Series in Biophysics, Vol. 3, pp. 81–89; Kadler et al., 1990, Biochem J. 268:339–343).

Human proα1(I) is encoded by the COL1A1 gene, which is located on chromosome 17q21.3-q22, and human proα2(I) is encoded by the COL1A2 gene, which is located on chromosome 7q21.3-q22. Oligonucleotide primers useful for amplifying and sequencing cDNA encoding the human proα1(I) chain of Type I procollagen have been described (Labhard et al., 1990, Matrix 10: 124–130).

The complete cDNA sequence corresponding to the COL1A1 gene has been reported (Chu et al., 1984, Nature 310:337–340; Tromp et al., 1988, Biochem. J. 253:919–922; Bernard et al., 1983, Biochem. 22:5213–5223). Furthermore, the nucleotide sequence of approximately 400 base pairs of the 5'-untranslated region, introns 1–26, and twenty-six nucleotides at the 5'-end of intron 27 of COL1A2 have been reported (Chu et al., 1985, J. Biol. Chem. 260:2315–2320; D'Alessio et al., 1988, Gene 67:105–113; Barsh et al., 1985 Proc. Natl. Acad. Sci. USA 82:2870–2874).

The complete cDNA sequence corresponding to the COL1A2 gene has been reported (Bernard et al., 1983, Biochem. 22:1139–1145; de Wet et al., 1987, J. Biol. Chem. 262:16032–16036; Kuivaniemi et al., 1988, Biochem. J. 252:633–640). Furthermore, the nucleotide sequence of certain non-coding regions of the COL1A2 gene have been reported, including the following sequences:
(i) 75 nucleotides located within intron 1
(ii) 318 nucleotides at the 3'-end of intron 5
(iii) 298 nucleotides at the 5'-end of intron 6
(iv) 30 nucleotides at the 3'-end of intron 26
(v) intron 27
(vi) intron 28
(vii) 25 nucleotides at the 5'-end of intron 29
(viii) intron 33
(Myers et al., 1983, J. Biol. Chem. 258:10128–10135; Myers et al., 1984, J. Biol. Chem. 259:12941–12944; Dickson et al., 1984, Proc. Natl. Acad. Sci. USA 81:4524–4528; Tromp et al., 1988, Proc. Natl. Acad. Sci. USA 85:5254–5258; Sherwood et al., 1990, Gene 89:238–244; Vasan et al., 1991, Am. J. Hum. Genet. 48:305–317; Ganguly et al., 1991, J. Biol. Chem. 266:12035–12040).

Alterations in the coding region of either the COL1A1 gene or the COL2A1 gene and gene alterations that decrease expression of either proα1(I) or proα2(I) have been associated with osteogenesis imperfecta, a genetic disease of children which is characterized by bone brittleness. Many, but not all, children afflicted with osteogenesis imperfecta also exhibit blueness of the sclerae of the eyes, poor dentition, and thin skin. These symptoms are thought to be associated with a decrease in the amount of Type I collagen in the corresponding tissue or with formation of abnormal Type I collagen fibrils therein. Bone brittleness associated with osteogenesis imperfecta is usually apparent early in childhood because the patients develop numerous fractures resulting from relatively minor trauma. It is thought that bone brittleness associated with decreased or abnormal Type I collagen expression can be confused with the symptoms of battered child syndrome. Many patients afflicted with mild osteogenesis imperfecta become fracture-free after the growth spurt associated with puberty, but develop a marked susceptibility to bone fracture later in life.

Alterations in Type I procollagen genes have been found in patients afflicted with some forms of Ehlers-Danlos syndrome (EDS; Weil et al., 1989, EMBO J. 8:1705; Weil et al., 1988, J. Biol. Chem. 263:8561; Weil et al., 1989, J. Biol. Chem. 264:16804; Vasan et al., 1991, Am. J. Hum. Genet. 48:305; Weil et al., 1990, J Biol. Chem. 265:16007). Some patients afflicted with osteoporosis have alterations in one or more of their Type I procollagen genes (Constantinou et al., 1990, Cytogenet. Cell Genet. 51:979; Nicholls et al., 1984, J. Med. Genet. 21:257–262).

Fibroblasts obtained from a patient afflicted with osteopenia and ankylosing spondylitis synthesized Type I procollagen having decreased thermal stability, an observation which suggests that an altered procollagen protein was involved in the patient's symptoms (Constantinou et al., 1990, Cytogenet. Cell Genet. 51:979). In another case, a structural defect in the proα2(I) chain was found in a family afflicted with osteoporosis and idiopathic scoliosis (Shapiro et al., 1989, Connect Tissue Res. 21:117–123). In a third case, a single base mutation that converted the codon encoding glycine-661 of proα2(I) to a codon encoding serine was reported in a woman afflicted with postmenopausal osteoporosis (Spotila et al., 1990, Am. J. Hum. Genet. 47: A237). In yet another case, a mutation that converted the codon encoding glycine-19 of proα1(I) to a codon encoding cysteine was reported in a patient afflicted with osteoporosis and joint hypermobility (Nicholls et al., 1984, J. Med. Genet. 21:257–262). Furthermore, an eleven-base-pair deletion was detected in the gene encoding proα2(I) in another patient afflicted with osteoporosis and joint hypermobility (Nicholls et al., 1984, J. Med. Genet. 21:257–262). Functional and structural abnormalities of Type I procollagen are also known to result in a number of clinically distinct inherited disorders which affect the strength of bone, ligaments, tendons, and other connective tissues (Prockop, 1990 Arth. Rheumat. 31:1–8). The significance of mutations affecting Type I procollagen structure or function no doubt remains unrecognized in numerous diseases and disorders affecting tissues which comprise Type I collagen.

Type IX Collagen

Type IX collagen is a component of hyaline cartilage and the vitreous body of the eye. The Type IX collagen molecule is a heterotrimer comprising three distinct gene products, α1(IX), α2(IX) and α3(IX), which are encoded by the COL9A1 gene, the COL9A2 gene, and the COL9A3 gene, respectively (van der Rest et al., 1987, In *Structure and Function of Collagen Types*, Mayne et al., eds., Academic Press, Orlando, pp. 195–221; Shaw et al., 1991, Trends Biochem. Sci. 16:191–194). The COL9A1 gene is located on chromosome 6q12-q14, and the COL9A2 gene is located on chromosome 1p32. The chromosomal location of the COL9A3 gene is located on chromosome 20q13.3 (Brewton et al., 1995, Genomics 30:329–336).

Each α chain comprises three collagenous domains, designated COL1, COL2, and COL3, numbered in the direction from the carboxyl- to the amino-terminus of the chain. The three collagenous domains are flanked by four small non-collagenous domains, designated NC1, NC2, NC3, and NC4 (van der Rest et al., 1988, J. Biol. Chem. 263:1615–1618; Vasios et al., 1988, J. Biol. Chem. 263:2324–2329; Vaughan et al., 1988, J. Cell. Biol. 106:991–997; Ninomiya et al., 1990, In *Extracellular Matrix Genes*, Sandell et al., eds., Academic press, San Diego, pp. 79–114; Brewton et al., 1995, Genomics 30:329–336).

The 339-amino-acid COL2 domain and the 137-amino-acid COL3 collagenous domain are identical in length in each the three α chains. The 115-amino-acid COL1 collagenous domains of α1(IX) and α2(IX) are nearly identical in length to the COL1 domain of α3(IX), which is 112 amino acids in length. As a consequence of the similar length of the collagenous regions of the three α chains, the chains are able to fold into an triple helix like that of the $(proα1(I))_2proα2(I)$ triple helix of Type I collagen, as described herein, wherein the Gly-X-Y tripeptide sequences of the three α chains are in register.

The non-collagenous domains vary in size among the three α chains of Type IX collagen. The NC3 domain consists of twelve amino acids in the α1(IX) chain, seventeen amino acids in the α2(IX) chain, and fifteen amino acids in the α3(IX) chain. The difference in size among the non-collagenous domains are thought to impart flexibility to the Type IX collagen molecule.

Type IX collagen is attached to the surface of Type II collagen fibers by lysine-derived covalent cross-links between the COL2 domain of α3(IX) and the C-telopeptide of Type II collagen and between the N-terminal end of the COL2 domains of all three α chains and the N-telopeptide of Type II collagen (Eyre et al., 1987, FEBS Lett. 220:337–341; van der Rest et al., 1988, J. Biol. Chem. 263:1615–1618; Wu et al., 1992, J. Biol. Chem. 267:23007–23014; Diab et al., 1996, Biochem. J. 314:327–332). Type IX collagen is thus a fibril-associated collagen having interrupted triple helices, and, as such, belongs to the FACIT subgroup of collagens (Gordon et al., 1990, Curr. Op. Cell Biol. 2:833–838).

When a triple-helical domain of Type IX collagen molecule is anchored to a Type II collagen fibril, the NC3 domain functions as a hinge, allowing the COL3 and NC4 domains to project away from the surface of the fibril. Thus, the COL3 and NC4 domains of Type IX collagen are capable of mediating interactions between Type II collagen fibrils in cartilage and non-collagenous proteins (van der Rest et al., 1988, J. Biol. Chem. 263:1615–1618; Vasios et al., 1988, J. Biol. Chem. 263:2324–2329; Vaughan et al., 1988, J. Cell. Biol. 106:991–997). The NC4 domain in the α1(IX) chain is unique in the sense that it occurs in two variant forms. In cartilaginous tissue, the NC4 domain of the α1(IX) chain has a longer sequence; in ocular tissue, the NC4 domain has a shorter sequence.

Type IX collagen is a proteoglycan. The NC3 domain of the α2(IX) chain comprises an attachment site for a glycosaminoglycan side chain (Bruckner et al., 1985, Proc. Natl. Acad. Sci. USA 82:2608–2612). Results from a recent study indicate that the NC1 domain of the three α chains of Type IX collagen encode all of the information necessary for glycosaminoglycan side chain selection and assembly (Mechling et al., 1996, J. Biol. Chem. 271:13781–13785).

Complete cDNA sequences of the chicken, human, and murine COL9A1 genes have been reported (Ninomiya et al., 1984, Proc. Natl. Acad. Sci. USA 81:3014–3018; Vasios et al., 1988, J. Biol. Chem. 263:2324–2329; Ninomiya et al., 1990, In: *Extracellular Matrix Genes*, Sandell et al., eds., Academic press, San Diego, pp. 79–114; Muragaki et al., 1990, Eur. J. Biochem. 192:703–708; Rokos et al., 1994, Matrix Biol. 14:1–8). Portions of the genomic structure of the chicken, human, murine, and rat COL9A1 genes have been reported (Lozano et al., 1985, Proc. Natl. Acad. Sci. USA 82:4050–4054; Ninomiya et al., 1990, In: *Extracellular Matrix Genes*, Sandell et al., eds., Academic press, San Diego, pp. 79–114; Muragaki et al., 1990, Proc. Natl. Acad. Sci. USA 87:2400–2404; Ting et al., 1993, J. Bone Min. Res. 8:1377–1387).

Complete cDNA sequences of the chicken, human, and murine COL9A2 genes have been reported (Ninomiya et al, 1985, Biochem. 24:4223–4229; Perälä et al., 1993, FEBS Lett. 319:177–180; Perälä et al., 1994, J. Biol. Chem. 269:5064–5071). The complete genomic structure of the chicken and murine COL9A2 genes have been reported (Ninomiya et al., 1990, In *Extracellular Matrix Genes*, Sandell et al., eds., Academic press, San Diego, pp. 79–114; Perälä et al., 1994, J. Biol. Chem. 269:5064–5071).

Complete cDNA sequences of the chicken and human COL9A3 genes have been reported (Brewton et al., 1992, Eur. J. Biochem. 205:443–449; Har-El et al., 1992, J. Biol. Chem. 267:10070–10076; Brewton et al., 1995, Genomics 30:329–336). The genomic structure of the COL9A3 gene has not been reported in any species to date.

Transgenic mice expressing a cDNA construct comprising the coding region of the COL9A1 gene having a large in-frame deletion in the COL2-domain-encoding region thereof develop abnormalities in cartilage collagen fiber structure, and exhibit a phenotype similar to human osteoarthritis and mild chondrodysplasia (Nakata et al., 1993, Proc. Natl. Acad. Sci. USA 90:2870–2874). Degenerative joint disease was also exhibited by transgenic mice which were homozygous for an inactivated COL9A1 gene (Fassler et al., 1994, Proc. Natl. Acad. Sci. USA 91:5070–5074), by transgenic mice which overexpressed the isolated NC4 domain of the α1(IX) chain (Haimes et al., 1996, Inflam. Res. 44(Suppl.2):S127–S128), and by transgenic mice which expressed a truncated COL9A2 gene having an in-frame deletion of a region which encoded 38 amino acids in the COL2 domain of α2(IX) (Perälä et al., 1994, J. Biol. Chem. 269:5064–5071). These findings indicate that Type IX collagen is not essential for cartilage development, but it is required for maintaining the integrity of cartilage structures.

Until the present invention, it has been possible to identify a mutation associated with a pathological condition in a human COL1 or COL9 gene only if the mutation was located within the coding sequence of one of the COL1A1, COL1A2, COL9A1, COL9A2, and COL9A3 genes, within one of introns 1–26 of the COL1A1 gene, within the 26 nucleotides located at the 5'-end of intron 27 of the COL1A1 gene, or within the approximately 350 nucleotides adjacent exon 1 of the COL1A1 gene, in the 5'-untranslated region thereof. Hence, a serious unmet need exists for methods and compositions which are useful for identifying mutations which are located in non-coding regions of the genes encoding the chains of Type I and Type IX collagen and which are associated with a pathological condition.

SUMMARY OF THE INVENTION

The invention relates to a method of detecting an alteration in a collagen gene of a human subject, wherein the alteration is associated with a pathological condition in the subject, the method comprising
(i) obtaining from the subject a sample nucleic acid comprising at least a portion of the gene, wherein the portion comprises at least one intronic nucleotide, a first site, and a second site;
(ii) determining the nucleotide sequence of the portion of the gene; and
(iii) comparing the nucleotide sequence of the portion of the gene with a consensus nucleotide sequence of the gene. A difference between the nucleotide sequence and the consensus nucleotide sequence is indicative of the presence in the subject of the alteration in the gene. The portion of the gene is selected from the group consisting of the segment of the COL1A1 gene extending in the 5'- to 3'-direction from and including the 78 nucleotides of intron 27 located adjacent exon 28 through the 3'-end of the COL1A1 gene, the segment of the COL1A2 gene extending in the 5'- to the 3'-direction from and including the 3'-end thereof through intron 4, the segment of the COL1A2 gene extending in the 5'- to the 3'-direction from and including the 2600 nucleotides at the 3'-end of intron 26 through the 340 nucleotides at the 5'-end of intron 26, the segment of the COL1A2 gene extending in the 5'- to the 3'-direction from and including the 775 nucleotides at the 3'-end of intron 29 through intron 32, the segment of the COL1A2 gene extending in the 5'- to the 3'-direction from and including intron 34 through the 5'-end of the COL1A2 gene, the COL9A1 gene, the COL9A2 gene, and the COL9A3 gene. The consensus nucleotide sequence of the COL1A1 gene is SEQ ID NO: 1; the consensus nucleotide sequence of the COL1A2 gene is SEQ ID NO: 2; that of the COL9A1 gene is SEQ ID NO: 3; that of the COL9A2 gene is SEQ ID NO: 4; and that of the COL9A3 gene comprises SEQ ID NO: 5 and SEQ ID NO: 640.

In one embodiment, the method of the invention further comprises the step of contacting the portion of the gene with a first intronic primer prior to determining the nucleotide sequence of the portion, the first intronic primer being either substantially complementary to or substantially homologous with the first site. Preferably, the first intronic primer has a sequence selected from the group consisting of SEQ ID NO: 273 through SEQ ID NO: 336, SEQ ID NO: 339 through SEQ ID NO: 379, SEQ ID NO: 382 through SEQ ID NO: 391, SEQ ID NO: 394 through SEQ ID NO: 477, SEQ ID NO: 480 through SEQ ID NO: 499, SEQ ID NO: 502 through SEQ ID NO: 563, and SEQ ID NO: 568 through SEQ ID NO: 639.

Another embodiment of the method of the invention further comprises the steps of contacting the portion of the gene with a first intronic primer homologous to the first site, contacting the portion of the gene with a second primer complementary to the second site, and amplifying the portion of the gene to obtain an amplified polynucleotide prior to determining the nucleotide sequence of the portion.

In another embodiment of the method of the invention, the method further comprises a CSGE step performed after the step of amplifying and prior to the step of determining the nucleotide sequence of the portion of the gene, the CSGE step comprising the steps of denaturing the amplified polynucleotide, annealing the amplified polynucleotide, and determining whether the amplified polynucleotide forms a heteroduplex, and wherein the step of determining the nucleotide sequence of the portion comprises determining the nucleotide sequence of the amplified polynucleotide.

In yet another embodiment of the method of the invention, the first intronic primer is either substantially complementary to or substantially homologous with a part of a non-coding region of the portion, wherein the non-coding region of the portion is selected from the group consisting of SEQ ID NO: 6, SEQ ID NO: 7, SEQ ID NO: 24 through SEQ ID NO: 58, SEQ ID NO: 60 through SEQ ID NO: 62, SEQ ID NO: 65 through SEQ ID NO: 83, and SEQ ID NO: 88 through SEQ ID NO: 215.

In a preferred embodiment of the method of the invention, the first intronic primer has a sequence selected from the group consisting of SEQ ID NO: 273 through SEQ ID NO: 336, SEQ ID NO: 339 through SEQ ID NO: 379, SEQ ID NO: 382 through SEQ ID NO: 391, SEQ ID NO: 394 through SEQ ID NO: 447, SEQ ID NO: 480 through SEQ ID NO: 499, SEQ ID NO: 502 through SEQ ID NO: 563, and SEQ ID NO: 568 through SEQ ID NO: 639. Also preferably, the first primer and the second primer are selected from the pairs of primers listed in FIGS. 21 through 25.

In still another embodiment of the method of the invention, the steps of contacting the portion of the gene with a first intronic primer homologous to the first site, contacting the portion of the gene with a second primer complementary to the second site, and amplifying the portion of the gene to obtain an amplified polynucleotide comprise the steps of contacting the portion of the gene with a plurality of pairs of intronic primers and amplifying the portion of the gene to obtain a plurality of amplified polynucleotides. In a variation of this embodiment, the method further comprises a CSGE step performed after the step of amplifying the portion and prior to the step of determining the nucleotide sequence of the portion, the CSGE step comprising the steps of denaturing the amplified polynucleotides, annealing the amplified polynucleotides, and determining whether any of the amplified polynucleotides forms a heteroduplex, wherein the step of determining the nucleotide sequence of the portion comprises determining the nucleotide sequence of any of the amplified polynucleotides which forms a heteroduplex. Preferably, each of the intronic primers is either substantially complementary to or substantially homologous with a part of a non-coding region of the portion. Also preferably, the length of every of the amplified polynucleotides is between about two hundred and about five hundred nucleotides. Also preferably, the length of the polynucleotide amplified using any one pair of the plurality of pairs of primers is different from the length of the polynucleotides amplified using every other pair of the plurality of pairs of primers.

In one embodiment of the method of the invention, a plurality of pairs of primers comprising pairs of primers sufficient to amplify substantially all exons and exon flanking regions of the gene is used. In this method, it is preferred that the length of every of the amplified polynucleotides is between about two hundred and about five hundred nucleotides, and wherein the length of the polynucleotide amplified using every single pair of the plurality of pairs of primers is different from the length of the polynucleotides amplified using every other pair of the plurality of pairs of primers.

In a variation of this embodiment of the method of the invention, the method further comprises a CSGE step performed after the step of amplifying the portion and prior to the step of determining the nucleotide sequence of the portion, the CSGE step comprising the steps of denaturing the amplified polynucleotides, annealing the amplified polynucleotides, and determining whether any of the amplified polynucleotides forms a heteroduplex, wherein the step of determining the nucleotide sequence of the portion comprises determining the nucleotide sequence of any of the amplified polynucleotides which forms a heteroduplex.

In a first embodiment of the method of the invention, the portion of the gene is a segment of the COL1A1 gene not including any non-coding sequence disclosed in the scientific literature prior to the invention and each of the pairs of primers is selected from the pairs of primers listed in FIG. 21. Preferably, the pathological condition is selected from the group consisting of osteoporosis, multiple epiphyseal dysplasia, osteogenesis imperfecta, shortness of stature, and low bone density.

In a second embodiment of the method of the invention, the portion of the gene is a segment of the COL1A2 gene not including any non-coding sequence disclosed in the scientific literature prior to the invention and each of the pairs of primers is selected from the pairs of primers listed in FIG. 22. Preferably, the pathological condition is selected from the group consisting of osteoporosis, multiple epiphyseal dysplasia, osteogenesis imperfecta, shortness of stature, and low bone density.

In a third embodiment of the method of the invention, the portion of the gene is the COL9A1 gene and each of the pairs of primers is selected from the pairs of primers listed in FIG. 23. Preferably, the pathological condition is selected from the group consisting of osteoarthritis, chondrodysplasia, multiple epiphyseal dysplasia, scoliosis, and degenerative joint disease.

In a fourth embodiment of the method of the invention, the portion of the gene is the COL9A2 gene and each of the pairs of primers is selected from the pairs of primers listed in FIG. 24. Preferably, the pathological condition is selected from the group consisting of osteoarthritis, chondrodysplasia, multiple epiphyseal dysplasia, scoliosis, and degenerative joint disease.

In a fifth embodiment of the method of the invention, the portion of the gene is the COL9A3 gene, and each of the pairs of primers is selected from the pairs of primers listed in FIG. 25. Preferably, the pathological condition is selected from the group consisting of osteoarthritis, chondrodysplasia, multiple epiphyseal dysplasia, scoliosis, and degenerative joint disease.

The invention also relates to an isolated nucleic acid comprising at least about fifteen consecutive nucleotides and having a nucleotide sequence which is either substantially complementary to or substantially homologous with a portion of a human collagen gene, wherein the portion of the gene includes at least one nucleotide located in a non-coding region.

The portion of the gene is preferably selected from the group consisting of the segment of the COL1A1 gene extending in the 5'- to 3'-direction from and including the 78 nucleotides of intron 27 located adjacent exon 28 through the 3'-end of the COL1A1 gene, the segment of the COL1A2 gene extending in the 5'- to the 3'-direction from and including the 3'-end thereof through intron 4, the segment of the COL1A2 gene extending in the 5'- to the 3'-direction from and including the 2600 nucleotides at the 3'-end of intron 26 through the 340 nucleotides at the 5'-end of intron 26, the segment of the COL1A2 gene extending in the 5'- to the 3'-direction from and including the 775 nucleotides at the 3'-end of intron 29 through intron 32, the segment of the COL1A2 gene extending in the 5'- to the 3'-direction from and including intron 34 through the 5'-end of the COL1A2 gene, the COL9A1 gene, the COL9A2 gene, and the COL9A3 gene.

Preferably, the isolated nucleic acid is completely complementary to or is completely homologous with the portion of the collagen gene. Also preferably, the portion includes at least three nucleotides located in a non-coding region. Preferably, the portion of the collagen gene comprises only nucleotides located in the non-coding region, wherein the non-coding region has a nucleotide sequence selected from the group consisting of SEQ ID NO: 6, SEQ ID NO: 7, SEQ ID NO: 24 through SEQ ID NO: 58, SEQ ID NO: 60 through SEQ ID NO: 62, SEQ ID NO: 65 through SEQ ID NO: 83, and SEQ ID NO: 88 through SEQ ID NO: 215.

In another embodiment, the isolated nucleic acid has a nucleotide sequence selected from the group consisting of SEQ ID NO: 273 through SEQ ID NO: 336, SEQ ID NO: 339 through SEQ ID NO: 379, SEQ ID NO: 382 through SEQ ID NO: 391, SEQ ID NO: 394 through SEQ ID NO: 447, SEQ ID NO: 480 through SEQ ID NO: 499, SEQ ID NO: 502 through SEQ ID NO: 563, and SEQ ID NO: 568 through SEQ ID NO: 639.

The invention also relates to a kit for detecting an alteration in a gene segment of a human collagen gene, the kit comprising a consensus sequence for the gene and a pair of intronic primers, each having a length of at least about fifteen consecutive nucleotides, wherein the gene segment comprises at least one nucleotide located in a non-coding region of the gene.

In the kit, the gene is selected from the group consisting of the segment of the COL1A1 gene extending in the 5'- to 3'-direction from and including the 78 nucleotides of intron 27 located adjacent exon 28 through the 3'-end of the COL1A1 gene, the segment of the COL1A2 gene extending in the 5'- to the 3'-direction from and including the 3'-end thereof through intron 4, the segment of the COL1A2 gene extending in the 5'- to the 3'-direction from and including the 2600 nucleotides at the 3'-end of intron 26 through the 340 nucleotides at the 5'-end of intron 26, the segment of the COL1A2 gene extending in the 5'- to the 3'-direction from and including the 775 nucleotides at the 3'-end of intron 29 through intron 32, the segment of the COL1A2 gene extending in the 5'- to the 3'-direction from and including intron 34 through the 5'-end of the COL1A2 gene, the COL9A1 gene, the COL9A2 gene, and the COL9A3 gene.

The consensus nucleotide sequence of the COL1A1 gene is SEQ ID NO: 1; the consensus nucleotide sequence of the COL1A2 gene is SEQ ID NO: 2; that of the COL9A1 gene is SEQ ID NO: 3; that of the COL9A2 gene is SEQ ID NO: 4; and that of the COL9A3 gene is listed in SEQ ID NO: 5 and SEQ ID NO: 640.

In one embodiment of the kit, the length of the gene segment is between about two hundred and about five hundred nucleotides. In another embodiment of the kit of the invention, the kit comprises at least one sequencing primer for determining the nucleotide sequence of at least a portion of the gene segment. In yet another embodiment of the kit of the invention, the pair of primers is selected from the group consisting of the pairs of primers listed in FIGS. 21 through 25. In still another embodiment, the kit comprises a plurality of the pairs of primers. In a first embodiment of the kit of the invention, the gene is a segment of the COL1A1 gene not including any non-coding sequence disclosed in the scientific literature prior to the invention and the first primer and the second primer are selected from the pairs of primers listed in FIG. 21. In a second embodiment of the kit of the invention, the gene is a segment of the COL1A2 gene not including any non-coding sequence disclosed in the scientific literature prior to the invention and the first primer and the second primer are selected from the pairs of primers listed in FIG. 22. In a third embodiment of the kit of the invention, the gene is the COL9A1 gene and the first primer and the second primer are selected from the pairs of primers listed in FIG. 23. In a fourth embodiment of the kit of the invention, the gene is the COL9A2 gene and the first primer and the second primer are selected from the pairs of primers listed in FIG. 24. In a fifth embodiment of the kit of the invention, the gene is the COL9A3 gene and the first primer and the second primer are selected from the pairs of primers listed in FIG. 25.

BRIEF DESCRIPTION OF THE DRAWINGS

FIG. 3, comprising FIGS. 3A–3G, depicts the nucleotide sequence of the introns of the human COL1A1 gene extending from a portion of intron 25 to the three nucleotides at the 5'-end of exon 52. Capital letters indicate terminal codons of exon sequences or five ambiguous bases in introns. The alternative bases in some cloned PCR products were G/T at position +185 of intron 46, A/C at position +291 of intron 46, T/C at position +112 of intron 49, A/G at position +126 of intron 49, and C/T at position +179 of intron 50, wherein numbering is in the 3'-direction from the 5'-end of the intron on the coding strand of the gene.

FIG. 4, comprising FIGS. 4A-1 through 4B-54, depicts the human COL1A1 gene. FIGS. 4A-1 through 4A-15 list a consensus nucleotide sequence of the human COL1A1 gene (SEQ ID NO: 1). FIGS. 4B-1 through 4B-54 list the consensus nucleotide sequences of the 5'-untranslated region (FIG. 4B-1; SEQ ID NO: 6), introns 1–50 (FIGS. 4B-2 through 4B-52; SEQ ID NOs: 7–56, respectively), and the 3'-untranslated region (FIGS. 4B-53 and 4B-54; SEQ ID NO: 57) of the COL1A1 gene.

FIG. 5, comprising FIGS. 5A-1 through 5B-58, depicts the human COL1A2 gene. FIGS. 5A-1 through 5A-31 list a consensus nucleotide sequence of the human COL1A2 gene (SEQ ID NO: 2). FIGS. 5B-1 through 5B-58 list the consensus nucleotide sequences of the 5'-untranslated region (FIG. 5B-1 and; SEQ ID NO: 58), introns 1–51 (FIGS. 5B-3 through 5B-57; SEQ ID NOs: 59–109, respectively), and the 3'-untranslated region (FIGS. 5B-58; SEQ ID NO: 110) of the COL1A2 gene.

FIG. 6 is a graph depicting a comparison of the lengths of the introns of the human and chicken COL1A2 genes. Intron sizes in the human gene are indicated by open circles, and intron sizes in the chicken gene are indicated by filled triangles.

FIG. 7 is an image depicting the results of CSGE analysis of amplification products derived from human subjects having single-base alterations in one allele of the individual's COL1A1 gene. Samples were obtained from individuals described in Table 2.

FIG. 8, comprising In FIG. 8A, a diagram of the genomic organization of the COL9A1 gene is depicted, wherein exon numbers are indicated above the diagram, and relative positions of the sequence on P1 clones P1-A and P1-B are indicated below the diagram. The position of alternate exon 1*, which is expressed in ocular tissue, is indicated. Also in FIG. 8A, a diagram of the genomic organization of the COL9A2 gene is depicted, wherein exon numbers are indicated above the diagram, and relative position of the sequence on a PAC clone, PAC-1, is depicted below the diagram. The scale used in FIG. 8A, in kilobases, is indicated along the bottom of the Figure. In FIG. 8B, the protein chains encoded by the COL9A1 and COL9A2 genes are represented. The amino acid length of each region of the proteins is indicated. The COL1, COL2, and COL3 regions are shaded. The exons which encode each of the regions is indicated, wherein E16, for example, refers to a portion of the protein encoded by exon 16. The α1(IX) chain depicted in FIG. 8B is designated "9α1" and represents the form of the protein expressed in cartilaginous tissue.

FIG. 9 is a schematic representation of the human COL9A3 gene. The scale used, in kilobases, is indicated along the central portion of the Figure. A restriction map of the COL9A3 gene region is depicted on the top portion of the Figure, and restriction sites for restriction endonucleases are indicated. Below the scale, the genomic organization of the gene is represented, wherein exons are numbered. Below this representation, the protein chain encoded by the gene is depicted. The lines connecting the representation of the gene with the depiction of the protein indicate the exons which encode the various regions of the protein. The numerals in parentheses next to the region names indicate the amino acid length of the region.

FIG. 10, comprising FIGS. 10A-1 through 10B-41, depicts the human COL9A1 gene. FIGS. 10A-1 through 10A-23 list a consensus nucleotide sequence of the human COL9A1 gene (SEQ ID NO: 3). FIGS. 10B-1 through 10B-41 list the consensus nucleotide sequences of the 5'-untranslated region (FIGS. 10B-1 and 10B-2; SEQ ID NO: 111), introns 1–37 (FIGS. 10B-3 through 10B-40; SEQ ID NOs: 112–148, respectively), and the 3'-untranslated region (FIG. 10B-41; SEQ ID NO: 149) of the COL9A1 gene.

FIG. 11, comprising FIGS. 11A-1 through 11B-38, depicts the human COL9A2 gene. FIGS. 11A-1 through 11A-19 list a consensus nucleotide sequence of the human COL9A2 gene (SEQ ID NO: 4). FIGS. 11B-1 through 11B-38 list the consensus nucleotide sequences of the 5'-untranslated region (FIG. 11B-1; SEQ ID NO: 150), introns 1–31 (FIGS. 11B-2 through 11B-37; SEQ ID NOs: 151–181, respectively), and the 3'-untranslated region (FIG. 10B-38; SEQ ID NO: 182) of the COL9A2 gene.

FIG. 12, comprising FIGS. 12A, 12B, and 12C, depicts the human COL9A3 gene. FIGS. 12A-1 through 12A-16 list a portion of the gene, comprising about three kilobases of the promoter through a 5'-portion of intron 26 thereof. FIGS. 12B-1 through 12B-5 list another portion of the gene, comprising a 3'-portion of intron 26 through the 3'-end of exon 32. The sequence depicted in FIG. 12A is SEQ ID NO: 5; the sequence in FIG. 12B is SEQ ID NO: 640. FIGS. 12C-1 through 12C-37 list the consensus nucleotide sequences of the 5'-untranslated region (FIGS. 12C-1, 12C-2, and 12C-3; SEQ ID NO: 183), introns 1–25 and the 5'-portion of intron 26 (FIGS. 12C-4 through 12C-34; SEQ ID NOs: 184–208 and 209, respectively), the 3'-portion of intron 26, and introns 27–31 (FIGS. 12C-35, 12C-36, and 12C-37; SEQ ID NOs: 210 and 211–215) of the COL9A3 gene.

FIG. 13 depicts the 3'-untranslated region of the COL9A1 gene, as determined by 3'-RACE analysis, as described herein.

FIG. 14 depicts alternate splicing patterns for exons 1 through 8 of the COL9A1 gene. The gene is depicted as a series of boxes and lines across the center of the Figure. The lines and legends above the gene indicate how the exons of the gene are spliced in, for example, cartilaginous tissue, wherein exons 1 through 8 are spliced to exon 6, which is spliced to exon 7, which is spliced to exon 8, which is spliced to the higher-numbered exons of the gene, which are not shown in the Figure. The lines and legends below the gene indicate how the exons of the gene are spliced in, for example, corneal tissue, wherein alternate exon 1* is spliced to exon 8, which is spliced to the higher-numbered exons of the gene.

FIG. 15 lists the nucleotide sequences of a region of intron 6 of each of the human ("H"), murine ("M"), and chicken ("C") COL9A1 genes, as described herein.

FIG. 16 depicts a comparison of the sizes of the introns in the human COL9A1 gene, depicted by filled circles connected by solid lines, and the sizes of the introns in the murine COL9A1 gene, depicted by open circles connected by broken lines. Intron number is indicated on the horizontal axis, and the size, in nucleotides, of each intron is indicated on the vertical axis. Introns in which Alu sequences have been detected are indicated by "+Alu".

FIG. 17 depicts the number of Gly-X-Y amino acid triplet sequences encoded by exons 2, 3, and 4 of the human COL9A3 and COL9A2 genes. Exons are shown to scale. The junction of the NC4 and COL3 domains is indicated.

FIG. 18, comprising

FIG. 19 depicts the nucleotide sequence of a region of the COL9A3 gene, including a repetitive GC-rich region in which a deletion occurred in individuals afflicted with MED. The normal sequence of the gene is shown on the top line. Two alternate sites where the deletion described herein may have occurred are indicated on the lower two lines.

FIG. 20, comprising FIGS. 20A and 20B, depicts alternate models whereby non-triple helical domains such as the NC2 region of Type IX collagen may have a role in aligning Gly-X-Y sequences so that they can assume a triple helical conformation. In Panel A, the conformation of a portion of a normal Type IX collagen fibril is depicted. In Panel B, the conformation of a portion of an altered Type IX collagen fibril is depicted, wherein a Gly-X-Y triplet has been altered or deleted in one chain of the fibril.

FIG. 21, comprising FIGS. 21A–21L, depicts pairs of oligonucleotide primers used for PCR amplification of the promoter region, exons and flanking sequences, and the polyadenylation signals of the COL1A1 gene. Primer sequences are listed with the 5'-end of the sequence at the left. The position ("pos") of each 5'-primer is indicated as the relative position of the 5'-most nucleotide of the gene sequence to which the 5'-primer is homologous. The position of the 5'-primer used to amplify the promoter is indicated relative to the transcription start site; the position of each 5'-primer used to amplify an exon and flanking regions is indicated relative to the 5'-end of the exon; the position of each 5'-primer used to amplify a polyadenylation signal is indicated relative to the 5'-end of the signal. The position of each 3'-primer is indicated as the relative position of the 3'-most nucleotide of the gene sequence to which the 3'-primer is complementary. The position of the 3'-primer used to amplify the promoter is indicated relative to the transcription start site; the position of each 3'-primer used to amplify an exon and flanking regions is indicated relative to the 3'-end of the exon; the position of each 3'-primer used to amplify a polyadenylation signal is indicated relative to the 3'-end of the signal. All relative positions are indicated such that a negative number represents a position in the direction of the 5'-end of the gene and a positive number represents a position in the direction of the 3'-end of the gene, relative to the corresponding reference position. All references to the gene in this figure legend refer to the coding strand thereof The length of each PCR amplification product made using a primer pair is indicated ("transcript length"). Two pairs of primers, each pair comprising the same 3'-primer, are shown for Exon 2. A SEQ ID NO is listed adjacent to each primer.

FIG. 22, comprising FIGS. 22A–22K, depicts pairs of oligonucleotide primers used for PCR amplification of the promoter region, exons and flanking sequences, and the polyadenylation signals of the COL1A2 gene. Primer sequences are listed with the 5'-end of the sequence at the left. Positions are indicated as in FIG. 21. The length of each PCR amplification product made using a primer pair is indicated ("transcript length"). The position indicated for the 3'-primer used to amplify the promoter is at nucleotide 28 of exon 1. A SEQ ID NO is listed adjacent to each primer.

FIG. 23, comprising FIGS. 23A–23H, depicts pairs of oligonucleotide primers used for PCR amplification of the promoter region and the exons and flanking sequences of the COL9A1 gene. Primer sequences are listed with the 5'-end of the sequence at the left. Positions are indicated as in FIG. 21. The length of each PCR amplification product made using a primer pair is indicated ("transcript length"). Primer positions located within an exon are indicated by "(Exon #)", wherein "#" is the exon number. A SEQ ID NO is listed adjacent to each primer.

FIG. 24, comprising FIGS. 24A–24F, depicts pairs of oligonucleotide primers used for PCR amplification of the exons and flanking sequences of the COL9A2 gene. Primer sequences are listed with the 5'-end of the sequence at the left. Positions are indicated as in FIG. 21. The length of each PCR amplification product made using a primer pair is indicated ("transcript length"). Primer positions located within an exon are indicated by "(Exon #)", wherein "#" is the exon number. The position of the 5'-primer used to amplify exon 24 is located in intron 22. A SEQ ID NO is listed adjacent to each primer.

FIG. 25, comprising FIGS. 25A–25F, depicts pairs of oligonucleotide primers used for PCR amplification of the exons and flanking sequences of the COL9A3 gene. Primer sequences are listed with the 5'-end of the sequence at the left. Positions are indicated as in FIG. 21. The length of each PCR amplification product made using a primer pair is indicated ("transcript length"). A SEQ ID NO is listed adjacent to each primer.

DETAILED DESCRIPTION OF THE INVENTION

Figure 1:
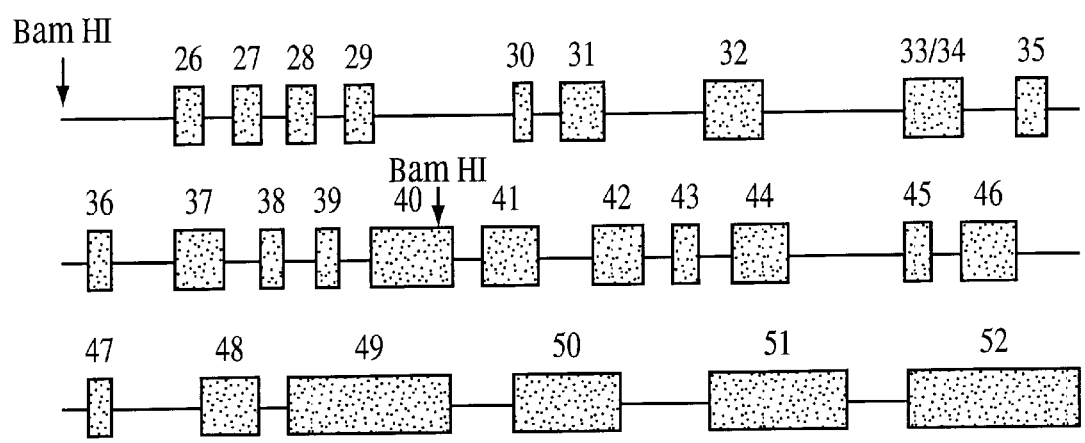
FIG. 1 is a schematic depiction of the 3'-portion of the human COL1A1 gene, comprising the portion extending from a portion of intron 25 through the 3'-end of the gene.

The present invention provides compositions and methods for detecting altered COL1 and COL9 gene sequences in a human subject. Prior art compositions and methods are useful only for detecting mutations in the coding sequences of COL1 or COL9 genes or in certain non-coding sequences of the COL1A1 gene. The compositions and methods of the present invention are superior to prior art compositions and methods in that they are useful for detecting mutations in both the coding sequences and the non-coding sequences of any of the COL1 or COL9 genes. Thus, the compositions and methods can be used to detect collagen gene alterations which affect either the primary sequence of a collagen protein chain, splicing of the mRNA encoding such chains, or regulation of expression of the genes encoding such chains.

The ability to detect abnormalities in a COL1 or COL9 gene permits one skilled in the art to determine whether a subject is predisposed to certain pathological conditions associated with an altered COL1 or COL9 gene sequence. Similarly, the ability to detect abnormalities in a COL1 or COL9 gene permits one skilled in the art to determine whether a subject presenting symptoms potentially attributable to a pathological condition associated with an altered COL1 or COL9 gene sequence is afflicted with that pathological condition. Furthermore, identification of an abnormality in a COL1 or COL9 gene of a subject is useful for designing a therapeutic nucleotide or gene therapy agent which can be administered to the subject to correct or alleviate the abnormality.

By way of example, one skilled in the art would, upon reading the present disclosure, appreciate that the compositions and methods described herein are useful for identifying human subjects who are afflicted with, or who are predisposed to be afflicted with, any of a number of pathological conditions associated with an altered COL1 or COL9 gene sequence including, but not limited to, osteoporosis, osteoarthritis, chondrodysplasia, multiple epiphyseal dysplasia, osteogenesis imperfecta, shortness of stature, scoliosis, low bone density, and degenerative joint disease. One skilled in the art would further appreciate that the compositions and methods described herein are useful for identifying an altered COL1 or COL9 gene sequence associated with a pathological condition, even if the association between the altered sequence and the pathological condition is not presently recognized.

The present invention also provides conformation-sensitive gel electrophoresis (CSGE) compositions and methods whereby alterations in a COL1 or COL9 gene may be easily identified.

The compositions of the present invention may be conveniently packaged in the form of a kit comprising numerous intronic primers, whereby the entire sequence of one or more COL1 or COL9 genes may be examined for the presence of genetic alterations. The kit of the invention provides the practitioner with the numerous reagents which are useful to practice the methods of the invention including, but not limited to, intronic primers, one or more consensus collagen gene sequences, oligonucleotides having sequences derived from portions of a consensus gene sequence, CSGE compositions, instructions, and the like.

It has now been determined that mutations in Type I procollagen genes increase the likelihood of developing osteoporosis. Predisposition for developing osteoporosis is therefore heritable. Although mutations in collagen genes have been demonstrated in diseases such as osteogenesis imperfecta, Ehlers-Danlos syndrome, and related disorders, it was heretofore unknown that mutations in Type I procollagen genes are linked to osteoporosis in the absence of any other evidence of a connective tissue disease or syndrome. Mutations in type I procollagen have been discovered to cause osteoporosis in a subset of patients afflicted with the disease.

When the compositions and methods of the invention are used to identify a mutation in a COL1 or COL9 gene of a first family member by scanning the entire gene of the first family member, it is possible to determine whether a second family member also has the mutation in his or her same COL1 or COL9 gene by using only a single primer pair which amplifies the mutated region of the affected gene. The invention conveniently provides kits comprising compositions which can be used to identify alterations anywhere within a COL1 or COL9 gene of a first family member and compositions which can be used to analyze a particular portion of an affected COL1 or COL9 gene in other family members to determine whether the other family members have the mutated gene.

If the existence in a subject of a pathological condition associated with an altered COL1 or COL9 gene sequence or a predisposition to develop such a pathological condition is detected early, effective treatment is more likely to be available prior to the onset of severe, less treatable symptoms. Also, members of families identified as being predisposed to such pathological conditions may choose to seek appropriate genetic counseling prior to reproduction.

PCR/CSGE Methods for Detecting an Altered Type I or Type IX Collagen Gene

The methods of the invention comprise detecting an alteration in a gene encoding a chain of Type I or Type IX collagen, relative to the consensus nucleotide sequence of the gene. The consensus nucleotide sequence of the human COL1A1 gene is listed in FIGS. 4A-1 through 4A-15 (SEQ ID NO: 1). The consensus nucleotide sequence of the human COL1A2 gene listed in FIGS. 5A-1 through 5A-31 (SEQ ID NO: 2). The consensus nucleotide sequence of the human COL9A1 gene is listed in FIGS. 10A-1 through 10A-23 (SEQ ID NO: 3). The consensus nucleotide sequence of the human COL9A2 gene is listed in FIGS. 11A-1 through 11A-19 (SEQ ID NO: 4). The consensus nucleotide sequence of the human COL9A3 gene is listed in FIGS. 12A-1 through 12B-5 (SEQ ID NOs: 5 and 640, respectively).

An alteration in a gene encoding a chain of Type I or Type IX collagen, relative to the consensus nucleotide sequence of the gene, may be detected by obtaining from a subject a nucleic acid comprising at least a portion of one allele of the gene, wherein the portion comprises at least one intronic nucleotide, determining the nucleotide sequence of the nucleic acid, and comparing the nucleotide sequence of the nucleic acid with the consensus nucleotide sequence of the gene, whereby a difference between the nucleotide sequence of the nucleic acid and the consensus nucleotide sequence indicates the presence of an alteration of the gene in the allele of the subject. Preferably, the collagen gene is selected from the group consisting of the segment of the COL1A1 gene extending in the 5'- to 3'-direction from and including the 68 nucleotides of intron 27 located adjacent exon 28 through the 3'-end of the COL1A1 gene, the COL1A2 gene, the COL9A1 gene, the COL9A2 gene, and the COL9A3 gene, and excluding published non-coding sequences of the COL1A2 gene. Published non-coding sequences of the COL1A2 gene include the following sequences:
(i) 75 nucleotides located within intron 1
(ii) 318 nucleotides at the 3'-end of intron 5
(iii) 298 nucleotides at the 5'-end of intron 6
(iv) 30 nucleotides at the 3'-end of intron 26
(v) intron 27
(vi) intron 28
(vii) 25 nucleotides at the 5'-end of intron 29
(viii) intron 33
(Myers et al., 1983, J. Biol. Chem. 258:10128–10135; Myers et al., 1984, J. Biol. Chem. 259:12941–12944; Dickson et al., 1984, Proc. Natl. Acad. Sci. USA 81:4524–4528; Tromp et al., 1988, Proc. Natl. Acad. Sci. USA 85:5254–5258; Sherwood et al., 1990, Gene 89:238–244; Vasan et al., 1991, Am. J. Hum. Genet. 48:305–317; Ganguly et al., 1991, J. Biol. Chem. 266:12035–12040). Because the nucleotide sequences of the non-coding regions in these collagen genes are described herein for the first time, it is now possible to construct primers which are useful for replicating the sequence of an exon and intronic sequences flanking one or both ends of the exon. Thus, one skilled in the art, armed with the present disclosure, can detect both alterations affecting the primary sequence of the collagen protein chains encoded by these genes and alterations affecting mRNA splicing, transcriptional regulation, or translational regulation in these genes.

Using a pair of such primers and well known PCR reagents, a portion of a genomic DNA molecule or a non-spliced mRNA molecule comprising a Type I or Type IX collagen gene may be amplified to provide an amplified DNA sequence. The amplified DNA sequence comprises an exon of the gene, a portion of a first non-coding region of the gene which is located 3' relative to the exon, and a portion of a second non-coding region of the gene which is located 5' relative to the exon. Thus, the amplified DNA sequence may comprise both the exon and non-coding sequences flanking the exon. Each non-coding sequence may comprise an intron, the 5'-untranslated region, or the 3'-untranslated region of the gene.

A pair of such primers comprises a first primer which is complementary to a sequence comprising a portion of the first non-coding region on one strand of the genomic DNA molecule and a second primer which is complementary to a sequence comprising a portion of the second non-coding region on the opposite strand of the genomic DNA molecule. Thus, "one strand" and "the opposite strand" of the genomic DNA molecule refer to the sense strand and the antisense strand thereof, or vice versa. Addition of PCR components, such as *Thermus aquaticus* DNA polymerase and deoxynucleotide triphosphates (dNTPs), to the suspension of primers and genomic DNA and thermal cycling of the suspension, as is well known in the art of PCR, results in amplification of the exon and non-coding sequences flanking the exon.

Primers which are useful for amplifying an exon and non-coding sequences flanking the exon of a Type I or Type IX collagen gene may be constructed using the corresponding consensus COL1A1, COL1A2, COL9A1, COL9A2, or COL9A3 gene sequence as described herein. Construction of primers useful for PCR amplification of a region of a gene is well within the level of ordinary skill in the art of PCR, when the worker is provided with one of the Type I or Type IX collagen gene consensus sequences described herein. Such construction is described, for example, in Innis et al.(ed., 1990, In: *PCR Protocols*, Academic Press, Inc., San Diego). Preferably, at least one primer of a pair of primers used to amplify an exon of a Type I or Type IX collagen gene is complementary to at least one nucleotide of a non-coding region of the gene, whereby at least one nucleotide of a non-coding region of the gene is amplified along with a nucleic acid comprising at least a portion of the exon or a longer portion of the non-coding region or both. More preferably, at least three nucleotides of a non-coding region of the gene are amplified along with the nucleic acid. Preferably, at least fifteen nucleotides of a non-coding region of the gene are amplified along with the nucleic acid. It is particularly preferred that the each primer of the pair of primers is complementary to a sequence which is located entirely within a non-coding region of the gene.

Preferably, the primers of the invention have a relationship with a non-coding sequence of one of the Type I or Type IX collagen genes described herein, wherein the relationship is selected from the group consisting of a homologous relationship and a complementary relationship. Restated another way, it is preferred that the primers of the invention are complementary to either a portion of a non-coding region on the coding strand of a nucleic acid comprising a portion of one of the Type I or Type IX collagen genes described herein or a portion of a non-coding region on the non-coding strand of a nucleic acid comprising a portion of one of these genes. Preferably, the primer of the invention is either homologous or complementary to a portion of a Type I or Type IX collagen gene described herein, wherein the portion is located entirely within a non-coding region of the gene. Preferably, the primer of the invention is either homologous or complementary to a portion of one of the non-coding regions of the COL1A1 gene listed in FIGS. 4B-1 through 4B-52 (SEQ ID NOs: 6–57), to a portion of one of the non-coding regions of the COL1A2 gene listed in FIGS. 5B-1 through 5B-57 (SEQ ID NOs: 58–110), to a portion of one of the non-coding regions of the COL9A1 gene listed in FIGS. 10B-1 through 10B-40 (SEQ ID NOs: 111–149), to a portion of one of the non-coding regions of the COL9A2 gene listed in FIGS. 11B-1 through 11B-37 (SEQ ID NOs: 150–182), or to a portion of one of the non-coding regions of the COL9A3 gene listed in FIGS. 12C-1 through 12C-34 (SEQ ID NOs: 183–215).

A primer that is homologous to a sequence may be entirely or partially homologous to the sequence, and that a primer that is complementary to a sequence may be entirely or partially complementary to the sequence. It is most preferred that each primer described herein is either entirely homologous or entirely complementary to the corresponding sequence. However, one skilled in the art would appreciate that primers which are partially homologous or partially complementary may be used in the methods and compositions described herein. Each primer may be at least 95% homologous or at least 95% complementary to the corresponding sequence. Each primer may also be at least 90% homologous or at least 90% complementary to the corresponding sequence. Furthermore, each primer may be at least 85% homologous or at least 85% complementary to the corresponding sequence. Further, each primer may be at least 80% homologous or at least 80% complementary to the corresponding sequence. It is important that each primer is sufficiently homologous or sufficiently complementary to the corresponding sequence that the primer will bind to the sequence with which binding is desired under the conditions used in the methods and compositions described herein.

In one aspect of the invention, the nucleotide sequence of an amplified nucleic acid sequence comprising an exon of a Type I or Type IX collagen gene and at least one nucleotide from a non-coding region adjacent the exon is determined, and the sequence is compared with the consensus nucleotide sequence of the gene. A difference between the sequence and the consensus sequence is an indication that the gene is an altered gene. The amplified nucleic acid sequence preferably comprises at least five nucleotides from a non-coding region of the gene corresponding to the amplified nucleic acid. More preferably, the amplified nucleic acid sequence comprises at least about twenty nucleotides from non-coding regions of the gene corresponding to the amplified nucleic acid, and more preferably the amplified nucleic acid sequence comprises at least about eighty such nucleotides.

The method of the invention may be used to determine the sequence of a portion of a coding region of a collagen gene obtained from a subject. By comparing the sequence of the coding portion of the subject's COL1 or COL9 gene with the sequence of the corresponding coding portion of the collagen gene obtained from a subject who is not afflicted with a pathological condition associated with an altered COL1 or COL9 gene sequence, the existence, genetic location, and sequence of an alteration of the COL1 or COL9 gene sequence of the subject may be determined. Consensus sequences of COL1 and COL9 genes are presented herein in FIGS. 4 and 5 and 10 through 12. Any of the primers described herein may be used to amplify the corresponding portion of the corresponding gene.

Relevant portions of the COL1 or COL9 gene sequences of subjects having a genetic relationship to an affected subject who has been determined to possess an altered COL1 or COL9 gene sequence may be screened using a simplified procedure. In this procedure, the PCR amplification and nucleotide sequencing procedures described in this Example are performed using only the primers useful for amplifying and sequencing the region(s) of the COL1 or COL9 gene which is altered in the affected subject. Using this simplified procedure, it may be conveniently determined whether a subject having a genetic relationship to an affected subject has the altered gene sequence.

One skilled in the art would appreciate that any pair of primers described herein is useful in the methods described in this Example. One skilled in the art would also appreciate that the methods described in this Example are useful for identifying an altered COL1 or COL9 gene sequence associated with any pathological condition associated with an altered COL1 or COL9 gene sequence including, but not limited to, osteoporosis, osteoarthritis, chondrodysplasia, multiple epiphyseal dysplasia, osteogenesis imperfecta, shortness of stature, scoliosis, low bone density, and degenerative joint disease. One skilled in the art would further appreciate that the methods described in this Example are useful for identifying an altered COL1 or COL9 gene sequence associated with a pathological condition even if the association between the altered sequence and the pathological condition is not presently recognized.

The PCR/CSGE methods of the present invention are useful for detection of any mutation in a COL1A1 or COL1A2 gene of a subject which is associated with a pathological condition. The PCR/CSGE methods of the present invention are applicable to detection of mutations in any Type I or Type IX collagen gene which is associated with a pathological condition, wherein a set of intronic primers have been adapted for use in the methods and wherein the set of intronic primers is useful for amplifying substantially all exons, exon flanking regions, and 3'- and 5'-untranslated regions of the gene. Such pathological conditions include, but are not limited to, osteoporosis, osteoarthritis, chondrodysplasia, multiple epiphyseal dysplasia, osteogenesis imperfecta, shortness of stature, scoliosis, low bone density, and degenerative joint disease. The compositions and methods described herein are useful for identifying an altered COL1A1 or COL1A2 gene sequence associated with a pathological condition, even if the association between the altered sequence and the pathological condition is not presently recognized.

Three sets of intronic primers are described herein in FIGS. 23, 24, and 25. These intronic primers have been designed for use in PCR/CSGE methods described elsewhere herein for screening the human COL9A1, COL9A2, and COL9A3 genes for alterations associated with a pathological condition. One skilled in the art would appreciate that the intronic primers and PCR/CSGE methods described herein are useful for detection of any mutation in a COL9A1, COL9A2, or COL9A3 gene of a subject which is associated with a pathological condition. Such pathological conditions include, but are not limited to, osteoporosis, osteoarthritis, chondrodysplasia, multiple epiphyseal dysplasia, osteogenesis imperfecta, shortness of stature, scoliosis, low bone density, and degenerative joint disease. One skilled in the art would further appreciate that the compositions and methods described herein are useful for identifying an altered COL9A1, COL9A2, or COL9A3 gene sequence associated with a pathological condition, even if the association between the altered sequence and the pathological condition is not presently recognized.

Any method of determining the nucleotide sequence of the amplified DNA sequence may be used in the methods of the invention including, but not limited to, the method of Sanger et al. (1977, Proc. Natl. Acad. Sci. USA 74:5463–5467) or Sambrook et al. (1989, In: *Molecular Cloning: A Laboratory Manual*, Cold Spring Harbor Laboratory, New York).

In a preferred method of determining the nucleotide sequence of an amplified DNA molecule, a sequencing primer complementary to a region of one strand of the amplified DNA molecule is used as a reactant in any of numerous DNA nucleotide sequence determination assays including, but not limited to, the method of Sanger et al. (1977, Proc. Natl. Acad. Sci. USA 74:5463–5467) or Sambrook et al. (1989, In: *Molecular Cloning: A Laboratory Manual*, Cold Spring Harbor Laboratory, New York). Preferably, the sequencing primer is a primer adapted for use with the exon of the amplified DNA molecule.

In a particularly preferred method of identifying an altered Type I or Type IX collagen gene, substantially all relevant segments of at least one Type I or Type IX collagen gene are amplified using the primers described herein, wherein a relevant segment comprises an exon, at least six nucleotides located sequentially adjacent the 5'-end of the exon in the corresponding non-coding region, and at least twenty nucleotides located sequentially adjacent the 3'-end of the exon in the corresponding 3'-non-coding region. Preferably, at least twenty or thirty nucleotides sequentially adjacent the 5'-end of the exon and at least twenty or thirty nucleotides sequentially adjacent the 3'-end of the exon are amplified.

By way of example, substantially all relevant segments of the COL1A1 gene may be amplified using every pair of primers depicted in FIG. 21 (SEQ ID NOs: 216–324); substantially all relevant segments of the COL1A2 gene may be amplified using every pair of primers depicted in FIG. 22 (SEQ ID NOs: 325–434); substantially all relevant segments of the COL9A1 gene may be amplified using every pair of primers depicted in FIG. 23 (SEQ ID NOs: 435–477, 480–499, and 502–513); substantially all relevant segments of the COL9A2 gene may be amplified using every pair of primers depicted in FIG. 24 (SEQ ID NOs: 514–563 and 568–575); substantially all relevant segments of the COL9A3 gene may be amplified using every pair of primers depicted in FIG. 25 (SEQ ID NOs: 576–639).

In another particularly preferred method of identifying an altered Type I or Type IX collagen gene, the primers used to amplify one or more sequences of the gene are selected such that the amplified DNA oligonucleotide is suitable for CSGE analysis.

Oligonucleotides suitable for CSGE analysis generally range in length from about fifteen base pairs to about two thousand base pairs. Preferably, such oligonucleotides range in length from about fifty base pairs to about fifteen hundred base pairs, even more preferably from about one hundred base pairs to about one thousand base pairs. Most preferably, an oligonucleotide suitable for CSGE analysis ranges in length from about two hundred base pairs to about five hundred base pairs.

According to the data presented herein, a pair of primers useful for amplification of a sequence for CSGE analysis should be selected such that the sum of the lengths of the sequence to which one primer of the pair is homologous, the sequence to which the other primer of the pair is complementary, and the sequence located between these two sequences is greater than or equal to about two hundred and less than or equal to about five hundred nucleotides. If more than one pair of primers is to be used to generate more than one amplified oligonucleotide in the same reaction mixture, it is preferred that the each amplified oligonucleotide have a length that is different than the length of all other amplified oligonucleotides produced in the mixture, so that every amplified oligonucleotide is identifiable as a discrete band following gel electrophoretic separation of the oligonucleotides in the reaction mixture.

Pairs of primers which have been designed such that the oligonucleotide amplified using any pair of the primers is suitable for CSGE analysis are depicted in FIG. 21 (SEQ ID NOs: 216–324), corresponding to primer pairs useful for amplifying COL1A1 gene sequences, in FIG. 22 (SEQ ID NOs: 325–434), corresponding to primer pairs useful for amplifying COL1A2 gene sequences, in FIG. 23 (SEQ ID NOs: 435–477, 480–499, and 502–513), corresponding to primer pairs useful for amplifying COL9A1 gene sequences, in FIG. 24 (SEQ ID NOs: 514–563 and 568–575), corresponding to primer pairs useful for amplifying COL9A2 gene sequences, and in FIG. 25 (SEQ ID NOs: 576–639), corresponding to primer pairs useful for amplifying COL9A3 gene sequences.

The primer pairs depicted in each of FIGS. 21 through 25 have been designed such that all primer pairs depicted in any one of the Figures may be used to amplify substantially all important regions of the corresponding gene, such that the amplified oligonucleotides made thereby are suitable for CSGE analysis. In addition, the design of the primers yields unique fragments in high yield when they are used to amplify gene sequences obtained from a human genome.

CSGE methods, reagents, and compositions have been described (Ganguly et al., 1993, Proc. Natl. Acad. Sci. USA 90:10325–10329; Ganguly et al., 1995, Electrophoresis 16:1830–1835; U.S. patent application Ser. No. 08/468, 551). One skilled in the art would appreciate that the selection of apparatus, sources of reagents, primer synthesis methods, and manual or automated gel imaging and analysis techniques useful in the CSGE methods described herein are within the level of ordinary skill in the art, given the disclosure provided herein.

The nucleic acid which is obtained from a subject for amplification using one or more pairs of primers described herein and subsequent CSGE analysis may be any type of nucleic acid obtained from essentially any cell or tissue of the subject. By way of example, the nucleic acid may be a single-stranded RNA molecule, an mRNA molecule, an mRNA molecule obtained prior to mRNA processing, a single-stranded DNA molecule, a double-stranded DNA molecule, or a complementary DNA (cDNA) molecule derived from an mRNA molecule. Preferably, the nucleic acid is either a cDNA molecule derived from an mRNA molecule obtained from a skin fibroblast of the subject or a double-stranded DNA molecule obtained from any cell of the subject. More preferably, the nucleic acid is a double-stranded DNA molecule obtained from a blood cell of the subject.

The subject may be a member of any species for which at least one intronic nucleotide sequence of at least one gene encoding a Type I or Type IX collagen chain is known. Preferably, the subject is a mammal, more preferably, a primate. Most preferably, the subject is a human.

In one aspect of the invention, pairs of primers which are useful for amplifying substantially all exons and exon flanking regions of a Type I or Type IX collagen gene are provided together in a kit for analyzing that gene. Such a kit comprises a plurality of pairs of primers, wherein at least one pair of primers is useful for amplification of a segment of the gene, the segment comprising at least one nucleotide located in a non-coding region of the gene. By way of example, all of the primer pairs depicted in FIG. 21 may be provided together in a kit useful for CSGE analysis of substantially all exons and exon flanking regions of the COL1A1 gene. Similarly, all of the primer pairs depicted in FIG. 22 may be provided together in a kit useful for CSGE analysis of substantially all exons and exon flanking regions of the COL1A2 gene. All of the primer pairs depicted in FIG. 23 may be provided together in a kit useful for CSGE analysis of substantially all exons and exon flanking regions of the COL9A1 gene. All of the primer pairs depicted in FIG. 24 may be provided together in a kit useful for CSGE analysis of substantially all exons and exon flanking regions of the COL9A2 gene. All of the primer pairs depicted in FIG. 25 may be provided together in a kit useful for CSGE analysis of substantially all exons and exon flanking regions of the COL9A3 gene.

In another aspect of the invention, a kit such as one of those described in the preceding paragraph further comprises a plurality of oligonucleotides generated by amplification of the consensus Type I or Type IX collagen gene using the primers of the kit. Although the kits described in the previous paragraph are useful for detecting heteromorphic alleles in a subject, these kits may not be able to detect the presence in a subject of two identical alleles of a Type I or Type IX collagen gene, wherein both alleles are altered relative to the consensus gene sequence. Kits which further comprise a plurality of oligonucleotides made by amplification of the consensus Type I or Type IX collagen gene using the primers of the kit can be used to detect altered gene sequences, even in subjects having two identical altered alleles. Sequences of a plurality of oligonucleotides are not provided herein, the method of obtaining such sequences being clear to one of ordinary skill in the art. To obtain such sequences, a set of primer pairs as described herein is used to amplify the exons and exon flanking regions of a nucleic acid having a sequence comprising the consensus gene sequence.

One skilled in the art would appreciate that the primers and probes described herein may be used in any set of reaction conditions wherein hybridization is possible between the primer or probe and a nucleic acid to which it is complementary. By way of example, the primers and probes may be used in standard PCR and hybridization conditions known in the art. The primers or probes may be supped, for example, in solution, in lyophilized form, affixed to a well of a 96-well plate, affixed to a particular region of a solid support such as a glass slide, a microchip, and the like.

Testing Subjects Genetically Related to a First Subject for an Altered Type I or Type IX Collagen Gene Once the location of an alteration in a gene encoding a chain of Type I or Type IX collagen is identified in a first subject using the PCR/CSGE methods described herein, simpler methods can be used to detect the presence of the same alteration in subjects who are genetically related to the first subject. The PCR/CSGE methods described herein are not only useful for detecting an altered collagen gene in a first subject who presents symptoms of a disease or disorder related to abnormal Type I or Type IX collagen production, but are also useful for designing protocols to screen subjects who are genetically related to the first subject for the presence of the altered gene. Non-limiting examples of methods of designing such protocols are described in this Example.

In one aspect, the PCR/CSGE methods described herein involve using a multiplicity of primer pairs to identify an alteration in one or more genes which encode a chain of Type I or Type IX collagen.

By way of example, a kit may be used which comprises pairs of primers which are useful for amplifying substantially all exons and exon flanking sequences of each of the COL1A1, COL1A2, COL9A1, COL9A2, and COL9A3 genes. The kit may also comprise all of the reagents necessary for CSGE analysis of the amplified sequences. Therefore, using this kit, a practitioner may detect the presence of heteromorphic alleles of any of the COL1A1, COL1A2, COL9A1, COL9A2, and COL9A3 genes in a first subject by identifying the presence of heteroduplex products in the CSGE gel. Furthermore, by identifying the particular amplified sequence in which heteroduplex formation occurs, the primer pair used to amplify the particular sequence is indicated as being useful for identifying the altered particular sequence in subjects genetically related to the first subject. Once this primer pair is identified, PCR amplification of the DNA of subjects who are genetically related to the first subject may be performed using only this primer pair, instead of using each of the multiplicity of primer pairs of the kit. Thus, once this primer pair is identified, PCR/CSGE methods of the invention may be performed using only a single pair of primers to identify heteroduplexes of the particular sequence in subjects genetically related to the first subject.

If the kit described in the preceding paragraph further comprises sequencing primers useful for determining the nucleotide sequence of each amplified sequence, then the sequencing primers may be used to determine the nucleotide sequence of the particular sequence in subjects genetically related to the first subject without the need to use the PCR/CSGE methods described herein for those subjects. Subjects who are homozygous for an altered Type I or Type IX collagen gene sequence may be identified using this method because the nucleotide sequence of the altered gene, rather than heteroduplex formation is used to determine whether the subjects have an allele comprising the altered sequence.

Alternately, once an altered Type I or a Type IX collagen gene has been identified in a first subject, the nucleotide sequence of the amplified sequence comprising the alteration may be determined, and an oligonucleotide probe which binds specifically to the altered sequence of the gene, but not to the normal sequence of the gene, may be designed using methods well known in the art. A single-stranded nucleic acid obtained from a subject genetically related to the first subject may be contacted with the oligonucleotide probe under hybridizing conditions, and the degree of hybridization between the probe and the single-stranded nucleic acid may be observed. Hybridization between the probe and the single-stranded nucleic acid is an indication that the subject has the same collagen gene alteration as the first subject.

By way of example, if an alteration of the COL1A1 gene of a first subject is identified at nucleotide 100, wherein the altered gene consists of a first nucleotide at that position and the normal COL1A1 gene consists of a different nucleotide at that position, an oligonucleotide probe may be made which is complementary to the altered gene sequence from nucleotide 90 through nucleotide 108 and which hybridizes with a portion of the gene comprising the altered region, but not with the same portion of the gene obtained from a normal individual. This probe may be contacted with a single-stranded nucleic acid obtained from a subject, whereby hybridization between the probe and the single-stranded nucleic acid is an indication that the single-stranded nucleic acid comprises a sequence which is homologous to nucleotides 90 to 108 of the altered COL1A1 gene. Alternately, primers may be designed based on the sequence of the COL1A1 gene described herein which are useful for amplifying a nucleic acid sequence comprising nucleotides 90 to 108 of the COL1A1 gene. DNA obtained from the subject may be amplified using PCR methods prior to contacting the oligonucleotide probe with the amplified DNA.

Single-stranded nucleic acid may be obtained from the subject in the form of a single-stranded nucleic acid or in the form of a double-stranded nucleic acid or may be synthesized using methods well known in the art from a single- or double-stranded nucleic acid obtained from the subject (e.g. Sambrook, et al., 1989, In: *Molecular Cloning: A Laboratory Manual*, Cold Spring Harbor Laboratory, New York).

Any known method of detecting the presence of a nucleotide sequence in a sample obtained from a subject may be used to detect the presence in the subject of an altered COL1 or COL9 gene sequence identified by the methods described herein. By way of example, nucleic acid hybridization assays such as dot or slot blot assays or Southern transfer of DNA fragments after separation on agarose gel are well known. Other methods apparent to one skilled in the art may be used including, but not limited to, restriction endonuclease digestion of amplified DNA followed by agarose gel electrophoresis and visualization of the DNA by ethidium bromide, if the alteration in the collagen gene has created or destroyed a restriction endonuclease recognition site.

The methods of detecting an alteration in a Type I or Type IX collagen gene are useful for diagnosing the cause of an existing disease or disorder associated with abnormal production of a Type I or Type IX collagen chain as well as for detecting a genetic predisposition of a subject to develop such a disease or disorder.

The compositions and methods described herein may be used to detect a predisposition for or to diagnose any disease or disorder associated with abnormal production of a Type I or Type IX collagen chain. Diseases and disorders associated with abnormal production of a Type I or Type IX collagen chain include both those diseases and disorders which are presently known to be associated with abnormal production of a Type I or Type IX collagen chain and those disease and disorders which are, but are not presently recognized as being, associated with abnormal production of a Type I or Type IX collagen chain. Diseases and disorders which are presently known to be associated with abnormal production of a Type I or Type IX collagen chain include, but are not limited to, osteoporosis, osteoarthritis, chondrodysplasia, multiple epiphyseal dysplasia, osteogenesis imperfecta, shortness of stature, scoliosis, low bone density, and degenerative joint disease.

Pathological Conditions Associated with Altered COL1 and COL9 Genes

The structures of various types of collagen in heritable collagen diseases has been reviewed (Prockop et al., 1984, New Eng. J. Med. 311:376–386; Prockop, 1985, J. Clin. Invest. 75:783–787; Prockop, 1986, Hosp. Pract., Feb. 15, 1986; Prockop, 1990, J. Biol. Chem. 265:15349–5352; Kuivaniemi et al., 1991, FASEB J. 5:2052–2060; Kuivaniemi et al., 1997, Hum. Mutat. 9:300–315). Numerous pathological conditions are associated with an alteration in a COL1 or a COL9 gene, including, but not limited to, osteoporosis, osteoarthritis, chondrodysplasia, multiple epiphyseal dysplasia, osteogenesis imperfecta, shortness of stature, scoliosis, low bone density, and degenerative joint disease.

Osteoporosis

Osteoporosis is an important cause of serious disability in humans. Osteoporosis is characterized by a marked decrease in bone mass (osteopenia) and an associated susceptibility to bone fracture resulting from relatively minor trauma. Two forms of osteoporosis have been described. Type I osteoporosis, also designated 'post-menopausal osteoporosis,' primarily affects women beginning ten to fifteen years after menopause. Type I osteoporosis is associated with a transient acceleration of bone loss that coincides with a decrease in estrogen level in women at menopause and is believed to be familial. Type II osteoporosis, also designated 'age-related osteoporosis,' occurs in patients over the age of about seventy and afflicts each gender with approximately equal frequency. Both types of osteoporosis are associated, at least in part, with insufficient accumulation of skeletal mass in young adulthood. Normally, bone mass increases until about age thirty and decreases thereafter. When a patient's bone density decreases below an approximate threshold value, the patient becomes susceptible to bone fracture caused by relatively minor trauma.

Bone loss due to osteoporosis cannot be effectively reversed by any known therapy. However, the rate of bone loss can be decreased by administration of estrogen or a related agent. It is generally not advisable to administer estrogen or a related agent in the relatively large dose necessary for efficacy against osteoporosis to all individuals. Estrogen therapy can have significant side effects, such as feminizing effects in men and increasing the incidence of cervical and breast cancer in women. However, if women predisposed to Type I osteoporosis can be identified early, it could be justifiable to accept the risk of administering estrogens or a related agent and to carefully monitor carcinogenesis so as to avoid the devastating effects of osteoporosis.

Bone is a complex structure, and its strength and resistance to fracture depends on a number of factors. A major contributor to bone strength is the network of Type I collagen fibrils that form a scaffold on which the mineral components of bone are deposited. Therefore, mutations which affect the amount or structure of Type I collagen are expected to affect the pathology of and the symptoms associated with osteoporosis.

Osteoarthritis

Osteoarthritis is a progressive disease of joints that is a cause of serious disability in humans. Osteoarthritis is defined as a progressive degeneration of the cartilaginous surfaces of joints which leads to stiffness, pain, and loss of mobility. Degeneration of the cartilaginous surfaces of joints associated with osteoarthritis can have a number of causes. For example, severe trauma to a joint or a bacterial infection in a joint can produce immediate or slowly progressive degeneration of the joint. A number of metabolic disturbances are also know to result in joint degeneration.

Cartilage and the membranes that line joints are complex structures. A major source of the strength of cartilage is the fibrils of Type II collagen. Type IX collagen, which is associated with Type II collagen, is essential for the maintenance of cartilage integrity under conditions of normal physical activity. Type II collagen fibrils are stretched into three-dimensional arcades primarily by the presence of another group of macromolecules called proteoglycans including, but not limited to, Type IX collagen. Proteoglycans are highly charged and, therefore, absorb water and salts and thereby extend the arcades of Type II collagen fibrils. As a result, a highly resilient structure is formed that can withstand the intermittent pounding and pressures that joints must undergo.

Collagens, proteoglycans, and other proteins found in the matrix of cartilage are synthesized by cells embedded within the matrix. The matrix is actively synthesized during embryonic development of certain tissues and during periods of growth. The rates of synthesis and degradation of the matrix are lower during adult life than earlier in life. However, throughout life, a continual slow synthesis and degradation of cartilage occurs, particularly in response to the pressures associated with physical activity.

The degeneration of joint cartilages that occurs in osteoarthritis is caused by a failure of the cartilage to maintain its structural integrity. In this process, the cartilage surface is eroded by physical pressures and is not adequately replaced by the new synthesis of cartilage. Instead of adequate repair of cartilage, secondary changes occur in the joint surface and in the joint. These changes include, for example, inflammatory responses characterized by invasion of white cells and macrophages, abnormal deposition of mineral in the form of calcium and phosphate within the joint space and in the cartilage itself, deposition of fibers of Type I and other collagens; that are not normally part of cartilage or the joint, abnormal growth of cartilage calls and matrix at locations adjacent to the joint surface and abnormal calcifications of the joints and associated structures. As part of the complex changes that occur, the cells of the cartilage or the invading cells from the blood stream begin to secrete degradative enzymes that further contribute to the degradation of the joint structures. As a primary component of cartilage that accounts for much of the maintenance of the structural integrity thereof, Type IX is likely to be associated with many diseases and disorders characterized by abnormal cartilage degradation, in addition to the diseases and disorders with which Type IX collagen is presently associated.

The term "osteoarthritis", as used herein, includes, but is not limited to, ankylosing spondylitis.

Chondrodysplasia

In the more severe diseases of cartilage known as chondrodysplasias, serious defects in the formation of cartilage are apparent early in life and there is a failure of joints to develop their normal size and shape. There is also a secondary failure of bone growth seen in these diseases. Moreover, there can be a failure of normal development of many tissues such as failure to achieve closure of normal partitions between oral and nasal passages, known as cleft palate, and improper development of the vitreous gel of the eye that causes severe myopia and retinal detachment.

Research has demonstrated that some forms of osteoarthritis and related conditions are caused by mutations in the genes that code for and, therefore, determine the structure of the collagens that are the major source of the strength of cartilage. Type IX collagen, for instance, is associated with Type II collagen in hyaline cartilage and in the vitreous body of the eye. Thus, alterations in one or more of the COL9 genes can be expected to result in the production of cartilage that does not have the strength of normal collagen, resulting in joint cartilage degeneration associated with normal physical activity.

Mutations affecting cartilage strength and durability produce drastic effects during growth and development. Some individuals who inherit mutated collagen genes develop severe chondrodysplasias and die in utero or shortly after birth. Alternatively, such individuals can have serious deformities such as dwarfism which shows severe malformation of joints and may be associated with conditions of severe myopia, myopia with retinal detachment and blindness, cataracts, cleft palate, and unusual facial appearance other similar mutations in the same genes may produce much milder effects and cause progressive generalized osteoarthritis in which affected individuals are apparently normal until middle age when they develop progressive stiffness, pain and then immobility of many joints.

Mutations of the gene for Type II procollagen and collagen have been shown to cause these disorders. Research suggests that some of the conditions are caused by mutations in other genes, such as the COL9 genes.

Multiple Epiphyseal Dysplasia

MED is a relatively common disorder which is characterized by symptoms ranging from mild joint stiffness, pain in large joints, early onset osteoarthritis, and mild to moderate shortness of stature (Briggs et al., 1994, Am. J. Hum. Genet. 55:678–684).

A mutation of a 5'-donor splice site was recently found in the third intron of the human COL9A2 gene in a family afflicted with multiple epiphyseal dysplasia (MED; Muragaki et al., 1990, Proc. Natl. Acad. Sci. USA 87:2400–2404). The mutation caused an in-frame deletion of a portion of the gene encoding twelve amino acids in the COL3 domain of α2(IX). Mutations in COMP, the gene encoding cartilage oligomeric matrix protein, cause Ribbing, Fairbank, or unclassified forms of MED (Briggs et al., 1995, Nature Genet. 10:330–336; Cohn et al., 1996, Ann. N.Y. Acad. Sci. 785:188–194; Ballo et al., 1997, Am. J. Med. Genet. 68:396–400). Furthermore, a linkage to the COMP or the COL9A2 genes has been excluded at least in one family afflicted with MED (Deere et al., 1995, Am. J. Hum. Genet. 56:698–704). ecause the COL9A1, COL9A2, and COL9A3 genes encode different chains of Type IX protein, and because mutations in COL9A2 are associated with MED, mutations in the COL9A1 and COL9A3 genes are also likely to be associated with MED.

Osteogenesis Imperfecta

Osteogenesis imperfecta (OI) is a heritable disorder that causes varying degrees of bone fragility and defects in several other tissues which are rich in Type I collagen. Almost 200 mutations in COL1A1 and COL1A2 have been detected in subjects afflicted with OI (Prockop, 1990, J. Biol. Chem. 265:15349–15352; Byers, 1993, In: *Connective tissue and its heritable disorders*, Royce et al., eds., Wiley-Liss, New York, pp 317–351; Prockop et al., 1995, Annu. Rev. Biochem. 64:403–434; Kuivaniemi et al., 1997, Hum. Mutat. 9:300–315). The most severe variants of the disease (OI types II, III, and IV) are caused primarily by single base substitutions that convert a codon for an obligate glycine in the triple helix of the proα1(I) or proα2(I) protein to a codon for an amino acid with a bulkier side chain, which distorts the conformation of the triple helix of the Type I collagen molecule. Most mutations in the mildest (Type I) variants of OI cause decreased expression of proα1(I) chains. Alterations resulting in decreased proα1(I) expression comprise an alteration of an amino-acid-encoding codon to a premature termination codon or an alteration of an RNA splicing site of the COL1A1 gene (Willing et al., 1994, Am. J. Hum. Genet. 55:638–647; Willing et al., 1992, Am. J. Hum. Genet. 51:508–515; Willing et al., 1996, Am. J. Hum. Genet. 59:799–809; Redford-Badwal et al., 1996, J. Clin. Invest. 97:1035–1040; Körkkö et al., 1997, Hum. Mutat. 9:148–156).

DNA linkage studies indicate that over 90% of subjects afflicted with OI have an altered COL1A2 or COL1A2 gene (Sykes et al., 1990, Am. J. Hum. Genet. 46:293–307). Practitioners employing prior art protocols have not been able to identify many altered COL1 and COL9 genes, no doubt owing in part to the capacity of such protocols to identify mutations only in the coding regions of the genes and in a very limited number corresponding non-coding sequences. Hence, a critical unmet need remains for compositions and protocols which are capable of identifying mutations in any part of any of the COL1 and COL9 genes.

Shortness of Stature

Because alteration of a subject's COL1A1 and COL1A2 gene can result in abnormalities in the bulk and strength of the subject's bones, particularly during development and growth of the subject, detection of an altered COL1A1 and COL1A2 gene in a subject is an indication that the subject is genetically predisposed to shortness of stature. By way of example, repeated bone fractures caused by an alteration in the subject's COL1A1 or COL1A2 gene can impede proper stature development. If the alteration in the COL1A1 or COL1A2 gene is identified prior to the onset of clinical symptoms of shortness of stature, the subject can be monitored closely for such symptoms and therapeutic intervention may begin before symptoms develop or shortly thereafter. Detection in an alteration in the COL1A1 or COL1A2 gene of a subject who has been diagnosed with shortness of stature can reveal the physiological cause of the condition, potentially eliminating the involvement of other causes and, where the subject is experiencing bone growth and development, permitting therapeutic intervention. It is understood that bone tissue generally develops continuously over the course of a subject's lifetime, old bone tissue being replaced by new bone tissue.

Similarly, the presence in a subject of abnormal cartilage can result in improper development of the stature of the subject, particularly where the abnormality of the subject's cartilage is caused by an alteration in the COL9A1, COL9A2, or COL9A3 gene of the subject.

Scoliosis

In light of the observation that a structural defect in the proα2(I) chain was found in a family afflicted with osteoporosis and idiopathic scoliosis (Shapiro et al., 1989, Connect Tissue Res. 21:117–123), the compositions and methods of the invention can be used to detect an altered COL1 or COL9 gene, wherein the altered gene causes the subject harboring the altered gene to be afflicted with scoliosis.

Degenerative Joint Disease

Because Type IX collagen appears to be required for maintaining the integrity of cartilage structures, it is expected that detection of altered COL9 gene sequences are associated with degenerative joint diseases including. Degenerative joint diseases include arthritis, osteoarthritis, rheumatism and other diseases which are characterized by irritation, inflammation, or erosion of joint cartilage or with stiffness, pain, or deformity of joints.

Other COL1- or COL9-Associated Diseases

It is clear that the compositions and methods of the invention can be used to identify any alteration in a COL1 or COL9 gene, whether the alteration is a neutral variant of the gene, an alteration which causes a disease or disorder recognized as being associated with an altered COL1 or COL9 gene, or an alteration which causes a disease or disorder which is, but is not recognized to be, associated with an altered COL1 or COL9 gene. By way of example, it is known that Type IX collagen is a component of the vitreous of the eye. It is therefore to be expected that certain alterations of the genes encoding Type IX collagen will result in degenerative and other disorders of the eye. Furthermore, the presence of Type IX collagen in cartilaginous structures causes one skilled in the art to expect that alterations in the genes encoding Type IX collagen can result in pathological conditions involving such structures, such as cleft palate. Type I collagen is a component of tooth tissue, and both Type I and Type IX collagens are components of the sound-transmitting and -detecting structures of the mammalian ear. Thus, it is to be expected that alterations in the genes encoding Type I collagen can be associated with diseases and disorders of the teeth and ear, and that alterations in the genes encoding Type IX collagen can be associated with diseases and disorders of the ear, such as deafness. It is emphasized that the compositions and methods of the invention are useful for detecting an alteration in a COL1 or COL9 gene, regardless of whether that alteration is presently known to result in affliction of the subject harboring the altered gene with a disease or disorder.

Disease- or disorder-causing alterations in a COL1 or COL9 gene may be distinguished from neutral variants of the gene in numerous ways. By way of example, alterations in a protein-encoding region of the gene which do not cause an alteration of the amino acid sequence of the protein can be neutral variants, although it is recognized that substitution of a codon encoding a particular amino acid for a rare codon encoding the same amino acid can result in decreased expression of the gene. Where the alteration in the gene results in an alteration of the amino acid sequence of a protein encoded by the gene, the consequence of the alteration of the amino acid sequence can be predicted by reference to data in the scientific literature regarding the function of the protein. By way of example, as described herein, substitution of the Gly residue in a Gly-X-Y triplet in the α chain portion of a collagen chain can cause deformation of the three-dimensional conformation of a collagen subunit comprising the collagen chain. Further by way of example, a recombinant collagen protein comprising a chain encoded by the altered collagen gene can be expressed by cells in culture, and abnormal characteristics of the cells, or of the collagen produced by the cells, can be determined. Disease- or disorder-causing alterations in collagen genes may also be distinguished from neutral variants of the genes by observing whether symptoms experienced by a subject afflicted with the disease or disorder who harbors a gene having an alteration are similarly experienced by other subjects, such as genetic relatives of the subject, who harbor a copy of the gene having the alteration. Coinheritance of the altered collagen gene and the symptoms of the disease or disorder indicates that the disease or disorder is associated with the alteration of the collagen gene. Furthermore, the presence of an alteration in a collagen gene obtained from a subject who is not afflicted with a disease or disorder is an indication that the alteration does not cause the disease or disorder.

Definitions

As used herein, the term "COL1 gene" means any gene encoding a chain of Type I collagen including, but not limited to, the human COL1A1 and COL1A2 genes and the vertebrate and mammalian homologs thereof including, but not limited to, the chicken and murine homologs thereof.

As used herein, the term "COL9 gene" means any gene encoding a chain of Type IX collagen including, but not limited to, the human COL9A1, COL9A2, and COL9A3 genes and the vertebrate and mammalian homologs thereof including, but not limited to, the chicken, murine, and rat homologs thereof.

As used herein, the terms "alteration" or "mutation" of a gene mean that the altered or mutated gene has a nucleotide sequence which differs from a consensus nucleotide sequence of the gene at one or more positions.

As used herein, a "neutral variant" of a gene means a gene which has an altered sequence which is not associated with a pathological condition.

As used herein, a "chain" of a protein means a single polyamino acid molecule in the protein. A protein "chain," as used herein, is frequently referred to in the art as a protein subunit. The term "chain" has been used herein to distinguish a chain of a protein from a "subunit" of a collagen molecule, as used herein.

As used herein, a "subunit" of a collagen molecule means an individual collagen protein molecule which is capable of being incorporated into a collagen fibril. It is understood by one skilled in the art that a single collagen fibril may include numerous collagen subunits, and that a single collagen subunit may comprise numerous protein chains. By way of example, a Type I collagen fibril obtained from bone tissue may comprise numerous Type I collagen protein subunits, each of which subunits comprises two proα1(I) chains and a proα2(I) chain.

As used herein, a "portion" of a collagen gene means a polymer comprising at least about fifteen consecutive nucleotides having a sequence substantially complementary to or substantially homologous with the nucleotide sequence of a human collagen gene, wherein said gene is selected from the group consisting of the segment of the COL1A1 gene extending in the 5'- to 3'-direction from and including the 78 nucleotides of intron 27 located adjacent exon 28 through the 3'-end of the COL1A1 gene, the COL1A2 gene, the COL9A1 gene, the COL9A2 gene, and the COL9A3 gene, and excluding published non-coding sequences of the COL1A2 gene. Published non-coding sequences of the COL1A2 gene include the following sequences:

(i) 75 nucleotides located within intron 1
(ii) 318 nucleotides at the 3'-end of intron 5
(iii) 298 nucleotides at the 5'-end of intron 6
(iv) 30 nucleotides at the 3'-end of intron 26
(v) intron 27
(vi) intron 28
(vii) 25 nucleotides at the 5'-end of intron 29
(viii) intron 33

(Myers et al., 1983, J. Biol. Chem. 258:10128–10135; Myers et al., 1984, J. Biol. Chem. 259:12941–12944; Dickson et al., 1984, Proc. Nati. Acad. Sci. USA 81:4524–4528; Tromp et al., 1988, Proc. Natl. Acad. Sci. USA 85:5254–5258; Sherwood et al., 1990, Gene 89:238–244; Vasan et al., 1991, Am. J. Hum. Genet. 48:305–317; Ganguly et al., 1991, J. Biol. Chem. 266:12035–12040).

As used herein, a "coding region" of a collagen gene is a portion of the nucleotide sequence of said gene which encodes at least a portion of the amino acid sequence of the protein chain encoded by the gene. The terms "coding region" and "exon" are used synonymously herein.

As used herein, an "exon flanking sequence" means an intronic nucleotide or an intronic polynucleotide which is sequentially adjacent a coding region of a gene. An exon flanking sequence preferably comprises at least about six, and preferably about twenty, nucleotides.

As used herein, two nucleotides or polynucleotides are "sequentially adjacent" if both of the nucleotides or polynucleotides are part of the same polymeric nucleic acid and if no other nucleotides are located between the two nucleotides or polynucleotides in the polymeric nucleic acid.

As used herein, "substantially all exons and exon flanking sequences" of a gene means at least most exons and exon flanking sequences of a gene. Preferably, "substantially all exons and exon flanking sequences" means at least about 75% of such sequences; more preferably, the term means at least about 90% of such sequences; even more preferably, the term means at least about 95% of such sequences.

As used herein, a "non-coding region" of a collagen gene is a portion of the nucleotide sequence of said gene which does not encode a portion of the amino acid sequence of the protein chain encoded by the gene. Non-coding regions of collagen genes include, but are not limited to, 5'-untranslated regions of such genes, introns in such genes, and 3'-untranslated regions of such genes.

As used herein, an "intronic nucleotide" is a nucleotide located in a non-coding region of a collagen gene including, but not limited to, a nucleotide located in the 5'-untranslated regions of said gene, a nucleotide located in an intron in said gene, and a nucleotide located in the 3'-untranslated region of said gene.

As used herein, a "part of a non-coding region" of a collagen gene means at least one nucleotide located in a non-coding region of said gene. Preferably, said part of a non-coding region comprises at least three such nucleotides, more preferably five, and even more preferably about fifteen such nucleotides.

As used herein, the terms "a first site" and "a second site" refer to nucleotide sequences of a portion of a collagen gene, wherein each of said first site and said second site comprise at least about fifteen consecutive nucleotides of the gene.

As used herein, an oligonucleotide "probe" means a polymer comprising nucleotide residues having a sequence whereby the probe is complementary to a nucleotide sequence of interest. An oligonucleotide probe preferably comprises at least about fifteen nucleotide residues, more preferably at least about eighteen. Probes preferably have a length between about fifteen and about thirty nucleotides. The nucleotide sequence of an oligonucleotide probe is determined by the nucleotide sequence of the nucleic acid to which binding of the probe is sought, the probe being complementary to that nucleic acid.

As used herein, an oligonucleotide "primer" means a polymer comprising nucleotide residues, having a sequence complementary to a known sequence, and having a free 3'-end suitable for extension by a nucleic acid polymerase, such as a DNA polymerase, whereby when the primer is annealed with the known sequence in the presence of the components of a nucleic acid polymerase reaction mixture, the primer is extended in the 3'-direction thereof, whereby the nucleotide sequence of the extended region of the primer has a sequence complementary to the sequence located adjacent the known sequence in the 5'-direction. An oligonucleotide primer preferably comprises at least about fifteen nucleotide residues, more preferably at least about eighteen. Primers preferably have a length between about twenty and about fifty nucleotides, more preferably between about thirty and forty nucleotides. The nucleotide sequence of a primer is determined by the nucleotide sequence of the nucleic acid to which binding of the primer is sought, the primer being complementary to that nucleic acid. As is well known in the art, the primers of a pair of primers useful for PCR methods are complementary to sequences which flank the nucleotide sequence of which amplification is desired.

As used herein, an "intronic primer" is a oligonucleotide primer comprising at least one nucleotide which is either complementary to or homologous with a nucleotide located in a non-coding region of a collagen gene including, but not limited to, a nucleotide located in the 5'-untranslated regions of said gene, a nucleotide located in an intron in said gene, and a nucleotide located in the 3'-untranslated region of said gene.

As used herein, a "sequencing primer" is an oligonucleotide primer which is complementary to at least a portion of a polynucleotide and which can be elongated by a DNA or RNA polymerizing enzyme such as DNA polymerase, whereby binding of the sequencing primer to the polynucleotide and elongation of the primer using methods well known in the art yields an oligonucleotide transcript which is complementary to at least a part of the polynucleotide.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'-ATTGCC-5' and 3'-TATGCG-5' share 50% homology.

As used herein, a first polynucleotide is "completely homologous" to a second polynucleotide if the nucleotide in every subunit position in the first polynucleotide is identical to the nucleotide in the same subunit position in the second polynucleotide. It is understood that, in addition to the region of complete homology, the second polynucleotide may comprise other nucleotide sequences.

As used herein, a first polynucleotide is "substantially homologous" to a second polynucleotide if the nucleotides in at least most subunit positions in the first polynucleotide are identical to the nucleotides in the same subunit positions in the second polynucleotide. Preferably, "substantially homologous" means that at least about 75% of nucleotides in the first polynucleotide are identical to the nucleotides in the same subunit positions in the second polynucleotide; more preferably, the term means that at least about 90% of nucleotides in the first polynucleotide are identical to the nucleotides in the same subunit positions in the second polynucleotide; even more preferably, the term means that at least about 95% of nucleotides in the first polynucleotide are identical to the nucleotides in the same subunit positions in the second polynucleotide. It is understood that, in addition to the region of substantial complementarity, both the first and the second polynucleotides may comprise other nucleotide sequences.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

As used herein, a first polynucleotide is "completely complementary" to a second polynucleotide if the nucleotide in every subunit position in the first polynucleotide is complementary to the nucleotide in the same subunit position in the second polynucleotide. It is understood that, in addition to the region of complete complementary, the second polynucleotide may comprise other nucleotide sequences.

As used herein, a first polynucleotide is "substantially complementary" to a second polynucleotide if the nucleotides in at least most subunit positions in the first polynucleotide are complementary to the nucleotides in the same subunit positions in the second polynucleotide. Preferably, "substantially complementary" means that at least about 75% of nucleotides in the first polynucleotide are complementary to the nucleotides in the same subunit positions in the second polynucleotide; more preferably, the term means that at least about 90% of nucleotides in the first polynucleotide are complementary to the nucleotides in the same subunit positions in the second polynucleotide; even more preferably, the term means that at least about 95% of nucleotides in the first polynucleotide are complementary to the nucleotides in the same subunit positions in the second polynucleotide. It is understood that, in addition to the region of substantial complementarity, both the first and the second polynucleotides may comprise other nucleotide sequences.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand.

As used herein, "identifying the nucleotide sequence" of a gene means either identifying the nucleotide sequence of the entire gene or identifying the nucleotide sequence of only part of the gene.

As used herein, a gene is "heteromorphic" if the gene exists in more than one allele in a subject, and at least one of the alleles has a nucleotide sequence which differs from the nucleotide sequence of at least one other allele at at least one nucleotide.

As used herein, the term "proband" means a subject afflicted with a pathological condition, who has been diagnosed as so afflicted independently of any diagnosis of a genetic relative.

As used herein, a first subject is "genetically related" to a second subject if the first subject and the second subject have each inherited genetic material from a common ancestor. It is understood that various degrees of genetic relationship exist between individuals, the degree of genetic relationship being greater the fewer number of generations which separate the subjects. By way of example, siblings having common parents are equally genetically related to the parents, although one sibling may be more nearly genetically related to a single grandparent than the other sibling. Continuing the example, the father and mother of the siblings are not necessarily closely genetically related to one another, and thus the siblings are more closely genetically related to each of their father and their mother than the father and mother are to one another. The degree of genetic relationship between two subjects may be determined by examining the genealogies of the two patients, by identifying common genetic markers shared by the two subjects, or by other methods known in the art.

As used herein, a "pathological condition associated with an altered collagen gene" means the existence of clinically-detectable symptoms resulting from expression of at least one of a COL1 gene or a COL9 gene having a nucleotide sequence which differs from the consensus nucleotide sequence of the gene at at least one position. The terms "pathological condition associated with an altered collagen gene," "pathological condition associated with an altered COL1 or COL9 gene," and "disease or disorder associated with abnormal production of a Type I or Type IX collagen chain" are generally used interchangeably herein. Pathological conditions associated with an alteration in a COL1 or a COL9 gene include, but are not limited to, osteoporosis, osteoarthritis, chondrodysplasia, multiple epiphyseal dysplasia, osteogenesis imperfecta, shortness of stature, scoliosis, low bone density, and degenerative joint disease.

As used herein, a "disease or disorder associated with abnormal production of a Type I or Type IX collagen chain" means a disease or disorder associated with production of an abnormal Type I or Type IX collagen chain or production of an abnormal amount of a normal Type I or Type IX collagen chain. Preferably, the disease or disorder associated with abnormal production of a Type I or Type IX collagen chain is one known to be associated with abnormal production of a Type I or Type IX collagen chain.

As used herein, "production of an abnormal Type I or Type IX collagen chain" means production of a Type I or Type IX collagen chain having an amino acid sequence different from the amino acid sequence encoded by the corresponding consensus gene sequence described herein.

As used herein, "production of an abnormal amount of a normal Type I or Type IX collagen chain" means production in a subject of a chain of Type I or Type IX collagen having the same amino acid sequence as that encoded by the corresponding consensus gene sequence described herein, but in an amount such that the ratio of production the chain to production of a different chain of the Type I or Type IX collagen differs from the ratio of production in individuals who do not have a pathological condition associated with an altered Type I or Type IX collagen gene. This level of collagen production is referred to herein as "normal." The normal ratio of production of the $\alpha 1(I)$ chain to production of the $\alpha 2(I)$ chain is two to one. The normal ratio of production of the $\alpha 1(IX)$ chain to production of the $\alpha 2(IX)$ chain is one to one. The normal ratio of production of the $\alpha 1(IX)$ chain to production of the $\alpha 3(IX)$ chain is one to one. The normal ratio of production of the $\alpha 2(IX)$ chain to production of the $\alpha 3(IX)$ chain is one to one. Preferably, the difference between the normal ratio and the ratio in a subject afflicted with a pathological condition associated with an altered Type I or Type IX collagen gene is at least about 1%; more preferably the difference is at least about 10%.

As used herein, the term "procollagen" means a gene product of a collagen gene which comprises at least one amino acid sequence which is present in the chain encoded by the collagen gene and which is not present in the mature $\alpha$ chain encoded by the collagen gene. By way of example, pro$\alpha 1(I)$ is a procollagen encoded by the COL1A1 gene. Pro$\alpha(I)$ comprises N-telopeptidic and C-telopeptidic amino acid sequences which are not present in the mature $\alpha(I)$ chain.

As used herein, the term "registration" refers to the alignment of Gly-X-Y tripeptide sequences of the collagen or procollagen chains of a collagen or procollagen subunit. Gly-X-Y tripeptide sequences are 'in register' when the first Gly-X-Y sequence, numbered from the carboxyl terminal end, of a first collagen or procollagen chain is able to hydrogen bond to the first Gly-X-Y sequence, numbered from the carboxyl terminal end, of each of the other two collagen or procollagen chains of the collagen or procollagen subunit.

As used herein, a "substantially pure PCR product" is an amplified nucleotide or plurality of amplified nucleotides which has been separated from the components of a PCR. Such components include a DNA polymerase, oligonucleotide primers, and the like. Methods of making substantially pure PCR products from PCR mixtures are well known in the art and include, for example, electrophoretic separation of PCR mixture components on an agarose gel following the reaction.

EXAMPLES

The invention is now described with reference to the following experimental examples. These examples are provided for the purpose of illustration only and the invention should in no way be construed as being limited to these examples but rather should be construed to encompass any and all variations which become evident as a result of the teaching provided herein.

Although the methods of the invention have been demonstrated in the first instance in humans, they are expected to be useful in other mammalian species, particularly commercially important species and laboratory animal species used in models of human disease.

Example 1

Determining the Presence of an Alteration in the Coding Region of a Collagen Gene of a Subject The following method may be used to determine the presence, genetic location, and sequence of an alteration in the coding region of a COL1 or COL9 gene of a subject. The method involves making and sequencing cDNA from mRNA obtained from cultured fibroblasts taken from the subject, and then comparing the cDNA sequence to a reference sequence, whereby alterations in the subject's sequence may be identified.

Complementary DNA (cDNA) molecules were prepared from mRNA encoding the proα1(I) chain and from mRNA encoding the proα2(I) chain of Type I collagen. These two cDNA molecules encode the entire coding sequence of each of the two chains.

To prepare cDNA, total cellular RNA was isolated from cultured skin fibroblasts by lysing the cells with the detergent, Sarcosyl, in the presence of guanidinium isothiocyanate. Isolated RNA was pelleted through a cesium chloride solution, as described (Maniatis et al., 1982, In: *Molecular Cloning: A Laboratory Manual*, Cold Spring Harbor Laboratory, Cold Spring Harbor, N.Y., p. 196). cDNA was synthesized using a commercial poly(A)+RNA kit purchased from BRL (Bethesda Research Laboratories, Bethesda, Md.) or Pharmacia (Pharmacia-LKB, Piscataway, N.J.) or using reverse transcriptase and a primer specific for the proα1(I) chain such as those provided in Table 1. Synthesis of cDNA using reverse transcriptase and primer was performed as described (Maniatis et al., 1982, In: *Molecular Cloning: A Laboratory Manual*, Cold Spring Harbor Laboratory, Cold Spring Harbor, N.Y., p. 213).

TABLE 1

Primers for amplifying the cDNA for the human proα1 (I) chain are presented herein

| CODE NO. | TARGET SEQUENCE[a] SENSE | ANTI-SENSE | PRIMER SEQUENCE | | | | | | | | |
|---|---|---|---|---|---|---|---|---|---|---|---|
| CDC27 | | Exon 41 | GGA EcoRI | ATT | CAA | GCG | TGG | TGT | GGT | CGG | CCT | G |
| CDC28 | Exon 44 | | GGG BamHI | GAT | CCC | TCA | CCA | CGA | TCA | CCA | CTC | T |
| CDC22 | | Exon 44 | GGA EcoRI | ATT | CCT | TGG | CCC | TGC | TGG | CAA | GAG | T |
| CDC26 | Intron 45 | | AAG BamHI | GAT | CCC | AGG | CGG | AAG | TTC | CAT | TGG | C |
| CDC30 | | Intron 44 | CCG EcoRI | GAA | TTC | CTG | GCC | AAG | AGC | TCA | TGC | T |
| CDC23 | Intron 46 | | AAG BamHI | GAT | CCC | CTC | CTA | TCC | CAC | AGC | ACA | G |
| 146F | | Intron 46 | ATG BamHI | GAT | CCA | TGC | TGT | GCT | GTG | GGA | TAG | G |
| E48R | Exon 48 | | ATG EcoRI | ATT | TCC | GTT | GAG | TCC | ATC | TTT | GCC | A |
| E48F | | Exon 48 | ATG BamHI | GAT | CCT | CGC | GGT | CGC | ACT | GGT | GAT | G |
| E50R | Exon 50 | | ATG EcoRI | AAT | TCC | AGC | CTT | GGT | TGG | GGT | CAA | T |
| E50F | | Exon 50 | ATG BamHI | GAT | CCA | TGT | CTG | GTT | CGG | CGA | GAG | C |
| E52R | Exon 52 | | ATG AEcoRI | AAT | TCT | CAA | TCA | CTG | TCT | TGC | CCC | |

[a]Primers were used in pairs, as follows: CDC27 (SEQ ID NO: 478) with CDC28 (SEQ ID NO: 479), CDC22 (SEQ ID NO: 500) with CDC26 (SEQ ID NO: 501), CDC30 (SEQ ID NO: 564) with CDC23 (SEQ ID NO: 565), 146F (SEQ ID NO: 566) with B48R (SEQ ID NO: 568), E48F (SEQ ID NO: 641) with E50R (SEQ ID NO: 642), and E50F (SEQ ID NO: 643) with E52R (SEQ ID NO: 644).
[b]Underlined nucleotides indicate sequences added to provide restriction sites used to clone the PCR products.

Double-stranded cDNA was synthesized using the method of Gubler et al. (1983, Gene 25:263–269), as amended by the manufacturers of the cDNA preparation kits. Single-stranded cDNA was synthesized using reverse transcriptase followed by alkaline hydrolysis of the RNA, as described (Maniatis et al., 1982, In: *Molecular Cloning: A Laboratory Manual*, Cold Spring Harbor Laboratory, Cold Spring Harbor, N.Y., pp. 214–216). Double- or single-stranded cDNA was amplified using a PCR kit (GeneAMp™ DNA Amplification Reagent Kit, Perkin Elmer Cetus, Norwalk, Conn.), according to the instructions provided by the manufacturer. Primers complementary to portions of cDNA of the proα1(I) gene were used in the PCR. The primers which were used are described in Table 1.

To obtain the nucleotide sequence of an amplified DNA sequence, PCR was performed using an unequal amount of two primers, so that an excess of single-stranded DNA synthesized using the prevalent primer resulted. Following PCR, single-stranded DNA (ssDNA) was sequenced using the dideoxynucleotide chain termination method using internal primers and a sequencing kit (Sequenase™; United States Biochemical Corp., Cleveland, Ohio).

In a typical experiment, cDNA was used as a PCR template with a pair of the primers described in Table 1. The PCR was permitted to proceed for thirty cycles, wherein a cycle is defined as permitting the reaction to proceed at 94° C. for ninety seconds, at 56° C. or 58° C. for sixty seconds, and at 74° C. for ninety seconds. The picomolar ratio of antisense primer to sense primer was 20:4. In a second PCR, about one percent of the first PCR product was used as template for a second PCR. The second PCR was permitted to proceed for twenty cycles, as described, in which the ratio of antisense:sense primers was 50:1. The second PCR product was purified, and the volume in which it was contained was reduced using an Ultrafree™ MC filtration unit (Millipore, Bedford, Mass.; No. UFC3TTK00) to yield a solution comprising substantially purified DNA. The sequence of the substantially purified DNA was determined using the dideoxynucleotide chain termination reaction, as described (Sanger et al., 1977, Proc. Nat. Acad. Sci. USA 74:5463–5467) using modified T7 DNA polymerase (United States Biochemical Corp., Cleveland, Ohio). Conventional and radioactive sequencing using $^{35}$S-dATP autoradiography and sequencing using fluorescently labeled primers and an ABI 370A automated sequencer (Applied Biosystems International, San Francisco, Calif.) were performed.

Example 2

Isolation and Characterization of the Nucleotide Sequence of the COL1A1 Gene, Including the Sequences of Introns 25 to 51

The nucleotide sequences of the entire coding region, the 5'-untranslated region, introns 1–26, and the twenty-six nucleotides of intron 27 located adjacent to exon 26 of COL1A1, have been reported, as described herein. This Example describes the sequencing of the entire human COL1A1 gene, including the 78 nucleotides of intron 27 which are adjacent exon 28 through and including the −3' end of the gene.

To analyze the sequence of COL1A1 extending from intron 25 to exon 40, a genomic fragment of the COL1A1 gene was cloned from DNA obtained from cultured skin fibroblasts of a subject afflicted with osteogenesis imperfecta (Tsuneyoshi et al., 1991, J. Biol. Chem. 266:15608–15613). Genomic DNA was digested with BamHI in order to generate a COL1A1 gene fragment having a length of about five kilobases. BamHI-digested genomic DNA was separated by electrophoresis on an agarose gel, and fragments having a length between about two and about six kilobases were electroeluted therefrom. Fragments were cloned into lambda phage vectors (Lambda-2AP, Stratagene, La Jolla, Calif.) to create a phage library. Individual phage clones from the phage library were screened for the presence of the COL1A1 gene using a cDNA probe (designated Hf-404) derived from COL1A1 mRNA (Maniatis et al., 1982, In: *Molecular Cloning: A Laboratory Manual*, Cold Spring Harbor Laboratory, Cold Spring Harbor, N.Y.; Bernard et al., 1983, Biochemistry 22:5213–5223). A phage clone comprising at least a portion of the COL1A1 gene was isolated. A deletion library was prepared from the nucleic acid encoded by the phage clone using exonuclease III and a commercial kit (Erase-a-base, Stratagene, La Jolla, Calif.). Double-stranded DNA obtained from the deletion library was used for dideoxynucleotide sequencing (Sanger et al., 1977, Proc. Natl. Acad. Sci. USA 74:5463–5467) using T7 polymerase (Sequenase™; U.S. Biochemical Corp., Cleveland, Ohio).

The nucleotide sequence of the 78 nucleotides of intron 27 which are adjacent exon 28 through and including the −3' end of the human COL1A1 gene is presented in FIG. 4.

Example 3

Post-Menopausal Osteoporosis and Reduced Bone Density in Members of a Family Having an Altered COL1A2 Gene The data presented in this Example establish an association between post-menopausal osteoporosis and an altered COL1A2 gene sequence. In addition, the data establish an association between an altered COL1A2 gene sequence and reduced bone density in subjects.

A fifty-two-year old female human subject was diagnosed with post-menopausal osteoporosis. The woman was Caucasian and was evaluated after having developed acute mid-thoracic pain. X-ray examination of the subject's spine revealed the presence of an anterior compression fracture of the ninth thoracic vertebra and generalized demineralization of the spinal column consistent with osteoporosis. Bone densitometry of the lumbar spine by dual-energy X-ray absorptiometry revealed that the subject's bone density was 0.75 g/cm$^2$, a value which is in the second lowest percentile for women of the same age, the mean normal value being 1.13 g/cm$^2$.

On physical examination of the subject, her sclerae were found to have a slightly bluish cast, her skin was not abnormally thin, and there was no hyperextensibility of her joints. Routine laboratory tests, including serum protein electrophoresis, were normal.

The woman had experienced a normal menopause seven years prior to examination. She had no history of any disease or use of drugs known to be associated with osteoporosis. However, she had experienced repeated fractures throughout her life, from early childhood on. Dermal fibroblasts were obtained from the woman, and Type I procollagen synthesized by those cells was examined by SDS-PAGE. Delayed migration of both the proα1(I) and proα2(I) chains derived from the secreted Type I procollagen was observed, relative to migration of chains obtained from individuals who did not exhibit symptoms of a pathological condition associated with an altered Type I or Type IX collagen gene. Differential migration was more apparent when fragments obtained by treating type I collagen obtained from the woman with a vertebrate collagenase were examined. Migration of vertebrate collagenase fragment A, comprising amino acid residues 1–775 of the woman's type I collagen, was retarded in the gel. However, migration of the B fragments, comprising amino acid residues 776–1,014 of the woman's type I collagen, was not retarded in the gel. Retarded migration of the woman's collagen fragment A was found to be caused by post-translational over-modification of the α chains. Incubation of the woman's fibroblasts in a solution comprising 0.3 mM α,α'-dipyridyl, which inhibits post-translational modification of the protein by prolyl hydroxylase and lysyl hydroxylase, abolished the difference in migration rates between collagen chains obtained from the woman and those obtained from individuals not afflicted with a pathological condition associated with an altered Type I or Type IX collagen gene.

Total RNA was extracted from the fibroblasts obtained from the woman and was used to synthesize single-stranded cDNA, as described herein. cDNA was used as a template for nine separate PCRs using primer pairs that resulted in amplification of all 3,052 base pairs of coding sequence of the triple-helical domains of each of the proα1(I) and proα2(I) chains. Heterozygous single-base mutations were detected in individual PCR products by denaturing and renaturing the PCR and treating the renatured DNA with a water-soluble carbodiimide, as described (Ganguly et al., 1990, Nucl. Acids Res. 18:3933–3939). Analysis by primer extension of each of the nine PCR products indicated that one comprised a sequence heteromorphism. The region in which the sequence difference was identified spanned nucleotides 1,951 to 2,813 of COL1A2, a portion of the coding region of the gene corresponding to amino acids 516 to 803 of the triple-helical domain of proα2(I). Further analysis indicated that a sequence variation was present in the region of the COL1A2 gene encoding amino acid residues 660 to 667 of the proα2(I) chain.

The region of the COL1A2 gene comprising the sequence variation that gave rise to the mismatch observed using the carbodiimide technique was sequenced. Nucleotide sequencing was performed using the PCR product which comprised the sequence heteromorph, as well as using three other PCR products that spanned the remainder of the coding sequences corresponding to the triple-helical domain of proα2(I). Analysis of the woman's COL1A2 gene sequence identified a single-base alteration at codon 661, which normally has the nucleotide sequence GGT and encodes glycine. One of the alleles in the woman's COL1A2 gene had the nucleotide sequence AGT at codon 661, encoding serine instead of glycine. PCR products derived from the woman's DNA contained both A and G in this codon, indicating that her DNA was heterozygous for the altered COL1A2 gene. Dideoxynucleotide sequencing of the three PCR products spanning the remainder of the coding sequences for the triple-helical of the proα2(I) chain did not reveal any nucleotide sequence difference that would alter the amino acid encoded by the corresponding codon.

To confirm the presence of the mutation in the genomic DNA of this woman, the genomic DNA was amplified using PCR using intronic primers described herein. PCR products were hybridized with an oligonucleotide having a sequence which was complementary to either the normal coding sequence of the COL1A2 gene or the normal coding sequence having a single-base alteration that converted G to A at codon 661. Both oligonucleotides hybridized to PCR products derived from the patient's genomic DNA. However, the oligonucleotide having the altered base did not hybridize to PCR products derived from fifty control samples of genomic DNA obtained from individuals who were afflicted with neither post-menopausal osteoporosis nor abnormally low bone density.

Further experiments involving hybridization of the normal primer and the primer having the altered base with PCR products derived from genetic relatives of the woman demonstrated that the mutation was not present in the genomic DNA of the patient's 89-year old mother, although she had severe thoracic kyphosis and radiographic evidence of age-related or Type II osteoporosis. The mutation was present in the genomic DNA of each of the patient's three sons, ages 24, 29, and 31. These individuals had each suffered one to four fractures following trauma as adolescents. Subsequent examination of the three sons demonstrated that none had any evidence of osteogenesis imperfecta or related genetic diseases. However, all three individuals had markedly reduced bone density.

The results presented in this example establish an association between an altered COL1A2 gene and post-menopausal osteoporosis and/or reduced bone density.

Example 4

PCR/CSGE Analysis of the COL1A1 and COL1A2 Genes of Fifteen Human Patients Afflicted with Mild (Type I) Osteogenesis Imperfecta Using Intronic Primers Although it has been estimated that over 90% of patients afflicted with osteogenesis imperfecta (OI) have a mutation in one or both of the COL1A1 and COL1A2 genes, it has been difficult to detect such mutations in all patients afflicted with the mildest forms of the disease, designated Type I OI. In this Example, the presence or absence of COL1A1 and COL1A2 mutations was examined by analysis of protein and mRNA synthesized in fibroblasts obtained from each of ten patients afflicted with Type I OI. No evidence of a mutation at the protein level was found in two of the ten patients, and no evidence of a mutation at the cDNA level was found in five of the ten patients.

Genomic DNA was obtained from the original ten patients and from an additional five patients afflicted with Type I OI. In order to assay the genomic DNA of these fifteen patients, it was necessary to identify a consensus sequence for both of the COL1A1 and COL1A2 genes, which is indicative of a normal non-mutated gene in each case. To identify these consensus sequences, it was necessary to obtain 90% of the sequence of the 38-kb COL1A2 gene and to sequence extensive regions of the 18-kb COL1A1 gene, including some regions for which sequence data had already been reported. Previously reported COL1A1 sequences did not appear to represent a consensus gene sequence.

The consensus sequences were used to develop intronic primers useful for PCR amplification of the 103 exons of the two genes and the flanking sequences bordering each of the exons. PCR amplification products were scanned for the presence of heteroduplexes by conformation sensitive gel electrophoresis (CSGE; Ganguly et al., 1993, Proc. Natl. Acad. Sci. USA 90:10325–10329; Ganguly et al., 1995, Electrophoresis 16:1830–1835), and products comprising heteroduplexes were sequenced. This method detected disease-causing mutations in thirteen of the fifteen patients and two additional probable disease-causing mutations in the remaining two patients. Analysis of the data described herein revealed common sequences for mutations resulting in null alleles.

The PCR/CSGE technique described in this Example greatly reduced the amount of DNA sequencing necessary to identify mutations in the genes of subjects afflicted with OI or with another pathological condition which is associated with an altered COL1 or COL9 gene.

The materials and methods used in this Example are now described.

Subjects

All subjects were probands who presented the typical phenotype of OI Type I. The major clinical symptoms manifested by each of them are summarized in Table 2.

Protein Analysis

Skin biopsy samples were obtained from each of subjects one through ten, and fibroblast cultures derived from each of these samples were established under culture conditions known in the art. About 35,000 cells/cm$^2$ were seeded onto the culture medium. Labeling of fibroblasts and purification of collagen was performed as reported (Nuytinck et al., 1996, Human. Genet. 97:324–329). Briefly, cells were labeled by adding to the culture medium BME medium (Basal Medium Eagle, Life Technologies, Gaithersburg, Md.) comprising one microcurie per milliliter $^{14}$C proline, 5% (v/v) dialyzed fetal calf serum (FCS), 0.05 milligrams per milliliter β-aminoproprionitrile and 0.025 milligrams per milliliter ascorbic acid. After twenty hours, the medium was removed and supplemented with protease inhibitors such that final concentrations were 0.1 milligrams per milliliter phenylmethylsulfonyl fluoride (PMSF), 0.1 milligrams per milliliter N-methylmaleimide, and 2 millimolar ethylenediaminetetraacetic acid (EDTA). The cell layer was trypsinized, and the cells were collected by centrifugation and lysed in a solution comprising 0.5% (v/v) Triton X-100 in 0.5 M acetic acid. The medium and lysed cells were pooled and centrifuged, and the supernatant was used for collagen analysis.

Collagens were isolated from the supernatant by alcohol precipitation and were resuspended in 0.5 M acetic acid. To convert procollagen to collagen, the samples were digested with 50 micrograms per milliliter pepsin for four hours at 15° C., Digestion was halted by adding 0.5 mg/ml pepstatin. SDS-PAGE was performed as described (Laemmli et al., 1970, Nature 227:680) using a 3% (w/v) stacking gel and a 5% (w/v) separating gel. Prior to loading, samples were lyophilized, redissolved in sample buffer comprising Tris-HCl, pH 6.8, 2 M urea, and 0.04% (w/v) bromphenol blue, and denatured for twenty minutes at 55° C., Electrophoresis was performed at 8° C. overnight using an applied voltage of 3.5 V/cm$^2$. Each gel was processed for fluorography by soaking it in a solution comprising 20% (w/v) 2,5-diphenyloxazole (PPO) in 100% (v/v) acetic acid, drying it, and exposing it to a sheet of Hyperfilm MP™ (Amersham, Arlington Heights, Ill.).

Analysis of DNA Polymorphism

Total RNA was isolated from cultured skin fibroblasts using the Trizol buffer (Life Technologies, Gaithersburg, Md.) method, according to the manufacturer's instructions. Prior to cDNA synthesis, RNA was treated with RNase-free DNase (Life Technologies, Gaithersburg, Md.) to prevent contamination by genomic DNA in the reverse transcriptase-PCR (RT-PCR) experiments. Moloney murine leukemia virus reverse transcriptase was used in combination with random hexanucleotide primers to synthesize cDNA from mRNA. MnlI polymorphisms in the COL1A1 gene were detected using primers and conditions as described (Sokolov et al., 1991, Hum. Genet. 88:125–129). After enzymatic digestion of the cDNA, fragment length was evaluated either by agarose gel electrophoresis or by separation on polyacrylamide gels and an automated laser fluorescent DNA sequencer (ALF™, Pharmacia LKB Biotechnology Inc., Piscataway, N.J.).

The four-base-pair insertion polymorphism at the 3'-end of the COL1A1 gene was detected by PCR amplification, wherein the sense primer had the sequence 5'-CCT TTC TGC TCC TTT CTC CA-3' (SEQ ID NO: 645) and the antisense primer had the sequence 5'-AGC AAC ACA GTT ACA CAA GG-3' (SEQ ID NO: 646). About 500 nanograms of genomic DNA was amplified by subjecting it to twenty-five PCR amplification cycles as follows: 94° C. for one minute, 56° C. for one minute, and 72° C. 1 minute. Amplification products were separated on a 6% (w/v) polyacrylamide gel using an automated laser fluorescent DNA sequencer (ALF™, Pharmacia LKB Biotechnology Inc., Piscataway, N.J.). A nucleotide having a length of 430 base pairs, designated allele A1, a nucleotide having a length of 434 base pairs, designated allele A2, or both, were identified by comparison to nucleotide size markers of known length.

Defining the Consensus Sequences of the 5'-Portion of the COL1A1 Gene

Identification of the consensus sequence of the 3'-portion of the COL1A1 gene has been described elsewhere herein.

To identify a consensus sequence of the 5'-portion of the COL1A1 gene, genomic DNA obtained from eight unrelated subjects afflicted with OI was amplified by PCR using primers based on published sequences of the COL1A1 gene (Chu et al., 1985, J. Biol. Chem. 260:2315–2320; D'Alessio et al., 1988, Gene 67:105–115; Määttä et al., 1991, FEBS Lett. 279:9–13; Westerhausen et al., 1991, Matrix 11:375–379). PCR reactions were carried out using a commercial DNA polymerase (Amplitaq Gold, Perkin Elmer Cetus, Norwalk, Conn.) in a 40 microliter reaction volume. The PCR was maintained at 95° C. for ten minutes, and then was subjected to thirty-five cycles as follows: 95° C. for forty seconds, 60° C. for forty seconds, and 72° C. for fifty seconds. Amplification products had sizes ranging from about one thousand to about twenty-five hundred nucleotides.

Nucleotide sequences of amplification products were defined by automated sequencing (ABI PRISM 377™ Sequencer, Perkin Elmer Cetus, Norwalk, Conn.; ABI PRISM™ Dye Therminator Cycle Sequencing Ready Kit with AmpliTaq™ DNA polymerase, Perkin Elmer Cetus, Norwalk, Conn.). Prior to sequencing, samples were treated with exonuclease I (Amersham, Arlington Heights, Ill.) to degrade residual PCR primers and shrimp alkaline phosphatase (Amersham, Arlington Heights, Ill.) to dephosphorylate residual nucleotides, as described (Hanke et al., 1994, BioTechniques 17:858–860; Werle et al., 1994, Nucl. Acids Res. 22:4354–4355).

Sequencing of the Human COL1A2 Gene

To sequence the 5'-end of the human COL1A2 gene, a fragment having a length of about fourteen kilobases spanning intron 1 to intron 21 was obtained from an EcoRI/EcoRI genomic fragment that had been cloned into a bacteriophage vector in the course of defining a mutation that caused OI, as described (Vasan et al., 1991, Am. J. Hum. Genet. 48:305–317). The fourteen kilobase fragment was broken at random positions by sonication, and the resulting fragments were separated by gel electrophoresis. Selected fragments were subcloned into a plasmid (pUC18), and sixty clones, each comprising a fragment, were isolated from *Escherichia coli* host cells. Plasmid DNA was isolated from thirteen color-selected colonies. The plasmids each comprised an insert having a size between about 500 and about 4,000 base pairs. About 90% of the sequence of the fourteen kilobase COL1A2 gene fragment was determined by shotgun sequencing of the inserts from the thirteen selected clones. The remainder of the sequence was determined by sequencing the original bacteriophage clone containing the fourteen kilobase genomic fragment using manual or automated procedures described herein and well known in the art.

To identify the sequence of the portions of the COL1A2 gene not represented in the fourteen kilobase bacteriophage fragment, a genomic P1 clone comprising the complete human COL1A2 gene was obtained by PCR screening of a human P1 library (Genome Systems, Inc., St. Louis, Mo.). PCR screening was performed using primers having sequences based on the reported sequence of human COL1A2 cDNA (de Wet et al., 1987, J. Biol. Chem. 262:16032–16036; Kuivaniemi et al., 1988, Biochem. J. 252:633–640). PCR primers used were C1PF1, which had the sequence 5'-GTA CAT TTC CTA GAG AAC TTG-3' (SEQ ID NO: 647), and C1PR1, which had the sequence 5'-CTA CTC TCA GCC CAG GAG GTC CTG-3' (SEQ ID NO: 648). The sequence of C1PF1 corresponded to sequences in intron 19 of COL1A2, and the sequence of C1PR1 corresponded to sequences in exon 21 and intron 21. Three P1 clones were identified as comprising at least a portion of the coding sequence of COL1A2: P1 clone DMPC-HFF#1 1250-E2, GS control #7403, P1 clone DMPC-HFF#1 1365-B1, GS control #7404, and P1 clone DMPC-HFF#1 1473-F6, GS control #7405. Because P1 clone #7407 was determined to comprise the entire coding sequences of the human COL1A2 gene, this clone was selected for detailed characterization of the gene.

To increase the yield of DNA, P1 clone #7407 was transferred from E. coli strain NS3529 to E. coli strain NS3516 via transduction. P1 plasmid DNA was isolated as described by Birnboim et al. (1979, Nucl. Acids Res. 7:1513–1523). Isolated P1 plasmid DNA was dissolved in water, and was further purified by spot dialysis using water separated from the DNA by a membrane (VSWP 02500; Millipore, Bedford, Mass.).

Nucleotide sequencing was carried out by cycle sequencing of P1 plasmid DNA using the dsDNA Cycle Sequencing System obtained from Life Technologies, Inc. (Gaithersburg, Md.) or the Cycle Sequencing Kit obtained from Pharmacia LKB Biotechnology Inc. (Piscataway, N.J.). Sequences of primers used for sequencing the COL1A2 gene were based on published COL1A2 sequences (Bernard et al., 1983, Biochem. 22:1139–1145; de Wet et al., 1987, J. Biol. Chem. 262:16032–16036; Kuivaniemi et al., 1988, Biochem. J. 252:633–640). Additional primer sequences were based on the sequences determined during the work described herein. The 5'-end of each primer was labeled using T4 polynucleotide kinase (U.S. Biochemical Corp., Cleveland, Ohio) and [γ-$^{33}$P]ATP (Dupont NEN, Wilmington, Del.). In cycle sequencing experiments, 0.5–2.0 micrograms of P1 plasmid DNA was used as the template, and thermal cycling was carried out using a commercial instrument (either a GeneAmp 9600™, Perkin Elmer Cetus, Norwalk, Conn., or a PTC 225 DNA Engine Tetrad™, MJ-Research, Inc., Watertown, Mass.). Some nucleotide sequences were obtained using the Terminator Cycle Sequencing Ready Reaction kit and an ABI PRISM 377™ DNA Sequencer (both obtained from Perkin Elmer Cetus, Norwalk, Conn.). Sequence data were analyzed using the Wisconsin Sequence Analysis Package, versions 8.0 and 8.1 for UNIX (Genetics Computer Group, Madison, Wis.) and the Editseq program of Lasergene software package (DNAStar, Inc., Madison, Wis.).

PCR/CSGE Mutation Analysis

Genomic DNA was extracted from blood samples or from cultured skin fibroblasts obtained from human subjects. The exons and the flanking sequences corresponding to the 51 exons of the COL1A1 gene and to the 52 exons of the COL1A2 gene were amplified using the primers depicted in FIGS. 21 and 22 [SEQ ID NOS. 216–324 and 325–434, respectively]. Genomic DNA was amplified by performing PCR in a 40 microliter reaction volume. The PCR was maintained at 95° C. for ten minutes, and then was subjected to thirty-five cycles as follows: 95° C. for forty seconds, 60° C. for forty seconds, and 72° C. for fifty seconds.

PCR amplification was followed by a heteroduplex formation step, wherein the products of the amplification were maintained at 95° C. for 5 minutes and then at 68° C. for 30 minutes. Samples containing heteroduplexes were identified by CSGE analysis, as described, except that the taurine buffer was not autoclaved (Ganguly et al., 1993, Proc. Natl. Acad. Sci. USA 90:10325–10329; Ganguly et al., 1995, Electrophoresis 16:1830–1835).

Samples containing heteroduplexes were treated with exonuclease I and shrimp alkaline phosphatase, as described (Hanke et al., 1994, BioTechniques 17:858–860; Werle et al., 1994, Nucl. Acids Res. 22:4354–4355), and were then analyzed either by PCR product sequencing using the Sequenase PCR Product Sequencing Kit (U.S. Biochemical Corp., Cleveland, Ohio) according to the manufacturer's instructions or by automated sequencing (ABI PRISM™ 377 Sequencer, and ABI PRISM™ Dye Therminator Cycle Sequencing Ready Kit with AmpliTaq™ DNA polymerase FS, both obtained from Perkin Elmer Cetus, Norwalk, Conn.). Alleles of PCR products that contained deletions in one allele were separated on and subsequently purified from agarose gels (QIAEX II™ Gel Extraction Kit, Qiagen, Chatsworth, Calif.), and about 60 nanograms of purified PCR product was cloned into plasmid pT7 (pT7 Blue T-Vector Kit, Novagen, Madison, Wis.) prior to sequencing.

The results of the experiments performed in this Example are now described.

Detection of COL1A1 and COL1A2 Mutations by Protein and mRNA Analysis

Fibroblasts obtained from ten subjects afflicted with Type I OI were examined to determine the ratio of newly synthesized chains of Type I and Type III procollagen. The fibroblasts were also examined for the presence of polymorphic COL1A1-derived mRNA, which reflects expression of two different alleles of the COL1A1 gene. As indicated in Table 2, a reduced ratio of newly synthesized Type I procollagen to newly synthesized Type III procollagen was detected in fibroblasts obtained from seven of the ten subjects tested and a slight reduction was detected in an eighth subject. This ratio was normal in fibroblasts obtained from two of the subjects.

TABLE 2

Mutations Detected in Subjects Afflicted with Type I OI

| Subject Number | Reduced Ratio of Procollagen I to Procollagen III | Absence of One COL1A1 Allele in mRNA[a,b] | Mutation Detected by CSGE Analysis | Identified Mutation in COL1A1 |
|---|---|---|---|---|
| 1 | + | + | + | $A^{+3}IVS22 \rightarrow G$ |
| 2 | + | + | + | $G^{-12}IVS20 \rightarrow A$ |
| 3 | + | + | + | $A^{+2}IVS5 \rightarrow G$ |
| 4 | + | + | + | del T nt 927 (E12) |
| 5 | + | NI | + | $Arg^{183} \rightarrow STOP$ |
| 6 | + | NI | + | del T nt 2192 (E31) |
| 7 | ±[c] | NI | + | del G nt 3198 (E43) |
| 8 | + | 0 | + | $G^{+1}IVS12 \rightarrow A$ |
| 9 | 0 | + | + | del T nt 2732 (E38) |
| 10 | 0 | NI | + | $Arg^{42} \rightarrow STOP$ |
| 11 | NA | NA | + | Ins C nt 1787 (B24) |
| 12 | NA | NA | + | $Arg^{519} \rightarrow STOP$ |
| 13 | NA | NA | + | Ins AC nt 1838 (E25) |
| 14 | NA | NA | + | $G^{-1}IVS25 \rightarrow A$ |
| 15 | NA | NA | + | $G^{-1}IVS18 \rightarrow A$ |

[a]NA means not assayed.
[b]NI indicates assay results that were non-informative, due to the fact that the subject was homozygous for the polymorphism.
[c]indicates that the subject exhibited a slight reduction in the ratio.

Fibroblasts obtained from the subjects were also examined to determine the presence or absence of a polymorphic base in the mRNA which indicated expression of COL1A1 alleles A1 and A2. One allele either was not expressed or was expressed at a reduced level in fibroblasts obtained from five subjects (subjects 1–4 and 9 in Table 2, including one in whom the collagen ratio was normal. The mRNA assay indicated that both COL1A1 alleles were expressed in one subject who was identified by the protein assay as expressing a decreased ratio of Type I to Type III collagen (i.e. subject 8 in Table 2). The mRNA assay results in cells obtained from four subjects were non-informative.

Examination of procollagen protein and mRNA encoding procollagen in cultured skin fibroblasts have been useful in the prior art in defining mutations that cause OI. However, as illustrated herein, these assays did not detect all COL1A1 and COL1A2 mutations, particularly in Type I OI. Furthermore, examination of protein and mRNA requires the use of skin biopsies from which fibroblasts are cultured for three weeks or more. Thus, examination of protein and mRNA is less convenient than is an assay based on genomic DNA, which DNA can easily be obtained from numerous physiological sources, including a blood sample. For these reasons, a test was developed which included PCR amplification of each of the 103 exons, the flanking sequences thereof, and the 5'- and 3'-untranslated regions of the COL1A1 and COL1A2 genes for the purpose of identifying genetic abnormalities therein.

Sequences of the COL1A1 and COL1A2 Genes

The nucleotide sequences of the COL1A1 and COL1A2 genes were determined, so that intronic PCR primers could be designed for analysis of the genes. Several groups had reported the nucleotide sequence of the coding sequence, introns 1–26, and the 5'-portion of intron 27 of the COL1A1 gene, as described herein. However, attempts to make intronic PCR primers based on published sequences for the 5'-half of the COL1A1 gene were largely unsuccessful, apparently because the published sequences did not represent the most frequent alleles of the gene. For this reason, about twelve kilobases of the sequence of the COL1A1 gene were sequenced in the present study, using samples derived from the genomic DNA of eight subjects. The consensus sequence for the complete eighteen kilobase COL1A1 gene has been submitted to GenBank (accession number AF017178), and is included herein at FIG. 4 (SEQ ID NO: 1). The genomic structure of COL1A1 is depicted herein at FIG. 1.

More than 250 differences were detected between the nucleotide sequences of the introns of the consensus COL1A1 gene and the nucleotide sequences reported for introns 1–27 thereof. It is thus apparent that the COL1A1 intron sequences reported herein and the sequences of primers derived therefrom have not been previously described.

Figure 2:
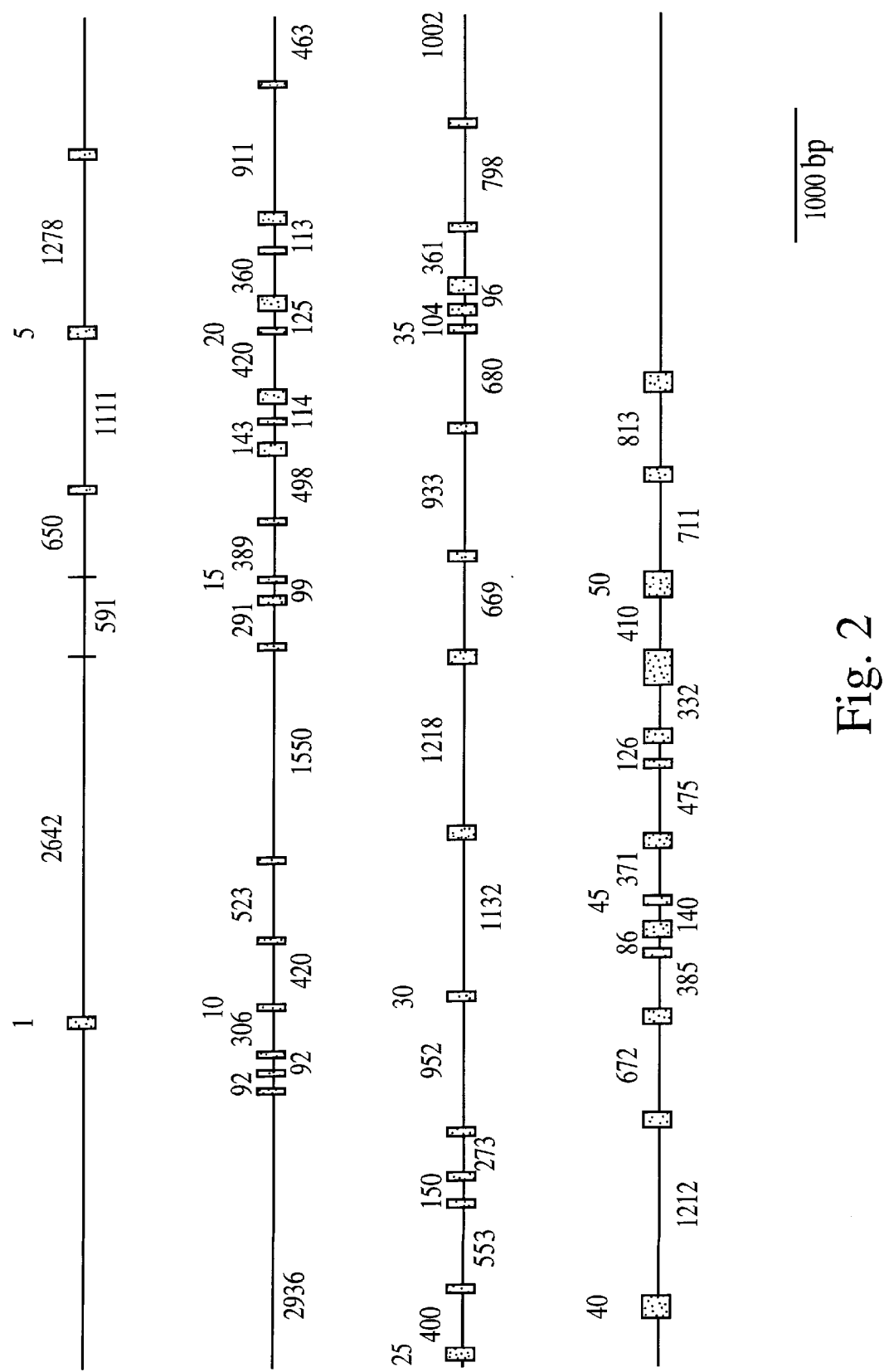
FIG. 2 is a schematic depiction of the human COL1A2 gene, extending from the 5'-untranslated region to the 3'-untranslated region thereof. Numbers in the larger font refer to intron numbers; numbers in the smaller font refer to the nucleotide length of each of the introns. The scale is indicated in the lower right, the bar representing a polynucleotide having a length of one thousand residues.

As described herein, the complete cDNA sequence of COL1A2 and portions of the non-coding region thereof have been reported in the prior art. The complete nucleotide sequence of COL1A2 reported herein includes about 30 kb of sequence which has not previously been reported. About 11 kb of new sequences from the 5'-end of the gene were obtained using a 14 kb EcoRI genomic fragment prepared for other purposes (Vasan et al., 1991, Am. J. Hum. Genet. 48:305–317). An additional 19 kb of new sequences of the COL1A2 gene were obtained using the P1 clone #7407. The complete sequence of the COL1A2 gene has been submitted to GenBank (accession number AF004877), and is described herein in FIG. 5 (SEQ ID NO: 2). The genomic structure of COL1A2 is depicted herein in FIG. 2.

Figure 6:
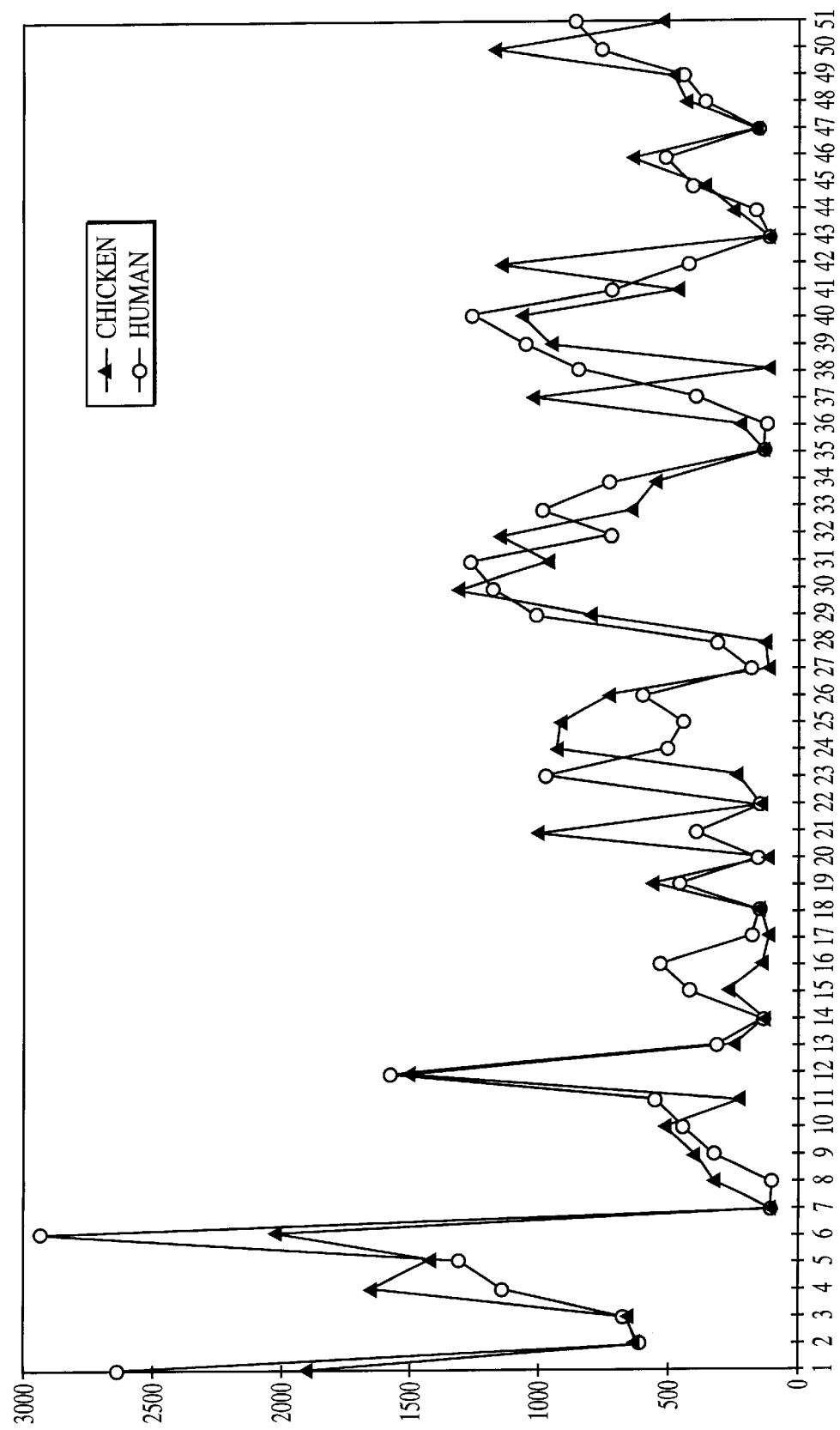

As depicted in FIG. 6, the lengths of the human COL1A2 introns were about the same as the lengths of the chicken COL1A2 introns (Boedtker et al., 1985, Ann. N.Y. Acad. Sci. 460:85–116). There were major differences in the lengths of human COL2A1 introns and chicken COL2A1 introns (Ala-Kokko et al., 1995, Biochem. J. 308:923–929).

Primers for PCR Amplification of the Exons and Flanking Regions of COL1A1 and COL1A2

The sequences of the human COL1A1 and COL1A2 genes described herein were used to design sequences for pairs of nucleotide primer useful for amplification of each of the 103 exons and at least 80 bp of both the 5'- and 3'-flanking sequences of the two genes. The non-coding regions of the COL1A1 gene are depicted herein in FIG. 4 (SEQ ID NOs: 6–57), and the non-coding regions of the COL1A2 gene are depicted herein in FIG. 5 (SEQ ID NOs: 58–110).

Conditions for PCR amplification were optimized so that each PCR amplification product could be detected as a discrete band by agarose gel electrophoresis and by polyacrylamide gel electrophoresis. In addition, the primers were designed so each of the amplification products made using the primer pairs generally had a length no greater than about 500 base pairs, so that the presence of a single-base substitution could be detected by heteroduplex analysis of an amplification product using CSGE (Ganguly et al., 1995, Electrophoresis 16:1830–1835). Thus, these primer pairs are useful for analyzing not only the coding regions of the COL1A1 and COL1A2 genes, but also for analyzing the intron-exon boundaries and the 5'- and 3'-ends of the genes for mutations associated with pathological conditions. The primers which were designed for use with the COL1A1 gene are depicted in FIG. 21 (SEQ ID NOs: 216–324), and the primers which were designed for use with the COL1A2 gene are depicted in FIG. 22 (SEQ ID NOs: 325–434). One skilled in the art would appreciate that other intronic primers can be made, based on the non-coding region nucleotide sequences described herein, which are useful for PCR/CSGE analysis of at lease a portion of the COL1A1 gene or the COL1A2 gene.

Figure 7:
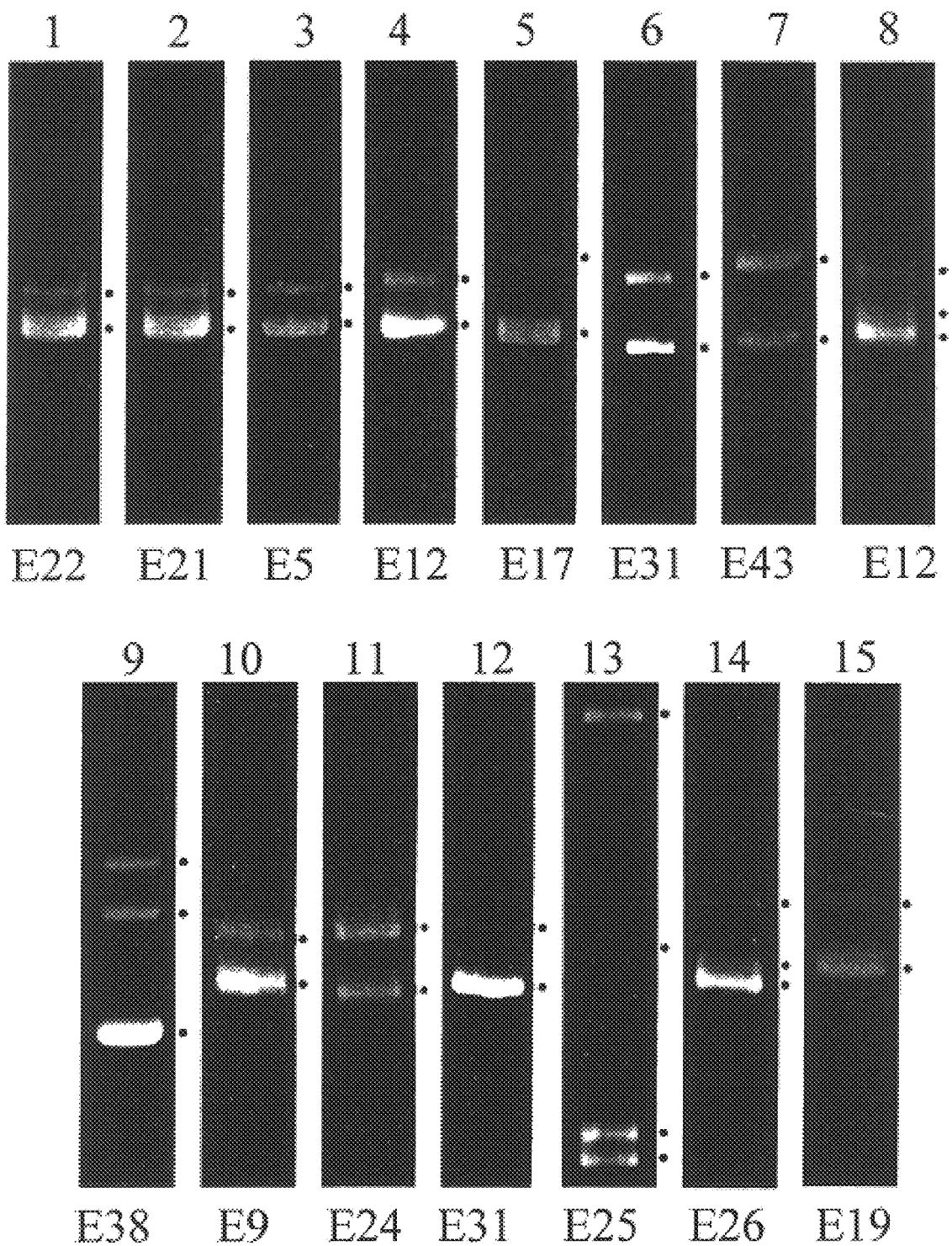

PCR/CSGE Detection of COL1A1 and COL1A2 Mutations in Human Subjects Afflicted with Type I OI The PCR/CSGE Mutation Analysis protocol described herein was used to identify mutations in fifteen subjects, including the ten subjects from whom fibroblast samples were obtained. Twenty-five polymorphisms in the COL1A1 gene and eighteen polymorphisms in the COL1A2 gene were detected. Most of the polymorphisms were found within an intron sequence of one of the two genes, and thus could not have been detected using primers corresponding to cDNA sequences derived from the genes. In addition, the presence of unique heteroduplexes was detected in each of the fifteen subjects, as depicted in FIG. 7. Nucleotide sequence analysis of each of the PCR amplification products which comprised a unique heteroduplex identified thirteen mutations. Five of the mutations were single base deletions or insertions (Subjects 4, 6, 7, 9 and 11 in Table 2), one mutation was a two-base-pair insertion (Subject 13), and three of the mutations were single base substitutions that converted a codon encoding Arg to a premature termination codon (Subjects 5, 10 and 12). Four mutations altered consensus sites of RNA splicing in the first two or last two bases of an intron (Probands 3, 8, 14 and 15). Thus, in order to screen type I and type IX collagen genes for disease/disorder-causing mutations, it is important to examine both coding regions and potential RNA splicing sites. Consensus RNA splicing sites have been described in the scientific literature (see, e.g., Shapiro et al., 1987, Nucl. Acids Res. 15:7155–7174; Jacob et al., 1989, Nucl. Acids Res. 17:2159–2180). Two alterations identified in the two other subjects were also likely to alter RNA splicing: one was at position +3 of intron 22 (subject 1); the second was at position −12 of intron 20 (subject 2). Intronic nucleotides are numbered such that the nucleotide which is located in the intron adjacent the 5'-end of an exon on the coding strand and which is located immediately adjacent the 5'-end of the exon is numbered "−1," the nucleotide located immediately adjacent the −1 nucleotide in the 5'-direction is numbered "−2," and so on. Similarly, the nucleotide which is located in the intron adjacent the 3'-end of an exon on the coding strand and which is located immediately adjacent the 3'-end of the exon is numbered "+1," the nucleotide located immediately adjacent the +1 nucleotide in the 3'-direction is numbered "+2," and so on. Although the nucleotides at these two positions are not conserved in all introns (Nakai et al., 1994, Gene 141:171–177), these two mutations were not found in one hundred other COL1A1 alleles. Furthermore, no other nucleotide sequence alterations were identified following amplification of all other regions of the COL1A1 and COL1A2 genes of these two subjects. Protein and mRNA data indicated that each of these two subjects expressed one COL1A1 allele at an abnormally low level. Two other observations supported the conclusion that the single base change at −12 of intron 20 in subject 2 was a disease-causing mutation. The same change was found in the affected father and sister of subject 2, but not in unaffected brother of subject 2. Also, the single base change at position-12 of intron 20 produced a 3'-consensus sequence for RNA splicing, i.e. it converted the nucleotide sequence 5'-(Pyrimidine)$_{11}$-CGG-3' to the sequence 5'-(Pyrimidine)$_{11}$-CAG-3', wherein (Pyrimidine)$_{11}$ means a sequence comprising eleven pyrimidine residues. The results therefore establish that definitive disease-causing mutations have been identified in thirteen subjects afflicted with Type I OI and probable disease-causing mutations have been identified in the other two. As indicated in Table 2, all of these mutations were in the COL1A1 gene.

Identification of Common Sequences for Mutations Causing COL1A1 Null Alleles

Comparison of COL1A1 mutations identified herein with previously defined mutations in OI-afflicted subjects identified common sequences for null allele mutations in the COL1A1 gene (Willing et al., 1994, Am. J. Hum. Genet. 55:638–647; Willing et al., 1996, Am. J. Hum. Genet. 59:799–809; Redford-Badwal et al., 1996, J. Clin. Invest. 97:1035–1040; Körkkö et al., 1997, Hum. Mutat. 9:148–156).

Single base substitutions that converted a CGA codon encoding arginine to a premature TGA termination codon were considered first. There were nine mutations that met this criterion, as indicated in Table 3. All were found in the COL1A1 gene in the sequence context 5'-C/GCC-CGA-GG/T-3', wherein "C/G" means that the nucleotide at that position may be C or G and "G/T" means that the nucleotide at that position may be G or T. Mutations comprising replacement of a codon encoding Arg with a termination codon were found in five of the six sequences having the indicated context in the wildtype COL1A1 gene. In contrast, no such mutations have been reported in the seven other sequence contexts in which arginine-encoding CGA codons exist in the wildtype COL1A2 gene, i.e. seven sequences in which a CGA codon is not preceded by G/CCC. These data establish that the sequence context 5'-C/GCC-CGA-GG/T-3' represents a site in the COL1A1 gene that is highly susceptible to mutation. Accordingly, primers, including, but not limited to, primer pairs and intronic primers, which can be used to amplify regions of the COL1A1 gene which comprise this sequence context are especially useful for identifying altered COL1A1 gene sequences.

TABLE 3

Common Sequences for Alteration of a CGA Codon to a Premature Termination Codon

| Sequence Context | Number of Mutations Reported | Exon Location of Reported Mutations | Amino Acid Number Corresponding to the Mutation | Reference[A] |
|---|---|---|---|---|
| CCC-CGA-GG | 1 | 9 | 42 | Herein |
| CCC-CGA-GG | 1 | 17 | 183 | Herein |
| GCC-CGA-GG | 2 | 19 | 237 | Herein and Willing '96 |
| CCC-CGA-GG | 2 | 31 | 519 | Willing '96 |
| CCC-CGA-gt | 3 | 47 | 963 | Willing '96 Kuivaniemi '97 |
| GAC-CGA-GA | 0 | 2 | | |
| CCC-CGA-GG | 0 | 4 | | |
| GGC-CGA-GA | 0 | 5 | | |
| GCT-CGA-GG | 0 | 11 | | |
| AAG-CGA-GG | 0 | 21 | | |
| GAG-CGA-GG | 0 | 26 | | |
| GGC-CGA-GT | 0 | 39 | | |
| GGA-CGA-GA | 0 | 43 | | |

[A]References: "Herein" refers to the present application; "Willing '96" refers to Willing et al., 1996, Am. J. Hum. Genet. 59:799–809; "Kuivaniemi '97" refers to Kuivaniemi et al., 1997, Hum. Mutat. 9:300–315.

Single base deletions or insertions which created frameshifts and premature termination codons in the COL1A1 gene were considered next. A total of fourteen such mutations have been reported in the COL1A1 gene, as indicated in Table 4. Nine of the fourteen mutations in the COL1A1 gene were contained within the sequence 5'-CCC-CCT-3'. Only five of the fourteen mutations were identified in other sequences. In the COL2A1 gene, six such mutations were reported and two are located in the sequence 5'-CCC-CCT-3' (Brown et al., 1992, Arch. Ophthalmol. 110:1589–1593; Brown et al., 1995, Hum. Molec. Genet. 4:141–142; Ahmad et al., 1995, Arch. Ophthalmol. 113:1454–1457; Ritvaniemie et al., 1993, Genomics 17:218–221). These observations are in accord with the observation of by Jego et al. (1992, Oncogene 8:209–213), that both single base insertions, single base deletions are likely to occur in duplicated sequences. In the case of collagens, the sequence 5'-CCC-CCT-3', encoding Pro-Pro or Pro-Hyp, is a common sequence in the COL1A1 gene.

Table 4. Null Allele Mutations Produced by Single Nucleotide Insertions or Deletions. Mutations were identified herein and by Körkkö et al. (1997, Hum. Mutat. 9:148–156), Willing et al. (1996, Am. J. Hum. Genet. 59:799–809), Willing et al. (1994, Am. J. Hum. Genet. 55:638–647), and Redford-Badwal et al. (1996, J. Clin. Invest. 97:1035–1040).

| Gene | Number of CCC-CCT Sequences in Gene | Number of Reported Single Base Insertions or Deletions Total | In CCC-CCT Sequence |
|---|---|---|---|
| COL1A1 | 30 | 14 | 9 |
| COL1A2 | 6 | 0 | 0 |
| COL2A1 | 16 | 6 | 2 |

No mutations in the COL1A2 gene were found by PCR/CSGE analysis of the genomic DNA obtained from the fifteen subjects afflicted with Type I OI. Therefore, mutations in the COL1A2 gene appear to be a rare cause of Type I OI, even though mutations in the gene can cause some severe variants of OI (Kuivaniemi et al., 1997, Hum. Mutat. 9:300–315). Individuals and mice which are heterozygous for a non-functional proα2(I) chain have decreased bone density (Dickson et al., 1984, Proc. Natl. Acad. Sci. USA 81:4524–4528; Chipman et al., 1993, Proc. Natl. Acad. Sci. USA 90:1701–1705; Saban et al., 1996, BioTechniques 21:190–192). Therefore, individuals with non-functional COL1A2 genes may have phenotypes that are milder than Type I OI and that overlap with osteoporosis.

Example 5

PCR/CSGE Analysis of the COL9A1 and COL9A2 Genes Using Intronic Primers

In this Example, the complete nucleic acid sequences of each of the human COL9A1 and COL9A2 genes are described. Primers useful for PCR/CSGE analysis of the genes are also described. PCR/CSGE screening methods have been described elsewhere herein. Sequences of the non-coding regions of these two genes are reported herein for the first time.

The materials and methods used in this Example are now described.

Screening of Genomic Library

PCR screening of a human genomic P1 library (Genome Systems, Inc., St. Louis, Mo.) was performed using primers based on the reported cDNA sequence of the human α1(IX) collagen chain (Muragaki et al., 1990). Initial PCR screening was performed using oligonucleotide MV-9B3, which has the nucleotide sequence 5'-CTT TCG CTA AGA GAG CCT GTG (SEQ ID NO: 649) and oligonucleotide MV-9R3, which has the nucleotide sequence 5'-GGA CTG AGC ACG CAG CTC TG (SEQ ID NO: 650). One P1 clone was identified which comprised at least a portion of the COL9A1 gene. This clone was designated P1-A and was clone DMC-HFF#1-1378-C8, GS control #5173.

A second screening involved the use of two primer pairs. The first primer pair comprised oligonucleotide PRIM-1, which has the nucleotide sequence 5'-GTT TCT GTG AGC CAG CCT CCT G (SEQ ID NO: 651), and oligonucleotide PRIM-2, which has the sequence 5'-GGC ACA GTG GCC CAC GAT AAG AC (SEQ ID NO: 652). The second primer pair comprised oligonucleotide PRIM-3, which has the nucleotide sequence 5'-TTT ATA TGA GTA TGA AGC AGG CAC (SEQ ID NO: 653), and oligonucleotide PRIM-4, which has the sequence 5'-TCT TGT TTA CCC TTG TGT ATC TAC (SEQ ID NO: 654). PCR screening of the P1 library described herein using these two primer pairs identified a P1 clone which comprised at least of portion of the COL9A1 gene. This clone was designated P1-B and was P1 clone DMPC-HFF#1-837-D10, GS control #13295.

To obtain genomic clones comprising the human COL9A2 gene sequence, PCR screening of a human genomic PAC library (Genome Systems, Inc., St. Louis, Mo.) was performed using a primer pair, the sequences of which were based on published sequences of cDNA encoding the human α2(IX) collagen chain (Perälä et al., 1994, J. Biol. Chem. 269:5064–5071). This primer pair comprised oligonucleotide TP-9, which has the nucleotide sequence 5'-GGC AGC CCA GGT ATT CGT GG (SEQ ID NO: 655) and oligonucleotide TP-10, which has the nucleotide sequence 5'-GCC CTG GTG GCC TGG ACT TC (SEQ ID NO: 656). The screening yielded one positive PAC clone, PAC-39-22G, GS control#6111, herein designated PAC-1.

Characterization of Genomic Clones

In order to increase the yield of DNA, both P1 clones were transferred from E. coli strain NS3529 to E. coli strain NS3516 via phage transduction. Isolation of P1 plasmid DNA and PAC plasmid DNA was done using the method of Birnboim et al. (1979, Nucl. Acids Res. 7:1513–1523). Isolated DNA was dissolved in water and further purified by spot dialysis using water separated from the DNA by a membrane as described elsewhere herein. The COL9A1 and COL9A2 genes were sequenced using primers based on published cDNA sequences of the genes. Additional sequencing primers were based on sequences identified in the experiments described herein.

Nucleotide sequencing was performed by cycle sequencing of P1 and PAC clones using the dsDNA Cycle Sequencing System obtained from Life Technologies, Inc (Gaithersburg, Md.) or the Cycle Sequencing Kit obtained from Pharmacia LKB Biotechnology Inc. (Piscataway, N.J.). Labeling was achieved by either labeling the 5'-end of the primer with T4 polynucleotide kinase (U.S. Biochemical Corp., Cleveland, Ohio) and [γ-$^{33}$P]ATP (Dupont NEN, Wilmington, Del.) or by including [α-$^{35}$S]dATP (Amersham Life Science, Arlington Heights, Ill.) in the sequencing reaction mixture. For cycle sequencing, 0.5 to 2.0 micrograms of P1 or PAC DNA was used as template and thermal cycling was performed using either a GeneAmp™ 9600 (Perkin Elmer Cetus, Norwalk, Conn.) or PTC-225 DNA Engine Tetrad™ (MJ-Research, Inc., Watertown, Mass.) instrument. Some nucleotide sequences were determined by automated sequencing of P1 or PAC DNA using the Dye Terminator Cycle Sequencing Ready Reaction kit and ABI PRISM™ 377 DNA Sequencer (both obtained from Perkin Elmer Cetus, Norwalk, Conn.).

Some intronic sequences for the COL9A1 and COL9A2 genes were PCR amplified and cloned into a pUC 18 vector (SureClone Ligation Kit™, Pharmacia LKB Biotechnology Inc., Piscataway, N.J.). Cloned plasmid DNA was isolated using the Wizard Plus Maxiprep DNA Purification System (Promega Corp., Madison, Wis.), and was sequenced using the dideoxynucleotide sequencing method (Sanger et al., 1977, Proc. Natl. Acad. Sci. USA 74:5463–5467) and T7 DNA polymerase (T7 Sequencing Kit, Pharmacia LKB Biotechnology Inc., Piscataway, N.J.).

The sizes of the longest introns of the COL9A1 gene were determined by PCR amplification of the intron (Expand Long Template PCR System; Boehringer-Mannheim, Indianapolis, Ind.) and by estimation of the size of the intron after agarose gel electrophoresis by comparison to nucleotides of known length. For each intron this was done using at least two forward and two reverse primers in all possible combinations and using the P1 DNA as template. Computerized analysis of all sequences was performed using the Wisconsin Sequence Analysis Package, versions 8.0 and 8.1 for UNIX (Genetics Computer Group, Madison, Wis.).

3'-RACE analyses

To define the 3'-end of the cDNA encoding α1(IX), a RT-PCR was performed. About 0.4 micrograms of total RNA obtained from human fetal cartilage (Baldwin et al., 1989, Biochem. J. 262:521–528) was reverse transcribed using the GeneAmp™ RNA PCR Kit obtained from Perkin Elmer Cetus (Norwalk, Conn.) and an oligo(dT) primer linked to a random sequence, namely 5'-GAC TGA TCA GCG AAT TCT ACG TCG C($T_{20}$) (SEQ ID NO: 657). Single-stranded cDNA was amplified by two sequential PCRs using nested forward primers designed to hybridize to the 3'-end of the cDNA, namely a primer designated RACE-1, which had the sequence 5'-CAG GGC TGG CAG GAA TTC CTG (SEQ ID NO: 658) and a primer designated RACE-2, which had the sequence 5'-AAT TCC TGG AGT GCC TGG AC (SEQ ID NO: 659). The reverse primer used with each of RACE-1 and RACE-2 had a sequence identical to the random sequence at the 5'-end of the oligo(dT) primer. The first PCR was performed in a volume of 25 microliters using 10 picomoles of the reverse primer and 10 picomoles of RACE-1. The PCR was maintained at 95° C. for ninety seconds, and was then subjected to forty cycles as follows: 95° C. for thirty seconds, 62° C. for thirty seconds, and 72° C. for thirty seconds. Two microliters of the reaction mixture was used as template for the second PCR. The reaction volume for the second PCR was 50 microliters, and 20 picomoles of the reverse primer and 20 picomoles of RACE-2 were used. The second PCR was subjected to the same reaction conditions as the first PCR, except that at the annealing temperature was 60° C. instead of 62° C., and that thirty cycles were performed instead of forty.

Agarose gel electrophoretic separation of the products of the second PCR demonstrated the presence of a product having a length of 380 base pairs. Cloning and sequencing of this RT-PCR product revealed a 229-base-pair stretch of 3'-untranslated sequence, followed by a stretch of adenine residues. No polyadenylation signal was detected. Because the signal was not detected, a second RT-PCR was performed as before using a new oligonucleotide, RACE-3, which had the sequence 5'-GGA AGA CAG CAG AGT CAT CAG (SEQ ID NO: 660). The sequence of RACE-3 was based on the sequence located 20 nucleotides in the 5'-direction relative to the stretch of adenine residues.

PCR was performed in a volume of 25 microliters using 10 picomoles of the reverse primer described herein and 10 picomoles of RACE-3. The PCR was maintained at 95° C. for ninety seconds, and was then subjected to forty cycles as follows: 95° C. for thirty seconds, 60° C. for thirty seconds, and 72° C. for ninety seconds. In addition to the expected 50-base-pair-length product derived by amplification of the intragenic stretch of adenine residues, another product having a length of about 200 nucleotides was detected. This RT-PCR product was cloned and the sequence was determined.

Cloning and Sequencing of the Murine COL9A 1 Gene

Genomic DNA was isolated from murine liver, as described (Ausubel et al., 1989, In: Current Protocols in Molecular Biology, Wiley, New York, Vol. 1, pp. 2.2.1–2.2.3) and 200 nanograms of this DNA was used as a template for PCR amplification of the sequences of exon 6, the alternative promoter, and exon 7 of the murine COL9A1 gene. The PCR was performed in a reaction volume of 50 microliters using 10 picomoles of primer M6F, which had the nucleotide sequence 5'-AGT TTG AAC TCC AGT GGG TGC (SEQ ID NO: 661), and 10 picomoles of M7R, which had the nucleotide sequence 5'-ACC TCA TCA GTG GTC TGG CTG (SEQ ID NO: 662). The sequences of primers M6F and M7R were based on published sequences of exons 6 and 7, respectively, of the murine COL9A1 gene (Muragaki et al., 1990, Eur. J. Biochem. 192:703–708). The PCR was maintained at 94.5° C. for ninety seconds, and was then subjected to 33 cycles as follows: 94.5° C. for thirty seconds, 60° C. for thirty seconds, and 72° C. for seventy-five seconds. The PCR product was cloned into a pUC18 vector and sequenced. The sequence for this portion of the murine COL9A 1 gene has been described in the literature.

The results obtained in the experiments of this Example are now described.

Characterization of Genomic Clones

Figure 8A:
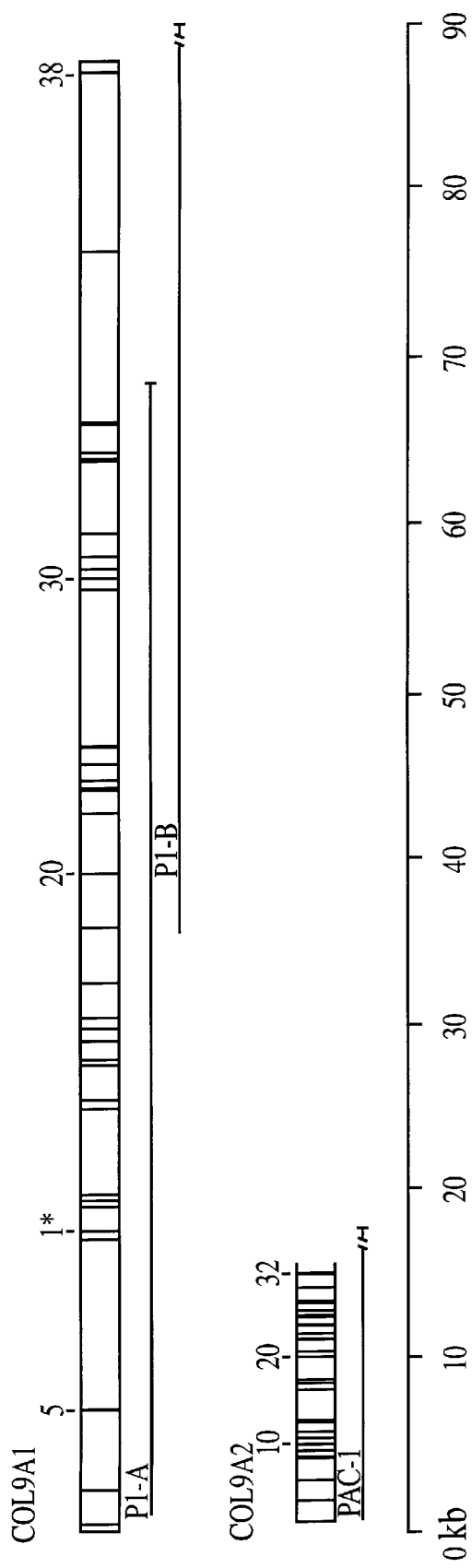
FIGS. 8A and 8B, depicts schematic representations of the human COL9A1 and COL9A2 genes and the gene products thereof.

PCR screening of a human P1 library for clones comprising at least a portion of the human COL9A1 gene sequence yielded two positive clones, P1-A and P1-B, which are schematically depicted in FIG. 8A. Clone P1-A comprised the 5'-end of the gene and extended in the 3'-direction therefrom beyond intron 36. Clone P1-B comprised the 3'-end of the gene and extended in the 5'-direction therefrom beyond intron 18. PCR screening of a human PAC library for clones comprising at least a portion of the human COL9A2 gene sequence identified one positive clone, PAC-1, which is schematically depicted in FIG. 8A. Clone PAC-1 comprised the entire coding sequence for the gene.

Genomic Structure and Domain Organization of the Human COL9A1 and COL9A2 Genes

The exon boundaries of the COL9A1 and COL9A2 genes were defined by nucleotide sequencing using primers based on corresponding cDNA sequences. The sizes of several large introns of the COL9A1 gene were also defined by PCR amplification and subsequent agarose gel electrophoresis. It was determined that the COL9A1 gene spans about 90 kb and comprises thirty-eight exons. The complete genomic organization and sequence were defined for the COL9A2 gene. It was determined that the gene is considerably more compact than the COL9A1 gene, in that it spans only about 15 kb even though it comprises thirty-two exons. The relative sizes of the introns and exons of the COL9A1 and COL9A2 genes are diagrammatically listed in FIG. 8A.

Figure 8B:
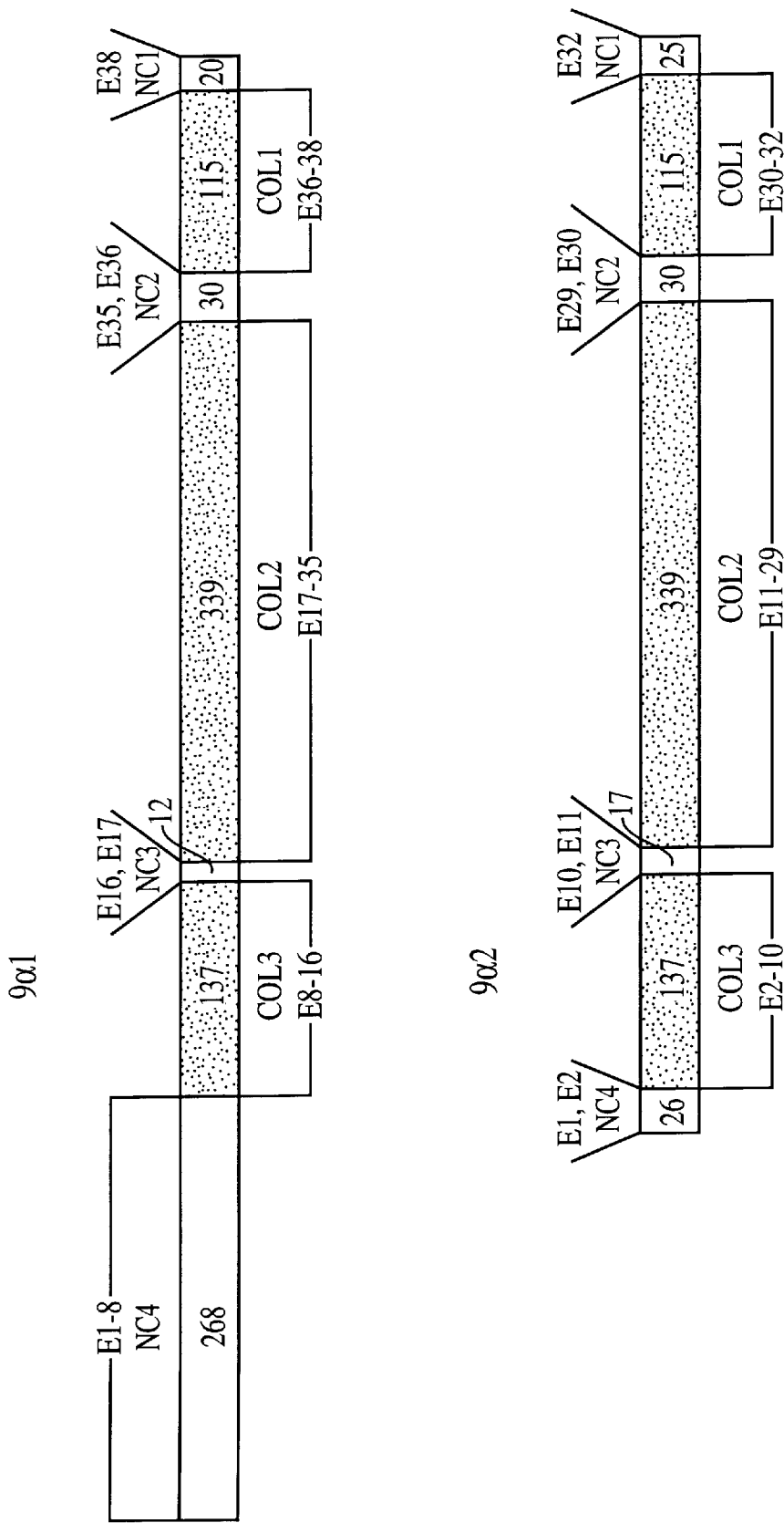

Because COL9A1 and COL9A2 encode the α1(IX) and α2(IX) chains of Type IX collagen, it was not surprising that the exon organization of these genes was identical except for the exons coding for NC4 domain, as schematically listed in FIG. 8B. The NC4 domain comprises the cartilage-specific domain of the α1(IX) collagen chain. Exon 16 of the COL9A1 gene is 33 base pairs in length, whereas the corresponding exon 10 of the COL9A2 gene is 48 base pairs in length. This difference of 15 base pairs explains the presence of five additional amino acids in the NC3 domain of the proα1(XI) chain, relative to the NC3 domain of the proα2(IX) chain.

The intron sizes of the two genes are markedly different, as schematically listed in FIG. 8A. The longest intron in the COL9A2 gene is intron 16 and has a length of 1,690 base pairs. Also, only five introns of COL9A2 are over 1,000 base pairs in length. In contrast, there are nineteen introns that are over 1,000 base pairs in length in the COL9A1 gene. Furthermore, three of the introns of the COL9A1 gene are about 10,000 base pairs in length. The largest introns of the two genes are not located in the 5'-end of the genes, as they are in the genes encoding fibrillar collagen (Ala-Kokko et al., 1995, Biochem. J. 308:923–929).

Comparison of the Human COL9A1 Gene with the Chicken, Murine, and Rat COL9A1 Genes The gene encoding the α1(IX) chain in chicken is about 100 kilobases in length (Ninomiya et al., 1990, In *Extracellular Matrix Genes*, Sandell et al., eds., Academic press, San Diego, pp. 79–114), and is similar in size to the human gene. However, the chicken gene has been only partially characterized, in that the sizes of only the first seventeen and the last two exons are known (Lozano et al., 1985, Proc. Natl. Acad. Sci. USA 82:4050–4054; Vasios et al., 1988, J. Biol. Chem. 263:2324–2329; Ninomiya et al., 1990, In *Extracellular Matrix Genes*, Sandell et al., eds., Academic press, San Diego, pp. 79–114). The sizes of the defined exons are the same in the chicken and human genes with two exceptions. Exon 6 is 78 base pairs in length in the chicken gene and 84 base pairs in length in the human gene (Ninomiya et al., 1990, In *Extracellular Matrix Genes*, Sandell et al., eds., Academic press, San Diego, pp. 79–114). The last (i.e. 3'-most) exon is about 1,000 base pairs in length in the chicken gene and about 550 base pairs in length in the human gene because of a difference in the lengths of the 3'-untranslated regions thereof.

Figure 14:
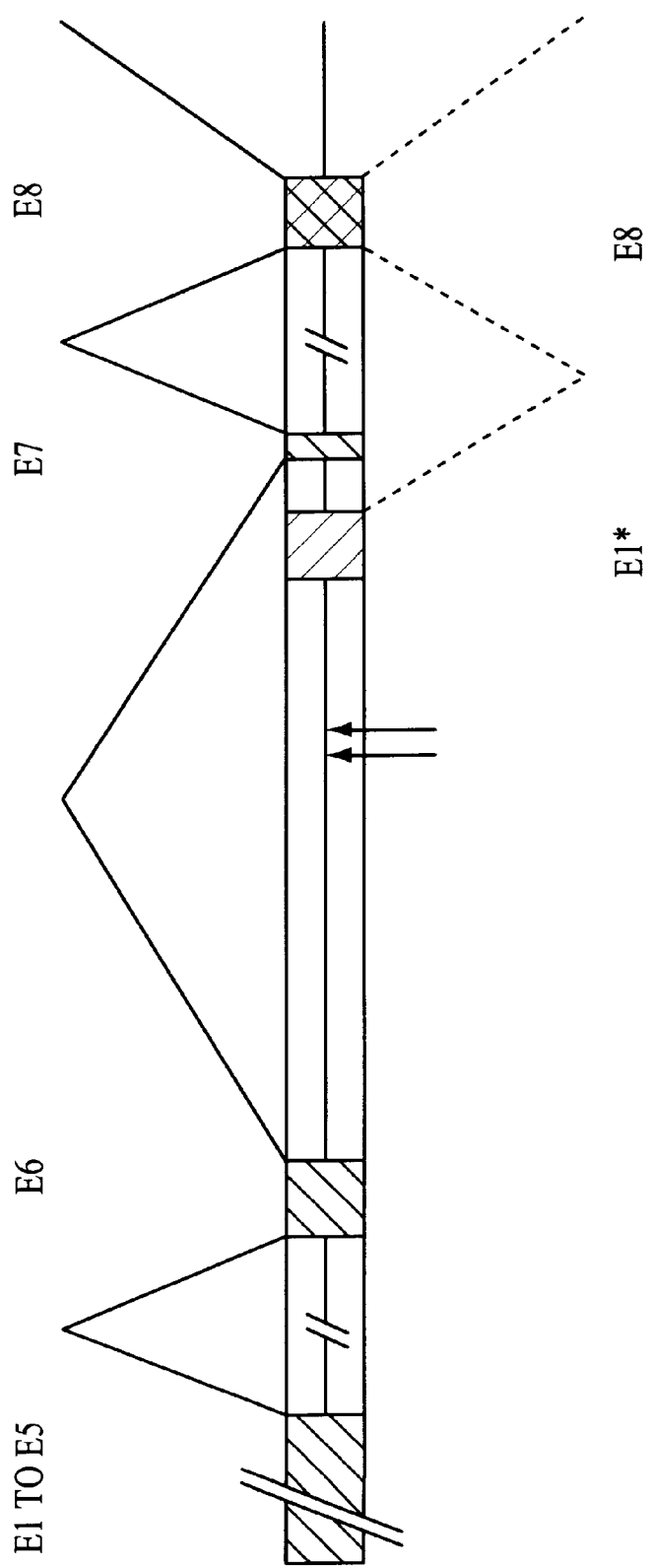
Figure 16:
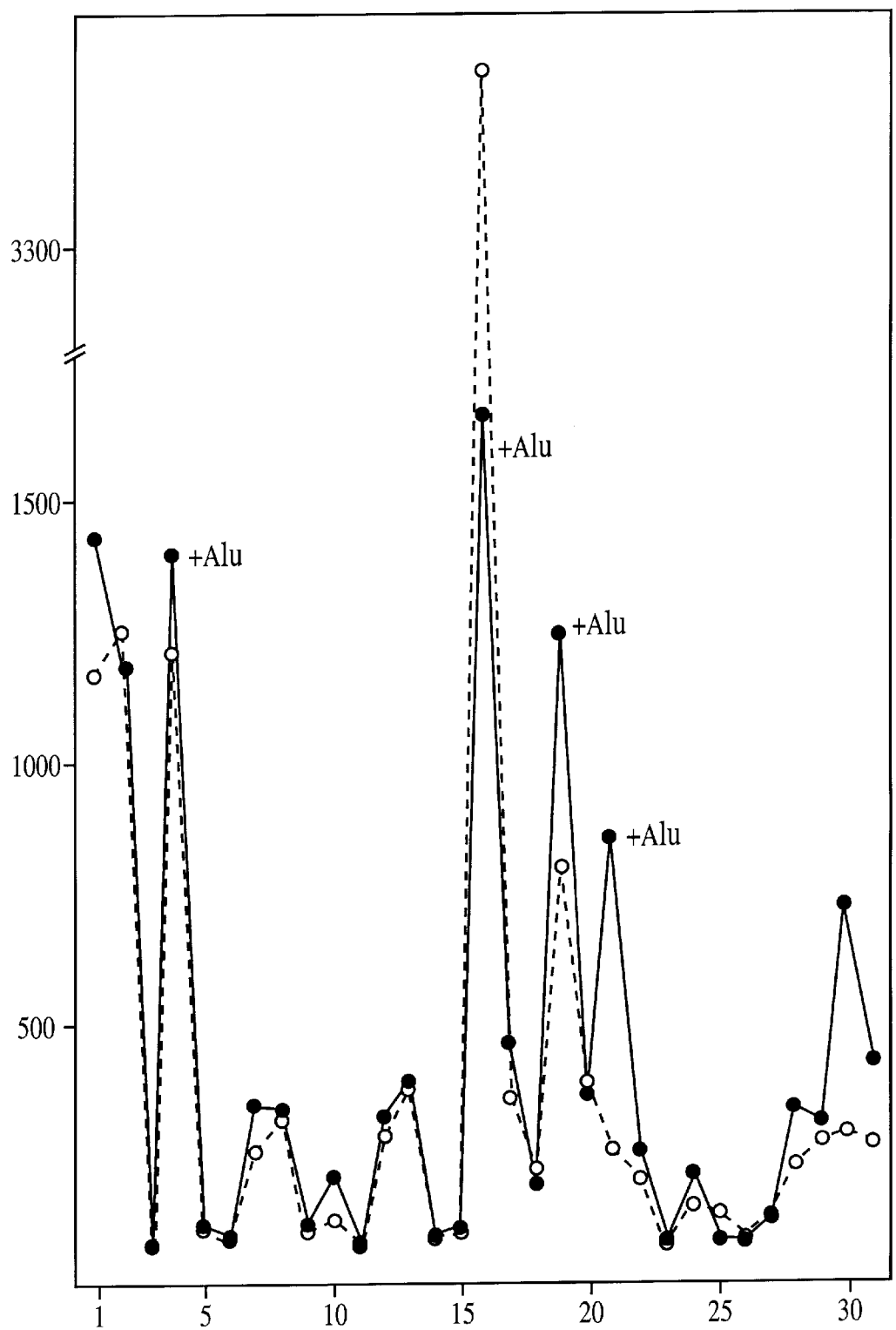

The alternative transcript of the COL9A1 gene is initiated in intron 6 thereof, as depicted in FIG. 14. The size of intron 6 is similar in the chicken and human genes, 663 and 820 base pairs, respectively, as indicated in Table 5.

TABLE 5

Comparison of the Lengths of COL9A1 Gene Segments

| Gene Segment[a] | Species | | | |
|---|---|---|---|---|
| | Human | Mouse | Chicken | Rat[b] |
| Exon 6 | 84 | 84 | 78 | ND |
| Intron 6 | 820 | 799 | 663 | ND |
| 5'-E6 → E1* | 686 | 662 | 549 | ND |
| Exon 1* | 72 | 78 | 72 | 78 |
| 5'-I1* → E7 | 62 | 59 | 42 | 57 |

[a]Abbreviations used: "5'-E6 → E1*" means the distance from the 5'-end of Exon 6 to Exon 1*
"5'-I1* → E7" means the distance from the 5'-end of Intron 1* to Exon 7
[b]"ND" means not determined.

To extend the comparison of COL9A1 gene sequences, intron 6 of the mouse gene was sequenced. The size of intron 6 in the mouse gene was 799 base pairs, and was similar to the intron size in the human and chicken genes. The nucleotide sequences from the 5'-end of intron 6 to the start of translation of the alternative exon 1* were compared in the human, chicken, and mouse genes. The sizes of these sequences were 685, 549, and 612 base pairs, respectively, in the human, chicken, and murine genes, as depicted in FIG. 15 and in Table 5). In addition to conserved size, the human, chicken, and murine sequences were also conserved, in that there was 72% sequence identity between the human and murine sequences, 65% sequence identity between the human and the chicken sequences, and 65% sequence identity between the mouse and the chick sequences. Because the cornea-specific transcription start site of the chicken gene is located 13 to 20 nucleotides downstream of a TAATAA box and 41 nucleotides downstream of a CCAAT box (Nishimura et al., 1989, J. Biol. Chem. 264:20033–20041), the analogous regions were analyzed for the presence of these sequences in the human and murine genes. The TAATAA and CCAAT sequences and their locations were conserved among the chicken, human, and murine genes, as depicted in FIG. 15. Thus, a COL9A1 cornea-specific promoter was identified in the human gene. The alternative start site in exon 1* of the human gene was similar to the alternative start site in exon 1* of the chicken gene.

Short sequences separated the 3'-end of exon 1 from the 5'-end of exon 7 in the COL9A1 genes of the various species. The length of this separation was 62 base pairs in the human gene, 48 base pairs in the chicken gene, 58 base pairs in the murine gene, and 57 base pairs in the rat gene. Among these genes, the distance separating the 3' end of exon 1* and the 5'-end of exon 7 was consistently less than 70 bp, the minimum size observed for any intron sequence (Fu et al., 1988, Mol. Cell. Biol. 8:3582–3590). The short size of this nucleotide sequence probably explains why splicing of RNA transcripts that begin in exon 1* occurs between the 3' end of exon 1* and the 5'-end of exon 8 in the cornea.

Although the human COL9A1 and COL9A2 genes encode similar chains of a single protein, they differ in size by a factor of about six. The difference in size is accounted for by much larger introns in the 90 kilobase COL9A1 gene. The comparison of the mouse and human COL9A2 genes demonstrated that the intron sizes are conserved to a high degree in the genes of the two species. Three introns that are larger in the human sequence are probably larger because of Alu sequence insertions. However, intron 16 in the mouse gene is twice the size of the corresponding human intron, even though the human intron comprises an Alu sequence.

In addition to providing information on conservation of gene structures, the results described herein provide a basis for identifying mutations in the COL9A1 and COL9A2 genes that are associated with human disorders including, but not limited to, multiple epiphyseal dysplasia (MED), osteoarthritis, and early onset osteoarthritis. Recent results demonstrate that mutations in the COL9A2 gene are associated with MED. Also, experiments in transgenic mice demonstrate that mutations in the COL9A1 gene can produce cartilage degeneration similar to osteoarthritis.

Example 6

PCR/CSGE Analysis of the COL9A3 Gene Using Intronic Primers

In this Example, the complete nucleic acid sequence of the human COL9A3 gene is described. Primers useful for PCR/CSGE analysis of the genes are also described. PCR/CSGE screening methods have been described elsewhere herein. Sequences of the non-coding regions of COL9A3 are reported herein for the first time. Two unrelated families having different nine base pair deletions in the same region of the COL1 domain of the COL9A3 gene are also described, wherein the deletions comprise neutral variants of the COL9A3 gene.

The materials and methods used in this Example are now described.

Isolation of Phage and P1 Clones for the Human COL9A3 Gene

Sequences of the human COL9A3 gene in phages and plasmids of human genomic libraries were identified by PCR amplification using primer pairs having sequences based on published cDNA sequences encoding human α3(IX) and on murine COL9A2 gene sequences (Brewton et al., 1995, Genomics 30:329–336; Perälä et al., 1994, J. Biol. Chem. 269:5064–5071). The COL9A3 gene was amplified using a primer pair comprising an oligonucleotide designated C93-F4, which has the nucleotide sequence 5'-CAG GAA AGC CGG GGA AAC CAG (SEQ ID NO: 663), corresponding the sequence of nucleotides 200 to 220 numbered in the 3'-direction relative to the translation start site identified in the human cDNA, and a second oligonucleotide designated C93-R5, which has the nucleotide sequence 5'-GTC CAT CTC GTC CAG TCA GAC (SEQ ID NO: 664), corresponding to the sequence of nucleotides 277 to 257 numbered in the 3'-direction relative to the translation start site. Sequences at the 3'-end of the COL9A3 gene were amplified using a pair of primers comprising an oligonucleotide designated C93-F32, which has the nucleotide sequence 5'-CCT GCC AAG GAG CCG TGT TAG G (SEQ ID NO: 665), corresponding to nucleotides 1997 to 2018 numbered in the 3'-direction relative to the translation start site and a second oligonucleotide designated C93-RUTR, which has the nucleotide sequence 5'-CCT TTT GAG GTA TGC TGT CAG GC (SEQ ID NO: 666), corresponding to nucleotides 2249 to 2227 numbered in the 3'-direction relative to the translation start site. The nucleotide sequences of primers C93-F4 and C93-R5 corresponded to sequences in exons 4 and 5, respectively, of cDNA derived from the human COL9A3 gene. The nucleotide sequences of primers C93-F32 and C93-RUTR corresponded to sequences in exon 32 of the murine COL9A2 gene.

PCR amplification was performed in a 40 microliter reaction volume comprising between about 50 and 100 nanograms of genomic DNA, 0.25 mM of each of the two primers, 200 micromolar of each dNTP, 1.5 millimolar $MgCl_2$, and 1 unit of Taq polymerase (AmpliTaq™, Perkin Elmer Cetus, Norwalk, Conn.). The PCR was subjected to thirty cycles as follows: 94° C. for one minute, 60° C. for one minute, and 72° C. for one minute. Amplification products exhibited single bands following agarose gel electrophoretic separation thereof. The amplification product made using primers C93-F4 and C93-R5 had a length of about 700 base pairs, and the amplification product made using primers C93-32F and C93-RUTR had a length of about 250 base pairs. These two amplification products were used for screening of human P1 library (Genome Systems, Inc.) to identify clones comprising at least a portion of the human COL9A3 gene. Screening of the library resulted in identification of three positive P1 clones designated P1-C93A, P1-C93B and, P1-C93C (having GS control numbers 12269, 12270, and 12271 and clone addresses DMPC-HFF#1-270-C3, DMPC-HFF#1-753-B10 and DMPC-HFF#1-1082-B5, respectively).

Characterization of P1 Clones

P1 DNA was isolated by culturing bacterial cells comprising a P1 clone overnight in 3 milliliters of Luria Broth (LB) comprising 25 μg/ml kanamycin. A 2.5 milliliter aliquot of the overnight culture was used to inoculate 75 milliliters of LB. After ninety minutes of incubation, isopropyl β-D-thiogalactopyranoside (IPTG) was added to a final concentration of 0.5 mM and the cells were incubated for an additional five hours. Cells were harvested by centrifugation of 10 milliliter aliquots of culture medium at 10,000×g for ten minutes. P1 DNA was isolated from harvested cells using a standard plasmid isolation protocol (Birnboim et al., 1979, Nucl. Acids Res. 7:1513–1523).

P1 clone DNA was sequenced by a cycle sequencing method using a Cycle Sequencing Kit supplied by Pharmacia LKB Biotechnology Inc. (Piscataway, N.J.). Sequences of the primers used for the sequencing method were based on published cDNA nucleotide sequences encoding human α3(IX) protein (Brewton et al., 1995, Genomics 30:329–336) or the nucleotide sequence of the murine COL9A2 gene (Perälä et al., 1994, J. Biol. Chem. 269:5064–5071). The introns between exons 10 and 11, between exons 12 and 13, between exons 26 and 27, and between exons 31 and 32 were amplified using an Expand Long Template PCR System kit supplied by Boehringer Mannheim (Indianapolis, Ind.). PCR products were purified using a commercial agarose gel extraction kit (QIAEX™ II Gel Extraction Kit, Qiagen, Chatsworth, Calif.), cloned into pUC18 vectors using the SureClone™ Ligation Kit supplied by Pharmacia LKB Biotechnology Inc. (Piscataway, N.J.), and sequenced using a T7 Sequencing Kit supplied by Pharmacia LKB Biotechnology Inc. (Piscataway, N.J.). Oligonucleotides produced during the sequencing reactions were separated using a 6% (w/v) polyacrylamide gel.

PCR/CSGE Mutation Analysis

PCR primers having nucleotide sequences derived from the nucleotide sequences of the introns of the human COL9A3 gene were used to amplify each exon, the 5'-untranslated region, and the 3'-untranslated region thereof. Primers were selected such that the length of each of the amplified sequences was between about 200 and about 400 base pairs. Each amplified sequence included at least 80 intron-encoded nucleotides, including a segment derived from the intron located at the 5'-end and a segment derived from the intron located at the 3'-end of the amplified exon sequence. Genomic DNA obtained from individual subjects was PCR-amplified in a 40 microliter reaction volume by subjecting the PCR to thirty cycles as follows: 94° C. for forty-five seconds, 60–62° C. for forty-five seconds, and 72° C. for one minute. Following amplification, the PCR products were maintained at 72° C. for ten minutes, denatured at 95° C. for five minutes, and reannealed at 68° C. for thirty minutes. Using this method, heteroduplexes were formed in PCR mixtures comprising genomic sequences having non-identical alleles of COL9A3.

PCR amplification products were analyzed by CSGE, as described, except that taurine buffer was not autoclaved (Ganguly et al., 1993, Proc. Natl. Acad. Sci. USA 90:10325–10329). The concentration and quality of amplification products was estimated analyzing 5 microliters of each product by gel electrophoresis using a 1.5% (w/v) agarose gel.

Each CSGE gel comprised 10% (w/v) polyacrylamide, wherein the ratio of acrylamide (Intermountain Scientific, Kaysville, Utah) to 1,4 bis(acryloyl)piperazine (BAP, Fluka, Ronkonkoma, N.Y.) was 99:1, 10% (v/v) ethylene glycol (Sigma Chemical Company, St. Louis, Mo.), 15% (v/v) formamide (Gibco, Grand Island, N.Y.), 0.1% (w/v) ammonium persulfate (U.S. Biochemical Corp., Cleveland, Ohio), 0.07% (v/v) TEMED (Sigma Chemical Company, St. Louis, Mo.), and 0.5×TTE buffer (which comprised 44 millimolar Tris, 14.5 millimolar Taurine, and 0.1 millimolar EDTA at pH 9.0). Electrophoresis was performed using a standard DNA sequencing apparatus and 0.5×TTE buffer as the electrode buffer. Prior to electrophoresis, between 3 and 15 microliters of an amplification product, comprising between about 25 and about 75 nanograms of DNA, was mixed with loading buffer to achieve final concentrations of 3% (v/v) glycerol, 0.025% (w/v) xylene cyanole FF, and 0.025% (w/v) bromphenol blue. Prior to loading the gel, electrical current was applied to the gel at a rate of 45 Watts for fifteen minutes. After loading, electrical current was applied to the gel at a rate of 45 Watts for five hours, the gel being maintained at room temperature throughout the procedure. Following electrophoresis, the gel was stained with ethidium bromide. Amplification products which were identified as containing heteroduplexes were analyzed by direct PCR sequencing using a T7 Sequenase PCR Product Sequencing Kit supplied by U.S. Biochemical Corp. (Cleveland, Ohio). PCR products were purified from agarose using a commercial kit (QIAEX™ II Gel Extraction Kit, Qiagen, Chatsworth, Calif.). PCR products were sequenced following cloning of about 60 nanograms of the purified product into a pUC18 vector, using the SureClone™ Ligation Kit supplied by Pharmacia LKB Biotechnology Inc. (Piscataway, N.J.). Several clones corresponding to each observed heteroduplex were sequenced to identify sequences for both alleles.

The results of the experiments presented in this Example are now described.

Characterization of genomic clones

Figure 9:
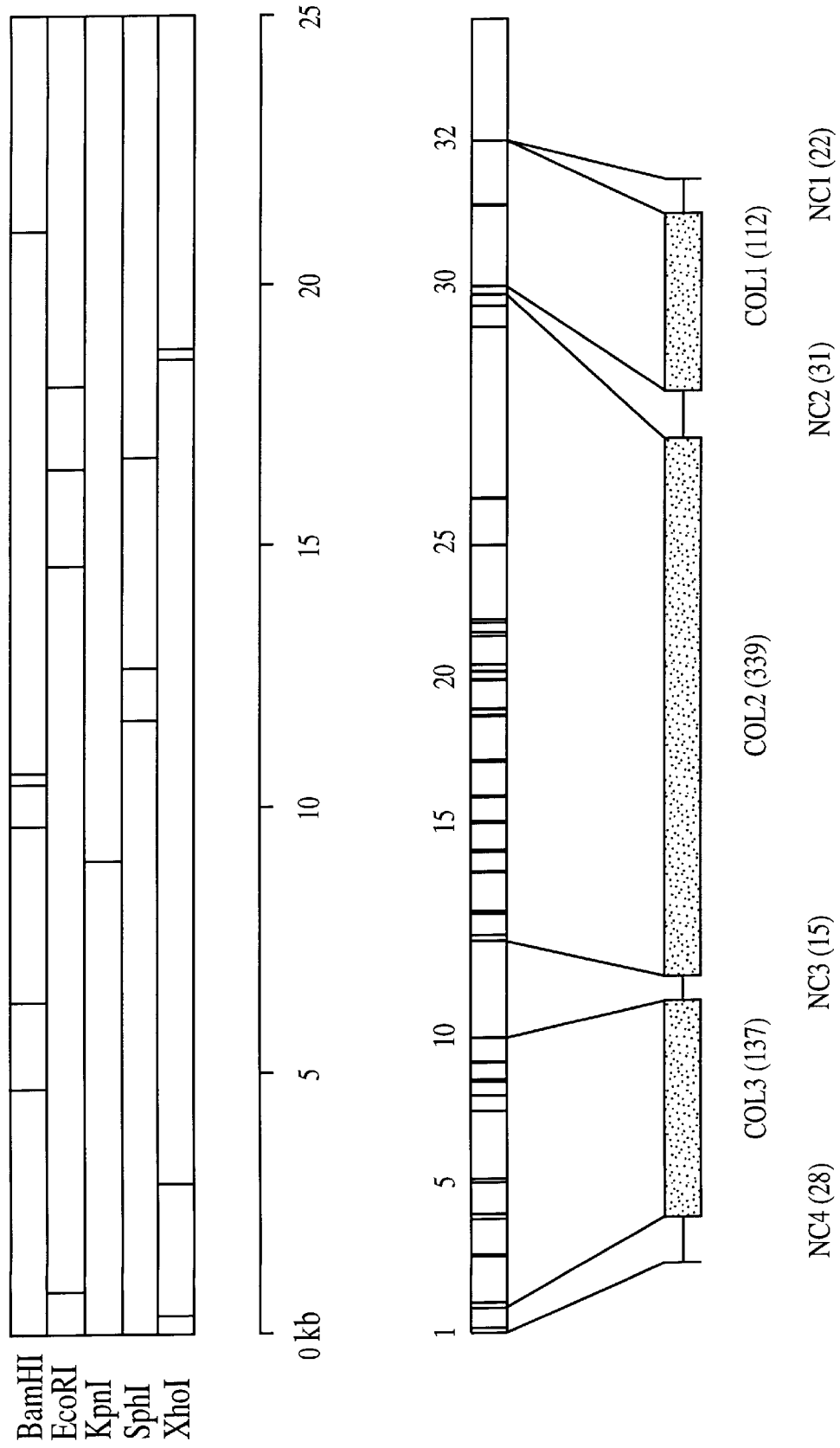

Screening of the human P1 library with the two PCR primer pairs designed to amplify the 5'-end and the 3'-end of the human COL9A3 gene identified three P1 clones, each of which comprised sequences corresponding to both ends of the gene. Thus, all three clones comprised the entire coding region of COL9A3. Clone P1-C93A was selected for detailed characterization of the gene. Nucleotide sequencing of the human COL9A3 gene was performed by direct sequencing of clone P1-C93A or by sequencing of plasmids comprising subclones thereof. Over 27 kilobases of nucleotide sequence was identified, and the results indicated that the COL9A3 gene has a length of about 24 kilobases and contains thirty-two exons, as depicted in FIG. 9). The nucleotide sequence of more than 3 kilobases of the untranslated region adjacent the 5'-end of the gene was identified. Restriction endonuclease sites in this region are depicted in FIG. 9.

Exon Organization and Domain Structure

The genomic structure of the human COL9A3 gene is depicted in FIGS. 9 and 12. The exon organization of the COL9A3 gene was compared with the exon organization of the murine gene encoding the α2 chain of Type IX collagen (Perälä et al., 1994, J. Biol. Chem. 269:5064–5071). The overall exon organization of these two genes exhibited considerable similarities. There were some unexpected differences in the lengths of the exons encoding the COL3 domain of each of the proteins, even though the size of the domain is identical in these genes. The COL3 domain comprises 137 amino acids in each of the two proteins, and is thus encoded by a sequence comprising 411 nucleotides. This domain is encoded by exons 2 through 10 in both genes. Also, in both genes, exon 2 encodes the junction between the NC4 and COL3 domains of the chain.

Figure 17:
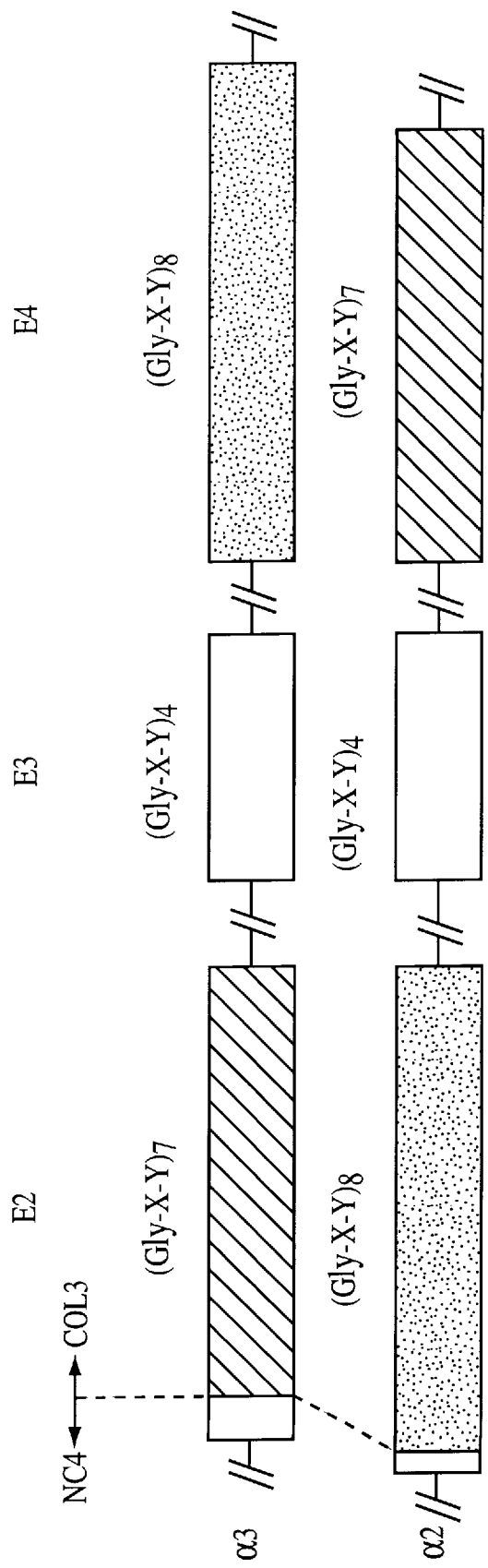

It was discovered that exon 2 of the human COL9A3 gene encodes one fewer collagen Gly-X-Y triplet than exon 2 of the murine COL9A2 gene. Nonetheless, the COL3 domains of the two proteins remain identical, because exon 4 of the human COL9A3 gene encodes one more collagen Gly-X-Y triplet than does exon 4 of the murine COL9A2 gene, as depicted in FIG. 17. In effect, deletion of nine nucleotides encoding one Gly-X-Y triplet from exon 2 of the human COL9A3 gene is compensated for by insertion of nine nucleotides encoding an additional Gly-X-Y triplet in exon 4.

Non-Coding Regions

The lengths of the introns of the human COL9A3 gene vary from 84 nucleotides to more than 3,000 nucleotides, as depicted in FIG. 12. Six of these introns are more than 1,000 nucleotides in length. The largest intron, intron 26, has a length of about 3,000 nucleotides, which can be explained in part by the observation that the intron comprises two Alu-repeats. In contrast to the murine COL9A2 gene and each of the genes encoding fibrillar collagen proteins which have been characterized to date, the first intron of the human COL9A3 gene is relatively small, and the large introns are located mostly in the 3'-end of the gene (Ala-Kokko, 1995, Biochem. J. 308:923–929).

Mutation Screening

A subject who was afflicted with MED and who was a member of a first family was examined to determine whether the subject's COL9A3 gene comprised an MED-causing mutation. The exons and flanking sequences of the subject's COL9A3 gene were amplified by PCR, and the amplification products were analyzed for the presence of heteroduplexes using CSGE analysis, as described herein.

Several neutral polymorphisms and one potential disease-causing mutation were identified. The potential disease-causing mutation was located in exon 30. Sequencing of the amplification product corresponding to exon 30 and the flanking sequences thereof indicated the presence of a nine nucleotide deletion in the exon, which caused a deletion in a Gly-Pro-Pro triplet in the 5'-end of the COL1 domain of the α3(IX) chain in the subject's DNA.

Figure 18A:
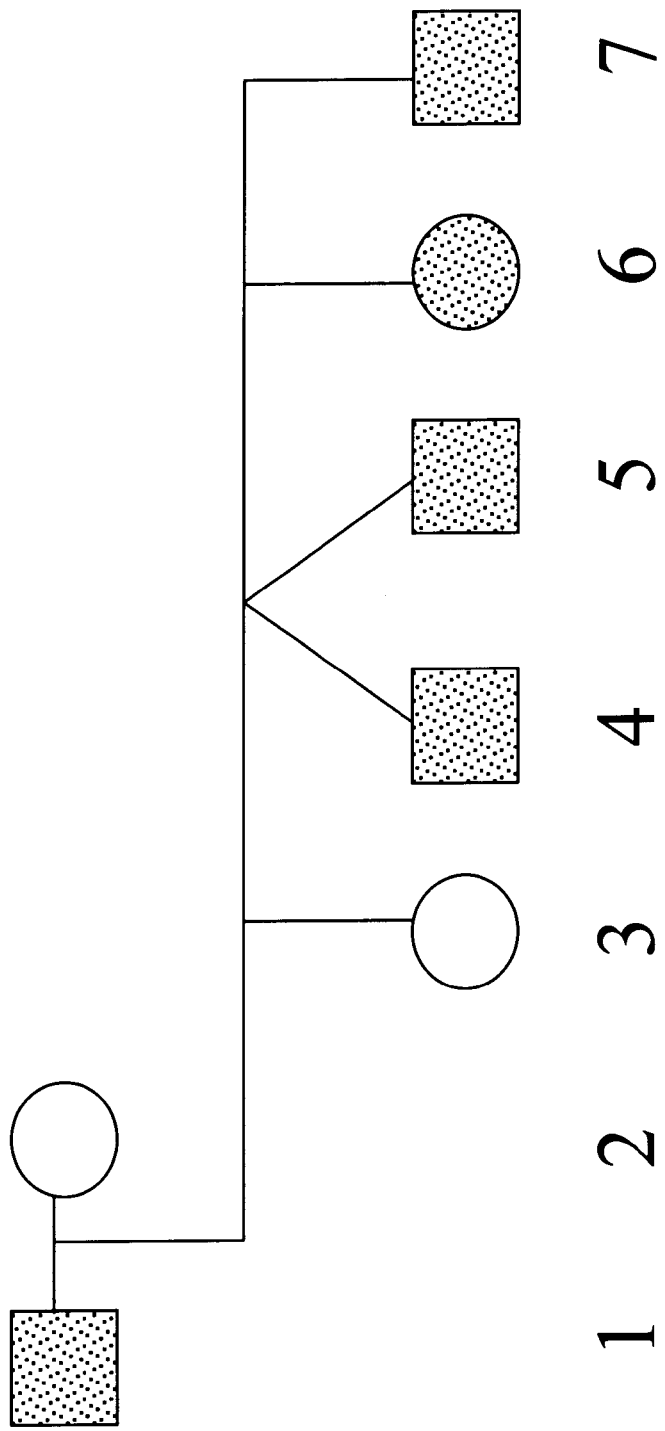
FIGS. 18A and 18B, depicts the results of CSGE analysis of exon 30 of the COL9A3 gene obtained from seven subjects from an MED-affected family. Affected family members are indicated by shaded symbols. Round symbols indicate female subjects and square symbols indicate male subjects. The five subjects shown below the other two subjects are the offspring of the two subjects. The pair of male subjects connected by a 'V'-shaped line are twins. Corresponding symbols and CSGE results are numbered identically in FIGS. 18A and 18B.
Figure 18B:

Other members of the first family were examined for the presence of the mutation. As depicted in FIG. 18, the COL9A3 genes of three affected members of the first family exhibited the deletion. However, the mutation was not demonstrated to be the sole or sufficient cause of the MED symptoms in the subjects. The COL9A3 gene of one unaffected member of the first family exhibited the deletion; furthermore, the COL9A3 genes of identical twins that were affected did not have the deletion. Hence, the deletion in the COL9A3 gene and the MED phenotype did not exclusively co-segregate in the first family.

The nucleotide sequence of the deleted region identified in the first family, which is depicted in FIG. 19 as "Del A1," indicated that the deletion occurred in a repetitive GC-rich region. Because of the repetitiveness of the sequences, the deletion could have occurred at either of two different sites. The nucleotide sequence of the deleted region in the second family also consisted of nine nucleotides of the COL9A3 gene which encoded a Gly-Pro-Pro triplet in the 5'-end of the COL1 domain. The deleted sequence in the second family was different from the deleted sequence in the first family, as depicted in FIG. 19 as "Del A2."

Because the three α chains of the type (IX) collagen triple helix must be of the same length and in register, the observation that different nine nucleotide deletions encoding a Gly-X-Y triplet occurred in two unrelated MED-affected individuals suggested that the deletions were associated with the disease state of the individuals. However, examination of affected and unaffected members of the family indicated there was no co-inheritance of the deletion with the disease phenotype. Therefore, the deletion must be a neutral variant of the COL9A3 gene. In Type IX collagen protein encoded by this variant, the protein apparently retains its normal function, even though each of the two the deletions shorten the COL1 domain of the α3(IX) chain, such that it lacks a Gly-X-Y triplet found in each of the α1(IX) and α2(IX) chains. It appears sufficient for normal Type IX collagen function that the three chains retain a continuous sequence of four or five Gly-X-Hyp or Gly-Pro-Hyp at the ends of the COL1 domain (Fertala et al. 1993, Biochem. J. 289:195–199; Westerhausen et al., 1990, J. Biol. Chem. 265:13995–14000).

Fibrillar collagens have been used as prototype proteins to study chain association and triple helix formation in collagens. According to the presently-understood model, the carboxyl-terminal propeptides of the three α chains of a collagen molecule associate and form intramolecular disulfide-bonded trimers. Formation of bonded trimers ensures correct registration of the α chains. Following disulfide bond formation, helix formation progresses in the direction from the carboxyl terminus toward the amino terminus of the collagen protein or region.

Figure 20:
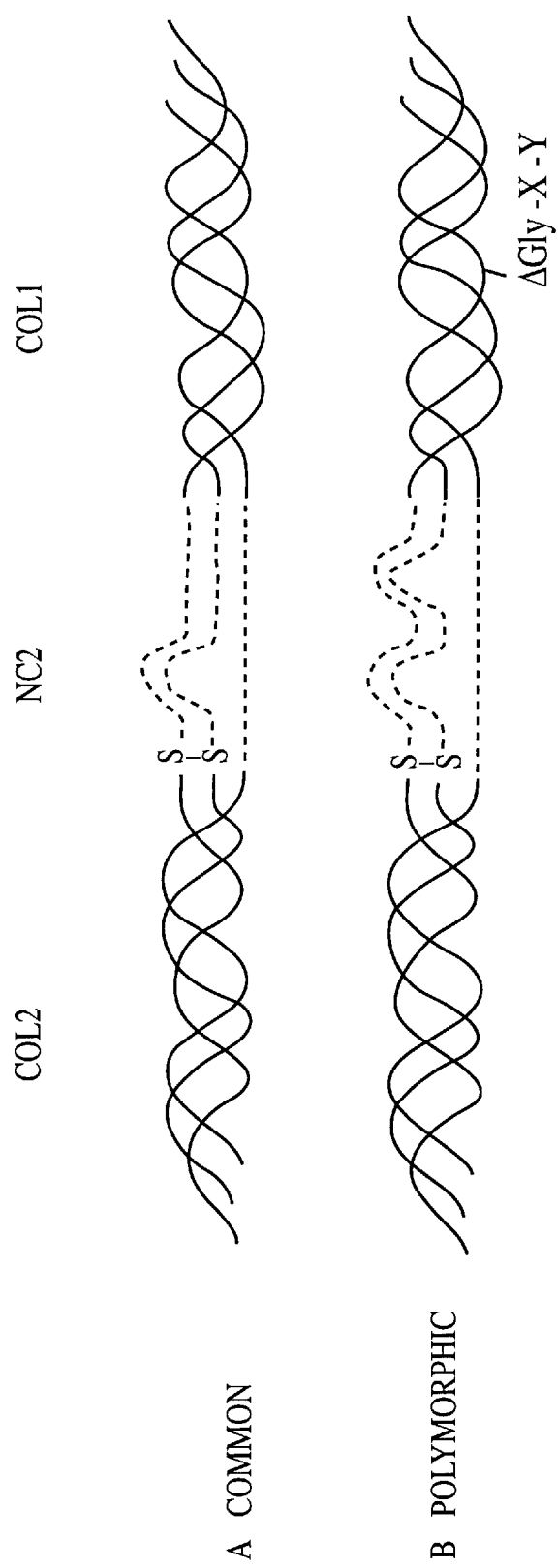

It has been demonstrated that the carboxyl terminal propeptides of fibrillar collagens contain all the information necessary for correct chain selection and association (Engel et al., 1991, Annu. Rev. Biophys. Biophys. Chem. 20:137–152). It has also been demonstrated that synthetic peptides comprising the entire NC1 domain and the carboxyl-terminal end of the COL1 domain each of the three α chains of Type IX collagen contain all the information necessary for chain selection and assembly (Mechling et al., 1996, J. Biol. Chem. 271:13781–13785). The correct assembly of collagen α chains is critical for biosynthesis of functional Type IX collagen because formation of the triple helix progresses in a zipper-like fashion. In FACIT collagens, non-triple helical domains such as the NC2 region of Type IX collagen may have a role in aligning Gly-X-Y sequences so that they can assume a triple helical conformation, as depicted in FIG. 20.

Oligonucleotide probes and primers may be labeled with a detectable label, using any labeling method known in the art, preferably using a radiolabel such as $^{32}$P. By way of example, oligonucleotides may be labeled with $^{32}$P using standard methods, such as treatment of an oligonucleotide with γ-$^{32}$P-ATP and $T_4$ polynucleotide kinase according to known methods (see, e.g. Sambrook, et al., 1989, In: *Molecular Cloning: A Laboratory Manual*, Cold Spring Harbor Laboratory, New York). Further by way of example, non-radiolabeled probes comprising biotinylated nucleotides introduced during oligonucleotide synthesis may also be used. Detection of biotinylated nucleotides may be accomplished by streptavidin and antibody-linked enzymes which generate a color reaction using, for example, the Genius™ system (Boehringer Mannheim Biochemicals, Indianapolis, Ind.).

Polymerase chain reaction (PCR) methods, as used herein, are described, for example, in U.S. Pat. No. 4,683,195 to Mullis et al., in U.S. Pat. No. 4,683,202 to Mullis, and in Innis et al., ed., 1990, In: *PCR Protocols*, Academic Press, Inc., San Diego. PCR primer and DNA probe labeling methods are described, for example, in U.S. Pat. No. 4,822,731 to Watson et al.

The disclosures of each and every patent, patent application, and publication cited herein are hereby incorporated herein by reference in their entirety.

Methods which were used but not described herein are well known and within the competence of one of ordinary skill in the art of molecular biology.

While this invention has been disclosed with reference to specific embodiments, it is apparent that other embodiments and variations of this invention may be devised by others skilled in the art without departing from the true spirit and scope of the invention. The appended claims are intended to be construed to include all such equivalent variations.

What is claimed is:

1. A method of detecting a collagen gene alteration associated with a pathological condition in a human subject, the method comprising obtaining from the subject a sample nucleic acid comprising a portion which consists of at least fifteen consecutive nucleotides of a segment of the gene, wherein the portion comprises at least one intronic nucleotide, a first site, and a second site;

determining the nucleotide sequence of the portion; and comparing the nucleotide sequence of the portion with the corresponding consensus nucleotide sequence of the gene, whereby a difference between the nucleotide sequence of the portion and the corresponding consensus nucleotide sequence indicates the presence of the collagen gene alteration in the subject, wherein the segment is the segment of the COL1A1 gene extending in the 5'- to 3'-direction from and including the 78 nucleotides of intron 27 located adjacent exon 28 through the 3'-end of intron 51 wherein the consensus nucleotide sequence of the COL1A1 gene is SEQ ID NO: 1.

2. The method of claim 1, further comprising contacting the sample nucleic acid with a first intronic primer prior to determining the nucleotide sequence of the portion, the first intronic primer being either substantially complementary to or substantially homologous with the first site.

3. The method of claim 2, wherein the first intronic primer has a sequence selected from the group consisting of SEQ ID NOs: 273–299 and 301–319.

4. The method of claim 1, further comprising contacting the sample nucleic acid with a first intronic primer homologous with the first site, contacting the sample nucleic acid with a second primer complementary to the second site, and amplifying the portion to obtain an amplified polynucleotide prior to determining the nucleotide sequence of the portion, wherein determining the nucleotide sequence of the portion comprises determining the nucleotide sequence of the amplified polynucleotide.

5. The method of claim 4, further comprising performing conformation-sensitive gel electrophoresis (CSGE) after amplifying the portion and prior to determining the nucleotide sequence of the portion, the CSGE comprising denaturing the amplified polynucleotide, annealing the amplified polynucleotide, and determining whether the amplified polynucleotide forms a heteroduplex.

6. The method of claim 4, wherein the first intronic primer is either substantially complementary to or substantially homologous with a part of a non-coding region of the segment that has a sequence selected from the group consisting of SEQ ID NOs: 6, 7, 24–57.

7. The method of claim 4, wherein the first intronic primer has a sequence selected from the group consisting of SEQ ID NOs: 273–299 and 301–319.

8. The method of claim 4, wherein the first primer and the second primer are selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 273 | SEQ ID NO: 274 |
| SEQ ID NO: 275 | SEQ ID NO: 276 |
| SEQ ID NO: 277 | SEQ ID NO: 278 |
| SEQ ID NO: 279 | SEQ ID NO: 280 |
| SEQ ID NO: 281 | SEQ ID NO: 282 |
| SEQ ID NO: 283 | SEQ ID NO: 284 |
| SEQ ID NO: 285 | SEQ ID NO: 286 |
| SEQ ID NO: 287 | SEQ ID NO: 288 |
| [SEQ ID NO: 289 | SEQ ID NO: 290 |
| SEQ ID NO: 291 | SEQ ID NO: 292 |
| SEQ ID NO: 293 | SEQ ID NO: 294 |
| SEQ ID NO: 295 | SEQ ID NO: 296 |
| SEQ ID NO: 297 | SEQ ID NO: 298 |
| SEQ ID NO: 299 | SEQ ID NO: 300 |
| SEQ ID NO: 301 | SEQ ID NO: 302 |
| SEQ ID NO: 303 | SEQ ID NO: 304 |

-continued

| Column 1 | Column 2 |
| --- | --- |
| SEQ ID NO: 305 | SEQ ID NO: 306 |
| SEQ ID NO: 307 | SEQ ID NO: 308 |
| SEQ ID NO: 309 | SEQ ID NO: 310 |
| SEQ ID NO: 311 | SEQ ID NO: 312 |
| SEQ ID NO: 313 | SEQ ID NO: 314 |
| SEQ ID NO: 315 | SEQ ID NO: 316 |
| SEQ ID NO: 317 | SEQ ID NO: 318 |
| SEQ ID NO: 319 | SEQ ID NO: 320 |
| SEQ ID NO: 325 | SEQ ID NO: 326 |
| SEQ ID NO: 327 | SEQ ID NO: 328 |
| SEQ ID NO: 329 | SEQ ID NO: 330 |
| SEQ ID NO: 331 | SEQ ID NO: 332 |
| SEQ ID NO: 333 | SEQ ID NO: 334 |
| SEQ ID NO: 335 | SEQ ID NO: 336 |
| SEQ ID NO: 339 | SEQ ID NO: 340 |
| SEQ ID NO: 341 | SEQ ID NO: 342 |
| SEQ ID NO: 343 | SEQ ID NO: 344 |
| SEQ ID NO: 345 | SEQ ID NO: 346 |
| SEQ ID NO: 347 | SEQ ID NO: 348 |
| SEQ ID NO: 349 | SEQ ID NO: 350 |
| SEQ ID NO: 351 | SEQ ID NO: 352 |
| SEQ ID NO: 353 | SEQ ID NO: 354 |
| SEQ ID NO: 355 | SEQ ID NO: 356 |
| SEQ ID NO: 357 | SEQ ID NO: 358 |
| SEQ ID NO: 359 | SEQ ID NO: 360 |
| SEQ ID NO: 361 | SEQ ID NO: 362 |
| SEQ ID NO: 363 | SEQ ID NO: 364 |
| SEQ ID NO: 365 | SEQ ID NO: 366 |
| SEQ ID NO: 367 | SEQ ID NO: 368 |
| SEQ ID NO: 369 | SEQ ID NO: 370 |
| SEQ ID NO: 371 | SEQ ID NO: 372 |
| SEQ ID NO: 373 | SEQ ID NO: 374 |
| SEQ ID NO: 375 | SEQ ID NO: 376 |
| SEQ ID NO: 377 | SEQ ID NO: 378 |
| SEQ ID NO: 379 | SEQ ID NO: 380 |
| SEQ ID NO: 381 | SEQ ID NO: 382 |
| SEQ ID NO: 383 | SEQ ID NO: 384 |
| SEQ ID NO: 385 | SEQ ID NO: 386 |
| SEQ ID NO: 387 | SEQ ID NO: 388 |
| SEQ ID NO: 389 | SEQ ID NO: 390 |
| SEQ ID NO: 391 | SEQ ID NO: 392 |
| SEQ ID NO: 393 | SEQ ID NO: 394 |
| SEQ ID NO: 395 | SEQ ID NO: 396 |
| SEQ ID NO: 397 | SEQ ID NO: 398 |
| SEQ ID NO: 399 | SEQ ID NO: 400 |
| SEQ ID NO: 401 | SEQ ID NO: 402 |
| SEQ ID NO: 403 | SEQ ID NO: 404 |
| SEQ ID NO: 405 | SEQ ID NO: 406 |
| SEQ ID NO: 407 | SEQ ID NO: 408 |
| SEQ ID NO: 409 | SEQ ID NO: 410 |
| SEQ ID NO: 411 | SEQ ID NO: 412 |
| SEQ ID NO: 413 | SEQ ID NO: 414 |
| SEQ ID NO: 415 | SEQ ID NO: 416 |
| SEQ ID NO: 417 | SEQ ID NO: 418 |
| SEQ ID NO: 419 | SEQ ID NO: 420 |
| SEQ ID NO: 421 | SEQ ID NO: 422 |
| SEQ ID NO: 423 | SEQ ID NO: 424 |
| SEQ ID NO: 425 | SEQ ID NO: 426 |
| SEQ ID NO: 427 | SEQ ID NO: 428 |
| SEQ ID NO: 429 | SEQ ID NO: 430 |
| SEQ ID NO: 431 | SEQ ID NO: 432 |
| SEQ ID NO: 433 | SEQ ID NO: 434 |
| SEQ ID NO: 435 | SEQ ID NO: 436 |
| SEQ ID NO: 437 | SEQ ID NO: 438 |
| SEQ ID NO: 439 | SEQ ID NO: 440 |
| SEQ ID NO: 441 | SEQ ID NO: 442 |
| SEQ ID NO: 443 | SEQ ID NO: 444 |
| SEQ ID NO: 445 | SEQ ID NO: 446 |
| SEQ ID NO: 447 | SEQ ID NO: 448 |
| SEQ ID NO: 449 | SEQ ID NO: 450 |
| SEQ ID NO: 451 | SEQ ID NO: 452 |
| SEQ ID NO: 453 | SEQ ID NO: 454 |
| SEQ ID NO: 455 | SEQ ID NO: 456 |
| SEQ ID NO: 457 | SEQ ID NO: 458 |
| SEQ ID NO: 459 | SEQ ID NO: 460 |
| SEQ ID NO: 461 | SEQ ID NO: 462 |
| SEQ ID NO: 463 | SEQ ID NO: 464 |

-continued

| Column 1 | Column 2 |
|---|---|
| SEQ ID NO: 465 | SEQ ID NO: 466 |
| SEQ ID NO: 467 | SEQ ID NO: 468 |
| SEQ ID NO: 469 | SEQ ID NO: 470 |
| SEQ ID NO: 471 | SEQ ID NO: 472 |
| SEQ ID NO: 475 | SEQ ID NO: 476 |
| SEQ ID NO: 475 | SEQ ID NO: 477 |
| SEQ ID NO: 478 | SEQ ID NO: 479 |
| SEQ ID NO: 480 | SEQ ID NO: 481 |
| SEQ ID NO: 482 | SEQ ID NO: 483 |
| SEQ ID NO: 484 | SEQ ID NO: 485 |
| SEQ ID NO: 486 | SEQ ID NO: 487 |
| SEQ ID NO: 488 | SEQ ID NO: 489 |
| SEQ ID NO: 490 | SEQ ID NO: 491 |
| SEQ ID NO: 492 | SEQ ID NO: 493 |
| SEQ ID NO: 494 | SEQ ID NO: 495 |
| SEQ ID NO: 496 | SEQ ID NO: 497 |
| SEQ ID NO: 498 | SEQ ID NO: 499 |
| SEQ ID NO: 502 | SEQ ID NO: 503 |
| SEQ ID NO: 504 | SEQ ID NO: 505 |
| SEQ ID NO: 506 | SEQ ID NO: 507 |
| SEQ ID NO: 508 | SEQ ID NO: 509 |
| SEQ ID NO: 510 | SEQ ID NO: 511 |
| SEQ ID NO: 512 | SEQ ID NO: 513 |
| SEQ ID NO: 514 | SEQ ID NO: 515 |
| SEQ ID NO: 516 | SEQ ID NO: 517 |
| SEQ ID NO: 518 | SEQ ID NO: 519 |
| SEQ ID NO: 520 | SEQ ID NO: 521 |
| SEQ ID NO: 522 | SEQ ID NO: 523 |
| SEQ ID NO: 524 | SEQ ID NO: 525 |
| SEQ ID NO: 526 | SEQ ID NO: 527 |
| SEQ ID NO: 528 | SEQ ID NO: 529 |
| SEQ ID NO: 530 | SEQ ID NO: 531 |
| SEQ ID NO: 532 | SEQ ID NO: 533 |
| SEQ ID NO: 534 | SEQ ID NO: 535 |
| SEQ ID NO: 536 | SEQ ID NO: 537 |
| SEQ ID NO: 538 | SEQ ID NO: 539 |
| SEQ ID NO: 540 | SEQ ID NO: 541 |
| SEQ ID NO: 542 | SEQ ID NO: 543 |
| SEQ ID NO: 544 | SEQ ID NO: 545 |
| SEQ ID NO: 546 | SEQ ID NO: 547 |
| SEQ ID NO: 548 | SEQ ID NO: 549 |
| SEQ ID NO: 550 | SEQ ID NO: 551 |
| SEQ ID NO: 552 | SEQ ID NO: 553 |
| SEQ ID NO: 554 | SEQ ID NO: 555 |
| SEQ ID NO: 556 | SEQ ID NO: 557 |
| SEQ ID NO: 558 | SEQ ID NO: 559 |
| SEQ ID NO: 560 | SEQ ID NO: 561 |
| SEQ ID NO: 562 | SEQ ID NO: 563 |
| SEQ ID NO: 568 | SEQ ID NO: 569 |
| SEQ ID NO: 570 | SEQ ID NO: 571 |
| SEQ ID NO: 572 | SEQ ID NO: 573 |
| SEQ ID NO: 574 | SEQ ID NO: 575 |
| SEQ ID NO: 576 | SEQ ID NO: 577 |
| SEQ ID NO: 578 | SEQ ID NO: 579 |
| SEQ ID NO: 580 | SEQ ID NO: 581 |
| SEQ ID NO: 582 | SEQ ID NO: 583 |
| SEQ ID NO: 584 | SEQ ID NO: 585 |
| SEQ ID NO: 586 | SEQ ID NO: 587 |
| SEQ ID NO: 588 | SEQ ID NO: 589 |
| SEQ ID NO: 590 | SEQ ID NO: 591 |
| SEQ ID NO: 592 | SEQ ID NO: 593 |
| SEQ ID NO: 594 | SEQ ID NO: 595 |
| SEQ ID NO: 596 | SEQ ID NO: 597 |
| SEQ ID NO: 598 | SEQ ID NO: 599 |
| SEQ ID NO: 600 | SEQ ID NO: 601 |
| SEQ ID NO: 602 | SEQ ID NO: 603 |
| SEQ ID NO: 604 | SEQ ID NO: 605 |
| SEQ ID NO: 606 | SEQ ID NO: 607 |
| SEQ ID NO: 608 | SEQ ID NO: 609 |
| SEQ ID NO: 610 | SEQ ID NO: 611 |
| SEQ ID NO: 612 | SEQ ID NO: 613 |
| SEQ ID NO: 614 | SEQ ID NO: 615 |
| SEQ ID NO: 616 | SEQ ID NO: 617 |
| SEQ ID NO: 618 | SEQ ID NO: 619 |
| SEQ ID NO: 620 | SEQ ID NO: 621 |
| SEQ ID NO: 622 | SEQ ID NO: 623 |
| SEQ ID NO: 624 | SEQ ID NO: 625 |

-continued

| Column 1 | Column 2 |
|---|---|
| SEQ ID NO: 626 | SEQ ID NO: 627 |
| SEQ ID NO: 628 | SEQ ID NO: 629 |
| SEQ ID NO: 630 | SEQ ID NO: 631 |
| SEQ ID NO: 632 | SEQ ID NO: 633 |
| SEQ ID NO: 634 | SEQ ID NO: 635 |
| SEQ ID NO: 636 | SEQ ID NO: 637 |
| SEQ ID NO: 638 | SEQ ID NO: 639]. |

9. The method of claim 4, wherein the sample nucleic acid is contacted with a plurality of pairs of primers and a plurality of portions of the segment are amplified to obtain a plurality of amplified polynucleotides.

10. The method of claim 9, further comprising performing CSGE after amplifying the portions and prior to determining the nucleotide sequence of the portions, the CSGE comprising denaturing the amplified polynucleotides, annealing the amplified polynucleotides, and determining whether any of the amplified polynucleotides forms a heteroduplex.

11. The method of claim 10, wherein each of the primers is either substantially complementary to or substantially homologous with a part of a non-coding region of the segment.

12. The method of claim 9, wherein the length of each amplified polynucleotide is between about two hundred and about five hundred nucleotides.

13. The method of claim 12, wherein the length of the polynucleotide amplified using each pair of primers is different than the length of the polynucleotides amplified using every other pair of primers.

14. The method of claim 9, wherein the plurality of pairs of primers comprises pairs of primers sufficient to amplify substantially all exons and exon flanking regions of the gene.

15. The method of claim 14, wherein the length of each amplified polynucleotide is between about two hundred and about five hundred nucleotides and is different from the length of every other amplified polynucleotide.

16. The method of claim 15, further comprising performing CSGE after amplifying the portions and prior to determining the nucleotide sequence of the portions, the CSGE comprising denaturing the amplified polynucleotides, annealing the amplified polynucleotides, and determining whether any of the amplified polynucleotides forms a heteroduplex.

17. The method of claim 16, wherein the segment is the segment of the COL1A1 gene extending in the 5'- to 3'-direction from and including the 78 nucleotides of intron 27 located adjacent exon 28 through the 3'-end of intron 51, and wherein each pair of primers comprises a first intronic primer and a second primer, the first intronic primer and second primer being selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 273 | SEQ ID NO: 274 |
| SEQ ID NO: 275 | SEQ ID NO: 276 |
| SEQ ID NO: 277 | SEQ ID NO: 278 |
| SEQ ID NO: 279 | SEQ ID NO: 280 |
| SEQ ID NO: 281 | SEQ ID NO: 282 |
| SEQ ID NO: 283 | SEQ ID NO: 284 |
| SEQ ID NO: 285 | SEQ ID NO: 286 |
| SEQ ID NO: 287 | SEQ ID NO: 288. |

18. The method of claim 17, wherein the pathological condition is selected from the group consisting of osteoporosis, multiple epiphyseal dysplasia, osteogenesis imperfecta, shortness of stature, and low bone density.

19. An isolated nucleic acid comprising at least about fifteen consecutive nucleotides,
  wherein the isolated nucleic acid is either completely complementary to or completely homologous with at least fifteen consecutive nucleotides of a segment of a human collagen gene, including at least one nucleotide of the segment located in a non-coding region of the gene, and
  wherein the segment is the segment of the COL1A1 gene (SEQ ID NO: 1) extending in the 5'- to 3'-direction from and including the 78 nucleotides of intron 27 located adjacent exon 28 through the 3'-end of intron 51.

20. The isolated nucleic acid of claim 19, wherein the nucleic acid is completely complementary to the segment.

21. The isolated nucleic acid of claim 19, wherein the nucleic acid is completely homologous to the segment.

22. The isolated nucleic acid of claim 19, wherein the isolated nucleic acid is complementary to or homologous with at least three nucleotides of the segment located in the non-coding region.

23. The isolated nucleic acid of claim 19, wherein the segment comprises only nucleotides located in the non-coding region and wherein the non-coding region has a nucleotide sequence selected from the group consisting of SEQ ID NOs: 6, 7, 24–57.

24. The isolated nucleic acid of claim 19, having a nucleotide sequence selected from the group consisting of SEQ ID NOs: 273–299 and 301–319.

25. A kit for detecting an alteration in a segment of a human collagen gene, the kit comprising a consensus sequence of the gene, a first intronic primer, and a second primer,
  wherein each of the first intronic primer and the second primer comprises at least about fifteen consecutive nucleotides,
  wherein the segment comprises at least one nucleotide located in a non-coding region of the gene, a first site, and a second site, the first intronic primer being substantially homologous with the first site and the second primer being substantially complementary to the second site,
  wherein the segment is the segment of the COL1A1 gene extending in the 5'- to 3'-direction from and including the 78 nucleotides of intron 27 located adjacent exon 28 through the 3'-end of intron 51
  wherein the consensus nucleotide sequence of the COL1A1 gene is SEQ ID NO: 1.

26. The kit of claim 25, wherein the length of the segment is between about two hundred and about five hundred nucleotides.

27. The kit of claim 25, further comprising at least one sequencing primer for determining the nucleotide sequence of at least a portion of the segment.

28. The kit of claim 25, wherein the first intronic primer and the second primer are selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 273 | SEQ ID NO: 274 |
| SEQ ID NO: 275 | SEQ ID NO: 276 |
| SEQ ID NO: 277 | SEQ ID NO: 278 |
| SEQ ID NO: 279 | SEQ ID NO: 280 |
| SEQ ID NO: 281 | SEQ ID NO: 282 |
| SEQ ID NO: 283 | SEQ ID NO: 284 |
| SEQ ID NO: 285 | SEQ ID NO: 286 |
| SEQ ID NO: 287 | SEQ ID NO: 288. |

29. The kit of claim 28, comprising a plurality of the pairs of primers.

30. The method of claim 8, wherein the first intronic primer and the second primer are selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 289 | SEQ ID NO: 290 |
| SEQ ID NO: 291 | SEQ ID NO: 292 |
| SEQ ID NO: 293 | SEQ ID NO: 294 |

31. The method of claim 8, wherein the first intronic primer and the second primer are selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 295 | SEQ ID NO: 296 |
| SEQ ID NO: 297 | SEQ ID NO: 298 |
| SEQ ID NO: 299 | SEQ ID NO: 300 |

32. The method of claim 8, wherein the first intronic primer and the second primer are selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 301 | SEQ ID NO: 302 |
| SEQ ID NO: 303 | SEQ ID NO: 304 |
| SEQ ID NO: 305 | SEQ ID NO: 306 |

33. The method of claim 8, wherein the first intronic primer and the second primer are selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 307 | SEQ ID NO: 308 |
| SEQ ID NO: 309 | SEQ ID NO: 310 |
| SEQ ID NO: 311 | SEQ ID NO: 312. |

34. The method of claim 8, wherein the first intronic primer and the second primer are selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 313 | SEQ ID NO: 314 |
| SEQ ID NO: 315 | SEQ ID NO: 316. |

35. The method of claim 8, wherein the first intronic primer and the second primer are selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 317 | SEQ ID NO: 318 |
| SEQ ID NO: 319 | SEQ ID NO: 320. |

36. The kit of claim 28, wherein the first intronic primer and the second primer are selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 289 | SEQ ID NO: 290 |
| SEQ ID NO: 291 | SEQ ID NO: 292 |
| SEQ ID NO: 293 | SEQ ID NO: 294. |

37. The kit of claim 28, wherein the first intronic primer and the second primer are selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 295 | SEQ ID NO: 296 |
| SEQ ID NO: 297 | SEQ ID NO: 298 |
| SEQ ID NO: 299 | SEQ ID NO: 300. |

38. The kit of claim 28, wherein the first intronic primer and the second primer are selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 301 | SEQ ID NO: 302 |
| SEQ ID NO: 303 | SEQ ID NO: 304 |
| SEQ ID NO: 305 | SEQ ID NO: 306. |

39. The kit of claim 28, wherein the first intronic primer and the second primer are selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 307 | SEQ ID NO: 308 |
| SEQ ID NO: 309 | SEQ ID NO: 310 |
| SEQ ID NO: 311 | SEQ ID NO: 312. |

40. The kit of claim 28, wherein the first intronic primer and the second primer are selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 313 | SEQ ID NO: 314 |
| SEQ ID NO: 315 | SEQ ID NO: 316. |

41. The kit of claim 28, wherein the first intronic primer and the second primer are selected such that when the first intronic primer has a sequence listed in Column 1 of the following table, the second primer has the sequence listed on the same line in Column 2 of the following table:

| Column 1 | Column 2 |
| --- | --- |
| SEQ ID NO: 317 | SEQ ID NO: 318 |
| SEQ ID NO: 319 | SEQ ID NO: 320.-- |

\* \* \* \* \*

SEQUENCE LISTING (1) GENERAL INFORMATION:

(iii) NUMBER OF SEQUENCES: 666

(2) INFORMATION FOR SEQ ID NO: 1:

(i) SEQUENCE CHARACTERISTICS:
      (A) LENGTH: 18609 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
GGGGCACCCC TACCCACTGG TTAGCCCACG CCATCCTGAG GACCCAGCTG CACCCCTACC      60
ACAGCACCTC GGGCCTAGGC TGGGCGGGGG GCTGGGGAGG CAGAGCTGCG AAGAGGGGAG     120
ATGTGGGGTG GACTCCCTTC CCTCCTCCTC CCCCTCTCCA TTCCAACTCC CAAATTGGGG     180
GCCGGGCCAG GCAGCTCTGA TTGGCTGGGG CACGGGCGGC CGGCTCCCCC TCTCCGAGGG     240
GCAGGGTTCC TCCCTGCTCT CCATCAGGAC AGTATAAAAG GGGCCCGGGC CAGTCGTCGG     300
AGCAGACGGG AGTTTCTCCT CGGGGTCGGA GCAGGAGGCA CGCGGAGTGT GAGGCCACGC     360
ATGAGCGGAC GCTAACCCCC TCCCCAGCCA CAAAGAGTCT ACATGTCTAG GTCTAGACA      420
TGTTCAGCTT TGTGGACCTC CGGCTCCTGC TCCTCTTAGC GGCCACCGCC CTCCTGACGC     480
ACGGCCAAGA GGAAGGCCAA GTCGAGGGCC AAGACGAAGA CAGTAAGTCC CAAACTTTTG     540
GGAGTGCAAG GATACTCTAT ATCGCGCCTT GCGCTTGGTC CCGGGGGCCG CGGCTTAAAA     600
CGAGACGTGG ATGATCCGGA GACTCGGGAA TGGAAGGGAG ATGATGAGGG CTCTTCCTCG     660
GCGCCCTGAG ACAGGAGGGA GCTCACCCTG GGGCGAGGTT GGGGTTGAAC GCGCCCCGGG     720
AGCGGGAGGT GAGGGTGGAG CGCCCCGTGA GTTGGTGCAA GAGAGAATCC CGAGAGCGCA     780
ACCGGGGAAG TGGGGATCAG GGTGCAGAGT GAGGAAAGTA CGTCGAAGAT GGGATGGGGG     840
CGCCGAGCGG GGCATTTGAA GCCCAAGATG TAGAAGCAAT CAGGAAGGCC GTGGGATGAT     900
TCATAAGGAA AGATTGCCCT CTCTGCGGGC TAGAGTGTTG CTGGGCCGTG GGGGTGCTGG     960
GCAGCCGCGG GAAGGGGGTG CGGAGCGTGG GCGGGTGGAG GATGAGAAAC TTTGGCGCGG    1020
ACTCGGCGGG GCGGGGTCCT TGCGCCCCCT GCTGACCGAT GCTGAGCACT GCGTCTCCCG    1080
GTCCAACGCT TACTGGGGCA GGAGCCGGAG CGGGAAGACC CGGGTTATTG CTGGGTGCGG    1140
ACCCCCACCT CTAGATCTGG AAAGTAAAGC CAGGGATGGG GCAGCCCAAG CCTCTTAAAG    1200
AGGTAGTCGG GCCGGTGAGG TCGGCCCCGC CCCGGCCCCA TTGCTTAGCG TTGCCCGACA    1260
CCTAGTGGCC GTCTGGGGAG CCGCTAGCGC GGTGGGAGTG GTTAGCTAAC TTCTGGACTA    1320
TTTGCGGACT TTTTGGTTCT TTGGCTAAAA GTGACCTGGA GGCATTGGCT GGCTTTGGGG    1380
GACTGGGGAT GGCCCCGAGA GCGGGCTTTT AAGATGTCTA GGTGCTGGAG GTTAGGGTGT    1440
CTCCTAATTT TGAGGTACAT TTCAAGTCTT GGGGGGGCGT CCCTTCCAAT CAGCCGCTCC    1500
CATTCTCTTA GCCCCGCCCC CGCCACCCCA CATGCCCAGG GAATGGGGGC GGGATGAGGG    1560
ATGGACCTCC CTTCTCTCCT CCCTCGCCCT CCTCCTGTCT CTACCACGCA AGCCACTCCC    1620
CACGAGCCTG CCCTCCCGAT GGGGCCCCTC CTATTCTCCC CCCGCCCTCC CCCTCTCACC    1680
CTGTGGTTTT ATTTCACTTG GCTTCAGCGC CAATGGGCTG AGGTTGGAGT TGGAAGCCAC    1740
CGCGGACTAA AGCTTTGTTT AAATTCCTGA GAACTGGAAA GAGTTACAGC CTCCCTGGCC    1800
```

-continued

```
AGGCGCCTCG GCGCTGTCAC CCGCGCTGAT GAGGAGCAGG CGAGCTTTTA AGGATTTGAG    1860

GAAAGAAGAA CGGGGGGAGG GGCGGGAAGT GAAAAATCCA AGTGTGCCTC TTAGACCCGG    1920

GGGAAAGGTG GTTAAGCTGG GGGTTGCAGT CACTACTGAC AACGCCCCTC TTCCGCCTGT    1980

CCCAGTCCCA CCAATCACCT GCGTACAGAA CGGCCTCAGG TACCATGACC GAGACGTGTG    2040

GAAACCCGAG CCCTGCCGGA TCTGCGTCTG CGACAACGGC AAGGTGTTGT GCGATGACGT    2100

GATCTGTGAC GAGACCAAGA ACTGCCCCGG CGCCGAAGTC CCCGAGGGCG AGTGCTGTCC    2160

CGTCTGCCCC GACGGCTCAG GTGCGGCTGC GCTCGGGGCC TGGGGCCTGG GGCTGGGGCT    2220

GGGGGTGGTC GGCGCTCGCT GGCCCTCCGT GCTGGAGGCC TCTGCCGACG GGAGCAGCAT    2280

TAGCAAACCT TGGCTCTAAC GGGCGTCTCT TCGTCCCCTA GAGTCACCCA CCGACCAAGA    2340

AACCACCGGC GTCGAAGTAA TCTCCTGCCC TCGAATTTTG CCCCTGCGCG GCCCGTGACT    2400

CCTCACAGTC CTCCCTTCTC TAACCTGGCC TCTTGTTTCT TCTCCCCCAA TCCCACAGGG    2460

ACCCAAGGGA GACACTGGCC CCCGAGGCCC AAGGGTAAGC GTTGCACTCT GGGCTGTGGG    2520

GGGCTGCAGG TGGGCATGGC TCTCGGCCCC ACGCTCACCC CGGCCCCGCC CTCTCCCCCT    2580

GCAGGGACCC GCAGGCCCCC CTGGCCGAGA TGGCATCCCT GGACAGCCTG GACTTCCCGG    2640

ACCCCCCGGA CCCCCCGGAC CTCCCGGACC CCCTGGCCTC GGAGGAGTAA GTGGAGAGGC    2700

CTTGTGTGTC CACTCTCCCC TGTTTTGTTT TTGTTTTTTG GCAGATGACA TAATTTTATA    2760

CTTTGAAATA ATTTCAAACT TACAGAAAAG TTGCAAGAAT CCTACAGGAA ACTCTCACAT    2820

ACCCTTCACA GTTTGTGACA TGTGCTTTAT TAGTCTCTGT TTATGTATAT GTATCTTTTT    2880

TTTTCTGAAC TGTTTGAGCA AGTTGCTAAC ATCAGGCTCT TTTGCGCCTA AATACTTAGG    2940

TGTGTTTTTC CTAAAAACAA GAGCATTCTC TTAACTGACC TACACAATGA TTAAATTCAC    3000

TCTCTAATGT GCAGTCCGTA CTCAAAGTTC ACCGATGTCC CGATAATGTC CTTTATAGAT    3060

TCCACCCCCC ACCACCCCAA TCTGGGATCC AGTCCAGGAT TATGTATTGC ATTTAATCAT    3120

CATGTCTCTA GTTCCACAA ATGTAGAACG TTCCTCAGAC TTTCTTTGTC TTTAGTGGCA    3180

CTGGGAGTTT TGATGAGTCC AGTTGTTTTG CAGACTGTCC CTCAATTTGG GATTGTCTCA    3240

TTAGATTAGA TGCAGGGATG CATCTTTGGC AGGAATGTCT TAAAAGCAAT GTTATTCTTC    3300

TCAGCACATC ACACCAGGAA GTGCATGATG TCAGTTTCTT CCATCCTCAG TGCCGTCTTC    3360

TGCCTTTCAA TTCACTGTCC TCACTCTGAC TTCTCTTGTT TGTTCTAGAA CTTTGCTCCC    3420

CAGCTGTCTT ATGGCTATGA TGAGAAATCA ACCGGAGGAA TTTCCGTGCC TGGCCCCATG    3480

GTGAGCCAGC AGGGGAGCA TGGATGACAG AAGAGAGAAT GGGTATCCAG AGGATGTGGG    3540

CATACGCGGC TGGTATACAC AGCTTGGGAG GTCCATATCA CCTTTGGGAC CTCAGAGTCC    3600

AGAAAGGATG CAAGACGACT GGGTGGTCCC AACAGGCATG AATGACTACA TCCACATGCT    3660

TTCCTACAGA GGGATCACCA TGACCCCCCT TTCTTCTCCC TCTATAGGGT CCCTCTGGTC    3720

CTCGTGGTCT CCCTGGCCCC CCTGGTGCAC CTGTGAGTAT CCAGGACGTC TTCATATGCC    3780

TCCTTGGGCT TTGGTCTTTT GGAGGGAAGA CTGGATGACG GGCAGGAGAG ATGCTCAGAG    3840

ATCTCTTGGT AAGATTGGAG AAGGTTGACA GGGACTTGTC TTCTAACCCA TCTTTTTCCT    3900

TCTTCTCAAG GGTCCCCAAG GCTTCCAAGG TCCCCCTGGT GAGCCTGGCG AGCCTGGAGC    3960

TTCAGTAAGC ACTCTCTATA CAGATTCATA CTCCTTCTAC AAACACACAG ACTCTCCTAT    4020

AGAAGAACTC CCAGGCCTGG GGTCTTCCTT ACCTCTTCCC TTCAATCCCA GCCTTCCCCT    4080

TCTTTTTTTC TTATCCATAT TCTAACCACC TCTTCTATCT TTTCTAGGGT CCCATGGGTC    4140
```

```
CCCGAGGTCC CCCAGGTCCC CCTGGAAAGA ATGGAGATGA TGTAAGTATC CCCAGCAAGA    4200

AGATACCATC TGACCCCATG GCCTCCATGG GTTGGGTCCT GCAATTTCCA CTCCACCACA    4260

TTTGGGAACG ATACTCAGAG GAAGGAGGGC AAGTCCTCTC TGATGCACGG ACTGCCCTGG    4320

AACAATGATC TTTTCGCTTA GTGAGATGAT TCCATGTCCC AACAAAGTG ACTGTTCTCC     4380

TCACCCCAGC CACCTTAGAG CAATCCCCAA CCCCATCCCT TTGGGAAAT TGGTGCGCAG     4440

ATGGTGAAAT TAAAATGCTG GTGACAGAAG TAGACAGAAA TTCCTTTAGA GGCACTCAGA    4500

TTTCACCAAA CGAAGGTTTC ACTGTAGATT TAAACTGAGC TCTAGATTCA AAGATAAGAT    4560

TCTGGGCCCC CAAACCTGAC CTGCAACAAT CCAAAGAAGA CTGAGACCTT CTCCACTTTT    4620

CCAGCCCCTA GGCGGTGGTG GGGAGGCAGA GGCATGATGG TCTTTTCTCT CCCTCTCAGG    4680

GGGAAGCTGG AAAACCTGGT CGTCCTGGTG AGCGTGGGCC TCCTGGGCCT CAGGTGAGCA    4740

GGGGGCTGTG GCTGAACCTG GCTTCACTG CACTTGGGCT TCATTTAGGA GCTGGGTCCA     4800

CAGTGATGTG TTCTAATGGC CCTTCCTTGT CTTCTTCATC TCTCTCCAGG GTGCTCGAGG    4860

ATTGCCCGGA ACAGCTGGCC TCCCTGGAAT GAAGGGACAC AGAGTGAGTC ACCTTTGAGT    4920

CATTTAAGCT CCCCAAGTCC CTAGCATACC CCCATCCAGT CCCAGCCTCT TCCCCAAAAG    4980

ATCCTGAGTT GCATCATGGT GGGTGGCAGC TACAGAAGTC CCAAGGGCCA GAGAGTGGAC    5040

ATCCAAAAGC ACTCCTCATG GAATCCCGAT TACCGATTGG GTGAGATCTT AGAGCCATTT    5100

GGGGTTTAGT CTAGCTCAGA AACAAAGGGA TGGCGGTGAT GACCTCCCAA GGCTCTTTCT    5160

CAGATCTAGG TGGATGTCAA GGCTGTTCCA CCCCCTCCAC AGGTTCTTAC CTTCTACCTC    5220

TTTCCTGCTT TAGGGTTTCA GTGGTTTGGA TGGTGCCAAG GGAGATGCTG GTCCTGCTGG    5280

TCCTAAGGTA AGAGGCTGTC TGAACATCAT GGTCCTCCAC ATCCCCAGAG TCCCACCATG    5340

AATGAATTTC TCACTCATTA TTCTCTGATC TACAGGGTGA GCCTGGCAGC CCTGGTGAAA    5400

ATGGAGCTCC TGGTCAGATG GTGAGTGTGC CCAGTTCCAG AGGGCAGGGA TGGGGCAGGA    5460

GGCAGGGGCA AGATGGAGGC CTGGGGGAAC AAGGCTGTCT CCCATCTCAT CTGACTTCTC    5520

TTGGTTTGGT TGTCAGGGCC CCCGTGGCCT GCCTGGTGAG AGAGGTCGCC CTGGAGCCCC    5580

TGGCCCTGCT GTAAGTACTC CTGGCCCCTT GGGGATCCC TGAGCTCTGG AAGGGGCTCC     5640

CCAGGAACTC TAGGGACTGG CCAGTGCTCA GTGGACTTAA CGGGGCTTCC CCTCTCTCCT    5700

GCAGGGTGCT CGTGGAAATG ATGGTGCTAC TGGTGCTGCC GGGCCCCCTG TGAGTGTGGC    5760

CTGTAGGCCT CAGGGCCTGG GAGTGGGGAG GGGTCTCAGT GTCTGCTCTT GGGGCTGACA    5820

ATGGGGGCAG GTTATGTTGG TCTGAACCCC AGGACTTCCT CTGTCCCAGG GTGTGACTTG    5880

CAGCTGCCAT CTCTTCCTTC TCGCTGACAT CTCCATTTCA TTCACAGGGT CCCACCGGCC    5940

CCGCTGGTCC TCCTGGCTTC CCTGGTGCTG TTGGTGCTAA GGTGAGACCC CCCACTCTCC    6000

TCTAAGCATG ACCCTCATGG GCCAAGGGGT TCATGTCTCC CTGTTCCCCA AACCAAAGGG    6060

ACCCAGAGTG GCAAGAGAGC AGCCCGTTCA CTAACACCTT TGTCCTGGGG TCTCCGTCTC    6120

TGATCTTAGA GTCCTGATCA TTGCTCTCCT GTCCCTGTCT CCCCTTCCTC CTGCCATCCC    6180

GAGAGGCAAG GTTGGGTTTC CCAGGGTGGC TTCTGATATG TCCTTTCTTC TGATTCAGGG    6240

TGAAGCTGGT CCCCAAGGGC CCCGAGGCTC TGAAGGTCCC CAGGGTGTGC GTGGTGAGCC    6300

TGGCCCCCCT GGCCCTGCTG GTGCTGCTGG CCCTGCTGTA AGTGTCCCCG ACTCAGTGTC    6360

CCCTTTGCCA CTTTCTAACC TCAGAGTCCT TGCCTGTTGC TGACACTCCT TTCTCTGTGC    6420

CACAGGGAAA CCCTGGTGCT GATGGACAGC CTGGTGCTAA AGGTGCCAAT GTAAGTATCC    6480

TGCCAGGCTT CAGTCCCACT CCTGCCGCCT GCAGCCTGCC TGCCCCTTTC CCTCTGCTCC    6540
```

```
TAGGCTCACG CCCTGGCTGT CTGCCTCCCA CAGGGTGCTC CTGGTATTGC TGGTGCTCCT      6600

GGCTTCCCTG GTGCCCGAGG CCCCTCTGGA CCCCAGGGCC CCGGCGGCCC TCCTGGTCCC      6660

AAGGGTAACA GCGTGAGTAC CAAACTCTCC CTTCTGCCCA CCCCATGCAC TGGCTCCAGT      6720

GCGGCTCTCA TCTGGGGAGC AGGAAGACGC AGGCCAACTG AGCGCCCCCG ACTCTCAGCT      6780

CATCCTCTTC TCCCCCCTTG CAGGGTGAAC CTGGTGCTCC TGGCAGCAAA GGAGACACTG      6840

GTGCTAAGGG AGAGCCTGTA AGTCTCCCCG CCATCCTTCT TGCAGCCCAG CCCACCCTGC      6900

CCTAGGAGCC CCCTGAGGGA AATCCAGAAA GGAAGAGGAG CCCCTAGTCT TCTGGGGGAG      6960

TCCCTGCCAC ACCCCCAGGA ACCCCTGACA CTGGAGGCCC AGCCTCAGCC GGCTCTGAGG      7020

CTGGCACAGG ATGGCCCCTC ACCACAGGCC GCCTCCTCCT CTCGGCCCTC TCCAGGGCCC      7080

TGTTGGTGTT CAAGGACCCC CTGGCCCTGC TGGAGAGGAA GGAAAGCGAG GAGCTCGAGG      7140

TGAACCCGGA CCCACTGGCC TGCCCGGACC CCCTGGCGAG CGTGTAAGTG TCCCTGCCCG      7200

CCCCCTCCCA CTCCACCCTC ATTGCCTGGC TGGTGCCTGT GTGTCGCGGA GTTCACTGGC      7260

CTCCTCTCCT CCTGCAGGGT GGACCTGGTA GCCGTGGTTT CCCTGGCGCA GATGGTGTTG      7320

CTGGTCCCAA GGTAACCTCT CCTTGCGGCC GGGGGGCTGA CCCTGCCGCT CCCTGGGCAT      7380

CTTCTTCCTC TTTTGGCCCG TGGCAAAGAG CCACAAACTT GAGACCCTAA CTGTTCCTGT      7440

GACTTCCCCC AACCAGGGTC CCGCTGGTGA ACGTGGTTCT CCTGGCCCCG CTGGCCCCAA      7500

AGGATCTCCT GGTGAAGCTG GTCGTCCCGG TGAAGCTGGT CTGCCTGGTG CCAAGGTGAG      7560

GCCCCAGGCT TTCAGCCTGG CTTGGCCAGG CCCTGACCAT CCCGTGTAGG GTCTGGGATG      7620

AGGCGTTCTG GATCAGGCCC AAGGGTCTGC CCTCTGGAGT CCTCCCCCAC CTCCATCATG      7680

CTTCTCCCCA AGTCCCACTC ATACCTCTCT GCCTCCCTAG GGTCTGACTG GAAGCCCTGG      7740

CAGCCCTGGT CCTGATGGCA AAACTGGCCC CCCTGTAAGT ATCACTCCCC CTGAACCCCC      7800

TGCCATTGTC CTGTCTGCCT CCCTGCTGTC CTCACTGCTG CTTTCGTGCC TCCCATCCTT      7860

AGGGTCCCGC CGGTCAAGAT GGTCGCCCCG GACCCCCAGG CCCACCTGGT GCCCGTGGTC      7920

AGGCTGGTGT GATGGGATTC CCTGGACCTA AAGGTGCTGC TGTGAGTATT AAGTGAGGAT      7980

CCATGAAGAG CCAGGGACAA ACACACCTGA GACTTGAAGG AGTCCTGGGC TCTGGGCTCA      8040

GCTGTGCCGC TGACCTGCCG TGTGGCCACT CACTCTCACT TTCTGGACCT CAGCCTCCCT      8100

ATCTGTAAAA TGAAAGACTT CTCGGCGGGG CACGGTGGCT CATGCCTGTA ATCCCAGCAC      8160

TTTGGGAGGC CAAGGCGGGC AGACCATGAG GTCAGGAGTT TGAGACCAGT CGGGCCAACA      8220

TAGTGAAACC ACGTCTCTAC TAAAAATACA AAAGATTAGC TGGGTGTGGT GGTGTGCACC      8280

TGTAACCCCA GCTAGTCAGG AGGCTGAGGC AGGAGAATTG CATGAACCCG GGAGGTGGAG      8340

GTTGCAGTGA GCTGAGATCA CGCCATTGCA CTCCAGCCTG GCAACAGTG CGAGATTCCA       8400

TCTCAAAAAA AAAAAAAAA AGAAGAAAGA AGAAAGAAA AAATGAAACA CTTCTCCAGG        8460

CTCCATGACC ACTGCTCTGT CCTGAAATAA GTGTTGTTGG TGGCCCTCCA CCCCGACACG      8520

TGGGATAGG ACAGGCCTTT GATATGATAG GCACCCCCAG TCTTGGTGGA TTCTTTGAGG       8580

TCCAAAAGGA GATAGCAGAG AAGATGAAAG CCCTTTGCAG TGCAGGCCAC AGCGGGCATC     8640

TAACAGGGAA AAGGCAGAGG AGCCTGGAAG GGCATCTTGG GAGGAGTGGG CTCAGAAAGG      8700

GCCCAGCAAG AAGCACCTGC AGGGGCATTC CCCGGGGGCC AAACAGTCTT TGAAAAGAA       8760

AGTCCCTTAA AAAGTCCCAC TCAGAGTAAA TGAGAGGCCC CAGGAGGCCC TGGCTTCTCA      8820

CTTCAGCCCC CTCAACCCTA ACTCCCTTTC TCCACAGGGA GAGCCCGGCA AGGCTGGAGA      8880
```

```
GCGAGGTGTT CCCGGACCCC CTGGCGCTGT CGTAAGTATC TCCTTTCCAT CCCTACCTCC    8940
TTCCCATTGC TGCCCCGGCA CTTTCTCCTC CCTGCAGGAG GGGTGCTAGA GGCCACGGTC    9000
CTCAGCTGCT CGGGGCCTCC TAACCCTGAG TTCCCCTTTG CTCTCTCCCT GCAGGGTCCT    9060
GCTGGCAAAG ATGGAGAGGC TGGAGCTCAG GGACCCCCTG GCCCTGCTGT GAGTGTCCCT    9120
GATGGGGAGA TCTGGGGAGC AGAAAAGGGG AGACACCCTC AGCCCCTCGT CTCCTCGGCC    9180
TCCCCGTGAC TGTAGTGTTC TCTCTGTGCA GGGTCCCGCT GGCGAGAGAG GTGAACAAGG    9240
CCCTGCTGGC TCCCCCGGAT TCCAGGTGAG GCCTCATGGC TGTCAGGATG CTGGGAGGTA    9300
GGGGTAGGAA ACACCTCTTT GGTCTCTTCC AGATTCTAAA CCTTCCCTCC CTTCTTCCCC    9360
CATTTCCCAC CTACAGGGTC TCCCTGGTCC TGCTGGTCCT CCAGGTGAAG CAGGCAAACC    9420
TGGTGAACAG GTAAGAGGGA GCAGCCGGCC AGAGGGTGG GAGATGCAGG GAATCCAGAG    9480
GGACAGGCCC CCGCCTCCTA GCTAATCAGA CAGCCATCAA CTAGAGGGAT TGAGGTTAGA    9540
CACCGGAAAG AACTTCCTCC CATGAAGGGA GCAGCACAGA GGGAAGTGGG GGCTGCATGA    9600
TTGCTAGTCT GGGTGACTTC TTTTAAGAGC TGCTGGAATA TGCTGTGACT TTCCCTCAAC    9660
CCTTGTATTG ATAAATCTTG GTCCATAGTT TGGGGAGGGG GGAAGCCTTT GACACATCCC    9720
TAGGAGGAAG AGAGGGGCTG TTTGGGATAA TCTCAATTCA GTGCTGAGAA GGGGTTCCTC    9780
TCTAATCACG GCCAGACCCC AGGAGGAAGG ACCGTGCTTT CCAGCAGAGT GGCCCCAGGT    9840
AGGTTTTGCT CACTGTCTGT TCCTCTCTCC CTCCCCCTCA GGGTGTTCCT GGAGACCTTG    9900
GCGCCCCTGG CCCCTCTGGA GCAAGAGTAA GTAGGCCTCT CTCGCTGCAT CCGTCAAGGT    9960
GCGTTGTACT TGGCCCTATC TCCAGAGCAG CCTTCACATG CCCTGTCCTT CCCTTCTAGG   10020
GCGAGAGAGG TTTCCCTGGC GAGCGTGGTG TGCAAGGTCC CCCTGGTCCT GCTGGTCCCC   10080
GAGGGGCCAA CGGTGCTCCC GGCAACGATG GTGCTAAGGT GAGGGCAGCG TGGAAGGGGC   10140
TCTGGCAAGT GGCCCAGGGA CCAGGTCTCA CCCCTCCTGC AGCAGGGGAT GGCGGGCCAT   10200
GACCAAAGCC ATGGAGATAG GGTGTGGGGT GGGGGGAAAA GACCAGGGCA GGGGCCCACA   10260
CACAGCCTGG AGTCTGGGCT GTGAGTCTTT TCATCTTTTC TCAAGGCTTG TCGTTGGCCT   10320
TGGAAACAAG CCTGGGAGAT ACCAAGCGGG GCTTAGGGCT GTGACCCACT CTTGGGGCCC   10380
CAGGCCTCAC TCCAGTCTTC TTGGTTGTCA CATAGGGTGA TGCTGGTGCC CCTGGAGCTC   10440
CCGGTAGCCA GGGCGCCCCT GGCCTTCAGG GAATGCCTGG TGAACGTGGT GCAGCTGGTC   10500
TTCCAGGGCC TAAGGGTGAC AGAGTAAGTT CAACCTTCCC CCTCCCCTGA GCCCTACATG   10560
GCTCCCATCT CTGCCTGCTT TGAATCTCTC AGCATCTCTC CTTCTCTCTG GGATCTGTCC   10620
CTCTTCTCGC TAATCCTCCC CTCTTCCCCT TTCCCCTCTG GCCTTTTTGC TGATGAATCC   10680
TCTCCCTGTG GTCCAGGCCC ATCTATCCCC ATGGGTTACC ATGGTGATGA GAGGTGGGGG   10740
CATCTCCTTG GTGGAGGCTC CCTTATTCAT CCCGCTACAC AAGTCAGGGG CCTCTTAACC   10800
TCAGTTCCAC CTGAGTCTCC AGGCAGGAAC CCTTTTTCCT GAAAGAATCT TGAGTCCTT    10860
GGCCCAGGTG GAGGCAGGGC AGAGCTGCAG AGGGCCTCTC AGGAAACCCA GACACAAGCA   10920
GAACACTATA GGTCACCTCC TTGCCCCACA CTGGAAATCT CAAGCTTATC CATGTCTTTA   10980
GGGTGATGCT GGTCCCAAAG GTGCTGATGG CTCTCCTGGC AAAGATGGCG TCCGTGGTCT   11040
GACCGGCCCC ATTGGTCCTC CTGGCCCTGC TGGTGCCCCT GGTGACAAGG TGAGGTGGCC   11100
GCCTCCCCAC CTTCTGCCCT AACACATAGC CTCCTCAGCA GGCCTGGGCA CGGTTCCGTG   11160
GGGTTGCGTT GGGAGAGCAG GTCCTGCCAA ACTGAGCTGT CAACCTGGGA ACCTGGAGGG   11220
ACCAGAAGGA GGGGAGGCTC TCCTGGGGTC ATCTACTAGG AGTATTCAGG GGAGGCCCTG   11280
```

```
ACCCTGAGCC TCTTGTCCCT TGCTCTCAGG GTGAAAGTGG TCCCAGCGGC CCTGCTGGTC    11340

CCACTGGAGC TCGTGGTGCC CCCGTAAGTA CAGAAGACCT GTTAAGACCC CATACTTGGC    11400

CCTTCCCTCC CTTCACACAG CACCCCTGGC CCTGTCTGTG CCTTCACCCC TTGCCTCTCC    11460

CCTCACCGCA TCCCCGCCTT CCCTCCTGTC AGACGCATCT CTCCAATCTG ACTCCTTTTC    11520

TTCTAGGGAG ACCGTGGTGA GCCTGGTCCC CCCGGCCCTG CTGGCTTTGC TGGCCCCCCT    11580

GTGAGTACCA AGACCCCCAT CATTTTTCAT CACCGACTGG GACCTGGGAC CTCGAGGGAC    11640

GGAATGAGGA CAAAGGCGTC AGCCATCCTC AGGGGAGAAG GGTGGAGACG GGATTGTTTC    11700

CCACCCAAGC ATCTTCCTGC CTCCATTACT GCTCCTCCCC CAGGTAGTGG AAACTCCTGC    11760

CTCCTTCCCT CCATTCACCG CCCTGCTTCC TCCCCCAGGG TGCTGACGGC CAACCTGGTG    11820

CTAAAGGCGA ACCTGGTGAT GCTGGTGCTA AAGGCGATGC TGGTCCCCCT GGCCCTGCCG    11880

GACCCGCTGG ACCCCCTGGC CCCATTGTGA GTGGCTTGGC CCTCTGTGCC CACGAGGCTG    11940

GTGGGCTGGG ACCCAGGACG GGTCCAGGCT TGATGCGTCT GTGCTCTCCT ACAGGGTAAT    12000

GTTGGTGCTC CTGGAGCCAA AGGTGCTCGC GGCAGCGCTG GTCCCCCTGT GAGTATCACC    12060

CGCCTCTCTG TTGAGCCTCT CCCCTCTCCC CAGGCAGCGG TGGCAGGTGA GGGCAGCTGG    12120

GTCGGATGAG TTGGCTGTTC TCCCTCTGAC TGTTCCTATG TTCTCTCCTT CCAGGGTGCT    12180

ACTGGTTTCC CTGGTGCTGC TGGCCGAGTC GGTCCTCCTG GCCCCTCTGT AAGTCTCTGC    12240

AGCAGAGTCC ACTGCTCTAG GTTGGGGGTG CTGGGTGGGG GCTGCCAGAA GGATGGTGGG    12300

GCTGACTGAG GACCCAATGA TGCACCAGAG CCCCCTGGAG TCTGACAGCC CCTCCTATCC    12360

TCATCCAGGG AAATGCTGGA CCCCCTGGCC CTCCTGGTCC TGCTGGCAAA GAAGGCGGCA    12420

AAGGTCCCCG TGGTGAGACT GGCCCTGCTG GACGTCCTGG TGAAGTTGGT CCCCCTGGTC    12480

CCCCTGGCCC TGCTGGCGAG AAAGGATCCC CTGGTGCTGA TGGTCCTGCT GTAAGTGCCA    12540

GCTCAGATCT CTGCAGCTCC GGAGGTGTGC AGAGCTGGGG AGGGGTCCCT GTGCTGCTGT    12600

CTGGCACCTC ACCCCTGTTT GCCTCCCAAA GGGTGCTCCT GGTACTCCCG GCCTCAAGG    12660

TATTGCTGGA CAGCGTGGTG TGGTCGGCCT GCCTGGTCAG AGAGGAGAGA GAGGCTTCCC    12720

TGGTCTTCCT GGCCCCTCTG TAAGTGCCCC CCTCACCTTG GGGGGCCCTG AGAAAAACCA    12780

TCACAGGACT TGGAGTGGGG CGGAGCCAAG GAGAACAGAT TTGGTAGAGA TGACTCCAGC    12840

GGACTCAAGG GTCCTCCCAG ACCCTATCTC TGGCCTGACT CTTTCTTCTC CCTTAGGGTG    12900

AACCTGGCAA ACAAGGTCCC TCTGGAGCAA GTGGTGAACG TGGTCCCCCT GGTCCCATGG    12960

GCCCCCCTGG ATTGGCTGGA CCCCCTGGTG AATCTGGACG TGAGGTGAGC AGTCCCCAGC    13020

CCCCATGCCA GTACCCTCAG CATGGCCATT GTGGCCTTGC CTAAGCCCTC TTCCCCGGCT    13080

GACTCTCACT TCTCTCTCTC TCTCTCTGCA GGGGGCTCCT GGTGCCGAAG GTTCCCCTGG    13140

ACGAGACGGT TCTCCTGGCG CCAAGGTAAG ATGGCAACAC TCCATGACCA CAGCCTTGTC    13200

TGCTGCTTCC CTGCCCCATC CTGGCCCTTC ACCCGGGGCT GACCCATATT CCCCTGCTCT    13260

CCCCGCCAGG GTGACCGTGG TGAGACCGGC CCCGCTGGAC CCCCTGGTGC TCCTGGTGCT    13320

CCTGTTGCCC CTGGCCCCGT TGGCCCTGCT GGCAAGAGTG GTGATCGTGG TGAGACTGTA    13380

AGTAGCTGGG CTCCAGTTCC CTGTACCTGG TCAGGCCAGG GACTCTTCAG GCCTCCTTAG    13440

AGGCCTGGGG ATGGGTGTCG GACTTCACCC AGGCAGGGGG AGGAAAGGAG ATCCTGCAAG    13500

ATGTCAGGGC CTTAATCCAA AAAACTGAGT TAAAGCTCAG CCCTAAGTCC CCTCTCCCAG    13560

ACAGGACCGC CTCTCCCATG AGTTGGCCCC AGCTCCCGTG AAGATTGCAG TGGGGAGGTT    13620
```

-continued

```
TCCCTGGGAG TTGGGAGAGA TGGCCACAGT GGGAAGCAGC TGAGGAGAGA GAGATCCAGC  13680
AGAGGGGAGG CCTCATCCTG CAGCCCCAGC CTCAGCCTTC CCTGGCCAAG AGCTCATGCT  13740
TTCCTTGCTC TCCCCAGGGT CCTGCTGGTC CCGCCGGTCC TGTCGGCCCT GTTGGCGCCC  13800
GTGGCCCCGC CGTAAGTACC CTGCTGTGTC CCCCATGCCT TCAGAACTCT ACAGATGCAG  13860
ACAGTGCCCC ACTCGATGCC AATGGAACTT CCGCCTGACA GTTTGTCCCT TTCTCTCTTC  13920
TAGGGACCCC AAGGCCCCCG TGGTGACAAG GGTGAGACAG GCGAACAGGG CGACAGAGGC  13980
ATAAAGGGTC ACCGTGGCTT CTCTGGCCTC CAGGGTCCCC CTGGCCCTCC TGTAAGTATG  14040
CTCAGCCCCT CCCCAGTCCC CATGCTGTGC TGTGGGATAG GAGGGGGAGC TTCGCCTCAG  14100
TTTCCCCCTC TGGATAGTCA TTCTTTCCCC TCCCTAGTGG GGACTGGGGT CTGAAGATTT  14160
GTGGGCATGT CCAAGTAGCT TCTGAGAGGG TGAGGGGTAC ACAGAGAGGG ATTATGGGAG  14220
AGGTCTCTGC CTATGGACAC CCTCGGGCTA GATTTCCAGA ATAATGAAGG GGCATGGGTT  14280
GCCCACACTG CCCTTGTCTC TCCAGCCAGG CCCTCAGGCT ACATTTGACG CTCACTGGGC  14340
CTGAACTGCC TTTTTTATCT GTCCTTCAGG GCTCTCCTGG TGAACAAGGT CCCTCTGGAG  14400
CCTCTGGTCC TGCTGGTCCC CGAGTAAGTC ATGCCTTCTC TCTCCTCTTC CTGAGCCCCA  14460
AGCCCAGGCT CACCTCGGGG ACCCTTGCCA GGACCCAGGC ACCCTTTGCC TCTCTGGAGA  14520
AGGGTTCAGG GACAGGGAGT GGGCAAAGAA AGGAAGAATC CTGAACAAAC AATCTGATCT  14580
AGCTTTGGCC TCTCTGCTCC CCAATCCGTC CTCCCCTGGC TCAGCGGCTG GGAGGAGCTA  14640
TGGCATGTCC TATGGAAAGA GGCTGAGGCT GGCTCTATGA GCCGTGGGGC CAGAGCCAGC  14700
AGGGAGGGTG GTGGGCCTCT CCTCCAGAGC TGGGGTTGTT CGGGCTTCTG GCAGCCTTTC  14760
TCAAACCATT TCCCCCACTC CAGGGTCCCC CTGGCTCTGC TGGTGCTCCT GGCAAAGATG  14820
GACTCAACGG TCTCCCTGGC CCCATTGGGC CCCCTGGTCC TCGCGGTCGC ACTGGTGATG  14880
CTGGTCCTGT TGTATGTAGC CCCTCATCCC CTCTGCTCAT GGCCTCCAG CCCCCATAGC  14940
ACTTGGATGC CGGAATCCCC ACTCTCTTCC CTCTCTGTGC AGGGTCCCCC CGGCCCTCCT  15000
GGACCTCCTG GTCCCCCTGG TCCTCCCAGC GCTGGTTTCG ACTTCAGCTT CCTGCCCCAG  15060
CCACCTCAAG AGAAGGCTCA CGATGGTGGC CGCTACTACC GGGCTGATGA TGCCAATGTG  15120
GTTCGTGACC GTGACCTCGA GGTGGACACC ACCCTCAAGA GCCTGAGCCA GCAGATCGAG  15180
AACATCCGGA GCCCAGAGGG AAGCCGCAAG AACCCCGCCC GCACCTGCCG TGACCTCAAG  15240
ATGTGCCACT CTGACTGGAA GAGTGGTGTG GGCCTGCCCT AGCCTCTCCC TCCTCCTAC  15300
TCCTGCCATG CCAGGGTCCC CATGCCCATA TGTGCCCCTA CCATATGGTG CTGGCTGCTC  15360
CCTTTCCCTG ACTCCATCTT GCCCTGCCCT ACCACAGGAG AGTACTGGAT TGACCCCAAC  15420
CAAGGCTGCA ACCTGGATGC CATCAAAGTC TTCTGCAACA TGGAGACTGG TGAGACCTGC  15480
GTGTACCCCA CTCAGCCCAG TGTGGCCCAG AAGAACTGGT ACATCAGCAA GAACCCCAAG  15540
GACAAGAGGC ATGTCTGGTT CGGCGAGAGC ATGACCGATG GATTCCAGGT GCGTGAGCTG  15600
GACCTCAGAG CCAGTGTTAG GAGATGGGCT AGCCCAGTGC TCAGAAGGGA CATGAAGTCC  15660
TGGAGTAGGT CTCTGCTAAG GGTGATGGAC AGAGCTGGGC TGGGAGGCAG GGGTCTCAGG  15720
TCCCTGCTAG TGGTTCAGAC ACAGGCTGCC GATGGGCAGG TGGTGCCCCT CTGATATAAC  15780
GGTGCATTGG GCAGCTCTCT GAGGACCCTG GACAGGAGGC CAGCAGGACT AGAGGTTCCC  15840
GCATAGCTCA CTCTTCCCTC TCTCTCCTCC CTGCAGTTCG AGTATGGCGG CCAGGGCTCC  15900
GACCCTGCCG ATGTGGCCAT CCAGCTGACC TTCCTGCGCC TGATGTCCAC CGAGGCCTCC  15960
CAGAACATCA CCTACCACTG CAAGAACAGC GTGGCCTACA TGGACCAGCA GACTGGCAAC  16020
```

-continued

```
CTCAAGAAGG CCCTGCTCCT CAAGGGCTCC AACGAGATCG AGATCCGCGC CGAGGGCAAC    16080

AGCCGCTTCA CCTACAGCGT CACTGTCGAT GGCTGCACGG TGAGTGCCCA GAATCCCCAG    16140

GCAGGGCCCC ACCTCTCCGG CCTTGGGCAT TTTGGCCAGG CCATAGTGCC CTCTCTCCAT    16200

CACTCCCACG TGGTAATGCC CCCTCCCGTT GTCTCCGCCC CACCCCAGAG TCACACCGGA    16260

GCCTGGGGCA AGACAGTGAT TGAATACAAA ACCACCAAGA CCTCCCGCCT GCCCATCATC    16320

GATGTGGCCC CCTTGGACGT TGGTGCCCCA GACCAGGAAT TCGGCTTCGA CGTTGGCCCT    16380

GTCTGCTTCC TGTAAACTCC CTCCATCCCA ACCTGGCTCC CTCCCACCCA ACCAACTTTC    16440

CCCCCAACCC GGAAACAGAC AAGCAACCCA AACTGAACCC CCCCAAAAGC CAAAAAATGG    16500

GAGACAATTT CACATGGACT TTGGAAAATA TTTTTTTCCT TTGCATTCAT CTCTCAAACT    16560

TAGTTTTTAT CTTTGACCAA CCGAACATGA CCAAAAACCA AAAGTGCATT CAACCTTACC    16620

AAAAAAAAAA AAAAAAAAAA AAGAATAAAT AAATAACTTT TTAAAAAAGG AAGCTTGGTC    16680

CACTTGCTTG AAGACCCATG CGGGGGTAAG TCCCTTTCTG CCCGTTGGGT TATGAAACCC    16740

CAATGCTGCC CTTTCTGCTC CTTTCTCCAC ACCCCCCTTG GCCTCCCCTC CACTCCTTCC    16800

CAAATCTGTC TCCCCAGAAG ACACAGGAAA CAATGTATTG TCTGCCCAGC AATCAAAGGC    16860

AATGCTCAAA CACCCAAGTG GCCCCCACCC TCAGCCCGCT CCTGCCCGCC CAGCACCCCC    16920

AGGCCCTGGG GACCTGGGGT TCTCAGACTG CCAAAGAAGC CTTGCCATCT GGCGCTCCCA    16980

TGGCTCTTGC AACATCTCCC CTTCGTTTTT GAGGGGTCA TGCCGGGGA GCCACCAGCC    17040

CCTCACTGGG TTCGGAGGAG AGTCAGGAAG GGCCACGACA AAGCAGAAAC ATCGGATTTG    17100

GGGAACGCGT GTCATCCCTT GTGCCGCAGG CTGGGCGGGA GAGACTGTTC TGTTCTGTTC    17160

CTTGTGTAAC TGTGTTGCTG AAAGACTACC TCGTTCTTGT CTTGATGTGT CACCGGGGCA    17220

ACTGCCTGGG GGCGGGGATG GGGGCAGGGT GGAAGCGGCT CCCCATTTTT ATACCAAAGG    17280

TGCTACATCT ATGTGATGGG TGGGGTGGGG AGGGAATCAC TGGTGCTATA GAAATTGAGA    17340

TGCCCCCCCA GGCCAGCAAA TGTTCCTTTT TGTTCAAAGT CTATTTTTAT TCCTTGATAT    17400

TTTTTCTTTC TTTTTTTTTT TTTTTGTGGA TGGGGACTTG TGAATTTTTC TAAAGGTGCT    17460

ATTTAACATG GGAGGAGAGC GTGTGCGCTC CAGCCCAGCC CGCTGCTCAC TTTCCACCCT    17520

CTCTCCACCT GCCTCTGGCT TCTCAGGCCT CTGCTCTCCG ACCTCTCTCC TCTGAAACCC    17580

TCCTCCACAG CTGCAGCCCA TCCTCCCGGC TCCCTCCTAG TCTGTCCTGC GTCCTCTGTC    17640

CCCGGGTTTC AGAGACAACT TCCCAAAGCA CAAAGCAGTT TTTCCCTAGG GGTGGGAGGA    17700

AGCAAAAGAC TCTGTACCTA TTTTGTATGT GTATAATAAT TTGAGATGTT TTTAATTATT    17760

TTGATTGCTG GAATAAAGCA TGTGGAAATG ACCCAAACAT AATCCGCAGT GGCCTCCTAA    17820

TTTCCTTCTT TGGAGTTGGG GGAGGGGTAG ACATGGGGAA GGGGCCTTGG GGTGATGGGC    17880

TTGCCTTCCA TTCCTGCCCT TTCCCTCCCC ACTATTCTCT TCTAGATCCC TCCATAACCC    17940

CACTCCCCTT TCTCTCACCC TTCTTATACC GCAAACCTTT CTACTTCCTC TTTCATTTTC    18000

TATTCTTGCA ATTTCCTTGC ACCTTTTCCA AATCCTCTTC TCCCCTGCAA TACCATACAG    18060

GCAATCCACG TGCACAACAC ACACACACAC TCTTCACATC TGGGGTTGTC CAAACCTCAT    18120

ACCCACTCCC CTTCAAGCCC ATCCACTCTC CACCCCCTGG ATGCCCTGCA CTTGGTGGCG    18180

GTGGGATGCT CATGGATACT GGGAGGGTGA GGGGAGTGGA ACCCGTGAGG AGGACCTGGG    18240

GGCCTCTCCT TGAACTGACA TGAAGGGTCA TCTGGCCTCT GCTCCCTTCT CACCCACGCT    18300

GACCTCCTGC CGAAGGAGCA ACGCAACAGG AGAGGGTCT GCTGAGCCTG GCGAGGGTCT    18360
```

```
GGGAGGGACC AGGAGGAAGG CGTGCTCCCT GCTCGCTGTC CTGGCCCTGG GGGAGTGAGG      18420

GAGACAGACA CCTGGGAGAG CTGTGGGAA GGCACTCGCA CCGTGCTCTT GGGAAGGAAG       18480

GAGACCTGGC CCTGCTCACC ACGGACTGGG TGCCTCGACC TCCTGAATCC CCAGAACACA      18540

ACCCCCCTGG GCTGGGGTGG TCTGGGGAAC CATCGTGCCC CCGCCTCCCG CCTACTCCTT      18600

TTTAAGCTT                                                              18609

(2) INFORMATION FOR SEQ ID NO: 2:

(i) SEQUENCE CHARACTERISTICS:
        (A) LENGTH: 38682 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 2:

CATTACCACC CTGAGTCATT TTGCTCAGAA TTAGTCTCTG ACTCTCAGCA ACACAGGACA        60

AATACACACA TATGCCCTGC AAAGGTAATT CAGCACAGTG GTAACAATGA TTCTTAGAAA       120

TCATTTCTCA CTCTTCTGAT ATGCAGAAAA AAATTTGTTA TGATGTAGTA TTGAAGTTTT       180

TCTTTCCTGA TAAAAATGAT TTCCACTTTA AAAGTTTTTT GTTAGTTCTG TAACGGTGAT       240

ATTTCAGGGA AATGTTAAAA ATGTTCTTGG AATATACAAT TCAACCTCAG GTCTTTTGTT       300

GTTGTTGTTC CTAGAACCTA GAAAACTTCA ACATTGTTG CCTAGTTAGA AAAAAATTTG        360

AATGTGGATT GCTCCCTGTA AACCCCCTTC TAGGAATGAC CAGTAACCCT TTCAAATTCT       420

TTCACTCCCA GTTACTTCAA AAAATCATCC AAAGTGGTCT CCCAAGTGAG TGCCTTTAAT       480

TAGAATAAAA CAAGAGTTTA TTATAGTTTT TGGTTATCCA CTTTTACTTG CATTAACCTT       540

TTTTTCTTCT TTTACATTTA GAAAGAGTAA CCTGCTTTAG AATAGTCCCT TTTATTTACA       600

GAAGCTGCTG ATGGAGTTAA CTTCTGCAGA AATTCTTCCT TAAGGCAAAG CAAAAAAGC       660

GGGGAGGGGG TGGGGGAAG GAAGGGAAAA AGATTCTCAG GGAACTACAG CCCACTTGCT       720

TCTGTTTCTT AGAGACAGAA CTGACCTAAA GATGCCCCCT TTGCGATGAC TTCTGGGATA      780

GAGCAGCACT CTAACTAGGC CCCCGCTGCC TCATGGGGAC CTTAGGCAAG TAGAGGAGAG      840

GCCTGACACA CACACACACA CACACACACA CACACACGCA CACGCGCGCG CGCGCGCACA      900

CACACACACA CAGCCTTTCA AACCTAGGGC CTGGAATGCC ATCCCAAGAG GCTTTAGAAA      960

AAGGCACAGG ACCTTTGGCC TCCCACCTCA GGGTCAAAGT ACCAGTTCCT CCTCTCCCTA     1020

GTAGGGAGTG GAGGGTTGGA TGGAGGCGGC CAGAGAAGAG GGAAGTTGGG TGCTGGGGAG     1080

AGAGTTAACA TCCACGTTGG TGGGCGCACT GCTTGGGGTG TTACCAGCGA AGATTACGAA     1140

GACCCCAAGC TCGAATCAGA AGGGCCTCTG GATGTGCTAG GGGAGGTGCT TGGGTGTAAC     1200

TGTAAGAGAT GGGACAGAGA GTAAGCAGCA AGGTCAAGAG GGACCGGGGG GCTCACGGGA     1260

GGGTTGAAGG GTCCAGGCTC AGGGTAGAAC TGGTAAATCC AGACAAGGAG CCCATGGAGA     1320

AGGGGAGGGG AGACTGGAAA CCATGAAAGA TCCCCCACCG CAGCCTCAGA AAGGAGAGAC     1380

TGAGAAATAA GTTCTCGGTC TCCAGGTCGG TTGGAGTCGT GTCGGAGTGC CAGACCATCC     1440

CCCAAAAGAC CCTCTTTGGA ATGAGCCTCA GCAAAGGCAA GCTAGGAGGT CGAAGGACTT     1500

CCCCAGGTGA CTCGGTCTAG TCTAGAGTTC GCAAAGCCTA TCCTCCCTGT AGCCGGGTGC     1560

CAAGCAGCCT CGAGCCTGCT CCCCAGCCCA CCTGCCAACA AAAGGCGCCC TCCGACTGCA     1620

ACCCAGCCCT CCACAGACAG GACCCGCCCT TTCCCGAAGT CATAAGACAA AGAGAGTGCA     1680
```

```
TCACTGCTGA AACAGTGGGC GCACACGAGC CCCAAAGCTA GAGAAAAGCT GGAAGGGGCT    1740

GGGGGCGGGG TGCAGGGGTG GAGGGCGGG GAGGCGGGCT CCGGCTGCGC CACGCTATCG     1800

AGTCTTCCCT CCCTCCTTCT CTGCCCCCTC CGCTCCCGCT GGAGCCCTCC ACCCTACAAG    1860

TGGCCTACAG GGCACAGGTG AGGCGGGACT GGACAGCTCC TGCTTTGATC GCCGGAGATC    1920

TGCAAATTCT GCCCATGTCG GGGCTGCAGA GCACTCCGAC GTGTCCCATA GTGTTTCCAA    1980

ACTTGGAAAG GGCGGGGGAG GGCGGGAGGA TGCGGAGGGC GGAGGTATGC AGACAACGAG    2040

TCAGAGTTTC CCCTTGAAAG CCTCAAAAGT GTCCACGTCC TCAAAAAGAA TGGAACCAAT    2100

TTAAGAAGCC AGCCCCGTGG CCACGTCCCT TCCCCCATTC GCTCCCTCCT CTGCGCCCCC    2160

GCAGGCTCCT CCCAGCTGTG GCTGCCCGGG CCCCAGCCC CAGCCCTCCC ATTGGTGGAG     2220

GCCCTTTTGG AGGCACCCTA GGGCCAGGGA AACTTTTGCC GTATAAATAG GGCAGATCCG    2280

GGCTTTATTA TTTTAGCACC ACGGCAGCAG GAGGTTTCGG CTAAGTTGGA GGTACTGGCC    2340

ACGACTGCAT GCCCGCGCCC GCCAGGTGAT ACCTCCGCCG GTGACCCAGG GGCTCTGCGA    2400

CACAAGGAGT CTGCATGTCT AAGTGCTAGA CATGCTCAGC TTTGTGGATA CGCGGACTTT    2460

GTTGCTGCTT GCAGTAACCT TATGCCTAGC AACATGCCAA TGTAAGTGCC TTCAGCTTGT    2520

TTGGGGGAGA CTGGGTAGAG AGGTTAGATG GGAGGGCACC CTGCCCTGAA AAGGAAAACC    2580

TGTAACCTGA ATTCCAGGTA CACTTGGAGG GCAGACTCTC AGGCATGTGG GAAAACGCCG    2640

GAATTGATAA GAAACATGGA AATTACTTTA AAAAATGAAA ACATAAAAGC CTTGCCAAAA    2700

GTTAGGGAAC TTTTCCTCTA AGTTCAGAGT GAGACAGTTA ACTCGGTCTG GCTCCTCAGC    2760

TTAGTAACCC CCAAAGGGAG CGGAAGGTCT TTTTCCCTAA GGATGAGATA TTAACGACCA    2820

ATGTGGTGGA GGAAGTCAAG GGCCTGCACC CCACAGGCCC CATAACCGCA CTGATGTCCA    2880

CCTTGTAAAA CTTGAGGCCT GCGTTAGAAA GCCCTTCAAC TGAGTAATGT AAAACTCACC    2940

TCCTAAGAGC TTTTATCTTC TGGGCATTGT AAGGCTTGTC CGGAGGAGGA GGATGACGAT    3000

GCTGATATGA TGATGGTTAT AAGGCGCCCT CTGGAGGAAG GAAAATGAAA GTACAGGGGA    3060

CAGGGCCTTA AGCAGATGGA ATCCCAATTA AAGCTTCTAC GGATTTATAC AGATTAATGA    3120

TCAGCATTTC TGGTTGGAGC CTTTCCCAGT GGCTAGTCAG TGAACCCTGG AAAGAAGAAT    3180

GGATGCTACT TGGAGTGGGT ACATTCTGAA AAGTAATATA AGTGTCTCAA TTCACTTTCT    3240

AGTCATGGAA ATGGTAACAT TTTTTAACTC AAATCTGCTC TAAATTTTGT TTGAGCCTGA    3300

GAATTACCCC TTTGACATGT TCCCAGTGAT AAGCAAACAT TATGAACGCA GCAAGTTGAG    3360

AAATATCAAC ATTGAGATGA GACTCAAGAG ACCGGGGTTT TTCCCATGAG TCTGACACCA    3420

ATTTGCTGCG TGACTTTGGG CAAGTCAAAC GGCCTTTTCT AAAATGTGAG ACAGAGATTA    3480

AAGGGACCCC AAGGCCACTT TCCAGCTCTA GGTTCCATGG CCAGACTTTC ATGTCAACAG    3540

AGAATGAAGA AGATCAGTCC GTTTTCATCT TGAAAATGGC TGCCAAAGTG CTAGACAAAG    3600

ATATTGACTA GATGGGGGAT GGTATTGTCT GACCACACCC AGTACTCCAA AAAGTTGTTC    3660

CACCCACACA GCACGGTGTC TACCACTGCA TAATTTCTAA TGCATTTGTG TGCTTGTGTG    3720

TGTGTGTGTG TGTGTGTGTC TGTGTGTCTG TGTGTCTCTT CCCCCTTCAT TCACTTTTAG    3780

TATACATACT GTGGATACTA AGGAGTAATT GCAGTGAACA AATTCACATT ACCGAGTTCA    3840

TATTTTTAAT GAGATCTTGA GAGTGGGAGG AAAGAGTCGG CTCCTAGAGA ATAAAATGAA    3900

GGCAGACTTA GGGAAATTTG AAGGTACAAA GGCAACTTAC CTTCTGATCA ACAGCCAACC    3960

ACAGTCTGGA ATAAATGTTA TCAAACACAC ATTCTTCAAA ATGGTCCGTG TCTGAGTAAT    4020

TAAAAGGCAA ATTTCCAAAA TCATAAGGAC TTCCGTTAAT CAAGTCAGGC ATAATTATTC    4080
```

-continued

```
TTCCTACTGA TGACACAATG AAGTAAACAT ATCATTCTTG TAATTTAACA GTAATTCTCG    4140

TAAATTGCCC TTAAATGTCA GTGCTGGATG TGGTCCACCC TCCTAAATTG TGACTGTTGC    4200

AACAGATGTT CTCACTTCAA ATAACGCACT TCTTGGCCAC CTAATTAAAG CAATTTTTGG    4260

GGTGATTCAT CCTACTGCAA GCTTGGCCAC ACTTGTATCC TGTATTAACC TATAATTTTT    4320

GTACCGTAGG AGAAGAATTC ACTCTTTAAG GACTTATAAC AATTATGGCA AAAGGGGGA    4380

TAGTACTTTT GTTTATTTTT TCTATTATTT TTCAAGATCT TTAATCCGGT TTTTCCATTT    4440

ATACAAAACT CTTTCTCCGA GACAAAAATG ATACATATTG GTAAAATGAT CTTACCTAAT    4500

TTAAGTGAAC TAATTTAAAG CAAAATTCAG ATGTCTGAAT TAATCCATTT TCATAGTTAA    4560

TAATGTGCAA ATTAGACCTT TTGGAAAAAG GATATTAAGA ATGGTACAAA CTCAATGAAG    4620

TACTAGGTAA CTTCAATGTT TTATAAAAAA GTAAGTCAGC TTCAATGTTT CATAAAAAAC    4680

AAATTCAATA TAGAATTTTA AGGTAACATA CTTTCCTAAA TTTTACCTTT TTTCGATATT    4740

TAGGTATTAA AAATGATCAA AATCATAAAT TATTTCCTCA TCAATTTACT AGTCTTACAT    4800

TCAGCGATTC ATCTGTGCAC TTTACCAGCT TAATTGCTAA GCATTCAAAA TATCCTTCAG    4860

ACACATTAAT ATTTCACAAC AGTTATAAAA TAGTAAATAA TTAATAATTT AATTCAAAAT    4920

ACATTTACAT ATTAATATTG CAAACAAATC ACCCTGCTGA TCCCTGCCAT ACTTTTGACC    4980

TGCATAATTT CTAGGTCATT AAAATATTCT TAAAAAAATA TAATTGGTCC TTAATTAGGT    5040

AATTCAATTC TATAAACTTG TTTCTCTATT TGTTAATTAT TGCTATTGAT CCATGAAGTG    5100

ATACTAATAA TTGTTTCCTA CTTTTTCTTT TTTTTTTCTA CAGCTTTACA AGAGGTGAGT    5160

AAAACTTTTT TTAGAATTTT TAAAAATACT TTGATTCCCT TGGCTACAGT GATGTCTTCT    5220

CTTGGAAGGG AAGAAGTTAC ATTAATATTG ACCATCCTAG ATTAAAACCT TTCTGGCTGC    5280

CTTAGAAAGT ACCCACCCAA TTTTCCAAAA TAGGCGGGGC TACTGAATAA GACTAGGTTT    5340

ATAAAATATT CATAAGAAAT ATAGAGTAAA TAATCCAATA GAAGTTTGAG TTTTAGGATC    5400

AGCTTCTATG AAGCAGAAGA TTTCACTGAG CTAGAGAATC TTTTCACTCC TTTGAATTA    5460

TTTGCAAAAG CACTTATTGT TAACACATTC TTAGCTCATG AGTTGAATTT GAGGCATAAG    5520

TACAGGTACG TATTGCTATG TATTTTTGTT CTGTAGGTAC ATATTTTTAT TTGACATGTT    5580

GGTAAAATTT TAAATTGTAG TTTGAAATAT TAAACTGAGA TAATAGTAAA TGCATAATGT    5640

AATGAATTGT GAAGGTATAT TTGTATACTA CACCAAAATG GAAGCTGTTT TTAAATATAT    5700

ATATACAATT TTCTTCATAA TAATCTTTGA TTTATTCTTT TCTAGGAAAC TGTAAGAAAG    5760

GTAAGAGTAC ACTACTTCTC CATAAATATC TAAAATTATC AGGGATAACA TAATTTAACT    5820

AAATTTATAG TAGACTATAG AAGGAAAATA CTTTATCAAA ATTTTGTTCA TATGAATATA    5880

CATTAGCTAA AGCATAAAAT AAAGTAGCTT TGATGTTTAA GATAACAAAG TTTAATTATC    5940

TTCTGGAATC ATCTGTAATT ACATTTATGT GATACAAACT GGTGATTTAC ATACAAAAGG    6000

AAAAAAAAAG ACTTGTTTTT ATTCTGGAGA TGGAAGGCAT ATTATGTTAA TTATAGGGAG    6060

TAAAAAAAGT TTATTTTAAA GGGTTTGACT ATATAAATGT GCTGTTAAAA ATGTAACAAA    6120

ATGATCATTT AATCTACAGT TATCATCTTA TTCAAAATGC TATGCATAGT ATTGTCCTAA    6180

TAGCTGAAGA CTATAGCAGC TTCCAATCCT CCAGCTGAAA AAAATTACG TATAATTACA    6240

ATTAAAATAT ATACTTTATC TATTGCATTG TGTCAATTTT TTATATGCTA TCTAATAACA    6300

TTGTAGTTAC ATCAGTCTTA CCAACTAATT ATTATCAAGA ATGATTTGTT TGTTCACTGG    6360

AAATTACTTC TTAGGCATTT ATTATTGTCC TGTTTGTATC TTTCCTGTAG GGCCCAGCCG    6420
```

```
GAGATAGAGG ACCACGTGGA GAAAGGGTGT GTAATTTTTG AACTATAAAG GGCTTCGTCC    6480

CGTATTTGAA TAACTATATG TTAGAAACTA CAGGAACTGG CAATTTATAA GAATATTATG    6540

TATCCAGATA ATTGTACACC CCTTTAAACA GGTAATGCAC TGCAGAAGAA GCGAATGAGC    6600

ATTATTATAT ATGATCAATA TTTGTTTTAG GTCAAAATTA CCGTTAAAAA AGAAAAACTG    6660

TTACAGTCAT ATTCTTTGCA TGGTCTACTT TCTTTATTTG TAATTGACCC ATCCAACACA    6720

TGCATAATGG AAATATATCT ACCTACCACC ACAGTCCTCT TTTTAACACA TTTCATTTGC    6780

TTTTGAACTA AGATCCCTTA GGTAGCTTGG AAATAATAGT GAATTAGTAG TCAGTAACAT    6840

GTTTCTCTGC TCAAATTCAT GCATGTACAA GTCAGGCTTA CATTTTATTT GTGGCATTCT    6900

TAAATCTCCC TGCTATGCTT ATTTGACATT TATAACTATG TGGTTTTGCA TTGTATAACA    6960

CTTTTGCCAA TATATGAATA CCTATATCTT ATATCTATTA GGAAGAGGAG ACTTACATGT    7020

ATTTCACTCA ATTTATTAGA AATAGAATTA AATCAGTTAA TTATTTTAAC AATACAAGTA    7080

GTTAATGATA GTAAATCTGC AGGATTTTCT CTCCTATGAT AAAGTGACCT TATTAACTGT    7140

CACATCAGTT AATTCATTCA CATGTAACAT ACCAAAACAA TTGAATCAGT TTGTCACAGT    7200

CAGAGATCGG CAATAAAAAT ACGATGTAAG TCCTTGTGCA CTGTTAAACA TATGAAGCAC    7260

GTGGAACCAT ACATTTTGGC TATAATTTTT ATATTTGAAT ACTGGAGCTT CAGTATGAAT    7320

TAATATTCAA TGGCCGAGAT AGTTCTTTAG GAAAACTACC CTGTGATATC TTAAGAGTTA    7380

TTAACCCTCT TTCTAAAATA GACTCATAAG TGAATTTCAA TCAATGACAA ATATAGTATA    7440

TTAAATTTCC ACCCTACTTG CACATAGAAA GGTCTGAACA ACTGATCTTA CCACATATAA    7500

TTCTTAGGTT TCTACAGGGC CTGTCTAACC TGACCTTACT CACTTTTTAC ATAACAGGGT    7560

CCACCAGGCC CCCCAGGCAG AGATGGTGAA GATGGTCCCA CAGGCCCTCC TGGTCCACCT    7620

GGTCCTCCTG GCCCCCTGG TCTCGGTGGG GTAAGGTGTC TTACGTATTG CTAACTTTTA    7680

GCTAACTTCA GTTGAAAGAA GGTTTATTGT GGAATTTATT TTTAGCAGTT AAGGGATAAT    7740

TCTTCCATTT GAAAATTAGT ATATTTTATT TCATTTATTT GGTTTTTTCA CTCAAGATTC    7800

TGCTTTACCC ATTCTCTTTG TGAGCCCTTG TCAATTACAG GACTGGTCTT TGTGTGCACT    7860

GAAGTTAGCT GTGGCCATCA TTACCATTAT TTAATTTGGA GATTTAATAT CTTTTATTAG    7920

TAAGGCACAA ATAAGAGGTG TTGCATTATT AAGGATTTTG ATTAGATTGA ACTGTGTAAG    7980

TGAAATCCCT GATCTTAAGC AATTTTACAA ACATCCTACG CTTTTTATTC TCCTTGACTT    8040

GAAGTCTGCT GAACCAACAT TCAAAGCGGT TTTAGGTTTA ATTTGCTTGA AACTAATTTG    8100

AGAAAAGTAC ATTTCCCTTT TTCATTAATA TCTTCTTTTA GCTTCATGTC TTTAACAATG    8160

GTATGAGTGC CAAATGACCT CACTGCAGGA AGGAAAACAT ATTTGCTTAA TTGGTTAGCA    8220

CTATGAATCA GAAGCCTGAT TCTAATACCC AACTGTATGT CAGTAAAATA AGACCTTTCT    8280

CCCCCAAAGA TCTTATTATG ATTGCTTATC TATGAATTGC ATTAAAAAGC AGCTTCTTTA    8340

ATAGAGCTAC CACTATAAGA GAGATCTTTA ACAGTAAAGT TATTACTGTG AACTAGTTTT    8400

TAGAAGTTTT ATCTTCCAAG GGGTATTTTA ATTTAATTTT CCTCTAAACT TGAAAACTCT    8460

TTATGCCCTT CCTGAAACTC CAGCAAGAAA AAGATCTCTT AGTCATTTTG TGTAGCTCCG    8520

GTGGGGAAGG GCAACAGGTG AAAATGTGAA GATGTCCTCT TGAGCTCTGT CTAATTTGTC    8580

AGGAGCCCTT AGTAACATTA AAAGTTTAGA AAGCTTCCCT TCCTCAGAGT AGAGGTAAAA    8640

GGTGGGAGTG GAGACACCGA GTTAAGGCAG AGGAAGGGCT CAAAAAGTAA AGTAGGGAAG    8700

TTCTCCATTT CAAAGAGGTG TCGGCCAAGT TTTTGACGTA CAGCTCTCAT AACTTTTTAG    8760

GAATTTAGTT CAATATAGAA TTTTAAACTA ATAATTATAT CAAAAACATT GCCCTCTTTT    8820
```

-continued

```
AAATAACAAC AGAAAAATAT TTACAAGTAG AATGAGAAAA TGAACTACAT GACTAGTAAC    8880

TAAAAATATT TTATATATAT ATATAATTTT TTTTTTTTAC TTCTCTAGAA CTTTGCTGCT    8940

CAGTATGATG GAAAAGGAGT TGGACTTGGC CCTGGACCAA TGGTATGCTT ATCTGTTTAT    9000

CTTAGCCAAA AAAATTGCTA AATAAATCAT TCATTTTATG TCACATTTTA CCACGCCATT    9060

TATTTAGCTA CCTAAGTTAA CACTCAATAC TTAGATTATA TAAAAACAAC TCTTTTTGTT    9120

TTCAAATTTA TGAAAACATA AGTTAAGGAG TTCACTTTTC TTTACAAAAG AAAGATTAAT    9180

TGATCTTTTA TGATTATATG ATCTTTTTGA TTATATGATC CTCATTAAGA TAGATCATAT    9240

ACTTATGTCC AAGAAATAAT CTTTGGACAT AGTAACCATA ACTTGGGCAA ATCAATTTAA    9300

TTTAAAACAG TAATCACTCT GATTAATTTT TTAATATTCT TTAACATTGC TTAGAATTTT    9360

AAGCAACACT TAGAGGCATA GAACTATTTA TTAAGTTCTC TGAACTTGTT GGAAAGGATC    9420

AACAAGTTCT ATCAGTCCA GCTAACTCAT TTTAAAATGG GAGAGTTTAA GCCCTTTTCT    9480

CAAAGTCATC CAGGTAACTA ATGACATAAC TAGAACTAGA TGCCAGGCAA GATGTCTAAT    9540

ATTTGCTTAC ATCATGGTTT ATGTACCTAG TCCTTGAATA AACCACTCAT TTAGTCAACA    9600

GATATTAATC AGATGCCTTC AATGGGCCCT AAACTGTATT AGGAACTGGG GAAATTACAA    9660

GGAATATGAC AGATTCTGAT CCTTCCTCAA GGAGTTAACA ATATAGGAAA TGTTTCTTTT    9720

TCTGAATTTT GACCAAAAAA ATCCTTTTTT AGTCTATTGA TTGTAAATCT ATATAGAAGA    9780

GAGTATGAGT AAAAATCTAG CATTTATGTC ACTCAGTACA AATATTCAGC ACCATACCCT    9840

ATCAGTGGAG CACCGCTTAG AAACATTCCC TATATGATGA TGATGATGAT GATGACTATT    9900

AACAAATGAA GCTTCTAACA AGCATTAGAG AGAAGTTTGA AGGGAAAAAT GCTAATACGA    9960

GCATGCAAAA TGTATACTAG CATATATGAA ATAGAGGGGA AAACTGCCAG AAGTCAAAGT    10020

GTTAGGTTGA TTAAGCACTA CAGAATTTAA TGTATACACA CACACGCAAT TTAGTGATTT    10080

TAATTAATTG TTTCAAAACA AAGGTATTTA TCTGCCCAAA GTCAACAAGG TCTTTAAAAT    10140

GTAAATTTTA CCTGAGCAGT GCACTTAGTG CTCTATCTTC AAAAGAAGAT GTTCTGCTGG    10200

AGCTAATGGC CCACAGTAAG CTAATATACT CTAAGGGTGA GATAATATTT TCTGTAAATT    10260

AAAACTCCCA CTTGAGAAAT AATGTACCTT TAATTGACGA CTTCTAATTC CCTAATTTTT    10320

TCTGGTAGTT TAAAATGTTC ATATCTGAAA TGAAAAAGTA GAGTGTTTCT TTTGGCTTTG    10380

TTTATATTGG ATTTTTGAAA TTAGCTGTTT CAGCTAATGC TGGACATTAG TCAGTTTTAA    10440

AGCAGTACCT ACATCTCAAG AAGAAGCAAG GGGGCGGAAA GTAAAGAGCT ACTAAATGTC    10500

ATTTTTAAAA AGCCCACTAA GCTGGGAAAA TTAAATATGGA TTTCAGATAC CCCTGTTTTC    10560

GGAACATCTG TCTTGGCATA AAGCAGAGTA TTTTACTTTG AAATATCAGT GAAATATAAT    10620

TTAAGCTTGC ACATCCACAC ACATGCACAG ACATATGTAA TCAACAGATA TCTGTTTCAC    10680

AAATAGGGAA GATAGGCAGC AATAAAGTAT TAAAATAATT TCCATGTTGG AAAATCAATA    10740

ACTATAAAAC CCCACAGGGT TCTTCTCTGA ATTAATGAGT AATCACAGCC TCCATGAAAT    10800

ACACTACATT TTATGTAAAT GAAATTGTTG CAAATACATG AAAAAATAAA TATAATTAGA    10860

AATTCATGAT GTCAAAGAAA ATTATTTTTT AATGTATGCC TAAAAAGCTA TTGTGATGGA    10920

AAAGTGACAG TTTCTTTTAA TGTCAGAGCA ATTTCTAAAA CCAAATGAAT AATTCTTATA    10980

ATTAAAATGA CGTACATTTT AGATAAAATC CATGTTATTT CACTCTAGGC ATTAATACAG    11040

TAAGGTAGGT TTGACTGCAG AGTCCCCACA GCTGATGTCA CGAACAAATT ACTTGAGACT    11100

GGTACATGAA ATATTTTCAG CATTATGAGG AACAGACCCT ACGGATGAGC TTACACAGGC    11160
```

```
ATTGATTACT GCAAAGAGGA GTCAAGAAAG TGTATTTAGC TTACAAACTA TTAACAGCCC   11220
TGTTTTACCC TACTTTTGTG CTATGGAAAC AACAAAGGGG AAAACAATCT TCCATCATTT   11280
GGGCCATATT TTCAACAATA ATATCATATA ATAGACTCTT CCAGAAGGCT GTTTCAATAA   11340
TGTTTTATTT TTCCTTCACC CCTCATTACA TCCACTTTTG TTTGACATTT TCATCAGTCA   11400
CCAATAACCC TTAGAGGAGC GATAAGGTTA TAACAAACTT CTCTCTAATC ATTAAGAAGG   11460
ACTTTTGATT CTTTTCAATT TATGTCCTTT GTGGCAATAA AAATACCAAT TCTTAGCTA    11520
AATATGACAT AGGAAGATGA CATATGATCA AAGATATCCA AATGGACATG CTTCATCTGC   11580
TGTATAGAAG ACAATTGTAT ATTCTGCACT TCTGCAAAGA CTGATTCACT TCATTGCATC   11640
AGAACAATCT CAATATGCCC AATTGTGCAC AACTTTAAGG AACCTATCTG CCCCGTCTAA   11700
TTCTCATTGA TTTCTGTTGA TATGGATTGG GAGAAAAGGA AAAGCAAAGG GAGAGAACTA   11760
GTGCAGGAAG TTTGAGTCCT TAAATTCTTC CTTGGGAGGA ATAAAAACTA TGGAATCAAA   11820
CCACAACAAT GGCACTGCTA AGTTGGTCAT GTCTGACCCC AGCCAACACC ATGACAACTT   11880
ATCAGTGCTA ACTGTTGATA TATCTGCTTT CTTTACAGGG CTTAATGGGA CCTAGAGGCC   11940
CACCTGGTGC AGCTGGAGCC CCAGTAAGTA CTGAAAGCTT GTAATGCCTC TTATGTAAAA   12000
AGACAGAGAA TTAAGAAATA AAGGCTTGGA GTATGACATT CTTTTTTTCT TTTAGGGCCC   12060
TCAAGGTTTC CAAGGACCTG CTGGTGAGCC TGGTGAACCT GGTCAAACTG TGAGTACATT   12120
TTTCCACCTT TGTGATAAGT TTTTTTCCAG GAAGTTTATG AATATAACCT TAGTGAAATG   12180
ATGGGTCTCC CATTTTCTTA GGGTCCTGCA GGTGCTCGTG GTCCAGCTGG CCCTCCTGGC   12240
AAGGCTGGTG AAGATGTAAG TATTTACTCT TAAGCACTTT CAAAATGCTA TTTAAATACT   12300
CTTGCCTCAA CAAGATTTTC TAGATTCAAA TTAAGTATTC TGCCAAAAGC TGAATATGCC   12360
TGACAGAACT CTTAATGTAT GGGAAATATT ATTTTAATGA AATATTAACT AACCTACTTG   12420
TATTAAGGGA AAGATTAAAT ATATATCTGG ATCCATATTT TTATGTGATA ACTTTCTCCC   12480
CTTTTGTAAA AACCAAGATT CCCCCATTTT GTCTGATAGT TTACCAAGAA GAAGTTGACT   12540
CTACAATGTT TTCATGTTTA GGGTCACCCT GGAAAACCCG GACGACCTGG TGAGAGAGGA   12600
GTTGTTGGAC CACAGGTGAG ACTTTTTACA TTGGTAGATA GCACAAACAT CATAGGCCTA   12660
TAAGATAGTT GCTAAAACTA GCATCAATCT AAATGACAAC ATAGATGTCA CCCAAACTCA   12720
TAACATGAAT CGAAGGCATC TAATAAAGAA AAAAGCCTAG TTAAAAAAAA ATGCATATAC   12780
ATTTTATTCA TGCAAATAAT GGAATATAAA TGACAGCAAG CATACCATAA GCAACTAAAT   12840
TGTGTTTTCT ACAAATACCG TATTATTAGT TACTCACATT AGAGCAAGTT AATTTGTCGC   12900
TCTGTGCTTA GAGGTATACT AGACTTTGGT TCAAAGCTTG AACTTTGATG AGAATAAATA   12960
CTTTGGAGGG AAGAAGTCAC TGTCTTTTTA TTTATGGTAA AACATTATTC ACCATCTTCT   13020
GTATTTCTTT CTAAGGGTGC TCGTGGTTTC CCTGGAACTC CTGGACTTCC TGGCTTCAAA   13080
GGCATTAGGG TGAGCACATT CTTTACTCAG AAGAGAGAAA ATGCCTATTA ATTTTTGGAA   13140
AAAACTCAAG TATGTTTAAA ATCTTGGGTG ACATATACTC ACTTTCAAAT CCCTGGAGTT   13200
TGCCAAAGGG AAGAAAGAGT TAAAGAGTCA GATTTCTTGA AGTAAAGTG GGGTGCAATT    13260
TTTTCAGTCT GTTCATAGCT ACCAAAAAAC AGGCTCACTA CAGAGAAAAT TATATAGAAC   13320
ATGTATTACT TATTGAGTAT TTACAACCGT CTGAAAATCA TAAAATTATT AAGGATGGAA   13380
AAGATGTGAG AGAACACCTA GTCCTCCATC CTTCTCTCTC AATGGCAAGA AAGTTAAGTG   13440
ACCTATCTAG GGCAATAGAC TGAGTTTGCT GGGACCTGGA ACACTGGACT TCTTTCTACT   13500
GCAGCAGACA AGACTTACCC AAGAGAGATT AATGGCAAAG ATATACAATA CAATTTTTAT   13560
```

```
TTGACCAAAC ACTATCATGG AACAGCATTT TATAATAAGG CTTTCCTTTC AGGGACACAA   13620

TGGTCTGGAT GGATTGAAGG GACAGCCCGG TGCTCCTGGT GTGAAGGTAA ATATTAAATT   13680

AGAAGCACTG TTTTTAAGCA CTTGATTGAA ATTCCCCATG ACCTCCAAAA AAGTATATTA   13740

TACTGAAGAC TACCCATATT ACAAAAAGTA TTTTTATTTT TTTTCTTTCC TGTACTTCAA   13800

ATCCCTCAAG GATGGGGACT ATGAGAGTCT GTGAAAAAAG GTCAATTATT AATATTTATT   13860

AAAATTCAAT ATCTATTAAA CAATTGAGAT AAAAATAATA TTAATAGTTT CTTGTTCCAT   13920

TTCCTTTCCT CCCTCTATAA TTCCAGTGTA TCTCTGCAGC CAAATAAAA GTAAATAAAC    13980

ATATAATCAG AGATTACGAC ACTCTGTATT ATTTTAAACT GTAAATTCTC CTTTGCCACA   14040

CACTAATTAG ATAGGTACAT TCATGTCGCT ATACACTTTT CAACCTCTTT CCTGTGATTT   14100

ATCTGTGCAC ACTCAAAAAA ATTTTAATTA GGTAATTAAA GTCTCAGAAG TGTGTTATCT   14160

CTTGGCTAGG CTCTTCTCTG ACAGCGTTTT CAACTATAAA ATGTTCTCTT TCCTATTAAG   14220

GAGATAATGT GATATTAAAG TGAATACCAA CGTAATTACA AATTAATGAG TAACGAATAC   14280

TAGCGGGACC AGAAATGAAC ATGAATATGG AGAATCTATT CTAACTTTCC AGCTGCCACA   14340

CAAATGGATA AGGTCAAACT CATTCTCCCA AGAGCCCGAT ATAACAGCTC AGACTACTAA   14400

TCACTGTATC CATAAAATGT TAGAGCTGCA AGGAGCTTTG GAGACCCCCT CATTTTGCAG   14460

AGGTGGGAAA CTGAGGCTTC GTGAGAGCAA TTGACTTGCC CAAAGTCACA CATCTAGAGG   14520

TTAGAAAGTC ATAGGCTAGA AATGATCCCC CCTTGCCACT TCAATGCTTA TTCCCAAAGA   14580

ATAGACTTCA CATAGAATCC TGGAAATTAA GGGTCCTTAT GAGGTCTCTT AAACCATATT   14640

TCCCCTATAT CTAAATCAGA TTATCTTTAA AAAAGTTCT TTTACATGTG CCATAGTATT     14700

AAATCCCACT ACTACTACTA CTACTACTAC TACCCTGGTT TTTACTCAGG ATAAGAATAT   14760

AGATTGGAAA TAAATATGAT GGCTCTAAAA AATACCATGA AGCTTCAATT TTTCATGCAC   14820

ATTTTATGAA AGTGATAACA CTGAGTGTTC AAAATAACTT TAAAAAGGAT AAATATGGTT   14880

ACATTGAAAG CAAATTTATC CTTTGCCATC TCTTTTTATG ATATTGTTTC TAGTATATAA   14940

TTGATATCCT GAATCTAAGG GAGAAATTGG GGAGGAGGTA CACTCAAATA ACCACATCTC   15000

CTTAGAACCT GGATATGTGG TACTATCTGA ATAAAAACTC ATGTTAGCAC ATTTTAAAAT   15060

CTGTGTGTCT GGCATAATTG AAAAACAATC TATATGTGTA AGAAATATTA TGAAGTATAT   15120

GAATGGTTCA AGTAAAAAA AATAGAGTAA AATTGCACTA TCAGGAAAAA TAATTGTTAT    15180

ATTTAATGAA CAAAAACTCA ATCCTTCTCC ATGTAGGGTG AACCTGGTGC CCCTGGTGAA   15240

AATGGAACTC CAGGTCAAAC AGTAAGTATT GACTACTTCA TTGTAAATTT AAATGTGTAC   15300

ACTCTTTATG AGATGGAACT TCTTTAATGT TTTTGCTAAT CACTGTATCC TTCAGCATTG   15360

TATTCTTTGA TGTTTTTCTA ATAGCCTTCT GATACTTAAT TGAAATCCAC TACTGTTTAG   15420

TTGGAATTAG AAGGCAACTT ATTTATTTTT AGTGTATTCT TGTACAGGTT GGAAACTGAA   15480

CAAAGCAAAT GATGCCTGTG ACTTTTTTTA AATTAGCATT CTGGATTTTA TTGAAAATAT   15540

TTCTGCTTCT AGGGAGCCCG TGGGCTTCCT GGTGAGAGAG GACGTGTTGG TGCCCCTGGC   15600

CCAGCTGTAA GTGCTTCCAT TTTTGTTCAG TTTCATCCTT TTAAAAAATC TTCTAATGGC   15660

TGTCATTTAA GTTTCCACCT GATCTTCCCT TTATTTTCTT CTTAGGGTGC CCGTGGCAGT   15720

GATGGAAGTG TGGGTCCCGT GGGTCCTGCT GTAAGTTTTG ACACTGGGGA GTTTGAAAGG   15780

AGTTGAGAAT GTGGGGTGGG TGCTGTCTTC TTCATTAATC TCTTACGAAA TAGCATCATT   15840

TCAGACACTT TACCAAATGT TCTGTGAGGT CTTTTGAAGG CTCCATTTAT AAGTAGTGTA   15900
```

```
                                                    -continued

AGCCATTTAT AAGTACCTGA ACTTTTGATT GATGTATAAA GCAAAATATC CCCACCCTGG    15960

ATACCATGAA TGTCTTGCCT TTGATGAGAT CCTAACGACA ACAGACTGGT TGTCAGTTTT    16020

TTTCTTTACT AATATAAACA GTGTCATGCC ACTGTAAGCA ACTTCAATCT TCTGCCATTG    16080

TTATTGTTTT CTTAATTTAC TTGGAGGAAA TTTCTTACCA CCTTCTGCTT TGATTTCAGG    16140

GTCCCATTGG GTCTGCTGGC CCTCCAGGCT TCCCAGGTGC CCCTGGCCCC AAGGTAAAAA    16200

CACTGGTGAC CATTGTCACT ACTTTGATAA ACTTTTTACT GTGATGTGAA AGATTGGAAC    16260

TGTGTTTGCA GATAAAGAGA TAATTACGAA ACAGTTACCT TAATTATTCC TTCCCTTCAA    16320

AATGGACATA GAATGACCAG TTTTCTCACT CTACATTTGA AATAGATCAT TTCTCTGCAC    16380

TGTGCACTGT GCCCATCGAT ATAGATGACA ACATGGAAAT TGTCTCTAGG ACTAGTTAGT    16440

TAGGACTGAC TGAGAACCAG AGTCAACCAC AGAGAGACAG AAGGAGAGGG AAGGTAGTAA    16500

CAGTAGCCAA GATGGCAGAA TCAAGCAAGG AAAATAGGAA ACCAAACTCA AATCTTGTAA    16560

TAAAACGGAT AAGAAAAATA ATTGCAATTT TGAAGTTTTA TGAAGACATT TCATAAAACT    16620

TGGCATCTTA AAAACAGATA TGCTGTTTCA TTATTTGCTG GTTAATTCCT TGGTTTAATT    16680

TCCTCTTTTA GGGTGAAATT GGAGCTATTG GTAACGCTGG TCCTGCTGGT CCCGCCGGTC    16740

CCCGTGGTGA AGTGGGTCTT CCAGGCCTCT CCGGCCCCGT TGGACCTCCT GTAAGTAGCC    16800

ACTGTCTTTA AACTTTATTG AGTAAAAGAA AACAAAGGTG GAGTATGGGG AAGAAGAAGA    16860

ATGAAGATGG GGTCAAAGAA GAACCGAAAT ATTCCAATTA ACTGTATATCC TTCTCCTTTC    16920

CTTTTCCTCA TAGGGTAATC CTGGAGCAAA CGGCCTTACT GGTGCCAAGG GTGCTGCTGT    16980

GAGTATACCT GTGTAGCTAA AATGTGCTGC TATGATTTTA AAGGCATTTA ATGTGTGCTG    17040

CCTCTACAGC CCATCACCTC CCTAATGGAC CACACTGCAT TTTCCTTCAT AGGGCCTTCC    17100

CGGCGTTGCT GGGGCTCCCG GCCTCCCTGG ACCCCGCGGT ATTCCTGGCC CTGTTGGTGC    17160

TGCCGGTGCT ACTGGTGCCA GAGGACTTGT TGTAAGTGGG CATGACTGTG GTTCTCATCA    17220

TCCTGAAATA CCACCTCTGC CATCATTTCA TCACTATCTA GACTTCCACT TGTAGTTTTA    17280

TTATTCCTAT TTTTCTCTTC CTTAGCATTT TTAGTTTATA TTTCTTATAT ATATATGTAC    17340

ACTCCCGTCT GCTATATGCA CACAGACATG CCCTTCCTGT TATCTTAAAT CATTACCTCA    17400

AGGTAAATGA GGCAAAGTTC TACAATATCA GTTTTGTCCC TTCGACCAAT AATACCATTC    17460

CCCTGTACTC AATTTAAATA TGAACAGGGT ACATTTCCTA GAGAACTTGA GCTTCTCTTT    17520

ACCTTGACCC ACAAATATTC TAAGAGATTT GTCTGCAAGA GAGTTTCAAC AAATGTTTGT    17580

CCTTTGACCA CTGTTCTGTA TTGAACCCTA GGGTGAGCCT GGTCCAGCTG GCTCCAAAGG    17640

AGAGAGCGGT AACAAGGGTG AGCCCGTAAG TAGCTCTATC ATCACACTTT TATAAAGTTA    17700

ATTGTTTTTC TCATTCCAGT TTCTCCAGCT GGACATAGTA TTAAAATTAT TTTTTTTACT    17760

CCCTCTTCTT TTGTTCTTTT CATTAAACAG GGCTCTGCTG GCCCCAAGG TCCTCCTGGT    17820

CCCAGTGGTG AAGAAGGAAA GAGAGGCCCT AATGGGGAAG CTGGATCTGC CGGCCCTCCA    17880

GGACCTCCTG GGCTGAGAGT AGGTTTCAAA TGCTCCCAAC ACCCTAACAC ACCAGAGGCA    17940

GATTATGATA CCCCTTCATT GGGAATTGGT CAAAATTACT GACTGTGTTT CTTAGGCAA     18000

AAAAAGCATC TGCTTTCCAT CTGCCTTATT AAATCAGTGA CTCTCAATTT AATATGTTAT    18060

AAAATTGGCC TGGAAACAAT GTTGACCTAC TTTTGCAGGA TGCTCATCTA TGAATTCCTC    18120

TAGGGGTTGG GTGAAGTGTT TTGGCTTGGT TTGTGTCTGT ATCTCCCCTG TAAGAGATCA    18180

TGCTATTTTT AACAAACTCT ACCTTATCAA AGCCAAGAGA TTTCTTTAAT TCTCTCTATT    18240

TCATGTACTT TCTTGCAGGG TAGTCCTGGT TCTCGTGGTC TTCCTGGAGC TGATGGCAGA    18300
```

-continued

```
GCTGGCGTCA TGGTAAGCTG TCTATCACTT ACTTCCTAGA AAGGGGCTTG CTGCTTCTGG    18360

TGGTGGGTGT GTCATTAGCT TTAGCATCCT CCTCCTCTAT CTGTTTTTTT TTTTTTTTTG    18420

AATAGGGCCC TCCTGGTAGT CGTGGTGCAA GTGGCCCTGC TGGAGTCCGA GGACCTAATG    18480

GAGATGCTGG TCGCCCTGGG GAGCCTGGTC TCATGGGACC CAGAGTAAGT TTCAAACTGA    18540

TTCTGAGCAA ATCACACCTG GCATTACTTC CTTCTTTAAA GGGTTGGTTA ATATTGAAGA    18600

TAACAATAAA AACATCAAAA GTAAATTTGT TAGTAGTCTT GCTGACAGTT GCATTTTTGA    18660

CTTTATCAAA GCTCAGTAGA TATTTTCATG CATTTAATTA GTTCATAAAT TTTCTATTTA    18720

TTACTTGATA CAATGGCTAT GAGGTTTTTG GAAGAATAGA TCTATTTTAA TATATCCAAA    18780

TTAGATTGGT CCTCCTATCA GCATGAATCT TTTATCTTAA TTTGTGAGTT TTATATAAGG    18840

TGTTCATGAA ATATATTAGG ACTATACATT TTTCGTTTAT TAGATTCATA AGTGAAGTCT    18900

TTTTCCTAGC AATCACAAAG TGCTGTAATG TATTCAGCAT CACACTAGCT ATGGAGAAAT    18960

AACCTCTAGG TCCATAGACA CACTAATCCA TAGCAATAGA GTAATTTTTT TGCCTCCATT    19020

ACCTCTTATG GGTGAATATC AACTGTAATT GTACCACAAA CAAGTAATAG GGACACCAAA    19080

TATAGCAATA AGAAATCCAC TTTGGAAATT GTTTACTAAA AGTATTAGTT TTTCTATTAT    19140

GAGGTAAATA ACGTGATACA TTTTGCCCAT ATACATGTTG CTTAACAGTT TCTTGAGATA    19200

TCTATAAAAG GATGAGTTGC ACTAAATTTC AATAAAAGGA AAGCCACAAA AAAATAGAAG    19260

AAAAATTTCA GAACTCTTTT CACACTTCCC AGCTAGTGGC TAATATTCCT AATGATTTAC    19320

CCTAGGCAAC AAACAAAAAG TCGGGGAAA AGGTGCCTTT GTTAGACTTC AGTTAATCTA    19380

AGGCTTGAGT ATGTAAGTTA AAGTGCCAAT ATAAAAACAT CCTCATTATT TATAGGGTCT    19440

TCCTGGTTCC CCTGGAAATA TCGGCCCCGC TGGAAAAGAA GGTCCTGTCG TAAGTATTGC    19500

TCATTTTCCC ATTATATTTT CAAGGACACT TATTGCACCC TTATCAAGTC TATTTTGTGG    19560

CTTATTTATA CATGAACACA TTGAAAATAA ATATCAGACA CATACATCAT CTGGGAATGC    19620

AGAGTAATAG ATTGTAATTA TGGAGTCCAA ATGAATACAG GACTGAAAGC AGAGCAGGGG    19680

AGAGAAAAAC ATGGCAGGGA AAATTGAAGC AGGTGACAAG GGGATGCAAG AGAAGGGAAT    19740

GAGGGAAATT GCATACATAC GAGATTGAAT TGGCTATGTG TGTACTGACA TCCTAGTTAG    19800

AAAAGGAAAA TGGATTCATA ATTTATTAAC GCTTTATACA AGAAGCTCTA TGCATTCAGA    19860

AAACTATTCT GTTTCATCCG TGGCAGCATC ATAAGCTTGA GGTTGTGAGA ATATGTTGAC    19920

ACTGAGTAAA CTTGAAATAA CTCTGCTTTC AGGGCCTCCC TGGCATCGAC GGCAGGCCTG    19980

GCCCAATTGG CCCCGTTGGA GCAAGAGGAG AGCCTGGCAA CATTGGATTC CCTGGACCCA    20040

AAGGCCCCAC TGTAAGAATC ACCACAACTT TCTTACCCTC AGCACTTTCT GTAGCCAAAT    20100

TTTACCAAAC TCTAGTATTT ATCTCCTGCG AATCAGTCCA GTCTCAGGGA GTTTCCTTTC    20160

AACACAGGAA AACTGCAGGC CACTTATCAC ATTAAAAGTT TACCTCTAGT GTATCCTTAT    20220

ATCCCTGCTA AAAATCCATC TCCTGAGCCC CATGCTTCCA CAGACACAGG GACATCTTAC    20280

TGTACATGGA GCTGCATGGT GATGGATCAT CCTTAGATAA CAGAAACCAC AGACTAGGGA    20340

TCTCAAAAGA ACACAAAAAC AAGCAGGATT CAACATTGCA AAATCACCGT GGTTAATTTG    20400

ACATTAAATG TGCAAAGCTG TTCTTTGTTT TGTTTTTCAT TTTTACTCTA GGGTGACCCT    20460

GGCAAAAACG GTGATAAAGG TCATGCTGGT CTTGCTGGTG CTCGGGTAGG TGCTAACTTG    20520

TGTACAGATC TATTCACATA GCATTCATCT AAGAACCACA CTTTTTTTTT TACACCATCT    20580

GATATCATTT TGTCACTTTC TTTTCAAGAT GGCATCCCCA GGGGTCCTTT TACTATCATA    20640
```

```
AAATGCCTTT TTAAAAACCA AACTTATAAA ACAGTGAGCA AAAACAAATC AGAATATACA    20700
TTAGGTCAAA AAATACAGAA GCACTTGGCT TTTATTTTAT TCATTTTGTA ATTAAAAGGG    20760
TATGAATATG TAGTAGCATT CTCTGGCCTT TATAAATTGC CTTGTGTCGC ATACTTCGCT    20820
TGAGTCATAT CAAAAGTTAG TAGGCAAACC CATAAATATA TATACCTACT ATGTACCCAC    20880
ACAAATTAAA AATTTAAAAA GTTAGTAGGC AGTATTTGGG CTTTCGTGGG AACCCACAAT    20940
GAGTTTAATT CATGCTAAAA TGACAAACTT GTTTTAAGGA AGTAATACCT GAGGCTTTGA    21000
GACATCTTAA ACTACCTGCT TGCAGCTAAC CATCAGCCTT TCTGTTAAAT ATTTTTAGGG    21060
TGCTCCAGGT CCTGATGGAA ACAATGGTGC TCAGGGACCT CCTGGACCAC AGGTGAGTAT    21120
TTCTCCCACT CTTGTGCTCT TCTGCACTAG AATGTATATA GTCCTCAAAC TGGCCATCTC    21180
CATTTTCAGT CCAAAAGTTA TACAGCTAGA CAACAGTGGT GACATACGTT GCTATTTATG    21240
CTCTCTTTCC TGTCACTTTC AGGGTGTTCA AGGTGGAAAA GGTGAACAGG GTCCCGCTGG    21300
TCCTCCAGGC TTCCAGGTAA GTCAACTCAA GCATATACAA TACTGCCTTT GGTCAGCCTA    21360
TTGAGCTGTA ATCACCATA CCGTACCTCT CTTCTCCACC ACAATAACAT GATTTCAGGA     21420
CTGAAGCAAA GAAAGGTGCA TTTTTTTCAA ACAAACTTTT GTGTAATGCT TAATAACATA    21480
CAATCGTGCT CATGTTGATA TTTGGTAGCC ACCACCCCA AACTCAATTA TTAGCAAATC     21540
TCCTGAACGT AGCCATGGGA TTGAGATTTG TATTTCTTTT CATTTTTAGG GTCTGCCTGG    21600
CCCCTCAGGT CCCGCTGGTG AAGTTGGCAA ACCAGGAGAA AGGGTGAGTA AAACAAGTAA    21660
TAGTAAGTAG TAACTACTAA ACTTGAGAAT TTCCCCCTGT TTAATACCCC ACTGCTATGC    21720
AATTATAATA TGTAAAAGAA AATTTCGTAT TTCATATGTT AATGATAGTG TTTTACATAC    21780
TTTGGTGCTG ATGGAGAGAA TGAGCCAAAT TACTTTAGTT CTGATTACTT TGTTTTACAG    21840
ATTTAATGAA ACATCACCTT ATGAAAGTAA AATCTATCAA TGAATATTTT ATTTAATAGC    21900
CTTACTTTTT GTATTGTTCT TGATAACGTT AAGATACAAA TTATTTCCTT CCCCATAGTG    21960
AAAAAGTAAA TGCACAATTT TCAATCAAAC TAGATCCCGA AAAATTCCTT TTGTGTTTTT    22020
CTTGGCATTC AGACATGACA CTACTATACA CAATCAGGGC ATGAGTTCTG AGTCATTTTC    22080
TCTCTAATTG TGATGAATGT GCCCCTATTT AGTTACATTC TGTGGCCTGG TCTCCTTTGT    22140
CAACAGTAGG ACATATTAAG GAGACAGCTG GTCAGTAATA AAAAGAGATA CACTTGGGTA    22200
TACAATTAAC TAGGCAATGT ACAGAATATG ATAATTTCTC TTAAGAAGAC GATCTGTTAT    22260
ACAGCTAAAA ATAGGCAACG TCTAATATTC ATTATTATTT ATCTTATTAT TGAAGGAAAT    22320
AGTCTGTCAC TTTTTAAAAA GCAATAAACT AAATAATGGG AAACAAATTT TTTGATACCA    22380
AGTTCTGGGA TGGATACATT TTTGTCGACC AATAAAATTC TCTCTTTCTG TATCTTTCCA    22440
TACTAAAAGT TGTTCTTATT AGCCTGTGTA CTTATGCACT CATGTAGATA CTGCCAGGTT    22500
TATTTCACTC TTTCCAAATT TTTCAAATAT TTTAATCATA AGTGAATTTA CAGATCACAC    22560
ACAGATTTCA TGCTTTATTC TCATGTTTTG TCTAGGGTCT CCATGGTGAG TTTGGTCTCC    22620
CTGGTCCTGC TGGTCCAAGA GTAAGTGTTA CTTCATTAAC TTTCATAAAC TCTGGCAATG    22680
TGTTTTAAA AGTAGTAGTG CTTTCTCCTT AAAGCCACTG ATGACCCTGC AACAAGTCTC     22740
TGATGCTCTT CTATAGTCAA ATGTAATCTG TAGAAAGCAT TAGATTTCTA AGTTGATAGA    22800
GAATTTTTTG TTTCATGGCT CATATTTCCT ATTCAATAAT TACATAGTTA TAAGAAACAC    22860
ATAAATCAAT ATATATTATA GTCAGTGATT TATATAGACA ACTATGCTAC ATTTGTGACA    22920
GTGGCTCAAC TTGAGCTAGG AAAAATAATA TGTTACTAAG ATATAAAGTT AATTTTGGCC    22980
ATGTGTGTTG ATGTTCAAAG CCTAAAGCCG AACTTATGAG TAGTCATATA AAGAAAAAAA    23040
```

```
AACTTAGTTT CTCTATGGGT ATTAGCATCA CTGAAATGAT TAATTTGCCC TGAAAGTATT    23100

CCATCATGTC ACTAGTTAAC ACATATGTAG GAAGCTCAAA GAACCCAACT TATAACAAGG    23160

TCCTTTGAAA CAGTTACAAC GTGGACCTAT GTGATAAATA TTTTGGGCTA TAGAATGCTA    23220

TGCTCTAGTG ATATTTAGAT GTAAATTGGA GATATTTAGA TAGACAGACA TATATATATA    23280

TACACAAATA CATATATCAA ATATACATAT GAATATTGTA ACTGTTATAT CATTATTACA    23340

CAGGGTTATA AAAGGGGGC ATAGATAGGA GAATATCTAA TGTTATCTAC ACCTGCCATT     23400

GCTATTCAAC TAAAATGACA CAATCTTTTC TTTGAATACT ACACATAACT GGCATCTGTT    23460

TTTACCTATG GATTTATCAC AGAAAAGACT CCTCAAAGAA GGGGAATGAA TTGCAAAAAT    23520

TGAATATTAT ACTCTAGAAG CAACGAATTC TGGAGTCGTA GTCATGGAAC ATTAGAGCTA    23580

AGTGACACTT TAGAGAATAT CTCATCAATC TCTTCATTTT ACTAGTGGAG AAATTAGGAA    23640

CAAAAGAAAT TTTAATTTGC TAATAAATGC AAACCAGGGC TCGGAAGCTA CACAAATGTA    23700

AACTCTCATA TGTAAAACAG TATCACTGAA AGTGATGAAT GGTGCAACAC TTCTTCTAAT    23760

CACTTTTTTC AGGGGGAACG CGGTCCCCCA GGTGAGAGTG GTGCTGCCGG TCCTACTGGT    23820

CCTATTGGAA GCCGAGGTCC TTCTGGACCC CCAGGGCCTG ATGGAAACAA GGTAAAATCT    23880

TATGTTTTCT ATATTGCTGG TTTGGCCCAG TCTGCCTGGA ATAAGTAGAC CCTTTACAAT    23940

AGAAAGATAA TTGTTTTTCA GATTTTTATT TATTTCCAGT TCTGTGATGA CTTCCCTCTC    24000

AGTAAACAGC AATCCGATTC CAGTGGACCT GAATTATTCT AAACAAACAA ACAATAGCAA    24060

CAAACTGTGG GGGAAAATTC AGAGTTCCCA AAACATAAAT GAATTAGTAT GGGTTGTCAC    24120

TCTTTTCTCC TCACGCTGTT TATGCTTTTG TTTTAATCTA GAAACATTGT ATTCATTGGA    24180

CATTATTTTC AGAGAAAATA ACTTTTTATC TTAACATCTC ATCCCATAGA GTAAAATTTC    24240

AACAAGTAGT CTGACTTTTA ATAATAAGAG TTTATGATGA TGAAAATTCA TTGGGCAATA    24300

CATTCACCCC CAAAAATTTG TCTGGAAACT TGTGTTCCAA AATAGAATCT GTGGTTTAGA    24360

TTTTAAAATA GATTAATAT ACATTCCTGA AAAAGAGATT ACCTTAACCA CAATAAAAAG    24420

AAGACAACAC ATATTATTTT CATTCTTAAC TCTAGGGAAA AAATGTAAAC ATTAGTTGCA    24480

AAAAGCTATT TTAGTGTATG GAAGGATGTT CTTGGGAAAA AAATAAAAAC ATAAAAGGGA    24540

GAGAGGAAAT AAAGAAACCA CGGTTTTGTG AGGTAGTACT TTCAAAGGGA TCTATGTATC    24600

TCAGAAGCTA GTCAACAGGT TTTAAGTATG TGGAATTGTA GGGTTTTATA TAAAAATGAA    24660

GATACAGTCT CTACTCTTAA GGAGATTAAA ACACAAACAT CTCCTCAATT GACAAGGTCT    24720

CTTTCCATGC TTTCTATCTG GGCTAAGAGA CTTATCCTTG AAAAATGTTT GTGGGTAAAC    24780

ATTTTTTACT CTCTGCTTCC CATTGTCCTA TCCTCTTCTC CATGCCTGCC ATCCTTAAGA    24840

GGACTGAAGC AGGTTATAGA GGAATCGCAG CTGTGCACTC CCACTACCCT CATCTCTTCA    24900

GTCACCATGT CATTAACAGC ATCTCTCTCT GCTATATTCT CCCTCCTTTC AATAGCCCAG    24960

CCTTCTTTGT GTTTCAAAGC AGGCAAGAAG CCTGTCTAGC TAGCTGTTTA AATTGGAATT    25020

CTTCTAGAGT TTGATTCTTC ATTTTCTTCT TTCTCCACTA AAATTGATTT CACATGTGTT    25080

TGACTCAAGG GTGAACCTGG TGTGGTTGGT GCTGTGGGCA CTGCTGGTCC ATCTGGTCCT    25140

AGTGGACTCC CAGGAGAGAG GGGTGCTGCT GGCATACCTG GAGGCAAGGG AGAAAAGGTA    25200

CGTGTTGACC CCTATTACAT ATTGTTGATG AACTCTAGTA AAGAAGGCTG CACAAGGATG    25260

CCCAAGTTTT CACAATTCTT GGCAGGTGGT CTGGTAGCAT TTTCATATCT ATCTATATAC    25320

ATTTCCCTCT ACCACCTAGC ACCTACACAT TTCTAAACTC ACTAATCTGG CAAGAAGTTC    25380
```

-continued

```
CTTGCTACCA TGGAATTTCA CACAAACAGA TGGTGTTGAG TAATACATGA GGCTCATTTT   25440

AATGCCACTA ACAATAATGC CTCATCCTGT CCTAATTAAT GGGAAGAAGC TACATTGAAC   25500

AGCTGTCAAC CATGCTGCTG CATTAGTTAT GCCGTAAGAG TGATCAGGCG CTGCAGCCCA   25560

TTGTGATGTT GCCTTACAAT TCTGTCCACA TGAATCTGTA CCTTGCTTGA TTATGCTTCA   25620

GGAGAGTGTA CGGAAATTAG AAAAGATTGT TTAACAATAA TCTGGAAATG GCCTTGAATT   25680

ATTTTTTCCT CATTATTTTT CTCGATTAAC ATTCTACAGA ATGGTAAGGA ATCGAGACAT   25740

TGCTAAAAAT CTTAAATGAC TGAAGGTATC ATAGCATCTT CTGTAAAAAA GAAAAAAACT   25800

TCATATTAAT TTCGATTCAA AATTTTGGTC AGAAAACAAA AAGTTGCTCT TGCTTTATAC   25860

TTTCAGGGTG AACCTGGTCT CAGAGGTGAA ATTGGTAACC CTGGCAGAGA TGGTGCTCGT   25920

GTGAGTAGAA TTTTGTTTGT ATGTTTCTTC GTACTTGGAT TTTTTTTTAT GTTGAATTGA   25980

GAATTTTCCA AATTCGAACT ACACACACTT TATTTATCAA GTTAATAAA ATAATATTCC    26040

TTCTCTCCTG GGCTATGACA ATAATATCAT TTTACAGTTC CAAAGGAAAA ATTAAAGGGA   26100

TTTAACCTCT TTGAAAATAA TATCCGAATT TTCTAACTTC CTAGTGTCAA TGATCCAACT   26160

ACAAAACTAT AGACCAAAAG CTTTAGGTTT AATAGAATAT TAAATGATGC TTCAAGTGAT   26220

AACAGAGATT AAAATAAATA AATAAATAAG TCTCCTATGC TTTAGGAAGC CGGGACCTCT   26280

AACAAGATTC TATAGTTATT CAAACCTACT CCCTAGAAAT TTATCACCCA AAGAGCAGCC   26340

CCAAAGATTA GCTGTTAATG CCATGAAGAT GCCAAAGATA ATCCCATGAC AGTCTAATTA   26400

CCTTATCTCG TATGTCAGCC TCATGGGTCT TCTAGGCCAC AGTCGGCCTG GATTCCTTTA   26460

TTCACCTCTC CTTCAGAGCT GAAAACTGAC TGTAGCACAT CTGTAATAGT CTTTCTTTTG   26520

AATCACATAG TTCTAACAGT TTCAAACAAG GCTACTCATT TGCTGCTCTC CAGGGAATTT   26580

TACAATAGCG GAAAGTTCAG ATCTCCCAAA TTTCTGACCT GCTATGACTT ACACATTTCC   26640

ATAACCTTTA TTACTGGAGT ACCCTCCTTC TGAGAGTGGC TTCTAATAGT CTTGTTAATT   26700

AGAACCAAAA TACATCAGAG GCCTTCTAGA TATCCAACCA GAGTGCAGTG AAAGTGTTCA   26760

GTCACTGTAT AAGCACAGAA AAAAGAATG ACAAGGTTCA CTTTTGATGA TACGGGGTGT    26820

TATTAATAAG ACATGTTTCC TTTTTGGTAC TAGGGTGCTC ATGGTGCTGT AGGTGCCCCT   26880

GGTCCTGCTG GAGCCACAGG TGACCGGGTA AGCATGCATT TCACTAAGC CAACAGCAAT    26940

ATCTAAAATT TCCCGCCTTC CCTAGTCCCA AAGAGCCCCA GCAATTCATT TTTATGGCTT   27000

GGTATAAAGC CTACTTATTT AAAAACCTAG CTATTGTGAT AGAGCAGCAG GAAACAAATG   27060

CTGTGTGTTT AAAATTACTT TTCCCTTCCT ATAGATTTGC CAGCTATCTG ATCTATACTC   27120

TAATCCCTAG CATTTGTTTT AAAGTCTCTC CATGTTGCGC ATTAACAATA TCCTAATGCA   27180

CTGAGGCTTC TCAAAGCCTT CAATTATTAC CAAAAAATCA ATAAAATACA TAGTGTGCCC   27240

ATTTCACATT GAACTCTCCA CTTAAAATAG ATCTTATTTA TTGTATTGCA AAGATTGCCA   27300

CAAATAGATC AGCCCCGTGT CCATCTAAAA ATTAAAATGT CCTCCTCCTG GTATTGTAGG   27360

CACTGATTTA TAGTGTTTTC TCAAGTGTAT AACCCATACC ACTTAACCCC CAAAATGAAT   27420

ATAGCATTAA GTAAAAATCC ACTTCATTTT ACTCTGTGAG ATGTGCGTCA GTTATCTCTT   27480

CCAAGGCAAC TAAGACTCTG TCTGTCCACC ACTGTTCTCT CTCCCTCCCA GTTCTTTGAG   27540

CATCTATGTC AGGCACATTA ACAGATTCAT CTTTGGTCCC ATTATAGGGC GAAGCTGGGG   27600

CTGCTGGTCC TGCTGGTCCT GCTGGTCCTG GGGAAGCCC TGTAAGTAAG AACCTGGGTC     27660

ATTTTGTATA CTCACACCTC ACAATGTTTA GACATTGATG AACCTAGGAT TGATAACACA   27720

TTTTTAAATC CCTTCTCCCA CCTAGGGTGA ACGTGGCGAG GTCGGTCCTG CTGGCCCCAA   27780
```

-continued

```
CGGATTTGCT GGTCCGGCTG TGAGTATCAC ATAATGAAGA TTAATCTGAA AACATCCTAA   27840

GTTGGGGAGT AGAGTGGGTC GGAATACCAG AGCTGTAACT GTTTATTTCC AACAGGGTGC   27900

TGCTGGTCAA CCGGGTGCTA AAGGAGAAAG AGGAGGCAAA GGGCCTAAGG GTGAAAACGG   27960

TGTTGTTGGT CCCACAGGCC CCGTTGGAGC TGCTGGCCCA GCTGTAAGTT GAATTCACTG   28020

GTGGTCCACA CAGCAGCTAC CCATTAGATC TTCCAATTAA ATATATATCC GTCAAGTGCC   28080

TGCTATGCAA CAGGGAATAT ACCAGATAGA AGATGGAAAA TAACGGAAGG ATTAACATTT   28140

GCACACTGCT TTACAAAGTA TAAAAGTTTC ATGAATATTG TTTTATTTTA ATTCTCTGAT   28200

AACCTCATAA GGGTGGTAAT ATTGAAGAAC ATTCTGACAC AGATAGTCAT TTTTTATTTC   28260

TATATTTTCT TCTAAGAGAT GCGGGAATGA TCCACTTGAA GAAAGAGTA GCATTTACAA    28320

GGGTTTGTTT GTGATTTGAC TCCATCTTTT TTGTTTGCAT TTAGGGTCCA AATGGTCCCC   28380

CCGGTCCTGC TGGAAGTCGT GGTGATGGAG GCCCCCCTGT GAGTATTACA ATGGACCTCT   28440

CGCCGCTTTT CTTTTTTCAG AATCTATTAA GGACACTTGA AAGTTTTGAA ATTTTTGGTA   28500

AATTTGGACT ACCATGAGGA AACTTTTGAG ATTCAAGTTC ATTCTATTCA GAGCAATTCC   28560

GATATTGATG TTAACTTGAA CTCAGCTGGA ACTCAGTGTA TGTTGCTATC AGCTCACTTG   28620

AGGTAATAAC CAAGGTGGGC CCTAGGCAGT TTAATTGTAA AGTCGGAAAA AATATTCCTT   28680

TTGGCGTTTA TTAATATGCC CCTTCTTCTG CCTGACCATG TCCTTCTCCT TTGCAGGCAA   28740

TGCTATCACA ACAATTCTCT AGAGACCCAG AGCTCCCCAA AAATGAACTT TACTGACTTC   28800

TTCTCTCACT GGACAGTGCT GAATTATCTA GGTCATTTGT TATTCTTTTG TCCATGAACA   28860

CCATTACCTA TTAAGTGTCC ATTTCCTTAC CACTCAGCCA GGTGGTAAAG ATAGTTATTA   28920

ATGTATACAC ATTAATGTGT AATAATGACA TAGTGTCTTA TCTTCATACC TTTACAACCA   28980

TAAGATAATA TGTCAGCATT TCAGAAAGGA CCATCCAAAC CTTAACGCAA AATATGGGCA   29040

TTGCAACTGG TAATATGCTG GTAAGGAAGA TGTGTGGAGA AGGAGGGCCT TCAGGGTCCT   29100

GGCTAAATAA TGCCCTATAT GAAGCTGCCT GATTTTCCAA AACAAAGAAA TTCCCATCTT   29160

ACCCAAATTC TTGGAGTTGA TGTTGACTGT GGAATTCTAA TGTGCTTGGC TCTTAGGGTA   29220

TGACTGGTTT CCCTGGTGCT GCTGGACGGA CTGGTCCCCC AGGACCCTCT GTAAGTAAAT   29280

CACTGTAAAC GTGTCTTCAT TTACTCTAGC CAAAAGGCCT GGCTTCTGAT AGGAAACTGG   29340

TAAGAAACTC TTCATGAAAA CACATCACTA ATATTCGCTA TTACTCTCCT GGTCTGAAGT   29400

CAGCTTTTCT GAACCATTAA GGTATTTCAT CACAAGTTAT ATTTTATAAT ATCAGTTTAA   29460

GAGGCTTTTA TTCATGTGAA CACCAGTCCC CTTTCAGGGG CATGGTCTTT TTGAAAAAAA   29520

AAAACAAAAA AACGAACAGT TTTAGCCACA TATCAGATAT TTCTATATCT AATTATCCTT   29580

TATGGCTAAC ATTCTGCCTC CATTGTTAAG GTATAATTGT TCCTGAATTT AAAGGTGGTT   29640

TGGCCTCTAA TTTAATTCTG ATTCAGACTC TCCTGTCAGG ACTCAAGAAA ATTTAATTAA   29700

TTACCAAGGA TTAAGTCTTC TGGTTAAGGT TTCTGGGAAA AAAAAATAGC AAAGATGTTG   29760

ATTTCTTGGA ATCCTTTTAC AGGTTCATAA CAGAAAAATC TTCATTCCCT GTAGGCATTT   29820

AATTAAACCT AGTTGAGAAG TGTGTGGGAT TCCTCAATTA TGAACAAAAC ACGTATATTG   29880

GCTTTCTTTA AAAAAAAAAA AAAGAAGAAA AAGAAAAGG CAAAGTCCTT CGAAACTCAG    29940

AGTCCCATTC ATTTATCATT AACTCCTATC ATTCTACATA GTTCTGATTC CAATATGCCA   30000

GGGTACCAGT GGCATGACAT TGTTTTTCCT CATAGAAATT TGCCATAGTC TCTCCTCCAT   30060

TATTTGGTTG GTTACAGCCT CATAAAGGAA GACAGGAGTT GCTTCTTTCT GCAAGAAAGA   30120
```

-continued

```
AGGTTAAAAA CTATAAATAT TTCCCCCAAA TGGCCAGGGT ATTATTTTAT TGCATCACAT   30180

TGTTTGCATC TTAAGATCTA GAATCTTTGC TGCTCTCTTC CAGGCCCTTG GTGATTAACA   30240

GAAAGGAAAT GACCTTGTAC ATTTGCTCAT AGGGTATTTC TGGCCCTCCT GGTCCCCCTG   30300

GTCCTGCTGG GAAAGAAGGG CTTCGTGGTC CTCGTGGTGA CCAAGGTCCA GTTGGCCGAA   30360

CTGGAGAAGT AGGTGCAGTT GGTCCCCCTG GCTTCGCTGG TGAGAAGGGT CCCTCTGGAG   30420

AGGCTGGTAC TGCTGTAAGT GATTTCCAAC TCCTCTTTCT TAATACCTTA TGCTGAATTA   30480

AAATAAAGCC CCTACACAGA TCTTCAAGTG CATCTATTT GTTGATGAGT ATTGCAGGCT   30540

CTCAAGTAGA GCTCAGTTGA GCCAGGAAAT CTGTCCAGCA CACACTGAGG GGCTGTGGCT   30600

TCCAAGATGC TCAGAAAGCA CAAATCGGGA AGACAATAAA TGAGGGAACT CAGTTTTATC   30660

ACAAAACCCT TAAAGCTATT GAAGGCACCT TACTGGTACC AGGATTAGAA CAGAGTCCCA   30720

TTGCTGTGGC CATCCTACTA CATATTAATC AATCTCAGTA GGCTACCAAT TCTTAAACA    30780

TACACTGTCC AGTATTAGTG CTACTCTGAA AGGTGCCCCT ATTAGACCTT AGAGGCCAAA   30840

GTCAAAATTT GCTTCCTTTT GATATACTGA TTTTACTGAT TTCCTTTTTG TTTTTGTTTT   30900

TTGTTTTTGT TTTTGTTTTT TTGTTTTGGG ATGGAGTTCC CCTCTGTTGC CCAGGCTGGA   30960

GTGCAGTGGC ACGATCTCAG CTCACTGCGA CTTCCGCTCC CAGTTCAAGT AATTATCTTG   31020

TCTCAGCCTC CGAGTAGCTG GGACTACAGG CACACACCAT CATGCCTAGC TAATTTTTGT   31080

ATTTTAGTAA AGACGGGGTT TCACCATATT GGTCAGGCTG GTCTCGATCT CCTGACCTCA   31140

GGTGATCCAC CCACCTTGAC CTCCTAAAGT GCTGGGATTA CACATGTGAG CCACCCCACC   31200

CAGCCTGATT TCCTTTCCTT TGTGTATATA CCCAGCAGTG TGATTGCTGG ATCTTATGGT   31260

AGTTCTATTT TTAGTTTTTT GAGGAACCCC TCCTACTATG TACAACTATT ATGTATCCAT   31320

AACAATTTAA ATTTTTTTAT TTGTTTCCCT GCCTAGAGGC TATAAAAACT CTATTTCACC   31380

ACCCCAAGTG TCTTTATAAA TCTCAACCAC ATATTTTTAA ATGTTGTGCC ATTGGTCTCA   31440

AGGATGAATC AGATACAAAA GTATTCATGC CAAGATGTAA ACTCACCGTC ATCACTAGAG   31500

AAAAGATATC CAAGGATATG TCCTAGTAAT AGGAGGTCAT TAGCCTTTTT CTAAGCTGAA   31560

GACAGTTTAT TCTCACAATC TTCAAGCCAA CCTGTGTTAT CACCTAGGGT CTTACCCATA   31620

ATACTCAGTA TTTTTTCTCT ATTTAGGGAC CTCCTGGCAC TCCAGGTCCT CAGGGTCTTC   31680

TTGGTGCTCC TGGTATTCTG GGTCTCCCTG GCTCGAGAGG TGAACGTGGT CTACCTGGTG   31740

TTGCTGGTGC TGTGGTGAGT GCTTGACAGT ATTCTGACTC CATTAACATA AGAAAAGATT   31800

TTAAAAGCTG CCACTTCAAA TGTGACAGAT TGATCACTGA ATAACTTCAC TTAAGATTTT   31860

TATTCATGGC ATTTTCTTTA TACAGATCAC ATGTCACTTA TCTAAGAAGC TTTAATACCA   31920

CCTTACTTAG ACACACACTA TAAAGACACA GCTTAATTAT GCAGAATGAT TTTTGGTTCT   31980

TTCCACGCAC TTAGGAACGA TACAATCTCT AATTGCGTTT ACTCCTCTGC AATATGAAAT   32040

GCTGGCATCA TTTATCCTGT AGGAAGAATG AAACTCTGGA AGTTCTGAAT CGTTCCATTA   32100

AACCTTATAC GTGACAACAA CTAGAAACCA TCTCATCTCC ATAAAATATA TCAACTTTTT   32160

GAATTCATTT CATTTGGGAT ACTGAATGAC ACGAGGCTCA CTTTTTACAG AGCAACATCC   32220

CGTGATTACA TAAAGCTGGC CATCTACATG TGGAGAAGGA GGGCAGAGAT GATACTAATG   32280

ATACTTCTTA CCATTGTGTG ACCCATTCAC ATTCAATTTA CCTTCTTCCT TCAAACTAGA   32340

ATCTCCTGAG TAGGGTTGTT TTGGAGGGGA AGGTTAGCAT TCCATCGAAT AAGGGGAATG   32400

TCATTTTATC TTCTCTGCCT GTTTAGGGTG AACCTGGTCC TCTTGGCATT GCCGGCCCTC   32460

CTGGGGCCCG TGGTCCTCCT GGTGCTGTGG GTAGTCCTGG AGTCAACGGT GCTCCTGGTG   32520
```

```
AAGCTGGTCG TGATGTGAGT CCAACACTTG GTTTGTAAAA TAAAACTGAG CAGGATTTCA    32580

TTGTGTGAAA CTTTATGTCC TGAGCTGAGG TTCTCTTCTT CCAAATTTCT GAACAAGATG    32640

GTCAAGCTTC TCCATAGTAT CTACACCTAG TACTGAAAAT ATGAAAATTG CTTAGGCCAA    32700

AGAATGGGCT TTTCAATAGC ACACTGCAAA ACTGGCCCAA GTATTTAAAA CATCTCTAAA    32760

AAATATCTAG GTTGGCAGGT TTTTATCCCT AGTTTTAACA GTCTGAAAGA GGGTTCGTTA    32820

CTGAGCACTG GAAGTGATGA AGACAGAGTA GCTACAACAT AGGGGCTGGT AGGCAGCAGA    32880

GCCTCACCAA CAGCCTTAAT TTGTGTGGTG TCTTCACAGG GCAACCCTGG GAACGATGGT    32940

CCCCCAGGTC GCGATGGTCA ACCCGGACAC AAGGTCAGTA CACTTTTCAT CTTTCTCTAA    33000

TTCAAAAGTG ATTAAAATGC AACCCAGATT GATGCTAAGC TTCATTTTGC CTTTGGTAGG    33060

GAGAGCGCGG TTACCCTGGC AATATTGGTC CCGTTGGTGC TGCAGGTGCA CCTGGTCCTC    33120

ATGGCCCCGT GGGTCCTGCT GGCAAACATG GAAACCGTGG TGAAACTGTA AGTTTGTGAA    33180

TACCAGTCCC TCAGTGCAGC ATTCTCGTGG GCTTCACTTC TGACTTCCCC ACACTTGGGG    33240

ATGGTGGAGG AGTGGGGAGG GGTATCTTGG GCCTAGCTAA GTTGTGTTTT TCTTTTTCAT    33300

TTCACAGGGT CCTTCTGGTC CTGTTGGTCC TGCTGGTGCT GTTGGCCCAA GAGGTCCTAG    33360

TGTATGTACA TGCTGAAGAT TTCTTTGCAA CACTAACATT TAGAGAGAAT CAGTCCAAAA    33420

CATCTGTTAA GAAAATAAAC AATATATCAG CTAGACTTAA TATTTTTAA AAATTTCAGT     33480

CCATGCTGAG AATTGATACA AATAACTTGA GCTATTTTAA ATCTCTTATG CTTGTTGTA    33540

TTAAACAATT ACAAGGATCT AGCCACTTTA CAGATAGCAC AACTAAAGCA GATTACCAGC    33600

AGAGGTGAGA GCCTAGCTAA ACCATTACAT GTCCTGAGTT ACCTTTGTAA ACGAATTAAG    33660

CAGTATTTGT GGTGAAGTGA GTGCCATTTT TTTAAAACGG TAAGTCTTAT CCATCCTTCT    33720

GTTTCTTTAT AGGGCCCACA AGGCATTCGT GGCGATAAGG GAGAGCCCGG TGAAAAGGGG    33780

CCCAGAGGTC TTCCTGGCTT CAAGGGACAC AATGGATTGC AAGGTCTGCC TGGTATCGCT    33840

GTAAGTAAAC TGTAGCCATC TCGCACATAA ACTGATCCTG AAGGCCTTCA GCTCAGAAGG    33900

ATTTTCATAT TTTCACTGCT ATTGTTCCAG TATAGCCTAT ATAATATCCA TTTCCCATTC    33960

TCTGGCTAAC TCCATCTCAC TCTTGGAGGT AATGCTATTT CATGCCAACA TGAAAGGTGA    34020

GGATTAAGGG AGATAGAAAT ATACAATACA ATAAAATCTC CTGGTAACAA TGTCCTTCAA    34080

CCCCACTTAA AATAAACATA ATTAGAGGAA TGACTAATAT TGCACTGCTG AAATAGGTTG    34140

TGAAAAAAAA TTGAATATAA TAGACATAAT GGGAGAAAAG AGCCCCACTT TACATTTTCA    34200

ATTTTCTCAA TCCGGAGTCC ATTTAACTAA AGTTTCCCAT TGAATTTGGA AAAAAAAAAA    34260

ATATGTCTCT TGACATGTGC TCTGAAAGTG TGATTTTCCT CTTCTGTCTT TAAAGGGTCA    34320

CCATGGTGAT CAAGGTGCTC CTGGCTCCGT GGGTCCTGCT GGTCCTAGGG TAGGTGGACT    34380

CAAGAGAAGA CAGTTCATCT CTGAAATAGA GGCTAAAGCG AGCAGTGAGC CCCAGGCTGC    34440

TGCTCCCTTG GTGGGATTCA CCAGCTCACA TGTACCTGGT GTCTGTCTTC CTTAGGGCCC    34500

TGCTGGTCCT TCTGGCCCTG CTGGAAAAGA TGGTCGCACT GGACATCCTG GTACGGTTGG    34560

ACCTGCTGGC ATTCGAGGCC CTCAGGGTCA CCAAGGCCCT GCTGTAAGTA TGATTTGGGG    34620

AAATAATAAA GAAGATCACG GACCTAAGGA ATGTTTCTT CAGACTAAAC CAAGACAACT    34680

TTGACAACCC ATTAAAGTTA GCCCCATTTC AATATATCCT CTAAAATATC TGGAAATTGT    34740

CTATATGCAA TGGGCTTGTT AAGTCCATCC CATGCAAGTG TGCCTGGGGG CTCGTTATTT    34800

ATTTATGTGA ACTTGATTAT TTTTTACTGA TGAGAACATG CTTCCGTGTG AAGCTCAACT    34860
```

```
GAAAATCTGC TGCCATGGAT GTCTCTCACT GTAAAAAAAT ATAAAGCCTC TCCTATCTAA   34920

CTTTCACCTT TGCAGGGCCC CCCTGGTCCC CCTGGCCCTC CTGGACCTCC AGGTGTAAGC   34980

GGTGGTGGTT ATGACTTTGG TTACGATGGA GACTTCTACA GGGCTGACCA GCCTCGCTCA   35040

GCACCTTCTC TCAGACCCAA GGACTATGAA GTTGATGCTA CTCTGAAGTC TCTCAACAAC   35100

CAGATTGAGA CCCTTCTTAC TCCTGAAGGC TCTAGAAAGA ACCCAGCTCG CACATGCCGT   35160

GACTTGAGAC TCAGCCACCC AGAGTGGAGC AGTGGTAGGT CAAGATGTCC AGACCAGACT   35220

GACCCTTCTC ACAAGTTGAG CTTTTCAAAA TTAGTTTCCA TTGACATTTA GAGTGAAAAT   35280

GCATTTGGGT AAAGATTACA TTATGTGAAA TCACACCCAA TTAATGGAGC GTCATCTTCT   35340

CCCAACCAGC ACCCAACCTC ATTTCCCTTA AAATGTATTT TTGCACTTTT CATAGTAATA   35400

AGTACCCTGA TTTGATTTTT CATGGAGGAG GGGAGGGAAG GAACTGTCTA ATCTTAAAAA   35460

TAGCCACCCT CTTCCTCTTA AATATGGGGT AGACAATCAA AAATGTTACT TATGAGAGTC   35520

AGTATCTTTC ATTAGTTATT ATTAGAATCT GTGTTCTGCT CAATGAGAAG TTTCATGATC   35580

TGAATGTTAT TTTCTTAAAA GGTTACTACT GGATTGACCC CAACCAAGGA TGCACTATGG   35640

AAGCCATCAA AGTATACTGT GATTTCCCTA CCGGCGAAAC CTGTATCCGG GCCCAACCTG   35700

AAAACATCCC AGCCAAGAAC TGGTATAGGA GCTCCAAGGA CAAGAAACAC GTCTGGCTAG   35760

GAGAAACTAT CAATGCTGGC AGCCAGGTGA GGAATCCCAC AAACACCTCT CCTTCTGCTA   35820

AATAATATTT TGGTAGGACT GTTTGTTAAT TATCTGCATT TTAATCTCTG ACAAAAATGG   35880

GCTTATTAAA AAAAGACCTG TTCCTTTCCT GGGTTCCAAT TTTGTGCCTA AATTGCACAT   35940

TAGAAGATGG ATTGATTGGA CACATCCATG TAATTCAAAG TTATTATTCA AATTTGACTT   36000

AATTGGTAAT CATTGAAAAA ACTGACTAAT GTCATTTAGT GTGAAGGAGC ACTGGCCAGC   36060

TATATGCCAC ACTCATACAT ATGCATTTTC AGAATGTGAG CAGCTTTTCT GAATTTTTAA   36120

TCAAACCTTT TCACCAACTT TACTGAATGC CTACTGGAAT TCCATAAATT ACAAAATGAC   36180

AGAAAAAGAA AAATGTCAGA ATTTCTACCT CCTCATTCTC TTATTCTAAA GAAGAACGAT   36240

ATGCAAAAAG GATTAATTGA AACAGATAAC TTTTTTAGAT GACCTTGCCT CAGTCTAGTA   36300

GGTCTTATGT TCATCTAGGT AACTGATACT TCAAAGACAA GTGAATTAAG TTTTCTTTAA   36360

AAGTACCCTT TTCCTAAGCT TGGATCTGAG TCTACTCTTC CTGAGATCTT TTTTTTTCTT   36420

TTTTTTTTTT TTCATGTTTG ACTCTTAGTA TCTGAGTCCT TCTCCACTTA ACTGGAATTT   36480

CATCCTATTT TCTGTAGTTT GAATATAATG TTGAAGGAGT GACTTCCAAG GAAATGGCTA   36540

CCCAACTTGC CTTCATGCGC CTGCTGGCCA ACTATGCCTC TCAGAACATC ACCTACCACT   36600

GCAAGAACAG CATTGCATAC ATGGATGAGG AGACTGGCAA CCTGAAAAAG GCTGTCATTC   36660

TACAGGGCTC TAATGATGTT GAACTTGTTG CTGAGGGCAA CAGCAGGTTC ACTTACACTG   36720

TTCTTGTAGA TGGCTGCTCT GTAAGTAATA GTGAAATATG GAATAGCTT TGGGAAGTGG    36780

GATGGAGGGG GTTCTAACTT AGACTGCCCC CAAGGGGGT CTAAAGGGGG GTTAAAAGAA    36840

CAGAAGAATG AGAGAACTAA CTTATTTCAT AAGTAAATTC AGTTTTTGTA TGTATTTTAT   36900

ATTTATTTAT TTATACGTAT TAATTTCGTA CTTAAATTCA GATGATAAAT TCAGAGTATT   36960

CTTATCAGAT AGTGCCTTCT GAAATGCTGA AATGTATACT ATGTCCATGC ATTGTTTTTT   37020

CTTTAGCATG TTTTTTAAAT GGTAATGTGT GCCCAGAACT TAAAATTTCT TGAGCTTCAG   37080

TGGCCTAAAC TATAATTTAT AGTTATGTGT ATTTTATTTT ACTTATTAGT ATGGCTACAT   37140

TTAACTTTTA ATGCTTTTTC TACAATATGC TATAAATATA AGAAAATTA AAATTCACTA    37200

ACAGCAAGAC TACATACCCA CCCAGGTCCC GCTCCCAAAG ACACACATAG AGGGACATAC   37260
```

```
ACACAACAAT CCTAAAAATG ACTTTGTAGA GATAGGTCAC TTGGAATGTG TGTTGAAATG    37320

TTGTTGGTTT TTTTGGTTGG TTTGTTTGTT TGTTTTTTGT TAGACTGATA GGGAGCCCCT    37380

CCCACTAAAG ACACCCTTGA TACTGTTATT TCAAGGATGA ACTTATTTAT CTGGGACAGA    37440

CATCTTCAGA ATGACACATG CCAAACAGTG GTTCTTATTA AATCAAAGGT TCAGATATTA    37500

TCAGATTCAG AAATAGTGAT GCTTTGTGTA TCTATTTTCT TCTCTTTAAA CAGAAAAAGA    37560

CAAATGAATG GGGAAAGACA ATCATTGAAT ACAAAACAAA TAAGCCATCA CGCCTGCCCT    37620

TCCTTGATAT TGCACCTTTG GACATCGGTG GTGCTGACCA TGAATTCTTT GTGGACATTG    37680

GCCCAGTCTG TTTCAAATAA ATGAACTCAA TCTAAATTAA AAAGAAAGA AATTTGAAAA     37740

AACTTTCTCT TTGCCATTTC TTCTTCTTCT TTTTTAACTG AAAGCTGAAT CCTTCCATTT    37800

CTTCTGCACA TCTACTTGCT TAAATTGTGG GCAAAGAGA AAAAGAAGGA TTGATCAGAG     37860

CATTGTGCAA TACAGTTTCA TTAACTCCTT CCCCCGCTCC CCCAAAAATT TGAATTTTTT    37920

TTTCAACACT CTTACACCTG TTATGGAAAA TGTCAACCTT TGTAAGAAAA CCAAAATAAA    37980

AATTGAAAAA TAAAAACCAT AAACATTTGC ACCACTTGTG GCTTTTGAAT ATCTTCCACA    38040

GAGGGAAGTT TAAAACCCAA ACTTCCAAAG GTTTAAACTA CCTCAAAACA CTTTCCCATG    38100

AGTGTGATCC ACATTGTTAG GTGCTGACCT AGACAGAGAT GAACTGAGGT CCTTGTTTTG    38160

TTTTGTTCAT AATACAAAGG TGCTAATTAA TAGTATTTCA GATACTTGAA GAATGTTGAT    38220

GGTGCTAGAA GAATTTGAGA AGAAATACTC CTGTATTGAG TTGTATCGTG TGGTGTATTT    38280

TTTAAAAAAT TTGATTTAGC ATTCATATTT TCCATCTTAT TCCCAATTAA AAGTATGCAG    38340

ATTATTTGCC CAAAGTTGTC CTCTTCTTCA GATTCAGCAT TTGTTCTTTG CCAGTCTCAT    38400

TTTCATCTTC TTCCATGGTT CCACAGAAGC TTTGTTTCTT GGGCAAGCAG AAAAATTAAA    38460

TTGTACCTAT TTTGTATATG TGAGATGTTT AAATAAATTG TGAAAAAAAT GAAATAAAGC    38520

ATGTTTGGTT TTCCAAAAGA ACATATTGAG TAAAATTCCT TGCTTCAATG CTCTTTGCAA    38580

TATAAATATG CATCTCTACC AGCCATTAGA CCAAGTGCCT CTGATTAGAT AGAAATTATG    38640

CAAAAAGGGC AGTTTGGTGT GGTAGAAGAG CAGAGAACGA GG                       38682

(2) INFORMATION FOR SEQ ID NO:3:

(i) SEQUENCE CHARACTERISTICS:
        (A) LENGTH: 24183 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

TCTGCTCAAC TCTGGTAGTC TCAGAGTTTA AGAATAAACA ACAAGTAGGG GGCTTGATGT      60

TACATTTTAT CAGGATTTCT ATCCATGAGG TAGAGAGAGG GAATGTGTAT TTAGTAATAG    120

GCATGGCACT TTGAAAAAGT TACTTCATTT TCTGCTTCCT CAACTTTCTT ATTTGGAGAA    180

TAAGGGTAAC TTCAGTCTTA CCTTATAATG TTGTTGTGAG AATTAAATGG CATTAAGCTT    240

TGAGCATTTT CAACAGACGG AGGTGCATAA TGAAGCGTTA GCTATGAAGA CGATGACAAA    300

TAATGATTGT TGGGTGTTAG ACCCTCTGCC TTTGATACCT CATTTAATTC TCAAAACCAT    360

TGTTTTAATG TAAGCATTTT CAATCTGTTT TACAGTTAGG GCATCTAGTT ACAGAAAGGT    420

GAAGTAACTC TCTCAAGGAC ACACAGCTAG TAAGCTTCAG AATAAACAGG GATTGAAACT    480

TAGGTTGATC GGGCACCAAG GCTCCCACGA GTTTCCACAC CTCTGCCTCC CAGTGGGCAC    540
```

-continued

```
ATTTTTACTG GAACCTCAGC CCTCTGAAAG CTTCCACTGT ATTCCTATAG CAGTTCTGAA      600
AGCTGCCATT GTACTCCTAT AGCAGATCTA AAAGCATCTA CTGTGTTCCT ATAGCACCTT      660
GCCTGGATCT TTCTGGTGAA TTTCCCCACA TCCTGATTTT ATTTTTTTCT TTTCAGCAAA      720
CTTTCCCCTG TAAATCCCTC CTTCAGTATA ACCTTGTTAG CTTTGAGGAC ACACCCCTAG      780
GCCTGGGCTC AGAGCGCTGC TTCTCCCCAC CCCTTTCCTT TGCTTCAGTT TAAAGTGTCA      840
CGAGATGCCT CTGGTTCTCT CCCTTTGCTT TTAGCCCTCA CCGGGGGCAG GAGGGACCAA      900
GGCTGGGCCA GAACACATAG TCCTAGGGTA ACAGTGAAGG GGTCGTGAGG GGACAGTGAC      960
TCCCTTCCAA CCCCTTCTTC ATAGGGACTG TTGGCAAACA AGAAAATCA ACTGGGAAAA      1020
TGAAGACCTG CTGGTAAGAC AATAACCCTG GAAAGAGTGG TGGGGAGATG GAGCTGGGGG     1080
TCCTCAGAAC CAAGGGTCTG TATTTTTTGC AGCAGTGGTA AGATGAGAGT AGGTGAGCCT     1140
CAAGGTGAGA GACAGAAAGA GAGACGGATG AGAGAGTAAG ACAAGAGGGC AAGCGTGAGA     1200
AACCGAAGAC AGACACAAAA AACCGAAGAC AGACAGAGGA AGGGAGAGAA AGTGACGGCC     1260
ACAGAAAAAG AGAGGAAGGA AATCAAAGGT GAAAGAAACC AGAGACAAAG AAATAGGTAC     1320
CAAAACAGTG AGATAGGTAG ATACCGAGAA GGTGAGATCA ATAAAACAAC AACGACAGTN     1380
NGTCTGGAAA CATGAGTTCC TTACATCTCT CAGTAGGGTT TCAAAGTAAA AATGAAGGCT     1440
GGGTGCGGTG GCTTATGCTT GTAATCCCAG CACTTTGGGA GGCCGAGGCG GGCGAATCAC     1500
GAGGTCAGGA GTTCAAGACC AGACTGACCA CCATGGTGAA ACCCTGTCTC CACTAAAAAT     1560
AGAAAAAGTA ACTGGGTGTG GTGGCACGTG CCTGTAATCC CAGTTACTCA GGAGGCTGAG     1620
GCAGGAGAGT CGTTTGAGCC CAGGAGGTGG AGGTTGCAAA GAGCCGAGAT CGCGCCATTG     1680
CACTCCAGCC TGGGTGACAG AGCGAGACTC CGTCTCAAAA AAAAAAAAA AAAAAAAGAA     1740
ATGAAAAAAA AACTATACTG TGATTTGATC ACCTTACATT AATTAGGTTT ACTAGGTTTG     1800
AAAATATGGA AGTATTTTCC ATCTGCGGGG ACTCCTGTTT CAGTCATTTT TCTTCTCTCT     1860
TCTTCAGGAA AATTCCAGTT TTCTTCTTTG TGTGCAGTTT CCTGGAACCC TGGGCATCTG     1920
CAGCTGTCAA GCGTCGCCCC AGTAAGGGCC ATAGTTTCTA GACTTTCAAA GATCACTTAT     1980
TCCCAGAAAT GATCAGGCAG GGCTGTGGCT GACTGAAGAC TGAGTGAGGC ATTCATAGTC     2040
CTTCACACCC TCACTCTTCA ATCCAGCTTT GGGGCACAGG GATACATTAG GTTCTGGTTT     2100
TCCATGGTCA ATCGTGGGTA TGGAAAGTRR RRCCTCTTCA AAACGAACAT TTTCCCAGCC     2160
AGATTATTAG AGCAACTTTG TGCCTTGCAT CCACCCCTTC CAGGATGAGT TGCAGGTGGA     2220
CAGATTATAA TCGTAGAGGC ATGGAGGTAA AGCCAAACAC TTTACCTCTA AGCAAGCTGG     2280
TATAATATTG AATTTTAAAT ATTTATTATT ATTGATACAT CCTGAAATCT TTTTTTTGTG     2340
GTCAATTGCT ATTTTCTGGT TCTAAATTTT ATTATTATTA TTATTATTTT ATTTTATTTT     2400
ATTATTATTA TACTTTAAGT TAGAGTGGAT GAAGTAGAAT GACATGCTAT CTCTTTTGCA     2460
GGATTCCCTG TCAATTCCAA TTCTAATGGT GGAAATGAAC TCTGTCCAAA GATCAGGATT     2520
GGCCAAGATG ACTTACCAGG TGAGTAGCAA TGTACCCTAT TGAAAATGCA TGCTTTCTAT     2580
AAACCTGATT TTTTTTTTTA TTTGGGAAAG TTGTGGAAAG AAATAAAACC AATCTCATTT     2640
TAGACTTTTC ATTTTGTATT CCCATTCTAT AGGGTTTGAT CTGATCTCTC AGTTCCAGGT     2700
AGATAAAGCA GCATCTAGAA GAGCTATCCA GAGAGTAGTG GGATCAGCTA CATTGCAGGT     2760
GGCTTACAAG TTGGGAAATA ATGTAGACTT CAGGATTCCA ACTAGGTAAT CTATCAAAAA     2820
TATTTTAATC TAATTATCTG ACTCAAATGC ATTAAAAATG GATAGCTATC CAATGTTAGA     2880
```

```
GTTTTCTTAT GANCAATGTT TCTTGGGATT ATAATTGTAT TTAAAGATGA AGAAATTTAT      2940

TTACCTGCCT ATCTTCAGTA CCTTAATACT GCATTTCGAT GTTTTCRRRR AAGCACGGAC      3000

CATGAATGTA CAGGAATGAT TGNACTTCTG TAAAGGTCTT TATGAACAGT CATGAAAGAA      3060

CAAACGGTAC ATAGGTTTTT ACACTGTAGC TTTTCTATAG GTCTGGCATC TAAAATGGCC      3120

TCAAAAGGGA ATGTGGTAAA TACATATGGG TACAGGAAAC AAGATGCATG TTTACTATTT      3180

AAAAATTTTA CTCAGGAATT TATATCCCAG TGGACTGCCT GAAGAATACT CCTTCTTGAC      3240

GACGTTTCGA ATGACTGGAA GCACTCTCAA AAAGAACTGG AACATTTGGC AGATTCAGGA      3300

TTCCTCTGGG AAGGAGCAAG TTGGCATAAA GATTAATGGC CAAACACAAT CTGTTGTATT      3360

TTCATACAAG GGACTGGATG GAAGTCTCCA ACAGCAGCC TTTTCGAATT TGTCCTCCTT       3420

GTTTGATTCC CAGTGGCATA AGATCATGAT TGGCGTGGAG AGGAGTAGTG CTACTCTTTT      3480

TGTTGACTGC AACAGGATTG AATCTTTACC TATAAAGCCA AGAGGCCCAA TTGACATTGA      3540

TGGCTTTGCT GTGCTGGGAA ACTTGCAGA TAATCCTCAA GTTTCTGTTC CAGTAAGTAT       3600

AAAACCACAC ACTATGGCAG ATTAAAGCAA AACTAGATTG GTAAAAATGA ACATCTCAAG      3660

CATCTTTGAT AATCAGCTGA GTGCAGCATG TCCCAGATGG AATTTGGAAT CAGAGGAAGT     3720

TAAGTAGATA GCTTCTGGTC TTGAGGAGCT TAAAGTTGGA AAGTGTTACA TGCCCACCTA      3780

GTGCACCCAG AGTCTTTCTG AGGCAACTTA GAAAGARRRR GTCCTTCTGA TTGCCACTTT      3840

TTTTTTCTGT CTCTAATCTC CCATCTAAAA TCTTACAGCA TATATTCCCT GTAGAGTTCA      3900

ATAGCCCTGG GTTTCAACCC AGACTCTGAC ACTTATTGGT TTGTGACTTG GACCGTTTCT     3960

GTTCTCTCTG AACCTCATCT TAGTAGGATC TACATCTTGA GATTGTCATC AGAACAGAAA     4020

TAGAAAGTCA GTGCTGGTGG TCTGTTTCCA GGCTAGGGGT ATGCTGAAAT AATTCAAAGC     4080

TAAAGACATC TATACCTAAT AATCAGAGAA ACTTGTGAAA GCTTCCAACC CATTTCCATT     4140

AGAAAACTTG TATTCAAGGA AAAGCCAAGA GTCCTGGTCC AGTGTGCTCA ACCAGTTCAA     4200

GTTGATTTCC AATTATTTAA CAATTAGACG CAACTCATCT CTCTCTTGAA TGACCAGCTT     4260

CAGTCGTCCA AAAAACCTTA CCTGACTGTC TACTACCTTT CTCCAGTTTG AACTTCAATG     4320

GATGCTGATC CATTGTGACC CCCTGCGGCC CAGGAGAGAA ACTTGCCATG AGCTGCCAGC    4380

CAGAATAACG GTGAGTCCCC TGACTACCTG CAAAGGCCAC TTCTACCCAG CTCAACCCTC     4440

TCCACCTCAC CACTTTCCCA TCTTGCCACC TCCCCAGCAC CCCTCCTCCC CACTCTCTTT     4500

CGCTAAGAGA GCCTGTGCTT TGCTGTACTG ACTAGAGAAA TATTAGGGAA GTACACTTCA    4560

TACTTTCGAC CTGGCGGGTA GAAACCACCT GCAGCCTGGC AGGTAGAAAC CACCTGCGGG    4620

TGTGTGGTTG TCCCTTTGGT AGCTTATGGA CCCTCCTCCC TTACTCTCAA ACATGTCCAA    4680

GAACACTTGA GTTCTACTGG CCAGCACTGG CACAGGCCAC CCGGGAAGGT CTCCGAGGAC    4740

AGCCAGAAGC TGCACTGGGG TGGATGGGAT GGAGGCAGAG CTGCGTGCTC AGTCCTCGCC    4800

TGTGCGGCGG CAGGGAAGGG GTTAAGGGCG ACTGTTGTCA TTCTATCCGT CCTCCCCTTC    4860

CCCCTAGCTC TCCTCCAATC CCAGGACCCT CTCCGGGGCC ATTCATAAAC AGGGGGNAAC    4920

GCGCCCCTCC CGGGCCTGGA CGCTTTGGCA ACCGCTACTC CCGGGGGTGC TTTTTCTGCA    4980

GGGACGAAGT GCCACCTATG CTAGTGGCGG GTCTGGAAGC CTAGAGGGGA ACCAGGCTGC    5040

AGAGCCGGGC CAAGGGATTA GCGGCGGGCG GCGGGCATGG CCTGGACTGC GCGGGACCGC    5100

GGGGCCCTGG GGCTGCTGCT GTTGGGGCTC TGCTTGTGCG CGGCTCAAGT AAGTTGCGAT    5160

CGAGTTTGAG GGGTGCTTTT CTCACTTTCT CCCCATCTTT TCTTCTCCAG CCCAGCCAGA    5220

CCACCGACGA GGTAAGTTGG GGGCAGGGAG TGTTTGCATT TTTCAAGCGC ACACGAGGAC    5280
```

```
AGGTCGGGGC GCACGGGTCG AGGGAGCTGT GAGAAAGGCG CGGANATCCC CAGGGCTCTC      5340

AGACCCGCGC TTCCTCCAGC CTCGAGCACC TGCCGCGAGT CCTATCGAAG TCCAGAGCCG      5400

TAGATGACCC CTTGGTCTAG AAGGGGGGC TCCTCCCCAA TCTGGGTCCT CCCTACTGCA       5460

RRRRAATGCA CTCTGCAGAG GTGAGAACCA GTGAAGCCTC CCCCAACCTT GGGGGCGTCA     5520

ATCCTGCTCT AGCCCCACAG TTTAGCTCAT TAGAATATGG CGGAGACCAA AGCTGCGCTT     5580

GCTTGGAGGT CTGAGACATT TTTGCGTTGG GTTGCAAAAC CCGGCCTCCT CTGGAAGGTA     5640

ACTTTTACCC CACGGAGGCG GGGGCTTCAG GGCACCGCGC TCAGTTGCTC CCTGTTGCCC     5700

GATGTGCTCC ACTAACCTAT GTCTGCTATT TTTGCCAGAG AGGTCCCCCG GGTGAGCAGG     5760

GTCCTCCCGG GCCTCCGGGC CCCCCTGGAG TTCCAGGCAT CGATGGCATC GACGTAAGTT     5820

TCTATCTCCA GGCCACCTCT GTTCCCCAGT CCTGCCCTTT CCTATTCTTT TCCCAGGGCT     5880

CCTGTGGGGT TTTTTTTTTT TCAGAGAGGA CCAGGGTCTC CCCTTCCTGC CACCCCACTT     5940

AAAGGCAGGA TCAGACATGG GCGAGAGTTG GGGGTAGGAT CCTAGGAACC CGGGGATTTT     6000

TGGAGGGAGA GGTGTCTCTG TTGTCCTTGT TGGTCATGAA CCTCCACGTT TGACCCTTAC     6060

ACCATCCCCA TCTGTGAAGT GAGCTCTCCT GGGATTGTCC CAGTGGGGTC CTCAGCCTAT     6120

CCCGCTCATA GACTGCTCTC TCTTTTTCTC CTACCCCTCC AGGGTGACCG AGGTCCTAAG     6180

GGCCCCCCGG GCCCCCCGGT AAGTTGATTG GAGCATATGG CGCTCCACTT CCTTCCTTTA    6240

GACGTGTTTT GCAGCCCCCT GTTTCTGAAG GGTCTCAACT TTGCACCTTT TTCTCTCCTG    6300

CCCCCGCACC CTTCTGCCCC TGCTCAGGGT CCTGCAGGTG AACCGGGAAA GCCAGGAGCT    6360

CCAGGCAAGC CTGGCACACC TGGCGCTGAT GTGAGTAGGC GAGTGCTGGG AGGGCGCCCA    6420

GCCTGGGGTG TGTGGTGGGT ACGAGTAAGT GTGTGTTTTG TGGGGGGGG AGGGAGAGAG     6480

AGAAAGAGAG AGAGAGAACG CGCTGTGGCT CTAAACTTGG CCTCCTGCCA GCGCCTGATT    6540

GATCCGTGGA ACTGGCAGCT TTTGCAAAARR RCCAAAGCA GAGACAAAAA ACACTGAATT    6600

ATTGAACCCT GTGATAAACA ATGCAGTTAG CAGGAAGTTA GGAGTATGAT ACAACTTATC    6660

AAGAAGAAAT AATCACAACA GGCAGATCTT CTGTTAATCT TTTGAGTAAG ACTATAGTAA    6720

GGTATTTCTT TATAAATATT TGCATCATAC TTATGTAACC ATCCTGTAGA CAATTAATAA    6780

ATAAAATGAA AGTTTTCTAC TTAGTGGTTT GCCTAAGGAT GTTATGATAG TTCTAACATC    6840

ATTGTCTTGC TCTATTAGGG ATTAACAGGA CCTGATGGAT CCCCTGGCTC CATTGGGTCA    6900

AAGGGACAAA AAGTAAGTTA GCCATCTGGC ATTAATTGCT AGTACGAAAA TGCTGAAGTA    6960

TAATTTATT GCAGTGTTTG CAAGCCAACT AACATTAAGT TATGAAGTAT CTAAAATGCA     7020

CTCGTTCAAC TAAAATTGTG TTTAAAAACA CCATGATGTG GAATACTATG CAGCCATAAA    7080

AAGGAACAAG ATCATGTCCT TTGCAGGGAC GTGGATGGAG CTGGAAGCCA TTARRRRCTA    7140

TGTAANNNNT GCACCNNCTG CACATGTACC CCTGAACTTA AAATAAAAGT TGGAAATTTA    7200

AAAAAAAAAA ACACCATAAT GGGGTGTTTT AATGCTNTCA ATATTTATGC AGTTTTCACA    7260

TTTACATATT CATGATATGA AAGGTCAGTA CAATGAAACT ATTTTATTT TTAGGGAGAA     7320

CCTGGTGTGC CTGGATCGCG TGGATTTCCA GTAAGTAAAT GTAAAGCTAC AGAATTGAAA    7380

ATTTCCTATC TTTAGGTAAA ATTCTGCCAT TGTGAAATCT TTTTATTTAT TTATTTATTT    7440

ATTTATTTAT TTATTATTAT ACTTTGGGTT TTAGGGTACA TGTGCAGTTT TCTGCATAAT    7500

ATACATGAGA NATAAGTTGA TGACATCTGG TATGGTAAGC ATTTCTACTA TGAGTGGAAA    7560

AATTTTAGAG AAGTTTGAAT GTACAGTAGA AAATATATAT NCTATTTGCA GGTGGTATTT    7620
```

```
CCCAGCAGAC AATTCCCTCT TTACCTGCCA TGATAGARRR RAGCAGAGCC GTGTTTGCTT    7680

TTCTTTATTC AGTGCTTTCT TTAGAATGAG CATCATTTTT AGTAATAGAG TTTATGGTTT    7740

ATTTTAGCTG AGTTATGTCT ACATTCATAT TTATACTAAG TATAAACCTC AAGCTATAAC    7800

CATTTTTATT GTACTCTTTT AGGGCCGTGG TATTCCTGGA CCCCCTGTAA GTATCACTTC    7860

ATCATTTATT TTTATGCAGT CTATAAAAAT GTCCTATTTC TCAAATCCCC ACCTTATTCT    7920

CCTACTAACG GTCTACTCAG TGGTGTTTAC AGTGTTCTAC CTGCAAGNTC TTAGGTGGCT    7980

ACTAAGGATA ACACCCTTAT TCTGCTANAC NNNATATTTA TTAATTTAGG AAATTTCTGC    8040

TGTATCTTAA GTAATTAAAG TTTGGTCAAA TGAGTTATTG TGTCATTGGA AACCAAAGCT    8100

AATACAGAAA TGTAAATCTA ATATTTATCA TATTTGATAT AATGTATGAT AGATTGTAAA    8160

AATATTCATA AATGACCATT TGCTTTGATT TGTTGACTTC AGGGTCCTCC TGGGACAGCA    8220

GGACTCCCTG GAGAGCTTGG CCGTGTAGGA CCTGTTGTGA GTACCACAGT GCACTTTGAT    8280

AGACGTTTGC TGATTTAATA GAAGATGTTA TTTGGGAAAG CAAATTACCC TAACTGTACA    8340

TTTCCACTTG CAAACCAAAA CATGGCAGAT GAATTTCATT CCAGTTTATA ATATTGATGT    8400

GAACCAGGAA TAATAATAAT TTTTGCAGAG TGATTTTAAT TTTTTCCTAA ATTTTTCAGC    8460

TAAACTTTTC TTCCCAACTT CCAGATTGTC AAGTAAGAGA GTGTCGTCCT CATTTTACAG    8520

ACTCTCAGCC AGGACTGGAG TCTAGTGGCT TTTGTATTAG GCTCCCTGCA TGANATAAAA    8580

GTGAATAGCC TAAAATTATT ACCATGTGTA TTTATGTTAG GNTCATTAAA TTATAATTRR    8640

RRAATGGCAC TAGCAGTATA GGTTGCTCTA GGTCCTCTGT AAATCAACCA AAAAAATAAG    8700

TAGTGTTTCC AATTTGCTNT CAGAGTAGAT AAAATGTTTG TCTGATAGAG AAGAATTGGC    8760

TTTGCNNTTT CCCCTAGCTT CTCTCTGACT TGTTTTATTA CCTCGGTGAG ACTGGAATGC    8820

CTTTATTACT CTCATTTTGT AGAACTAATT GGATAACGGG CCACCCATCG ATTTTGGTGG    8880

CAGGTCTATG CATGGCTGAG CTCGGTGGGG NNNNCCAGTA ATACCATTCT CTTATGCCTC    8940

ACTGGTNTTA TGTACTGTGT TTTGACACAT GTATAACCAC TGTGTCGCAA TTTTCAAATA    9000

ACTTAGGGTG ACCCTGGGAG AAGAGGACCA CCTGGCCCCC CTGGTCCCCC AGGACCCAGA    9060

GTAAGTTATT TGCAGCTTGA ATTTCTGTTT GTGTCTGAGA GTCAGGGTTG AAAAAAATCT    9120

AAGAATCCAA AATGGAAGTT CCTATTAATT GAGTCATTGT CCCAAATTTN CAAAACGGCT    9180

ATCAATTTTT CCATGCACTC AAGGGCATGG TTCTGTTTAG GGCAAGAAGT AGAAGAATCA    9240

CAATAATTTA AAAGGTGGTT TTTATAGGGT ATATCTTACT CATTACTTTT GAAGTCTTTT    9300

GACAGTTGTG ATGTCTCAAA TGCTCAAAAC TTAGATATAT AAATGAAGCA TTTTCAAATG    9360

AACTAGTTTT TACAAAGGTT TTCATAGTAA GAAAAATTTA AAGAATATGA GTTTAAATGG    9420

AAGGTAATTC ATATTTTTAT TTGTAATTCA GAGTTCCCCA CATTTTCTAT TTTGCCTCTT    9480

ATTTCGTTTC CCTTCAATGT CTTCCCAAAA TAATCTACTG CAATTCATGG CTCTCCAAAG    9540

AGAACATGCC CATGAGTCAG GATTNTAGAA TATTAGCATA TTATCTGGTT TCTTATATTT    9600

TATTAAACAA ATATATTTTA TACTTTTGCC TGATGAGCTT TCTAGTATTA GTATGTTTGA    9660

ATTCATTATT TAATTGTATT CTGAACCTTA ATATTTTGTT TACTTTAGGG AACAATTGGC    9720

TTTCATGATG GAGATCCATT GGTAAGATGC TTTCCTTTGA ACAAAATATA GTTTTAATTC    9780

AAAGACCATA TAGCCTGCAG ATGAGTTTTC TTTAAAAGAT TTCCCTGGAA TATTCTATGT    9840

GTCTGTGTTT TCCTTTCACT CAAATGGCAG AGCAGTCTGT AACACTAGTG GACTAGTGGC    9900

TTGCATCTAC TCAGACTAAT AATTTTTCAT TATAGATGTA TCTTTGTTCT TCTATGATCT    9960

TTTTACTTTA TGACTAAGAC ATGCTTTTRR RRCTGGCTTT AAATGTGAAA TAATAATAAT    10020
```

-continued

```
AAAAAGGAAA GGGGTGTTTA GAATTATTCA ATGAATATTA TTGCAATGGA GTTCTGTAAC   10080

TGGAATCCCT TAAAAGATA CTGTCACAAA GCGGGAGTCC TAGTTTATGC ACTCTGTCTG    10140

TCTTTCTTTC TCTTTGTTCC CTCTCTCCCT GGCAGTGTCC CAATGCCTGT CCACCAGGTC   10200

GCTCAGGATA TCCAGGCCTA CCAGGCATGA GGGTAAGAGA ATAACTTCCA GTATTTTAAG   10260

AGTATTATCC ACAGATAAAA TGGAGCCTTT ACTTTAAGCA TTAGCCTTCC TGGTGCAGAG   10320

ACCCCACTTG GATGATCAGG CGAGTAGTGC TTATTCAGTC CTAGCAATTC CAGTTGCCCT   10380

TGACATGTAT TCCTGTATTC CTACCAAGAC ATGGAGGTTT AATCATAGGA TGGCTTTCTA   10440

GTTCAGGGAA GAAATACCAA TAAAATACAT TGGATTGAGA GACTTTRRRR CCTTCCTCCA   10500

CCATCAGGAA GGAGGTGGGA ATGGAGGAGG CCGAAGGGTT TTCAGAGCAG CCTTCAGAGG   10560

GCAGGGGATA GCCAGCTGAG CTTGGTCAAG GCTGTCACTT CTGAAAGGTT AAGTTACTGG   10620

AACTAGAGAA GACTTAATGC TCCTAACCCG TGTGAGGAAG TTGGAGAAAT AGGGAATAGG   10680

GATCTAGGAA ATAGCAGGCA AGTATCAATG AATCACATTG CTGAACTAGG TAATGAAGTG   10740

TATTATTCTA GAGCAGTGTT TTTCTATTAA GTAACACTGA TATTAATTAT ATATGGCAGT   10800

CATGGTGCTG TTAAGGTCAT TTAAGGCATT AATTTTCTTT GTGACATAAC TCATTTCTTA   10860

GTAATACATT GGCACTGATT TAGGGAAGCA GGATCACTTT ATGAGCCTTC TGATCACTTT   10920

CTGTACCAAA CTCAAGACAA TTACTTATTT TGCATTTGTT AGGGTCATAA AGGGCTAAA    10980

GGAGAAATTG GTGAACCAGG AAGACAAGGA CACAAGGTAA GGAAAATGGG TATTTAGTGG   11040

ATAAATTGTG ATTAGGAGTT ATTGGTCACT TTCATTATAA GAAATTAGGA ATTATAGGAA   11100

ATAATGAACC TCGATATTTT ACCATTCTTT TTAAAATAAT GATTGATAAG TTCTAAGCAG   11160

ATGCATCAAT ATTTGACTAA ATATCATATT CTGAAGTTGT TCATTTACAA TAAAACACTT   11220

ACAAATAAGG CACCAGACAT TTTCATTTTT TTCTGTCACT ACCTTTTCTT TTCTTTTCAA   11280

ATCAATCACA CTCAGCTTTT TTCCTTGATG CTATGATAGC AACATTATT CAGCAGTTGT    11340

TCCACTTCAC CAGCAARRRR TTTCTTGATA TCTTTGTCTC TCTTCCTCTT TCCCCCACTT   11400

TAGAAAAACT TTGAAAGAAT AACATCTAAA TGTTACTGGT ATTTTATAGT TAAATGGTGG   11460

TATTTTGGTG ACATTTTATA TGTAGGCTTC TCTGTATTTT CTGAATGTTC TACAATTAAT   11520

TTGGACTACC CATATAAATA ATTTAAGAAA GTAGAATAAT TCAGGAGTCA CCAAGTTAAC   11580

TTAAAACATA ATGAGTTAGA CCAAGCCTAT TTCTATGTTC GTTGCTAGA ATAACATTTG    11640

GTGTGCTTTT CTTTTTTCTT TTTTTTCTTT AGGGTGAAGA AGGTGACCAG GGAGAACTCG   11700

GAGAAGTTGG AGCTCAAGGA CCTCCAGTAA AGTATTTTTT AAAAAATATT TAACTAGGAT   11760

ATGTAAATAT TCTTTTTTTT CATGACTGTT GGAATATTTT CTATTTAGCA GTTGGATGAA   11820

TAGCATTACA TGAACTTGGT GTCCTCTATT TTCCACCACG CCAGCACTGG GGATAACTA    11880

CTTCTTCAAA ATAGGAGAGG GTCTTCATTA TATATTCTAG CACTTTTTA ACAGAAAAAT    11940

TCTACCTATA ATTTACATAC ATTCGTTTAC CAGATTTCAG GGCCAGGCAA TTGAAAAGCA   12000

AATACTAAGC ACAAAAGGAT GATACTCATC TTTTATGTTC TATCGTATTA TCACATGATA   12060

TAATGAGAAA ATTTTGTGTG TTCTAAATAT GCAGTAGGTA TATCATTTAT TGGATTAATG   12120

TAGCTTATTC CAGTATGCAA TCATTATAAT TAATTAAAAC ATTCTTAATT GCTCATATCA   12180

TGTCTTTTAA TAAAAAATTG GTCCCTCGTG CTTTAGCAGA TTTCTGCCAA TAATATTCAR   12240

RRRACATGCC ATGAAGGAAG TGGGAATGAT AGTGTAAGTT CTACATACAA GTTAAAAGGT   12300

AAGTCAAACA TATTATCACA ATTTCTCTTA TGCTGGTATT TACTTTTTTT GTCATAAGTG   12360
```

```
ATTTTGTCAA CTCCAGTTTT GTGTAAGACT TCAGAATTTT ATAAAAAGGT TTACCATCAG    12420
AAGAATTCTC CTTGGACTTT CTAAACTAGA AATGTTTGTC TATATATATA TAGTTACTAT    12480
TTCTTGGTAT TACCTTTGGT TATGATAATA CCCATTGTCT AGATCAGCTT TTGTGATGAG    12540
ATTTTTAAAA ATCTTTGCTT CAACTAAAAT AATTCACTTC TCTTTTTCAC ATTTCCAGGG    12600
AGCCCAGGGT TTGCGAGGCA TCACCGGCAT AGTTGGGGAC AAAGGGGAAA AAGTAAGATG    12660
GTGATGACAA TAATATAATA CCAAAATGTG TTAAATATTT AAAATTTTGG CCATTTAAAC    12720
ATAACTTTTT ATCTTCAACA ACTTTTTTTT TTTTTTTTTT GAGATGGAGT TTCACTCTTG    12780
TTGCCCAGGC TGGAGTGCAA TGGCGCGATC TTGGCTCACT GCAACCTCTG CCTCCTGGGT    12840
TCAAGCGATT CTCCTGTCTC AGCATCACGA GTAGAGCAGC TGGGATTACA GGCGCCTGCC    12900
ACCACGCCRR RRTTACCTGA GGTGCCTGAG NAATTACTCC TCAGGGATCA CTGTGTGTAT    12960
NACAGGCACA AAACCTCCTT TTCATCTGGC TATTAAATTT CTTTAGAAAG ATGGATGCTT    13020
CCTTTAACAT ACATGACTGA TCTCAGTTTT TTTCCATTGT CTTGTTTTTT TGCAGGGTGC    13080
TCGGGGCTTA GATGGTGAAC CTGGGCCTCA GGGTCTTCCT GGTGCACCTG TAAGTGATTT    13140
TCCTTCCACA AAACCCAATG ATAGATTTTT TTTTTTTTGC TATGTATGCA TGTGTGTGCA    13200
GTATTGTTTA TGTGTGAATA ATTAAAGTGG AAAAGTGGAC AATTTATATA TATATGTTTA    13260
AATTTAAATT TAATTAAGAC AGGTATCTTT CTCGGGTACA TAGAAATGTT CTTCTGACTT    13320
GACATGATTT TTTTCTTCAT AGATTAAGCC AAATTATTAA GTATTTATGT TTGCGTGTTT    13380
TCCTTTTCTT TGGTTATTAG GACGCCTTGA GTCTCAGTAA CTATCTCGTT TCTRRRRACA    13440
GAGGCATAGT GCATTTAAGG GGAAAACAAA AGACCATCAA GTGTCAGTTA TCTCTATGGC    13500
AATATCCATT TTTAAGACAA TTCCGTTTTT ATAAAAAGAC TTCTTCATCT AGGCTTCCTT    13560
GATAGAGCAA AGCCATTGTG GTGGAAGACT AATAGTTTGG TGACGTGGAT GATACTTTCT    13620
AATTTTTAAA AGTTGATTAA TAAGTAACTT TTGCTTGTAT TAACAAAATT TTATTTTCAT    13680
ACAGGGTGAT CAAGGACAGC GAGGACCTCC AGGAGAAGCA GGTCCCAAAG GAGATAGAGT    13740
GAGTTTAAAT TCAGTCACTC CAAGCCTCCT GCTTTTCAGT GTCATCTGCT GATTATGCTG    13800
ATCTCTTTGA CAAGTCTAAG TATTATGTTA ACTGAACATG TCTTGTCTAT TCTTTCTCTT    13860
CCTCCCTGCA GGGGGCTGAA GGTGCTAGAG GAATTCCTGG TCTCCCTGGG CCCAAAGGAG    13920
ACACGGTATG TCCTGAGCTG TAGTCATCAA GCACATTTTT CAGTGATCAT TGACTTGCAA    13980
TGAAACTTTA GAAAATAATG AAGGGAAAAA GAATGTGACT GTGTGTAAGA GACAGTATGT    14040
TTCTTTGTGT GTGTTTAGGG TTTGCCAGGT GTGGATGGCC GTGATGGGAT CCCTGGAATG    14100
CCTGGAACAA AGGTAGGCTG TGTAATTTAC TCCAAGAGTG AGTGGGGCTG TCTCTGCCCT    14160
GGCCAACTGA GTGTGGCATT TCCATTACTA AATCACCAAA AGATTTATTT AGCTAGCTTT    14220
GGCTTTTTCC CTTCCTTTAA TTTTTGAATC AAGTGTCAAA TATGAAATAC TTACTAGAAT    14280
AGTATAATTA TTTGCTTGGT TTCAGGAACT CAGTAAAATT GCCCTGTTGA TGAAAGTAAG    14340
TTGAGAGAGA CTGTGCATTT TGGTTGAATT ATGTCCTATT TCCCACCCTA CTCCCCCACC    14400
CTAAATTAAG TCACTTTATA AAAGTGCATG TAAAGTCAGC TGTTGGGACA ATCCTTTTAC    14460
TTAAAACGTC TGTGCTCCTC CGTTTCTTAA AAGAAATACA GCAGCTCATA CAGGTTCAAT    14520
CATGTGATAA AAGCTTTTTT TGCAGGGTGA ACCAGGAAAA CCTGGGCCTC CTGGTGATGC    14580
AGGATTGCAT GGGTTACCAG TAAGTATTTG ATTCTTTACA TGTTAATTGG TTTATATACA    14640
TGTTTTAAAG ATATACATTT TGGGGAGAGA CATGCTACCT AATCTGATAA GTTCTGGGGA    14700
AGATATGATG TTTTACTTTT ACATTTTTAC AATTTACATT TGTATTTTAT ATTTTATACT    14760
```

```
TTTTCTCTGA ATAGCTATTT GTGTAATAAC TGTAAATAAT AGGCTTTAAT TTTATGCTTT    14820

GGATTCCTTT TCTCTCTTTA GTTTACTCAG TCTTTTTTTA CATATTTTTT AACTAACCCT    14880

AAGCTGTAGG CCAGTGTGAT ATATTTCATT CCACTTTAAA CCGGTTCTAA AGCTCTTGTT    14940

AGTAGGATTA AGCAACAAGA GTGCTGAGAG TATACTCAGG TGACCCCTTA GATTATGTAC    15000

TATTTTTRRR RCCTAGTAGA GCTCCTCTTG ACCTGAAAGT GGTACTGGAT TCTAATTTGG    15060

GAAGTTTGTC CTTGAAAAGT AACTTTAGTT TAAAGACAAG ATTTGCTTTA AGGGTACTTA    15120

GCTTTAACAA GCCAGATATA GTAAAGTCAT GCCCTCTAAA CTGTGGGTAA TTCTATAAAT    15180

GACTGTGCAG AGTTTGGGAA CTAGGAAGCA TCTTCCTTAC ATTAAAGCTT TGAGGTTACC    15240

ATGATTCCCT CAGCCTCCCT GCAGTGTGCA GTGGGCTTGG CATCTCATGG ATTCTCAGAG    15300

GAGGTGATTA AACTCGGATT GTGTATGTAT TCTTTTAGGG TGTACCTGGA ATTCCTGGTG    15360

CAAAGGGTGT TGCTGGTGAA AAGGTAAAAT ATTTTAAAAT TTAAGTTAAT ATCTTTCTTA    15420

ATTTCTTTAT TATTTACTAA CGTATTTGTA ATTTTTAATA TTTTCAGCAT GTGTTTTATT    15480

TTATATTTGG CCCTAGGGAG AAATAAAAAG GTAAATGTGT TAAGGCTTCA AATACTAATC    15540

TTTTTCCTAG CTACAGAAAG CATACTTTGA CAAAATGCTG CTAATTAGAT TTCCTTAATG    15600

RRRRTGACAT TTGACCTTTA ATATATTTCT CAGACTCACA GACAATATCT TGAATCTAAA    15660

GGATTTCGAT GTATCTAACA AGAAAGAGAT TCTGCACATT CCCAGATNCT CAGTGTGAAA    15720

GCAGGGAATT AATGCTATTC AAATGTAAGA GATCCCAGTC TGGGTAAGGC AGATTGATGA    15780

TTATGCTTAC TTCAGCATGA GTTACTTTGA ATGTTGCATT TTACCCTTAG GGTAGCACAG    15840

GTGCTCCAGG GAAGCCTGGT CAGATGGGAA ATTCAGGCAA ACCGGTAAGA CACCATTTTA    15900

CCTCTCCTGA AGTTCTAACC TGTTGTAATC AGTAGGTGTT AACTTTTTTT CTACCTTCCT    15960

TCCTGATAAC AGGGCCAACA GGGGCCTCCA GGAGAGGTGG GACCCGAGG ACCCCGGGGG     16020

CTTCCTGTGA GTATTCCTTG CTGTTCTTTC CTAAAGCACC TTCTCAGGAC TTTGCTGGAT    16080

GTTCTTCCAT TCATTCATCC ATCCATCCAT GAATGCTGTC TGATGTTTGA GCCCATGCTA    16140

GTCCAAGACA CACAAGGAGA TGAAATGCTA TTTAGATGCA CAGCATGCCT TTTCAGAAAA    16200

TGGAAACAAA AATAAAGTGC TTCAAAAARR RRCTTCAGAA ACTTCAGAAA TTTTTACCAT    16260

CTGTGTCTTT TTGAAGTTGC AATAGTAATT TAAAGGCAAA CATATCTATT ATGTGTTTCT    16320

TTTTTCACTC TGTTGAGGTT TAAGATCATT TGCCAGATGT TGCTTTGAAA TGTTCTGTAG    16380

ACCTGAGAAT TTATTCTGTG TTCTAGGCAC TGTGCAGAAT TCCAAATTAA TATTTAACAA    16440

TACCTTAAGA ACACATAATC TAAGTGAGGG CTTAAAACAT GGACACAAAT AACCATAATA    16500

AAAGTTAGGA TGTGATTTAG ATGTTGAAAG TGACTAATTG CCATTTCATA TACATGCATA    16560

GCTATCATTT CTAAACGTCT GTAATCACAG TAAACAGCAT TCGAATCATT CAATGCAAGA    16620

TGAACACAGG ATGCTGTAGG CACTATGTAG GATGGCCTAT GCCTTTAGCT GAAGGAAAAA    16680

AACCTAGGTA GGATGTTATT TTATTTACAT AGTAACTAAG CATTTGAATT TTGGCAAAAT    16740

ATCCAATTGA CAATGTTTGT GTTTTTACAG GGCAGTAGAG GAGAATTAGG ACCAGTGGGA    16800

TCCCCAGGCC TACCAGGTAA ACTGGTAAGT AGAAAAGTTT CGTTTATTTG CCTTCTACGA    16860

AACACAATGC ATTTTAAAA ATAAGCAAGA GGAGAAAACA ATTTACAATT GAATTACCTG     16920

TACTTGATTT CTCTTGTTAT GTGAATATGA GAACAATGTA AAGGGGAAAT TTCAAATTAT    16980

GGGTAGGATA CCCTCAGAGG GTATTTTAAT CTGCGTGGTT TGTAGCATCC ATTTTTAAAC    17040

CTGGTGAAAT GTGAAGTGCT GCATTTGGCC TCTGGTTGTT CTTGGAATGG CAGAAAACAG    17100
```

-continued

```
AGTGAATGGT GCCTTTTACT TCCTGTGCAG TGCTTGTTTA CATAGCTAGA GGAGCAGCAG   17160
CGCCATTGCA GGCAGTGCGN NGGTGNNGNG GGCTTGACTG AAAAAGCCTA CTGTTGCCAA   17220
GGAGTGCAAG GGGAACTGAG GACCTTAGGG TGGAGTGAAG GCTGGGAGAA CATTGGCCCC   17280
GCCCTCTTCT CCTGAGAATA TGAAAGAGAG GCAAACCCAA GAAGCAGAGT TCAACCAACC   17340
ACAGCACGTT TATTTTAGAC ACAAGTCAAC ACACCCAAGG TTGTTTCTGC CTTCCGTGCT   17400
TTCAGTGTTG CAGTGACAGT AACTCCGGGG ACTTTGTTTT TGCTTTCCAG GGTTCTCTGG   17460
GTAGCCCTGG CCTCCCTGGC TTGCCTGGGC CCCCTGGACT TCCTGGAATG AAAGGTGACA   17520
GGGTAAGAGC TCCAGCACTC CAGAAGGTTC TTTATTTGGA AGGGTGATTT CTACCATGTT   17580
GAGAAACAAA GCTTGCTTTT GGCCCTGTGG AGAATTTTCT AGAATTTATC ATAAACAGCT   17640
ATCAAGAAAG ATATTTTAAA TTACTCAGAG TTGAGATTAA GAAGCAAAAA GTCTATTAAT   17700
ATAATTTAAC AGAAGGAAAA AAAGCTGAGA AAAGTAAAAA CTGTCCGTTG TAATCACACT   17760
TTCTACTTAG CCCTCAATTT ACATTTCTAC TAGTCAAATT TTATGAGGAT GTGACTCAGA   17820
GAATGCCCCA AGTTCAGAG CCTCTTGGAA AATTGTGACC TAATGTGGAA ACTTATGTTT   17880
TGGTCCTGAT TCTTGTTGGG TGGTGAGGAG TGGGAACGTC CTCTCCCATC ACATTATCCG   17940
TACTTGTGCT TATCCACCCA CCCAATAAGG TTCACTTGAA ATTATATAAA CAGTTGAAAA   18000
TACTGAAAAA GTATTATATT TTATTTATTA CAGGGTGTAG TCGGTGAACC GGGTCCAAAG   18060
GGTGAACAGG TCAGTCTTAT TATTTAATTG GTATAAAATG CAATGTTTGA TATGCACCAT   18120
TTCACAAGCA AGGGGGAATG GCTGGTTTAT GGGGGTTAAT AAAACCATGA AGGCTAACAG   18180
TTTTTCTCAA TGTGTTCATA GTGAGTGAAA CCTGGTGTTG AGTTTGGTCC GCAGCATTGT   18240
TTACTATTTT AACAAGCTGG AGCTAAAGAT GGCTCTGCTC CAGGACTGCA CACTGTCTTT   18300
CCTTTGAAGA GCGTGGCTCT GTCTCTGGTT CACGGAATTG GTTTATTCAT ATCCAATGAG   18360
CCTTCCACAG CCACATTAGA ATGTCTTAGG TTTTTCTTGA TCAAGACCTC AGCAAATAAA   18420
CTGTTTATAT GAATTAGACT CAGTCCTTTC CCTGGGTTCC TTTTTCTACT GTAGATTCCC   18480
TATTTCAAGG GCCAATTATA AAATTGTTGA ATATGGTCAT TTATCCTTCA TTCTAGCTGA   18540
AACTCAGCCT CACCTTCTGG CTTTCCTCTC CGCTATTTTC TGATTGGGAC TAACCACTGA   18600
CAGCTAGATT GGAAAGCCGC TGAGAGCATT TTGTATTTCT GCATGATTCT GGGAACACTG   18660
TGGGCACTTA TGAATGCTTA TCAATGTTTA CTGGTTAAAA TTGGGCAATG GGACTAAGAA   18720
TTTTAAAATG TAACCTTTTA TCTTAATTTT TAGGGTGCCT CTGGTGAAGA AGGTGAAGCA   18780
GGAGAAAGGG GGGAACTTGT AAGATTTTTT TTTTCTGGTT AATGATGAAG CTTTACCAAT   18840
TTTGAACTGT TAGAAGTATA TATATATACT TCTAACACAG TTCAAAATTG GTATATATAT   18900
ATATGTGGTT ATTTTCTGGA CACTGTTATC CTCACTGCCT TCTTTAAAGG TTATGATGTT   18960
TCTCCTATCA GCTAACAAAA GTCTCCCAAG ATTGCAGCCA ARRRRAATTC TTGACACCTA   19020
GCATTTGAGA TCTGGATGAA ACCCTGGAAA GCTCTGATTC AACCCTNTTA NTTAACAGAN   19080
NAATTAGCCA AAGGCTGGGA GGCTACATAG CTTACAGAGG GTCACAGAGT TAAGTAGAAC   19140
TGAGATTAGA ATCCAAAATT GGAGTCTAAT ATTTTTTTGC AGTGCCAGAG TTAATCTGTT   19200
CATGGTTTTC CGTATTTTAG TAGCACAATA ACTTTTAAAG TGTTTCAGG AAATTATCAA    19260
ATGTGAATAC ATTGTTCTAA CATAAATTTC TTTTATTGAT TTAGGGAGAT ATAGGATTAC   19320
CTGGCCCAAA GGGATCTGTA AGTATGGTGA ATAGTAATGG TATAAAAAAA TTAAAAACAT   19380
TAATAAAGCT GTAGAATATA TAATATTCTG CTTTATGAAA TCATTATGTA ACATTCAATT   19440
CTTTTTTTTT TTTGAGATGG AGTCTCACTC TGTCGCCCAG GCGTGAATGC AGTGGTGCAA   19500
```

```
TCTTGGCTCA CTGCAACCTC TGCCTCCTGG GTTCAAGCAA TTCTCCTGCC TTAGCCTCCC    19560
AAGTAGCTGG GATTACAGGC ATGCACCACC ATGCCCGGCT AATTTTTGTA TTTTTAGTAG    19620
AGATGGGGTT TCACCATGTT GGTCAGACTG GTCTCGAATT CCTTACCTCA GGTGATCTGG    19680
CCCACCTCAG CCTCCCAAAG TGCTGGGTTT ACAGGRRRRA GATGGGTAAG TTGTGTAGCA    19740
TTATGTGTCT TCACCTTGCA GTGAAGGTTT TGTAACCTCT GAAAGAACAC CTGTTAGGAT    19800
GCAGAGTGCA GGAAACCGCA AATTTCATAT AAGTGTTTAT ATGAGTATGA AGCAGGCACA    19860
TTCTTTATGC TTAGCCCTGG TTTGATAGTG TGCAATTGTG TTCCAGGCAG GTAATCCTGG    19920
GGAACCTGGC TTGAGAGGGC CTGAGGGAAG TCGGGGCTT CCTGGAGTGG AAGGACCAAG     19980
AGGACCACCT GGACCCCGGG GTGTGCAGGG AGAACAGGGT GCCACCGGCC TGCCTGGTGT    20040
CCAGGGCCCT CCGGTGAGTG GTGGGCAGCT TCTGTGGTTT CCCTCTGGAG ACTCCATCCC    20100
ACAGCAGGAG GGCTGTTCTA GGCATCAGCT TCTCAACAAG TTCTCTTGTA AATCCAGCCA    20160
CCTGGCTCCT TGCAGAGTCT GTCAGTTTAC AACTTAACAA TGTTCTCTTT ATGGTTTCAT    20220
GCATAAACTG CCTTTTTTTC TTTTCTGTCC CAGGGTAGAG CACCGACAGA TCAGCACATT    20280
AAGCAGGTTT GCATGAGAGT CATACAAGGT AAATAAATCA CAATGGTTTG ACTTTTTCCA    20340
CCATCAACTC TTGTTTCTTA AGATTTTATT CTTGTAGATA CACAAGGGTA AACAAGAGTG    20400
ACTTTTTGTG TGCCTTAAAG ATAGGACATT TAGGGTAATA TTAATGCCAA TTCTGTTTTT    20460
CCAACTATTG GCATCCACAA TAGTATACAG CCCGTAGCCT CAATGTAAAA TATTACTTTT    20520
CTGGTTATCC TGCCTTTTTT TTTTTTTTT TTGTTTTGTT TTTTTGCCAT GGGGGCTAAT     20580
TTATAACAAA GTGCACACAC ACACACACAC ACACTTTTTT CCTTTGGAAC ACAAGATTCT    20640
TAGTTGTCTC TCCCCGTCCT TAAGACCCTA GCCACTTAGT GTGTACCTAG CACTGACCTA    20700
GGCTTTCTCT ACATTTTGTG AGAAGTAAAT GACAGACTCC ATGCCCATAA GAAGCATAAG    20760
GACATTATCG CCATTCATGT ACACATATGT AAAAACAATC AATAACCAGC ATTTACCAAA    20820
ATTATGCACA ATTTTCATAC TTGTTAACCC TTATCAAAAT TTATCTGTAG CTATGGCAAT    20880
TGTTATTTGT TTCAGAATTG GTCTAGTTAT AAAAACACAC AGAAAATGAA GATGTGCAAA    20940
AGCACCCTAT AGCTGAGGAG TTCTGTAACA CTGAAGCCTA CAGCTAGTTA CAGTATTCTG    21000
GTGTAGCTAA CTTTGTCATG AAGAGATACT CTTTTGTATG TTCACTAGGC AGTCTAGTTT    21060
GTCTAGGAGA CTTGAGAAGT TTTCCAGAAC CAAATAGGAA TGAAACATTC ACTTCTATAT    21120
TTGAAAAGCA ATATAGGCCT CTTCATTGCA GACATTTTGT CCTGAAAGTC TATTTTAGTT    21180
TTAAACATAT CTAAAAAATT ATTATTCCAT GCAAACTCTT ACTTATATAA GCAAATTTAA    21240
AATACTCACA TTTAAACAAT TTAAAAATGT TGGGTAGAAA TTTGTTTCCA TTTCATATTC    21300
TCCTTTACCC TCTAAGTTTA AAAAATATTA CATGAGAATA TTTCCCTTAG AATGTTTTCA    21360
TGGGGATATT TTGTTGTAGG CCATGCCTTT AGTGGGTGAT TCTGAATCTA TTTAATGGTT    21420
CCTGAAAAAG CCCACACAGT TATTAATTTT TAAGACTAAC TCTGACCATT CCCAAGAAAC    21480
AAGTTATTTT TAATGTTTGT TGTCTATTTC AAGCATGGAA AAAACTTCTG AGAAGGAGGG    21540
TTTATAAGAA GCTGTGACTC CTGGGGATAT TTCAGTTTAT ATAATATCTT CAAACTAAGA    21600
ATGTGAGGCG AGGTCTCAAA TGGTGCTGAA TATTAATTCT GGACAATGTT CTTGGCTTTT    21660
AAAAACTGTC TGGACATCTG CTTCACATAT GTTAAGAAAC TCTTTTTCTT CCCATCCTGG    21720
GTTTTCAGAT ACCCAGCAGG GATTCAGGTG ACATCCTTCC AGAACATCAT TCACCCCAAA    21780
GCCTGTAGTT TAAGATTTTT GTGAATCCCA CCCCCTGCTA CCTCCCTCCC CGTGCCCTGA    21840
```

```
CTCTGTCTCA GAACAACAGG ACCAAATATA TCCAGGGAGA GCTGCATCAA ACAGCACCAG    21900

CGAAGCTNTC TGGCAGAAAG CCCACAGAGA AATTATCCAA CTTTATTCAT TTCTTACTAC    21960

CAATTTTGAA GATCTGGTGA CACATTTAGA AAAAAAGGCA TTTGGAATAC CTCTCTTTTC    22020

ATTAGAATAA CTTTTATGTT TCTGACACTT CTGGGTTGTT TTGTTTATTC TCTTTTAGAA    22080

CATTTTGCTG AGATGGCTGC CAGTCTTAAG CGTCCAGACT CAGGTGCCAC TGGGCTTCCT    22140

GGAAGGCCTG GCCCTCCTGG TCCCCCCGGC CCTCCTGGAG AGAATGGTTT CCCAGGCCAG    22200

ATGGGAATTC GTGGCCTTCC GGGCATTAAG GGTCCCCCTG GTGCTCTTGG TTTGAGGGGA    22260

CCTAAAGGTA AGTCATCTTG CCCATGTGGA ACCAAAGAAC ACAACCTTTT TCAGATGTAT    22320

AATCTGTATC AAGCTCGAGG AATTTATGTT TTACCAATTT CTGAATATCC AGTGAGATAA    22380

GATGTATTAT TCTCTTTTCA ATAGTGACGG TGAAGATTCA AAAACTGTTA TATAATATTC    22440

CCTTGACCCT GCTCTACCAC AACAGTAGAC CAAATACTAG AARRRRCATT CCAGTATCTA    22500

TGAATATAAT AATTTGATTT TCCCCCCTTA GATCTATTAA TAGATGAACT TGATTTTTGC    22560

CTTGCTACAT ACTCACTACA ATCTAGTTTA TGGCAATTTC ATGACCTTTT GGTTTCTGAA    22620

TTTTAGATTT GCTGAAAGTT TAAAGATGCG GAAGTTTATT TTTATAGATA TGTAGAAAAA    22680

TAACATTTCT TTAATGTAAT GCAGGTGACT TGGGAGAAAA GGGGGAGCGT GGCCCTCCAG    22740

GAAGAGGTCC CAACGGTTTG CCAGGAGCTA TAGGTCTCCC AGGTAAGTGT GTTGTATAGC    22800

TGAGAGGAGG AGGTAGCGAA ATTGGTAGCA AGTACACAGC CTGAATTGAA TAAAATTTTA    22860

AAATAATTGT TATTTGATCA CTTAAGCATA TTAATTATTC AGAATGGCTA GCATAGATTT    22920

TTCAAGACCA GCTTTAGTAA AGAATTAAAT GATCTGTAAA TCAAATCAGA AAATAGGTAT    22980

CAGGACTTGA AATACTAATT TCCTTAAATA GATGCTTCAA GAAAAATAGT GTCAAGGTCC    23040

AGGCACAATG CACTTGTTAT AAAATTCTGA ATAAATTGGA TCCTATCTAT TTCTAAAGCA    23100

GGTGATAGTT TCCTGTTTTT TTTTAATCTA AAATGCCAGA GCAGTAGGAA GATTAGCCTG    23160

TTTTTAATCT CTTGCACAAG GAGTAACTGA AATTTTATTT TTAAAGCTCC CCTTTCAAAC    23220

ACCCAGARRR RGAACTATTT AACATTTTTT CATATGAAGT CTTTAAAATC CAGGGGTGTT    23280

TGATCCTTAG TTCATCTCCA TTGGGCCTCA TCACATTTCA GCTCTCAATA GGCACCTGTG    23340

GCTGGAGGCT ACCATGGTGC ACGGTGCAGC TCTACTGATG GAAATGGGGG TTAGAGACAC    23400

TGAGGTCTCT TTCTGCTTTT AATTTCCATG AAAACCCAAG TCCAAGGAAG GGATCTTATT    23460

ATCATCATCA TCATCATCAT CACCAATCAT CACCAGTCAT CATCCATCGT TCCAAAAGC    23520

GTTTGTTAAA CCCCTTATCT GAGCGCTGCT GAGCCATGCC CTCTGCCAGT TTGCATCAAT    23580

GAGGATTCTC CTGTTCACAT GTGCAATCTT CTGTGTGTTT CAGGTGACCC AGGCCCTGCC    23640

AGCTATGGGA AAAATGGCCG AGACGGTGAG CGAGGCCCCC CAGGGCTGGC AGGAATTCCT    23700

GGAGTGCCTG GACCCCCGGG ACCTCCTGGG CTTCCCGGTT TCTGTGAGCC AGCCTCCTGC    23760

ACCATGCAGG CTGGTCAGCG AGCATTTAAC AAAGGGCCTG ACCCTTGAAA GGCTTACTGC    23820

TGCATGGCTG TCTGCATGAA CCACGCCTGG TGAAGGAGCC TGGGTGAGAA ACACCATCCA    23880

AAGCTGGGGC AAAGATGATT ACCTTCAGCA TGATTACAAT GTATTACCTT CAGTATGATT    23940

ACAGAAGTCC TACTTGACAA TCACATATAG AAGAACGGTG CTATTCAGTA AGTTCTCTTT    24000

CCTTTCCCTT GGAGGGAAGA CAGCAGAGTC ATCAGTTAAA AAAAAAAAAA AAGAAAACCA    24060

AACACCTCCC TTGAACAAAT TTATACTCCT GTTCCCAGGA TCTTGAGCTT TAGTGTGCTA    24120

TACCTATGTG TCTTATCGTG GGCCACTGTG CCAATAAACA AAAACAACTG TTTGGTTTAC    24180

CTC                                                                 24183
```

(2) INFORMATION FOR SEQ ID NO: 4:

(i) SEQUENCE CHARACTERISTICS:
        (A) LENGTH: 17606 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 4:

```
ATATATATAT ATATATGGAC TATTAGTATC CCCATTTTAC AGATGAGGAA AATGAGACTT      60

CATAGAGTTN GGGGTGCCTG TGGTCATATC TATAATTGTG AAAAAGTCAG ATTCCAAAGC     120

ATTTTACCAA TATTGCCTAA GTGAGTGGGA GGGAAGGGAA GGCTCTCTGG AGTCGGGCTA     180

TGCTGGACAG CGGGGTTCGG AAACTCTGGT GAATAAAGTG GTAGTTGTTT CTATGAACAT     240

GGAGTGAGAA GGCCCAATCC TAAACACACC AGTGCTTAAG GCAGCTGCAG AGAATTAAAG     300

GCAATAGAAA AAGGGGAGCT GGATGGCAGG AGCTTGGATG GGGAAGACTT CAAGGGCAGG     360

TGAAGATGCC AACAGCTTCC TGCCTGGAGG ACCGAAGAAG GGTTGGGCTT CACTGCAGAC     420

CTCCAGGAGA CAGATTTGCT TCTTGGGACA GAGTAGGGAG GTGAAAGCGA GGTGAGGAAG     480

TTCGGGGTGG GGGAGGTGCA CACAGTTCCA CTAAAGAGTT GGAAGAGGCC GATGGAGTAT     540

TCATGAGACG GCTGATCCAG GAAGGACTGT GGCATATTAA TATGGAAAAG GCCTGTTTGT     600

TTGTGCTTGG AGAGGAAGGA GCCAGAGGAG AGGGGAGCAA GGTGGGCGGG AGCTGGGGAG     660

AGCCTGCAGC AAGATCTGCA GAGCCCGAGG TGCTCTCGGC ATGGGCCCTG GAGAGGACGT     720

AGGGTAAGTG ATGGGCACA GGCNGTGCGT CAGGGGGAAG GTGCTGGGGC CTGAAGGTCC     780

CGAGGGGAAC NTCAGACGGC CTTATGCCTT CTCACAAAGA AACTGGACCA TCATTTCCGA     840

CCCGCACCCC GGTCGCCCCT CGAGGACAGA GGGTGGGCGC AGGAGGCTGG ACCGAGCGGG     900

GCGGAGCTGG ATGCCTGGCG CCGGCATCCC TCCCGGCAAC CCCCCGGTC CTCTCAGGTG     960

ACAGTCACGC CCGGCCCCCG CCCCGCCCCC CGCATATTCA AGGAGCCCCA GCCCACCCTG    1020

CCCGCGAACA GCCAGCGCTG GAGGAGCGCC GGGAGACTCT GCCGTCGGTG CGTGCGCGGA    1080

CACGCACCCG TCCCCCTTGG TCTCGCCGCC AGCCATGGCC GCCGCTACGG CCTCCCCCCG    1140

CAGCCTCCTT GTTCTCCTCC AGGTGGTAGT GCTCGCTCTG GCGCAGATTG TAAGTTTCGC    1200

AGCCCCTCCG CTGCCAGGGT CCAGGGTGCG GGGTCTGGAG TCCGGATGG AGGAGCTCTG    1260

CCTGTGTCCC GCGCCTACTG ACACCCCTAG CCCGAGAGGC CACCTGAGGA CAGCGCCGCG    1320

CGAGGTCCCC TCGGTGGGTG CATACATGGT GCCCATCGCG GCACGTGAAT GGAGGTGGCT    1380

GAGCGGAGAG TCAAACGGGA CCCGTCCCCA GACGCGCGGC CCGGCCCGGG ACAGGCAGCG    1440

TGGGCAGGA GCTGGCGCCC GGTCCTGGCA GCCCGGGGAG CCCAGGTGGC GGGCATACAA    1500

TGGTGCTCAT TCACCCGATG CGCAGCATCC GCCCCCGCCG CTTCCCAGGG GGCGCCGGCT    1560

CCAACCAGAC GCCGCTGTCG CCCCGAGGCG GCTTNTCGGC CCTGCCCGCC TACCCACGTC    1620

TCCCTTCCGA GGGCCGCCGG GGGCTGCGGG CGCGCGGGTA GGGCAGAGAC TGGGCCCGGT    1680

CGGGTGCTGG GTGTGGTTTC GAGCTCGCAT GCGGGGCGCC AGCCTGGCAC TTCGCGGCCT    1740

GGGGAGGTCG TGGGCACCGG GACCCCTGCA TGGGTCCGAG CTGGCTTCTT AAAAGGGCCG    1800

CCTTTTAAGA TCTCTGATCT GTTCAGAGAT GGGCAGCAGG ATGGGACTC TCCAGCTGTG    1860

AGCTCGCCTC ATCTTGATAT GACTTGTGAC CTCCCTGAAA CCTCACACCC ACCCAGGGGC    1920

ATTGAATTGC AGGCAAACGG GATCCAGAGA GAGGGTCTGC TTTCTGGGAG GTGCCGGCTC    1980
```

-continued

```
CTCCTGCTCC CCTGCAGCAG TCAGGGCTTA GCAGAGGGAG GACCGGGCAG CTGTGCTGCC    2040

GAAGGGCGC  TCCGAGTGGG AAGATAGTAC CCGCTTCACC TCCCTACACC TCCTTTCTCT    2100

GCGCCTCCCC CACTTTCCGT CGGGTTTTCC CGCACCATGG GGAGAGGAGG AGGCGCTGTC    2160

TCTGCCTGTC GTTCACGTAA GAACAACAAC CCGAGCCACC GCTCACTGAG GCCGGCAGC    2220

CTGCTAGGCA CAACCTTACA TTCCATCTGT GATTTATTTG AGCTGTCCAC GTCTCCATCT    2280

ATTCCCCACG CGACCGCGCA AGGGCAAACT GGCACAGTGG AAGGAGTCGG GCAGATCCAG    2340

GGCGGACTCC TGCGCCGCCG CCCACTCTCA GTGACCATGG ACCCTTCACG TTCTGAGCCA    2400

GTTTCTTCGA CTGCAAACTG GGGCCCGTAA TAGGGCCCGC TCCCGGTTCT GAGTATTCTG    2460

TAAGATAATG AATGCATGTA ATGCACACAG TGCCTGCTAT ACAGAAGATT CTCAATACGT    2520

GGGAGTTCGC GGAAGAGCTG CGCCCCTAGG ANNCTCCCAG GGTGNNTGCA GCCCCGGGGA    2580

CGCCCAGCTT CCTGCACTGT CTGAGGACTG CCCCACCCCG TGTGTGTTTT TCAGAGAGGT    2640

CCACCGGGAG AGCGGGGCCC CCCGGGTCCC CCGGGACCGC CGGGAGTGCC TGGATCCGAC    2700

GGCATCGACG TAAGTCTCTA ACCTGAGACC AGGGCGGGAG GGAGGCGGCA GACAAAGGAG    2760

AACTTTGTGA GCGCTGTGGT GGGGGTGGGG ACTTCGGGGT GCCCGGAGAT GTAGTGCCCC    2820

TCGTCGCCAA TAGNNCCCGC CCNNACCACA AGGACGCCGT TTGTTCTGCA AAAACCTCAA    2880

ACCAGCCCTG ACATNCGGAG CCCGTTATAG CCGCCGACAG ACAAGGAGCT GCTGTTCAGT    2940

CCGCCGGCCG CAGCTCACAG CGANGGNNNN TCCCCCTCCT CTCCTTTCCC CTCCTTGTGG    3000

GGTAGGAGGC GACTCAACCC CTCACCCTGC CTCTGGCACA TCTGGACGCT TCTTCAGGTT    3060

CGCTTGGGAG CCTTGGCCAG ACCACCGACC AGCTTGGGCC AGACTCCTGT CTCTTCCCTT    3120

CGGTTTTCTC TCCCCGATTT AGAATCAGCT GGGCTTGTTC CTGCAGGGTG AGGGTTAAAT    3180

ACCTCATTCT GAAAGCTCCC GCAGGAGGGC CGCTTGATGT TTACCAGTCT GGACAGACTT    3240

CTATTCAACC TGTGCCCCCA CCCCCCAAAC ACAGGATGCT GGCCCCGGC CAGGCCCTGG    3300

CTGCTGAGGG CTCTGAAATG CCTGGAGGCC TCTCTGGGC TGAATCGCAC TCTACCGGCC    3360

CTGCCTGCCC ACCACCAAGG GTCCTTTGGC ACTGGAAGGA GGTCCTTCCC TCCTTGGGAA    3420

CACTGAATTT CCCCCTTGCA GTCCCCCTTG GTCCTTGCCA CTGGCTCAGC TTCCCGTTCT    3480

CCTGCCCTGC AGTCTGGAAT AGAGCTGCTG CCCAACTCGC TCATCCCCCT TCACGTTTCT    3540

CTAAAAGCCC CAACCTTCCT CCCACACGTG CCCAAATCCA AGAGGCATNA GCTTGGAGCC    3600

CCCAGCCCTG GTAGTGGGTC TCACAGCTGG CACCTCATGA CATCAGCATG TCTGTACCTT    3660

CTTGCATGTT GCTGTCACCC TCTCCAGCCC GGCCAGGGTT ATTCTCATGC TCCTGTGATT    3720

TGTTTTTGGT TTTTATTTTT GAGGAAAAGG GGGCTCTTTT CCCAAAGATT GCAAGGCTTA    3780

GGGGACCTGG ACAGAAGAGA GGAGAGTGAG GAGAGCCTTT GGGAGCGGCC TGCCAGGGCC    3840

TGTGTGTGCC CACTTGGGGT AGTGTGAGCC GTAGTGTGCT GTCTCACCAA CTTGTATCTT    3900

GCAGGGTGAC AATGGGCCCC CTGGAAAAGC TGGCCCTCCG GTGAGTGCTT TATCCTCTTT    3960

GGCCTTTGAC CCTTCCTGCT CTTGCCCTCC TCTGGCTCAT GTTTGTTCCA TCTCTGTTTT    4020

CAAGGGACCC AAGGGCGAGC CTGGCAAAGC TGGGCCAGAT GGGCCAGACG GAAGCCCGG    4080

GATTGATGTG AGTAGCTGAG TGTCGGGTGG GCAGGGTAG GCTCTGCCAA TTGACCTCCA    4140

GGGCCTGGCT CTGGCATCTT CACTGATCTG TTCAGAGATG GGCAGCAGGA TGGAGATTCT    4200

CCAGCTGTGA GCCCCCCTCA CCTTGATATG ACTTGTGACC TTCCTGGAAC CTCACTCTCA    4260

CCCAGGGTCA TTGATTTGCA GGCAACCGGG GTCCAGAGAG AGGGTCTGCT TTCTGGGAGG    4320
```

```
TGCAGGTTCC TCCTGCTACC CCTCAGCAGT CAGGACTTAG TCTCACATTT CTGGCCTCCA    4380

AGGATCAGGC TGAATATGTT GGGTGGGGCT GTCCTTGTGT GCCCTGTCCT TTCCTCCGCT    4440

CTTCCCCTGA CCCCTACCCA CAGCCCCAGG CATGACTCAG GAGAGAAACA TCATTTAGCT    4500

GATACCACAG AGCTCCCAGG GGGACCCCCA AGGTCACAGG CTCTTGAACA CAGCCAGCCC    4560

CAGGGGCATG AGGACAACAT CTGATGGGGG TTACACTGGG TCAGTCACTG AAAGATGGGA    4620

GAAAGGAGAA ACCCCCATGA CTTGCCTCTG CCCTGCTGGC TCATGAGGTG TGACCAGGGC    4680

TGGGACAGTC ACCAGGACCC CTTCAAACTC ATCCACACCC TGCAACGATT ACAAGGCATA    4740

TTGCCTTCTA TGTTGCATCA GTTCTCACAT CCACCCAGAG AGGCACCCAG ATGAGAAACT    4800

AAGGCTCAGA AAAAGTTGCC AATGGCCTGG CGTGGTGGCT TATGCCTGTA ATCCCAGCAC    4860

TTTGGGAGGC CGAGGTGGGC AGATTACTTG AGGTCAGGAG CTCAAGACCA GCCTGGCCAA    4920

CATGGCGAAA CCCCATCTCT ACTAAAAATA CAAAAATTAC CCAAGCGTGG TGGCGCATGC    4980

CCCTGGTCCT AGCTACTTGG GAGGCTGGGG CACAAGAATC ATTTGAACCC AGGAAGCGGG    5040

GGTTGCAGTG AGCTGAGACT GTGCCACTGC ACTCCAGCCT GAGCAACAGA GTGAGACTGT    5100

GTCTCAATTG AAAAAAAAAA GAAAGAAAAA GAAAAGAGAA AGGAAAGAAA AGAAAAGAAA    5160

ATGAAAAAGT TGTCAAGGTA GGACATCAAG CAAATGACCA ATCTTGACCC ATGGCTAGGT    5220

CTTCTAGACT CCTGAACCCG GAGGCATGAA GCCTGGGTCT GGCATAAAGC CAAATCTTTG    5280

GGCTTTGGTT TCTCATCTTT CAAAAGAAGG GAATTGTTCT GCCTGCCTCC TAGGGTTACT    5340

ATGGGAACTG GGGAAAAGGA AGAAAGGTG TGGAGGTTCC TAGGCCTTCA TGAGGTGTGG    5400

CAAAAAGGAG CCTCGGCCCA CCCAGGAGGG ACCCTTGAAC CTGCCCTGCT CTGTGGGTCA    5460

GGGAGCAGGT TGGCCCTCAT TGATCTACAT TTTCATTCTT CCCCAGGGTT TAACTGGAGC    5520

CAAGGGGGAG CCTGGCCCCA TGGGATCCC TGGAGTCAAG GTAAGGGGCC TGCTGGGGCC    5580

TCAGCGTGGG CAATCTAGGG CCAGCGTTTG GGAGTGGCTG TAGAGAGGAA GTAGGAGCCG    5640

GGGAAACCCC AGCCTCTGAG CCTTTCTCGT TGCTTCTGCA GGGCCAGCCC GGGCTTCCTG    5700

GTCCTCCTGG CCTTCCGGTG AGTACAACCT GCAAGGCTTC GAGGGACTCT TGGGGAGAG    5760

GGGACCTGCA GAGGGAGCCA TGAAGCCAAT TTTCTTTCTT TCTGTTCCAG GGCCCTGGTT    5820

TTGCTGGACC TCCTGTAAGT CCTCAGGGAT GGGGCAGGAT CCCCAGAACT CCCAGGGAAG    5880

GAGGGGACAA CAGAAAGGCT TCGAGGGNAT GGCCACCATG GGAAGGAGCC AGCTTGCTGT    5940

GATAGTGTCA GGAATAAGTG GACCTGCCAG AGACCCAGGG CCAGCCCACT CTGGGCCTGT    6000

CCACTGGCTC TGNAATTCTC TGGTCCTTAA AGCCTCAGTC TGTCAGTCTC TCTGGGGTTG    6060

GCAAAAAAAA AAAAAAAGTA AAAGTGGAGA ACGGGCTTT GGGTGCCTGT CTCTACCTTT    6120

GTGCCCAGGG TATCTGACCC TCTGAGGCAT CCTGACCATC AACTCTCTGC TCCCCAGGGG    6180

CCTCCTGGAC CTGTTGGCCT CCCTGGTGAG ATTGGAATCC GAGGCCCAA GGTGAGCCTC    6240

AGCCACCCTC TGTTCACTGC CTCCTGCCTT CTATCTCCAA GCTGGCAAGC TGGGTGGTCT    6300

TTCTGGAAGT TCCTGGGCCT GCTCCTGGCC ACTGGGAAAC TCCTCCAGGT CTGGGGCAGA    6360

AACCCCTCCT ATGAGCCCAC CCGGCACTAG GTCTTTTAGG GACNGCTGGC CCCATCCCCT    6420

GTCAATCAGG CCTTCATCTC CCAAGATGGT GGATCTCACA AAGTGACCGG GAAGACAGGG    6480

TGGAGAGGGC AGAGGCAGGA CCTGGAGGAG GGCACTAGGG TAAGCTGGTA AGGGCTGGTC    6540

AGGGGTATGA TTTGGGCTTC TTTTGCTTCC AGGGGGACCC TGGACCAGAT GGACCATCGG    6600

GGCCCCCAGG ACCCCCTGGG AAACCTGTAA GTGTCCCCAG ACCCCCGACA TGGCAAAGTG    6660

CAGGGGAAGG AGAAGGGTCT TTGAGCAAGC CTGCGGCGGG AAAGGGTCAG GCCAAGCTCC    6720
```

```
ATCTTCATGT CTCCTCTCAG GGTCGCCCGG GAACCATCCA GGGTCTGGAA GGCAGTGCGG    6780
ATTTCCTGGT GAGAGACGAG GTCTGGGGCG GGGCTAACAC AGGGGGGCGG GGCCACAGAG    6840
ATGGGGAGGC GGGGCCACGG AGATGGGGGT GTCTGGAGAG ATGGGGAGGG GCTGCAGTGC    6900
AGGGGTTCCA CCAGGTGAGG CGGAGGAGAG CACGGGGCTT GGAGAGATGG GGGCGCACTG    6960
CCCAGCTGAT CACAGGACCC TGTGGGATTT TCTGTTTCCA GTGTCCAACC AACTGTCCAC    7020
CCGGAATGAA AGGTCCCCCA GGGCTGCAGG GAGTGAAGGT GAGAGCTCCT GGCCTGAATC    7080
TTGGGAGGGT GGTGCAGGTG ACAGGAGGGG ACCTCGTATT GAGCTCTCTC CTTCCCTTCA    7140
GGGGCATGCG GCAAACGCG GGATTCTGGG TGATCCTGGC CACCAGGGGA AGCCGGTGAG     7200
TGCAAGGGCT GAGGGCTGTG GGTCAGGGAT ACGTGGAGAT GGTCCTACAG GGCTCTGTCC    7260
CCTTCTTCGT CCCTTCCCCT TCCCCTGTGG GTTCTGGGGA CAGAGCCTTG AGCCGGNGGC    7320
TGGAGGCCTG TGCTCCAGGT CGGCATGTCT CTGGTCATGT CTCCTTGCTT GGCTTTTCTC    7380
TATCTGTAAC ACAGGACTGT AGGGTTCGTA GTAGTCCCTC CCGTCTGCTT GTGCTGGGGA    7440
AAAGAGGTGG TATCTTTGCT TGTCTGTATA TGTGTCTTTC CATCTGCCTG CCTGTCTGAC    7500
AGCTCATCCC TGCCCTTTAG GGTCCCAAGG GAGATGTGGG TGCCTCTGGA GAGCAAGGCA    7560
TCCCTGGACC ACCGGTAAGG AACACCTTGC CTCAGTGGCC CTCTTCTCCC TCACCCCAGG    7620
AGCCCTTCAT GGAGTCATTC CCCTGCTCAG GCCTCTAGCT TGTAAAAGAG ACACCTGTGT    7680
CTAGCTGGGA GCATCTCTGG ATGGGAGAT GGAGGCTGAA ATTGTCAGGA ATGAGGGACA     7740
GGAACCAAAG CTGTCAGCAA GAAGCCCAGG CTGAGGTCCA GGTCTGCCAC TGTCCCTTTG    7800
AGTAATGCAG TGAGTCCCTC CTCATCTCTG AACCTCCATG TCCCATCCAT GAGACAGAGA    7860
CTCTGCTGCC TACCTCAAAA GGGCACTGTA AGATTGAAGG TGGGCATCAG ACAAGGTATC    7920
ATGAAGTGGG CCTTGCAATT GCCATTGCTG TCATTTTTCT TTCTCAACAG GGTCCCCAGG    7980
GCATCAGGGG CTACCCAGGC ATGGCAGGGC CCAAGGGAGA GACGGTAAGT GAATCTTGGG    8040
GTGTTCTACA AGAGCTTCCA GGAGCTGCCT TCTGGCCCCT GGAGTTCAGC CAGGACTGAC    8100
CTGCAACCCT TTCCTCTCCC CAGGGCCCTC ATGGATATAA AGGCATGGTG GGCGCTATCG    8160
GTGCCACTGG GCCACCGGTA AGCCTCTTTT TGCTCCCCTA CCCCTGAGGC TGGAGCTCCT    8220
ACAGCTACAG CCACAGAGTG GGCATGGCTC CCCCTGAGCC TGTGTGACCT GGATTCCTGC    8280
TTGTCTTTCT TGCCAGGGTG AGGAAGGTCC TAGGGACCG CCAGGCCGAG CTGGGGAGAA     8340
GGGTGACGAG GTGAGTCCTC AGGCACCCAT TGTTCAGTCA GGNCCCCTGG GGAGTACTGG    8400
GCAGGACAAG GCACCCCCTA AGGCTGTGTG TGTGAGAGTG CATGAGTGTG TGCGTGAGTG    8460
TGAATGTGTA GTGTGTGTGA GTGTGTAGTG TGTGTGTGTG TAGACTGTGT GTATATGAGT    8520
GTATGTGTAC AGTGTGTATG TGTGAGGCTG TCTGTGAGTG TGTGTAGTAT GTGTATGTGA    8580
GTGTGTGAGG ATATCTCTGA GTGTGTGTGT GTGACTGTGA GTGTATGTAT GTGTGTGTGA    8640
GTGAGTGTGT GTGTGTCTGC CCAAGTGGGT GACCTGCTGG GGAGGACCAT CTGTGCCAAG    8700
AGCCCAGTCA GCCCAAATTC AGACTTTAGG CGANNNTGGG ATCCAGTCCC ATGGTCACTG    8760
GGGCCAGACA ATGAGATTCC AGCAAATCAG CCATGGGGCT AATGGGATTT GGTCTCGATC    8820
CCAGTTCTCT TAACTCTTTT TTTTTTTTTT TCCCAATTAA TAGACCTGTT GGGGGAAGCG    8880
GTTTTAAGTT TACAGAAAAA TGGAGCAGAA AACACAGTTA ACTGTTATTA TTATTTAGTT    8940
TTTTAAATTA TTTTCTTTTC TTTTTAAAAA TTAAAAAATT CTTATACTTT TATTTTTCTA    9000
TTAGACAGCA GAGATCATCT AGTTGTTTTG TTTTGTTTTG TTTTTGAGAT GGAGTTTTAT    9060
```

```
TCTTGTTGCC CAGGCTGGAG TGCATGGTGC GATCTCGGCT CACTGCAACC TCCGCCTCCC    9120
TGGTTCAAGA GATTCTCTTG CCTCAGCCAC CCAAGTGGCT GGGATTACAG GCATGCGCCA    9180
CCATGCTCAG CTAATTTTGT ATTTTTAGTA GAGACAGGGT TTCACCATGT TAGGCTGGTC    9240
TCGAACTCCT GACNTCAGGT GANCCACCTG CCTCGGCCTC CCAAAGTGCT GGGATTACAG    9300
GTGTGAGCCA ACACGCCCAG CAATATCTAG TTTTTTAATG CAATTTTTTA ACTATACAGA    9360
AAACCAGTGA GAGTGATATA AAGAATCCCC ATGTACCTAT CACAGGTTCC AANTCAGTTA    9420
TTAACATTTT GTCAGTCTTG TGTCCTCTAT CCCCCAGACC CCTCCTTCCT TTGATTTTGT    9480
TATTGCTTTG CTCTGATGTT TTCAAGTAAA TCCTTAACAT CCTATCATCT CAGCCCTAGA    9540
TACTTTTGTA CATATCTCTA AACAATAAGC ACTCATTCTC ACATAATCAC ATTATCACAA    9600
CTGACAAAAT AAACAAGTAC TCCCTAACAT CATCTAATGG CCAGTCTCTG TTCAGTTTTT    9660
CCCAATTATC TCAAAAATGT CTTTTCCTGG TTCTTGTTCA AATCAAGACT CACACAGCAT    9720
CCACACACTG CATTCGGTTG TTGTGTTCCT TTGGCTGAGT GGATTGTGGG GCCTTGGCCA    9780
AGGTCTCAGT GGATTCTGGC TCCCACCCCT GCTCTGGCTC AGCCCAGCCT GGCCTCCTGG    9840
CACTGACTTC TCCTCCCTCC TGCTGGTGCC AGGGCAGGAA GGGTACTCCC AAGGCTCTCT    9900
CCTCCGGCCC CTGCATGGTG TGGCCTGTGC CAGAGGAACT CTGGGACCTA GAGGCCACTG    9960
TTCTCAGTGG TTCCCCTCTC TGCACAGCCA GACAGGGGCC CAACATCCTG AGGGTGACCT   10020
GATCTCTCTC CGCTTTGCAG GGCAGCCCAG GTATTCGTGG ACCCCAGGGG ATCACAGGCC   10080
CGAAAGGAGC AACGGTAGGT GCCAGAGGCC TAGGCCCACC AGGACAGAGG CCAGGGCCCA   10140
GCTGCTTTGT CCAAACCCCC AGAAGAGAAG CCTGGGATGC TAGTCTGAAC TCTGCAACTG   10200
GTGGGCTGGC TCCATAACCT CAGGAAATGC CTCCCTTTCT GTGCCTCAGT TTCTTCACCT   10260
GTAAACAGGG GTGATGACAT ACGGGAGGTC ATGGGGAGCT TGCAGCAGTC GGGGACACCA   10320
CCCTCCACAC TAGGGAAGGA CTGTGTTCCG TGACCCTCAT CCCCTTCCCA CTTCAACTCC   10380
CCTCCCCCAG TTGGCCAGTG GGGCTTCCTG GGATGACCAG AGCCACTCCC TCCCTGCACA   10440
CTGCAGCTGT CTCAGAGGAA CAGGGGTGGG TGGCCAGACC CCAGACATCT CCGCATTATC   10500
ACTCTCCCTT GAACTTTCCT CCTGGGTAGG GCCCCCAGG CATCAACGGC AAGGATGGGA   10560
CCCCAGGCAC GCCTGGCATG AAGGTAGGAG TGGGGCTGCT GATGGGACTG GGCAGGGGC   10620
AGGACCTTGA GTCCTGGATT CTAGACACCA AGAGCCTGGG GCCCTCAGGT CATGGACATG   10680
CCCTTTCTTG CCTCTGGATC TCAGTTTCCC TACCTGCATC TGGGTAGAAG CCATGGCCCT   10740
CTGGCTGGAG CTTTAATTTG TATCTTTGGT TATCTGTCTA TCCCAGGGCA GTGCAGGACA   10800
GGCGGGACAG CCCGGAAGTC CAGGCCACCA GGGCCTAGCG GTAAGTGTCA GGTGGAGCCA   10860
CAGGGGCTGG CCAGGGGCTA GTGGCTGATG AGGTTAGAAT CCACACACAC CCGGGGCTCT   10920
TGCTCAATCA CCACCTCTTG CCTTGTTACC AACTCTGTGG CCCCTGGNCT GGCGAAGGCT   10980
TCATTACTTG GACAATTACT CTAGCCTTCT CTTTGGCCAT TCCAGTCCTC CATGTTGGCT   11040
AAATGGGATC TGACCATTTC TGCACTATAG CACCTTCCAT GGCTCCCCAC CGCCTCCAGG   11100
AAAAAGTCAT TCAGTCCAGT CCTTCAATAA GTAGTTATTG AGGTCGGGTG CAGTGGCTCA   11160
TGCCTATAAT CCCAGCACTT CAGGAGGCTC AGCTGAGTGG ATCACTTGAG GTCAGGAGTT   11220
CAAAACCAGC CTGGCCAATG TGGTGACACC CCGTCTCTAC TAAAAATACA AAAATTAGCT   11280
GGGCGTGGCG GCTCATGCCT GTAATCTCAG CTACTCAGGA GGCTGAGGCA GGAGAATTGC   11340
TTGAGCCCAG GAGGCGAGGT TGCACTGAGC CAAGATTACA CCACTGCACT CCAGCCTGGG   11400
TAACAGAGCA AGACTCCATC TCAAAAAAAA AAAAAAAAA AATAGTTATT GAGTATCTGA   11460
```

```
GGTATACTAA GTGGCAGGTA AACAATTATA AATAGGACAG ATGCAATCTT TGTCTTTCAT   11520

GGCTCATCTT ACCATTCAAT GACCACCATA ATCTGACCCC AACCTGCCCC TCCTGCCATA   11580

TCAGCAATGG CCCCTCTCTG TCCTTTCCCT TCTCAACAGG CCTTGGCTTT TCTGCCTCCA   11640

CACCTTTAGG CCTTTGCTGG TCCCTCTGTT TGAAATGCCC TTTCTGGTCT CTTTGTGCCT   11700

TCTTATCGTT CAGGGCCATC TCCATTCCAT ACCTCCTGGA GTCCAGTCCA TGGGAGCCTG   11760

CCCTCCCTCC CTGTGGGGGT ACTGAGTGGC CAAACCTGTT TCTGTGCACA CATGCAGACT   11820

TGTGTTCCTG CGTGCACTCA CATGGGCTCA GGCACCTGAG AGCACATATC CATCTCTTCC   11880

ACGTAGACCC CAGGTCCTGG AANACAGGCC ATTCTCTGTG CCCCACTCCT CTGNCACCAC   11940

TGTGGGAATG TACAGTNAAG TTCATCATGC CGTGGCTGGA CCTTCTGTTG TTCAGCTCCC   12000

ACAGGTGGGG GAAATCTGGA TTGGGGATGG GAAGCAAAGC AGCAGGTGCA TGGGGCTCCC   12060

TCATGCCAGG GCAGAAACTG ACTTCAACTT CTTTCTGCAG GGTGTGCCAG GCCAGCCTGG   12120

GACAAAAGGA GGCCCTGGAG ACCAGGTGAG GCGATCCCAA GCTGGGGACA GAATTGAGCA   12180

AGGAAGTCTG GGGCCAGGAA GACAGCAAGG CCCAGGCCTC AGCCAAGTCT CAGAGGCTCA   12240

GCCAGAACAT AAGCCCCTTG GGCCTAACCA CCTCCCTCCT GCCACCTCCC ACCCATCATG   12300

CACTCCTCAG CCTGCCTCAG TGCAGATAGG ATGGCATGGC TTAAAATCCA GAGGAGAAAC   12360

AAACAGGAAA ATCAGGAGCC AAGAGGATTG AACCAAGAAT ACCCTCTTCC CCGTCCCAGC   12420

TCATCTGGTT CCAGGCTCTG TTTAGGCTTC GTTGGGTTTC CCTGAGGCCA AGGGCTGACT   12480

GGGCCACCCA GACTGACCTG AGAACTGTTT TCCTGCAGGG TGAGCCGGGC CCGCAGGGCC   12540

TTCCTGGATT CTCTGGTCCC CCTGGGAAAG AGGTAAATGC CCCCTGCACT GACACAAGGG   12600

TTCCTGCTTT AGGGTGAGGC CATGGGGTGG AGCCTAACCT AGGGAGAGCT CCGAGTTAGT   12660

CTGGCTCTGC CTGACCCAAT GATTCAGGGA AGCTCTTTCT CCTCCCTGGG CCTGTTTCCC   12720

TATGTACATT GCAGGGAGGG TGGGGACTGG CTCTGTTCTG GAGTGTGACT TTCCTAGATG   12780

GCCAAGTTGA TGGGCTGGGA ATCCAACAGG CAGAGTTGTT CGTTCATTTA TTCATTGCAT   12840

AAACATTCAC TAAACACTTG CAACTATGAG TCTCCTCTTC ATATGGAGGG TATAGTTTAA   12900

TGGAAGAAAT AGACATGAAA TAAATGATCA CGCCGGGGGC NNNNNCACGC CTGTAATCCC   12960

AGCATTTTGG GAGGCTGAGG CGGGTGGATC ACGAGGTCAG GAGATCCAGA CCGCGGTGAA   13020

ACCCCGTCTC TACTAAAAAT ACAAAAAATT AGCTGGGGGC GGTGGCAGGC ACCTGTAGTC   13080

CCAGCTACTC TGGAGGCTGA GGCAGGAGAA TGGCATGAAC CCGGGAGGCG GAGCTTGCAG   13140

TGAGCGGAGA TCGCGCCACT GCATTCCAGC CTGGGTGACA GAGCAAGACT CCCTCTCAAA   13200

AAAAAAAAAA AAAAAAAAAA AGAAAGAAAG AAATGATCAC ATGATAAGTA ATTCAAATTG   13260

TGTTGGGTCC TTTGAAAGAA AACTACAGGG ACCCAAAACC ATGGAACAGG TGGTCTGGGA   13320

AACCTTCCCT GATGAAGCAA ATTAGCTGAG ACCCAGGGTA GGGAGGGGCT GGCCAGGTGT   13380

GGAAGGGTGG GTTCCACCAG GTCAAACGCT TAGCCCCAAT TTCTCCTTCC TCCAGGGAGA   13440

GCCAGGGCCT CGAGGAGAAA TTGGTCCCCA GGGCATCATG GGACAGAAGG TAAGTGCCTG   13500

GCACAATGGC CCCTCCCCGG GGGCCTCTGC GGCAGCTGGC ACTGCTGGAT ACAGCATCTG   13560

CTCCGTGCAG CCCGTGAGAT GCCTCCCCAG GCAGGGCCTA GGTTTGCTTT GCTGGTCTGC   13620

CAAGTGGAGA AAGGACCCCC TGCCAGTGAC AGCAGGAATG GAGGGCACCC TGACCATGCG   13680

GTGCCAGGCC TCGGTGCGGG AGGCTACCCC TGCTGAGAGC TGCTGAGGTT GTGACCTTCT   13740

CTTTCCATTT CAGGGTGACC AAGGCGAGAG GGGTCCAGTG GGGCAACCAG GCCCTCAGGG   13800
```

```
AAGGCAGGTG AGTGCAGGCC AGCTAAGGTG GGCAGGGCGT CATATCCAGG CCCCTCATTC   13860

CATTTATTCC TTTGGTTTCT TTTCTCCTCA GGGCCCTAAG GGGGAGCAGG GCCCCCCCGG   13920

AATTCCAGGG CCCCAAGGCT TGCCAGGCGT CAAAGGAGAC AAGGTGCCAG ATGGGGCTGG   13980

GAAACNCCTG GGAAAGGGGC CCTATAACAG GGGGAGTGGG GTCGGCAGGA CTCAGANCCT   14040

TCCGGAGCCT CCAAACCTGC GGNTCTCAGG GTTCTGGTCT GGTCGGCGAG GCGGAGTTGG   14100

AAAGAGGGGT GTGGCCGAAA GTTAGGTGGG GGACCCCGTG GAGGGGGGAG CTCGCCAAAC   14160

CCCTCACTGC CCGCTTTCTC CAGGGCTCCC CAGGGAAGAC CGGGCCCCGC GGCAAAGTGG   14220

TGAGTTCCAG CACCCCTGTT CCCAGCGACC CCCAACCCTG CTCTGCGTCC CCGCCGCCAC   14280

CGCGCGTCTG ACCCGTGGTT CTCTCTGCAG GGTGACCCAG GGGTGGCCGG CCTCCCCGGA   14340

GAGAAAGGCG AGAAGGTGAG CGCGCGCCTA GGGAAGGGCG GGGAGCGGCG GCTGGCCCGG   14400

GGTCCNNGGC TTCGTGACCG CTGCTCCTTG TGCCTGCAGG GCGAGTCCGG CGAGCCGGGG   14460

CCCAAGGGAC AGGTGAGTCC TCCCCTCCCG GCGTTCTCCG ACTTTCCTGG GCGGCCACTC   14520

CCTTCCTCGA CCCCCACCCC CCACTCTCGC CCACCCGGGC GCCTTCTCAC CCGGCTCTGC   14580

TCCCACCCCC ATCCCCCCGC AGCAAGGAGT ACGTGGAGAA CCCGGCTACC CTGGCCCCAG   14640

CGGGGATGCG GGCGCCCCAG GGGTTCAGGG CTACCCTGGT CCCCCCGGCC CTCGAGGACT   14700

GGCCGGGAAC CGAGGCGTGC CAGGACAGCC CGGGAGACAG GGCGTGGAGG TGAGTCGGGC   14760

CCCGGGGTAG GAGGTGCTTC TTCTAGGTAG ATCTGTTCTG GGGTGCGGCT TACCCGCCAA   14820

AGGCTAGGGA TTCCCAGAGA CTCACCGACT TCCCCGAGAC TGGTTCCAAG CCCCAGAGCA   14880

GACAGGAAGG CTGTGAGTGC AGCCTGAGGG ATTACCCCGC GACCTTCCCA AGTAAGCCCT   14940

TGGCCCTGCC CAGGTACAAT CTGTTCCTCA GCTTGGGAAT TAATGACTCA ACACCAGAGT   15000

CTCCTCCATG GCGGCCTCAC GCTCAGCCAG GTGGGATAGG AGCGGTGGGC CCTTGTAGCC   15060

AGGGGCTTCT TCCTGAAAGC CTCTGCTTTC AGGGCCGGGA TGCCACTGAC CAGCACATCG   15120

TGGATGTGGC GCTGAAGATG CTGCAAGGTG AGGGGCAGCA ACCCCTCCTC ACAGTCAGTT   15180

CGAGGGCATC GCCGCCCCCT CACCCCCTCC CGGAGCCTCC ACGTGTTCAC TTGTCTGAAA   15240

ATCTGGAGTC CTGGGGGCTC CTTCCAGTCC AGTCTCTGAA GGGTTTTGGG ACCTTGAATA   15300

AGTCACTCTG GGCCTTTGAC TTCCGCAAAA CAGAGCCCAC GGAAGGTGGT GCTTTTCTGT   15360

CTGCAAACCT AGGGGCCAGG GCCCATCGGA ATGCTCTGCC TCCCCTAGTG TTACTGCTGA   15420

CACCCATCTC ATAGACTTCC CTCTCCCTCC TNCTCNCTCC CTCCAGAGCA ACTGGCAGAG   15480

GTCGCCGTGA GTGCCAAGCG GGAAGCCCTG GGTGCGGTGG GCATGATGGG TCCTCCAGGA   15540

CCTCCTGGGC CCCCTGGGTA CCCAGGCAAG CAGGGCCCCC ATGGGCACCC TGGCCCTCGG   15600

GGCGTTCCTG GCATCGTGGG AGCCGTGGGT CAGATCGGCA ACACGGGCC CAAGGGTGAG   15660

TGCTCCTCTG CGGTGGGCAT GGGGGCCAGG CAGTGAGGAT TTGTCCAGGC CGGCCCTTTC   15720

CCCATTCCCT TCTCAGGATG ACATACAGAC CCTTCCCCGG TTCCTCAGCC ACATGGTCCA   15780

GGAGACACTC CTGGNCTCTT TCCTAGTAGC AAACGGATGG CAATGAATGT ACTATGTTAT   15840

CACTCGGGGT TTCTGGGGTT TGTTTTTGAA TGTGCTTAGT GGTACCCCAT AAGCATCTTT   15900

CCATGTCAAT AGAGATNGGG CGGCAGACCA GCAGAGCAGT AAAGCAGGCA GGCTGGAGCC   15960

ACACACGGGT GTGAATCCAG ACTCCCCTTT CTCATCGTGG CTCTCAGACG AGTTACCTGC   16020

TAATTTCCCT GGGCCTTAGG TTTACTATCT GTAAAATGGG GNCACTGAAA GTACCAACCT   16080

CATCATGTGG CAGTGAGGAC TATCCTTAGA GTAGTTTACA TAGAGTTTGT CTTAGTTCAC   16140

TGAGACACAG TAAATGCTAG ATATTGTTAT GCTTGCTTTC CTGTAATAAA CTTTATTGGT   16200
```

```
TACATAATCT TCCATCCTTT GTCTGCACCT TCCTTTATTT AACAAGCCCT GCGTGACCAT     16260

TTCCAACTTT CCTCTATTAC AAACTAGCAC AAAACAGGAA TAATTTCTTT GCGTGAAACA     16320

TAGCAAAAAA TAGAGGAAAA GCATTTTCCA ATTCTGAAAA ATGAAGATTT CCTTTTTTGT     16380

CTACAGGAAA ACGTGGAGAG AAGGGTGATC CAGGAGAAGT GGGACGGGGG CACCCCGGGA     16440

TGCCTGGGCC CCCAGGGATC CCAGGTAAGC CATTGGCCCT GCCCAGCTGC AGTGTGTTCC     16500

TCAGCTTGGG AATTAATGAC GTGTGGACAC TGCGGTCTCC TCCATGGCGG CCTCACGCTC     16560

AGCCAGCTCA GTCCTTGATA CCCAGCTTCT GCACCCCTTT GGAGCACCCC GGAGTCTCTG     16620

GGTGGTTCCA GCTCTGGAAG CTGGGCCTCT CAGGACTTCC CAGGATCCAC CACCATCACT     16680

TCACAGAGGT GATGGAAGGG ATGTTTGCTC CCAAAGCTCA CTGATTGGGA GCTGGGGGTA     16740

GGGGACAATC ACAGAATCTC TGCCTCTGGG GCAGAGTCCT TTCTCCTATG GTGTTTTGGC     16800

CTCATTTTCT CCATCTGAAA AGTTTCCCCA CCTTCAAAAT TCTGGGCCTG AGACAAGAGG     16860

TGCCCCTAAT GTCTTGACTT TCTCCTGTTC ACAGGACTCC CTGGCCGGCC TGGCCAGGCA     16920

ATCAACGGCA AGGATGGAGA TCGAGGGTCC CCAGGGGCTC CAGGAGAGGC AGGTCGACCT     16980

GGCCTGCCAG GCCCCGTGGG GCTGCCGGGC TTCTGTGAAC CTGCCGCCTG CCTTGGAGCT     17040

TCGGCCTATG CCTCTGCCCG CCTTACAGAG CCTGGATCCA TCAAGGGGCC TTGAGCATCA     17100

GGCCCAGACA GAGCCTGGAG GCATCCTGGC GGGAAGGACC AGGTCCCCTC TGGTGGACAT     17160

GCACCCATCC CCAGTCCAGG AAACCATCTC CCCCAGGACC TTCTGTCTGG GACTCAGGAG     17220

TCCTAAGGAA AAGGAATTCT AAAACATGGG GGAAGGGGAG GTAGAGCACT GATGGGTGAA     17280

AAAGTGAGGC CAACACACAG GGCAAGTGGT GTCGATGGAG TCGAAGCGCT GAAGGAATAG     17340

GGCGGCTTTC CTTCCAGCGA GCATCATTCG GCTGTTACCA AAACAAACAT CTTAATCTGC     17400

ACCTTCCTCC ACTGGCCATC TTGTCCTTGG GTCAGTGGGA CATGGGCACC TCGGGAGGCC     17460

CGGGCCCTGC CCAGCTACAG TTCCACCCCT CAGCTTGAGG ACCAATACTG AGGTCTATGC     17520

CAGTTCCTGA TCCCATCTCA CTCTCTGGAC CTACTAGGTG ACTGCTGCTG GGGTGACTCC     17580

CCTGAGGCGG CTATACCCTT AAGCCA                                         17606
```

(2) INFORMATION FOR SEQ ID NO: 5:

(i) SEQUENCE CHARACTERISTICS:
        (A) LENGTH: 20084 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
GCTCTCCCCT GCGCCCCTGT CTTTGTAAAT TGACCCTTCT GGAGTGGGGG GCGGCGGGCA       60

GGGCTGCTTT TCTTAGTCTG ATACCAAGCA AGGCCTTTTC TGAATAAATT CATTTGACTT      120

TGAGTCTTTG GTATGGACCG GGGTCCTGTT GGGTGGCTGG TAGGGCTGGT GTCACAGCTG      180

ATGTCCCTCC AGGCTCCAGT GGCTGGCCTG GCCCGGCTAC CGCCTCACAT TGCTCCACCA      240

GGTGCCTGTG GGGCAGAGT GGTGGCCCAG CCCTCCCCAC ACACCCACTT GGCCACACAG       300

TCCCCAGGCA TGAACAGGTG GGCAGGCTGC AGCCTCCCAG AGCCTCTGAA GGTGGAACCG      360

AGGTCCCTCA GCAGGCTTTT GCCACCTAGT TGAAGATGAG TCTGGGGCTT CCCTTGGGGT      420

TGGCCGGGGC AGTGCTTGTG CATGGTGGGG TCTGGACCAG GCCTTTCTGC CTGCTGTGAT      480

CTGGGATGCG CTGCTGTGCC TCGGGCAGGC TTGGCAGTAC TCTCTGGCGG GCCCCTTGGC      540
```

```
TCCCTCAGGT CTGGTGGAGA CCAGGTGTGC CCCCAGGGCA GTCCCTCCCT GCAGTCTGCC      600
CTTGTCACCC TGGGCCAGGA CCCCCCGCTT CCCGGTTCCC CTACATTTCT ACATCAGCAG      660
GGTAAGGGGC TTTTTGTGGG GCCTCAGAGG AGGGGCCAGA CACTTGTCTT TGCTCAGTGA      720
AGGACAGGGC AGACCTGGGG CACCCCTGGG TGGGAGGGTT AAAGCTGTAG ACCCTGGTAC      780
CACTTCAGAT AAAATGCCCA GCTCCCATCT GGTGGCACCG GATACACGAG CCGGAAGTCA      840
CTGGGAGGAG ACACCCGAGG TTCAATAATC CCCCAGAGCT GCGTGGGGAA GCTGTGGGAC      900
CCCTGGTGCC TCAAGTGTGG CTCAGGGGAT TCCTGCCATG GAGGGAAACT GAGGCAGTGA      960
GCTGGACATA GGGCTAGAAG TGCAGTCACT GGGGCAGCGC CCGGCAGATC CAGCGTCCCC     1020
AGTCCAGGCC GTTGTGGGGC TGGAGTCGGT GAAAATCAGC GCCTGAAGTG AGGAGCCTGT     1080
TGGAGCAGCC CTGGGGGCCG ATGCCTGGCG GTGGGCACCT GGGGCCAGCA GGCAGTGCTG     1140
GCCAGCCAAC CCGGGCTTCA GGGAGAGTTG ACCCACAACA GGCGGGCAGC AGGAGGCTCT     1200
GCCCACTCAA AAGTGAGCCG GGGGAGGCTG AGCTCTGACA GTGCCCACCC TCTGCCTAGG     1260
ATCTGCCTGG AGCTGGGGGT GGTTTTTTGA GGGGCTTGAA GGTGGTTCGG GGGGGACACC     1320
AAGCAGGTGT CCCAGGCATG AGGTGGCTCC CCTGGCCTGA GGTGAAGGCC AGCTGTGTTT     1380
TGTCTGATTT GGGTCAGATA GCAGTCCTTG CTGACTGCAT GCTGGGCATC ATGGGGATAG     1440
GCAAAGTGGG GTGTGGGGCC AGGGACCAGG GGAGAGCCAC TGAGGAGGGG GCTGGCCACA     1500
GGGTCATCTT GCCAGGTGGA ACTGGTAGGG AGGACTTATC CTGTCCCCCA GACCCTGGGC     1560
TTGGGGTGGG GCTGGTGCTG GGAGCCCCTA AGGCCCCCTG CTGTCTGGGC TGACCTGCTC     1620
CACTCACCTC TCCCCGTAAT CAAAAGTCCT CTGTTAGGAA GCTCTGTGCC AGGATGACTT     1680
GGACTCCTCA GGAGGGTGGG CCTTTTCAGC TCCTCCCACC TCGCCTGATG GAATTCGCAC     1740
ACACCCCTCC CAGCCCAGCC ACCGCGCTCA CCCAGCAGTG AAGGGAGAAT CTCCCTCCAC     1800
TCACTTCACC GCGGGAGAGA TTAGAGCGAC ACTATTATTT TGAGACAGGG TCTCACTCTC     1860
TTGCCCAGGC AGGAGTGCAG TGGCGCCGTC TTGGCTCACT GCAGCCCCGA CCTTACAGGC     1920
TCAAGCGATC CTCTTGCCTC AGCCTCCCGT GTAGCGTGGA CTACAGGCGA GCACCACCAT     1980
GCCCAGCCGA TGTTTTAATT TTTGGTAGAC ATGAGGCCTC CCTCTGTCTC AAGCTGGCC      2040
ACGCCCGGCC GATGTTTCAA TTTTTGGTAG AGATGAGGCC TCCCTCTGTC GCCAGGCTGA     2100
CTGCGCCCGG CCAGAGTGCG GTGCTCCTGC TGAGCAGTTT TGCGCCCACT CCCCTCTCAT     2160
CCCCTCCCGC CCTTGCTAAC TCACAGCATT GCAACAGTCA TGAGTCCCCA CCTGCCGAAA     2220
GGAAGCTCCT GCAGCCCCCT ACAACCCCCA GGGCAGCCTT TCTCGGGAAT TTTCAAGATT     2280
CCTGGGGGAG GGGCTGGCAT CTGCGCCTTC ACTGAGCCTA CAGGCAACTG GAAGCTTTGA     2340
GTCCCCTAGG GCAGCGACTG CCCTGGCAGC CTGAGGCAGA GCTTGGCCGG ACCTGGCGAC     2400
CCCTGAGCTT CTGGGAAATG GACATGGCCA GCACCGCCTT CAGGTTCCTG CCCAGGGCAC     2460
GGTTCCTTCA GGCCGGGGAT CCCGGGGAGG GGTTCTTCCC CTCGGCCAGG GTCATCGTTT     2520
TGCGATCTCT CCTGGGAGTC TGGGTTTGGA GTCTGGTCTT AGCCGGTAGC AACTGACGTG     2580
GCCTGACCAC CCGGCCCGTC CAGGTCCACG GGTGAGGGGC GCGGTGGGG GTGCTCCCAG      2640
CCCAGCAGGC AGCGCTGGAC AGTGACCCCG GAGCGGAAC CAGGGCTGCG CTGGGCACTG      2700
ACCGGGCCCT GGTACCGGGG ATTCACCCTC CCCGGGGTGT CCCTGGGCCT TGGGTCGCCT     2760
GGGTCCGCTC CGGCGCCTGG GGAGGGATCT GCGGCTTCGG AAACTCGCGG GTCTCCCCTG     2820
CCCCTCCCTG AAGGCGGCCC TTCAGCGCCC GGCCGTTCCG CCCCCACACT CGGGTTGAGG     2880
```

```
AGCAAGGAGA GAAAAGAGCG TCTTTCTCTC TTGCTCAAAG CTGCGTGTGC GCAACGCGCC    2940

AGTCCCAGGA TAATTTTAAC TCGCGGCCGG AGAGAACGCG CCGCCCGCCC GGCGTCTTTT    3000

TTGTTTTCGC CCAGGCGGGC TGGACGGCGG CGCGGGGCGG GTGGAACCCC CCACGCAGGT    3060

GGGCCCGGCT GAATGGGGGG CTTGTGCAGG CGGGGCGGG AAGGGGAAGG GGAAGGGGCC    3120

GCCCACCTCC CGCCCCGCCC GCCCGCGCGC CGCCCGCCCC GACGCCGCAG CTCAGACTCC    3180

GCTCAGCCAT GGCCGGGCCG CGCGCGTGCG CGCCGCTCCT GCTCCTGCTC CTCCTCGGGC    3240

AGCTTCTGGC GGCCGCCGGG GCGCAGGTGA GCGCGAGATC CGGGCTCTGA GGCTGGACGT    3300

GGAGCCGCGA CCTCCCCAGC CCCGAACCCG CCACTCCGGG GTGCCCGCGC AGTCACGACG    3360

CCCCCAGCCC GTGTCGCCGT CGGGGAGAGG AGTCGCCAGC GCCTCGGGAT GAGCCCCGTC    3420

CGGCCGCGTC CTCGATGGGT CCTCGCTGGC CCGGGCGGCC GCCGCCGCCT CCTCTGGGAG    3480

CACAAGGGGG CCTTTGTTCC CGCCGCCGGA GGGAGGCGGG GGACACACTC GGCGGGGGCG    3540

CCTGCCTCGA GGCTTTGGGT CTCACCGAGG AGAGCGGCGG TCGTCGCAGG CCCCGGAGCC    3600

GCTCGGGACC CGGGAGGAGG GGACGCCGGG TCAGGCCACG GGGCACCTG CGCTCCTTAA    3660

TGAGTTTTCT CCGTTTCAGA GAGTGGGACT CCCCGGCCCC CCCGGCCCCC CAGGGCCGCC    3720

CGGGAAGCCC GGCCAGGACG GCATTGACGT GAGTTTGGGG GTGGGGAGGG CCCCGAGCGC    3780

TCTGGGGTTC TGGCTCTGGC CCCCACCTCC CTGAGCTCCC CGGCCTGATG GAGAGAAAAC    3840

CAGGCCCCAC CTCCCAGAGC CGGGGTGACA TCAGGGACA GCCAGTGCCT TCACGGGATG    3900

GGGGTGGCCC TGCGGGACTG CTGGTGGGTA GGGGTGGAGG GTGTCATGTG GTGGTCCTCC    3960

ACCCAGAATT CCGGCACTGA GGTGTGTGTC TCTGGGTCCC TGAGGGGCCC GTGCCCCTGT    4020

GTTCGGGGTT CTGGCCTCTG GCTGAAGTGG GAGAGGCACG TCCTTTGGGT GGTTGGGGGC    4080

CGGGGTCTTG TTGGAGGCTG CTGGGCTCTG GAGCCAGCCA TGGAGGGGCT TAGGAGCCGA    4140

CTCAGTCCTG AGATGATGTC CCCTATGGGT ATCTCAGGAC TGGTGTGGGC CAAGCAGCAG    4200

GAGGAGGCGG CTGAAATTCT ACAATTGTGC CTCCCTCGGA GGGACCGTCT GGGGTGAACC    4260

TCCCCATGTG ACCACCACCA GGGCAGGAGT CCCCTCAGGG CCTGTCCACG CTGTGTGGTC    4320

CCCGTGGAGG GCTGTGGAGG GCTGCACCAA GAGCCCCCCA TGACCCACCC TCTGCCCCCC    4380

TGCCCAGCTC GGCCTCAATG GCCATAGCCT CCTTCCAGTC TGTCCAGTTC ACCCCTTTGC    4440

CCAGTGCTGC CCCACACATG GGAGGGTGCC CTCTAGGTAG GGATCGGGGG CTCAGGGGCC    4500

CCTTTTGTCT GCTGGGGCTG GGGCTCTGGG GCTGATTTGG AGGCCAGCGC TGCTCTTTTC    4560

CCGAGGCGGG GTTCTTGAGG GACCCCTGAT TTTCAGGGTT ACATGTGGGT GTCTTTCCTC    4620

ACAGGGAGAA GCTGGTCCTC CAGGTCTGCC TGGGCCCCG GTGAGTGTCC CTGGCTGGGG    4680

AGACAGCCTT TTTCCAGTCT GGAGAGAAAG GGGGAACTCA GAACAGAGGG GTCATTGATA    4740

TCCTGTCTCA TCCTGCCGGA GCCCGGGTTG CCTGAGGGGA GGCCTCAGAG GCTTGGAGC    4800

AGGCCTGGAG CCAGCGGGGC GGAGGGGAGT GTGGGCTCAG CCTCTGCACA TGTTCAGGGC    4860

AGGGCCTGGG TTTGAAGCTT TCTTTGGACC AGCGCCAGGC AGGCGGGACC GGGGCTGATA    4920

CAGCTTCAGG TCCCCCAGGC CTGAGGTCAC CTGGAGCCCT CCCACCTTCT TCAGTTCCTG    4980

GGGTTGAGGG TCCTGGGGCT CAGAGCCCTG TCTGGGCCCA CTGGGGGTCC GACAGAGATG    5040

CCTGCTGGCC CTTAGCCAGG GAGGCCGAGG TGACCAGACG AAGGTGTTAC AGATGCCACT    5100

GAGGGATGGG GCGGGCAGCC TTCCTGGGCC AGCAAGGTGT GGGCAAGCAG GACACACGAG    5160

CCCCAGCTGA GCCGGGTCTG CCAGACAGTA GGGGGGACCC AGGAGAGGGG CCCATCCCGT    5220

ATGTTGGGCT GGGGGAAGTG GAAAGCATTT TGCTTCATTG CTGAAGCCTG GGCTCCAGGC    5280
```

```
CAGACCCCGC CTTCACATCT CTGCCCTTTC CTCCTGCACA GGGACCAAAG GGGGCCCCAG    5340

GAAAGCCGGG GAAACCAGGA GAGGCTGGGC TGCCGGGACT GCCGGGTGTG GATGTGAGTG    5400

CGCCTGCCCC TCCCCGCCAT GCCCCACTCC CCGCTCCGGG TCCCTGGAGG AGTCCGGCCC    5460

TAATTGCTGT TGTCCAGCTG GGCCTGCTCA GGCGGGAAGC CCAGTCCTGA GAGAAGTCTC    5520

CAGAAGTCCC CCAACAGGGG TCCTTTGGCC TTCATCCCAG ACGCCACCAG CATCTGGCAG    5580

GGGACAGAGC CAGCCCAGTG GAGTCGGAAG TCCCGCCAGC CCTCCTTGCT TGTCCAGGAA    5640

TGAGTGCCCA TTGTCAGGAC CTTCTGCCCA CTGCTGGCCT CACTTAGTCA TCTTGGGCTC    5700

CAGGCCAGCC CCAGGCCACG GAGTTTGTTC GGAGGAAGCC GGGCCTGAGA AGTGAGCTGT    5760

CCAGTCCTGC TGGGTTGGTC CCCGTGGCCT GACTACAGCA GGTGCCTCCG TTGCTGGCTT    5820

CCCGCTGGCT GCCCCCTCCC TCCTCCCAGC CTCTGGCTAC AGCAGGCAGA CAGTGGACAG    5880

GGCCAAGAGA GGAGGCTGCC ACCCTAAGGG TCTTCTATGC CTCTCTGGAC TCACCAAGGG    5940

AAGGGTCCGT GCTTCCATTT TTGCCTGGGG GGTGGCATGT GCTTCCCATG TGGCCCCTCG    6000

AGCTCGCCCT CTGCCTCTCC CCAGGGTCTG ACTGGACGAG ATGGACCCCC TGGACCCAAG    6060

GGTGCCCCTG GGAACGGGT AAGTGCCTGC GCCGAACCCA GTGGCTTGGG TTCAGAGGTG    6120

AGGTCCCCTG GCCACCTCTG GCTGCTCTGT GTCCACAAGG CCAAGGAGCT GGTAGTTCCA    6180

AGGACAGCTG CCCTGCCCGT GCCTGGGGTG GAGGGCAGA AGGGCAGGGT GCCAAGTGGC    6240

CAGTCCCCTG TGCCTGCCTC CCTGCCTCAC CTCCACGTAT GGTCAGAGTT GTCCTGGTAT    6300

CCAGACCATG GCAGGGAGAA GGGGGATGGT TTGGGGGAAC CCACCCCAGG TGCCTCCTCA    6360

GAATGTCCCT GAAGCCCCCA AGCCCTGGGC AGACCACCAC CAGGGACCCC CGGGCACGCA    6420

GCCTGCAGAG TCCCCTGTGC CTGCCTGTTG GACACTGAAT CCTTTACCCT GACGGAGCGG    6480

CACCACCACC CAAGGGTGCC TTTCTCCCCT TGTGGCTTCT GAGTACAAAC CCGAAGCCAG    6540

CAATCCCTCT TTGGCTTCAT AAGACGTGGC TGTCAGCCAA CCGGGTGCCA CTGGCCCCAG    6600

GCGCAAAGCA TCACAGAGGG CAGGAAGGCT GGGCTGGGA CACGAGGACA CAGCCCTGCC    6660

CTTGGGGACC CTTGGGAGCT CGTCAGGGCA TGAGGCGGAT TCTGAGCTGA AAACAGGAGG    6720

GAAACAGTAG CTGCTGGCCA GCGAGTCCGT GGTGCCCAGG GGTGTGGGGT GGGCTGGTCC    6780

CAGGCTTTCA GGAGGGGCCT CCAGCCTCAG CACAGGGCCC GTGCGTGCCG TCCAGGGAAT    6840

GAGGCATTTC AGGCAGCAGG GGCCAGACAG GGCCAGAGGG TGTGGAGGGC AGACAGGGCC    6900

TGGCTGCCAA GGCTCTGGGG CTCGCTGACG TGGGCGGGGG CTGAGGACTC AGCAGGCTCC    6960

GTGGGTGGGT TATCGGGAGG GCTTCCTGGT GGAGACAGGC ACCCCGGGTC ACTTCGGTGC    7020

CTCTCAGCCC TGCCTCAGGT TGCACCTTCT TGCAGCGAGC GCTGGGACTC TGGTGCCATC    7080

TGTCTCCAGC AGCTCCCCAG GACGGCAAAG ACCCTCCAGG TCAAGAGGGC TCAGAGGCCT    7140

GCCCCTCTGT GAAGTGGGGA CTTGGACCCT GTTGTCCTGG GAGTTGGAGT TGTGACGTCA    7200

CACTTCAGAG GGAGGGGATT GGGTTTGCAA ATAGAGGCCC AGCCAACCTA GACGCCTGCT    7260

TTCCTCCCAC AGGGAAGTCT GGGACCCCCG GGGCCGCCCG GCTGGGGGT GAGTATGGAG    7320

TGTGGTCCTC TCCTCTCCAT GGGAGTTTGG GGAGCTGGAG AGTCTGGTCT AAATGGGGTG    7380

GCCTCCAGGA ATCCCAGGGA CCATCCCTGG CCCTCTCATC TGCAGCCTCT CCGGAGCTGG    7440

TGCCTGGATG GGGTCCTGGT GCCCTCTCTG GGCTGGGACC AGACACCCAT CCCTGGAACC    7500

GCCCTTTCCC CAGGACCCAC CTGAGCCATC TTAGGGAGGG GTGAGCGCAG CCCTTCTTGT    7560

GCCTGGCAGG CTCTGACCCC ATGTTTGGCT TTGCAGGGCA AAGGCCTCCC TGGACCCCCC    7620
```

```
GTGAGTACTG ACAACCCTTG GGGCCCTGAG CAAGCACGCA AGTCCCGAGA GCCTGCCAGG    7680

CTGGGATGTC CCAAACCGTG CCTGGGGGTG GGGCTTCTCA GGGGCAGCCA TCTGACCACC    7740

CCATACTTGG AGCCCCTCTC CTTCGGAGGC GGCACAGGCC ACCCTGGGTG GGGATCCTCG    7800

GGGCTTCCGG GTGCAGACCT CCCCACCTCT CTTTACTTCC CTCCAGGGAG AGGCAGGAGT    7860

GAGCGGCCCC CCAGGTGGGA TCGGCCTCCG CGGCCCCCCG GTGAGTGGCT GTCCCAGAGC    7920

CCCTCAGAGT GTGCTCACCT GTGGCCTCCA CCCCAGACT CAACAGCCAG GGGTCCCTTC    7980

CCCTCTCCCT TTTCCCTTTC TCCCCCAACC CCACCTTGGG TTGTTGGTAG AAGCCCTGGC    8040

CAATGATCCA GACCCGACCT CAGGACGCAG ACACCAGCAC AGTCCGTGGG AGTGGGGGCT    8100

GGTGGGAGCT GGGCGTGTCC ACCTCCCTGG GAGAAGCCGG GCACCTCACT CAGGTGGGGG    8160

CTGGTCCCAC TCTGTCTAAG TCATACCCCC TCCCCAGGGA CCTTCTGGAC TCCCCGGCCT    8220

CCCTGGTCCC CCAGGACCTC CCGGACCCCC TGTAAGTACT GGGCAGAGGC TCTAAGAAGT    8280

GCTGGGCATG GACTAGGACA CTGGGTTGGC CCCTCCCCAT TCCCCCTCCC CAGGCTCCAT    8340

GCCCCTCCGA GATCTCCTAA CCCTAACTTG GCCACTCCCC AGGAACAGTC AATGGTGGGG    8400

GCAGTGGGCT GTGCTAGGCC AGCCAACTTG GGATGGTCAG GACTCAGGTC CCCATGCCAT    8460

CCTGCCCCAA GGACAGGTGG ATTCTGTCGT TGTCACATAC CCTGTGGGTG GGCCAGCAGC    8520

TCCCAGCACT GGCCACTTGG GGGACAGGAT GAAGGGTCTC CAAGTCCCCT GGTGGATGGG    8580

GAAGGTTGTG GTCCGTCAGA GAGTGGGTGG GTGGGTTGGG TGGCTGCAGG TGGCTGGGGA    8640

GGGCGGGAGA ATGTCAGCTG TCTCTTTTTG TCTTAGGGAC ACCCAGGAGT CCTCCCTGAA    8700

GGCGCTACTG ACCTTCAGGT AGGCACTTGA AGCCATTTGT TAAGGGTGCT GGGGGGTGCC    8760

TACCTTGGGG GGAGGGGTTC TGGCCTGGAG AGGGGCTTGT CCATACTGGC AAGAAGGCAG    8820

GCCCGAGCCC TCCCTGGGGA CAGGAGCTCA GAGCAGACAG CTCGGGCACA ACCTGGCAGA    8880

GAGGCTGGCT GGGACCTCCC CCTCCCCCTT CCCACCCTCC TCACCACCGT CTAGACCTGC    8940

ACTGTCCCTC ATGAAGCCAC CAGGCGCATG GAGCTGTACA AATGTAATGA ATCACAATCA    9000

TGTCACAGAG CCATCCAGCT CCCCTGCGTC ATCCGCAGAG GGCGCCCTTG CCACAGATG    9060

GCGACAGAAC TGGAGTCTGA GACCCACCTT TATCTTGATC TTTGAGCCTT GTCATTTGCC    9120

TGAAAAGAAA ACAGGCTCAG GTCAGGCGCA GTGGCTCAGG CCTGTAATCC CAGCACTTTG    9180

GGAGGCCCAG ACAGGAGGAT CGCTTAAGCT CAGGAGTTTG AGACCAGCCT GGGCAACATA    9240

GTGAGATCTT TGTCTCTACA AAAAATTGTT AAAGTAGCCA GACGTGGTGG CGTGCCTGTT    9300

GTCCTAGCTA CTTGGATGGC TGTGGTGGGA GGATCACTTG AGCCCAGGAG GCAGTGGTTG    9360

CAGGGTGCTG TGATCAAGCC ACTGCACTCC AGCGTGACGA GCCAAGCTAA GCCTGTCTCA    9420

AAAAAATGAA GAGGAAAGAA AATGGGCTTC GGAGGCCACG GATCCATCTC TCCTCTCTGT    9480

TTGGCCGTCC GTGGTGGCAG TCAGCGCCTT GTTTCCATAG AGAGGTTTGA TAGTTTTGAA    9540

GGGAAAAGCT CGGCCCACTC TGACCTGACC ACCGACGCTG TCTACCAGCC TCTCTCCTCA    9600

CCCCACCCCG GGGCCTAGGT GCCTGGCCAG CCTGTGTCCC AGAAGGGAGG CTTTAGGGAA    9660

CCTTCCAGAA TGTGGTGCGT GGTTGGGCCC CCGATCGTGG GCTGAGTGGG GCAGGGGCTA    9720

AAGATACGGG TCTGCACCCT TGGCCTGGCC TGCCCATTGC AGCTGTAGGA TCATCTAGAA    9780

GCAGCCCTGG GTTTCCTGAG CATCAGACCT GTTGCCTGGG CTCACAGTGC CCTCCTAAA    9840

AGCCCCATGC CGAGCACATT CCTGTGCTGA GGATGGGCCC GACCTGAGGC TGCTGAAGGC    9900

CCCCTGCAGT GCCGGCCGGG ACTGTGCTGA ATGGCTGCTT TGATAGCCAG TGTCTGCCGT    9960

GGGCCGGCTG CTCCATGCAG CCCCTGCTGA CTTGGCCAGT GCTGAAGGAG ACCCTGTCTG   10020
```

-continued

```
TGTCCTGTCC CAGTGCCATC TCCTGTACGA GTGGCCTCCT GGGGTCCCGT CACTGTGTGG    10080

AGTGGCCTCC TGGGGTCCCG TCACTGTGTG GAGTGGCCTC CTGGGGTCCT GTCACCCAGA    10140

GTGTCCCGAC ACCCGCGCCG GAGTGGCCTC CCGGGGCCCG TCACCCACGC GGAGTGGCCT    10200

CCTGGGGTCC CGTCACTGTG TGGAGTGGCC TCCTGGGGTC CCGTCACTGT GTGGAGTGGC    10260

CTCCTGGGGT CCTGTCACCA TGAGGAGTGG CCTCCCGGGG TCCCGTCACC GTGCAGAGTG    10320

GCCTCCTGGG GTCCCATCAT CTGTGCGGAG TGGCCTCCTG GGGTCCCGTC ACTGATGCGG    10380

AGTGGCCTCC TGGGGTCCTG TCACCGTGAG GAGTGGCCTC CCGGGGTCCC GTCACCGTGC    10440

AGAGTGGCCT CCTGGGGTCC CGCGGGCGCT GACCCCTGCG TCGACGTCCT GCTCTGTTTG    10500

GCTGGGAGGG GTCTGACTGC TCTGTTTTCC GACAGTGCCC AAGTATCTGC CCGCCAGGTC    10560

CCCCAGGGCC CCCTGGAATG CCAGGGTTCA AGGTGAGTCA CGGGTGACTG GGACCCAAGC    10620

ACCACCCTGT GCTGGGCAGG AGGCAGCTGG GCTCCCATGG GGCTGTGGAG GTGGCGGGTC    10680

CAGAAAGCTG GACCCTGGTT CCACGGTTGC CCCAGGAAGA AAGCTAGGCC AGCCTCCTTG    10740

TCCCGCCTTC AGCACCCCAG TGACACGCTG ATGTGGCCAG GCTGGGACTG GCCATAGGCA    10800

TCAGAGACTG CGGGGGAGAG CTAGCCTCAA GCTCCCACCC CAGCCCAGCC CTGGCCCGCT    10860

CCTGACCGCA GAGCGCCCTC ATGTGGGGTC CTAGCGCCTC TCAGGCCTCA GTTTCCCCAT    10920

GAGGGCCCAG ACCCGCGGTC CTGTGCGCTG CCGTGTGGCG GGCCCTGGGC TGACTGACCC    10980

TGCAGGCCTC ACTTCAGTGT TGCCAGGGAG GGGGTGTCGG GGGGTCTGGG TGGGGCAGTG    11040

ACCCCACATT TGCTTGCAGG GACCCACTGG CTACAAAGGC GAGCAGGGGG AAGTCGGCAA    11100

GGACGGCGAG AAGGTGAAGC TGCCGCACAG CAGCTGGGGA GGAGCTGGGG ACTGGAGGCT    11160

GGGCTCCGGC GGGAGGGAGG GGCTGGGCTC CGGCGGTGGG GAGGGACCGT TTCATGGGTG    11220

CACCTGCACT GGCACCTTCT GTGCTGTCTT CCAGATAGGG CCTGGCTGGT CAGAGCTGGG    11280

TGATTTAGGC TGGGTCCTGG ACAGACCCCG TCCTGCCTGG CCTCGCTGTG GAAGCTCCCT    11340

GGTTTGTGTC TGTGGCCGGG GCGAGGGGCA TCTGTGAGGA TGGCTGGCTT TAGCCTGTAG    11400

CCTCCCCTCA CCTGTGGTCG CTGTCCGTGG AGGGTGTCTG TCCATGGTCA CCTGCAGGCC    11460

GGGGGACCAG GTCTGGGATG CCCTTTAGCG TGGCTGGAGT GATCAGATGA GGAGACCCCA    11520

GGTGCACATC AGAGGGGTCC CTGCTTGGCC ACGAGGAGGG GCCTGGACAG GGCTGAAGGG    11580

CCTTGTGGGA ACAGTGACCA CGGACCCCGG CCCGGCAGGG CGAGGCCACC GAGACTCGCG    11640

GGACTGCTCT GGAACTGTGG GCAAGTGTCC CCTTCACAGA GCCTCCAAGG CCCAGCTGTG    11700

AAGCGGGCAA CACCCCCAGC TGCTTGGGCT TGAGTAGGGT GACTGGAGGC ACCGAAAGGT    11760

GCAAGGAGAG CCAGACTGGG CCGCTGACCA CCCTATCCCC TCTGTTTCAG GGTGACCCTG    11820

GCCCCCCTGG GCCCGCCGGC CTCCCGGGCA GCGTGGGGCT GCAGGTGAGG CTAGGAAGGG    11880

GTAAGGATGG TGGGATGGGA ACTCAGCCCA CAGAGTGATC AAGCCCTGCA CATATCTACC    11940

CCCGAGGGGG CCAGCTCCGG CTGGGGGGTG TTTGGCCAAC ACCCAGGCAC AGGAGCGCGA    12000

CCTGGCTGGG GGTCCCACCT CTGCCAAGGC TGCTGACCTC AAGGCTGGTG CCCCCTCCCT    12060

CTGGGGACC TGAGCTGAGG CTGAGGGCTC ATGGAAGACA CCAGGGCTCC CAGGGGTACC    12120

CCGAGGGCCT TGGCCCTGGG TGATCCCCGG GGTGGAGGTG CAGCCCCAGC CTCTGCATCT    12180

GTGCCTCTCT CTCGCAGGGC CCCCGGGGAT TACGAGGACT GCCAGGGCCA CTCGGGCCCC    12240

CTGGGGACCG GGTAAGTCCT GCAGCCCCTA GTGGGGCCG GCCAGGTGGC TGGGGGCCTG    12300

GTTGTCTGCA CCTCCAGACT TCAGATGGGC CCCGTGAGTG ACACTCTGAA GCAGCCGGCA    12360
```

-continued

```
CCCTGGCTCT GGCCATCGCC ACTGTGGCGC AGGCCTTGCT CTGGGCCCCT GTTCTCGCAT    12420
GTGCCTGGGC GAGAGCTGAC AGTCGGCGCT CACTGATGCC CGCACGCGGT CCCAGGCTGC    12480
TGTGAGGGCT GTTCACGCGT GTGCCCGGGC GAGGGCTGAT GAACTCTGCT CGCTGACACC    12540
CACACACACG GTCCCAGGCT GCTGTGAGGG CTGTTGTGGC TTAGGCCAGA GCAGGAGGGG    12600
AAGCAGGGAT TTGGAGACTA CTAGGTGGCA TCTTGGGGGA ACTTGCTGGG GAGCCCTAGA    12660
GGAAGGGCTG CTTGTGTCTG GGCCGCCCCT GAGGGAGCAC TGGGGGGATG CCAGCCAGGC    12720
CTCAGACAAG AGGACCCCGG ATCCCCTCTC TCCTCTGCAG GGTCCCATTG GGTTCCGAGG    12780
GCCGCCTGGG ATCCCAGGAG CGCCTGGGAA AGCGGTACGT GTGTCAGTGG ACGGTGGGCG    12840
CCATGCCACG TGACCTCTCT CCCCTTTCCC TCTGCTCCTC TCAGACGCCC CCAGCCCCAC    12900
TGGGGCCCCT CTTCTCTGGC TGAGCTGTTC CCTGGACACC CTGGGAGGGC TTGTGGCATG    12960
GGTACGGGGG TGCTTACCAA TGGAATCCAT TCTTTGTGAG ACATTCGCCT CCTTTCTGGT    13020
TCTGGACGTG GAATGAGGGG TCACCATCGT CCTTCTGGCA CCTCCAGCCA TCTCTGACCA    13080
CTCCTGGAGG GTCCAGGCCT GGAGGGGCCC CCATCCCACT CTCTGACCAC TCCTGGAGGG    13140
CTGTCCCCCG CCCGGGCCTG GAGGGGCCCC CGTCCTACTC TCCGACCATC TCCATGGTGT    13200
TAACTCTGTC CCTGCCCCAC CTCATCCTTT CCAGGGTGAC CGAGGCGAGA GGGGCCCAGA    13260
AGGGTTCCGC GGCCCCAAGG GTGACCTCGT AAGTGAGAGG GAAGTTGGTT CCCTGGGTCC    13320
TTATGTGGAA GAACCCAATT TCCCTCCTGA CTCGTGCTGG GGAGGGGGAC ACACTTGGGA    13380
GTGAGACTGC AAGGGGCTGC CTGGGTGGGC CTGGGGGTGC GTGGGGGTGA GCCTGACCCT    13440
GGAGGGCCCG AGATCTCTCC CTGGCCCCAG CCGTTCTCCC AGAGCCACAT GGGAGCTCTG    13500
TGGCCCCCTG CAGAGCGGCC CACGGGCCTG GAGGGACCAG GCTCCAGGGC TTGGATCCTG    13560
CCCCCAGAGA AAACGGCTCT CGGGTTGAGC AAGTGAACAT AAGGAAAGTC CAGAGGCAGC    13620
CAAGCGTTCC AGGAGTGGAA CTGAAGTGAC CGTCCCCAGA CTGGTCAGCC TCCACACCTC    13680
CCTCGACTGA GCCCTGGCAG CCGGAGTGCA GGGAGCCGCC GTGCCGTCCT GCAGCATCTG    13740
TGGATCCAAA CACAGTTTTC TCCACGCACC CACAGGCCCC AGGGTGGTTG GTCGGGGGTG    13800
GCCCCTGCCG CTGCCCACCA TAGCTCCTTG GTGTCCCCGA GCAGCTGGCC GGAGAATGCG    13860
TGAGGCCGTC TGGGAAGAGA CTGCCACTGC TTCTGTCACT TGTGTGTCCT CTAGGGCAGA    13920
CCTGGTCCCA AGGGAACCCC CGGAGTGGCC GGGCCAAGCG GAGAGCCGGT GAGTGCACGT    13980
GGCTGCTCAT GGAATGCTCC TCCCCCGGGT CCTGGGTATG TACAGGTGGA GATGGCATTC    14040
AGAAGGGCTG GAGCTCAGTG CCCTCTGCTG TGGCCATCTT GAAATCTGGG TTAACGGTGG    14100
AACAGCCCCG CAGCCCCACA CATTTCTCTC TTGCCCAGAG CCTCACGAGT GTGCAGGAGT    14160
AGGGGCCTCA GGCTGGGTTT ACCTGCACAG AGGACACGGG AAGTAAGGGT GGGTGGGTAG    14220
CACCACTGGG CAGAGGTGGG CACTCCCAGG GTCCCGGGCA CCCGTGCGGG CACCTTCCTT    14280
CCTGCTGGGT GCCCACCCTC AGCCCAGACC TGAGCTCCCT TCTAGCCCCT CGTGTTGCCT    14340
CTGCCCCGGA GTAGTGCCCT GTCTTGGGAC ACCCAGCAGT TGGCTGTGTC CTGATTCCAA    14400
AACCAGTCCA GGGTGGACCG AGGCAGGCCT GCCTAAGGCC TCAGTTTCCC CACCGTAAAA    14460
TGGGCCAGAA CCAAACTTCC TTAGGGCACC ATGATGTGCC TGGTGGACGA GGCCTCGGGC    14520
GTCAGCACTG CATCAGCACC GCCTCTGCCA CCCACCCGCA CCCCTGACCT GTGCGGTCAC    14580
CGAGGTAGCA CTGGTTGCCA CACGGCCACC TTGGTCATGA AACCAGATAA CTGCCAGGGT    14640
GTGGGGCAG ACACAGTTTT AGGTTGATGG GGAAGGAGGC TGCCCCCAGG GCGGGACTGT    14700
AGAGGGAGGG AGGGGGGCCA CTGCCCGACG GGCCTTACTC ATCCCTTGTC CCCAGGGCAT    14760
```

```
GCCAGGCAAG GACGGCCAGA ATGGCGTGCC AGGACTCGAT GGCCAGAAGG TTGGCATGGG    14820

GCTCAGGGTG TGACGGGAGG GAGGGGGCTG GAGGGGAGTT CGGCCTCCCG AGGCCTCAGC    14880

CTCCCCTTCC GCACCCCAAT CTCTGTCCTC ACAGGGAGAG GCTGGTCGCA ACGGTGCTCC    14940

GGGAGAGAAG GGCCCCAACG GGCTGCCGGT GAGTGCCCGG CGGGTGGGGC CAGCCTGGGG    15000

CGCCACAGCT TCTGCCTGCT CAGTGGCCCA TGTTGGGCTG GGTGGGTTGG TCACTGTAGG    15060

GCCGACTCCC TGTGAGGGGT TCTGGGGCCT GTGTCCATCA GGGCCTGGCA CAACCCCTGG    15120

TGCCCAGTGG TGCTGTGGAC GGTTGCCTGT ATGTTTGCAT GTGTGTGCTT ATTCGTGTGT    15180

ACATGGGACA TGTGTGAACA TGTTGATGGC CATCCCTGGA TGCCGTGCGG TCATCACCCC    15240

CATGGGCTCT GAGTAGGGGC TCCTGCATCC AAGGCCAGGG AGGCTGTCAA ATCCTCACCT    15300

CAGGTCCACA AGGCTGGGAG AAGTTGGCCC TGCCTTTGGG TGCACTCACT CTGGCCCCGG    15360

CGCCCTGCCT GCGTGCACGC CCCTGGGTGC TGCTGCCGGC GTGCAATGTA ACTGGCAGCC    15420

CTGACCGCAA GCTCTCTCCT GGCAGGGCCT CCCTGGACGA GCGGGTCCA AAGGCGAGAA    15480

GGGAGAACGG GTATGTGGCT GCAGCGCTTT CTCTCTGGGA GGGGAGGCGA GGGGCCGGGA    15540

GGCAAGGGGC TGGGCAGCGA GTGCAGGTGT AGGCAGGCAC TCACAGCTCT CCTTCCTCTA    15600

CAGGGCAGAG CTGGGGAGCT GGGTGAGGCC GGCCCCTCTG GAGAGCCAGG CGTCCCTGTG    15660

AGTATCTGCG GCGCCCCAGA CCCCTCCCCA TCCAGCCTGT GTGCAGACCC TGCCCTGACA    15720

CCCTCCTTCC TTTCCCTGTA GGGAGATGCT GGCATGCCTG GGGAGCGCGG TGAGGCTGGC    15780

CACCGGGGCT CAGCGGTGAG TGCAGGGACA TGGCCCGGGG TCGGGGGTTA GCACTGAGCC    15840

ATTGGCACAT GGCCCCAGTT TCTGAGCAGG CCGGGGTGGC ATTTGGTTGC CTTGATGGGC    15900

CAGGCCCACA AAAGCCTAGG ATGCCAGGAG GTGTGGGGCC CCATCTTCTT GTCCCTCACC    15960

CGCTGGGAGA CGGTCGGGGC CAGGCCGGAG CTGCCCTGTT TTCAAGCCTT CTATGCTGAG    16020

CCCAGCCTTG TGCCCCCATA GACTGAGATA ATGACAGCAC CAGCCACAGG GCCCTGGTGG    16080

GGGGAGCCAG GGGCATGGGT GCCTGGCCCC GAGTCTGGCC TGACAAATTG GGTCCAGGGT    16140

ATGCCGAGTT CTGAGACCCC CTAAACTGCC CTGGGAGGTA GCCCTGCCTT TGTCCCCAGC    16200

AACCCAGCCA GGTGGCTTAG AACCGGCTCC TGTGTCCACC CACTCTGGGG GAAGGCTGAG    16260

CCAGGCTCCC TGGGGCCTCT TGGGGAGTCC TCGAACCCTG AGACATCCGC TCACACCTCA    16320

CCTTTGTCTT CCAGGGGGCC CTCGGCCCAC AAGGCCCTCC CGGAGCCCCT GGTGTCCGAG    16380

GCTTCCAGGT GGGTGAGGTT GGGGCAAGGG CCTGGCATGG GGGGCGGCA CACCCAGACG    16440

GGCCAGACCC GACAGTATGG GCACTGACGA GCCAGGACCT CCTTCCCCAG GGCCAGAAGG    16500

GCAGCATGGG AGACCCGGC CTTCCAGGCC CCCAGGGCCT CCGAGGTGAC GTGGGCGACC    16560

GGGTAAGTGG CCCTCTCAGC AGGAAGCTCC CCTGCACCCC CTCTACCCAT GTACCACAGT    16620

CCCCCACCCC CCACCACAGT CCCCTGGGAC GCAGACAGGG AGAGGCCCTT GCAGCTCCCA    16680

GTGGGAAATC TGGCCATGGG CAGTGTCTCC CTGCGTGGCG GAGGCAGTGG CATCAGGGCC    16740

CCGACTGTGG CCCCTTTGGC CCCTCTGACC TTCCACGTGT TGTTCCTTGT GGGTGGGAGG    16800

CTGCGGGAGC CTGGGCGCTC TGCCTCCTGC CCTGCGTAGA CGCCTGGCGG GACCTGCACA    16860

CGGTCAGTGT TCATTCCTCA AGATCGTGGA GGCTGAGGCT CAAGAGCCAC GCCTGCTCCC    16920

GCCTAGCGGG TGTCTGTGGA GGCGCGGTTG ACAGAGGATC ACGTTGCTAT AAAATAGGTT    16980

TGAACACCAT GTCCCAAGTG ACTGTAACGG TCACAGCTTC TACCTCGTCA AGACTTTTTC    17040

CTGCTGGTCT TGCAGCAGCT GCAGCATTAG CTCCTTGGGG GTCCGGGCAG AAGCGGGGCA    17100
```

-continued

```
CGGCCTACCC AGGGCCCCAG CTCACTGGAA GGAGCCTGTG GGTCTGGTCT GGGCCCCAGC   17160

CATGCTCCAC CAGGTCCTTG GGGACCTCGT GTGCCTGCTG TGGCCACCTC TGCTGGGCAG   17220

ACAGACCCCT TTTTAGATGT CAATCCCGAG AAGCCTCCAG GACACGGCTG CAGATGCCCC   17280

GTCATTCCAG GGTGATGGTC ATTCCAGGGT GATGGCCGGG GCTGTGGACA CCACCACCCC   17340

TAGGGGGATA GCGGGCTGTT TGTTGGCCTC CAGGCAGGAC ATTCCAGAGG TGGGGGCCAT   17400

GCCAGCAACC TCAGGGCCTC CGAGAGATGG TAGGGCTGGC ACCCCCTGCG GGCACTGCGC   17460

CTGTCCCAGG TGTGGGTGGG GCCTGGTGGC TGAATTTCCC TTTCACTTTA AACTCACGGG   17520

AAAGTCTCCT GCTTTTCTGC CCTTTGGGCC AGTTCTCACT TATGTGGCCA TGTGAGCAAA   17580

TGGACATTTT TTAAAGGGAT TCATAGCAAC TCCCAGACAT GTCCTCATTT CACAATGCCG   17640

GGGGAAGGTG ATTAGATGAG CTTTTGCATC TTTGACTCTA CTGTGATGGA ATTATCCTGC   17700

AATTGTGCAG AAACACCCGC ACGAATTCAC GGGTGTTACA AACAGTGCAA ACCTAACGGG   17760

ACTTCACTAC CCACAAGGGG AGGCTGGACA GAGCCATCGG GCCCAGAGGC TGTGAACGTG   17820

AGCTTGGCCT TTGGGCCTGT GTCTGGGAGC CGGTGTTCAC AGAAGCCCTT TGTGCAGCAC   17880

AGATGGAGAT GTGGGAGGT GTTTACCATT CCTGGGCCCA GGGCAGGCTC ACTTTAGGGA   17940

TTCCTGCCAT TCCTCTAATC CAGAGCCTTC TCTCCACACC CAGGGTCCGG GAGGTGCCGC   18000

AGGCCCTAAG GGAGACCAGG TGAGCTGGGC ACAGGCTGGG GCAAAAGGAA TGAAGGCAAA   18060

GCTGCACAGC TTCTCCCAGG CTCCTCCTGT CCCGGCTCTG GCCCTGGCTG TGTTTTCGGG   18120

ACACTGAGCC TCCTTTCTCC TCTTGCCGTG TCTGTCAGTC GCCCTTTCTG GCTCCTGCCC   18180

CTCCTGCTTA GCACAGCGAA AGCAGCTCTG GGCACCCAGC CCCCAGGCAC GCCCCGGCAT   18240

CCGCCGCTGC CTTCCTGGGT GCAAACAGCT GGCCATGAGT GTCCCTGCAT GGCTCTGGGT   18300

GCACAGAAGC TGCTTCTAGT CCAGGAGGCA CCAATGGGAA CTCTCAAAGG GACAGAGGTG   18360

TGTCCTGCCA TCCTTCCGGA GAACTGACAG AGGGCAGGGG CTAGGCTCTG CGTGTGTGTT   18420

TTGCAGGCAG ATTCGAAATG CATTTCTGCT GTTCGAAGCA CTCTTCTTTT TGGAAAAGTG   18480

TCAGGGTGGG TGGGGCCATG GCCGTGGCTG CCCCGCCCTC CTGCAGTGCC TGCTCTGGGT   18540

GGGGCCCGTG GTCTGGCTGC CCCGCCCTCC TGCTGAGCCT GCTCTCACTT CTAGGCACAA   18600

GGCCTTTCCA TACCGCGCTG GAGGCCTGCA GCCATCGAAC CCCCACCGCA GGTTCTGCTT   18660

GGCAGAAAAA CCTCATTATG CAAACAAATG TCTTCCGTTT TTTGGCCCCG CCCCTGCCTG   18720

CAGGTCTCCC AAGGGCTGTG TTTGGAGCGG GTTAAAAGGC AGCCCTGGGG CCTGGGCTTT   18780

TGGCCTCGAC CTTAAGATGA ACATTACACC TACGGAGGCT TGAGAGCAGG GACTTTAAGG   18840

CATGAAGTCC CTACTCATGC ATGAACAGCT CTTTTAACTT TGGGGTGTAT CGTTTTCAGG   18900

GTATTGCAGG TTCCGACGGT CTTCCTGGGG ATAAAGGAGA ACTGGTGAGT AATTAGGTAA   18960

CCTCACTGTT ACCAACAGCT GGGAGCGAGG TCGCCACTGT GGCTGGGGAA CAGTCCTGGG   19020

GACAGGGTCA AAATCTGCAG CTCCCGGTGG AAGATCGGCA GCTCTGCTGG GCAGCGTGGG   19080

GATGGAGCAG GGTCGGGCAG AGGCCTTGGC CACTGGCCAT CCCTTAGCAA GTGGGCTGGG   19140

CCTGGCAGGG AAACTCAGCG GCTCTGGAGT CTGACCTGAC CCGGTGCTCA GACGTGTGGG   19200

CTCCCGCACT CTGCCCCGTG GAGTGGCACC TGCATGAAGC AGTCACAGCT GCATTTTTGT   19260

TTTTTTGTTT TTGGTTTTTT GGGGTTTCTT GTTTTTTGTT TTGAGACGAG TCTCACTCTG   19320

TCACCCAGGC TGGAGTGCAG TGGCGCGATC TCGGCTCGCT GCAAGCTCCG CCTCCCGGGT   19380

TCACGCCATT CTCCTGCCTC AGCCTCCCAA GTACCTGGGA CTACAGGCGC CCGCCACCAT   19440

GCCCAGCTAA TTTTTTGTAT TTTTAGTAGA GACGGGGTTT CACCGTGTTA GGCCAGGATG   19500
```

```
GTCTCCATCT CCTGACCTCG TGATCATCCC GCCTTGGTCT CTCAAAGTGC TGGGATTACA      19560

GGCGTGACGA CCGGGCCCGG CCGGGGTTTT TTTTGAGACG AAGTTTTGCT CTGTTGCCCA      19620

GGCTGGAGCA CAGTGGCGCG ATCTCGGTTC ACTGCAGCCT CTGCCTCCTG GGTCAAGCGA      19680

TTTTCAGCCT CAGCCTCCTG AGTAGCCAGG ATTATAGGCC CTCCCACAGT CGACTAATTT      19740

TTTGTGTTTT GGGGGGTTTT GTTTGTTTGT TTGTTTTTGA GATGGAGTCT CGCTCTTTCG      19800

CCAGGCTGGA GCGCAGTGAC GCCATCTCGG CTCACTGCAA CCTTCCCAGT TCAAGCGATT      19860

CTCCTGCCTC AGCTTCCTGA ATAGCTGGGA TTACAGGCGC CCGCCACCAC GCCCAGCTAA      19920

TGTTTGTATT TTTAGTAGAG ACAAGGTTTC ACCATGCTGG CCAGGCTGGT CTCGAATTCC      19980

CGACCTCAGG CAATCTGCCC GCCTCGGCCT CCAAAGTGCT GGGATTACAG GTACGAGCCA      20040

CCGCCCCTGG CCTAATTTTT GTATTTTTAG TAGAGACGGG TTTC                      20084
```

(2) INFORMATION FOR SEQ ID NO: 6:

(i) SEQUENCE CHARACTERISTICS:
        (A) LENGTH: 419 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 6:

```
GGGGCACCCC TACCCACTGG TTAGCCCACG CCATCCTGAG GACCCAGCTG CACCCCTACC        60

ACAGCACCTC GGGCCTAGGC TGGGCGGGGG GCTGGGAGG CAGAGCTGCG AAGAGGGGAG       120

ATGTGGGGTG GACTCCCTTC CCTCCTCCTC CCCCTCTCCA TTCCAACTCC CAAATTGGGG      180

GCCGGGCCAG GCAGCTCTGA TTGGCTGGGG CACGGGCGGC CGGCTCCCCC TCTCCGAGGG      240

GCAGGGTTCC TCCCTGCTCT CCATCAGGAC AGTATAAAAG GGGCCCGGGC CAGTCGTCGG      300

AGCAGACGGG AGTTTCTCCT CGGGGTCGGA GCAGGAGGCA CGCGGAGTGT GAGGCCACGC      360

ATGAGCGGAC GCTAACCCCC TCCCCAGCCA CAAAGAGTCT ACATGTCTAG GGTCTAGAC      419
```

(2) INFORMATION FOR SEQ ID NO: 7:

(i) SEQUENCE CHARACTERISTICS:
        (A) LENGTH: 1463 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 7:

```
GTAAGTCCCA AACTTTTGGG AGTGCAAGGA TACTCTATAT CGCGCCTTGC GCTTGGTCCC       60

GGGGGCCGCG GCTTAAAACG AGACGTGGAT GATCCGGAGA CTCGGGAATG GAAGGGAGAT      120

GATGAGGGCT CTTCCTCGGC GCCCTGAGAC AGGAGGGAGC TCACCCTGGG GCGAGGTTGG      180

GGTTGAACGC GCCCCGGGAG CGGGAGGTGA GGGTGGAGCG CCCCGTGAGT TGGTGCAAGA      240

GAGAATCCCG AGAGCGCAAC CGGGGAAGTG GGGATCAGGG TGCAGAGTGA GGAAAGTACG      300

TCGAAGATGG GATGGGGGCG CCGAGCGGGG CATTTGAAGC CCAAGATGTA GAAGCAATCA      360

GGAAGGCCGT GGGATGATTC ATAAGGAAAG ATTGCCCTCT CTGCGGGCTA GAGTGTTGCT      420

GGGCCGTGGG GGTGCTGGGC AGCCGCGGGA AGGGGTGCG GAGCGTGGGC GGGTGGAGGA      480

TGAGAAACTT TGGCGCGGAC TCGGCGGGGC GGGGTCCTTG CGCCCCCTGC TGACCGATGC      540
```

```
TGAGCACTGC GTCTCCCGGT CCAACGCTTA CTGGGGCAGG AGCCGGAGCG GGAAGACCCG    600

GGTTATTGCT GGGTGCGGAC CCCCACCTCT AGATCTGGAA AGTAAAGCCA GGGATGGGGC    660

AGCCCAAGCC TCTTAAAGAG GTAGTCGGGC CGGTGAGGTC GGCCCCGCCC CGGCCCCATT    720

GCTTAGCGTT GCCCGACACC TAGTGGCCGT CTGGGGAGCC GCTAGCGCGG TGGGAGTGGT    780

TAGCTAACTT CTGGACTATT TGCGGACTTT TTGGTTCTTT GGCTAAAAGT GACCTGGAGG    840

CATTGGCTGG CTTTGGGGGA CTGGGATGG CCCCGAGAGC GGGCTTTTAA GATGTCTAGG    900

TGCTGGAGGT TAGGGTGTCT CCTAATTTTG AGGTACATTT CAAGTCTTGG GGGGGCGTCC    960

CTTCCAATCA GCCGCTCCCA TTCTCTTAGC CCCGCCCCG CCACCCCACA TGCCCAGGGA   1020

ATGGGGCGG GATGAGGGAT GGACCTCCCT TCTCTCCTCC CTCGCCCTCC TCCTGTCTCT   1080

ACCACGCAAG CCACTCCCCA CGAGCCTGCC CTCCCGATGG GGCCCCTCCT ATTCTCCCCC   1140

CGCCCTCCCC CTCTCACCCT GTGGTTTTAT TTCACTTGGC TTCAGCGCCA ATGGGCTGAG   1200

GTTGGAGTTG GAAGCCACCG CGGACTAAAG CTTTGTTTAA ATTCCTGAGA ACTGGAAAGA   1260

GTTACAGCCT CCCTGGCCAG GCGCCTCGGC GCTGTCACCC GCGCTGATGA GGAGCAGGCG   1320

AGCTTTTAAG GATTTGAGGA AAGAAGAACG GGGGGAGGGG CGGGAAGTGA AAAATCCAAG   1380

TGTGCCTCTT AGACCCGGGG GAAAGGTGGT TAAGCTGGGG GTTGCAGTCA CTACTGACAA   1440

CGCCCCTCTT CCGCCTGTCC CAG                                          1463

(2) INFORMATION FOR SEQ ID NO: 8:

(i) SEQUENCE CHARACTERISTICS:
        (A) LENGTH: 141 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 8:

GTGCGGCTGC GCTCGGGGCC TGGGGCCTGG GGCTGGGGCT GGGGGTGGTC GGCGCTCGCT    60

GGCCCTCCGT GCTGGAGGCC TCTGCCGACG GGAGCAGCAT TAGCAAACCT TGGCTCTAAC   120

GGGCGTCTCT TCGTCCCCTA G                                             141

(2) INFORMATION FOR SEQ ID NO: 9:

(i) SEQUENCE CHARACTERISTICS:
        (A) LENGTH: 102 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 9:

GTAATCTCCT GCCCTCGAAT TTTGCCCCTG CGCGGCCCGT GACTCCTCAC AGTCCTCCCT    60

TCTCTAACCT GGCCTCTTGT TTCTTCTCCC CCAATCCCAC AG                      102

(2) INFORMATION FOR SEQ ID NO: 10:

(i) SEQUENCE CHARACTERISTICS:
        (A) LENGTH: 90 base pairs
        (B) TYPE: nucleic acid
        (C) STRANDEDNESS: double
        (D) TOPOLOGY: linear (ii) MOLECULE TYPE: DNA (genomic)
```

(xi) SEQUENCE DESCRIPTION: SEQ ID NO: 10:

```
GTAAGCGTTG CACTCTGGGC TGTGGGGGGC TGCAGGTGGG CATGGCTCTC GGCCCCACGC      60

TCACCCCGGC CCCGCCCTCT CCCCCTGCAG                                      90
```

(2) INFORMATION FOR SEQ ID NO: 11:

(i) SEQUENCE CHARACTERISTICS:
        (A) LENGTH: 722 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 11:

```
GTAAGTGGAG AGGCCTTGTG TGTCCACTCT CCCCTGTTTT GTTTTTGTTT TTTGGCAGAT      60

GACATAATTT TATACTTTGA AATAATTTCA AACTTACAGA AAAGTTGCAA GAATCCTACA     120

GGAAACTCTC ACATACCCTT CACAGTTTGT GACATGTGCT TTATTAGTCT CTGTTTATGT     180

ATATGTATCT TTTTTTTTCT GAACTGTTTG AGCAAGTTGC TAACATCAGG CTCTTTTGCG     240

CCTAAATACT TAGGTGTGTT TTTCCTAAAA ACAAGAGCAT TCTCTTAACT GACCTACACA     300

ATGATTAAAT TCACTCTCTA ATGTGCAGTC CGTACTCAAA GTTCACCGAT GTCCCGATAA     360

TGTCCTTTAT AGATTCCACC CCCCACCACC CCAATCTGGG ATCCAGTCCA GGATTATGTA     420

TTGCATTTAA TCATCATGTC TCTAGTTTCC ACAAATGTAG AACGTTCCTC AGACTTTCTT     480

TGTCTTTAGT GGCACTGGGA GTTTTGATGA GTCCAGTTGT TTTGCAGACT GTCCCTCAAT     540

TTGGGATTGT CTCATTAGAT TAGATGCAGG GATGCATCTT TGGCAGGAAT GTCTTAAAAG     600

CAATGTTATT CTTCTCAGCA CATCACACCA GGAAGTGCAT GATGTCAGTT TCTTCCATCC     660

TCAGTGCCGT CTTCTGCCTT TCAATTCACT GTCCTCACTC TGACTTCTCT TGTTTGTTCT     720

AG                                                                    722
```

(2) INFORMATION FOR SEQ ID NO: 12:

(i) SEQUENCE CHARACTERISTICS:
        (A) LENGTH: 227 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 12:

```
GTGAGCCAGC AGGGGAGCA TGGATGACAG AAGAGAGAAT GGGTATCCAG AGGATGTGGG       60

CATACGCGGC TGGTATACAC AGCTTGGGAG GTCCATATCA CCTTTGGGAC CTCAGAGTCC     120

AGAAAGGATG CAAGACGACT GGGTGGTCCC AACAGGCATG AATGACTACA TCCACATGCT     180

TTCCTACAGA GGGATCACCA TGACCCCCCT TTCTTCTCCC TCTATAG                   227
```

(2) INFORMATION FOR SEQ ID NO: 13:

(i) SEQUENCE CHARACTERISTICS:
        (A) LENGTH: 158 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 13:

```
GTGAGTATCC AGGACGTCTT CATATGCCTC CTTGGGCTTT GGTCTTTTGG AGGGAAGACT        60

GGGATGAGGG CAGGAGAGAT GCTCAGAGAT CTCTTGGTAA GATTGGAGAA GGTTGACAGG       120

GACTTGTCTT CTAACCCATC TTTTTCCTTC TTCTCAAG                               158

(2) INFORMATION FOR SEQ ID NO: 14:

(i) SEQUENCE CHARACTERISTICS:
        (A) LENGTH: 163 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 14:

GTAAGCACTC TCTATACAGA TTCATACTCC TTCTACAAAC ACACAGACTC TCCTATAGAA        60

GAACTCCCAG GCCTGGGGTC TTCCTTACCT CTTCCCTTCA ATCCCAGCCT TCCCCTTCTT       120

TTTTTCTTAT CCATATTCTA ACCACCTCTT CTATCTTTTC TAG                         163

(2) INFORMATION FOR SEQ ID NO: 15:

(i) SEQUENCE CHARACTERISTICS:
        (A) LENGTH: 498 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

GTAAGTATCC CCAGCAAGAA GATACCATCT GACCCCATGG CCTCCATGGG TTGGGTCCTG        60

CAATTTCCAC TCCACCACAT TTGGGAACGA TACTCAGAGG AAGGAGGGCA AGTCCTCTCT       120

GATGCACGGA CTGCCCTGGA ACAATGATCT TTTCGCTTAG TGAGATGATT CCATGTCCCC       180

AACAAAGTGA CTGTTCTCCT CACCCCAGCC ACCTTAGAGC AATCCCCAAC CCCATCCCTT       240

TGGGAAATT GGTGCGCAGA TGGTGAAATT AAAATGCTGG TGACAGAAGT AGACAGAAAT        300

TCCTTTAGAG GCACTCAGAT TTCACCAAAC GAAGGTTTCA CTGTAGATTT AAACTGAGCT       360

CTAGATTCAA AGATAAGATT CTGGGCCCCC AAACCTGACC TGCAACAATC CAAAGAAGAC       420

TGAGACCTTC TCCACTTTTC CAGCCCCTAG GCGGTGGTGG GGAGGCAGAG GCATGATGGT       480

CTTTTCTCTC CCTCTCAG                                                    498

(2) INFORMATION FOR SEQ ID NO: 16:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 16:

GTGAGCAGGG GGCTGTGGCT GAACCTGGGC TTCACTGCAC TTGGGCTTCA TTTAGGAGCT        60

GGGTCCACAG TGATGTGTTC TAATGGCCCT TCCTTGTCTT CTTCATCTCT CTCCAG          116

(2) INFORMATION FOR SEQ ID NO: 17:

(i) SEQUENCE CHARACTERISTICS:
        (A) LENGTH: 330 base pairs
        (B) TYPE: nucleic acid
```

(C) STRANDEDNESS: double
        (D) TOPOLOGY: linear (ii) MOLECULE TYPE: DNA (genomic)

(xi) SEQUENCE DESCRIPTION: SEQ ID NO: 17:

GTGAGTCACC TTTGAGTCAT TTAAGCTCCC CAAGTCCCTA GCATACCCCC ATCCAGTCCC    60

AGCCTCTTCC CCAAAAGATC CTGAGTTGCA TCATGGTGGG TGGCAGCTAC AGAAGTCCCA   120

AGGGCCAGAG AGTGGACATC CAAAAGCACT CCTCATGGAA TCCCGATTAC CGATTGGGTG   180

AGATCTTAGA GCCATTTGGG GTTTAGTCTA GCTCAGAAAC AAAGGGATGG CGGTGATGAC   240

CTCCCAAGGC TCTTTCTCAG ATCTAGGTGG ATGTCAAGGC TGTTCCACCC CCTCCACAGG   300

TTCTTACCTT CTACCTCTTT CCTGCTTTAG                                    330

(2) INFORMATION FOR SEQ ID NO: 18:

(i) SEQUENCE CHARACTERISTICS:
        (A) LENGTH: 88 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 18:

GTAAGAGGCT GTCTGAACAT CATGGTCCTC CACATCCCCA GAGTCCCACC ATGAATGAAT    60

TTCTCACTCA TTATTCTCTG ATCTACAG                                      88

(2) INFORMATION FOR SEQ ID NO: 19:

(i) SEQUENCE CHARACTERISTICS:
        (A) LENGTH: 116 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 19:

GTGAGTGTGC CCAGTTCCAG AGGGCAGGGA TGGGGCAGGA GGCAGGGGCA AGATGGAGGC    60

CTGGGGGAAC AAGGCTGTCT CCCATCTCAT CTGACTTCTC TTGGTTTGGT TGTCAG       116

(2) INFORMATION FOR SEQ ID NO: 20:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 20:

GTAAGTACTC CTGGCCCCTT GGGGGATCCC TGAGCTCTGG AAGGGGCTCC CCAGGAACTC    60

TAGGGACTGG CCAGTGCTCA GTGGACTTAA CGGGGCTTCC CCTCTCTCCT GCAG         114

(2) INFORMATION FOR SEQ ID NO: 21:

(i) SEQUENCE CHARACTERISTICS:
        (A) LENGTH: 178 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 21:

GTGAGTGTGG CCTGTAGGCC TCAGGGCCTG GGAGTGGGGA GGGGTCTCAG TGTCTGCTCT        60

TGGGGCTGAC AATGGGGGCA GGTTATGTTG GTCTGAACCC CAGGACTTCC TCTGTCCCAG       120

GGTGTGACTT GCAGCTGCCA TCTCTTCCTT CTCGCTGACA TCTCCATTTC ATTCACAG        178

(2) INFORMATION FOR SEQ ID NO: 22:

(i) SEQUENCE CHARACTERISTICS:
           (A) LENGTH: 257 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO: 22:

GTGAGACCCC CCACTCTCCT CTAAGCATGA CCCTCATGGG CCAAGGGGTT CATGTCTCCC        60

TGTTCCCCAA ACCAAAGGGA CCCAGAGTGG CAAGAGAGCA GCCCGTTCAC TAACACCTTT       120

GTCCTGGGGT CTCCGTCTCT GATCTTAGAG TCCTGATCAT TGCTCTCCTG TCCCTGTCTC       180

CCCTTCCTCC TGCCATCCCG AGAGGCAAGG TTGGGTTTCC CAGGGTGGCT TCTGATATGT       240

CCTTTCTTCT GATTCAG                                                      257

(2) INFORMATION FOR SEQ ID NO: 23:

(i) SEQUENCE CHARACTERISTICS:
           (A) LENGTH: 88 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO: 23:

GTAAGTGTCC CCGACTCAGT GTCCCCTTTG CCACTTTCTA ACCTCAGAGT CCTTGCCTGT        60

TGCTGACACT CCTTTCTCTG TGCCACAG                                          88

(2) INFORMATION FOR SEQ ID NO: 24:

(i) SEQUENCE CHARACTERISTICS:
           (A) LENGTH: 103 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO: 24:

GTAAGTATCC TGCCAGGCTT CAGTCCCACT CCTGCCGCCT GCAGCCTGCC TGCCCCTTTC        60

CCTCTGCTCC TAGGCTCACG CCCTGGCTGT CTGCCTCCCA CAG                         103

(2) INFORMATION FOR SEQ ID NO: 25:

(i) SEQUENCE CHARACTERISTICS:
           (A) LENGTH: 131 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO: 25:

```
GTGAGTACCA AACTCTCCCT TCTGCCCACC CCATGCACTG GCTCCAGTGC GGCTCTCATC      60

TGGGGAGCAG GAAGACGCAG GCCAACTGAG CGCCCCCGAC TCTCAGCTCA TCCTCTTCTC     120

CCCCCTTGCA G                                                         131

(2) INFORMATION FOR SEQ ID NO: 26:

(i) SEQUENCE CHARACTERISTICS:
        (A) LENGTH: 218 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 26:

GTAAGTCTCC CCGCCATCCT TCTTGCAGCC CAGCCCACCC TGCCCTAGGA GCCCCCTGAG      60

GGAAATCCAG AAAGGAAGAG GAGCCCCTAG TCTTCTGGGG GAGTCCCTGC CACACCCCCA     120

GGAACCCCTG ACACTGGAGG CCCAGCCTCA GCCGGCTCTG AGGCTGGCAC AGGATGGCCC     180

CTCACCACAG GCCGCCTCCT CCTCTCGGCC CTCTCCAG                             218

(2) INFORMATION FOR SEQ ID NO: 27:

(i) SEQUENCE CHARACTERISTICS:
        (A) LENGTH: 94 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 27:

GTAAGTGTCC CTGCCCGCCC CCTCCCACTC CACCCTCATT GCCTGGCTGG TGCCTGTGTG      60

TCGCGGAGTT CACTGGCCTC CTCTCCTCCT GCAG                                  94

(2) INFORMATION FOR SEQ ID NO: 28:

(i) SEQUENCE CHARACTERISTICS:
        (A) LENGTH: 125 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 28:

GTAACCTCTC CTTGCGGCCG GGGGGCTGAC CCTGCCGCTC CCTGGGCATC TTCTTCCTCT      60

TTTGGCCCGT GGCAAAGAGC CACAAACTTG AGACCCTAAC TGTTCCTGTG ACTTCCCCCA     120

ACCAG                                                                125

(2) INFORMATION FOR SEQ ID NO: 29:

(i) SEQUENCE CHARACTERISTICS:
        (A) LENGTH: 165 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 29:

GTGAGGCCCC AGGCTTTCAG CCTGGCTTGG CCAGGCCCTG ACCATCCCGT GTAGGGTCTG      60
```

GGATGAGGCG TTCTGGATCA GGCCCAAGGG TCTGCCCTCT GGAGTCCTCC CCCACCTCCA    120

TCATGCTTCT CCCCAAGTCC CACTCATACC TCTCTGCCTC CCTAG    165

(2) INFORMATION FOR SEQ ID NO: 30:

(i) SEQUENCE CHARACTERISTICS:
        (A) LENGTH: 88 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 30:

GTAAGTATCA CTCCCCCTGA ACCCCCTGCC ATTGTCCTGT CTGCCTCCCT GCTGTCCTCA    60

CTGCTGCTTT CGTGCCTCCC ATCCTTAG    88

(2) INFORMATION FOR SEQ ID NO: 31:

(i) SEQUENCE CHARACTERISTICS:
        (A) LENGTH: 896 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 31:

GTGAGTATTA AGTGAGGATC CATGAAGAGC CAGGGACAAA CACACCTGAG ACTTGAAGGA    60

GTCCTGGGCT CTGGGCTCAG CTGTGCCGCT GACCTGCCGT GTGGCCACTC ACTCTCACTT    120

TCTGGACCTC AGCCTCCCTA TCTGTAAAAT GAAAGACTTC TCGGCGGGGC ACGGTGGCTC    180

ATGCCTGTAA TCCCAGCACT TTGGGAGGCC AAGGCGGGCA GACCATGAGG TCAGGAGTTT    240

GAGACCAGTC GGGCCAACAT AGTGAAACCA CGTCTCTACT AAAAATACAA AAGATTAGCT    300

GGGTGTGGTG GTGTGCACCT GTAACCCCAG CTAGTCAGGA GGCTGAGGCA GGAGAATTGC    360

ATGAACCCGG GAGGTGGAGG TTGCAGTGAG CTGAGATCAC GCCATTGCAC TCCAGCCTGG    420

GCAACAGTGC GAGATTCCAT CTCAAAAAAA AAAAAAAAA GAAGAAAGAA AGAAAGAAAA    480

AATGAAACAC TTCTCCAGGC TCCATGACCA CTGCTCTGTC CTGAAATAAG TGTTGTTGGT    540

GGCCCTCCAC CCCGACACGT GGGGATAGGA CAGGCCTTTG ATATGATAGG CACCCCCAGT    600

CTTGGTGGAT TCTTTGAGGT CCAAAAGGAG ATAGCAGAGA AGATGAAAGC CCTTTGCAGT    660

GCAGGCCACA GCGGGCATCT AACAGGGAAA AGGCAGAGGA GCCTGGAAGG GCATCTTGGG    720

AGGAGTGGGC TCAGAAAGGG CCCAGCAAGA AGCACCTGCA GGGGCATTCC CCGGGGGCCA    780

AACAGTCTTT TGAAAAGAAA GTCCCTTAAA AAGTCCCACT CAGAGTAAAT GAGAGGCCCC    840

AGGAGGCCCT GGCTTCTCAC TTCAGCCCCC TCAACCCTAA CTCCCTTTCT CCACAG    896

(2) INFORMATION FOR SEQ ID NO: 32:

(i) SEQUENCE CHARACTERISTICS:
        (A) LENGTH: 143 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 32:

GTAAGTATCT CCTTTCCATC CCTACCTCCT TCCCATTGCT GCCCCGGCAC TTTCTCCTCC    60

```
CTGCAGGAGG GGTGCTAGAG GCCACGGTCC TCAGCTGCTC GGGGCCTCCT AACCCTGAGT     120

TCCCCTTTGC TCTCTCCCTG CAG                                            143
```

(2) INFORMATION FOR SEQ ID NO: 33:

(i) SEQUENCE CHARACTERISTICS:
        (A) LENGTH: 103 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 33:

```
GTGAGTGTCC CTGATGGGGA GATCTGGGGA GCAGAAAAGG GGAGACACCC TCAGCCCCTC     60

GTCTCCTCGG CCTCCCCGTG ACTGTAGTGT TCTCTCTGTG CAG                      103
```

(2) INFORMATION FOR SEQ ID NO: 34:

(i) SEQUENCE CHARACTERISTICS:
        (A) LENGTH: 111 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 34:

```
GTGAGGCCTC ATGGCTGTCA GGATGCTGGG AGGTAGGGGT AGGAAACACC TCTTTGGTCT     60

CTTCCAGATT CTAAACCTTC CCTCCCTTCT TCCCCCATTT CCCACCTACA G             111
```

(2) INFORMATION FOR SEQ ID NO: 35:

(i) SEQUENCE CHARACTERISTICS:
        (A) LENGTH: 451 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

```
GTAAGAGGGA GCAGCCGGCC AGAGGGGTGG GAGATGCAGG GAATCCAGAG GGACAGGCCC     60

CCGCCTCCTA GCTAATCAGA CAGCCATCAA CTAGAGGGAT TGAGGTTAGA CACCGGAAAG    120

AACTTCCTCC CATGAAGGGA GCAGCACAGA GGGAAGTGGG GGCTGCATGA TTGCTAGTCT    180

GGGTGACTTC TTTTAAGAGC TGCTGGAATA TGCTGTGACT TTCCCTCAAC CCTTGTATTG    240

ATAAATCTTG GTCCATAGTT TGGGGAGGGG GGAAGCCTTT GACACATCCC TAGGAGGAAG    300

AGAGGGGCTG TTTGGGATAA TCTCAATTCA GTGCTGAGAA GGGGTTCCTC TCTAATCACG    360

GCCAGACCCC AGGAGGAAGG ACCGTGCTTT CCAGCAGAGT GGCCCCAGGT AGGTTTTGCT    420

CACTGTCTGT TCCTCTCTCC CTCCCCCTCA G                                   451
```

(2) INFORMATION FOR SEQ ID NO: 36:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 36:

```
GTAAGTAGGC CTCTCTCGCT GCATCCGTCA AGGTGCGTTG TACTTGGCCC TATCTCCAGA        60

GCAGCCTTCA CATGCCCTGT CCTTCCCTTC TAG                                    93

(2) INFORMATION FOR SEQ ID NO: 37:

(i) SEQUENCE CHARACTERISTICS:
        (A) LENGTH: 297 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 37:

GTGAGGGCAG CGTGGAAGGG GCTCTGGCAA GTGGCCCAGG GACCAGGTCT CACCCCTCCT        60

GCAGCAGGGA ATGGCGGGCC ATGACCAAAG CCATGGAGAT AGGGTGTGGG GTGGGGGAA        120

AAGACCAGGG CAGGGGCCCA CACACAGCCT GGAGTCTGGG CTGTGAGTCT TTTCATCTTT       180

TCTCAAGGCT TGTCGTTGGC CTTGGAAACA AGCCTGGGAG ATACCAAGCG GGCTTAGGG        240

CTGTGACCCA CTCTTGGGGC CCCAGGCCTC ACTCCAGTCT TCTTGGTTGT CACATAG          297

(2) INFORMATION FOR SEQ ID NO: 38:

(i) SEQUENCE CHARACTERISTICS:
        (A) LENGTH: 458 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 38:

GTAAGTTCAA CCTTCCCCCT CCCCTGAGCC CTACATGGCT CCCATCTCTG CCTGCTTTGA        60

ATCTCTCAGC ATCTCTCCTT CTCTCTGGGA TCTGTCCCTC TTCTCGCTAA TCCTCCCCTC       120

TTCCCCTTTC CCCTCTGGCC TTTTTGCTGA TGAATCCTCT CCCTGTGGTC CAGGCCCATC       180

TATCCCCATG GGTTACCATG GTGATGAGAG GTGGGGGCAT CTCCTTGGTG GAGGCTCCCT       240

TATTCATCCC GCTACACAAG TCAGGGGCCT CTTAACCTCA GTTCCACCTG AGTCTCCAGG       300

CAGGAACCCT TTTTCCTGAA AGAATCTTTG AGTCCTTGGC CCAGGTGGAG GCAGGGCAGA       360

GCTGCAGAGG GCCTCTCAGG AAACCCAGAC ACAAGCAGAA CACTATAGGT CACCTCCTTG       420

CCCCACACTG GAAATCTCAA GCTTATCCAT GTCTTTAG                               458

(2) INFORMATION FOR SEQ ID NO: 39:

(i) SEQUENCE CHARACTERISTICS:
        (A) LENGTH: 220 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 39:

GTGAGGTGGC CGCCTCCCCA CCTTCTGCCC TAACACATAG CCTCCTCAGC AGGCCTGGGC        60

ACGGTTCCGT GGGGTTGCGT TGGGAGAGCA GGTCCTGCCA AACTGAGCTG TCAACCTGGG       120

AACCTGGAGG GACCAGAAGG AGGGGAGGCT CTCCTGGGGT CATCTACTAG GAGTATTCAG       180

GGGAGGCCCT GACCCTGAGC CTCTTGTCCC TTGCTCTCAG                             220
```

(2) INFORMATION FOR SEQ ID NO: 40:

(i) SEQUENCE CHARACTERISTICS:
        (A) LENGTH: 163 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 40:

```
GTAAGTACAG AAGACCTGTT AAGACCCCAT ACTTGGCCCT TCCCTCCCTT CACACAGCAC      60

CCCTGGCCCT GTCTGTGCCT TCACCCCTTG CCTCTCCCCT CACCGCATCC CCGCCTTCCC     120

TCCTGTCAGA CGCATCTCTC CAATCTGACT CCTTTTCTTC TAG                       163
```

(2) INFORMATION FOR SEQ ID NO: 41:

(i) SEQUENCE CHARACTERISTICS:
        (A) LENGTH: 218 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 41:

```
GTGAGTACCA AGACCCCCAT CATTTTTCAT CACCGACTGG GACCTGGGAC CTCGAGGGAC      60

GGAATGAGGA CAAAGGCGTC AGCCATCCTC AGGGGAGAAG GGTGGAGACG GGATTGTTTC     120

CCACCCAAGC ATCTTCCTGC CTCCATTACT GCTCCTCCCC CAGGTAGTGG AAACTCCTGC     180

CTCCTTCCCT CCATTCACCG CCCTGCTTCC TCCCCCAG                             218
```

(2) INFORMATION FOR SEQ ID NO: 42:

(i) SEQUENCE CHARACTERISTICS:
        (A) LENGTH: 88 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 42:

```
GTGAGTGGCT TGGCCCTCTG TGCCCACGAG GCTGGTGGGC TGGGACCCAG GACGGGTCCA      60

GGCTTGATGC GTCTGTGCTC TCCTACAG                                         88
```

(2) INFORMATION FOR SEQ ID NO: 43:

(i) SEQUENCE CHARACTERISTICS:
        (A) LENGTH: 126 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 43:

```
GTGAGTATCA CCCGCCTCTC TGTTGAGCCT CTCCCCTCTC CCCAGGCAGC GGTGGCAGGT      60

GAGGGCAGCT GGGTCGGATG AGTTGGCTGT TCTCCCTCTG ACTGTTCCTA TGTTCTCTCC     120

TTCCAG                                                                126
```

(2) INFORMATION FOR SEQ ID NO: 44:

(i) SEQUENCE CHARACTERISTICS:

(A) LENGTH: 140 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 44:

GTAAGTCTCT GCAGCAGAGT CCACTGCTCT AGGTTGGGGG TGCTGGGTGG GGGCTGCCAG      60

AAGGATGGTG GGGCTGACTG AGGACCCAAT GATGCACCAG AGCCCCCTGG AGTCTGACAG     120

CCCCTCCTAT CCTCATCCAG                                                140

(2) INFORMATION FOR SEQ ID NO: 45:

(i) SEQUENCE CHARACTERISTICS:
        (A) LENGTH: 101 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 45:

GTAAGTGCCA GCTCAGATCT CTGCAGCTCC GGAGGTGTGC AGAGCTGGGG AGGGGTCCCT      60

GTGCTGCTGT CTGGCACCTC ACCCCTGTTT GCCTCCCAAA G                        101

(2) INFORMATION FOR SEQ ID NO: 46:

(i) SEQUENCE CHARACTERISTICS:
        (A) LENGTH: 157 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 46:

GTAAGTGCCC CCCTCACCTT GGGGGGCCCT GAGAAAAACC ATCACAGGAC TTGGAGTGGG      60

GCGGAGCCAA GGAGAACAGA TTTGGTAGAG ATGACTCCAG CGGACTCAAG GGTCCTCCCA     120

GACCCTATCT CTGGCCTGAC TCTTTCTTCT CCCTTAG                              157

(2) INFORMATION FOR SEQ ID NO: 47:

(i) SEQUENCE CHARACTERISTICS:
        (A) LENGTH: 107 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 47:

GTGAGCAGTC CCCAGCCCCC ATGCCAGTAC CCTCAGCATG GCCATTGTGG CCTTGCCTAA      60

GCCCTCTTCC CCGGCTGACT CTCACTTCTC TCTCTCTCTC TCTGCAG                  107

(2) INFORMATION FOR SEQ ID NO: 48:

(i) SEQUENCE CHARACTERISTICS:
        (A) LENGTH: 104 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 48:

```
GTAAGATGGC AACACTCCAT GACCACAGCC TTGTCTGCTG CTTCCCTGCC CCATCCTGGC     60

CCTTCACCCG GGGCTGACCC ATATTCCCCT GCTCTCCCCG CCAG                      104
```

(2) INFORMATION FOR SEQ ID NO: 49:

(i) SEQUENCE CHARACTERISTICS:
        (A) LENGTH: 380 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 49:

```
GTAAGTAGCT GGGCTCCAGT TCCCTGTACC TGGTCAGGCC AGGGACTCTT CAGGCCTCCT     60

TAGAGGCCTG GGGATGGGTG TCGGACTTCA CCCAGGCAGG GGGAGGAAAG GAGATCCTGC    120

AAGATGTCAG GGCCTTAATC CAAAAAACTG AGTTAAAGCT CAGCCCTAAG TCCCCTCTCC    180

CAGACAGGAC CGCCTCTCCC ATGAGTTGGC CCCAGCTCCC GTGAAGATTG CAGTGGGGAG    240

GTTTCCCTGG GAGTTGGGAG AGATGGCCAC AGTGGGAAGC AGCTGAGGAG AGAGAGATCC    300

AGCAGAGGGG AGGCCTCATC CTGCAGCCCC AGCCTCAGCC TTCCCTGGCC AAGAGCTCAT    360

GCTTTCCTTG CTCTCCCCAG                                                380
```

(2) INFORMATION FOR SEQ ID NO: 50:

(i) SEQUENCE CHARACTERISTICS:
        (A) LENGTH: 112 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 50:

```
GTAAGTACCC TGCTGTGTCC CCCATGCCTT CAGAACTCTA CAGATGCAGA CAGTGCCCCA     60

CTCGATGCCA ATGGAACTTC CGCCTGACAG TTTGTCCCTT TCTCTCTTCT AG            112
```

(2) INFORMATION FOR SEQ ID NO: 51:

(i) SEQUENCE CHARACTERISTICS:
        (A) LENGTH: 338 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 51:

```
GTAAGTATGC TCAGCCCCTC CCCAGTCCCC ATGCTGTGCT GTGGGATAGG AGGGGGAGCT     60

TCGCCTCAGT TTCCCCCTCT GGATAGTCAT TCTTTCCCCT CCCTAGTGGG GACTGGGGTC    120

TGAAGATTTG TGGGCATGTC CAAGTAGCTT CTGAGAGGGT GAGGGGTACA CAGAGAGGGA    180

TTATGGGAGA GGTCTCTGCC TATGGACACC CTCGGGCTAG ATTTCCAGAA TAATGAAGGG    240

GCATGGGTTG CCCACACTGC CCTTGTCTCT CCAGCCAGGC CCTCAGGCTA CATTTGACGC    300

TCACTGGGCC TGAACTGCCT TTTTTATCTG TCCTTCAG                            338
```

(2) INFORMATION FOR SEQ ID NO: 52:

(i) SEQUENCE CHARACTERISTICS:

(A) LENGTH: 360 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 52:

GTAAGTCATG CCTTCTCTCT CCTCTTCCTG AGCCCCAAGC CCAGGCTCAC CTCGGGGACC        60

CTTGCCAGGA CCCAGGCACC CTTTGCCTCT CTGGAGAAGG GTTCAGGGAC AGGGAGTGGG       120

CAAAGAAAGG AAGAATCCTG AACAAACAAT CTGATCTAGC TTTGGCCTCT CTGCTCCCCA       180

ATCCGTCCTC CCCTGGCTCA GCGGCTGGGA GGAGCTATGG CATGTCCTAT GGAAAGAGGC       240

TGAGGCTGGC TCTATGAGCC GTGGGGCCAG AGCCAGCAGG GAGGGTGGTG GGCCTCTCCT       300

CCAGAGCTGG GGTTGTTCGG GCTTCTGGCA GCCTTTCTCA AACCATTTCC CCCACTCCAG       360

(2) INFORMATION FOR SEQ ID NO: 53:

(i) SEQUENCE CHARACTERISTICS:
        (A) LENGTH: 91 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 53:

GTATGTAGCC CCTCATCCCC TCTGCTCATG GCCCTCCAGC CCCCATAGCA CTTGGATGCC        60

GGAATCCCCA CTCTCTTCCC TCTCTGTGCA G                                      91

(2) INFORMATION FOR SEQ ID NO: 54:

(i) SEQUENCE CHARACTERISTICS:
        (A) LENGTH: 132 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 54:

GTGTGGGCCT GCCCTAGCCT CTCCCTCCCT CCTACTCCTG CCATGCCAGG GTCCCCATGC        60

CCATATGTGC CCCTACCATA TGGTGCTGGC TGCTCCCTTT CCCTGACTCC ATCTTGCCCT       120

GCCCTACCAC AG                                                          132

(2) INFORMATION FOR SEQ ID NO: 55:

(i) SEQUENCE CHARACTERISTICS:
        (A) LENGTH: 288 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 55:

GTGCGTGAGC TGGACCTCAG AGCCAGTGTT AGGAGATGGG CTAGCCCAGT GCTCAGAAGG        60

GACATGAAGT CCTGGAGTAG GTCTCTGCTA AGGGTGATGG ACAGAGCTGG GCTGGGAGGC       120

AGGGGTCTCA GGTCCCTGCT AGTGGTTCAG ACACAGGCTG CCGATGGGCA GGTGGTGCCC       180

CTCTGATATA ACGGTGCATT GGGCAGCTCT CTGAGGACCC TGGACAGGAG GCCAGCAGGA       240

CTAGAGGTTC CCGCATAGCT CACTCTTCCC TCTCTCTCCT CCCTGCAG                   288

(2) INFORMATION FOR SEQ ID NO: 56:

(i) SEQUENCE CHARACTERISTICS:
        (A) LENGTH: 129 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 56:

```
GTGAGTGCCC AGAATCCCCA GGCAGGGCCC CACCTCTCCG GCCTTGGGCA TTTTGGCCAG      60
GCCATAGTGC CCTCTCTCCA TCACTCCCAC GTGGTAATGC CCCCTCCCGT TGTCTCCGCC     120
CCACCCCAG                                                             129
```

(2) INFORMATION FOR SEQ ID NO: 57:

(i) SEQUENCE CHARACTERISTICS:
        (A) LENGTH: 2214 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 57:

```
ACTCCCTCCA TCCCAACCTG GCTCCCTCCC ACCCAACCAA CTTTCCCCCC AACCCGGAAA      60
CAGACAAGCA ACCCAAACTG AACCCCCCCA AAAGCCAAAA AATGGGAGAC AATTTCACAT     120
GGACTTTGGA AAATATTTTT TTCCTTTGCA TTCATCTCTC AAACTTAGTT TTTATCTTTG     180
ACCAACCGAA CATGACCAAA AACCAAAAGT GCATTCAACC TTACCAAAAA AAAAAAAAAA     240
AAAAAAAGAA TAAATAAATA ACTTTTTAAA AAAGGAAGCT TGGTCCACTT GCTTGAAGAC     300
CCATGCGGGG GTAAGTCCCT TTCTGCCCGT TGGGTTATGA AACCCCAATG CTGCCCTTTC     360
TGCTCCTTTC TCCACACCCC CCTTGGCCTC CCCTCCACTC CTTCCCAAAT CTGTCTCCCC     420
AGAAGACACA GGAAACAATG TATTGTCTGC CCAGCAATCA AAGGCAATGC TCAAACACCC     480
AAGTGGCCCC CACCCTCAGC CCGCTCCTGC CCGCCCAGCA CCCCCAGGCC CTGGGGACCT     540
GGGGTTCTCA GACTGCCAAA GAAGCCTTGC CATCTGGCGC TCCCATGGCT CTTGCAACAT     600
CTCCCCTTCG TTTTTGAGGG GGTCATGCCG GGGGAGCCAC CAGCCCCTCA CTGGGTTCGG     660
AGGAGAGTCA GGAAGGGCCA CGACAAAGCA GAAACATCGG ATTTGGGGAA CGCGTGTCAT     720
CCCTTGTGCC GCAGGCTGGG CGGGAGAGAC TGTTCTGTTC TGTTCCTTGT GTAACTGTGT     780
TGCTGAAAGA CTACCTCGTT CTTGTCTTGA TGTGTCACCG GGGCAACTGC CTGGGGGCGG     840
GGATGGGGGC AGGGTGGAAG CGGCTCCCCA TTTTTATACC AAAGGTGCTA CATCTATGTG     900
ATGGGTGGGG TGGGGAGGGA ATCACTGGTG CTATAGAAAT TGAGATGCCC CCCCAGGCCA     960
GCAAATGTTC CTTTTTGTTC AAAGTCTATT TTTATTCCTT GATATTTTTT CTTTCTTTTT    1020
TTTTTTTTTT GTGGATGGGG ACTTGTGAAT TTTTCTAAAG GTGCTATTTA ACATGGGAGG    1080
AGAGCGTGTG CGCTCCAGCC CAGCCCGCTG CTCACTTTCC ACCCTCTCTC CACCTGCCTC    1140
TGGCTTCTCA GGCCTCTGCT CTCCGACCTC TCTCCTCTGA AACCCTCCTC CACAGCTGCA    1200
GCCCATCCTC CCGGCTCCCT CCTAGTCTGT CCTGCGTCCT CTGTCCCCGG GTTTCAGAGA    1260
CAACTTCCCA AAGCACAAAG CAGTTTTTCC CTAGGGGTGG GAGGAAGCAA AAGACTCTGT    1320
ACCTATTTTG TATGTGTATA ATAATTTGAG ATGTTTTTAA TTATTTTGAT TGCTGGAATA    1380
```

| | | | | |
|---|---|---|---|---|
| AAGCATGTGG | AAATGACCCA | AACATAATCC | GCAGTGGCCT | CCTAATTTCC | TTCTTTGGAG | 1440 |
| TTGGGGGAGG | GGTAGACATG | GGGAAGGGGC | CTTGGGGTGA | TGGGCTTGCC | TTCCATTCCT | 1500 |
| GCCCTTTCCC | TCCCCACTAT | TCTCTTCTAG | ATCCCTCCAT | AACCCCACTC | CCCTTTCTCT | 1560 |
| CACCCTTCTT | ATACCGCAAA | CCTTTCTACT | TCCTCTTTCA | TTTTCTATTC | TTGCAATTTC | 1620 |
| CTTGCACCTT | TTCCAAATCC | TCTTCTCCCC | TGCAATACCA | TACAGGCAAT | CCACGTGCAC | 1680 |
| AACACACACA | CACACTCTTC | ACATCTGGGG | TTGTCCAAAC | CTCATACCCA | CTCCCCTTCA | 1740 |
| AGCCCATCCA | CTCTCCACCC | CCTGGATGCC | CTGCACTTGG | TGGCGGTGGG | ATGCTCATGG | 1800 |
| ATACTGGGAG | GGTGAGGGGA | GTGGAACCCG | TGAGGAGGAC | CTGGGGGCCT | CTCCTTGAAC | 1860 |
| TGACATGAAG | GGTCATCTGG | CCTCTGCTCC | CTTCTCACCC | ACGCTGACCT | CCTGCCGAAG | 1920 |
| GAGCAACGCA | ACAGGAGAGG | GGTCTGCTGA | GCCTGGCGAG | GGTCTGGGAG | GGACCAGGAG | 1980 |
| GAAGGCGTGC | TCCCTGCTCG | CTGTCCTGGC | CCTGGGGGAG | TGAGGGAGAC | AGACACCTGG | 2040 |
| GAGAGCTGTG | GGGAAGGCAC | TCGCACCGTG | CTCTTGGGAA | GGAAGGAGAC | CTGGCCCTGC | 2100 |
| TCACCACGGA | CTGGGTGCCT | CGACCTCCTG | AATCCCAGA | ACACAACCCC | CCTGGGCTGG | 2160 |
| GGTGGTCTGG | GGAACCATCG | TGCCCCCGCC | TCCCGCCTAC | TCCTTTTTAA | GCTT | 2214 |

(2) INFORMATION FOR SEQ ID NO: 58:

(i) SEQUENCE CHARACTERISTICS:
        (A) LENGTH: 2431 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 58:

| | | | | | |
|---|---|---|---|---|---|
| CATTACCACC | CTGAGTCATT | TTGCTCAGAA | TTAGTCTCTG | ACTCTCAGCA | ACACAGGACA | 60 |
| AATACACACA | TATGCCCTGC | AAAGGTAATT | CAGCACAGTG | GTAACAATGA | TTCTTAGAAA | 120 |
| TCATTTCTCA | CTCTTCTGAT | ATGCAGAAAA | AAATTTGTTA | TGATGTAGTA | TTGAAGTTTT | 180 |
| TCTTTCCTGA | TAAAAATGAT | TTCCACTTTA | AAAGTTTTTT | GTTAGTTCTG | TAACGGTGAT | 240 |
| ATTTCAGGGA | AATGTTAAAA | ATGTTCTTGG | AATATACAAT | TCAACCTCAG | GTCTTTTGTT | 300 |
| GTTGTTGTTC | CTAGAACCTA | GAAAACTTCA | AACATTGTTG | CCTAGTTAGA | AAAAAATTTG | 360 |
| AATGTGGATT | GCTCCCTGTA | AACCCCCTTC | TAGGAATGAC | CAGTAACCCT | TTCAAATTCT | 420 |
| TTCACTCCCA | GTTACTTCAA | AAAATCATCC | AAAGTGGTCT | CCCAAGTGAG | TGCCTTTAAT | 480 |
| TAGAATAAAA | CAAGAGTTTA | TTATAGTTTT | TGGTTATCCA | CTTTTACTTG | CATTAACCTT | 540 |
| TTTTTCTTCT | TTTACATTTA | GAAAGAGTAA | CCTGCTTTAG | AATAGTCCCT | TTTATTTACA | 600 |
| GAAGCTGCTG | ATGGAGTTAA | CTTCTGCAGA | AATTCTTCCT | TAAGGCAAAG | CAAAAAAAGC | 660 |
| GGGGAGGGGG | TGGGGGGAAG | GAAGGGAAAA | AGATTCTCAG | GGAACTACAG | CCCACTTGCT | 720 |
| TCTGTTTCTT | AGAGACAGAA | CTGACCTAAA | GATGCCCCCT | TTGCGATGAC | TTCTGGGATA | 780 |
| GAGCAGCACT | CTAACTAGGC | CCCCGCTGCC | TCATGGGGAC | CTTAGGCAAG | TAGAGGAGAG | 840 |
| GCCTGACACA | CACACACACA | CACACACACA | CACACACGCA | CACGCGCGCG | CGCGCGCACA | 900 |
| CACACACACA | CAGCCTTTCA | AACCTAGGGC | CTGGAATGCC | ATCCCAAGAG | GCTTTAGAAA | 960 |
| AAGGCACAGG | ACCTTTGGCC | TCCCACCTCA | GGGTCAAAGT | ACCAGTTCCT | CCTCTCCCTA | 1020 |
| GTAGGGAGTG | GAGGGTTGGA | TGGAGGCGGC | CAGAGAAGAG | GGAAGTTGGG | TGCTGGGGAG | 1080 |
| AGAGTTAACA | TCCACGTTGG | TGGGCGCACT | GCTTGGGGTG | TTACCAGCGA | AGATTACGAA | 1140 |

```
GACCCCAAGC TCGAATCAGA AGGGCCTCTG GATGTGCTAG GGGAGGTGCT TGGGTGTAAC      1200

TGTAAGAGAT GGGACAGAGA GTAAGCAGCA AGGTCAAGAG GGACCGGGGG GCTCACGGGA      1260

GGGTTGAAGG GTCCAGGCTC AGGGTAGAAC TGGTAAATCC AGACAAGGAG CCCATGGAGA      1320

AGGGGAGGGG AGACTGGAAA CCATGAAAGA TCCCCCACCG CAGCCTCAGA AAGGAGAGAC      1380

TGAGAAATAA GTTCTCGGTC TCCAGGTCGG TTGGAGTCGT GTCGGAGTGC CAGACCATCC      1440

CCCAAAAGAC CCTCTTTGGA ATGAGCCTCA GCAAAGGCAA GCTAGGAGGT CGAAGGACTT      1500

CCCCAGGTGA CTCGGTCTAG TCTAGAGTTC GCAAAGCCTA TCCTCCCTGT AGCCGGGTGC      1560

CAAGCAGCCT CGAGCCTGCT CCCCAGCCCA CCTGCCAACA AAAGGCGCCC TCCGACTGCA      1620

ACCCAGCCCT CCACAGACAG GACCCGCCCT TTCCCGAAGT CATAAGACAA AGAGAGTGCA      1680

TCACTGCTGA AACAGTGGGC GCACACGAGC CCCAAAGCTA GAGAAAAGCT GGAAGGGGCT      1740

GGGGGCGGGG TGCAGGGGTG GAGGGCGGGG GAGGCGGGCT CCGGCTGCGC CACGCTATCG      1800

AGTCTTCCCT CCCTCCTTCT CTGCCCCCTC CGCTCCCGCT GGAGCCCTCC ACCCTACAAG      1860

TGGCCTACAG GGCACAGGTG AGGCGGGACT GGACAGCTCC TGCTTTGATC GCCGGAGATC      1920

TGCAAATTCT GCCCATGTCG GGGCTGCAGA GCACTCCGAC GTGTCCCATA GTGTTTCCAA      1980

ACTTGGAAAG GGCGGGGGAG GGCGGGAGGA TGCGGAGGGC GGAGGTATGC AGACAACGAG      2040

TCAGAGTTTC CCCTTGAAAG CCTCAAAAGT GTCCACGTCC TCAAAAAGAA TGGAACCAAT      2100

TTAAGAAGCC AGCCCCGTGG CCACGTCCCT TCCCCCATTC GCTCCCTCCT CTGCGCCCCC      2160

GCAGGCTCCT CCCAGCTGTG GCTGCCCGGG CCCCCAGCCC CAGCCCTCCC ATTGGTGGAG      2220

GCCCTTTTGG AGGCACCCTA GGGCCAGGGA AACTTTTGCC GTATAAATAG GGCAGATCCG      2280

GGCTTTATTA TTTTAGCACC ACGGCAGCAG GAGGTTTCGG CTAAGTTGGA GGTACTGGCC      2340

ACGACTGCAT GCCCGCGCCC GCCAGGTGAT ACCTCCGCCG GTGACCCAGG GGCTCTGCGA      2400

CACAAGGAGT CTGCATGTCT AAGTGCTAGA C                                    2431
```

(2) INFORMATION FOR SEQ ID NO: 59:

(i) SEQUENCE CHARACTERISTICS:
        (A) LENGTH: 2642 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 59:

```
GTAAGTGCCT TCAGCTTGTT TGGGGAGAC TGGGTAGAGA GGTTAGATGG GAGGGCACCC        60

TGCCCTGAAA AGGAAAACCT GTAACCTGAA TTCCAGGTAC ACTTGGAGGG CAGACTCTCA      120

GGCATGTGGG AAAACGCCGG AATTGATAAG AAACATGGAA ATTACTTTAA AAAATGAAAA      180

CATAAAAGCC TTGCCAAAAG TTAGGGAACT TTTCCTCTAA GTTCAGAGTG AGACAGTTAA      240

CTCGGTCTGG CTCCTCAGCT TAGTAACCCC CAAAGGGAGC GGAAGGTCTT TTTCCCTAAG      300

GATGAGATAT TAACGACCAA TGTGGTGGAG GAAGTCAAGG GCCTGCACCC CACAGGCCCC      360

ATAACCGCAC TGATGTCCAC CTTGTAAAAC TTGAGGCCTG CGTTAGAAAG CCCTTCAACT      420

GAGTAATGTA AAACTCACCT CCTAAGAGCT TTTATCTTCT GGGCATTGTA AGGCTTGTCC      480

GGAGGAGGAG GATGACGATG CTGATATGAT GATGGTTATA AGGCGCCCTC TGGAGGAAGG      540

AAAATGAAAG TACAGGGGAC AGGGCCTTAA GCAGATGGAA TCCAATTAA AGCTTCTACG       600

GATTTATACA GATTAATGAT CAGCATTTCT GGTTGGAGCC TTTCCCAGTG CTAGTCAGT       660
```

```
GAACCCTGGA AAGAAGAATG GATGCTACTT GGAGTGGGTA CATTCTGAAA AGTAATATAA      720

GTGTCTCAAT TCACTTTCTA GTCATGGAAA TGGTAACATT TTTTAACTCA AATCTGCTCT      780

AAATTTTGTT TGAGCCTGAG AATTACCCCT TTGACATGTT CCCAGTGATA AGCAAACATT      840

ATGAACGCAG CAAGTTGAGA AATATCAACA TTGAGATGAG ACTCAAGAGA CCGGGGTTTT      900

TCCCATGAGT CTGACACCAA TTTGCTGCGT GACTTTGGGC AAGTCAAACG GCCTTTTCTA      960

AAATGTGAGA CAGAGATTAA AGGGACCCCA AGGCCACTTT CCAGCTCTAG GTTCCATGGC     1020

CAGACTTTCA TGTCAACAGA GAATGAAGAA GATCAGTCCG TTTTCATCTT GAAAATGGCT     1080

GCCAAAGTGC TAGACAAAGA TATTGACTAG ATGGGGGATG GTATTGTCTG ACCACACCCA     1140

GTACTCCAAA AAGTTGTTCC ACCCACACAG CACGGTGTCT ACCACTGCAT AATTTCTAAT     1200

GCATTTGTGT GCTTGTGTGT GTGTGTGTGT GTGTGTGTCT GTGTGTCTGT GTGTCTCTTC     1260

CCCCTTCATT CACTTTTAGT ATACATACTG TGGATACTAA GGAGTAATTG CAGTGAACAA     1320

ATTCACATTA CCGAGTTCAT ATTTTTAATG AGATCTTGAG AGTGGGAGGA AAGAGTCGGC     1380

TCCTAGAGAA TAAAATGAAG GCAGACTTAG GGAAATTTGA AGGTACAAAG GCAACTTACC     1440

TTCTGATCAA CAGCCAACCA CAGTCTGGAA TAAATGTTAT CAAACACACA TTCTTCAAAA     1500

TGGTCCGTGT CTGAGTAATT AAAAGGCAAA TTTCCAAAAT CATAAGGACT TCCGTTAATC     1560

AAGTCAGGCA TAATTATTCT TCCTACTGAT GACACAATGA AGTAAACATA TCATTCTTGT     1620

AATTTAACAG TAATTCTCGT AAATTGCCCT TAAATGTCAG TGCTGGATGT GGTCCACCCT     1680

CCTAAATTGT GACTGTTGCA ACAGATGTTC TCACTTCAAA TAACGCACTT CTTGGCCACC     1740

TAATTAAAGC AATTTTTGGG GTGATTCATC CTACTGCAAG CTTGGCCACA CTTGTATCCT     1800

GTATTAACCT ATAATTTTTG TACCGTAGGA GAAGAATTCA CTCTTTAAGG ACTTATAACA     1860

ATTATGGCAA AAGGGGGAT AGTACTTTTG TTTATTTTTT CTATTATTTT TCAAGATCTT     1920

TAATCCGGTT TTTCCATTTA TACAAAACTC TTTCTCCGAG ACAAAAATGA TACATATTGG     1980

TAAAATGATC TTACCTAATT TAAGTGAACT AATTTAAAGC AAAATTCAGA TGTCTGAATT     2040

AATCCATTTT CATAGTTAAT AATGTGCAAA TTAGACCTTT TGGAAAAAGG ATATTAAGAA     2100

TGGTACAAAC TCAATGAAGT ACTAGGTAAC TTCAATGTTT TATAAAAAAG TAAGTCAGCT     2160

TCAATGTTTC ATAAAAAACA AATTCAATAT AGAATTTTAA GGTAACATAC TTTCCTAAAT     2220

TTTACCTTTT TTCGATATTT AGGTATTAAA AATGATCAAA ATCATAAATT ATTTCCTCAT     2280

CAATTTACTA GTCTTACATT CAGCGATTCA TCTGTGCACT TTACCAGCTT AATTGCTAAG     2340

CATTCAAAAT ATCCTTCAGA CACATTAATA TTTCACAACA GTTATAAAAT AGTAAATAAT     2400

TAATAATTTA ATTCAAAATA CATTTACATA TTAATATTGC AAACAAATCA CCCTGCTGAT     2460

CCCTGCCATA CTTTTGACCT GCATAATTTC TAGGTCATTA AAATATTCTT AAAAAAATAT     2520

AATTGGTCCT TAATTAGGTA ATTCAATTCT ATAAACTTGT TTCTCTATTT GTTAATTATT     2580

GCTATTGATC CATGAAGTGA TACTAATAAT TGTTTCCTAC TTTTTCTTTT TTTTTCTAC     2640

AG                                                                    2642
```

(2) INFORMATION FOR SEQ ID NO: 60:

(i) SEQUENCE CHARACTERISTICS:
        (A) LENGTH: 591 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 60:

| | | | | | |
|---|---|---|---|---|---|
| GTGAGTAAAA | CTTTTTTTAG | AATTTTTAAA | AATACTTTGA | TTCCCTTGGC | TACAGTGATG | 60
| TCTTCTCTTG | GAAGGGAAGA | AGTTACATTA | ATATTGACCA | TCCTAGATTA | AAACCTTTCT | 120
| GGCTGCCTTA | GAAAGTACCC | ACCCAATTTT | CCAAAATAGG | CGGGGCTACT | GAATAAGACT | 180
| AGGTTTATAA | AATATTCATA | AGAAATATAG | AGTAAATAAT | CCAATAGAAG | TTTGAGTTTT | 240
| AGGATCAGCT | TCTATGAAGC | AGAAGATTTC | ACTGAGCTAG | AGAATCTTTT | CACTCCTTTG | 300
| GAATTATTTG | CAAAAGCACT | TATTGTTAAC | ACATTCTTAG | CTCATGAGTT | GAATTTGAGG | 360
| CATAAGTACA | GGTACGTATT | GCTATGTATT | TTTGTTCTGT | AGGTACATAT | TTTTATTTGA | 420
| CATGTTGGTA | AAATTTTAAA | TTGTAGTTTG | AAATATTAAA | CTGAGATAAT | AGTAAATGCA | 480
| TAATGTAATG | AATTGTGAAG | GTATATTTGT | ATACTACACC | AAAATGGAAG | CTGTTTTTAA | 540
| ATATATATAT | ACAATTTTCT | TCATAATAAT | CTTTGATTTA | TTCTTTTCTA | G | 591

(2) INFORMATION FOR SEQ ID NO: 61:

(i) SEQUENCE CHARACTERISTICS:
        (A) LENGTH: 650 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 61:

| | | | | | |
|---|---|---|---|---|---|
| GTAAGAGTAC | ACTACTTCTC | CATAAATATC | TAAAATTATC | AGGGATAACA | TAATTTAACT | 60
| AAATTTATAG | TAGACTATAG | AAGGAAAATA | CTTTATCAAA | ATTTTGTTCA | TATGAATATA | 120
| CATTAGCTAA | AGCATAAAAT | AAAGTAGCTT | TGATGTTTAA | GATAACAAAG | TTTAATTATC | 180
| TTCTGGAATC | ATCTGTAATT | ACATTTATGT | GATACAAACT | GGTGATTTAC | ATACAAAAGG | 240
| AAAAAAAAAG | ACTTGTTTTT | ATTCTGGAGA | TGGAAGGCAT | ATTATGTTAA | TTATAGGGAG | 300
| TAAAAAAAGT | TTATTTTAAA | GGGTTTGACT | ATATAAATGT | GCTGTTAAAA | ATGTAACAAA | 360
| ATGATCATTT | AATCTACAGT | TATCATCTTA | TTCAAAATGC | TATGCATAGT | ATTGTCCTAA | 420
| TAGCTGAAGA | CTATAGCAGC | TTCCAATCCT | CCAGCTGAAA | AAAAATTACG | TATAATTACA | 480
| ATTAAAATAT | ATACTTTATC | TATTGCATTG | TGTCAATTTT | TTATATGCTA | TCTAATAACA | 540
| TTGTAGTTAC | ATCAGTCTTA | CCAACTAATT | ATTATCAAGA | ATGATTTGTT | TGTTCACTGG | 600
| AAATTACTTC | TTAGGCATTT | ATTATTGTCC | TGTTTGTATC | TTTCCTGTAG | | 650

(2) INFORMATION FOR SEQ ID NO: 62:

(i) SEQUENCE CHARACTERISTICS:
        (A) LENGTH: 1111 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 62:

| | | | | | |
|---|---|---|---|---|---|
| GTGTGTAATT | TTTGAACTAT | AAAGGGCTTC | GTCCCGTATT | TGAATAACTA | TATGTTAGAA | 60
| ACTACAGGAA | CTGGCAATTT | ATAAGAATAT | TATGTATCCA | GATAATTGTA | CACCCCTTTA | 120
| AACAGGTAAT | GCACTGCAGA | AGAAGCGAAT | GAGCATTATT | ATATATGATC | AATATTTGTT | 180
| TTAGGTCAAA | ATTACCGTTA | AAAAAGAAAA | ACTGTTACAG | TCATATTCTT | TGCATGGTCT | 240
| ACTTTCTTTA | TTTGTAATTG | ACCCATCCAA | CACATGCATA | ATGGAAATAT | ATCTACCTAC | 300

```
CACCACAGTC CTCTTTTTAA CACATTTCAT TTGCTTTTGA ACTAAGATCC CTTAGGTAGC      360

TTGGAAATAA TAGTGAATTA GTAGTCAGTA ACATGTTTCT CTGCTCAAAT TCATGCATGT      420

ACAAGTCAGG CTTACATTTT ATTTGTGGCA TTCTTAAATC TCCCTGCTAT GCTTATTTGA      480

CATTTATAAC TATGTGGTTT TGCATTGTAT AACACTTTTG CCAATATATG AATACCTATA      540

TCTTATATCT ATTAGGAAGA GGAGACTTAC ATGTATTTCA CTCAATTTAT TAGAAATAGA      600

ATTAAATCAG TTAATTATTT TAACAATACA AGTAGTTAAT GATAGTAAAT CTGCAGGATT      660

TTCTCTCCTA TGATAAAGTG ACCTTATTAA CTGTCACATC AGTTAATTCA TTCACATGTA      720

ACATACCAAA ACAATTGAAT CAGTTTGTCA CAGTCAGAGA TCGGCAATAA AAATACGATG      780

TAAGTCCTTG TGCACTGTTA AACATATGAA GCACGTGGAA CCATACATTT TGGCTATAAT      840

TTTTATATTT GAATACTGGA GCTTCAGTAT GAATTAATAT TCAATGGCCG AGATAGTTCT      900

TTAGGAAAAC TACCCTGTGA TATCTTAAGA GTTATTAACC CTCTTTCTAA AATAGACTCA      960

TAAGTGAATT TCAATCAATG ACAAATATAG TATATTAAAT TTCCACCCTA CTTGCACATA     1020

GAAAGGTCTG AACAACTGAT CTTACCACAT ATAATTCTTA GGTTTCTACA GGGCCTGTCT     1080

AACCTGACCT TACTCACTTT TTACATAACA G                                   1111

(2) INFORMATION FOR SEQ ID NO: 63:

(i) SEQUENCE CHARACTERISTICS:
        (A) LENGTH: 1278 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 63:

GTAAGGTGTC TTACGTATTG CTAACTTTTA GCTAACTTCA GTTGAAAGAA GGTTTATTGT       60

GGAATTTATT TTTAGCAGTT AAGGGATAAT TCTTCCATTT GAAAATTAGT ATATTTATT      120

TCATTTATTT GGTTTTTTCA CTCAAGATTC TGCTTTACCC ATTCTCTTTG TGAGCCCTTG      180

TCAATTACAG GACTGGTCTT TGTGTGCACT GAAGTTAGCT GTGGCCATCA TTACCATTAT      240

TTAATTTGGA GATTTAATAT CTTTTATTAG TAAGGCACAA ATAAGAGGTG TTGCATTATT      300

AAGGATTTTG ATTAGATTGA ACTGTGTAAG TGAAATCCCT GATCTTAAGC AATTTTACAA      360

ACATCCTACG CTTTTTATTC TCCTTGACTT GAAGTCTGCT GAACCAACAT TCAAAGCGGT      420

TTTAGGTTTA ATTTGCTTGA AACTAATTTG AGAAAAGTAC ATTTCCCTTT TTCATTAATA      480

TCTTCTTTTA GCTTCATGTC TTTAACAATG GTATGAGTGC CAAATGACCT CACTGCAGGA      540

AGGAAAACAT ATTTGCTTAA TTGGTTAGCA CTATGAATCA GAAGCCTGAT TCTAATACCC      600

AACTGTATGT CAGTAAAATA AGACCTTTCT CCCCCAAAGA TCTTATTATG ATTGCTTATC      660

TATGAATTGC ATTAAAAAGC AGCTTCTTTA ATAGAGCTAC CACTATAAGA GAGATCTTTA      720

ACAGTAAAGT TATTACTGTG AACTAGTTTT TAGAAGTTTT ATCTTCCAAG GGTATTTTA      780

ATTTAATTTT CCTCTAAACT TGAAAACTCT TTATGCCCTT CCTGAAACTC AGCAAGAAA      840

AAGATCTCTT AGTCATTTTG TGTAGCTCCG GTGGGGAAGG GCAACAGGTG AAAATGTGAA      900

GATGTCCTCT TGAGCTCTGT CTAATTTGTC AGGAGCCCTT AGTAACATTA AAAGTTTAGA      960

AAGCTTCCCT TCCTCAGAGT AGAGGTAAAA GGTGGGAGTG GAGACACCGA GTTAAGGCAG     1020

AGGAAGGGCT CAAAAAGTAA AGTAGGGAAG TTCTCCATTT CAAAGAGGTG TCGGCCAAGT     1080

TTTTGACGTA CAGCTCTCAT AACTTTTTAG GAATTTAGTT CAATATAGAA TTTTAAACTA     1140
```

-continued

| | |
|---|---|
| ATAATTATAT CAAAAACATT GCCCTCTTTT AAATAACAAC AGAAAAATAT TTACAAGTAG | 1200 |
| AATGAGAAAA TGAACTACAT GACTAGTAAC TAAAAATATT TTATATATAT ATATAATTTT | 1260 |
| TTTTTTTTAC TTCTCTAG | 1278 |

(2) INFORMATION FOR SEQ ID NO: 64:

(i) SEQUENCE CHARACTERISTICS:
        (A) LENGTH: 2936 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 64:

| | |
|---|---|
| GTATGCTTAT CTGTTTATCT TAGCCAAAAA AATTGCTAAA TAAATCATTC ATTTTATGTC | 60 |
| ACATTTTACC ACGCCATTTA TTTAGCTACC TAAGTTAACA CTCAATACTT AGATTATATA | 120 |
| AAAACAACTC TTTTTGTTTT CAAATTTATG AAAACATAAG TTAAGGAGTT CACTTTTCTT | 180 |
| TACAAAGAA AGATTAATTG ATCTTTTATG ATTATATGAT CTTTTTGATT ATATGATCCT | 240 |
| CATTAAGATA GATCATATAC TTATGTCCAA GAAATAATCT TTGGACATAG TAACCATAAC | 300 |
| TTGGGCAAAT CAATTTAATT TAAAACAGTA ATCACTCTGA TTAATTTTTT AATATTCTTT | 360 |
| AACATTGCTT AGAATTTTAA GCAACACTTA GAGGCATAGA ACTATTTATT AAGTTCTCTG | 420 |
| AACTTGTTGG AAAGGATCAA CAAGTTCTAT CTAGTCCAGC TAACTCATTT TAAAATGGGA | 480 |
| GAGTTTAAGC CCTTTTCTCA AAGTCATCCA GGTAACTAAT GACATAACTA GAACTAGATG | 540 |
| CCAGGCAAGA TGTCTAATAT TTGCTTACAT CATGGTTTAT GTACCTAGTC CTTGAATAAA | 600 |
| CCACTCATTT AGTCAACAGA TATTAATCAG ATGCCTTCAA TGGGCCCTAA ACTGTATTAG | 660 |
| GAACTGGGGA AATTACAAGG AATATGACAG ATTCTGATCC TTCCTCAAGG AGTTAACAAT | 720 |
| ATAGGAAATG TTTCTTTTTC TGAATTTTGA CCAAAAAAAT CCTTTTTTAG TCTATTGATT | 780 |
| GTAAATCTAT ATAGAAGAGA GTATGAGTAA AAATCTAGCA TTTATGTCAC TCAGTACAAA | 840 |
| TATTCAGCAC CATACCCTAT CAGTGGAGCA CCGCTTAGAA ACATTCCCTA TATGATGATG | 900 |
| ATGATGATGA TGACTATTAA CAAATGAAGC TTCTAACAAG CATTAGAGAG AAGTTTGAAG | 960 |
| GGAAAAATGC TAATACGAGC ATGCAAAATG TATACTAGCA TATATGAAAT AGAGGGGAAA | 1020 |
| ACTGCCAGAA GTCAAAGTGT TAGGTTGATT AAGCACTACA GAATTAATG TATACACACA | 1080 |
| CACGCAATTT AGTGATTTTA ATTAATTGTT TCAAAACAAA GGTATTTATC TGCCCAAAGT | 1140 |
| CAACAAGGTC TTTAAAATGT AAATTTTACC TGAGCAGTGC ACTTAGTGCT CTATCTTCAA | 1200 |
| AAGAAGATGT TCTGCTGGAG CTAATGGCCC ACAGTAAGCT AATATACTCT AAGGGTGAGA | 1260 |
| TAATATTTTC TGTAAATTAA AACTCCCACT TGAGAAATAA TGTACCTTTA ATTGACGACT | 1320 |
| TCTAATTCCC TAATTTTTTC TGGTAGTTTA AAATGTTCAT ATCTGAAATG AAAAAGTAGA | 1380 |
| GTGTTTCTTT TGGCTTTGTT TATATTGGAT TTTTGAAATT AGCTGTTTCA GCTAATGCTG | 1440 |
| GACATTAGTC AGTTTTAAAG CAGTACCTAC ATCTCAAGAA GAAGCAAGGG GGCGGAAAGT | 1500 |
| AAAGAGCTAC TAAATGTCAT TTTTAAAAAG CCCACTAAGC TGGGAAAATT AATATGGATT | 1560 |
| TCAGATACCC CTGTTTTCGG AACATCTGTC TTGGCATAAA GCAGAGTATT TTACTTTGAA | 1620 |
| ATATCAGTGA AATATAATTT AAGCTTGCAC ATCCACACAC ATGCACAGAC ATATGTAATC | 1680 |
| AACAGATATC TGTTTCACAA ATAGGGAAGA TAGGCAGCAA TAAAGTATTA AAATAATTTC | 1740 |
| CATGTTGGAA AATCAATAAC TATAAAACCC CACAGGGTTC TTCTCTGAAT TAATGAGTAA | 1800 |

```
TCACAGCCTC CATGAAATAC ACTACATTTT ATGTAAATGA AATTGTTGCA AATACATGAA    1860

AAAATAAATA TAATTAGAAA TTCATGATGT CAAAGAAAAT TATTTTTTAA TGTATGCCTA    1920

AAAAGCTATT GTGATGGAAA AGTGACAGTT TCTTTTAATG TCAGAGCAAT TTCTAAAACC    1980

AAATGAATAA TTCTTATAAT TAAAATGACG TACATTTTAG ATAAAATCCA TGTTATTTCA    2040

CTCTAGGCAT TAATACAGTA AGGTAGGTTT GACTGCAGAG TCCCCACAGC TGATGTCACG    2100

AACAAATTAC TTGAGACTGG TACATGAAAT ATTTTCAGCA TTATGAGGAA CAGACCCTAC    2160

GGATGAGCTT ACACAGGCAT TGATTACTGC AAAGAGGAGT CAAGAAAGTG TATTTAGCTT    2220

ACAAACTATT AACAGCCCTG TTTTACCCTA CTTTTGTGCT ATGGAAACAA CAAAGGGGAA    2280

AACAATCTTC CATCATTTGG GCCATATTTT CAACAATAAT ATCATATAAT AGACTCTTCC    2340

AGAAGGCTGT TTCAATAATG TTTTATTTTT CCTTCACCCC TCATTACATC CACTTTTGTT    2400

TGACATTTTC ATCAGTCACC AATAACCCTT AGAGGAGCGA TAAGGTTATA ACAAACTTCT    2460

CTCTAATCAT TAAGAAGGAC TTTTGATTCT TTTCAATTTA TGTCCTTTGT GGCAATAAAA    2520

ATACCAATTT CTTAGCTAAA TATGACATAG GAAGATGACA TATGATCAAA GATATCCAAA    2580

TGGACATGCT TCATCTGCTG TATAGAAGAC AATTGTATAT TCTGCACTTC TGCAAAGACT    2640

GATTCACTTC ATTGCATCAG AACAATCTCA ATATGCCCAA TTGTGCACAA CTTTAAGGAA    2700

CCTATCTGCC CCGTCTAATT CTCATTGATT TCTGTTGATA TGGATTGGGA GAAAAGGAAA    2760

AGCAAAGGGA GAGAACTAGT GCAGGAAGTT TGAGTCCTTA AATTCTTCCT TGGGAGGAAT    2820

AAAAACTATG GAATCAAACC ACAACAATGG CACTGCTAAG TTGGTCATGT CTGACCCCAG    2880

CCAACACCAT GACAACTTAT CAGTGCTAAC TGTTGATATA TCTGCTTTCT TTACAG       2936
```

(2) INFORMATION FOR SEQ ID NO: 65:

(i) SEQUENCE CHARACTERISTICS:
        (A) LENGTH: 92 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 65:

```
GTAAGTACTG AAAGCTTGTA ATGCCTCTTA TGTAAAAAGA CAGAGAATTA AGAAATAAAG    60

GCTTGGAGTA TGACATTCTT TTTTTCTTTT AG                                   92
```

(2) INFORMATION FOR SEQ ID NO: 66:

(i) SEQUENCE CHARACTERISTICS:
        (A) LENGTH: 92 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 66:

```
GTGAGTACAT TTTTCCACCT TGTGATAAG TTTTTTTCCA GGAAGTTTAT GAATATAACC    60

TTAGTGAAAT GATGGGTCTC CCATTTTCTT AG                                  92
```

(2) INFORMATION FOR SEQ ID NO: 67:

(i) SEQUENCE CHARACTERISTICS:
        (A) LENGTH: 306 base pairs
        (B) TYPE: nucleic acid (C) STRANDEDNESS: double
        (D) TOPOLOGY: linear (ii) MOLECULE TYPE: DNA (genomic)

(xi) SEQUENCE DESCRIPTION: SEQ ID NO: 67:

```
GTAAGTATTT ACTCTTAAGC ACTTTCAAAA TGCTATTTAA ATACTCTTGC CTCAACAAGA      60

TTTTCTAGAT TCAAATTAAG TATTCTGCCA AAAGCTGAAT ATGCCTGACA GAACTCTTAA     120

TGTATGGGAA ATATTATTTT AATGAAATAT TAACTAACCT ACTTGTATTA AGGGAAAGAT     180

TAAATATATA TCTGGATCCA TATTTTTATG TGATAACTTT CTCCCCTTTT GTAAAAACCA     240

AGATTCCCCC ATTTTGTCTG ATAGTTTACC AAGAAGAAGT TGACTCTACA ATGTTTTCAT     300

GTTTAG                                                                306
```

(2) INFORMATION FOR SEQ ID NO: 68:

(i) SEQUENCE CHARACTERISTICS:
        (A) LENGTH: 420 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 68:

```
GTGAGACTTT TTACATTGGT AGATAGCACA AACATCATAG GCCTATAAGA TAGTTGCTAA      60

AACTAGCATC AATCTAAATG ACAACATAGA TGTCACCCAA ACTCATAACA TGAATCGAAG     120

GCATCTAATA AAGAAAAAAG CCTAGTTAAA AAAAAATGCA TATACATTTT ATTCATGCAA     180

ATAATGGAAT ATAAATGACA GCAAGCATAC CATAAGCAAC TAAATTGTGT TTTCTACAAA     240

TACCGTATTA TTAGTTACTC ACATTAGAGC AAGTTAATTT GTCGCTCTGT GCTTAGAGGT     300

ATACTAGACT TTGGTTCAAA GCTTGAACTT TGATGAGAAT AAATACTTTG GAGGGAAGAA     360

GTCACTGTCT TTTTATTTAT GGTAAAACAT TATTCACCAT CTTCTGTATT TCTTTCTAAG     420
```

(2) INFORMATION FOR SEQ ID NO: 69:

(i) SEQUENCE CHARACTERISTICS:
        (A) LENGTH: 523 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 69:

```
GTGAGCACAT TCTTTACTCA GAAGAGAGAA AATGCCTATT AATTTTTGGA AAAAACTCAA      60

GTATGTTTAA AATCTTGGGT GACATATACT CACTTTCAAA TCCCTGGAGT TTGCCAAAGG     120

GAAGAAAGAG TTAAAGAGTC AGATTTCTTG AAAGTAAAGT GGGGTGCAAT TTTTTCAGTC     180

TGTTCATAGC TACCAAAAAA CAGGCTCACT ACAGAGAAAA TTATATAGAA CATGTATTAC     240

TTATTGAGTA TTTACAACCG TCTGAAAATC ATAAAATTAT TAAGGATGGA AAAGATGTGA     300

GAGAACACCT AGTCCTCCAT CCTTCTCTCT CAATGGCAAG AAAGTTAAGT GACCTATCTA     360

GGGCAATAGA CTGAGTTTGC TGGGACCTGG AACACTGGAC TTCTTTCTAC TGCAGCAGAC     420

AAGACTTACC CAAGAGAGAT TAATGGCAAA GATATACAAT ACAATTTTTA TTTGACCAAA     480

CACTATCATG GAACAGCATT TTATAATAAG GCTTTCCTTT CAG                       523
```

(2) INFORMATION FOR SEQ ID NO: 70:

(i) SEQUENCE CHARACTERISTICS:
        (A) LENGTH: 1550 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 70:

| | | | | |
|---|---|---|---|---|
| GTAAATATTA | AATTAGAAGC | ACTGTTTTTA | AGCACTTGAT | TGAAATTCCC | CATGACCTCC | 60 |
| AAAAAAGTAT | ATTATACTGA | AGACTACCCA | TATTACAAAA | AGTATTTTTA | TTTTTTTTCT | 120 |
| TTCCTGTACT | TCAAATCCCT | CAAGGATGGG | GACTATGAGA | GTCTGTGAAA | AAAGGTCAAT | 180 |
| TATTAATATT | TATTAAAATT | CAATATCTAT | TAAACAATTG | AGATAAAAAT | AATATTAATA | 240 |
| GTTTCTTGTT | CCATTTCCTT | TCCTCCCTCT | ATAATTCCAG | TGTATCTCTG | CAGCCAAAAT | 300 |
| AAAAGTAAAT | AAACATATAA | TCAGAGATTA | CGACACTCTG | TATTATTTTA | AACTGTAAAT | 360 |
| TCTCCTTTGC | CACACACTAA | TTAGATAGGT | ACATTCATGT | CGCTATACAC | TTTTCAACCT | 420 |
| CTTTCCTGTG | ATTTATCTGT | GCACACTCAA | AAAAATTTTA | ATTAGGTAAT | TAAAGTCTCA | 480 |
| GAAGTGTGTT | ATCTCTTGGC | TAGGCTCTTC | TCTGACAGCG | TTTTCAACTA | TAAAATGTTC | 540 |
| TCTTTCCTAT | TAAGGAGATA | ATGTGATATT | AAAGTGAATA | CCAACGTAAT | TACAAATTAA | 600 |
| TGAGTAACGA | ATACTAGCGG | GACCAGAAAT | GAACATGAAT | ATGGAGAATC | TATTCTAACT | 660 |
| TTCCAGCTGC | CACACAAATG | GATAAGGTCA | AACTCATTCT | CCCAAGAGCC | CGATATAACA | 720 |
| GCTCAGACTA | CTAATCACTG | TATCCATAAA | ATGTTAGAGC | TGCAAGGAGC | TTTGGAGACC | 780 |
| CCCTCATTTT | GCAGAGGTGG | GAAACTGAGG | CTTCGTGAGA | GCAATTGACT | TGCCCAAAGT | 840 |
| CACACATCTA | GAGGTTAGAA | AGTCATAGGC | TAGAAATGAT | CCCCCCTTGC | CACTTCAATG | 900 |
| CTTATTCCCA | AAGAATAGAC | TTCACATAGA | ATCCTGGAAA | TTAAGGGTCC | TTATGAGGTC | 960 |
| TCTTAAACCA | TATTTCCCCT | ATATCTAAAT | CAGATTATCT | TTAAAAAAAG | TTCTTTTACA | 1020 |
| TGTGCCATAG | TATTAAATCC | CACTACTACT | ACTACTACTA | CTACTACCCT | GGTTTTTACT | 1080 |
| CAGGATAAGA | ATATAGATTG | GAAATAAATA | TGATGGCTCT | AAAAAATACC | ATGAAGCTTC | 1140 |
| AATTTTTCAT | GCACATTTTA | TGAAAGTGAT | AACACTGAGT | GTTCAAAATA | ACTTTAAAAA | 1200 |
| GGATAAATAT | GGTTACATTG | AAAGCAAATT | TATCCTTTGC | CATCTCTTTT | TATGATATTG | 1260 |
| TTTCTAGTAT | ATAATTGATA | TCCTGAATCT | AAGGGAGAAA | TTGGGGAGGA | GGTACACTCA | 1320 |
| AATAACCACA | TCTCCTTAGA | ACCTGGATAT | GTGGTACTAT | CTGAATAAAA | ACTCATGTTA | 1380 |
| GCACATTTTA | AAATCTGTGT | GTCTGGCATA | ATTGAAAAAC | AATCTATATG | TGTAAGAAAT | 1440 |
| ATTATGAAGT | ATATGAATGG | TTCAAAGTAA | AAAAAATAGA | GTAAAATTGC | ACTATCAGGA | 1500 |
| AAAATAATTG | TTATATTTAA | TGAACAAAAA | CTCAATCCTT | CTCCATGTAG | | 1550 |

(2) INFORMATION FOR SEQ ID NO: 71:

(i) SEQUENCE CHARACTERISTICS:
        (A) LENGTH: 291 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 71:

| | | | | | |
|---|---|---|---|---|---|
| GTAAGTATTG | ACTACTTCAT | TGTAAATTTA | AATGTGTACA | CTCTTTATGA | GATGGAACTT | 60 |
| CTTTAATGTT | TTTGCTAATC | ACTGTATCCT | TCAGCATTGT | ATTCTTTGAT | GTTTTTCTAA | 120 |

TAGCCTTCTG ATACTTAATT GAAATCCACT ACTGTTTAGT TGGAATTAGA AGGCAACTTA      180

TTTATTTTTA GTGTATTCTT GTACAGGTTG GAAACTGAAC AAAGCAAATG ATGCCTGTGA      240

CTTTTTTTAA ATTAGCATTC TGGATTTTAT TGAAAATATT TCTGCTTCTA G              291

(2) INFORMATION FOR SEQ ID NO: 72:

(i) SEQUENCE CHARACTERISTICS:
        (A) LENGTH: 99 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 72:

GTAAGTGCTT CCATTTTTGT TCAGTTTCAT CCTTTTAAAA AATCTTCTAA TGGCTGTCAT      60

TTAAGTTTCC ACCTGATCTT CCCTTTATTT TCTTCTTAG                             99

(2) INFORMATION FOR SEQ ID NO: 73:

(i) SEQUENCE CHARACTERISTICS:
        (A) LENGTH: 389 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 73:

GTAAGTTTTG ACACTGGGGA GTTTGAAAGG AGTTGAGAAT GTGGGGTGGG TGCTGTCTTC      60

TTCATTAATC TCTTACGAAA TAGCATCATT TCAGACACTT TACCAAATGT TCTGTGAGGT      120

CTTTTGAAGG CTCCATTTAT AAGTAGTGTA AGCCATTTAT AAGTACCTGA ACTTTTGATT      180

GATGTATAAA GCAAAATATC CCCACCCTGG ATACCATGAA TGTCTTGCCT TTGATGAGAT      240

CCTAACGACA ACAGACTGGT TGTCAGTTTT TTTCTTTACT AATATAAACA GTGTCATGCC      300

ACTGTAAGCA ACTTCAATCT TCTGCCATTG TTATTGTTTT CTTAATTTAC TTGGAGGAAA      360

TTTCTTACCA CCTTCTGCTT TGATTTCAG                                       389

(2) INFORMATION FOR SEQ ID NO: 74:

(i) SEQUENCE CHARACTERISTICS:
        (A) LENGTH: 498 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 74:

GTAAAAACAC TGGTGACCAT TGTCACTACT TTGATAAACT TTTTACTGTG ATGTGAAAGA      60

TTGGAACTGT GTTTGCAGAT AAAGAGATAA TTACGAAACA GTTACCTTAA TTATTCCTTC      120

CCTTCAAAAT GGACATAGAA TGACCAGTTT TCTCACTCTA CATTTGAAAT AGATCATTTC      180

TCTGCACTGT GCACTGTGCC CATCGATATA GATGACAACA TGGAAATTGT CTCTAGGACT      240

AGTTAGTTAG GACTGACTGA GAACCAGAGT CAACCACAGA GAGACAGAAG GAGAGGGAAG      300

GTAGTAACAG TAGCCAAGAT GGCAGAATCA AGCAAGGAAA ATAGGAAACC AAACTCAAAT      360

CTTGTAATAA AACGGATAAG AAAAATAATT GCAATTTTGA AGTTTTATGA AGACATTTCA      420

TAAAACTTGG CATCTTAAAA ACAGATATGC TGTTTCATTA TTTGCTGGTT AATTCCTTGG      480

TTTAATTTCC TCTTTTAG                                                  498

(2) INFORMATION FOR SEQ ID NO: 75:

(i) SEQUENCE CHARACTERISTICS:
        (A) LENGTH: 143 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 75:

GTAAGTAGCC ACTGTCTTTA AACTTTATTG AGTAAAAGAA AACAAAGGTG GAGTATGGGG       60

AAGAAGAAGA ATGAAGATGG GGTCAAAGAA GAACCGAAAT ATTCCAATTA ACTGATATCC      120

TTCTCCTTTC CTTTTCCTCA TAG                                             143

(2) INFORMATION FOR SEQ ID NO: 76:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 76:

GTGAGTATAC CTGTGTAGCT AAAATGTGCT GCTATGATTT TAAAGGCATT TAATGTGTGC       60

TGCCTCTACA GCCCATCACC TCCCTAATGG ACCACACTGC ATTTTCCTTC ATAG            114

(2) INFORMATION FOR SEQ ID NO: 77:

(i) SEQUENCE CHARACTERISTICS:
        (A) LENGTH: 420 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 77:

GTAAGTGGTC ATGACTGTGG TTCTCATCAT CCTGAAATAC CACCTCTGCC ATCATTTCAT       60

CACTATCTAG ACTTCCACTT GTAGTTTTAT TATTCCTATT TTTCTCTTCC TTAGCATTTT      120

TAGTTTATAT TTCTTATATA TATATGTACA CTCCCGTCTG CTATATGCAC ACAGACATGC      180

CCTTCCTGTT ATCTTAAATC ATTACCTCAA GGTAAATGAG GCAAAGTTCT ACAATATCAG      240

TTTTGTCCCT TCGACCAATA ATACCATTCC CCTGTACTCA ATTTAAATAT GAACAGGGTA      300

CATTTCCTAG AGAACTTGAG CTTCTCTTTA CCTTGACCCA CAAATATTCT AAGAGATTTG      360

TCTGCAAGAG AGTTTCAACA AATGTTTGTC CTTTGACCAC TGTTCTGTAT TGAACCCTAG      420

(2) INFORMATION FOR SEQ ID NO: 78:

(i) SEQUENCE CHARACTERISTICS:
        (A) LENGTH: 125 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 78:

```
GTAAGTAGCT CTATCATCAC ACTTTTATAA AGTTAATTGT TTTTCTCATT CCAGTTTCTC      60

CAGCTGGACA TAGTATTAAA ATTATTTTTT TTACTCCCTC TTCTTTTGTT CTTTTCATTA     120

AACAG                                                                 125
```

(2) INFORMATION FOR SEQ ID NO: 79:

(i) SEQUENCE CHARACTERISTICS:
        (A) LENGTH: 360 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 79:

```
GTAGGTTTCA AATGCTCCCA ACACCCTAAC ACACCAGAGG CAGATTATGA TACCCCTTCA      60

TTGGGAATTG GTCAAAATTA CTGACTGTGT TTTCTTAGGC AAAAAAAGCA TCTGCTTTCC     120

ATCTGCCTTA TTAAATCAGT GACTCTCAAT TTAATATGTT ATAAAATTGG CCTGGAAACA     180

ATGTTGACCT ACTTTTGCAG GATGCTCATC TATGAATTCC TCTAGGGGTT GGGTGAAGTG     240

TTTTGGCTTG GTTTGTGTCT GTATCTCCCC TGTAAGAGAT CATGCTATTT TTAACAAACT     300

CTACCTTATC AAAGCCAAGA GATTTCTTTA ATTCTCTCTA TTTCATGTAC TTTCTTGCAG     360
```

(2) INFORMATION FOR SEQ ID NO: 80:

(i) SEQUENCE CHARACTERISTICS:
        (A) LENGTH: 113 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 80:

```
GTAAGCTGTC TATCACTTAC TTCCTAGAAA GGGGCTTGCT GCTTCTGGTG GTGGGTGTGT      60

CATTAGCTTT AGCATCCTCC TCCTCTATCT GTTTTTTTTT TTTTTTTGAA TAG            113
```

(2) INFORMATION FOR SEQ ID NO: 81:

(i) SEQUENCE CHARACTERISTICS:
        (A) LENGTH: 911 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 81:

```
GTAAGTTTCA AACTGATTCT GAGCAAATCA CACCTGGCAT TACTTCCTTC TTTAAAGGGT      60

TGGTTAATAT TGAAGATAAC AATAAAAACA TCAAAAGTAA ATTTGTTAGT AGTCTTGCTG     120

ACAGTTGCAT TTTTGACTTT ATCAAAGCTC AGTAGATATT TTCATGCATT TAATTAGTTC     180

ATAAATTTTC TATTTATTAC TTGATACAAT GGCTATGAGG TTTTTGGAAG AATAGATCTA     240

TTTTAATATA TCCAAATTAG ATTGGTCCTC CTATCAGCAT GAATCTTTTA TCTTAATTTG     300

TGAGTTTTAT ATAAGGTGTT CATGAAATAT ATTAGGACTA TACATTTTTC GTTTATTAGA     360

TTCATAAGTG AAGTCTTTTT CCTAGCAATC ACAAAGTGCT GTAATGTATT CAGCATCACA     420

CTAGCTATGG AGAAATAACC TCTAGGTCCA TAGACACACT AATCCATAGC AATAGAGTAA     480

TTTTTTTGCC TCCATTACCT CTTATGGGTG AATATCAACT GTAATTGTAC CACAAACAAG     540
```

-continued

| | |
|---|---|
| TAATAGGGAC ACCAAATATA GCAATAAGAA ATCCACTTTG GAAATTGTTT ACTAAAAGTA | 600 |
| TTAGTTTTTC TATTATGAGG TAAATAACGT GATACATTTT GCCCATATAC ATGTTGCTTA | 660 |
| ACAGTTTCTT GAGATATCTA TAAAAGGATG AGTTGCACTA AATTTCAATA AAAGGAAAGC | 720 |
| CACAAAAAAA TAGAAGAAAA ATTTCAGAAC TCTTTTCACA CTTCCCAGCT AGTGGCTAAT | 780 |
| ATTCCTAATG ATTTACCCTA GGCAACAAAC AAAAAGTCGG GGGAAAAGGT GCCTTTGTTA | 840 |
| GACTTCAGTT AATCTAAGGC TTGAGTATGT AAGTTAAAGT GCCAATATAA AAACATCCTC | 900 |
| ATTATTTATA G | 911 |

(2) INFORMATION FOR SEQ ID NO: 82:

(i) SEQUENCE CHARACTERISTICS:
        (A) LENGTH: 463 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 82:

| | |
|---|---|
| GTAAGTATTG CTCATTTTCC CATTATATTT TCAAGGACAC TTATTGCACC CTTATCAAGT | 60 |
| CTATTTTGTG GCTTATTTAT ACATGAACAC ATTGAAAATA AATATCAGAC ACATACATCA | 120 |
| TCTGGGAATG CAGAGTAATA GATTGTAATT ATGGAGTCCA AATGAATACA GGACTGAAAG | 180 |
| CAGAGCAGGG GAGAGAAAAA CATGGCAGGG AAAATTGAAG CAGGTGACAA GGGGATGCAA | 240 |
| GAGAAGGGAA TGAGGGAAAT TGCATACATA CGAGATTGAA TTGGCTATGT GTGTACTGAC | 300 |
| ATCCTAGTTA GAAAAGGAAA ATGGATTCAT AATTTATTAA CGCTTTATAC AAGAAGCTCT | 360 |
| ATGCATTCAG AAAACTATTC TGTTTCATCC GTGGCAGCAT CATAAGCTTG AGGTTGTGAG | 420 |
| AATATGTTGA CACTGAGTAA ACTTGAAATA ACTCTGCTTT CAG | 463 |

(2) INFORMATION FOR SEQ ID NO: 83:

(i) SEQUENCE CHARACTERISTICS:
        (A) LENGTH: 400 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 83:

| | |
|---|---|
| GTAAGAATCA CCACAACTTT CTTACCCTCA GCACTTTCTG TAGCCAAATT TTACCAAACT | 60 |
| CTAGTATTTA TCTCCTGCGA ATCAGTCCAG TCTCAGGGAG TTTCCTTTCA ACACAGGAAA | 120 |
| ACTGCAGGCC ACTTATCACA TTAAAAGTTT ACCTCTAGTG TATCCTTATA TCCCTGCTAA | 180 |
| AAATCCATCT CCTGAGCCCC ATGCTTCCAC AGACACAGGG ACATCTTACT GTACATGGAG | 240 |
| CTGCATGGTG ATGGATCATC CTTAGATAAC AGAAACCACA GACTAGGGAT CTCAAAAGAA | 300 |
| CACAAAAACA AGCAGGATTC AACATTGCAA AATCACCGTG GTTAATTTGA CATTAAATGT | 360 |
| GCAAAGCTGT TCTTTGTTTT GTTTTTCATT TTTACTCTAG | 400 |

(2) INFORMATION FOR SEQ ID NO: 84:

(i) SEQUENCE CHARACTERISTICS:
        (A) LENGTH: 553 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 84:

| | | | | | |
|---|---|---|---|---|---|
| GTAGGTGCTA | ACTTGTGTAC | AGATCTATTC | ACATAGCATT | CATCTAAGAA | CCACACTTTT | 60
| TTTTTTACAC | CATCTGATAT | CATTTTGTCA | CTTTCTTTTC | AAGATGGCAT | CCCCAGGGGT | 120
| CCTTTTACTA | TCATAAAATG | CCTTTTTAAA | AACCAAACTT | ATAAAACAGT | GAGCAAAAAC | 180
| AAATCAGAAT | ATACATTAGG | TCAAAAAATA | CAGAAGCACT | TGGCTTTTAT | TTTATTCATT | 240
| TTGTAATTAA | AAGGGTATGA | ATATGTAGTA | GCATTCTCTG | GCCTTTATAA | ATTGCCTTGT | 300
| GTCGCATACT | TCGCTTGAGT | CATATCAAAA | GTTAGTAGGC | AAACCCATAA | ATATATATAC | 360
| CTACTATGTA | CCCACACAAA | TTAAAAATTT | AAAAAGTTAG | TAGGCAGTAT | TTGGGCTTTC | 420
| GTGGGAACCC | ACAATGAGTT | TAATTCATGC | TAAAATGACA | AACTTGTTTT | AAGGAAGTAA | 480
| TACCTGAGGC | TTTGAGACAT | CTTAAACTAC | CTGCTTGCAG | CTAACCATCA | GCCTTTCTGT | 540
| TAAATATTTT | TAG | | | | | 553

(2) INFORMATION FOR SEQ ID NO: 85:

(i) SEQUENCE CHARACTERISTICS:
        (A) LENGTH: 150 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 85:

| | | | | | |
|---|---|---|---|---|---|
| GTGAGTATTT | CTCCCACTCT | TGTGCTCTTC | TGCACTAGAA | TGTATATAGT | CCTCAAACTG | 60
| GCCATCTCCA | TTTTCAGTCC | AAAAGTTATA | CAGCTAGACA | ACAGTGGTGA | CATACGTTGC | 120
| TATTTATGCT | CTCTTTCCTG | TCACTTTCAG | | | | 150

(2) INFORMATION FOR SEQ ID NO: 86:

(i) SEQUENCE CHARACTERISTICS:
        (A) LENGTH: 273 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 86:

| | | | | | |
|---|---|---|---|---|---|
| GTAAGTCAAC | TCAAGCATAT | ACAATACTGC | CTTTGGTCAG | CCTATTGAGC | TGTAAATCAC | 60
| CATACCGTAC | CTCTCTTCTC | CACCACAATA | ACATGATTTC | AGGACTGAAG | CAAAGAAAGG | 120
| TGCATTTTTT | TCAAACAAAC | TTTTGTGTAA | TGCTTAATAA | CATACAATCG | TGCTCATGTT | 180
| GATATTTGGT | AGCCACCACC | CCCAAACTCA | ATTATTAGCA | AATCTCCTGA | ACGTAGCCAT | 240
| GGGATTGAGA | TTTGTATTTC | TTTTCATTTT | TAG | | | 273

(2) INFORMATION FOR SEQ ID NO: 87:

(i) SEQUENCE CHARACTERISTICS:
        (A) LENGTH: 952 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 87:

```
GTGAGTAAAA CAAGTAATAG TAAGTAGTAA CTACTAAACT TGAGAATTTC CCCCTGTTTA      60

ATACCCCACT GCTATGCAAT TATAATATGT AAAAGAAAAT TTCGTATTTC ATATGTTAAT     120

GATAGTGTTT TACATACTTT GGTGCTGATG GAGAGAATGA GCCAAATTAC TTTAGTTCTG     180

ATTACTTTGT TTTACAGATT TAATGAAACA TCACCTTATG AAAGTAAAAT CTATCAATGA     240

ATATTTTATT TAATAGCCTT ACTTTTTGTA TTGTTCTTGA TAACGTTAAG ATACAAATTA     300

TTTCCTTCCC CATAGTGAAA AAGTAAATGC ACAATTTTCA ATCAAACTAG ATCCCGAAAA     360

ATTCCTTTTG TGTTTTTCTT GGCATTCAGA CATGACACTA CTATACACAA TCAGGGCATG     420

AGTTCTGAGT CATTTTCTCT CTAATTGTGA TGAATGTGCC CCTATTTAGT TACATTCTGT     480

GGCCTGGTCT CCTTTGTCAA CAGTAGGACA TATTAAGGAG ACAGCTGGTC AGTAATAAAA     540

AGAGATACAC TTGGGTATAC AATTAACTAG GCAATGTACA GAATATGATA ATTTCTCTTA     600

AGAAGACGAT CTGTTATACA GCTAAAAATA GGCAACGTCT AATATTCATT ATTATTTATC     660

TTATTATTGA AGGAAATAGT CTGTCACTTT TTAAAAAGCA ATAAACTAAA TAATGGGAAA     720

CAAATTTTTT GATACCAAGT TCTGGGATGG ATACATTTTT GTCGACCAAT AAAATTCTCT     780

CTTTCTGTAT CTTTCCATAC TAAAAGTTGT TCTTATTAGC CTGTGTACTT ATGCACTCAT     840

GTAGATACTG CCAGGTTTAT TTCACTCTTT CCAAATTTTT CAAATATTTT AATCATAAGT     900

GAATTTACAG ATCACACACA GATTTCATGC TTTATTCTCA TGTTTTGTCT AG            952

(2) INFORMATION FOR SEQ ID NO: 88:

(i) SEQUENCE CHARACTERISTICS:
        (A) LENGTH: 1132 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 88:

GTAAGTGTTA CTTCATTAAC TTTCATAAAC TCTGGCAATG TGTTTTTAAA AGTAGTAGTG      60

CTTTCTCCTT AAAGCCACTG ATGACCCTGC AACAAGTCTC TGATGCTCTT CTATAGTCAA     120

ATGTAATCTG TAGAAAGCAT TAGATTTCTA AGTTGATAGA GAATTTTTTG TTTCATGGCT     180

CATATTTCCT ATTCAATAAT TACATAGTTA TAAGAAACAC ATAAATCAAT ATATATTATA     240

GTCAGTGATT TATATAGACA ACTATGCTAC ATTTGTGACA GTGGCTCAAC TTGAGCTAGG     300

AAAAATAATA TGTTACTAAG ATATAAAGTT AATTTTGGCC ATGTGTGTTG ATGTTCAAAG     360

CCTAAAGCCG AACTTATGAG TAGTCATATA AGAAAAAAA AACTTAGTTT CTCTATGGGT     420

ATTAGCATCA CTGAAATGAT TAATTTGCCC TGAAAGTATT CCATCATGTC ACTAGTTAAC     480

ACATATGTAG GAAGCTCAAA GAACCCAACT TATAACAAGG TCCTTTGAAA CAGTTACAAC     540

GTGGACCTAT GTGATAAATA TTTTGGGCTA TAGAATGCTA TGCTCTAGTG ATATTTAGAT     600

GTAAATTGGA GATATTTAGA TAGACAGACA TATATATATA TACACAAATA CATATATCAA     660

ATATACATAT GAATATTGTA ACTGTTATAT CATTATTACA CAGGGTTATA AAAGGGGGC     720

ATAGATAGGA GAATATCTAA TGTTATCTAC ACCTGCCATT GCTATTCAAC TAAAATGACA     780

CAATCTTTTC TTTGAATACT ACACATAACT GGCATCTGTT TTTACCTATG GATTTATCAC     840

AGAAAAGACT CCTCAAAGAA GGGGAATGAA TTGCAAAAAT TGAATATTAT ACTCTAGAAG     900

CAACGAATTC TGGAGTCGTA GTCATGGAAC ATTAGAGCTA AGTGACACTT TAGAGAATAT     960

CTCATCAATC TCTTCATTTT ACTAGTGGAG AAATTAGGAA CAAAAGAAAT TTTAATTTGC    1020
```

```
TAATAAATGC AAACCAGGGC TCGGAAGCTA CACAAATGTA AACTCTCATA TGTAAAACAG    1080

TATCACTGAA AGTGATGAAT GGTGCAACAC TTCTTCTAAT CACTTTTTC AG            1132
```

(2) INFORMATION FOR SEQ ID NO: 89:

(i) SEQUENCE CHARACTERISTICS:
        (A) LENGTH: 1218 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 89:

```
GTAAAATCTT ATGTTTTCTA TATTGCTGGT TTGGCCCAGT CTGCCTGGAA TAAGTAGACC      60

CTTTACAATA GAAAGATAAT TGTTTTTCAG ATTTTTATTT ATTTCCAGTT CTGTGATGAC     120

TTCCCTCTCA GTAAACAGCA ATCCGATTCC AGTGGACCTG AATTATTCTA AACAAACAAA     180

CAATAGCAAC AAACTGTGGG GGAAAATTCA GAGTTCCCAA AACATAAATG AATTAGTATG     240

GGTTGTCACT CTTTTCTCCT CACGCTGTTT ATGCTTTTGT TTTAATCTAG AAACATTGTA     300

TTCATTGGAC ATTATTTTCA GAGAAAATAA CTTTTTATCT TAACATCTCA TCCCATAGAG     360

TAAAATTTCA ACAAGTAGTC TGACTTTTAA TAATAAGAGT TTATGATGAT GAAAATTCAT     420

TGGGCAATAC ATTCACCCCC AAAAATTTGT CTGGAAACTT GTGTTCCAAA ATAGAATCTG     480

TGGTTTAGAT TTTAAAATAG ATTTAATATA CATTCCTGAA AAAGAGATTA CCTTAACCAC     540

AATAAAAAGA AGACAACACA TATTATTTTC ATTCTTAACT CTAGGGAAAA AATGTAAACA     600

TTAGTTGCAA AAAGCTATTT TAGTGTATGG AAGGATGTTC TTGGGAAAAA AATAAAAACA     660

TAAAAGGGAG AGAGGAAATA AAGAAACCAC GGTTTTGTGA GGTAGTACTT TCAAAGGGAT     720

CTATGTATCT CAGAAGCTAG TCAACAGGTT TTAAGTATGT GGAATTGTAG GGTTTTATAT     780

AAAAATGAAG ATACAGTCTC TACTCTTAAG GAGATTAAAA CACAAACATC TCCTCAATTG     840

ACAAGGTCTC TTTCCATGCT TTCTATCTGG GCTAAGAGAC TTATCCTTGA AAAATGTTTG     900

TGGGTAAACA TTTTTTACTC TCTGCTTCCC ATTGTCCTAT CCTCTTCTCC ATGCCTGCCA     960

TCCTTAAGAG GACTGAAGCA GGTTATAGAG GAATCGCAGC TGTGCACTCC CACTACCCTC    1020

ATCTCTTCAG TCACCATGTC ATTAACAGCA TCTCTCTCTG CTATATTCTC CCTCCTTTCA    1080

ATAGCCCAGC CTTCTTTGTG TTTCAAAGCA GGCAAGAAGC CTGTCTAGCT AGCTGTTTAA    1140

ATTGGAATTC TTCTAGAGTT TGATTCTTCA TTTTCTTCTT TCTCCACTAA AATTGATTTC    1200

ACATGTGTTT GACTCAAG                                                  1218
```

(2) INFORMATION FOR SEQ ID NO: 90:

(i) SEQUENCE CHARACTERISTICS:
        (A) LENGTH: 669 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 90:

```
GTACGTGTTG ACCCCTATTA CATATTGTTG ATGAACTCTA GTAAAGAAGG CTGCACAAGG      60

ATGCCCAAGT TTTCACAATT CTTGGCAGGT GGTCTGGTAG CATTTTCATA TCTATCTATA     120

TACATTTCCC TCTACCACCT AGCACCTACA CATTTCTAAA CTCACTAATC TGGCAAGAAG     180

TTCCTTGCTA CCATGGAATT TCACACAAAC AGATGGTGTT GAGTAATACA TGAGGCTCAT     240
```

```
TTTAATGCCA CTAACAATAA TGCCTCATCC TGTCCTAATT AATGGGAAGA AGCTACATTG      300

AACAGCTGTC AACCATGCTG CTGCATTAGT TATGCCGTAA GAGTGATCAG GCGCTGCAGC      360

CCATTGTGAT GTTGCCTTAC AATTCTGTCC ACATGAATCT GTACCTTGCT TGATTATGCT      420

TCAGGAGAGT GTACGGAAAT TAGAAAAGAT TGTTTAACAA TAATCTGGAA ATGGCCTTGA      480

ATTATTTTTT CCTCATTATT TTTCTCGATT AACATTCTAC AGAATGGTAA GGAATCGAGA      540

CATTGCTAAA AATCTTAAAT GACTGAAGGT ATCATAGCAT CTTCTGTAAA AAGAAAAAA       600

ACTTCATATT AATTTCGATT CAAAATTTTG GTCAGAAAAC AAAAAGTTGC TCTTGCTTTA      660

TACTTTCAG                                                             669

(2) INFORMATION FOR SEQ ID NO: 91:

(i) SEQUENCE CHARACTERISTICS:
        (A) LENGTH: 933 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 91:

GTGAGTAGAA TTTTGTTTGT ATGTTTCTTC GTACTTGGAT TTTTTTTTAT GTTGAATTGA       60

GAATTTTCCA AATTCGAACT ACACACACTT TATTTATCAA GTTTAATAAA ATAATATTCC      120

TTCTCTCCTG GGCTATGACA ATAATATCAT TTTACAGTTC CAAAGGAAAA ATTAAAGGGA      180

TTTAACCTCT TTGAAAATAA TATCCGAATT TTCTAACTTC CTAGTGTCAA TGATCCAACT      240

ACAAAACTAT AGACCAAAAG CTTTAGGTTT AATAGAATAT TAAATGATGC TTCAAGTGAT      300

AACAGAGATT AAAATAAATA AATAAATAAG TCTCCTATGC TTTAGGAAGC CGGGACCTCT      360

AACAAGATTC TATAGTTATT CAAACCTACT CCCTAGAAAT TTATCACCCA AGAGCAGCC      420

CCAAAGATTA GCTGTTAATG CCATGAAGAT GCCAAAGATA ATCCCATGAC AGTCTAATTA      480

CCTTATCTCG TATGTCAGCC TCATGGGTCT TCTAGGCCAC AGTCGGCCTG GATTCCTTTA      540

TTCACCTCTC CTTCAGAGCT GAAAACTGAC TGTAGCACAT CTGTAATAGT CTTTCTTTTG      600

AATCACATAG TTCTAACAGT TTCAAACAAG GCTACTCATT TGCTGCTCTC CAGGGAATTT      660

TACAATAGCG GAAAGTTCAG ATCTCCCAAA TTTCTGACCT GCTATGACTT ACACATTTCC      720

ATAACCTTTA TTACTGGAGT ACCCTCCTTC TGAGAGTGGC TTCTAATAGT CTTGTTAATT      780

AGAACCAAAA TACATCAGAG GCCTTCTAGA TATCCAACCA GAGTGCAGTG AAAGTGTTCA      840

GTCACTGTAT AAGCACAGAA AAAAGAATG ACAAGGTTCA CTTTTGATGA TACGGGGTGT       900

TATTAATAAG ACATGTTTCC TTTTTGGTAC TAG                                  933

(2) INFORMATION FOR SEQ ID NO: 92:

(i) SEQUENCE CHARACTERISTICS:
        (A) LENGTH: 680 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 92:

GTAAGCATGC ATTTTCACTA AGCCAACAGC AATATCTAAA ATTTCCCGCC TTCCCTAGTC       60

CCAAAGAGCC CCAGCAATTC ATTTTTATGG CTTGGTATAA AGCCTACTTA TTTAAAAACC      120
```

```
TAGCTATTGT GATAGAGCAG CAGGAAACAA ATGCTGTGTG TTTAAAATTA CTTTTCCCTT      180

CCTATAGATT TGCCAGCTAT CTGATCTATA CTCTAATCCC TAGCATTTGT TTTAAAGTCT      240

CTCCATGTTG CGCATTAACA ATATCCTAAT GCACTGAGGG TTCTCAAAGC CTTCAATTAT      300

TACCAAAAAA TCAATAAAAT ACATAGTGTG CCCATTTCAC ATTGAACTCT CCACTTAAAA      360

TAGATCTTAT TTATTGTATT GCAAAGATTG CCACAAATAG ATCAGCCCCG TGTCCATCTA      420

AAAATTAAAA TGTCCTCCTC CTGGTATTGT AGGCACTGAT TTATAGTGTT TTCTCAAGTG      480

TATAACCCAT ACCACTTAAC CCCCAAAATG AATATAGCAT TAAGTAAAAA TCCACTTCAT      540

TTTACTCTGT GAGATGTGCG TCAGTTATCT CTTCCAAGGC AACTAAGACT CTGTCTGTCC      600

ACCACTGTTC TCTCTCCCTC CCAGTTCTTT GAGCATCTAT GTCAGGCACA TTAACAGATT      660

CATCTTTGGT CCCATTATAG                                                  680
```

(2) INFORMATION FOR SEQ ID NO: 93:

(i) SEQUENCE CHARACTERISTICS:
        (A) LENGTH: 104 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 93:

```
GTAAGTAAGA ACCTGGGTCA TTTTGTATAC TCACACCTCA CAATGTTTAG ACATTGATGA       60

ACCTAGGATT GATAACACAT TTTTAAATCC CTTCTCCCAC CTAG                       104
```

(2) INFORMATION FOR SEQ ID NO: 94:

(i) SEQUENCE CHARACTERISTICS:
        (A) LENGTH: 96 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 94:

```
GTGAGTATCA CATAATGAAG ATTAATCTGA AAACATCCTA AGTTGGGGAG TAGAGTGGGT       60

CGGAATACCA GAGCTGTAAC TGTTTATTTC CAACAG                                 96
```

(2) INFORMATION FOR SEQ ID NO: 95:

(i) SEQUENCE CHARACTERISTICS:
        (A) LENGTH: 361 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 95:

```
GTAAGTTGAA TTCACTGGTG GTCCACACAG CAGCTACCCA TTAGATCTTC CAATTAAATA       60

TATATCCGTC AAGTGCCTGC TATGCAACAG GGAATATACC AGATAGAAGA TGGAAAATAA      120

CGGAAGGATT AACATTTGCA CACTGCTTTA CAAAGTATAA AAGTTTCATG AATATTGTTT      180

TATTTTAATT CTCTGATAAC CTCATAAGGG TGGTAATATT GAAGAACATT CTGACACAGA      240

TAGTCATTTT TTATTTCTAT ATTTTCTTCT AAGAGATGCG GGAATGATCC ACTTGAAGAA      300

AAGAGTAGCA TTTACAAGGG TTTGTTTGTG ATTTGACTCC ATCTTTTTTG TTTGCATTTA      360
```

| G | 361 |

(2) INFORMATION FOR SEQ ID NO: 96:

(i) SEQUENCE CHARACTERISTICS:
        (A) LENGTH: 798 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 96:

| GTGAGTATTA | CAATGGACCT | CTCGCCGCTT | TTCTTTTTTC | AGAATCTATT | AAGGACACTT | 60 |
| GAAAGTTTTG | AAATTTTTGG | TAAATTTGGA | CTACCATGAG | GAAACTTTTG | AGATTCAAGT | 120 |
| TCATTCTATT | CAGAGCAATT | CCGATATTGA | TGTTAACTTG | AACTCAGCTG | GAACTCAGTG | 180 |
| TATGTTGCTA | TCAGCTCACT | TGAGGTAATA | ACCAAGGTGG | GCCCTAGGCA | GTTTAATTGT | 240 |
| AAAGTCGGAA | AAAATATTCC | TTTTGGCGTT | TATTAATATG | CCCCTTCTTC | TGCCTGACCA | 300 |
| TGTCCTTCTC | CTTTGCAGGC | AATGCTATCA | CAACAATTCT | CTAGAGACCC | AGAGCTCCCC | 360 |
| AAAAATGAAC | TTTACTGACT | TCTTCTCTCA | CTGGACAGTG | CTGAATTATC | TAGGTCATTT | 420 |
| GTTATTCTTT | TGTCCATGAA | CACCATTACC | TATTAAGTGT | CCATTTCCTT | ACCACTCAGC | 480 |
| CAGGTGGTAA | AGATAGTTAT | TAATGTATAC | ACATTAATGT | GTAATAATGA | CATAGTGTCT | 540 |
| TATCTTCATA | CCTTTACAAC | CATAAGATAA | TATGTCAGCA | TTTCAGAAAG | GACCATCCAA | 600 |
| ACCTTAACGC | AAAATATGGG | CATTGCAACT | GGTAATATGC | TGGTAAGGAA | GATGTGTGGA | 660 |
| GAAGGAGGGC | CTTCAGGGTC | CTGGCTAAAT | AATGCCCTAT | ATGAAGCTGC | CTGATTTTCC | 720 |
| AAAACAAAGA | AATTCCCATC | TTACCCAAAT | TCTTGGAGTT | GATGTTGACT | GTGGAATTCT | 780 |
| AATGTGCTTG | GCTCTTAG | | | | | 798 |

(2) INFORMATION FOR SEQ ID NO: 97:

(i) SEQUENCE CHARACTERISTICS:
        (A) LENGTH: 1002 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 97:

| GTAAGTAAAT | CACTGTAAAC | GTGTCTTCAT | TTACTCTAGC | CAAAAGGCCT | GGCTTCTGAT | 60 |
| AGGAAACTGG | TAAGAAACTC | TTCATGAAAA | CACATCACTA | ATATTCGCTA | TTACTCTCCT | 120 |
| GGTCTGAAGT | CAGCTTTTCT | GAACCATTAA | GGTATTTCAT | CACAAGTTAT | ATTTTATAAT | 180 |
| ATCAGTTTAA | GAGGCTTTTA | TTCATGTGAA | CACCAGTCCC | CTTTCAGGGG | CATGGTCTTT | 240 |
| TTGAAAAAAA | AAAACAAAAA | AACGAACAGT | TTTAGCCACA | TATCAGATAT | TTCTATATCT | 300 |
| AATTATCCTT | TATGGCTAAC | ATTCTGCCTC | CATTGTTAAG | GTATAATTGT | TCCTGAATTT | 360 |
| AAAGGTGGTT | TGGCCTCTAA | TTTAATTCTG | ATTCAGACTC | TCCTGTCAGG | ACTCAAGAAA | 420 |
| ATTTAATTAA | TTACCAAGGA | TTAAGTCTTC | TGGTTAAGGT | TTCTGGGAAA | AAAAAATAGC | 480 |
| AAAGATGTTG | ATTTCTTGGA | ATCCTTTTAC | AGGTTCAATA | CAGAAAAATC | TTCATTCCCT | 540 |
| GTAGGCATTT | AATTAAACCT | AGTTGAGAAG | TGTGTGGGAT | TCCTCAATTA | TGAACAAAAC | 600 |
| ACGTATATTG | GCTTTCTTTA | AAAAAAAAAA | AAGAAGAAA | AAGAAAAGG | CAAAGTCCTT | 660 |
| CGAAACTCAG | AGTCCCATTC | ATTTATCATT | AACTCCTATC | ATTCTACATA | GTTCTGATTC | 720 |

| CAATATGCCA GGGTACCAGT GGCATGACAT TGTTTTTCCT CATAGAAATT TGCCATAGTC | 780 |

| TCTCCTCCAT TATTTGGTTG GTTACAGCCT CATAAAGGAA GACAGGAGTT GCTTCTTTCT | 840 |

| GCAAGAAAGA AGGTTAAAAA CTATAAATAT TTCCCCCAAA TGGCCAGGGT ATTATTTTAT | 900 |

| TGCATCACAT TGTTTGCATC TTAAGATCTA GAATCTTTGC TGCTCTCTTC CAGGCCCTTG | 960 |

| GTGATTAACA GAAAGGAAAT GACCTTGTAC ATTTGCTCAT AG | 1002 |

(2) INFORMATION FOR SEQ ID NO: 98:

(i) SEQUENCE CHARACTERISTICS:
        (A) LENGTH: 1212 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 98:

| GTAAGTGATT TCCAACTCCT CTTTCTTAAT ACCTTATGCT GAATTAAAAT AAAGCCCCTA | 60 |

| CACAGATCTT CAAGTGGCAT CTATTTGTTG ATGAGTATTG CAGGCTCTCA AGTAGAGCTC | 120 |

| AGTTGAGCCA GGAAATCTGT CCAGCACACA CTGAGGGGCT GTGGCTTCCA AGATGCTCAG | 180 |

| AAAGCACAAA TCGGGAAGAC AATAAATGAG GGAACTCAGT TTTATCACAA AACCCTTAAA | 240 |

| GCTATTGAAG GCACCTTACT GGTACCAGGA TTAGAACAGA GTCCCATTGC TGTGGCCATC | 300 |

| CTACTACATA TTAATCAATC TCAGTAGGCT ACCAATTTCT TAAACATACA CTGTCCAGTA | 360 |

| TTAGTGCTAC TCTGAAAGGT GCCCCTATTA GACCTTAGAG GCCAAAGTCA AAATTTGCTT | 420 |

| CCTTTTGATA TACTGATTTT ACTGATTTCC TTTTTGTTTT TGTTTTTTGT TTTTGTTTTT | 480 |

| GTTTTTTTGT TTTGGGATGG AGTTCCCCTC TGTTGCCCAG GCTGGAGTGC AGTGGCACGA | 540 |

| TCTCAGCTCA CTGCGACTTC CGCTCCCAGT TCAAGTAATT ATCTTGTCTC AGCCTCCGAG | 600 |

| TAGCTGGGAC TACAGGCACA CCACCATCATG CCTAGCTAAT TTTTGTATTT TAGTAAAGAC | 660 |

| GGGGTTTCAC CATATTGGTC AGGCTGGTCT CGATCTCCTG ACCTCAGGTG ATCCACCCAC | 720 |

| CTTGACCTCC TAAAGTGCTG GGATTACACA TGTGAGCCAC CCCACCCAGC CTGATTTCCT | 780 |

| TTCCTTTGTG TATATACCCA GCAGTGTGAT TGCTGGATCT TATGGTAGTT CTATTTTTAG | 840 |

| TTTTTTGAGG AACCCCTCCT ACTATGTACA ACTATTATGT ATCCATAACA ATTTAAATTT | 900 |

| TTTTATTTGT TTCCCTGCCT AGAGGCTATA AAAACTCTAT TTCACCACCC CAAGTGTCTT | 960 |

| TATAAATCTC AACCACATAT TTTTAAATGT TGTGCCATTG GTCTCAAGGA TGAATCAGAT | 1020 |

| ACAAAAGTAT TCATGCCAAG ATGTAAACTC ACCGTCATCA CTAGAGAAAA GATATCCAAG | 1080 |

| GATATGTCCT AGTAATAGGA GGTCATTAGC CTTTTTCTAA GCTGAAGACA GTTTATTCTC | 1140 |

| ACAATCTTCA AGCCAACCTG TGTTATCACC TAGGGTCTTA CCCATAATAC TCAGTATTTT | 1200 |

| TTCTCTATTT AG | 1212 |

(2) INFORMATION FOR SEQ ID NO: 99:

(i) SEQUENCE CHARACTERISTICS:
        (A) LENGTH: 672 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 99:

```
GTGAGTGCTT GACAGTATTC TGACTCCATT AACATAAGAA AAGATTTTAA AAGCTGCCAC      60

TTCAAATGTG ACAGATTGAT CACTGAATAA CTTCACTTAA GATTTTTATT CATGGCATTT     120

TCTTTATACA GATCACATGT CACTTATCTA AGAAGCTTTA ATACCACCTT ACTTAGACAC     180

ACACTATAAA GACACAGCTT AATTATGCAG AATGATTTTT GGTTCTTTCC ACGCACTTAG     240

GAACGATACA ATCTCTAATT GCGTTTACTC CTCTGCAATA TGAAATGCTG GCATCATTTA     300

TCCTGTAGGA AGAATGAAAC TCTGGAAGTT CTGAATCGTT CCATTAAACC TTATACGTGA     360

CAACAACTAG AAACCATCTC ATCTCCATAA AATATATCAA CTTTTTGAAT TCATTTCATT     420

TGGGATACTG AATGACACGA GGCTCACTTT TTACAGAGCA ACATCCCGTG ATTACATAAA     480

GCTGGCCATC TACATGTGGA GAAGGAGGGC AGAGATGATA CTAATGATAC TTCTTACCAT     540

TGTGTGACCC ATTCACATTC AATTTACCTT CTTCCTTCAA ACTAGAATCT CCTGAGTAGG     600

GTTGTTTTGG AGGGGAAGGT TAGCATTCCA TCGAATAAGG GGAATGTCAT TTTATCTTCT     660

CTGCCTGTTT AG                                                        672

(2) INFORMATION FOR SEQ ID NO: 100:

(i) SEQUENCE CHARACTERISTICS:
        (A) LENGTH: 385 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 100:

GTGAGTCCAA CACTTGGTTT GTAAAATAAA ACTGAGCAGG ATTTCATTGT GTGAAACTTT      60

ATGTCCTGAG CTGAGGTTCT CTTCTTCCAA ATTTCTGAAC AAGATGGTCA AGCTTCTCCA     120

TAGTATCTAC ACCTAGTACT GAAAATATGA AAATTGCTTA GGCCAAAGAA TGGGCTTTTC     180

AATAGCACAC TGCAAAACTG GCCCAAGTAT TTAAAACATC TCTAAAAAAT ATCTAGGTTG     240

GCAGGTTTTT ATCCCTAGTT TTAACAGTCT GAAAGAGGGT TCGTTACTGA GCACTGGAAG     300

TGATGAAGAC AGAGTAGCTA CAACATAGGG GCTGGTAGGC AGCAGAGCCT CACCAACAGC     360

CTTAATTTGT GTGGTGTCTT CACAG                                          385

(2) INFORMATION FOR SEQ ID NO: 101:

(i) SEQUENCE CHARACTERISTICS:
        (A) LENGTH: 86 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 101:

GTCAGTACAC TTTTCATCTT TCTCTAATTC AAAAGTGATT AAAATGCAAC CCAGATTGAT      60

GCTAAGCTTC ATTTTGCCTT TGGTAG                                          86

(2) INFORMATION FOR SEQ ID NO: 102:

(i) SEQUENCE CHARACTERISTICS:
        (A) LENGTH: 140 base pairs
        (B) TYPE: nucleic acid
        (C) STRANDEDNESS: double
        (D) TOPOLOGY: linear (ii) MOLECULE TYPE: DNA (genomic)
```

(xi) SEQUENCE DESCRIPTION: SEQ ID NO: 102:

GTAAGTTTGT GAATACCAGT CCCTCAGTGC AGCATTCTCG TGGGCTTCAC TTCTGACTTC     60

CCCACACTTG GGGATGGTGG AGGAGTGGGG AGGGGTATCT TGGGCCTAGC TAAGTTGTGT    120

TTTTCTTTTT CATTTCACAG                                                140

(2) INFORMATION FOR SEQ ID NO :103:

(i) SEQUENCE CHARACTERISTICS:
        (A) LENGTH: 371 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 103:

GTATGTACAT GCTGAAGATT TCTTTGCAAC ACTAACATTT AGAGAGAATC AGTCCAAAAC     60

ATCTGTTAAG AAAATAAACA ATATATCAGC TAGACTTAAT ATTTTTTAAA AATTTCAGTC    120

CATGCTGAGA ATTGATACAA ATAACTTGAG CTATTTTAAA TCTCTTATGC TTGTTTGTAT    180

TAAACAATTA CAAGGATCTA GCCACTTTAC AGATAGCACA ACTAAAGCAG ATTACCAGCA    240

GAGGTGAGAG CCTAGCTAAA CCATTACATG TCCTGAGTTA CCTTTGTAAA CGAATTAAGC    300

AGTATTTGTG GTGAAGTGAG TGCCATTTTT TTAAAACGGT AAGTCTTATC CATCCTTCTG    360

TTTCTTTATA G                                                          371

(2) INFORMATION FOR SEQ ID NO: 104:

(i) SEQUENCE CHARACTERISTICS:
        (A) LENGTH: 475 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 104:

GTAAGTAAAC TGTAGCCATC TCGCACATAA ACTGATCCTG AAGGCCTTCA GCTCAGAAGG     60

ATTTTCATAT TTTCACTGCT ATTGTTCCAG TATAGCCTAT ATAATATCCA TTTCCCATTC    120

TCTGGCTAAC TCCATCTCAC TCTTGGAGGT AATGCTATTT CATGCCAACA TGAAAGGTGA    180

GGATTAAGGG AGATAGAAAT ATACAATACA ATAAAATCTC CTGGTAACAA TGTCCTTCAA    240

CCCCACTTAA AATAAACATA ATTAGAGGAA TGACTAATAT TGCACTGCTG AAATAGGTTG    300

TGAAAAAAAA TTGAATATAA TAGACATAAT GGGAGAAAAG AGCCCCACTT TACATTTTCA    360

ATTTTCTCAA TCCGGAGTCC ATTTAACTAA AGTTTCCCAT TGAATTTGGA AAAAAAAAAA    420

ATATGTCTCT TGACATGTGC TCTGAAAGTG TGATTTTCCT CTTCTGTCTT TAAAG         475

(2) INFORMATION FOR SEQ ID NO: 105:

(i) SEQUENCE CHARACTERISTICS:
        (A) LENGTH: 126 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 105:

GTAGGTGGAC TCAAGAGAAG ACAGTTCATC TCTGAAATAG AGGCTAAAGC GAGCAGTGAG     60

```
CCCCAGGCTG CTGCTCCCTT GGTGGGATTC ACCAGCTCAC ATGTACCTGG TGTCTGTCTT    120

CCTTAG                                                                126
```

(2) INFORMATION FOR SEQ ID NO: 106:

(i) SEQUENCE CHARACTERISTICS:
        (A) LENGTH: 332 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 106:

```
GTAAGTATGA TTTGGGGAAA TAATAAAGAA GATCACGGAC CTAAGGAATG TTTTCTTCAG     60

ACTAAACCAA GACAACTTTG ACAACCCATT AAAGTTAGCC CCATTTCAAT ATATCCTCTA    120

AAATATCTGG AAATTGTCTA TATGCAATGG GCTTGTTAAG TCCATCCCAT GCAAGTGTGC    180

CTGGGGCTC GTTATTTATT TATGTGAACT TGATTATTTT TTACTGATGA AACATGCTT     240

CCGTGTGAAG CTCAACTGAA AATCTGCTGC CATGGATGTC TCTCACTGTA AAAAAATATA   300

AAGCCTCTCC TATCTAACTT TCACCTTTGC AG                                 332
```

(2) INFORMATION FOR SEQ ID NO: 107:

(i) SEQUENCE CHARACTERISTICS:
        (A) LENGTH: 410 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 107:

```
GTGGTAGGTC AAGATGTCCA GACCAGACTG ACCCTTCTCA CAAGTTGAGC TTTTCAAAAT     60

TAGTTTCCAT TGACATTTAG AGTGAAAATG CATTTGGGTA AAGATTACAT TATGTGAAAT    120

CACACCCAAT TAATGGAGCG TCATCTTCTC CCAACCAGCA CCCAACCTCA TTTCCCTTAA   180

AATGTATTTT TGCACTTTTC ATAGTAATAA GTACCCTGAT TTGATTTTTC ATGGAGGAGG    240

GGAGGGAAGG AACTGTCTAA TCTTAAAAAT AGCCACCCTC TTCCTCTTAA ATATGGGGTA   300

GACAATCAAA AATGTTACTT ATGAGAGTCA GTATCTTTCA TTAGTTATTA TTAGAATCTG   360

TGTTCTGCTC AATGAGAAGT TCATGATCT GAATGTTATT TTCTTAAAAG              410
```

(2) INFORMATION FOR SEQ ID NO: 108:

(i) SEQUENCE CHARACTERISTICS:
        (A) LENGTH: 711 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 108:

```
GTGAGGAATC CCACAAACAC CTCTCCTTCT GCTAAATAAT ATTTTGGTAG GACTGTTTGT     60

TAATTATCTG CATTTTAATC TCTGACAAAA ATGGGCTTAT TAAAAAAAGA CCTGTTCCTT    120

TCCTGGGTTC CAATTTTGTG CCTAAATTGC ACATTAGAAG ATGGATTGAT TGGACACATC   180

CATGTAATTC AAAGTTATTA TTCAAATTTG ACTTAATTGG TAATCATTGA AAAAACTGAC   240

TAATGTCATT TAGTGTGAAG GAGCACTGGC CAGCTATATG CCACACTCAT ACATATGCAT   300
```

```
TTTCAGAATG TGAGCAGCTT TTCTGAATTT TTAATCAAAC CTTTTCACCA ACTTTACTGA      360

ATGCCTACTG GAATTCCATA AATTACAAAA TGACAGAAAA AGAAAAATGT CAGAATTTCT      420

ACCTCCTCAT TCTCTTATTC TAAAGAAGAA CGATATGCAA AAAGGATTAA TTGAAACAGA      480

TAACTTTTTT AGATGACCTT GCCTCAGTCT AGTAGGTCTT ATGTTCATCT AGGTAACTGA      540

TACTTCAAAG ACAAGTGAAT TAAGTTTTCT TTAAAAGTAC CCTTTTCCTA AGCTTGGATC      600

TGAGTCTACT CTTCCTGAGA TCTTTTTTTT TCTTTTTTTT TTTTTTCATG TTTGACTCTT      660

AGTATCTGAG TCCTTCTCCA CTTAACTGGA ATTTCATCCT ATTTTCTGTA G              711

(2) INFORMATION FOR SEQ ID NO: 109:

(i) SEQUENCE CHARACTERISTICS:
        (A) LENGTH: 813 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 109:

GTAAGTAATA GTGAAATATG GAATAGCTT TGGGAAGTGG GATGGAGGGG GTTCTAACTT        60

AGACTGCCCC CAAGGGGGT CTAAAGGGGG GTTAAAAGAA CAGAAGAATG AGAGAACTAA      120

CTTATTTCAT AAGTAAATTC AGTTTTTGTA TGTATTTAT ATTTATTTAT TTATACGTAT      180

TAATTTCGTA CTTAAATTCA GATGATAAAT TCAGAGTATT CTTATCAGAT AGTGCCTTCT      240

GAAATGCTGA AATGTATACT ATGTCCATGC ATTGTTTTTT CTTTAGCATG TTTTTTAAAT      300

GGTAATGTGT GCCCAGAACT TAAAATTTCT TGAGCTTCAG TGGCCTAAAC TATAATTTAT      360

AGTTATGTGT ATTTTATTTT ACTTATTAGT ATGGCTACAT TTAACTTTTA ATGCTTTTTC      420

TACAATATGC TATAAATATA AGAAAAATTA AAATTCACTA ACAGCAAGAC TACATACCCA      480

CCCAGGTCCC GCTCCCAAAG ACACACATAG AGGGACATAC ACACAACAAT CCTAAAAATG      540

ACTTTGTAGA GATAGGTCAC TTGGAATGTG TGTTGAAATG TTGTTGGTTT TTTTGGTTGG      600

TTTGTTTGTT TGTTTTTTGT TAGACTGATA GGGAGCCCCT CCCACTAAAG ACACCCTTGA      660

TACTGTTATT TCAAGGATGA ACTTATTTAT CTGGGACAGA CATCTTCAGA ATGACACATG      720

CCAAACAGTG GTTCTTATTA AATCAAAGGT TCAGATATTA TCAGATTCAG AAATAGTGAT      780

GCTTTGTGTA TCTATTTTCT TCTCTTTAAA CAG                                  813

(2) INFORMATION FOR SEQ ID NO: 110:

(i) SEQUENCE CHARACTERISTICS:
        (A) LENGTH: 982 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 110:

ATGAACTCAA TCTAAATTAA AAAGAAAGA AATTTGAAAA AACTTTCTCT TTGCCATTTC        60

TTCTTCTTCT TTTTTAACTG AAAGCTGAAT CCTTCCATTT CTTCTGCACA TCTACTTGCT      120

TAAATTGTGG GCAAAAGAGA AAAAGAAGGA TTGATCAGAG CATTGTGCAA TACAGTTTCA      180

TTAACTCCTT CCCCCGCTCC CCCAAAAATT TGAATTTTTT TTTCAACACT CTTACACCTG      240

TTATGGAAAA TGTCAACCTT TGTAAGAAAA CCAAAATAAA AATTGAAAAA TAAAAACCAT      300

AAACATTTGC ACCACTTGTG GCTTTTGAAT ATCTTCCACA GAGGGAAGTT TAAAACCCAA      360
```

| | |
|---|---|
| ACTTCCAAAG GTTTAAACTA CCTCAAAACA CTTTCCCATG AGTGTGATCC ACATTGTTAG | 420 |
| GTGCTGACCT AGACAGAGAT GAACTGAGGT CCTTGTTTTG TTTTGTTCAT AATACAAAGG | 480 |
| TGCTAATTAA TAGTATTTCA GATACTTGAA GAATGTTGAT GGTGCTAGAA GAATTTGAGA | 540 |
| AGAAATACTC CTGTATTGAG TTGTATCGTG TGGTGTATTT TTTAAAAAAT TTGATTTAGC | 600 |
| ATTCATATTT TCCATCTTAT TCCCAATTAA AAGTATGCAG ATTATTTGCC CAAAGTTGTC | 660 |
| CTCTTCTTCA GATTCAGCAT TTGTTCTTTG CCAGTCTCAT TTTCATCTTC TTCCATGGTT | 720 |
| CCACAGAAGC TTTGTTTCTT GGGCAAGCAG AAAAATTAAA TTGTACCTAT TTTGTATATG | 780 |
| TGAGATGTTT AAATAAATTG TGAAAAAAAT GAAATAAAGC ATGTTTGGTT TTCCAAAAGA | 840 |
| ACATATTGAG TAAAATTCCT TGCTTCAATG CTCTTTGCAA TATAAATATG CATCTCTACC | 900 |
| AGCCATTAGA CCAAGTGCCT CTGATTAGAT AGAAATTATG CAAAAGGGC AGTTTGGTGT | 960 |
| GGTAGAAGAG CAGAGAACGA GG | 982 |

(2) INFORMATION FOR SEQ ID NO: 111:

(i) SEQUENCE CHARACTERISTICS:
        (A) LENGTH: 1867 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 111:

| | |
|---|---|
| TCTGCTCAAC TCTGGTAGTC TCAGAGTTTA AGAATAAACA ACAAGTAGGG GGCTTGATGT | 60 |
| TACATTTTAT CAGGATTTCT ATCCATGAGG TAGAGAGAGG GAATGTGTAT TTAGTAATAG | 120 |
| GCATGGCACT TTGAAAAAGT TACTTCATTT TCTGCTTCCT CAACTTTCTT ATTTGGAGAA | 180 |
| TAAGGGTAAC TTCAGTCTTA CCTTATAATG TTGTTGTGAG AATTAAATGG CATTAAGCTT | 240 |
| TGAGCATTTT CAACAGACGG AGGTGCATAA TGAAGCGTTA GCTATGAAGA CGATGACAAA | 300 |
| TAATGATTGT TGGGTGTTAG ACCCTCTGCC TTTGATACCT CATTTAATTC TCAAAACCAT | 360 |
| TGTTTTAATG TAAGCATTTT CAATCTGTTT TACAGTTAGG GCATCTAGTT ACAGAAAGGT | 420 |
| GAAGTAACTC TCTCAAGGAC ACACAGCTAG TAAGCTTCAG AATAAACAGG GATTGAAACT | 480 |
| TAGGTTGATC GGGCACCAAG GCTCCCACGA GTTTCCACAC CTCTGCCTCC CAGTGGGCAC | 540 |
| ATTTTTACTG GAACCTCAGC CCTCTGAAAG CTTCCACTGT ATTCCTATAG CAGTTCTGAA | 600 |
| AGCTGCCATT GTACTCCTAT AGCAGATCTA AAAGCATCTA CTGTGTTCCT ATAGCACCTT | 660 |
| GCCTGGATCT TTCTGGTGAA TTTCCCCACA TCCTGATTTT ATTTTTTTCT TTTCAGCAAA | 720 |
| CTTTCCCCTG TAAATCCCTC CTTCAGTATA ACCTTGTTAG CTTTGAGGAC ACACCCCTAG | 780 |
| GCCTGGGCTC AGAGCGCTGC TTCTCCCCAC CCCTTTCCTT TGCTTCAGTT TAAAGTGTCA | 840 |
| CGAGATGCCT CTGGTTCTCT CCCTTTGCTT TTAGCCCTCA CCGGGGCAG GAGGGACCAA | 900 |
| GGCTGGGCCA GAACACATAG TCCTAGGGTA ACAGTGAAGG GGTCGTGAGG GGACAGTGAC | 960 |
| TCCCTTCCAA CCCCTTCTTC ATAGGGACTG TTGGCAAACA AAGAAAATCA ACTGGGAAAA | 1020 |
| TGAAGACCTG CTGGTAAGAC AATAACCCTG GAAAGAGTGG TGGGGAGATG GAGCTGGGGG | 1080 |
| TCCTCAGAAC CAAGGGTCTG TATTTTTTGC AGCAGTGGTA AGATGAGAGT AGGTGAGCCT | 1140 |
| CAAGGTGAGA GACAGAAAGA GAGACGGATG AGAGAGTAAG ACAAGAGGGC AAGCGTGAGA | 1200 |
| AACCGAAGAC AGACACAAAA AACCGAAGAC AGACAGAGGA AGGGAGAGAA AGTGACGGCC | 1260 |
| ACAGAAAAAG AGAGGAAGGA AATCAAAGGT GAAAGAAACC AGAGACAAAG AAATAGGTAC | 1320 |

| CAAAACAGTG AGATAGGTAG ATACCGAGAA GGTGAGATCA ATAAAACAAC AACGACAGTN | 1380 |
| NGTCTGGAAA CATGAGTTCC TTACATCTCT CAGTAGGGTT TCAAAGTAAA AATGAAGGCT | 1440 |
| GGGTGCGGTG GCTTATGCTT GTAATCCCAG CACTTTGGGA GGCCGAGGCG GGCGAATCAC | 1500 |
| GAGGTCAGGA GTTCAAGACC AGACTGACCA CCATGGTGAA ACCCTGTCTC CACTAAAAAT | 1560 |
| AGAAAAAGTA ACTGGGTGTG GTGGCACGTG CCTGTAATCC CAGTTACTCA GGAGGCTGAG | 1620 |
| GCAGGAGAGT CGTTTGAGCC CAGGAGGTGG AGGTTGCAAA GAGCCGAGAT CGCGCCATTG | 1680 |
| CACTCCAGCC TGGGTGACAG AGCGAGACTC CGTCTCAAAA AAAAAAAAAA AAAAAAGAA | 1740 |
| ATGAAAAAAA AACTATACTG TGATTTGATC ACCTTACATT AATTAGGTTT ACTAGGTTTG | 1800 |
| AAAATATGGA AGTATTTTCC ATCTGCGGGG ACTCCTGTTT CAGTCATTTT TCTTCTCTCT | 1860 |
| TCTTCAG | 1867 |

(2) INFORMATION FOR SEQ ID NO: 112:

(i) SEQUENCE CHARACTERISTICS:
        (A) LENGTH: 520 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 112:

| GTAAGGGCCA TAGTTTCTAG ACTTTCAAAG ATCACTTATT CCCAGAAATG ATCAGGCAGG | 60 |
| GCTGTGGCTG ACTGAAGACT GAGTGAGGCA TTCATAGTCC TTCACACCCT CACTCTTCAA | 120 |
| TCCAGCTTTG GGGCACAGGG ATACATTAGG TTCTGGTTTT CCATGGTCAA TCGTGGGTAT | 180 |
| GGAAAGTNNN NCCTCTTCAA AACGAACATT TTCCCAGCCA GATTATTAGA GCAACTTTGT | 240 |
| GCCTTGCATC CACCCCTTCC AGGATGAGTT GCAGGTGGAC AGATTATAAT CGTAGAGGCA | 300 |
| TGGAGGTAAA GCCAAACACT TTACCTCTAA GCAAGCTGGT ATAATATTGA ATTTTAAATA | 360 |
| TTTATTATTA TTGATACATC CTGAAATCTT TTTTTTGTGG TCAATTGCTA TTTTCTGGTT | 420 |
| CTAAATTTTA TTATTATTAT TATTATTTTA TTTTATTTTA TTATTATTAT ACTTTAAGTT | 480 |
| AGAGTGGATG AAGTAGAATG ACATGCTATC TCTTTTGCAG | 520 |

(2) INFORMATION FOR SEQ ID NO: 113:

(i) SEQUENCE CHARACTERISTICS:
        (A) LENGTH: 133 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 113:

| GTGAGTAGCA ATGTACCCTA TTGAAAATGC ATGCTTTCTA TAAACCTGAT TTTTTTTTTT | 60 |
| ATTTGGGAAA GTTGTGGAAA GAAATAAAAC CAATCTCATT TTAGACTTTT CATTTTGTAT | 120 |
| TCCCATTCTA TAG | 133 |

(2) INFORMATION FOR SEQ ID NO: 114:

(i) SEQUENCE CHARACTERISTICS:
        (A) LENGTH: 390 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 114:

| | | | | | |
|---|---|---|---|---|---|
|GTAATCTATC|AAAAATATTT|TAATCTAATT|ATCTGACTCA|AATGCATTAA|AAATGGATAG|60|
|CTATCCAATG|TTAGAGTTTT|CTTATGANCA|ATGTTTCTTG|GGATTATAAT|TGTATTTAAA|120|
|GATGAAGAAA|TTTATTTACC|TGCCTATCTT|CAGTACCTTA|ATACTGCATT|TCGATGTTTT|180|
|CNNNNAAGCA|CGGACCATGA|ATGTACAGGA|ATGATTGNAC|TTCTGTAAAG|GTCTTTATGA|240|
|ACAGTCATGA|AAGAACAAAC|GGTACATAGG|TTTTTACACT|GTAGCTTTTC|TATAGGTCTG|300|
|GCATCTAAAA|TGGCCTCAAA|AGGGAATGTG|GTAAATACAT|ATGGGTACAG|GAAACAAGAT|360|
|GCATGTTTAC|TATTTAAAAA|TTTTACTCAG| | | |390|

(2) INFORMATION FOR SEQ ID NO: 115:

(i) SEQUENCE CHARACTERISTICS:
        (A) LENGTH: 714 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 115:

| | | | | | |
|---|---|---|---|---|---|
|GTAAGTATAA|AACCACACAC|TATGGCAGAT|TAAAGCAAAA|CTAGATTGGT|AAAAATGAAC|60|
|ATCTCAAGCA|TCTTTGATAA|TCAGCTGAGT|GCAGCATGTC|CCAGATGGAA|TTTGGAATCA|120|
|GAGGAAGTTA|AGTAGATAGC|TTCTGGTCTT|GAGGAGCTTA|AAGTTGGAAA|GTGTTACATG|180|
|CCCACCTAGT|GCACCCAGAG|TCTTTCTGAG|GCAACTTAGA|AAGANNNNGT|CCTTCTGATT|240|
|GCCACTTTTT|TTTTCTGTCT|CTAATCTCCC|ATCTAAAATC|TTACAGCATA|TATTCCCTGT|300|
|AGAGTTCAAT|AGCCCTGGGT|TTCAACCCAG|ACTCTGACAC|TTATTGGTTT|GTGACTTGGA|360|
|CCGTTTCTGT|TCTCTCTGAA|CCTCATCTTA|GTAGGATCTA|CATCTTGAGA|TTGTCATCAG|420|
|AACAGAAATA|GAAAGTCAGT|GCTGGTGGTC|TGTTTCCAGG|CTAGGGGTAT|GCTGAAATAA|480|
|TTCAAAGCTA|AAGACATCTA|TACCTAATAA|TCAGAGAAAC|TTGTGAAAGC|TTCCAACCCA|540|
|TTTCCATTAG|AAAACTTGTA|TTCAAGGAAA|AGCCAAGAGT|CCTGGTCCAG|TGTGCTCAAC|600|
|CAGTTCAAGT|TGATTTCCAA|TTATTTAACA|ATTAGACGCA|ACTCATCTCT|CTCTTGAATG|660|
|ACCAGCTTCA|GTCGTCCAAA|AAACCTTACC|TGACTGTCTA|CTACCTTTCT|CCAG|714|

(2) INFORMATION FOR SEQ ID NO: 116:

(i) SEQUENCE CHARACTERISTICS:
        (A) LENGTH: 686 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 116:

| | | | | | |
|---|---|---|---|---|---|
|GTGAGTCCCC|TGACTACCTG|CAAAGGCCAC|TTCTACCCAG|CTCAACCCTC|TCCACCTCAC|60|
|CACTTTCCCA|TCTTGCCACC|TCCCCAGCAC|CCCTCCTCCC|CACTCTCTTT|CGCTAAGAGA|120|
|GCCTGTGCTT|TGCTGTACTG|ACTAGAGAAA|TATTAGGGAA|GTACACTTCA|TACTTTCGAC|180|
|CTGGCGGGTA|GAAACCACCT|GCAGCCTGGC|AGGTAGAAAC|CACCTGCGGG|TGTGTGGTTG|240|
|TCCCTTTGGT|AGCTTATGGA|CCCTCCTCCC|TTACTCTCAA|ACATGTCCAA|GAACACTTGA|300|

```
GTTCTACTGG CCAGCACTGG CACAGGCCAC CCGGGAAGGT CTCCGAGGAC AGCCAGAAGC    360

TGCACTGGGG TGGATGGGAT GGAGGCAGAG CTGCGTGCTC AGTCCTCGCC TGTGCGGCGG    420

CAGGGAAGGG GTTAAGGGCG ACTGTTGTCA TTCTATCCGT CCTCCCCTTC CCCCTAGCTC    480

TCCTCCAATC CCAGGACCCT CTCCGGGGCC ATTCATAAAC AGGGGGNAAC GCGCCCCTCC    540

CGGGCCTGGA CGCTTTGGCA ACCGCTACTC CCGGGGGTGC TTTTTCTGCA GGGACGAAGT    600

GCCACCTATG CTAGTGGCGG GTCTGGAAGC CTAGAGGGGA ACCAGGCTGC AGAGCCGGGC    660

CAAGGGATTA GCGGCGGGCG GCGGGC                                        686

(2) INFORMATION FOR SEQ ID NO: 117:

(i) SEQUENCE CHARACTERISTICS:
         (A) LENGTH: 62 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 117:

GTAAGTTGCG ATCGAGTTTG AGGGGTGCTT TTCTCACTTT CTCCCCATCT TTTCTTCTCC     60

AG                                                                   62

(2) INFORMATION FOR SEQ ID NO: 118:

(i) SEQUENCE CHARACTERISTICS:
         (A) LENGTH: 507 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 118:

GTAAGTTGGG GGCAGGGAGT GTTTGCATTT TTCAAGCGCA CACGAGGACA GGTCGGGGCG     60

CACGGGTCGA GGGAGCTGTG AGAAAGGCGC GGANATCCCC AGGGCTCTCA GACCCGCGCT    120

TCCTCCAGCC TCGAGCACCT GCCGCGAGTC CTATCGAAGT CCAGAGCCGT AGATGACCCC    180

TTGGTCTAGG AAGGGGGGCT CCTCCCCAAT CTGGGTCCTC CCTACTGCAN NNNAATGCAC    240

TCTGCAGAGG TGAGAACCAG TGAAGCCTCC CCCAACCTTG GGGGCGTCAA TCCTGCTCTA    300

GCCCCACAGT TTAGCTCATT AGAATATGGC GGAGACCAAA GCTGCGCTTG CTTGGAGGTC    360

TGAGACATTT TTGCGTTGGG TTGCAAAACC CGGCCTCCTC TGGAAGGTAA CTTTTACCCC    420

ACGGAGGCGG GGGCTTCAGG GCACCGCGCT CAGTTGCTCC CTGTTGCCCG ATGTGCTCCA    480

CTAACCTATG TCTGCTATTT TTGCCAG                                       507

(2) INFORMATION FOR SEQ ID NO: 119:

(i) SEQUENCE CHARACTERISTICS:
         (A) LENGTH: 349 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 119:

GTAAGTTTCT ATCTCCAGGC CACCTCTGTT CCCCAGTCCT GCCCTTTCCT ATTCTTTTCC     60

CAGGGCTCCT GTGGGGTTTT TTTTTTTTCA GAGAGGACCA GGGTCTCCCC TTCCTGCCAC    120
```

```
CCCACTTAAA GGCAGGATCA GACATGGGCG AGAGTTGGGG GTAGGATCCT AGGAACCCGG      180

GGATTTTTGG AGGGAGAGGT GTCTCTGTTG TCCTTGTTGG TCATGAACCT CCACGTTTGA      240

CCCTTACACC ATCCCCATCT GTGAAGTGAG CTCTCCTGGG ATTGTCCCAG TGGGGTCCTC      300

AGCCTATCCC GCTCATAGAC TGCTCTCTCT TTTTCTCCTA CCCCTCCAG                  349

(2) INFORMATION FOR SEQ ID NO: 120:

(i) SEQUENCE CHARACTERISTICS:
        (A) LENGTH: 129 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 120:

GTAAGTTGAT TGGAGCATAT GGCGCTCCAC TTCCTTCCTT TAGACGTGTT TTGCAGCCCC      60

CTGTTTCTGA AGGGTCTCAA CTTTGCACCT TTTTCTCTCC TGCCCCCGCA CCCTTCTGCC      120

CCTGCTCAG                                                              129

(2) INFORMATION FOR SEQ ID NO: 121:

(i) SEQUENCE CHARACTERISTICS:
        (A) LENGTH: 468 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 121:

GTGAGTAGGC GAGTGCTGGG AGGGCGCCCA GCCTGGGGTG TGTGGTGGGT ACGAGTAAGT      60

GTGTGTTTTG TGGGGGGGGG AGGGAGAGAG AGAAAGAGAG AGAGAGAACG CGCTGTGGCT      120

CTAAACTTGG CCTCCTGCCA GCGCCTGATT GATCCGTGGA ACTGGCAGCT TTTGCAAANN      180

NNCCAAAGCA GAGACAAAAA ACACTGAATT ATTGAACCCT GTGATAAACA ATGCAGTTAG      240

CAGGAAGTTA GGAGTATGAT ACAACTTATC AAGAAGAAAT AATCACAACA GGCAGATCTT      300

CTGTTAATCT TTTGAGTAAG ACTATAGTAA GGTATTTCTT TATAAATATT TGCATCATAC      360

TTATGTAACC ATCCTGTAGA CAATTAATAA ATAAAATGAA AGTTTTCTAC TTAGTGGTTT      420

GCCTAAGGAT GTTATGATAG TTCTAACATC ATTGTCTTGC TCTATTAG                   468

(2) INFORMATION FOR SEQ ID NO: 122:

(i) SEQUENCE CHARACTERISTICS:
        (A) LENGTH: 402 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 122:

GTAAGTTAGC CATCTGGCAT TAATTGCTAG TACGAAAATG CTGAAGTATA ATTTTATTGC      60

AGTGTTTGCA AGCCAACTAA CATTAAGTTA TGAAGTATCT AAAATGCACT CGTTCAACTA      120

AAATTGTGTT TAAAACACC ATGATGTGGA ATACTATGCA GCCATAAAAA GGAACAAGAT      180

CATGTCCTTT GCAGGGACGT GGATGGAGCT GGAAGCCATT ANNNNCTATG TAANNNNTGC      240

ACCNNCTGCA CATGTACCCC TGAACTTAAA ATAAAGTTG GAAATTTAAA AAAAAAAAC       300
```

-continued

```
ACCATAATGG GGTGTTTTAA TGCTNTCAAT ATTTATGCAG TTTTCACATT TACATATTCA      360

TGATATGAAA GGTCAGTACA ATGAAACTAT TTTTATTTTT AG                         402
```

(2) INFORMATION FOR SEQ ID NO: 123:

(i) SEQUENCE CHARACTERISTICS:
        (A) LENGTH: 472 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 123:

```
GTAAGTAAAT GTAAAGCTAC AGAATTGAAA ATTTCCTATC TTTAGGTAAA ATTCTGCCAT       60

TGTGAAATCT TTTTATTTAT TTATTTATTT ATTTATTTAT TTATTATTAT ACTTTGGGTT      120

TTAGGGTACA TGTGCAGTTT TCTGCATAAT ATACATGAGA NATAAGTTGA TGACATCTGG      180

TATGGTAAGC ATTTCTACTA TGAGTGGAAA AATTTTAGAG AAGTTTGAAT GTACAGTAGA      240

AAATATATAT NCTATTTGCA GGTGGTATTT CCCAGCAGAC AATTCCCTCT TTACCTGCCA      300

TGATAGANNN NAGCAGAGCC GTGTTTGCTT TTCTTTATTC AGTGCTTTCT TTAGAATGAG      360

CATCATTTTT AGTAATAGAG TTTATGGTTT ATTTTAGCTG AGTTATGTCT ACATTCATAT      420

TTATACTAAG TATAAACCTC AAGCTATAAC CATTTTTATT GTACTCTTTT AG             472
```

(2) INFORMATION FOR SEQ ID NO: 124:

(i) SEQUENCE CHARACTERISTICS:
        (A) LENGTH: 356 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 124:

```
GTAAGTATCA CTTCATCATT TATTTTATG CAGTCTATAA AAATGTCCTA TTTCTCAAAT        60

CCCCACCTTA TTCTCCTACT AACGGTCTAC TCAGTGGTGT TTACAGTGTT CTACCTGCAA      120

GNTCTTAGGT GGCTACTAAG GATAACACCC TTATTCTGCT ANACNNNATA TTTATTAATT      180

TAGGAAATTT CTGCTGTATC TTAAGTAATT AAAGTTTGGT CAAATGAGTT ATTGTGTCAT      240

TGGAAACCAA AGCTAATACA GAAATGTAAA TCTAATATTT ATCATATTTG ATATAATGTA      300

TGATAGATTG TAAAAATATT CATAAATGAC CATTTGCTTT GATTTGTTGA CTTCAG         356
```

(2) INFORMATION FOR SEQ ID NO: 125:

(i) SEQUENCE CHARACTERISTICS:
        (A) LENGTH: 750 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 125:

```
GTGAGTACCA CAGTGCACTT TGATAGACGT TTGCTGATTT AATAGAAGAT GTTATTTGGG       60

AAAGCAAATT ACCCTAACTG TACATTTCCA CTTGCAAACC AAAACATGGC AGATGAATTT      120

CATTCCAGTT TATAATATTG ATGTGAACCA GGAATAATAA TAATTTTTGC AGAGTGATTT      180

TAATTTTTTC CTAAATTTTT CAGCTAAACT TTTCTTCCCA ACTTCCAGAT TGTCAAGTAA      240
```

-continued

```
GAGAGTGTCG TCCTCATTTT ACAGACTCTC AGCCAGGACT GGAGTCTAGT GGCTTTTGTA      300

TTAGGCTCCC TGCATGANAT AAAAGTGAAT AGCCTAAAAT TATTACCATG TGTATTTATG      360

TTAGGNTCAT TAAATTATAA TTNNNNAATG GCACTAGCAG TATAGGTTGC TCTAGGTCCT      420

CTGTAAATCA ACCAAAAAAA TAAGTAGTGT TTCCAATTTG CTNTCAGAGT AGATAAAATG      480

TTTGTCTGAT AGAGAAGAAT TGGCTTTGCN NTTTCCCCTA GCTTCTCTCT GACTTGTTTT      540

ATTACCTCGG TGAGACTGGA ATGCCTTTAT TACTCTCATT TTGTAGAACT AATTGGATAA      600

CGGGCCACCC ATCGATTTTG GTGGCAGGTC TATGCATGGC TGAGCTCGGT GGGGNNNNCC      660

AGTAATACCA TTCTCTTATG CCTCACTGGT NTTATGTACT GTGTTTTGAC ACATGTATAA      720

CCACTGTGTC GCAATTTTCA AATAACTTAG                                      750
```

(2) INFORMATION FOR SEQ ID NO: 126:

(i) SEQUENCE CHARACTERISTICS:
        (A) LENGTH: 648 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 126:

```
GTAAGTTATT TGCAGCTTGA ATTTCTGTTT GTGTCTGAGA GTCAGGGTTG AAAAAAATCT       60

AAGAATCCAA AATGGAAGTT CCTATTAATT GAGTCATTGT CCCAAATTTN CAAAACGGCT      120

ATCAATTTTT CCATGCACTC AAGGGCATGG TTCTGTTTAG GGCAAGAAGT AGAAGAATCA      180

CAATAATTTA AAAGGTGGTT TTTATAGGGT ATATCTTACT CATTACTTTT GAAGTCTTTT      240

GACAGTTGTG ATGTCTCAAA TGCTCAAAAC TTAGATATAT AAATGAAGCA TTTTCAAATG      300

AACTAGTTTT TACAAAGGTT TTCATAGTAA GAAAAATTTA AAGAATATGA GTTTAAATGG      360

AAGGTAATTC ATATTTTTAT TTGTAATTCA GAGTTCCCCA CATTTTCTAT TTTGCCTCTT      420

ATTTCGTTTC CCTTCAATGT CTTCCCAAAA TAATCTACTG CAATTCATGG CTCTCCAAAG      480

AGAACATGCC CATGAGTCAG GATTNTAGAA TATTAGCATA TTATCTGGTT TCTTATATTT      540

TATTAAACAA ATATATTTTA TACTTTTGCC TGATGAGCTT TCTAGTATTA GTATGTTTGA      600

ATTCATTATT TAATTGTATT CTGAACCTTA ATATTTTGTT TACTTTAG                  648
```

(2) INFORMATION FOR SEQ ID NO: 127:

(i) SEQUENCE CHARACTERISTICS:
        (A) LENGTH: 434 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 127:

```
GTAAGATGCT TTCCTTTGAA CAAAATATAG TTTTAATTCA AAGACCATAT AGCCTGCAGA       60

TGAGTTTTCT TTAAAAGATT TCCCTGGAAT ATTCTATGTG TCTGTGTTTT CCTTTCACTC      120

AAATGGCAGA GCAGTCTGTA ACACTAGTGG ACTAGTGGCT TGCATCTACT CAGACTAATA      180

ATTTTTCATT ATAGATGTAT CTTTGTTCTT CTATGATCTT TTTACTTTAT GACTAAGACA      240

TGCTTTTNNN NCTGGCTTTA AATGTGAAAT AATAATAATA AAAAGGAAAG GGTGTTTAG      300

AATTATTCAA TGAATATTAT TGCAATGGAG TTCTGTAACT GGAATCCCTT AAAAAGATAC      360

TGTCACAAAG CGGGAGTCCT AGTTTATGCA CTCTGTCTGT CTTTCTTTCT CTTTGTTCCC      420
```

TCTCTCCCTG GCAG                                                        434

(2) INFORMATION FOR SEQ ID NO: 128:

(i) SEQUENCE CHARACTERISTICS:
        (A) LENGTH: 730 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 128:

GTAAGAGAAT AACTTCCAGT ATTTTAAGAG TATTATCCAC AGATAAAATG GAGCCTTTAC      60

TTTAAGCATT AGCCTTCCTG GTGCAGAGAC CCCACTTGGA TGATCAGGCG AGTAGTGCTT     120

ATTCAGTCCT AGCAATTCCA GTTGCCCTTG ACATGTATTC CTGTATTCCT ACCAAGACAT     180

GGAGGTTTAA TCATAGGATG GCTTTCTAGT TCAGGAAGA AATACCAATA AAATACATTG      240

GATTGAGAGA CTTTNNNNCC TTCCTCCACC ATCAGGAAGG AGGTGGGAAT GGAGGAGGCC     300

GAAGGGTTTT CAGAGCAGCC TTCAGAGGGC AGGGGATAGC CAGCTGAGCT TGGTCAAGGC     360

TGTCACTTCT GAAAGGTTAA GTTACTGGAA CTAGAGAAGA CTTAATGCTC CTAACCCGTG     420

TGAGGAAGTT GGAGAAATAG GGAATAGGGA TCTAGGAAAT AGCAGGCAAG TATCAATGAA     480

TCACATTGCT GAACTAGGTA ATGAAGTGTA TTATTCTAGA GCAGTGTTTT TCTATTAAGT     540

AACACTGATA TTAATTATAT ATGGCAGTCA TGGTGCTGTT AAGGTCATTT AAGGCATTAA     600

TTTTCTTTGT GACATAACTC ATTTCTTAGT AATACATTGG CACTGATTTA GGGAAGCAGG     660

ATCACTTTAT GAGCCTTCTG ATCACTTTCT GTACCAAACT CAAGACAATT ACTTATTTTG     720

CATTTGTTAG                                                           730

(2) INFORMATION FOR SEQ ID NO: 129:

(i) SEQUENCE CHARACTERISTICS:
        (A) LENGTH: 656 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 129:

GTAAGGAAAA TGGGTATTTA GTGGATAAAT TGTGATTAGG AGTTATTGGT CACTTTCATT      60

ATAAGAAATT AGGAATTATA GGAAATAATG AACCTCGATA TTTTACCATT CTTTTTAAAA    120

TAATGATTGA TAAGTTCTAA GCAGATGCAT CAATATTTGA CTAAATATCA TATTCTGAAG    180

TTGTTCATTT ACAATAAAAC ACTTACAAAT AAGGCACCAG ACATTTTCAT TTTTTTCTGT    240

CACTACCTTT TCTTTTCTTT TCAAATCAAT CACACTCAGC TTTTTTCCTT GATGCTATGA    300

TAGCCAACAT TATTCAGCAG TTGTTCCACT TCACCAGCAA NNNNTTTCTT GATATCTTTG    360

TCTCTCTTCC TCTTTCCCCC ACTTTAGAAA AACTTTGAAA GAATAACATC TAAATGTTAC    420

TGGTATTTTA TAGTTAAATG GTGGTATTTT GGTGACATTT TATATGTAGG CTTCTCTGTA    480

TTTTCTGAAT GTTCTACAAT TAATTTGGAC TACCCATATA AATAATTTAA GAAAGTAGAA    540

TAATTCAGGA GTCACCAAGT TAACTTAAAA CATAATGAGT TAGACCAAGC CTATTTCTAT    600

GTTCGTTTGC TAGAATAACA TTTGGTGTGC TTTTCTTTTT TCTTTTTTTT CTTTAG        656

(2) INFORMATION FOR SEQ ID NO: 130:

(i) SEQUENCE CHARACTERISTICS:
    (A) LENGTH: 872 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO: 130:

```
GTAAAGTATT TTTTAAAAAA TATTTAACTA GGATATGTAA ATATTCTTTT TTTTCATGAC      60

TGTTGGAATA TTTTCTATTT AGCAGTTGGA TGAATAGCAT TACATGAACT TGGTGTCCTC     120

TATTTTCCAC CACGCCAGCA CTGGGGGATA ACTACTTCTT CAAAATAGGA GAGGGTCTTC     180

ATTATATATT CTAGCACTTT TTTAACAGAA AAATTCTACC TATAATTTAC ATACATTCGT     240

TTACCAGATT TCAGGGCCAG GCAATTGAAA AGCAAATACT AAGCACAAAA GGATGATACT     300

CATCTTTTAT GTTCTATCGT ATTATCACAT GATATAATGA GAAAATTTTG TGTGTTCTAA     360

ATATGCAGTA GGTATATCAT TTATTGGATT AATGTAGCTT ATTCCAGTAT GCAATCATTA     420

TAATTAATTA AAACATTCTT AATTGCTCAT ATCATGTCTT TTAATAAAAA ATTGGTCCCT     480

CGTGCTTTAG CAGATTTCTG CCAATAATAT TCANNNNACA TGCCATGAAG GAAGTGGGAA     540

TGATAGTGTA AGTTCTACAT ACAAGTTAAA AGGTAAGTCA AACATATTAT CACAATTTCT     600

CTTATGCTGG TATTTACTTT TTTTGTCATA AGTGATTTTG TCAACTCCAG TTTTGTGTAA     660

GACTTCAGAA TTTTATAAAA AGGTTTACCA TCAGAAGAAT TCTCCTTGGA CTTTCTAAAC     720

TAGAAATGTT TGTCTATATA TATATAGTTA CTATTTCTTG GTATTACCTT TGGTTATGAT     780

AATACCCATT GTCTAGATCA GCTTTTGTGA TGAGATTTTT AAAAATCTTT GCTTCAACTA     840

AAATAATTCA CTTCTCTTTT TCACATTTCC AG                                   872
```

(2) INFORMATION FOR SEQ ID NO: 131:

(i) SEQUENCE CHARACTERISTICS:
        (A) LENGTH: 423 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 131:

```
GTAAGATGGT GATGACAATA ATATAATACC AAAATGTGTT AAATATTTAA AATTTTGGCC      60

ATTTAAACAT AACTTTTTAT CTTCAACAAC TTTTTTTTTT TTTTTTTTGA GATGGAGTTT     120

CACTCTTGTT GCCCAGGCTG GAGTGCAATG GCGCGATCTT GGCTCACTGC AACCTCTGCC     180

TCCTGGGTTC AAGCGATTCT CCTGTCTCAG CATCACGAGT AGAGCAGCTG GGATTACAGG     240

CGCCTGCCAC CACGCCNNNN TTACCTGAGG TGCCTGAGNA ATTACTCCTC AGGGATCACT     300

GTGTGTATNA CAGGCACAAA ACCTCCTTTT CATCTGGCTA TTAAATTTCT TTAGAAAGAT     360

GGATGCTTCC TTTAACATAC ATGACTGATC TCAGTTTTTT TCCATTGTCT TGTTTTTTG     420

CAG                                                                   423
```

(2) INFORMATION FOR SEQ ID NO: 132:

(i) SEQUENCE CHARACTERISTICS:
        (A) LENGTH: 555 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 132:

| | | | | | |
|---|---|---|---|---|---|
| GTAAGTGATT | TTCCTTCCAC | AAAACCCAAT | GATAGATTTT | TTTTTTTTTG | CTATGTATGC | 60 |
| ATGTGTGTGC | AGTATTGTTT | ATGTGTGAAT | AATTAAAGTG | GAAAAGTGGA | CAATTTATAT | 120 |
| ATATATGTTT | AAATTTAAAT | TTAATTAAGA | CAGGTATCTT | TCTCGGGTAC | ATAGAAATGT | 180 |
| TCTTCTGACT | TGACATGATT | TTTTTCTTCA | TAGATTAAGC | CAAATTATTA | AGTATTTATG | 240 |
| TTTGCGTGTT | TTCCTTTTCT | TTGGTTATTA | GGACGCCTTG | AGTCTCAGTA | ACTATCTCGT | 300 |
| TTCTNNNNAC | AGAGGCATAG | TGCATTTAAG | GGGAAAACAA | AAGACCATCA | AGTGTCAGTT | 360 |
| ATCTCTATGG | CAATATCCAT | TTTTAAGACA | ATTCCGTTTT | TATAAAAAGA | CTTCTTCATC | 420 |
| TAGGCTTCCT | TGATAGAGCA | AAGCCATTGT | GGTGGAAGAC | TAATAGTTTG | GTGACGTGGA | 480 |
| TGATACTTTC | TAATTTTTAA | AAGTTGATTA | ATAAGTAACT | TTTGCTTGTA | TTAACAAAAT | 540 |
| TTTATTTTCA | TACAG | | | | | 555 |

(2) INFORMATION FOR SEQ ID NO: 133:

(i) SEQUENCE CHARACTERISTICS:
        (A) LENGTH: 133 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 133:

| | | | | | |
|---|---|---|---|---|---|
| GTGAGTTTAA | ATTCAGTCAC | TCCAAGCCTC | CTGCTTTTCA | GTGTCATCTG | CTGATTATGC | 60 |
| TGATCTCTTT | GACAAGTCTA | AGTATTATGT | TAACTGAACA | TGTCTTGTCT | ATTCTTTCTC | 120 |
| TTCCTCCCTG | CAG | | | | | 133 |

(2) INFORMATION FOR SEQ ID NO: 134:

(i) SEQUENCE CHARACTERISTICS:
        (A) LENGTH: 133 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 134:

| | | | | | |
|---|---|---|---|---|---|
| GTATGTCCTG | AGCTGTAGTC | ATCAAGCACA | TTTTTCAGTG | ATCATTGACT | TGCAATGAAA | 60 |
| CTTTAGAAAA | TAATGAAGGG | AAAAAGAATG | TGACTGTGTG | TAAGAGACAG | TATGTTTCTT | 120 |
| TGTGTGTGTT | TAG | | | | | 133 |

(2) INFORMATION FOR SEQ ID NO: 135:

(i) SEQUENCE CHARACTERISTICS:
        (A) LENGTH: 433 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 135:

| | | | | | |
|---|---|---|---|---|---|
| GTAGGCTGTG | TAATTTACTC | CAAGAGTGAG | TGGGGCTGTC | TCTGCCCTGG | CCAACTGAGT | 60 |
| GTGGCATTTC | CATTACTAAA | TCACCAAAAG | ATTTATTTAG | CTAGCTTTGG | CTTTTTCCCT | 120 |

```
TCCTTTAATT TTTGAATCAA GTGTCAAATA TGAAATACTT ACTAGAATAG TATAATTATT      180

TGCTTGGTTT CAGGAACTCA GTAAAATTGC CCTGTTGATG AAAGTAAGTT GAGAGAGACT      240

GTGCATTTTG GTTGAATTAT GTCCTATTTC CCACCCTACT CCCCCACCCT AAATTAAGTC      300

ACTTTATAAA AGTGCATGTA AAGTCAGCTG TTGGGACAAT CCTTTTACTT AAAACGTCTG      360

TGCTCCTCCG TTTCTTAAAA GAAATACAGC AGCTCATACA GGTTCAATCA TGTGATAAAA      420

GCTTTTTTTG CAG                                                        433
```

(2) INFORMATION FOR SEQ ID NO: 136:

(i) SEQUENCE CHARACTERISTICS:
        (A) LENGTH: 739 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 136:

```
GTAAGTATTT GATTCTTTAC ATGTTAATTG GTTTATATAC ATGTTTTAAA GATATACATT       60

TTGGGGAGAG ACATGCTACC TAATCTGATA AGTTCTGGGG AAGATATGAT GTTTTACTTT      120

TACATTTTTA CAATTTACAT TTGTATTTTA TATTTTATAC TTTTTCTCTG AATAGCTATT      180

TGTGTAATAA CTGTAAATAA TAGGCTTTAA TTTTATGCTT TGGATTCCTT TTCTCTCTTT      240

AGTTTACTCA GTCTTTTTTT ACATATTTTT TAACTAACCC TAAGCTGTAG GCCAGTGTGA      300

TATATTTCAT TCCACTTTAA ACCGGTTCTA AAGCTCTTGT TAGTAGGATT AAGCAACAAG      360

AGTGCTGAGA GTATACTCAG GTGACCCCTT AGATTATGTA CTATTTTTNN NNCCTAGTAG      420

AGCTCCTCTT GACCTGAAAG TGGTACTGGA TTCTAATTTG GGAAGTTTGT CCTTGAAAAG      480

TAACTTTAGT TTAAAGACAA GATTTGCTTT AAGGGTACTT AGCTTTAACA AGCCAGATAT      540

AGTAAAGTCA TGCCCTCTAA ACTGTGGGTA ATTCTATAAA TGACTGTGCA GAGTTTGGGA      600

ACTAGGAAGC ATCTTCCTTA CATTAAAGCT TTGAGGTTAC CATGATTCCC TCAGCCTCCC      660

TGCAGTGTGC AGTGGGCTTG GCATCTCATG GATTCTCAGA GGAGGTGATT AAACTCGGAT      720

TGTGTATGTA TTCTTTTAG                                                  739
```

(2) INFORMATION FOR SEQ ID NO: 137:

(i) SEQUENCE CHARACTERISTICS:
        (A) LENGTH: 447 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 137:

```
GTAAAATATT TTAAAATTTA AGTTAATATC TTTCTTAATT TCTTTATTAT TTACTAACGT       60

ATTTGTAATT TTTAATATTT TCAGCATGTG TTTTATTTTA TATTTGGCCC TAGGGAGAAA      120

TAAAAAGGTA AATGTGTTAA GGCTTCAAAT ACTAATCTTT TTCCTAGCTA CAGAAAGCAT      180

ACTTTGACAA AATGCTGCTA ATTAGATTTC CTTAATGNNN NTGACATTTG ACCTTTAATA      240

TATTTCTCAG ACTCACAGAC AATATCTTGA ATCTAAAGGA TTTCGATGTA TCTAACAAGA      300

AAGAGATTCT GCACATTCCC AGATNCTCAG TGTGAAAGCA GGGAATTAAT GCTATTCAAA      360

TGTAAGAGAT CCCAGTCTGG GTAAGGCAGA TTGATGATTA TGCTTACTTC AGCATGAGTT      420

ACTTTGAATG TTGCATTTTA CCCTTAG                                         447
```

(2) INFORMATION FOR SEQ ID NO: 138:

(i) SEQUENCE CHARACTERISTICS:
        (A) LENGTH: 88 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 138:

```
GTAAGACACC ATTTTACCTC TCCTGAAGTT CTAACCTGTT GTAATCAGTA GGTGTTAACT      60

TTTTTTCTAC CTTCCTTCCT GATAACAG                                        88
```

(2) INFORMATION FOR SEQ ID NO: 139:

(i) SEQUENCE CHARACTERISTICS:
        (A) LENGTH: 744 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 139:

```
GTGAGTATTC CTTGCTGTTC TTTCCTAAAG CACCTTCTCA GGACTTTGCT GGATGTTCTT      60

CCATTCATTC ATCCATCCAT CCATGAATGC TGTCTGATGT TTGAGCCCAT GCTAGTCCAA     120

GACACACAAG GAGATGAAAT GCTATTTAGA TGCACAGCAT GCCTTTTCAG AAAATGGAAA     180

CAAAAATAAA GTGCTTCAAA AANNNNCTTC AGAAACTTCA GAAATTTTTA CCATCTGTGT     240

CTTTTTGAAG TTGCAATAGT AATTTAAAGG CAAACATATC TATTATGTGT TTCTTTTTTC     300

ACTCTGTTGA GGTTTAAGAT CATTTGCCAG ATGTTGCTTT GAAATGTTCT GTAGACCTGA     360

GAATTTATTC TGTGTTCTAG GCACTGTGCA GAATTCCAAA TTAATATTTA ACAATACCTT     420

AAGAACACAT AATCTAAGTG AGGGCTTAAA ACATGGACAC AAATAACCAT AATAAAAGTT     480

AGGATGTGAT TTAGATGTTG AAAGTGACTA ATTGCCATTT CATATACATG CATAGCTATC     540

ATTTCTAAAC GTCTGTAATC ACAGTAAACA GCATTCGAAT CATTCAATGC AAGATGAACA     600

CAGGATGCTG TAGGCACTAT GTAGGATGGC CTATGCCTTT AGCTGAAGGA AAAAAACCTA     660

GGTAGGATGT TATTTTATTT ACATAGTAAC TAAGCATTTG AATTTTGGCA AAATATCCAA     720

TTGACAATGT TTGTGTTTTT ACAG                                           744
```

(2) INFORMATION FOR SEQ ID NO: 140:

(i) SEQUENCE CHARACTERISTICS:
        (A) LENGTH: 626 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 140:

```
GTAAGTAGAA AAGTTTCGTT TATTTGCCTT CTACGAAACA CAATGCATTT TTAAAAATAA      60

GCAAGAGGAG AAAACAATTT ACAATTGAAT TACCTGTACT TGATTTCTCT TGTTATGTGA     120

ATATGAGAAC AATGTAAAGG GGAAATTTCA AATTATGGGT AGGATACCCT CAGAGGGTAT     180

TTTAATCTGC GTGGTTTGTA GCATCCATTT TTAAACCTGG TGAAATGTGA AGTGCTGCAT     240

TTGGCCTCTG GTTGTTCTTG GAATGGCAGA AAACAGAGTG AATGGTGCCT TTTACTTCCT     300
```

```
GTGCAGTGCT TGTTTACATA GCTAGAGGAG CAGCAGCGCC ATTGCAGGCA GTGCGNNGGT        360

GNNGNGGGCT TGACTGAAAA AGCCTACTGT TGCCAAGGAG TGCAAGGGGA ACTGAGGACC        420

TTAGGGTGGA GTGAAGGCTG GGAGAACATT GGCCCCGCCC TCTTCTCCTG AGAATATGAA        480

AGAGAGGCAA ACCCAAGAAG CAGAGTTCAA CCAACCACAG CACGTTTATT TTAGACACAA        540

GTCAACACAC CCAAGGTTGT TTCTGCCTTC CGTGCTTTCA GTGTTGCAGT GACAGTAACT        600

CCGGGGACTT TGTTTTTGCT TTCCAG                                             626

(2) INFORMATION FOR SEQ ID NO: 141:

(i) SEQUENCE CHARACTERISTICS:
        (A) LENGTH: 511 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 141:

GTAAGAGCTC CAGCACTCCA GAAGGTTCTT TATTTGGAAG GGTGATTTCT ACCATGTTGA         60

GAAACAAAGC TTGCTTTTGG CCCTGTGGAG AATTTTCTAG AATTTATCAT AAACAGCTAT        120

CAAGAAAGAT ATTTTAAATT ACTCAGAGTT GAGATTAAGA AGCAAAAAGT CTATTAATAT        180

AATTTAACAG AAGGAAAAAA AGCTGAGAAA AGTAAAAACT GTCCGTTGTA ATCACACTTT        240

CTACTTAGCC CTCAATTTAC ATTTCTACTA GTCAAATTTT ATGAGGATGT GACTCAGAGA        300

ATGCCCCAAG TTCCAGAGCC TCTTGGAAAA TTGTGACCTA ATGTGGAAAC TTATGTTTTG        360

GTCCTGATTC TTGTTGGGTG GTGAGGAGTG GGAACGTCCT CTCCCATCAC ATTATCCGTA        420

CTTGTGCTTA TCCACCCACC CAATAAGGTT CACTTGAAAT TATATAAACA GTTGAAAATA        480

CTGAAAAAGT ATTATATTTT ATTTATTACA G                                       511

(2) INFORMATION FOR SEQ ID NO: 142:

(i) SEQUENCE CHARACTERISTICS:
        (A) LENGTH: 684 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 142:

GTCAGTCTTA TTATTTAATT GGTATAAAAT GCAATGTTTG ATATGCACCA TTTCACAAGC         60

AAGGGGAAT GGCTGGTTTA TGGGGGTTAA TAAAACCATG AAGGCTAACA GTTTTTCTCA        120

ATGTGTTCAT AGTGAGTGAA ACCTGGTGTT GAGTTTGGTC CGCAGCATTG TTTACTATTT        180

TAACAAGCTG GAGCTAAAGA TGGCTCTGCT CCAGGACTGC ACACTGTCTT TCCTTTGAAG        240

AGCGTGGCTC TGTCTCTGGT TCACGGAATT GGTTTATTCA TATCCAATGA GCCTTCCACA        300

GCCACATTAG AATGTCTTAG GTTTTTCTTG ATCAAGACCT CAGCAAATAA ACTGTTTATA        360

TGAATTAGAC TCAGTCCTTT CCCTGGGTTC CTTTTTCTAC TGTAGATTCC CTATTTCAAG        420

GGCCAATTAT AAAATTGTTG AATATGGTCA TTTATCCTTC ATTCTAGCTG AAACTCAGCC        480

TCACCTTCTG GCTTTCCTCT CCGCTATTTT CTGATTGGGA CTAACCACTG ACAGCTAGAT        540

TGGAAAGCCG CTGAGAGCAT TTTGTATTTC TGCATGATTC TGGGAACACT GTGGGCACTT        600

ATGAATGCTT ATCAATGTTT ACTGGTTAAA ATTGGGCAAT GGGACTAAGA ATTTTAAAAT        660
```

```
GTAACCTTTT ATCTTAATTT TTAG                                              684

(2) INFORMATION FOR SEQ ID NO: 143:

(i) SEQUENCE CHARACTERISTICS:
        (A) LENGTH: 506 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 143:

GTAAGATTTT TTTTTTCTGG TTAATGATGA AGCTTTACCA ATTTTGAACT GTTAGAAGTA         60

TATATATATA CTTCTAACAC AGTTCAAAAT TGGTATATAT ATATATGTGG TTATTTTCTG        120

GACACTGTTA TCCTCACTGC CTTCTTTAAA GGTTATGATG TTTCTCCTAT CAGCTAACAA        180

AAGTCTCCCA AGATTGCAGC CAANNNNAAT TCTTGACACC TAGCATTTGA GATCTGGATG        240

AAACCCTGGA AAGCTCTGAT TCAACCCTNT TANTTAACAG ANNAATTAGC CAAAGGCTGG        300

GAGGCTACAT AGCTTACAGA GGGTCACAGA GTTAAGTAGA ACTGAGATTA GAATCCAAAA        360

TTGGAGTCTA ATATTTTTTT GCAGTGCCAG AGTTAATCTG TTCATGGTTT TCCGTATTTT        420

AGTAGCACAA TAACTTTTAA AGTGTTTTCA GGAAATTATC AAATGTGAAT ACATTGTTCT        480

AACATAAATT TCTTTTATTG ATTTAG                                            506

(2) INFORMATION FOR SEQ ID NO: 144:

(i) SEQUENCE CHARACTERISTICS:
        (A) LENGTH: 569 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 144:

GTAAGTATGG TGAATAGTAA TGGTATAAAA AAATTAAAAA CATTAATAAA GCTGTAGAAT         60

ATATAATATT CTGCTTTATG AAATCATTAT GTAACATTCA ATTCTTTTTT TTTTTTGAGA        120

TGGAGTCTCA CTCTGTCGCC CAGGCGTGAA TGCAGTGGTG CAATCTTGGC TCACTGCAAC        180

CTCTGCCTCC TGGGTTCAAG CAATTCTCCT GCCTTAGCCT CCCAAGTAGC TGGGATTACA        240

GGCATGCACC ACCATGCCCG GCTAATTTTT GTATTTTTAG TAGAGATGGG GTTTCACCAT        300

GTTGGTCAGA CTGGTCTCGA ATTCCTTACC TCAGGTGATC TGGCCCACCT CAGCCTCCCA        360

AAGTGCTGGG TTTACAGGNN NNAGATGGGT AAGTTGTGTA GCATTATGTG TCTTCACCTT        420

GCAGTGAAGG TTTTGTAACC TCTGAAAGAA CACCTGTTAG GATGCAGAGT GCAGGAAACC        480

GCAAATTTCA TATAAGTGTT TATATGAGTA TGAAGCAGGC ACATTCTTTA TGCTTAGCCC        540

TGGTTTGATA GTGTGCAATT GTGTTCCAG                                         569

(2) INFORMATION FOR SEQ ID NO: 145:

(i) SEQUENCE CHARACTERISTICS:
        (A) LENGTH: 200 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 145:
```

```
GTGAGTGGTG GGCAGCTTCT GTGGTTTCCC TCTGGAGACT CCATCCCACA GCAGGAGGGC      60

TGTTCTAGGC ATCAGCTTCT CAACAAGTTC TCTTGTAAAT CCAGCCACCT GGCTCCTTGC     120

AGAGTCTGTC AGTTTACAAC TTAACAATGT TCTCTTTATG GTTTCATGCA TAAACTGCCT     180

TTTTTTCTTT TCTGTCCCAG                                                 200
```

(2) INFORMATION FOR SEQ ID NO: 146:

(i) SEQUENCE CHARACTERISTICS:
        (A) LENGTH: 1770 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 146:

```
GTAAATAAAT CACAATGGTT TGACTTTTTC CACCATCAAC TCTTGTTTCT TAAGATTTTA      60

TTCTTGTAGA TACACAAGGG TAAACAAGAG TGACTTTTTG TGTGCCTTAA AGATAGGACA     120

TTTAGGGTAA TATTAATGCC AATTCTGTTT TTCCAACTAT TGGCATCCAC AATAGTATAC     180

AGCCCGTAGC CTCAATGTAA AATATTACTT TTCTGGTTAT CCTGCCTTTT TTTTTTTTTT     240

TTTTGTTTTG TTTTTTTGCC ATGGGGCTA ATTTATAACA AAGTGCACAC ACACACACAC     300

ACACACTTTT TTCCTTTGGA ACACAAGATT CTTAGTTGTC TCTCCCGTC CTTAAGACCC     360

TAGCCACTTA GTGTGTACCT AGCACTGACC TAGGCTTTCT CTACATTTTG TGAGAAGTAA     420

ATGACAGACT CCATGCCCAT AAGAAGCATA AGGACATTAT CGCCATTCAT GTACACATAT     480

GTAAAAACAA TCAATAACCA GCATTTACCA AAATTATGAC ACATTTTCAT ACTTGTTAAC     540

CCTTATCAAA ATTTATCTGT AGCTATGGCA ATTGTTATTT GTTTCAGAAT TGGTCTAGTT     600

ATAAAAACAC ACAGAAAATG AAGATGTGCA AAAGCACCCT ATAGCTGAGG AGTTCTGTAA     660

CACTGAAGCC TACAGCTAGT TACAGTATTC TGGTGTAGCT AACTTTGTCA TGAAGAGATA     720

CTCTTTTGTA TGTTCACTAG GCAGTCTAGT TTGTCTAGGA GACTTGAGAA GTTTTCCAGA     780

ACCAAATAGG AATGAAACAT TCACTTCTAT ATTTGAAAAG CAATATAGGC CTCTTCATTG     840

CAGACATTTT GTCCTGAAAG TCTATTTTAG TTTTAAACAT ATCTAAAAAA TTATTATTCC     900

ATGCAAACTC TTACTTATAT AAGCAAATTT AAAATACTCA CATTTAAACA ATTTAAAAAT     960

GTTGGGTAGA AATTTGTTTC CATTTCATAT TCTCCTTTAC CCTCTAAGTT TAAAAAATAT    1020

TACATGAGAA TATTTCCCTT AGAATGTTTT CATGGGGATA TTTTGTTGTA GGCCATGCCT    1080

TTAGTGGGTG ATTCTGAATC TATTTAATGG TTCCTGAAAA AGCCCACACA GTTATTAATT    1140

TTTAAGACTA ACTCTGACCA TTCCCAAGAA ACAAGTTATT TTTAATGTTT GTTGTCTATT    1200

TCAAGCATGG AAAAAACTTC TGAGAAGGAG GGTTTATAAG AAGCTGTGAC TCCTGGGGAT    1260

ATTTCAGTTT ATATAATATC TTCAAACTAA GAATGTGAGG CGAGGTCTCA AATGGTGCTG    1320

AATATTAATT CTGGACAATG TTCTTGGCTT TTAAAAACTG TCTGGACATC TGCTTCACAT    1380

ATGTTAAGAA ACTCTTTTTC TTCCCATCCT GGGTTTTCAG ATACCCAGCA GGGATTCAGG    1440

TGACATCCTT CCAGAACATC ATTCACCCCA AAGCCTGTAG TTTAAGATTT TTGTGAATCC    1500

CACCCCCTGC TACCTCCCTC CCCGTGCCCT GACTCTGTCT CAGAACAACA GGACCAAATA    1560

TATCCAGGGA GAGCTGCATC AAACAGCACC AGCGAAGCTN TCTGGCAGAA AGCCCACAGA    1620

GAAATTATCC AACTTTATTC ATTTCTTACT ACCAATTTTG AAGATCTGGT GACACATTTA    1680

GAAAAAAAGG CATTTGGAAT ACCTCTCTTT TCATTAGAAT AACTTTTATG TTTCTGACAC    1740
```

```
TTCTGGGTTG TTTTGTTTAT TCTCTTTTAG                                     1770

(2) INFORMATION FOR SEQ ID NO: 147:

(i) SEQUENCE CHARACTERISTICS:
        (A) LENGTH: 437 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 147:

GTAAGTCATC TTGCCCATGT GGAACCAAAG AACACAACCT TTTTCAGATG TATAATCTGT       60

ATCAAGCTCG AGGAATTTAT GTTTTACCAA TTTCTGAATA TCCAGTGAGA TAAGATGTAT      120

TATTCTCTTT TCAATAGTGA CGGTGAAGAT TCAAAAACTG TTATATAATA TTCCCTTGAC      180

CCTGCTCTAC CACAACAGTA GACCAAATAC TAGAANNNNC ATTCCAGTAT CTATGAATAT      240

AATAATTTGA TTTTCCCCCC TTAGATCTAT TAATAGATGA ACTTGATTTT TGCCTTGCTA      300

CATACTCACT ACAATCTAGT TTATGGCAAT TTCATGACCT TTTGGTTTCT GAATTTTAGA      360

TTTGCTGAAA GTTAAAGAT GCGGAAGTTT ATTTTTATAG ATATGTAGAA AAATAACATT       420

TCTTTAATGT AATGCAG                                                    437

(2) INFORMATION FOR SEQ ID NO: 148:

(i) SEQUENCE CHARACTERISTICS:
        (A) LENGTH: 841 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 148:

GTAAGTGTGT TGTATAGCTG AGAGGAGGAG GTAGCGAAAT TGGTAGCAAG TACACAGCCT       60

GAATTGAATA AAATTTTAAA ATAATTGTTA TTTGATCACT TAAGCATATT AATTATTCAG      120

AATGGCTAGC ATAGATTTTT CAAGACCAGC TTTAGTAAAG AATTAAATGA TCTGTAAATC      180

AAATCAGAAA ATAGGTATCA GGACTTGAAA TACTAATTTC CTTAAATAGA TGCTTCAAGA      240

AAAATAGTGT CAAGGTCCAG GCACAATGCA CTTGTTATAA AATTCTGAAT AAATTGGATC      300

CTATCTATTT CTAAAGCAGG TGATAGTTTC CTGTTTTTTT TTAATCTAAA ATGCCAGAGC      360

AGTAGGAAGA TTAGCCTGTT TTTAATCTCT TGCACAAGGA GTAACTGAAA TTTTATTTTT      420

AAAGCTCCCC TTTCAAACAC CCAGANNNNG AACTATTTAA CATTTTTTCA TATGAAGTCT      480

TTAAAATCCA GGGGTGTTTG ATCCTTAGTT CATCTCCATT GGGCCTCATC ACATTTCAGC      540

TCTCAATAGG CACCTGTGGC TGGAGGCTAC CATGGTGCAC GGTGCAGCTC TACTGATGGA      600

AATGGGGGTT AGAGACACTG AGGTCTCTTT CTGCTTTTAA TTTCCATGAA AACCCAAGTC      660

CAAGGAAGGG ATCTTATTAT CATCATCATC ATCATCATCA CCAATCATCA CCAGTCATCA      720

TCCATCGTTT CCAAAAGCGT TTGTTAAACC CCTTATCTGA GCGCTGCTGA GCCATGCCCT      780

CTGCCAGTTT GCATCAATGA GGATTCTCCT GTTCACATGT GCAATCTTCT GTGTGTTTCA      840

G                                                                     841

(2) INFORMATION FOR SEQ ID NO: 149:

(i) SEQUENCE CHARACTERISTICS:
        (A) LENGTH: 378 base pairs
```

(B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 149:

```
TGAAAGGCTT ACTGCTGCAT GGCTGTCTGC ATGAACCACG CCTGGTGAAG GAGCCTGGGT      60

GAGAAACACC ATCCAAAGCT GGGGCAAAGA TGATTACCTT CAGCATGATT ACAATGTATT     120

ACCTTCAGTA TGATTACAGA AGTCCTACTT GACAATCACA TATAGAAGAA CGGTGCTATT     180

CAGTAAGTTC TCTTTCCTTT CCCTTGGAGG GAAGACAGCA GAGTCATCAG TTAAAAAAAA     240

AAAAAAAGAA AACCAAACAC CTCCCTTGAA CAAATTTATA CTCCTGTTCC CAGGATCTTG     300

AGCTTTAGTG TGCTATACCT ATGTGTCTTA TCGTGGGCCA CTGTGCCAAT AAACAAAAAC     360

AACTGTTTGG TTTACCTC                                                   378
```

(2) INFORMATION FOR SEQ ID NO: 150:

(i) SEQUENCE CHARACTERISTICS:
        (A) LENGTH: 1114 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 150:

```
ATATATATAT ATATATGGAC TATTAGTATC CCCATTTTAC AGATGAGGAA AATGAGACTT      60

CATAGAGTTN GGGGTGCCTG TGGTCATATC TATAATTGTG AAAAAGTCAG ATTCCAAAGC     120

ATTTTACCAA TATTGCCTAA GTGAGTGGGA GGGAAGGGAA GGCTCTCTGG AGTCGGGCTA     180

TGCTGGACAG CGGGGTTCGG AAACTCTGGT GAATAAAGTG GTAGTTGTTT CTATGAACAT     240

GGAGTGAGAA GGCCCAATCC TAAACACACC AGTGCTTAAG GCAGCTGCAG AGAATTAAAG     300

GCAATAGAAA AAGGGGAGCT GGATGGCAGG AGCTTGGATG GGGAAGACTT CAAGGGCAGG     360

TGAAGATGCC AACAGCTTCC TGCCTGGAGG ACCGAAGAAG GGTTGGGCTT CACTGCAGAC     420

CTCCAGGAGA CAGATTTGCT TCTTGGGACA GAGTAGGGAG GTGAAAGCGA GGTGAGGAAG     480

TTCGGGGTGG GGGAGGTGCA CACAGTTCCA CTAAAGAGTT GGAAGAGGCC GATGGAGTAT     540

TCATGAGACG GCTGATCCAG GAAGGACTGT GGCATATTAA TATGGAAAAG GCCTGTTTGT     600

TTGTGCTTGG AGAGGAAGGA GCCAGAGGAG AGGGGAGCAA GGTGGGCGGG AGCTGGGGAG     660

AGCCTGCAGC AAGATCTGCA GAGCCCGAGG TGCTCTCGGC ATGGGCCCTG GAGAGGACGT     720

AGGGTAAGTG ATGGGCACA GGCNGTGCGT CAGGGGGAAG GTGCTGGGGC CTGAAGGTCC     780

CGAGGGGAAC NTCAGACGGC CTTATGCCTT CTCACAAAGA AACTGGACCA TCATTTCCGA     840

CCCGCACCCC GGTCGCCCCT CGAGGACAGA GGGTGGGCGC AGGAGGCTGG ACCGAGCGGG     900

GCGGAGCTGG ATGCCTGGCG CCGGCATCCC TCCCGGCAAC CCCCCCGGTC CTCTCAGGTG     960

ACAGTCACGC CCGGCCCCCG CCCCGCCCCC CGCATATTCA AGGAGCCCCA GCCCACCCTG    1020

CCCGCGAACA GCCAGCGCTG GAGGAGCGCC GGGAGACTCT GCCGTCGGTG CGTGCGCGGA    1080

CACGCACCCG TCCCCCTTGG TCTCGCCGCC AGCC                                1114
```

(2) INFORMATION FOR SEQ ID NO: 151:

(i) SEQUENCE CHARACTERISTICS:
        (A) LENGTH: 1445 base pairs
        (B) TYPE: nucleic acid (C) STRANDEDNESS: double
        (D) TOPOLOGY: linear (ii) MOLECULE TYPE: DNA (genomic)

(xi) SEQUENCE DESCRIPTION: SEQ ID NO: 151:

| | | | | | |
|---|---|---|---|---|---|
| GTAAGTTTCG | CAGCCCCTCC | GCTGCCAGGG | TCCAGGGTGC | GGGGTCTGGA | GTCCGGGATG | 60 |
| GAGGAGCTCT | GCCTGTGTCC | CGCGCCTACT | GACACCCCTA | GCCCGAGAGG | CCACCTGAGG | 120 |
| ACAGCGCCGC | GCGAGGTCCC | CTCGGTGGGT | GCATACATGG | TGCCCATCGC | GGCACGTGAA | 180 |
| TGGAGGTGGC | TGAGCGGAGA | GTCAAACGGG | ACCCGTCCCC | AGACGCGCGG | CCCGGCCCGG | 240 |
| GACAGGCAGC | GTGGGGCAGG | AGCTGGCGCC | CGGTCCTGGC | AGCCCGGGGA | GCCCAGGTGG | 300 |
| CGGGCATACA | ATGGTGCTCA | TTCACCCGAT | GCGCAGCATC | CGCCCCCGCC | GCTTCCCAGG | 360 |
| GGGCGCCGGC | TCCAACCAGA | CGCCGCTGTC | GCCCCGAGGC | GGCTTNTCGG | CCCTGCCCGC | 420 |
| CTACCCACGT | CTCCCTTCCG | AGGGCCGCCG | GGGCTGCGG | GCGCGCGGGT | AGGGCAGAGA | 480 |
| CTGGGCCCGG | TCGGGTGCTG | GGTGTGGTTT | CGAGCTCGCA | TGCGGGGCGC | CAGCCTGGCA | 540 |
| CTTCGCGGCC | TGGGGAGGTC | GTGGGCACCG | GGACCCCTGC | ATGGGTCCGA | GCTGGCTTCT | 600 |
| TAAAAGGGCC | GCCTTTTAAG | ATCTCTGATC | TGTTCAGAGA | TGGGCAGCAG | GATGGAGACT | 660 |
| CTCCAGCTGT | GAGCTCGCCT | CATCTTGATA | TGACTTGTGA | CCTCCCTGAA | ACCTCACACC | 720 |
| CACCCAGGGG | CATTGAATTG | CAGGCAAACG | GGATCCAGAG | AGAGGGTCTG | CTTTCTGGGA | 780 |
| GGTGCCGGCT | CCTCCTGCTC | CCCTGCAGCA | GTCAGGGCTT | AGCAGAGGGA | GGACCGGGCA | 840 |
| GCTGTGCTGC | CGAAGGGGCG | CTCCGAGTGG | GAAGATAGTA | CCCGCTTCAC | CTCCCTACAC | 900 |
| CTCCTTTCTC | TGCGCCTCCC | CCACTTTCCG | TCGGGTTTTC | CCGCACCATG | GGAGAGGAG | 960 |
| GAGGCGCTGT | CTCTGCCTGT | CGTTCACGTA | AGAACAACAA | CCCGAGCCAC | CGCTCACTGA | 1020 |
| GGGCCGGCAG | CCTGCTAGGC | ACAACCTTAC | ATTCCATCTG | TGATTTATTT | GAGCTGTCCA | 1080 |
| CGTCTCCATC | TATTCCCCAC | GCGACCGCGC | AAGGGCAAAC | TGGCACAGTG | GAAGGAGTCG | 1140 |
| GGCAGATCCA | GGGCGGACTC | CTGCGCCGCC | GCCCACTCTC | AGTGACCATG | GACCCTTCAC | 1200 |
| GTTCTGAGCC | AGTTTCTTCG | ACTGCAAACT | GGGGCCCGTA | ATAGGGCCCG | CTCCCGGTTC | 1260 |
| TGAGTATTCT | GTAAGATAAT | GAATGCATGT | AATGCACACA | GTGCCTGCTA | TACAGAAGAT | 1320 |
| TCTCAATACG | TGGGAGTTCG | CGGAAGAGCT | GCGCCCCTAG | GANNCTCCCA | GGGTGNNTGC | 1380 |
| AGCCCCGGGG | ACGCCCAGCT | TCCTGCACTG | TCTGAGGACT | GCCCCACCCC | GTGTGTGTTT | 1440 |
| TTCAG | | | | | | 1445 |

(2) INFORMATION FOR SEQ ID NO: 152:

(i) SEQUENCE CHARACTERISTICS:
        (A) LENGTH: 1195 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 152:

| | | | | | |
|---|---|---|---|---|---|
| GTAAGTCTCT | AACCTGAGAC | CAGGGCGGGA | GGGAGGCGGC | AGACAAAGGA | GAACTTTGTG | 60 |
| AGCGCTGTGG | TGGGGGTGGG | GACTTCGGGG | TGCCCGGAGA | TGTAGTGCCC | CTCGTCGCCA | 120 |
| ATAGNNCCCG | CCCNNACCAC | AAGGACGCCG | TTTGTTCTGC | AAAAACCTCA | AACCAGCCCT | 180 |
| GACATNCGGA | GCCCGTTATA | GCCGCCGACA | GACAAGGAGC | TGCTGTTCAG | TCCGCCGGCC | 240 |
| GCAGCTCACA | GCGANGGNNN | NTCCCCCTCC | TCTCCTTTCC | CCTCCTTGTG | GGGTAGGAGG | 300 |

```
CGACTCAACC CCTCACCCTG CCTCTGGCAC ATCTGGACGC TTCTTCAGGT TCGCTTGGGA      360

GCCTTGGCCA GACCACCGAC CAGCTTGGGC CAGACTCCTG TCTCTTCCCT TCGGTTTTCT      420

CTCCCCGATT TAGAATCAGC TGGGCTTGTT CCTGCAGGGT GAGGGTTAAA TACCTCATTC      480

TGAAAGCTCC CGCAGGAGGG CCGCTTGATG TTTACCAGTC TGGACAGACT TCTATTCAAC      540

CTGTGCCCCC ACCCCCCAAA CACAGGATGC TGGCCCCCGG CCAGGCCCTG GCTGCTGAGG      600

GCTCTGAAAT GCCTGGAGGC CTCTCTGGGG CTGAATCGCA CTCTACCGGC CCTGCCTGCC      660

CACCACCAAG GGTCCTTTGG CACTGGAAGG AGGTCCTTCC CTCCTTGGGA ACACTGAATT      720

TCCCCCTTGC AGTCCCCCTT GGTCCTTGCC ACTGGCTCAG CTTCCCGTTC TCCTGCCCTG      780

CAGTCTGGAA TAGAGCTGCT GCCCAACTCG CTCATCCCCC TTCACGTTTC TCTAAAAGCC      840

CCAACCTTCC TCCCACACGT GCCCAAATCC AAGAGGCATN AGCTTGGAGC CCCCAGCCCT      900

GGTAGTGGGT CTCACAGCTG GCACCTCATG ACATCAGCAT GTCTGTACCT TCTTGCATGT      960

TGCTGTCACC CTCTCCAGCC CGGCCAGGGT TATTCTCATG CTCCTGTGAT TTGTTTTTGG     1020

TTTTTATTTT TGAGGAAAAG GGGGCTCTTT TCCCAAAGAT TGCAAGGCTT AGGGGACCTG     1080

GACAGAAGAG AGGAGAGTGA GGAGAGCCTT TGGGAGCGGC CTGCCAGGGC CTGTGTGTGC     1140

CCACTTGGGG TAGTGTGAGC CGTAGTGTGC TGTCTCACCA ACTTGTATCT TGCAG         1195

(2) INFORMATION FOR SEQ ID NO: 153:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 153:

GTGAGTGCTT TATCCTCTTT GGCCTTTGAC CCTTCCTGCT CTTGCCCTCC TCTGGCTCAT       60

GTTTGTTCCA TCTCTGTTTT CAAG                                             84

(2) INFORMATION FOR SEQ ID NO: 154:

(i) SEQUENCE CHARACTERISTICS:
        (A) LENGTH: 1419 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 154:

GTGAGTAGCT GAGTGTCGGG TGGGGCAGGG TAGGCTCTGC CAATTGACCT CCAGGGCCTG       60

GCTCTGGCAT CTTCACTGAT CTGTTCAGAG ATGGGCAGCA GGATGGAGAT TCTCCAGCTG      120

TGAGCCCCCC TCACCTTGAT ATGACTTGTG ACCTTCCTGG AACCTCACTC TCACCCAGGG      180

TCATTGATTT GCAGGCAACC GGGGTCCAGA GAGAGGGTC GCTTTCTGGG AGGTGCAGGT      240

TCCTCCTGCT ACCCCTCAGC AGTCAGGACT TAGTCTCACA TTTCTGGCCT CCAAGGATCA      300

GGCTGAATAT GTTGGGTGGG GCTGTCCTTG TGTGCCCTGT CCTTTCCTCC GCTCTTCCCC      360

TGACCCCTAC CCACAGCCCC AGGCATGACT CAGGAGAGAA ACATCATTTA GCTGATACCA      420

CAGAGCTCCC AGGGGACCC CCAAGGTCAC AGGCTCTTGA ACACAGCCAG CCCCAGGGGC      480

ATGAGGACAA CATCTGATGG GGGTTACACT GGGTCAGTCA CTGAAAGATG GGAGAAAGGA      540
```

```
GAAACCCCCA TGACTTGCCT CTGCCCTGCT GGCTCATGAG GTGTGACCAG GGCTGGGACA      600

GTCACCAGGA CCCCTTCAAA CTCATCCACA CCCTGCAACG ATTACAAGGC ATATTGCCTT      660

CTATGTTGCA TCAGTTCTCA CATCCACCCA GAGAGGCACC CAGATGAGAA ACTAAGGCTC      720

AGAAAAAGTT GCCAATGGCC TGGCGTGGTG GCTTATGCCT GTAATCCCAG CACTTTGGGA      780

GGCCGAGGTG GGCAGATTAC TTGAGGTCAG GAGCTCAAGA CCAGCCTGGC CAACATGGCG      840

AAACCCCATC TCTACTAAAA ATACAAAAAT TACCCAAGCG TGGTGGCGCA TGCCCCTGGT      900

CCTAGCTACT TGGGAGGCTG GGCACAAGA ATCATTTGAA CCCAGGAAGC GGGGGTTGCA       960

GTGAGCTGAG ACTGTGCCAC TGCACTCCAG CCTGAGCAAC AGAGTGAGAC TGTGTCTCAA     1020

TTGAAAAAAA AAGAAAGAA AAAGAAAGA GAAAGGAAAG AAAAGAAAAG AAAATGAAAA       1080

AGTTGTCAAG GTAGGACATC AAGCAAATGA CCAATCTTGA CCCATGGCTA GGTCTTCTAG    1140

ACTCCTGAAC CCGGAGGCAT GAAGCCTGGG TCTGGCATAA AGCCAAATCT TTGGGCTTTG    1200

GTTTCTCATC TTTCAAAAGA AGGGAATTGT TCTGCCTGCC TCCTAGGGTT ACTATGGGAA    1260

CTGGGGAAAA GGAAAGAAAG GTGTGGAGGT TCCTAGGCCT TCATGAGGTG TGGCAAAAAG    1320

GAGCCTCGGC CCACCCAGGA GGGACCCTTG AACCTGCCCT GCTCTGTGGG TCAGGGAGCA    1380

GGTTGGCCCT CATTGATCTA CATTTTCATT CTTCCCCAG                            1419

(2) INFORMATION FOR SEQ ID NO: 155:

(i) SEQUENCE CHARACTERISTICS:
        (A) LENGTH: 121 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 155:

GTAAGGGGCC TGCTGGGGCC TCAGCGTGGG CAATCTAGGG CCAGCGTTTG GGAGTGGCTG       60

TAGAGAGGAA GTAGGAGCCG GGGAAACCCC AGCCTCTGAG CCTTTCTCGT TGCTTCTGCA     120

G                                                                    121

(2) INFORMATION FOR SEQ ID NO: 156:

(i) SEQUENCE CHARACTERISTICS:
        (A) LENGTH: 93 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 156:

GTGAGTACAA CCTGCAAGGC TTCGAGGGAC TCTTGGGGGA GAGGGACCT GCAGAGGGAG       60

CCATGAAGCC AATTTTCTTT CTTTCTGTTC CAG                                  93

(2) INFORMATION FOR SEQ ID NO: 157:

(i) SEQUENCE CHARACTERISTICS:
        (A) LENGTH: 343 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 157:
```

```
GTAAGTCCTC AGGGATGGGG CAGGATCCCC AGAACTCCCA GGGAAGGAGG GGACAACAGA       60

AAGGCTTCGA GGGNATGGCC ACCATGGGAA GGAGCCAGCT TGCTGTGATA GTGTCAGGAA      120

TAAGTGGACC TGCCAGAGAC CCAGGGCCAG CCCACTCTGG GCCTGTCCAC TGGCTCTGNA      180

ATTCTCTGGT CCTTAAAGCC TCAGTCTGTC AGTCTCTCTG GGGTTGGCAA AAAAAAAAA      240

AAAGTAAAAG TGGAGAAACG GGCTTTGGGT GCCTGTCTCT ACCTTTGTGC CCAGGGTATC      300

TGACCCTCTG AGGCATCCTG ACCATCAACT CTCTGCTCCC CAG                       343
```

(2) INFORMATION FOR SEQ ID NO: 158:

(i) SEQUENCE CHARACTERISTICS:
        (A) LENGTH: 341 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 158:

```
GTGAGCCTCA GCCACCCTCT GTTCACTGCC TCCTGCCTTC TATCTCCAAG CTGGCAAGCT       60

GGGTGGTCTT TCTGGAAGTT CCTGGGCCTG CTCCTGGCCA CTGGGAAACT CCTCCAGGTC      120

TGGGGCAGAA ACCCCTCCTA TGAGCCCACC CGGCACTAGG TCTTTTAGGG ACNGCTGGCC      180

CCATCCCCTG TCAATCAGGC CTTCATCTCC CAAGATGGTG GATCTCACAA AGTGACCGGG      240

AAGACAGGGT GGAGAGGGCA GAGGCAGGAC CTGGAGGAGG GCACTAGGGT AAGCTGGTAA      300

GGGCTGGTCA GGGGTATGAT TTGGGCTTCT TTTGCTTCCA G                         341
```

(2) INFORMATION FOR SEQ ID NO: 159:

(i) SEQUENCE CHARACTERISTICS:
        (A) LENGTH: 114 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 159:

```
GTAAGTGTCC CCAGACCCCC GACATGGCAA AGTGCAGGGG AAGGAGAAGG GTCTTTGAGC       60

AAGCCTGCGG CGGGAAAGGG TCAGGCCAAG CTCCATCTTC ATGTCTCCTC TCAG           114
```

(2) INFORMATION FOR SEQ ID NO: 160:

(i) SEQUENCE CHARACTERISTICS:
        (A) LENGTH: 213 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 160:

```
GTGAGAGACG AGGTCTGGGG CGGGGCTAAC ACAGGGGGGC GGGGCCACAG AGATGGGGAG       60

GCGGGGCCAC GGAGATGGGG GTGTCTGGAG AGATGGGGAG GGGCTGCAGT GCAGGGGTTC      120

CACCAGGTGA GGCGGAGGAG AGCACGGGGC TTGGAGAGAT GGGGGCGCAC TGCCCAGCTG      180

ATCACAGGAC CCTGTGGGAT TTTCTGTTTC CAG                                  213
```

(2) INFORMATION FOR SEQ ID NO: 161:

(i) SEQUENCE CHARACTERISTICS:

(A) LENGTH: 83 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 161:

GTGAGAGCTC CTGGCCTGAA TCTTGGGAGG GTGGTGCAGG TGACAGGAGG GGACCTCGTA      60

TTGAGCTCTC TCCTTCCCTT CAG      83

(2) INFORMATION FOR SEQ ID NO: 162:

(i) SEQUENCE CHARACTERISTICS:
            (A) LENGTH: 325 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 162:

GTGAGTGCAA GGGCTGAGGG CTGTGGGTCA GGGATACGTG GAGATGGTCC TACAGGGCTC      60

TGTCCCCTTC TTCGTCCCTT CCCCTTCCCC TGTGGGTTCT GGGGACAGAG CCTTGAGCCG     120

GNGGCTGGAG GCCTGTGCTC CAGGTCGGCA TGTCTCTGGT CATGTCTCCT TGCTTGGCTT     180

TTCTCTATCT GTAACACAGG ACTGTAGGGT TCGTAGTAGT CCCTCCCGTC TGCTTGTGCT     240

GGGGAAAAGA GGTGGTATCT TTGCTTGTCT GTATATGTGT CTTTCCATCT GCCTGCCTGT     300

CTGACAGCTC ATCCCTGCCC TTTAG      325

(2) INFORMATION FOR SEQ ID NO: 163:

(i) SEQUENCE CHARACTERISTICS:
            (A) LENGTH: 396 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 163:

GTAAGGAACA CCTTGCCTCA GTGGCCCTCT TCTCCCTCAC CCCAGGAGCC CTTCATGGAG      60

TCATTCCCCT GCTCAGGCCT CTAGCTTGTA AAAGAGACAC CTGTGTCTAG CTGGGAGCAT     120

CTCTGGATGG GGAGATGGAG GCTGAAATTG TCAGGAATGA GGGACAGGAA CCAAAGCTGT     180

CAGCAAGAAG CCCAGGCTGA GGTCCAGGTC TGCCACTGTC CCTTTGAGTA ATGCAGTGAG     240

TCCCTCCTCA TCTCTGAACC TCCATGTCCC ATCCATGAGA CAGAGACTCT GCTGCCTACC     300

TCAAAAGGGC ACTGTAAGAT TGAAGGTGGG CATCAGACAA GGTATCATGA AGTGGGCCTT     360

GCAATTGCCA TTGCTGTCAT TTTTCTTTCT CAACAG      396

(2) INFORMATION FOR SEQ ID NO: 164:

(i) SEQUENCE CHARACTERISTICS:
            (A) LENGTH: 99 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 164:

GTAAGTGAAT CTTGGGGTGT TCTACAAGAG CTTCCAGGAG CTGCCTTCTG GCCCCTGGAG      60

TTCAGCCAGG ACTGACCTGC AACCCTTTCC TCTCCCCAG                                   99

(2) INFORMATION FOR SEQ ID NO: 165:

(i) SEQUENCE CHARACTERISTICS:
        (A) LENGTH: 119 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 165:

GTAAGCCTCT TTTTGCTCCC CTACCCCTGA GGCTGGAGCT CCTACAGCTA CAGCCACAGA           60

GTGGGCATGG CTCCCCCTGA GCCTGTGTGA CCTGGATTCC TGCTTGTCTT TCTTGCCAG           119

(2) INFORMATION FOR SEQ ID NO: 166:

(i) SEQUENCE CHARACTERISTICS:
        (A) LENGTH: 1690 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 166:

GTGAGTCCTC AGGCACCCAT TGTTCAGTCA GGNCCCCTGG GGAGTACTGG GCAGGACAAG           60

GCACCCCCTA AGGCTGTGTG TGTGAGAGTG CATGAGTGTG TGCGTGAGTG TGAATGTGTA          120

GTGTGTGTGA GTGTGTAGTG TGTGTGTGTG TAGACTGTGT GTATATGAGT GTATGTGTAC          180

AGTGTGTATG TGTGAGGCTG TCTGTGAGTG TGTGTAGTAT GTGTATGTGA GTGTGTGAGG          240

ATATCTCTGA GTGTGTGTGT GTGACTGTGA GTGTATGTAT GTGTGTGTGA GTGAGTGTGT          300

GTGTGTCTGC CCAAGTGGGT GACCTGCTGG GGAGGACCAT CTGTGCCAAG AGCCCAGTCA          360

GCCCAAATTC AGACTTTAGG CGANNNTGGG ATCCAGTCCC ATGGTCACTG GGCCAGACA           420

ATGAGATTCC AGCAAATCAG CCATGGGCT AATGGGATTT GGTCTCGATC CCAGTTCTCT          480

TAACTCTTTT TTTTTTTTTT TCCCAATTAA TAGACCTGTT GGGGGAAGCG GTTTTAAGTT          540

TACAGAAAAA TGGAGCAGAA AACACAGTTA ACTGTTATTA TTATTTAGTT TTTTAAATTA          600

TTTTCTTTTC TTTTTAAAAA TTAAAAAATT CTTATACTTT TATTTTTCTA TTAGACAGCA          660

GAGATCATCT AGTTGTTTTG TTTTGTTTTG TTTTTGAGAT GGAGTTTTAT TCTTGTTGCC          720

CAGGCTGGAG TGCATGGTGC GATCTCGGCT CACTGCAACC TCCGCCTCCC TGGTTCAAGA          780

GATTCTCTTG CCTCAGCCAC CCAAGTGGCT GGGATTACAG GCATGCGCCA CCATGCTCAG          840

CTAATTTTGT ATTTTTAGTA GAGACAGGGT TTCACCATGT TAGGCTGGTC TCGAACTCCT          900

GACNTCAGGT GANCCACCTG CCTCGGCCTC CCAAAGTGCT GGGATTACAG GTGTGAGCCA          960

ACACGCCCAG CAATATCTAG TTTTTTAATG CAATTTTTTA ACTATACAGA AAACCAGTGA         1020

GAGTGATATA AAGAATCCCC ATGTACCTAT CACAGGTTCC AANTCAGTTA TTAACATTTT         1080

GTCAGTCTTG TGTCCTCTAT CCCCCAGACC CCTCCTTCCT TTGATTTTGT TATTGCTTTG         1140

CTCTGATGTT TTCAAGTAAA TCCTTAACAT CCTATCATCT CAGCCCTAGA TACTTTTGTA         1200

CATATCTCTA AACAATAAGC ACTCATTCTC ACATAATCAC ATTATCACAA CTGACAAAAT         1260

AAACAAGTAC TCCCTAACAT CATCTAATGG CCAGTCTCTG TTCAGTTTTT CCCAATTATC         1320

TCAAAAATGT CTTTTCCTGG TTCTTGTTCA AATCAAGACT CACACAGCAT CCACACACTG         1380

```
CATTCGGTTG TTGTGTTCCT TTGGCTGAGT GGATTGTGGG GCCTTGGCCA AGGTCTCAGT    1440

GGATTCTGGC TCCCACCCCT GCTCTGGCTC AGCCCAGCCT GGCCTCCTGG CACTGACTTC    1500

TCCTCCCTCC TGCTGGTGCC AGGGCAGGAA GGGTACTCCC AAGGCTCTCT CCTCCGGCCC    1560

CTGCATGGTG TGGCCTGTGC CAGAGGAACT CTGGGACCTA GAGGCCACTG TTCTCAGTGG    1620

TTCCCCTCTC TGCACAGCCA GACAGGGGCC CAACATCCTG AGGGTGACCT GATCTCTCTC    1680

CGCTTTGCAG                                                          1690

(2) INFORMATION FOR SEQ ID NO: 167:

(i) SEQUENCE CHARACTERISTICS:
         (A) LENGTH: 435 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 167:

GTAGGTGCCA GAGGCCTAGG CCCACCAGGA CAGAGGCCAG GGCCCAGCTG CTTTGTCCAA      60

ACCCCCAGAA GAGAAGCCTG GGATGCTAGT CTGAACTCTG CAACTGGTGG GCTGGCTCCA     120

TAACCTCAGG AAATGCCTCC CTTTCTGTGC CTCAGTTTCT TCACCTGTAA ACAGGGGTGA     180

TGACATACGG GAGGTCATGG GGAGCTTGCA GCAGTCGGGG ACACCACCCT CCACACTAGG     240

GAAGGACTGT GTTCCGTGAC CCTCATCCCC TTCCCACTTC AACTCCCCTC CCCCAGTTGG     300

CCAGTGGGGC TTCCTGGGAT GACCAGAGCC ACTCCCTCCC TGCACACTGC AGCTGTCTCA     360

GAGGAACAGG GGTGGGTGGC CAGACCCCAG ACATCTCCGC ATTATCACTC TCCCTTGAAC     420

TTTCCTCCTG GGTAG                                                    435

(2) INFORMATION FOR SEQ ID NO: 168:

(i) SEQUENCE CHARACTERISTICS:
         (A) LENGTH: 203 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 168:

GTAGGAGTGG GGCTGCTGAT GGGACTGGGG CAGGGGCAGG ACCTTGAGTC CTGGATTCTA      60

GACACCAAGA GCCTGGGGCC CTCAGGTCAT GGACATGCCC TTTCTTGCCT CTGGATCTCA     120

GTTTCCCTAC CTGCATCTGG GTAGAAGCCA TGGCCCTCTG GCTGGAGCTT TAATTTGTAT     180

CTTTGGTTAT CTGTCTATCC CAG                                           203

(2) INFORMATION FOR SEQ ID NO: 169:

(i) SEQUENCE CHARACTERISTICS:
         (A) LENGTH: 1260 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 169:

GTAAGTGTCA GGTGGAGCCA CAGGGGCTGG CCAGGGGCTA GTGGCTGATG AGGTTAGAAT      60

CCACACACAC CCGGGGCTCT TGCTCAATCA CCACCTCTTG CCTTGTTACC AACTCTGTGG     120
```

```
CCCCTGGNCT GGCGAAGGCT TCATTACTTG GACAATTACT CTAGCCTTCT CTTTGGCCAT      180

TCCAGTCCTC CATGTTGGCT AAATGGGATC TGACCATTTC TGCACTATAG CACCTTCCAT      240

GGCTCCCCAC CGCCTCCAGG AAAAAGTCAT TCAGTCCAGT CCTTCAATAA GTAGTTATTG      300

AGGTCGGGTG CAGTGGCTCA TGCCTATAAT CCCAGCACTT CAGGAGGCTC AGCTGAGTGG      360

ATCACTTGAG GTCAGGAGTT CAAAACCAGC CTGGCCAATG TGGTGACACC CCGTCTCTAC      420

TAAAAATACA AAAATTAGCT GGGCGTGGCG GCTCATGCCT GTAATCTCAG CTACTCAGGA      480

GGCTGAGGCA GGAGAATTGC TTGAGCCCAG GAGGCGAGGT TGCACTGAGC CAAGATTACA      540

CCACTGCACT CCAGCCTGGG TAACAGAGCA AGACTCCATC TCAAAAAAAA AAAAAAAAAA      600

AATAGTTATT GAGTATCTGA GGTATACTAA GTGGCAGGTA AACAATTATA AATAGGACAG      660

ATGCAATCTT TGTCTTTCAT GGCTCATCTT ACCATTCAAT GACCACCATA ATCTGACCCC      720

AACCTGCCCC TCCTGCCATA TCAGCAATGG CCCCTCTCTG TCCTTTCCCT TCTCAACAGG      780

CCTTGGCTTT TCTGCCTCCA CACCTTTAGG CCTTTGCTGG TCCCTCTGTT TGAAATGCCC      840

TTTCTGGTCT CTTTGTGCCT TCTTATCGTT CAGGGCCATC TCCATTCCAT ACCTCCTGGA      900

GTCCAGTCCA TGGGAGCCTG CCCTCCCTCC CTGTGGGGGT ACTGAGTGGC CAAACCTGTT      960

TCTGTGCACA CATGCAGACT TGTGTTCCTG CGTGCACTCA CATGGGCTCA GGCACCTGAG     1020

AGCACATATC CATCTCTTCC ACGTAGACCC CAGGTCCTGG AANACAGGCC ATTCTCTGTG     1080

CCCCACTCCT CTGNCACCAC TGTGGGAATG TACAGTNAAG TTCATCATGC CGTGGCTGGA     1140

CCTTCTGTTG TTCAGCTCCC ACAGGTGGGG GAAATCTGGA TTGGGGATGG GAAGCAAAGC     1200

AGCAGGTGCA TGGGGCTCCC TCATGCCAGG GCAGAAACTG ACTTCAACTT CTTTCTGCAG     1260

(2) INFORMATION FOR SEQ ID NO: 170:

(i) SEQUENCE CHARACTERISTICS:
         (A) LENGTH: 373 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 170:

GTGAGGCGAT CCCAAGCTGG GGACAGAATT GAGCAAGGAA GTCTGGGGCC AGGAAGACAG       60

CAAGGCCCAG GCCTCAGCCA AGTCTCAGAG GCTCAGCCAG AACATAAGCC CCTTGGGCCT      120

AACCACCTCC CTCCTGCCAC CTCCCACCCA TCATGCACTC CTCAGCCTGC CTCAGTGCAG      180

ATAGGATGGC ATGGCTTAAA ATCCAGAGGA GAAACAAACA GGAAAATCAG GAGCCAAGAG      240

GATTGAACCA AGAATACCCT CTTCCCCGTC CCAGCTCATC TGGTTCCAGG CTCTGTTTAG      300

GCTTCGTTGG GTTTCCCTGA GGCCAAGGGC TGACTGGGCC ACCCAGACTG ACCTGAGAAC      360

TGTTTTCCTG CAG                                                       373

(2) INFORMATION FOR SEQ ID NO: 171:

(i) SEQUENCE CHARACTERISTICS:
         (A) LENGTH: 863 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 171:

GTAAATGCCC CCTGCACTGA CACAAGGGTT CCTGCTTTAG GGTGAGGCCA TGGGGTGGAG       60
```

```
CCTAACCTAG GGAGAGCTCC GAGTTAGTCT GGCTCTGCCT GACCCAATGA TTCAGGGAAG    120

CTCTTTCTCC TCCCTGGGCC TGTTTCCCTA TGTACATTGC AGGGAGGGTG GGGACTGGCT    180

CTGTTCTGGA GTGTGACTTT CCTAGATGGC CAAGTTGATG GGCTGGGAAT CCAACAGGCA    240

GAGTTGTTCG TTCATTTATT CATTGCATAA ACATTCACTA AACACTTGCA ACTATGAGTC    300

TCCTCTTCAT ATGGAGGGTA TAGTTTAATG GAAGAAATAG ACATGAAATA AATGATCACG    360

CCGGGGGCNN NNNCACGCCT GTAATCCCAG CATTTTGGGA GGCTGAGGCG GGTGGATCAC    420

GAGGTCAGGA GATCCAGACC GCGGTGAAAC CCCGTCTCTA CTAAAAATAC AAAAAATTAG    480

CCTGGGGCGG TGGCAGGCAC CTGTAGTCCC AGCTACTCTG GAGGCTGAGG CAGGAGAATG    540

GCATGAACCC GGGAGGCGGA GCTTGCAGTG AGCGGAGATC GCGCCACTGC ATTCCAGCCT    600

GGGTGACAGA GCAAGACTCC CTCTCAAAAA AAAAAAAAAA AAAAAAAAAG AAAGAAAGAA    660

ATGATCACAT GATAAGTAAT TCAAATTGTG TTGGGTCCTT TGAAAGAAAA CTACAGGGAC    720

CCAAAACCAT GGAACAGGTG GTCTGGGAAA CCTTCCCTGA TGAAGCAAAT TAGCTGAGAC    780

CCAGGGTAGG GAGGGGCTGG CCAGGTGTGG AAGGGTGGGT TCCACCAGGT CAAACGCTTA    840

GCCCCAATTT CTCCTTCCTC CAG                                          863
```

(2) INFORMATION FOR SEQ ID NO: 172:

(i) SEQUENCE CHARACTERISTICS:
        (A) LENGTH: 264 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 172:

```
GTAAGTGCCT GGCACAATGG CCCCTCCCCG GGGGCCTCTG CGGCAGCTGG CACTGCTGGA     60

TACAGCATCT GCTCCGTGCA GCCCGTGAGA TGCCTCCCCA GGCAGGGCCT AGGTTTGCTT    120

TGCTGGTCTG CCAAGTGGAG AAAGGACCCC CTGCCAGTGA CAGCAGGAAT GGAGGGCACC    180

CTGACCATGC GGTGCCAGGC CTCGGTGCGG GAGGCTACCC CTGCTGAGAG CTGCTGAGGT    240

TGTGACCTTC TCTTTCCATT TCAG                                          264
```

(2) INFORMATION FOR SEQ ID NO: 173:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 173:

```
GTGAGTGCAG GCCAGCTAAG GTGGGCAGGG CGTCATATCC AGGCCCCTCA TTCCATTTAT     60

TCCTTTGGTT TCTTTTCTCC TCAG                                           84
```

(2) INFORMATION FOR SEQ ID NO: 174:

(i) SEQUENCE CHARACTERISTICS:
        (A) LENGTH: 220 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 174:

```
GTGCCAGATG GGGCTGGGAA ACNCCTGGGA AAGGGGCCCT ATAACAGGGG GAGTGGGGTC     60

GGCAGGACTC AGANCCTTCC GGAGCCTCCA AACCTGCGGN TCTCAGGGTT CTGGTCTGGT    120

CGGCGAGGCG GAGTTGGAAA GAGGGGTGTG GCCGAAAGTT AGGTGGGGGA CCCCGTGGAG    180

GGGGGAGCTC GCCAAACCCC TCACTGCCCG CTTTCTCCAG                          220
```

(2) INFORMATION FOR SEQ ID NO: 175:

(i) SEQUENCE CHARACTERISTICS:
        (A) LENGTH: 91 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 175:

```
GTGAGTTCCA GCACCCCTGT TCCCAGCGAC CCCCAACCCT GCTCTGCGTC CCCGCCGCCA     60

CCGCGCGTCT GACCCGTGGT TCTCTCTGCA G                                    91
```

(2) INFORMATION FOR SEQ ID NO: 176:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 176:

```
GTGAGCGCGC GCCTAGGGAA GGGCGGGGAG CGGCGGCTGG CCCGGGGTCC NNGGCTTCGT     60

GACCGCTGCT CCTTGTGCCT GCAG                                            84
```

(2) INFORMATION FOR SEQ ID NO: 177:

(i) SEQUENCE CHARACTERISTICS:
        (A) LENGTH: 130 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 177:

```
GTGAGTCCTC CCCTCCCGGC GTTCTCCGAC TTTCCTGGGC GGCCACTCCC TTCCTCGACC     60

CCCACCCCCC ACTCTCGCCC ACCGGGCGC CTTCTCACCC GGCTCTGCTC CCACCCCCAT    120

CCCCCCGCAG                                                           130
```

(2) INFORMATION FOR SEQ ID NO: 178:

(i) SEQUENCE CHARACTERISTICS:
        (A) LENGTH: 343 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 178:

```
GTGAGTCGGG CCCCGGGGTA GGAGGTGCTT CTTCTAGGTA GATCTGTTCT GGGGTGCGGC     60
```

-continued

```
TTACCCGCCA AAGGCTAGGG ATTCCCAGAG ACTCACCGAC TTCCCCGAGA CTGGTTCCAA      120

GCCCCAGAGC AGACAGGAAG GCTGTGAGTG CAGCCTGAGG GATTACCCCG CGACCTTCCC     180

AAGTAAGCCC TTGGCCCTGC CCAGGTACAA TCTGTTCCTC AGCTTGGGAA TTAATGACTC      240

AACACCAGAG TCTCCTCCAT GGCGGCCTCA CGCTCAGCCA GGTGGGATAG GAGCGGTGGG     300

CCCTTGTAGC CAGGGGCTTC TTCCTGAAAG CCTCTGCTTT CAG                       343
```

(2) INFORMATION FOR SEQ ID NO: 179:

(i) SEQUENCE CHARACTERISTICS:
        (A) LENGTH: 319 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 179:

```
GTGAGGGGCA GCAACCCCTC CTCACAGTCA GTTCGAGGGC ATCGCCGCCC CCTCACCCCC      60

TCCCGGAGCC TCCACGTGTT CACTTGTCTG AAAATCTGGA GTCCTGGGGG CTCCTTCCAG     120

TCCAGTCTCT GAAGGGTTTT GGGACCTTGA ATAAGTCACT CTGGGCCTTT GACTTCCGCA     180

AAACAGAGCC CACGGAAGGT GGTGCTTTTC TGTCTGCAAA CCTAGGGGCC AGGGCCCATC     240

GGAATGCTCT GCCTCCCCTA GTGTTACTGC TGACACCCAT CTCATAGACT TCCCTCTCCC     300

TCCTNCTCNC TCCCTCCAG                                                  319
```

(2) INFORMATION FOR SEQ ID NO: 180:

(i) SEQUENCE CHARACTERISTICS:
        (A) LENGTH: 731 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 180:

```
GTGAGTGCTC CTCTGCGGTG GGCATGGGGG CCAGGCAGTG AGGATTTGTC CAGGCCGGCC      60

CTTTCCCCAT TCCCTTCTCA GGATGACATA CAGACCCTTC CCCGGTTCCT CAGCCACATG     120

GTCCAGGAGA CACTCCTGGN CTCTTTCCTA GTAGCAAACG GATGGCAATG AATGTACTAT     180

GTTATCACTC GGGGTTTCTG GGGTTTGTTT TTGAATGTGC TTAGTGGTAC CCCATAAGCA     240

TCTTTCCATG TCAATAGAGA TNGGGCGGCA GACCAGCAGA GCAGTAAAGC AGGCAGGCTG     300

GAGCCACACA CGGGTGTGAA TCCAGACTCC CCTTTCTCAT CGTGGCTCTC AGACGAGTTA     360

CCTGCTAATT TCCCTGGGCC TTAGGTTTAC TATCTGTAAA ATGGGNCAC TGAAAGTACC      420

AACCTCATCA TGTGGCAGTG AGGACTATCC TTAGAGTAGT TTACATAGAG TTTGTCTTAG     480

TTCACTGAGA CACAGTAAAT GCTAGATATT GTTATGCTTG CTTTCCTGTA ATAAACTTTA     540

TTGGTTACAT AATCTTCCAT CCTTTGTCTG CACCTTCCTT TATTTAACAA GCCCTGCGTG     600

ACCATTTCCA ACTTTCCTCT ATTACAAACT AGCACAAAAC AGGAATAATT TCTTTGCGTG     660

AAACATAGCA AAAATAGAG GAAAAGCATT TTCCAATTCT GAAAAATGAA GATTTCCTTT      720

TTTGTCTACA G                                                          731
```

(2) INFORMATION FOR SEQ ID NO: 181:

(i) SEQUENCE CHARACTERISTICS:
        (A) LENGTH: 430 base pairs (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 181:

```
GTAAGCCATT GGCCCTGCCC AGCTGCAGTG TGTTCCTCAG CTTGGGAATT AATGACGTGT      60
GGACACTGCG GTCTCCTCCA TGGCGGCCTC ACGCTCAGCC AGCTCAGTCC TTGATACCCA     120
GCTTCTGCAC CCCTTTGGAG CACCCCGGAG TCTCTGGGTG GTTCCAGCTC TGGAAGCTGG     180
GCCTCTCAGG ACTTCCCAGG ATCCACCACC ATCACTTCAC AGAGGTGATG GAAGGGATGT     240
TTGCTCCCAA AGCTCACTGA TTGGGAGCTG GGGGTAGGGG ACAATCACAG AATCTCTGCC     300
TCTGGGGCAG AGTCCTTTCT CCTATGGTGT TTTGGCCTCA TTTTCTCCAT CTGAAAAGTT     360
TCCCCACCTT CAAAATTCTG GGCCTGAGAC AAGAGGTGCC CCTAATGTCT TGACTTTCTC     420
CTGTTCACAG                                                            430
```

(2) INFORMATION FOR SEQ ID NO: 182:

(i) SEQUENCE CHARACTERISTICS:
        (A) LENGTH: 515 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 182:

```
TGAGCATCAG GCCCAGACAG AGCCTGGAGG CATCCTGGCG GGAAGGACCA GGTCCCCTCT      60
GGTGGACATG CACCCATCCC CAGTCCAGGA AACCATCTCC CCCAGGACCT TCTGTCTGGG     120
ACTCAGGAGT CCTAAGGAAA AGGAATTCTA AACATGGGG GAAGGGGAGG TAGAGCACTG      180
ATGGGTGAAA AAGTGAGGCC AACACACAGG GCAAGTGGTG TCGATGGAGT CGAAGCGCTG     240
AAGGAATAGG GCGGCTTTCC TTCCAGCGAG CATCATTCGG CTGTTACCAA ACAAACATC      300
TTAATCTGCA CCTTCCTCCA CTGGCCATCT TGTCCTTGGG TCAGTGGGAC ATGGGCACCT     360
CGGGAGGCCC GGGCCCTGCC CAGCTACAGT TCCACCCCTC AGCTTGAGGA CCAATACTGA     420
GGTCTATGCC AGTTCCTGAT CCCATCTCAC TCTCTGGACC TACTAGGTGA CTGCTGCTGG     480
GGTGACTCCC CTGAGGCGGC TATACCCTTA AGCCA                                515
```

(2) INFORMATION FOR SEQ ID NO: 183:

(i) SEQUENCE CHARACTERISTICS:
        (A) LENGTH: 3188 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 183:

```
GCTCTCCCCT GCGCCCCTGT CTTTGTAAAT TGACCCTTCT GGAGTGGGGG GCGGCGGGCA      60
GGGCTGCTTT TCTTAGTCTG ATACCAAGCA AGGCCTTTTC TGAATAAATT CATTTGACTT     120
TGAGTCTTTG GTATGGACCG GGGTCCTGTT GGGTGGCTGG TAGGGCTGGT GTCACAGCTG     180
ATGTCCCTCC AGGCTCCAGT GGCTGGCCTG GCCCGGCTAC CGCCTCACAT TGCTCCACCA     240
GGTGCCTGTG GGGGCAGAGT GGTGGCCCAG CCCTCCCCAC ACACCCACTT GGCCACACAG     300
TCCCCAGGCA TGAACAGGTG GGCAGGCTGC AGCCTCCCAG AGCCTCTGAA GGTGGAACCG     360
```

```
AGGTCCCTCA GCAGGCTTTT GCCACCTAGT TGAAGATGAG TCTGGGGCTT CCCTTGGGGT    420

TGGCCGGGGC AGTGCTTGTG CATGGTGGGG TCTGGACCAG GCCTTTCTGC CTGCTGTGAT    480

CTGGGATGCG CTGCTGTGCC TCGGGCAGGC TTGGCAGTAC TCTCTGGCGG GCCCCTTGGC    540

TCCCTCAGGT CTGGTGGAGA CCAGGTGTGC CCCCAGGGCA GTCCCTCCCT GCAGTCTGCC    600

CTTGTCACCC TGGGCCAGGA CCCCCCGCTT CCCGGTTCCC CTACATTTCT ACATCAGCAG    660

GGTAAGGGGC TTTTTGTGGG GCCTCAGAGG AGGGGCCAGA CACTTGTCTT TGCTCAGTGA    720

AGGACAGGGC AGACCTGGGG CACCCCTGGG TGGGAGGGTT AAAGCTGTAG ACCCTGGTAC    780

CACTTCAGAT AAAATGCCCA GCTCCCATCT GGTGGCACCG GATACACGAG CCGGAAGTCA    840

CTGGGAGGAG ACACCCGAGG TTCAATAATC CCCCAGAGCT GCGTGGGGAA GCTGTGGGAC    900

CCCTGGTGCC TCAAGTGTGG CTCAGGGGAT TCCTGCCATG GAGGGAAACT GAGGCAGTGA    960

GCTGGACATA GGGCTAGAAG TGCAGTCACT GGGGCAGCGC CCGGCAGATC CAGCGTCCCC   1020

AGTCCAGGCC GTTGTGGGGC TGGAGTCGGT GAAAATCAGC GCCTGAAGTG AGGAGCCTGT   1080

TGGAGCAGCC CTGGGGCCG ATGCCTGGCG GTGGGCACCT GGGGCCAGCA GGCAGTGCTG   1140

GCCAGCCAAC CCGGGCTTCA GGGAGAGTTG ACCCACAACA GGCGGGCAGC AGGAGGCTCT   1200

GCCCACTCAA AAGTGAGCCG GGGGAGGCTG AGCTCTGACA GTGCCCACCC TCTGCCTAGG   1260

ATCTGCCTGG AGCTGGGGGT GGTTTTTTGA GGGGCTTGAA GGTGGTTCGG GGGGGACACC   1320

AAGCAGGTGT CCCAGGCATG AGGTGGCTCC CCTGGCCTGA GGTGAAGGCC AGCTGTGTTT   1380

TGTCTGATTT GGGTCAGATA GCAGTCCTTG CTGACTGCAT GCTGGGCATC ATGGGGATAG   1440

GCAAAGTGGG GTGTGGGGCC AGGGACCAGG GGAGAGCCAC TGAGGAGGGG GCTGGCCACA   1500

GGGTCATCTT GCCAGGTGGA ACTGGTAGGG AGGACTTATC CTGTCCCCCA GACCCTGGGC   1560

TTGGGGTGGG GCTGGTGCTG GGAGCCCCTA AGGCCCCCTG CTGTCTGGGC TGACCTGCTC   1620

CACTCACCTC TCCCCGTAAT CAAAAGTCCT CTGTTAGGAA GCTCTGTGCC AGGATGACTT   1680

GGACTCCTCA GGAGGGTGGG CCTTTTCAGC TCCTCCCACC TCGCCTGATG GAATTCGCAC   1740

ACACCCCTCC CAGCCCAGCC ACCGCGCTCA CCCAGCAGTG AAGGGAGAAT CTCCCTCCAC   1800

TCACTTCACC GCGGGAGAGA TTAGAGCGAC ACTATTATTT TGAGACAGGG TCTCACTCTC   1860

TTGCCCAGGC AGGAGTGCAG TGGCGCCGTC TTGGCTCACT GCAGCCCCGA CCTTACAGGC   1920

TCAAGCGATC CTCTTGCCTC AGCCTCCCGT GTAGCGTGGA CTACAGGCGA GCACCACCAT   1980

GCCCAGCCGA TGTTTTAATT TTTGGTAGAC ATGAGGCCTC CCTCTGTCTC CAAGCTGGCC   2040

ACGCCCGGCC GATGTTTCAA TTTTTGGTAG AGATGAGGCC TCCCTCTGTC GCCAGGCTGA   2100

CTGCGCCCGG CCAGAGTGCG GTGCTCCTGC TGAGCAGTTT TGCGCCCACT CCCCTCTCAT   2160

CCCCTCCCGC CCTTGCTAAC TCACAGCATT GCAACAGTCA TGAGTCCCCA CCTGCCGAAA   2220

GGAAGCTCCT GCAGCCCCCT ACAACCCCCA GGGCAGCCTT TCTCGGGAAT TTTCAAGATT   2280

CCTGGGGGAG GGCTGGCAT CTGCGCCTTC ACTGAGCCTA CAGGCAACTG GAAGCTTTGA   2340

GTCCCCTAGG GCAGCGACTG CCCTGGCAGC CTGAGGCAGA GCTTGGCCGG ACCTGGCGAC   2400

CCCTGAGCTT CTGGGAAATG GACATGGCCA GCACCGCCTT CAGGTTCCTG CCCAGGGCAC   2460

GGTTCCTTCA GGCCGGGGAT CCCGGGGAGG GGTTCTTCCC CTCGGCCAGG GTCATCGTTT   2520

TGCGATCTCT CCTGGGAGTC TGGGTTTGGA GTCTGGTCTT AGCCGGTAGC AACTGACGTG   2580

GCCTGACCAC CCGGCCCGTC CAGGTCCACG GGTGAGGGGC CGCGGTGGGG GTGCTCCCAG   2640

CCCAGCAGGC AGCGCTGGAC AGTGACCCCG GAGCGGGAAC CAGGGCTGCG CTGGGCACTG   2700
```

```
ACCGGGCCCT GGTACCGGGG ATTCACCCTC CCCGGGGTGT CCCTGGGCCT TGGGTCGCCT      2760

GGGTCCGCTC CGGCGCCTGG GGAGGGATCT GCGGCTTCGG AAACTCGCGG GTCTCCCCTG      2820

CCCCTCCCTG AAGGCGGCCC TTCAGCGCCC GGCCGTTCCG CCCCCACACT CGGGTTGAGG      2880

AGCAAGGAGA GAAAAGAGCG TCTTTCTCTC TTGCTCAAAG CTGCGTGTGC GCAACGCGCC      2940

AGTCCCAGGA TAATTTTAAC TCGCGGCCGG AGAGAACGCG CCGCCCGCCC GGCGTCTTTT      3000

TTGTTTTCGC CCAGGCGGGC TGGACGGCGG CGCGGGGCGG GTGGAACCCC CCACGCAGGT      3060

GGGCCCGGCT GAATGGGGGG CTTGTGCAGG CGGGGGCGGG AAGGGGAAGG GGAAGGGGCC      3120

GCCCACCTCC CGCCCCGCCC GCCCGCGCGC CGCCCGCCCC GACGCCGCAG CTCAGACTCC      3180

GCTCAGCC                                                              3188

(2) INFORMATION FOR SEQ ID NO: 184:

(i) SEQUENCE CHARACTERISTICS:
        (A) LENGTH: 413 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 184:

GTGAGCGCGA GATCCGGGCT CTGAGGCTGG ACGTGGAGCC GCGACCTCCC CAGCCCCGAA       60

CCCGCCACTC CGGGGTGCCC GCGCAGTCAC GACGCCCCCA GCCCGTGTCG CCGTCGGGGA      120

GAGGAGTCGC CAGCGCCTCG GGATGAGCCC CGTCCGGCCG CGTCCTCGAT GGGTCCTCGC      180

TGGCCCGGGC GGCCGCCGCC GCCTCCTCTG GGAGCACAAG GGGGCCTTTG TTCCCGCCGC      240

CGGAGGGAGG CGGGGGACAC ACTCGGCGGG GGCGCCTGCC TCGAGGCTTT GGGTCTCACC      300

GAGGAGAGCG GCGGTCGTCG CAGGCCCCGG AGCCGCTCGG GACCCGGGAG GAGGGGACGC      360

CGGGTCAGGC CACGGGGGCA CCTGCGCTCC TTAATGAGTT TTCTCCGTTT CAG            413

(2) INFORMATION FOR SEQ ID NO: 185:

(i) SEQUENCE CHARACTERISTICS:
        (A) LENGTH: 876 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 185:

GTGAGTTTGG GGGTGGGGAG GGCCCCGAGC GCTCTGGGGT TCTGGCTCTG GCCCCCACCT       60

CCCTGAGCTC CCCGGCCTGA TGGAGAGAAA ACCAGGCCCC ACCTCCCAGA GCCGGGGTGA      120

CATCAGGGGA CAGCCAGTGC CTTCACGGGA TGGGGTGGC CCTGCGGGAC TGCTGGTGGG      180

TAGGGGTGGA GGGTGTCATG TGGTGGTCCT CCACCCAGAA TTCCGGCACT GAGGTGTGTG      240

TCTCTGGGTC CCTGAGGGGC CCGTGCCCCT GTGTTCGGGG TTCTGGCCTC TGGCTGAAGT      300

GGGAGAGGCA CGTCCTTTGG GTGGTTGGGG GCCGGGGTCT TGTTGGAGGC TGCTGGGCTC      360

TGGAGCCAGC CATGGAGGGG CTTAGGAGCC GACTCAGTCC TGAGATGATG TCCCCTATGG      420

GTATCTCAGG ACTGGTGTGG GCCAAGCAGC AGGAGGAGGC GGCTGAAATT CTACAATTGT      480

GCCTCCCTCG GAGGGACCGT CTGGGGTGAA CCTCCCCATG TGACCACCAC CAGGGCAGGA      540

GTCCCCTCAG GGCCTGTCCA CGCTGTGTGG TCCCCGTGGA GGGCTGTGGA GGGCTGCACC      600

AAGAGCCCCC CATGACCCAC CCTCTGCCCC CCTGCCCAGC TCGGCCTCAA TGGCCATAGC      660
```

| | |
|---|---|
| CTCCTTCCAG TCTGTCCAGT TCACCCCTTT GCCCAGTGCT GCCCCACACA TGGGAGGGTG | 720 |
| CCCTCTAGGT AGGGATCGGG GGCTCAGGGG CCCCTTTTGT CTGCTGGGGC TGGGGCTCTG | 780 |
| GGGCTGATTT GGAGGCCAGC GCTGCTCTTT TCCCGAGGCG GGGTTCTTGA GGGACCCCTG | 840 |
| ATTTTCAGGG TTACATGTGG GTGTCTTTCC TCACAG | 876 |

(2) INFORMATION FOR SEQ ID NO: 186:

(i) SEQUENCE CHARACTERISTICS:
        (A) LENGTH: 661 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 186:

| | |
|---|---|
| GTGAGTGTCC CTGGCTGGGG AGACAGCCTT TTTCCAGTCT GGAGAGAAAG GGGGAACTCA | 60 |
| GAACAGAGGG GTCATTGATA TCCTGTCTCA TCCTGCCGGA GCCCGGGTTG CCTGAGGGGA | 120 |
| GGCCTCAGAG GGCTTGGAGC AGGCCTGGAG CCAGCGGGGC GGAGGGGAGT GTGGGCTCAG | 180 |
| CCTCTGCACA TGTTCAGGGC AGGGCCTGGC TTTGAAGCTT TCTTTGGACC AGCGCCAGGC | 240 |
| AGGCGGGACC GGGGCTGATA CAGCTTCAGG TCCCCCAGGC CTGAGGTCAC CTGGAGCCCT | 300 |
| CCCACCTTCT TCAGTTCCTG GGGTTGAGGG TCCTGGGGCT CAGAGCCCTG TCTGGGCCCA | 360 |
| CTGGGGGTCC GACAGAGATG CCTGCTGGCC CTTAGCCAGG GAGGCCGAGG TGACCAGACG | 420 |
| AAGGTGTTAC AGATGCCACT GAGGGATGGG GCGGGCAGCC TTCCTGGGCC AGCAAGGTGT | 480 |
| GGGCAAGCAG GACACACGAG CCCCAGCTGA GCCGGGTCTG CCAGACAGTA GGGGGGACCC | 540 |
| AGGAGAGGGG CCCATCCCGT ATGTTGGGCT GGGGGAAGTG GAAAGCATTT TGCTTCATTG | 600 |
| CTGAAGCCTG GGCTCCAGGC CAGACCCCGC CTTCACATCT CTGCCCTTTC CTCCTGCACA | 660 |
| G | 661 |

(2) INFORMATION FOR SEQ ID NO: 187:

(i) SEQUENCE CHARACTERISTICS:
        (A) LENGTH: 631 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 187:

| | |
|---|---|
| GTGAGTGCGC CTGCCCCTCC CCGCCATGCC CCACTCCCCG CTCCGGGTCC CTGGAGGAGT | 60 |
| CCGGCCCTAA TTGCTGTTGT CCAGCTGGGC CTGCTCAGGC GGGAAGCCCA GTCCTGAGAG | 120 |
| AAGTCTCCAG AAGTCCCCCA ACAGGGGTCC TTTGGCCTTC ATCCCAGACG CCACCAGCAT | 180 |
| CTGGCAGGGG ACAGAGCCAG CCCAGTGGAG TCGGAAGTCC CGCCAGCCCT CCTTGCTTGT | 240 |
| CCAGGAATGA GTGCCCATTG TCAGGACCTT CTGCCCACTG CTGGCCTCAC TTAGTCATCT | 300 |
| TGGGCTCCAG GCCAGCCCCA GGCCACGGAG TTTGTTCGGA GGAAGCCGGG CCTGAGAAGT | 360 |
| GAGCTGTCCA GTCCTGCTGG GTTGGTCCCC GTGGCCTGAC TACAGCAGGT GCCTCCGTTG | 420 |
| CTGGCTTCCC GCTGGCTGCC CCCTCCCTCC TCCCAGCCTC TGGCTACAGC AGGCAGACAG | 480 |
| TGGACAGGGC CAAGAGAGGA GGCTGCCACC CTAAGGGTCT TCTATGCCTC TCTGGACTCA | 540 |
| CCAAGGGAAG GGTCCGTGCT TCCATTTTTG CCTGGGGGGT GGCATGTGCT TCCCATGTGG | 600 |

```
CCCCTCGAGC TCGCCCTCTG CCTCTCCCCA G                                     631
```

(2) INFORMATION FOR SEQ ID NO: 188:

(i) SEQUENCE CHARACTERISTICS:
        (A) LENGTH: 1194 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 188:

```
GTAAGTGCCT GCGCCGAACC CAGTGGCTTG GGTTCAGAGG TGAGGTCCCC TGGCCACCTC      60
TGGCTGCTCT GTGTCCACAA GGCCAAGGAG CTGGTAGTTC AAGGACAGC TGCCCTGCCC      120
GTGCCTGGGG TGGAGGGGCA GAAGGGCAGG GTGCCAAGTG GCCAGTCCCC TGTGCCTGCC     180
TCCCTGCCTC ACCTCCACGT ATGGTCAGAG TTGTCCTGGT ATCCAGACCA TGGCAGGGAG     240
AAGGGGATG GTTTGGGGGA ACCCACCCCA GGTGCCTCCT CAGAATGTCC CTGAAGCCCC      300
CAAGCCCTGG GCAGACCACC ACCAGGGACC CCCGGGCACG CAGCCTGCAG AGTCCCCTGT     360
GCCTGCCTGT TGGACACTGA ATCCTTTACC CTGACGGAGC GGCACCACCA CCCAAGGGTG     420
CCTTTCTCCC CTTGTGGCTT CTGAGTACAA ACCCGAAGCC AGCAATCCCT CTTTGGCTTC     480
ATAAGACGTG GCTGTCAGCC AACCGGGTGC CACTGGCCCC AGGCGCAAAG CATCACAGAG     540
GGCAGGAAGG CTGGGCTGGG GACACGAGGA CACAGCCCTG CCCTTGGGGA CCCTTGGGAG     600
CTCGTCAGGG CATGAGGCGG ATTCTGAGCT GAAAACAGGA GGGAAACAGT AGCTGCTGGC     660
CAGCGAGTCC GTGGTGCCCA GGGGTGTGGG GTGGGCTGGT CCCAGGCTTT CAGGAGGGGC     720
CTCCAGCCTC AGCACAGGGC CCGTGCGTGC CGTCCAGGGA ATGAGGCATT TCAGGCAGCA    780
GGGGCCAGAC AGGGCCAGAG GGTGTGGAGG GCAGACAGGG CCTGGCTGCC AAGGCTCTGG    840
GGCTCGCTGA CGTGGGCGGG GGCTGAGGAC TCAGCAGGCT CCGTGGGTGG GTTATCGGGA    900
GGGCTTCCTG GTGGAGACAG GCACCCCGGG TCACTTCGGT GCCTCTCAGC CCTGCCTCAG    960
GTTGCACCTT CTTGCAGCGA GCGCTGGGAC TCTGGTGCCA TCTGTCTCCA GCAGCTCCCC   1020
AGGACGGCAA AGACCCTCCA GGTCAAGAGG GCTCAGAGGC CTGCCCCTCT GTGAAGTGGG   1080
GACTTGGACC CTGTTGTCCT GGGAGTTGGA GTTGTGACGT CACACTTCAG AGGGAGGGGA   1140
TTGGGTTTGC AAATAGAGGC CCAGCCAACC TAGACGCCTG CTTTCCTCCC ACAG         1194
```

(2) INFORMATION FOR SEQ ID NO: 189:

(i) SEQUENCE CHARACTERISTICS:
        (A) LENGTH: 288 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 189:

```
GTGAGTATGG AGTGTGGTCC TCTCCTCTCC ATGGGAGTTT GGGGAGCTGG AGAGTCTGGT      60
CTAAATGGGG TGGCCTCCAG GAATCCCAGG GACCATCCCT GGCCCTCTCA TCTGCAGCCT     120
CTCCGGAGCT GGTGCCTGGA TGGGGTCCTG GTGCCCTCTC TGGGCTGGGA CCAGACACCC     180
ATCCCTGGAA CCGCCCTTTC CCCAGGACCC ACCTGAGCCA TCTTAGGGAG GGGTGAGCGC     240
AGCCCTTCTT GTGCCTGGCA GGCTCTGACC CCATGTTTGG CTTTGCAG                 288
```

(2) INFORMATION FOR SEQ ID NO: 190:

(i) SEQUENCE CHARACTERISTICS:
        (A) LENGTH: 226 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 190:

```
GTGAGTACTG ACAACCCTTG GGGCCCTGAG CAAGCACGCA AGTCCCGAGA GCCTGCCAGG      60

CTGGGATGTC CCAAACCGTG CCTGGGGGTG GGGCTTCTCA GGGGCAGCCA TCTGACCACC     120

CCATACTTGG AGCCCCTCTC CTTCGGAGGC GGCACAGGCC ACCCTGGGTG GGGATCCTCG     180

GGGCTTCCGG GTGCAGACCT CCCCACCTCT CTTTACTTCC CTCCAG                   226
```

(2) INFORMATION FOR SEQ ID NO: 191:

(i) SEQUENCE CHARACTERISTICS:
        (A) LENGTH: 297 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 191:

```
GTGAGTGGCT GTCCCAGAGC CCCTCAGAGT GTGCTCACCT GTGGCCTCCA CCCCCAGACT      60

CAACAGCCAG GGGTCCCTTC CCCTCTCCCT TTTCCCTTTC TCCCCCAACC CCACCTTGGG     120

TTGTTGGTAG AAGCCCTGGC CAATGATCCA GACCCGACCT CAGGACGCAG ACACCAGCAC     180

AGTCCGTGGG AGTGGGGGCT GGTGGGAGCT GGGCGTGTCC ACCTCCCTGG GAGAAGCCGG     240

GCACCTCACT CAGGTGGGGG CTGGTCCCAC TCTGTCTAAG TCATACCCCC TCCCCAG        297
```

(2) INFORMATION FOR SEQ ID NO: 192:

(i) SEQUENCE CHARACTERISTICS:
        (A) LENGTH: 425 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 192:

```
GTAAGTACTG GGCAGAGGCT CTAAGAAGTG CTGGGCATGG ACTAGGACAC TGGGTTGGCC      60

CCTCCCCATT CCCCCTCCCC AGGCTCCATG CCCCTCCGAG ATCTCCTAAC CCTAACTTGG     120

CCACTCCCCA GGAACAGTCA ATGGTGGGGG CAGTGGGCTG TGCTAGGCCA GCCAACTTGG     180

GATGGTCAGG ACTCAGGTCC CCATGCCATC CTGCCCCAAG GACAGGTGGA TTCTGTCGTT     240

GTCACATACC CTGTGGGTGG GCCAGCAGCT CCCAGCACTG GCCACTTGGG GGACAGGATG     300

AAGGGTCTCC AAGTCCCCTG GTGGATGGGG AAGGTTGTGG TCCGTCAGAG AGTGGGTGGG     360

TGGGTTGGGT GGCTGCAGGT GGCTGGGGAG GGCGGGAGAA TGTCAGCTGT CTCTTTTTGT     420

CTTAG                                                                 425
```

(2) INFORMATION FOR SEQ ID NO: 193:

(i) SEQUENCE CHARACTERISTICS:
        (A) LENGTH: 1817 base pairs
        (B) TYPE: nucleic acid
        (C) STRANDEDNESS: double (D) TOPOLOGY: linear (ii) MOLECULE TYPE: DNA (genomic)

(xi) SEQUENCE DESCRIPTION: SEQ ID NO: 193:

| | | | | | |
|---|---|---|---|---|---|
| GTAGGCACTT | GAAGCCATTT | GTTAAGGGTG | CTGGGGGGTG | CCTACCTTGG | GGGGAGGGGT | 60 |
| TCTGGCCTGG | AGAGGGGCTT | GTCCATACTG | GCAAGAAGGC | AGGCCCGAGC | CCTCCCTGGG | 120 |
| GACAGGAGCT | CAGAGCAGAC | AGCTCGGGCA | CAACCTGGCA | GAGAGGCTGG | CTGGGACCTC | 180 |
| CCCCTCCCCC | TTCCCACCCT | CCTCACCACC | GTCTAGACCT | GCACTGTCCC | TCATGAAGCC | 240 |
| ACCAGGCGCA | TGGAGCTGTA | CAAATGTAAT | GAATCACAAT | CATGTCACAG | AGCCATCCAG | 300 |
| CTCCCCTGCG | TCATCCGCAG | AGGGCGCCCT | TGGCCACAGA | TGGCGACAGA | ACTGGAGTCT | 360 |
| GAGACCCACC | TTTATCTTGA | TCTTTGAGCC | TTGTCATTTG | CCTGAAAAGA | AAACAGGCTC | 420 |
| AGGTCAGGCG | CAGTGGCTCA | GGCCTGTAAT | CCCAGCACTT | TGGGAGGCCC | AGACAGGAGG | 480 |
| ATCGCTTAAG | CTCAGGAGTT | TGAGACCAGC | CTGGGCAACA | TAGTGAGATC | TTTGTCTCTA | 540 |
| CAAAAAATTG | TTAAAGTAGC | CAGACGTGGT | GGCGTGCCTG | TTGTCCTAGC | TACTTGGATG | 600 |
| GCTGTGGTGG | GAGGATCACT | TGAGCCCAGG | AGGCAGTGGT | TGCAGGGTGC | TGTGATCAAG | 660 |
| CCACTGCACT | CCAGCGTGAC | GAGCCAAGCT | AAGCCTGTCT | CAAAAAAATG | AAGAGGAAAG | 720 |
| AAAATGGGCT | TCGGAGGCCA | CGGATCCATC | TCTCCTCTCT | GTTTGGCCGT | CCGTGGTGGC | 780 |
| AGTCAGCGCC | TTGTTTCCAT | AGAGAGGTTT | GATAGTTTTG | AAGGGAAAAG | CTCGGCCCAC | 840 |
| TCTGACCTGA | CCACCGACGC | TGTCTACCAG | CCTCTCTCCT | CACCCCACCC | CGGGGCCTAG | 900 |
| GTGCCTGGCC | AGCCTGTGTC | CCAGAAGGGA | GGCTTTAGGG | AACCTTCCAG | AATGTGGTGC | 960 |
| GTGGTTGGGC | CCCCGATCGT | GGGCTGAGTG | GGGCAGGGGC | TAAAGATACG | GGTCTGCACC | 1020 |
| CTTGGCCTGG | CCTGCCCATT | GCAGCTGTAG | GATCATCTAG | AAGCAGCCCT | GGGTTTCCTG | 1080 |
| AGCATCAGAC | CTGTTGCCTG | GGCTCACAGT | GCCCCTCCTA | AAAGCCCCAT | GCCGAGCACA | 1140 |
| TTCCTGTGCT | GAGGATGGGC | CCGACCTGAG | GCTGCTGAAG | GCCCCCTGCA | GTGCCGGCCG | 1200 |
| GGACTGTGCT | GAATGGCTGC | TTTGATAGCC | AGTGTCTGCC | GTGGGCCGGC | TGCTCCATGC | 1260 |
| AGCCCCTGCT | GACTTGGCCA | GTGCTGAAGG | AGACCCTGTC | TGTGTCCTGT | CCCAGTGCCA | 1320 |
| TCTCCTGTAC | GAGTGGCCTC | CTGGGGTCCC | GTCACTGTGT | GGAGTGGCCT | CCTGGGGTCC | 1380 |
| CGTCACTGTG | TGGAGTGGCC | TCCTGGGGTC | CTGTCACCCA | GAGTGTCCCG | ACACCCGCGC | 1440 |
| CGGAGTGGCC | TCCCGGGGCC | CGTCACCCAC | GCGGAGTGGC | CTCCTGGGGT | CCCGTCACTG | 1500 |
| TGTGGAGTGG | CCTCCTGGGG | TCCCGTCACT | GTGTGGAGTG | GCCTCCTGGG | GTCCTGTCAC | 1560 |
| CATGAGGAGT | GGCCTCCCGG | GGTCCCGTCA | CCGTGCAGAG | TGGCCTCCTG | GGTCCCATC | 1620 |
| ATCTGTGCGG | AGTGGCCTCC | TGGGGTCCCG | TCACTGATGC | GGAGTGGCCT | CCTGGGGTCC | 1680 |
| TGTCACCGTG | AGGAGTGGCC | TCCCGGGGTC | CCGTCACCGT | GCAGAGTGGC | CTCCTGGGGT | 1740 |
| CCCGCGGGCG | CTGACCCCTG | CGTCGACGTC | CTGCTCTGTT | TGGCTGGGAG | GGGTCTGACT | 1800 |
| GCTCTGTTTT | CCGACAG | | | | | 1817 |

(2) INFORMATION FOR SEQ ID NO: 194:

(i) SEQUENCE CHARACTERISTICS:
        (A) LENGTH: 467 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 194:

```
GTGAGTCACG GGTGACTGGG ACCCAAGCAC CACCCTGTGC TGGGCAGGAG GCAGCTGGGC      60

TCCCATGGGG CTGTGGAGGT GGCGGGTCCA GAAAGCTGGA CCCTGGTTCC ACGGTTGCCC     120

CAGGAAGAAA GCTAGGCCAG CCTCCTTGTC CCGCCTTCAG CACCCCAGTG ACACGCTGAT     180

GTGGCCAGGC TGGGACTGGC CATAGGCATC AGAGACTGCG GGGAGAGCT AGCCTCAAGC      240

TCCCACCCCA GCCCAGCCCT GGCCCGCTCC TGACCGCAGA GCGCCCTCAT GTGGGTCCT      300

AGCGCCTCTC AGGCCTCAGT TTCCCCATGA GGGCCCAGAC CCGCGGTCCT GTGCGCTGCC    360

GTGTGGCGGG CCCTGGGCTG ACTGACCCTG CAGGCCTCAC TTCAGTGTTG CCAGGGAGGG    420

GGTGTCGGGG GGTCTGGGTG GGGCAGTGAC CCCACATTTG CTTGCAG                   467
```

(2) INFORMATION FOR SEQ ID NO: 195:

(i) SEQUENCE CHARACTERISTICS:
  (A) LENGTH: 697 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO: 195:

```
GTGAAGCTGC CGCACAGCAG CTGGGGAGGA GCTGGGGACT GGAGGCTGGG CTCCGGCGGG      60

AGGGAGGGGC TGGGCTCCGG CGGTGGGGAG GGACCGTTTC ATGGGTGCAC CTGCACTGGC     120

ACCTTCTGTG CTGTCTTCCA GATAGGGCCT GGCTGGTCAG AGCTGGGTGA TTTAGGCTGG     180

GTCCTGGACA GACCCCGTCC TGCCTGGCCT CGCTGTGGAA GCTCCCTGGT TTGTGTCTGT     240

GGCCGGGGCG AGGGGCATCT GTGAGGATGG CTGGCTTTAG CCTGTAGCCT CCCCTCACCT     300

GTGGTCGCTG TCCGTGGAGG GTGTCTGTCC ATGGTCACCT GCAGGCCGGG GGACCAGGTC    360

TGGGATGCCC TTTAGCGTGG CTGGAGTGAT CAGATGAGGA GACCCCAGGT GCACATCAGA    420

GGGGTCCCTG CTTGGCCACG AGGAGGGGCC TGGACAGGGC TGAAGGGCCT TGTGGGAACA    480

GTGACCACGG ACCCCGGCCC GGCAGGGCGA GGCCACCGAG ACTCGCGGGA CTGCTCTGGA    540

ACTGTGGGCA AGTGTCCCCT TCACAGAGCC TCCAAGGCCC AGCTGTGAAG CGGGCAACAC    600

CCCCAGCTGC TTGGGCTTGA GTAGGGTGAC TGGAGGCACC GAAAGGTGCA AGGAGAGCCA    660

GACTGGGCCG CTGACCACCC TATCCCCTCT GTTTCAG                              697
```

(2) INFORMATION FOR SEQ ID NO: 196:

(i) SEQUENCE CHARACTERISTICS:
  (A) LENGTH: 333 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO: 196:

```
GTGAGGCTAG GAAGGGGTAA GGATGGTGGG ATGGGAACTC AGCCCACAGA GTGATCAAGC      60

CCTGCACATA TCTACCCCCG AGGGGGCCAG CTCCGGCTGG GGGGTGTTTG GCCAACACCC     120

AGGCACAGGA GCGCGACCTG GCTGGGGGTC CCACCTCTGC CAAGGCTGCT GACCTCAAGG    180

CTGGTGCCCC CTCCCTCTGG GGGACCTGAG CTGAGGCTGA GGGCTCATGG AAGACACCAG    240

GGCTCCCAGG GGTACCCCGA GGGCCTTGGC CCTGGGTGAT CCCCGGGGTG GAGGTGCAGC    300

CCCAGCCTCT GCATCTGTGC CTCTCTCTCG CAG                                  333
```

(2) INFORMATION FOR SEQ ID NO: 197:

(i) SEQUENCE CHARACTERISTICS:
        (A) LENGTH: 509 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 197:

```
GTAAGTCCTG CAGCCCCTAG TGGGGGCCGG CCAGGTGGCT GGGGGCCTGG TTGTCTGCAC      60
CTCCAGACTT CAGATGGGCC CCGTGAGTGA CACTCTGAAG CAGCCGGCAC CCTGGCTCTG     120
GCCATCGCCA CTGTGGCGCA GGCCTTGCTC TGGGCCCCTG TTCTCGCATG TGCCTGGGCG     180
AGAGCTGACA GTCGGCGCTC ACTGATGCCC GCACGCGGTC CCAGGCTGCT GTGAGGGCTG     240
TTCACGCGTG TGCCCGGGCG AGGGCTGATG AACTCTGCTC GCTGACACCC ACACACACGG     300
TCCCAGGCTG CTGTGAGGGC TGTTGTGGCT TAGGCCAGAG CAGGAGGGGA AGCAGGGATT     360
TGGAGACTAC TAGGTGGCAT CTTGGGGGAA CTTGCTGGGG AGCCCTAGAG GAAGGGCTGC     420
TTGTGTCTGG GCCGCCCCTG AGGGAGCACT GGGGGGATGC CAGCCAGGCC TCAGACAAGA     480
GGACCCCGGA TCCCCTCTCT CCTCTGCAG                                       509
```

(2) INFORMATION FOR SEQ ID NO: 198:

(i) SEQUENCE CHARACTERISTICS:
        (A) LENGTH: 420 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 198:

```
GTACGTGTGT CAGTGGACGG TGGGCGCCAT GCCACGTGAC CTCTCTCCCC TTTCCCTCTG      60
CTCCTCTCAG ACGCCCCCAG CCCCACTGGG GCCCCTCTTC TCTGGCTGAG CTGTTCCCTG     120
GACACCCTGG GAGGGCTTGT GGCATGGGTA CGGGGGTGCT TACCAATGGA ATCCATTCTT     180
TGTGAGACAT TCGCCTCCTT TCTGGTTCTG GACGTGGAAT GAGGGGTCAC CATCGTCCTT     240
CTGGCACCTC CAGCCATCTC TGACCACTCC TGGAGGGTCC AGGCCTGGAG GGCCCCCAT      300
CCCACTCTCT GACCACTCCT GGAGGGCTGT CCCCCGCCCG GGCCTGGAGG GGCCCCCGTC     360
CTACTCTCCG ACCATCTCCA TGGTGTTAAC TCTGTCCCTG CCCCACCTCA TCCTTTCCAG     420
```

(2) INFORMATION FOR SEQ ID NO: 199:

(i) SEQUENCE CHARACTERISTICS:
        (A) LENGTH: 626 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 199:

```
GTAAGTGAGA GGGAAGTTGG TTCCCTGGGT CCTTATGTGG AAGAACCCAA TTTCCCTCCT      60
GACTCGTGCT GGGGAGGGGG ACACACTTGG GAGTGAGACT GCAAGGGGCT GCCTGGGTGG     120
GCCTGGGGGT GCGTGGGGGT GAGCCTGACC CTGGAGGGCC CGAGATCTCT CCCTGGCCCC     180
AGCCGTTCTC CCAGAGCCAC ATGGGAGCTC TGTGGCCCCC TGCAGAGCGG CCCACGGGCC     240
```

```
TGGAGGGACC AGGCTCCAGG GCTTGGATCC TGCCCCCAGA GAAAACGGCT CTCGGGTTGA        300

GCAAGTGAAC ATAAGGAAAG TCCAGAGGCA GCCAAGCGTT CCAGGAGTGG AACTGAAGTG        360

ACCGTCCCCA GACTGGTCAG CCTCCACACC TCCCTCGACT GAGCCCTGGC AGCCGGAGTG        420

CAGGGAGCCG CCGTGCCGTC CTGCAGCATC TGTGGATCCA AACACAGTTT TCTCCACGCA        480

CCCACAGGCC CCAGGGTGGT TGGTCGGGGG TGGCCCCTGC CGCTGCCCAC CATAGCTCCT        540

TGGTGTCCCC GAGCAGCTGG CCGGAGAATG CGTGAGGCCG TCTGGGAAGA GACTGCCACT        600

GCTTCTGTCA CTTGTGTGTC CTCTAG                                            626
```

(2) INFORMATION FOR SEQ ID NO: 200:

(i) SEQUENCE CHARACTERISTICS:
        (A) LENGTH: 787 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 200:

```
GTGAGTGCAC GTGGCTGCTC ATGGAATGCT CCTCCCCCGG GTCCTGGGTA TGTACAGGTG         60

GAGATGGCAT TCAGAAGGGC TGGAGCTCAG TGCCCTCTGC TGTGGCCATC TTGAAATCTG        120

GGTTAACGGT GGAACAGCCC CGCAGCCCCA CACATTTCTC TCTTGCCCAG AGCCTCACGA        180

GTGTGCAGGA GTAGGGGCCT CAGGCTGGGT TTACCTGCAC AGAGGACACG GGAAGTAAGG        240

GTGGGTGGGT AGCACCACTG GGCAGAGGTG GGCACTCCCA GGGTCCCGGG CACCCGTGCG        300

GGCACCTTCC TTCCTGCTGG GTGCCCACCC TCAGCCCAGA CCTGAGCTCC CTTCTAGCCC        360

CTCGTGTTGC CTCTGCCCCG GAGTAGTGCC CTGTCTTGGG ACACCCAGCA GTTGGCTGTG        420

TCCTGATTCC AAAACCAGTC CAGGGTGGAC CGAGGCAGGC CTGCCTAAGG CCTCAGTTTC        480

CCCACCGTAA AATGGGCCAG AACCAAACTT CCTTAGGGCA CCATGATGTG CCTGGTGGAC        540

GAGGCCTCGG GCGTCAGCAC TGCATCAGCA CCGCCTCTGC CACCCACCCG CACCCCTGAC        600

CTGTGCGGTC ACCGAGGTAG CACTGGTTGC CACACGGCCA CCTTGGTCAT GAAACCAGAT        660

AACTGCCAGG GTGTGGGGGC AGACACAGTT TTAGGTTGAT GGGAAGGAG GCTGCCCCCA         720

GGGCGGGACT GTAGAGGGAG GGAGGGGGGC CACTGCCCGA CGGGCCTTAC TCATCCCTTG        780

TCCCCAG                                                                 787
```

(2) INFORMATION FOR SEQ ID NO: 201:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 201:

```
GTTGGCATGG GGCTCAGGGT GTGACGGGAG GGAGGGGGCT GGAGGGGAGT TCGGCCTCCC         60

GAGGCCTCAG CCTCCCCTTC CGCACCCCAA TCTCTGTCCT CACAG                       105
```

(2) INFORMATION FOR SEQ ID NO: 202:

(i) SEQUENCE CHARACTERISTICS:
        (A) LENGTH: 477 base pairs
        (B) TYPE: nucleic acid

```
        (C) STRANDEDNESS: double
        (D) TOPOLOGY: linear (ii) MOLECULE TYPE: DNA (genomic)

(xi) SEQUENCE DESCRIPTION: SEQ ID NO: 202:

GTGAGTGCCC GGCGGGTGGG GCCAGCCTGG GGCGCCACAG CTTCTGCCTG CTCAGTGGCC       60

CATGTTGGGC TGGGTGGGTT GGTCACTGTA GGGCCGACTC CCTGTGAGGG GTTCTGGGGC      120

CTGTGTCCAT CAGGGCCTGG CACAACCCCT GGTGCCCAGT GGTGCTGTGG ACGGTTGCCT      180

GTATGTTTGC ATGTGTGTGC TTATTCGTGT GTACATGGGA CATGTGTGAA CATGTTGATG      240

GCCATCCCTG GATGCCGTGC GGTCATCACC CCCATGGGCT CTGAGTAGGG GCTCCTGCAT      300

CCAAGGCCAG GGAGGCTGTC AAATCCTCAC CTCAGGTCCA CAAGGCTGGG AGAAGTTGGC      360

CCTGCCTTTG GGTGCACTCA CTCTGGCCCC GGCGCCCTGC CTGCGTGCAC GCCCCTGGGT      420

GCTGCTGCCG GCGTGCAATG TAACTGGCAG CCCTGACCGC AAGCTCTCTC CTGGCAG        477

(2) INFORMATION FOR SEQ ID NO: 203:

(i) SEQUENCE CHARACTERISTICS:
        (A) LENGTH: 113 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 203:

GTATGTGGCT GCAGCGCTTT CTCTCTGGGA GGGGAGGCGA GGGGCCGGGA GGCAAGGGGC       60

TGGGCAGCGA GTGCAGGTGT AGGCAGGCAC TCACAGCTCT CCTTCCTCTA CAG            113

(2) INFORMATION FOR SEQ ID NO: 204:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 204:

GTGAGTATCT GCGGCGCCCC AGACCCCTCC CCATCCAGCC TGTGTGCAGA CCCTGCCCTG       60

ACACCCTCCT TCCTTTCCCT GTAG                                             84

(2) INFORMATION FOR SEQ ID NO: 205:

(i) SEQUENCE CHARACTERISTICS:
        (A) LENGTH: 539 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 205:

GTGAGTGCAG GGACATGGCC CGGGGTCGGG GGTTAGCACT GAGCCATTGG CACATGGCCC       60

CAGTTTCTGA GCAGGCCGGG GTGGCATTTG GTTGCCTTGA TGGGCCAGGC CCACAAAAGC     120

CTAGGATGCC AGGAGGTGTG GGGCCCCATC TTCTTGTCCC TCACCCGCTG GGAGACGGTC     180

GGGGCCAGGC CGGAGCTGCC CTGTTTTCAA GCCTTCTATG CTGAGCCCAG CCTTGTGCCC     240

CCATAGACTG AGATAATGAC AGCACCAGCC ACAGGGCCCT GGTGGGGGGA GCCAGGGGCA     300
```

```
TGGGTGCCTG GCCCCGAGTC TGGCCTGACA AATTGGGTCC AGGGTATGCC GAGTTCTGAG      360

ACCCCCTAAA CTGCCCTGGG AGGTAGCCCT GCCTTTGTCC CCAGCAACCC AGCCAGGTGG      420

CTTAGAACCG GCTCCTGTGT CCACCCACTC TGGGGGAAGG CTGAGCCAGG CTCCCTGGGG      480

CCTCTTGGGG AGTCCTCGAA CCCTGAGACA TCCGCTCACA CCTCACCTTT GTCTTCCAG      539
```

(2) INFORMATION FOR SEQ ID NO: 206:

(i) SEQUENCE CHARACTERISTICS:
        (A) LENGTH: 102 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 206:

```
GTGGGTGAGG TTGGGGCAAG GGCCTGGCAT GGGGGGGCGG CACACCCAGA CGGGCCAGAC       60

CCGACAGTAT GGGCACTGAC GAGCCAGGAC CTCCTTCCCC AG                         102
```

(2) INFORMATION FOR SEQ ID NO: 207:

(i) SEQUENCE CHARACTERISTICS:
        (A) LENGTH: 1421 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 207:

```
GTAAGTGGCC CTCTCAGCAG GAAGCTCCCC TGCACCCCCT CTACCCATGT ACCACAGTCC       60

CCCACCCCCC ACCACAGTCC CCTGGGACGC AGACAGGGAG AGGCCCTTGC AGCTCCCAGT      120

GGGAAATCTG GCCATGGGCA GTGTCTCCCT GCGTGGCGGA GGCAGTGGCA TCAGGGCCCC      180

GACTGTGGCC CCTTTGGCCC CTCTGACCTT CCACGTGGTG TTCCTTGTGG GTGGGAGGCT      240

GCGGGAGCCT GGGCGCTCTG CCTCCTGCCC TGCGTAGACG CCTGGCGGGA CCTGCACACG      300

GTCAGTGTTC ATTCCTCAAG ATCGTGGAGG CTGAGGCTCA AGAGCCACGC CTGCTCCCGC      360

CTAGCGGGTG TCTGTGGAGG CGCGGTTGAC AGAGGATCAC GTTGCTATAA AATAGGTTTG      420

AACACCATGT CCCAAGTGAC TGTAACGGTC ACAGCTTCTA CCTCGTCAAG ACTTTTTCCT      480

GCTGGTCTTG CAGCAGCTGC AGCATTAGCT CCTTGGGGGT CCGGGCAGAA GCGGGGCACG      540

GCCTACCCAG GGCCCCAGCT CACTGGAAGG AGCCTGTGGG TCTGGTCTGG GCCCCAGCCA      600

TGCTCCACCA GGTCCTTGGG GACCTCGTGT GCCTGCTGTG GCCACCTCTG CTGGGCAGAC      660

AGACCCCTTT TTAGATGTCA ATCCCGAGAA GCCTCCAGGA CACGGCTGCA GATGCCCCGT      720

CATTCCAGGG TGATGGTCAT TCCAGGGTGA TGGCCGGGGC TGTGGACACC ACCACCCCTA      780

GGGGGATAGC GGGCTGTTTG TTGGCCTCCA GGCAGGACAT TCCAGAGGTG GGGGCCATGC      840

CAGCAACCTC AGGGCCTCCG AGAGATGGTA GGGCTGGCAC CCCCTGCGGG CACTGCGCCT      900

GTCCCAGGTG TGGGTGGGGC CTGGTGGCTG AATTTCCCTT TCACTTTAAA CTCACGGGAA      960

AGTCTCCTGC TTTTCTGCCC TTTGGGCCAG TTCTCACTTA TGTGGCCATG TGAGCAAATG     1020

GACATTTTTT AAAGGGATTC ATAGCAACTC CCAGACATGT CCTCATTTCA CAATGCCGGG     1080

GGAAGGTGAT TAGATGAGCT TTTGCATCTT TGACTCTACT GTGATGGAAT TATCCTGCAA     1140

TTGTGCAGAA ACACCCGCAC GAATTCACGG GTGTTACAAA CAGTGCAAAC CTAACGGGAC     1200
```

| | |
|---|---|
| TTCACTACCC ACAAGGGGAG GCTGGACAGA GCCATCGGGC CCAGAGGCTG TGAACGTGAG | 1260 |
| CTTGGCCTTT GGGCCTGTGT CTGGGAGCCG GTGTTCACAG AAGCCCTTTG TGCAGCACAG | 1320 |
| ATGGAGATGT GGGGAGGTGT TTACCATTCC TGGGCCCAGG GCAGGCTCAC TTTAGGGATT | 1380 |
| CCTGCCATTC CTCTAATCCA GAGCCTTCTC TCCACACCCA G | 1421 |

(2) INFORMATION FOR SEQ ID NO: 208:

(i) SEQUENCE CHARACTERISTICS:
        (A) LENGTH: 880 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 208:

| | |
|---|---|
| GTGAGCTGGG CACAGGCTGG GGCAAAAGGA ATGAAGGCAA AGCTGCACAG CTTCTCCCAG | 60 |
| GCTCCTCCTG TCCCGGCTCT GGCCCTGGCT GTGTTTTCGG GACACTGAGC CTCCTTTCTC | 120 |
| CTCTTGCCGT GTCTGTCAGT CGCCCTTTCT GGCTCCTGCC CCTCCTGCTT AGCACAGCGA | 180 |
| AAGCAGCTCT GGGCACCCAG CCCCCAGGCA CGCCCCGGCA TCCGCCGCTG CCTTCCTGGG | 240 |
| TGCAAACAGC TGGCCATGAG TGTCCCTGCA TGGCTCTGGG TGCACAGAAG CTGCTTCTAG | 300 |
| TCCAGGAGGC ACCAATGGGA ACTCTCAAAG GGACAGAGGT GTGTCCTGCC ATCCTTCCGG | 360 |
| AGAACTGACA GAGGGCAGGG GCTAGGCTCT GCGTGTGTGT TTTGCAGGCA GATTCGAAAT | 420 |
| GCATTTCTGC TGTTCGAAGC ACTCTTCTTT TTGGAAAAGT GTCAGGGTGG GTGGGGCCAT | 480 |
| GGCCGTGGCT GCCCCGCCCT CCTGCAGTGC CTGCTCTGGG TGGGGCCCGT GGTCTGGCTG | 540 |
| CCCCGCCCTC CTGCTGAGCC TGCTCTCACT TCTAGGCACA AGGCCTTTCC ATACCGCGCT | 600 |
| GGAGGCCTGC AGCCATCGAA CCCCCACCGC AGGTTCTGCT TGGCAGAAAA ACCTCATTAT | 660 |
| GCAAACAAAT GTCTTCCGTT TTTTGGCCCC GCCCCTGCCT GCAGGTCTCC CAAGGGCTGT | 720 |
| GTTTGGAGCG GGTTAAAAGG CAGCCCTGGG GCCTGGGCTT TTGGCCTCGA CCTTAAGATG | 780 |
| AACATTACAC CTACGGAGGC TTGAGAGCAG GGACTTTAAG GCATGAAGTC CCTACTCATG | 840 |
| CATGAACAGC TCTTTTAACT TTGGGGTGTA TCGTTTTCAG | 880 |

(2) INFORMATION FOR SEQ ID NO: 209:

(i) SEQUENCE CHARACTERISTICS:
        (A) LENGTH: 1140 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 209:

| | |
|---|---|
| GTGAGTAATT AGGTAACCTC ACTGTTACCA ACAGCTGGGA GCGAGGTCGC CACTGTGGCT | 60 |
| GGGGAACAGT CCTGGGGACA GGGTCAAAAT CTGCAGCTCC CGGTGGAAGA TCGGCAGCTC | 120 |
| TGCTGGGCAG CGTGGGGATG GAGCAGGGTC GGGCAGAGGC CTTGGCCACT GGCCATCCCT | 180 |
| TAGCAAGTGG GCTGGGCCTG GCAGGGAAAC TCAGCGGCTC TGGAGTCTGA CCTGACCCGG | 240 |
| TGCTCAGACG TGTGGGCTCC CGCACTCTGC CCCGTGGAGT GGCACCTGCA TGAAGCAGTC | 300 |
| ACAGCTGCAT TTTTGTTTTT TTGTTTTTGG TTTTTTGGGG TTTCTTGTTT TTGTTTTGA | 360 |
| GACGAGTCTC ACTCTGTCAC CCAGGCTGGA GTGCAGTGGC GCGATCTCGG CTCGCTGCAA | 420 |
| GCTCCGCCTC CCGGGTTCAC GCCATTCTCC TGCCTCAGCC TCCCAAGTAC CTGGGACTAC | 480 |

-continued

```
AGGCGCCCGC CACCATGCCC AGCTAATTTT TTGTATTTTT AGTAGAGACG GGGTTTCACC      540

GTGTTAGGCC AGGATGGTCT CCATCTCCTG ACCTCGTGAT CATCCCGCCT TGGTCTCTCA      600

AAGTGCTGGG ATTACAGGCG TGACGACCGG GCCCGGCCGG GGTTTTTTTT GAGACGAAGT      660

TTTGCTCTGT TGCCCAGGCT GGAGCACAGT GGCGCGATCT CGGTTCACTG CAGCCTCTGC      720

CTCCTGGGTC AAGCGATTTT CAGCCTCAGC CTCCTGAGTA GCCAGGATTA TAGGCCCTCC      780

CACAGTCGAC TAATTTTTTG TGTTTTGGGG GGTTTTGTTT GTTTGTTTGT TTTTGAGATG      840

GAGTCTCGCT CTTTCGCCAG GCTGGAGCGC AGTGACGCCA TCTCGGCTCA CTGCAACCTT      900

CCCAGTTCAA GCGATTCTCC TGCCTCAGCT TCCTGAATAG CTGGGATTAC AGGCGCCCGC      960

CACCACGCCC AGCTAATGTT TGTATTTTTA GTAGAGACAA GGTTTCACCA TGCTGGCCAG     1020

GCTGGTCTCG AATTCCCGAC CTCAGGCAAT CTGCCCGCCT CGGCCTCCAA AGTGCTGGGA     1080

TTACAGGTAC GAGCCACCGC CCCTGGCCTA ATTTTTGTAT TTTTAGTAGA GACGGGTTTC     1140
```

(2) INFORMATION FOR SEQ ID NO: 210:

(i) SEQUENCE CHARACTERISTICS:
        (A) LENGTH: 1022 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 210:

```
CTCCCAAAGT GCTGGGATTA CAGGCGTGAG CCACCTCGCC CAGCCCATTT AGTGAATTCT       60

TAGACAACAC TGACAAATGG ACCCTGGAAA TCCCAGAAGC TGCCCTACGT GGCCACTGTT      120

GCTGGTGGGG TGAGCAGAGC CCCTTGCAGG CGGAAAACCT AAGGCTTTGC TCTCAGCTAC      180

TCGCACGGTC GGGCTGTGTG AGGTGACCCC CTACCCTCCT GGCCTCCGCG GAGCATGCTG      240

TCTGGGCCCG GTCGGTCCCT CTGCTGTGCG GTTAGACTGT GTCAGTCTGT ATTCTGCAGC      300

TGTAACAGAA CACCGCAGCT TGGGTAGTTT ACAAGGGAAA GAGATCCATG TGGCTCCTAG      360

TTCTGGAGGC TGGGAAGCCC AAGACCGAGG GGTGCATCCA TCGAGGGCCT CCCCACTGCG      420

TCATTCCATG GTGGAAGGCA GAAGGGCCAA GAGGAGGTGC CAGAGAGAGA AAGGGGCCCA      480

ACCCATCCTT TTCATGAGGA ACCCACTGCG GAGACAACGG TGTTAGTTTA CTCCGGAGAG      540

CCGAGCTCTC AAACCTAATC ACCTCTTAAT AGCATTGCAG TGCAGTGGCC GTTCAATTGC      600

AGCATGTGTT TTGGAGGAGA CATTAACCCG GCTGACTGTG TGTTGACGCA CCTGGGGCCA      660

GTCATTCCTG AGGACCCAGC TGGAGGGGGT TCCAGGGTTT TAGGGCAGAG AGGTTCAGCC      720

CAGCATTAGG CGTGTTAGTA AGAAAAAGGA ATGGAAGCAA AGTAAGCGTG TGTAAGAGAC      780

AGCACCGTGC AGCTAACAAA GTCACTCTTC CCAGGAAAGT AAGTTTTTAA AAACTCAATC      840

AATCAGTGCA ATCACAGAAA TATAAAAAAT GTATATAGAA GAACGGAAGG AACCACTGTC      900

AATATTTGGA TGTAGTCTAA TAGCAGGTGT GTGGATGATT TGATTTATTT TATCCTCAAC      960

TGGCTACTTC CCACCCACCC AACAATACAC TTAGTTCAAA CACACAACTT TTCTCTTCAC     1020

AG                                                                   1022
```

(2) INFORMATION FOR SEQ ID NO: 211:

(i) SEQUENCE CHARACTERISTICS:
        (A) LENGTH: 229 base pairs
        (B) TYPE: nucleic acid
        (C) STRANDEDNESS: double

```
         (D) TOPOLOGY: linear (ii) MOLECULE TYPE: DNA (genomic)

(xi) SEQUENCE DESCRIPTION: SEQ ID NO: 211:

GTGAGTGCCC GGCGACTGTT CCGATGACAC CATCCATGGG CCCTGCTGGC TTCCTGCCCA      60

CCTCTGGGCA ACCAGGCACC CTGCAGGCAC TGCCCAGATC CGAGATGTAA AAAAGCTTGC     120

TCTGGTCAAG GCTGGGCAAG ACGGCTCGTG CCGGCTGGGA AGAGCACGT CGGGGTGGCT      180

CTGGGCTCCT GGGCTGGCCC CTGACCCACC TTCCTCTGTT CCTCTGCAG                 229

(2) INFORMATION FOR SEQ ID NO: 212:

(i) SEQUENCE CHARACTERISTICS:
        (A) LENGTH: 144 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 212:

GTACGTCGCT TTTCCGGCTT TTCCAGCTTT CACAGGGTTG AGATCGTGTT TTTTCCGGAA      60

GGAAGTTACT TTGCGGGGTG ACGGTGGGAA TGCCTCACCG AGGCTGCCGC CCCCATGCTG     120

ACGAATGTGT GGGGTGAATT CCAG                                            144

(2) INFORMATION FOR SEQ ID NO: 213:

(i) SEQUENCE CHARACTERISTICS:
        (A) LENGTH: 547 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 213:

GTAAGTCAGC CACCTGCACC GGCTGCAGCG GGGCCCATCC CCGCCTGGGG GTCCCGTGCC      60

TGGGGCTACA CAGAAGCCAA CGTGCCACTG CTTTCCAGCC AAAGTGAGCC CCTAGCACTC     120

ACCCCGCCTG TTAGCCCTTG GGGGTCCACG TCCGCCTTGG GTCTGCTGTC CTCTGCACTA     180

GAGGATGGCC CACGCTCCCG CCCCGGATTC AACCAGATTC CCAGCACGCA GCAGACGCCC     240

TAAAGCCTGC TGAATGCAAT GGGTACAAGA ACAGCGGAGT GTGCCCCTGT GGCTGGCAGG     300

GCAGGTCCCT AAACACCCCC AAGGGCACTT CCTTCACCTT CCCACTCAGG CTTCTCAGGC     360

TCCAAGGGGT TGGGGTCCT TTCTAGCTCC AGCATTCATC ACCCCAAAGC AGTTAAACCA      420

TTTTCCATCA ATCAGAAGGA AAACTTGCTT CTGGAAGACA GCACCGAGTA GATATTTTAT     480

GCTTTACGTA ACAATACTTC TGATGATCCT CTCTCGAGTA AACGCCTGCA CCCTTGTTTT     540

CCCAAAG                                                               547

(2) INFORMATION FOR SEQ ID NO: 214:

(i) SEQUENCE CHARACTERISTICS:
        (A) LENGTH: 1419 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 214:
```

-continued

```
GTGAGTGTTT GACCCCATGA CACGGTCACC CTGCTGTAAA AATCCCTGAG ACTGACTTGT      60

TAGTAGGCGC TGCTTCTGGT GCCTGCCATG CGCCCTCAGG GGTAACCCCT GGAACGTGGG     120

GGCCTCTCAT GTTTTGGGGC CTAGCGCATG TTAACTCCTT GGTAATCCTG TGGGAACTGG     180

AACATTTTTA ACATGTGATG TTTTTCTCAA ATACCATTAG AACAATATTT GGCAGGGAGG     240

GATTGATTTA AAATGTGACG AAGGCTGGGC GCCGTGGCTC ACGCCTGTAA TCCCAACACT     300

TTGGGGGGCT GAGGTGGGCA GATCACGAGG TCGGGAGTTC AAGACCAGCC TGACCAACAT     360

GGTGAAACCC TGTCTCTACT AAAAATACAA AAATTAGCTG GCATGGTGG CACACGCCTG      420

TAATCCCAGC TACTCAGGAG GCTGAGGCAG GAGAATCTCT TGAACCCTGA AGGCAGAGGT     480

TGCAGCGAGC TGAGATCGCA GGATTGCACT CCAGCTTGGG CGACAGAGCG AGACTCCGTC     540

TCCATAAAAG AAAAAAAAAA TGTGAGGAAT GGCCGGGTGC GGTGGCTCAT GCCTGTAATC     600

CCAGCACGTT GGGAGGACGA GGCAGGTGGA TTACTGAAG TCAGGAGTTC AAGACCAGCC      660

TGGTCAACAT GGTGAAACCC CGCCTCTACT AAAAATACAA AATTAGCCAG GCAAAACACA     720

GATGTAAGAT TTGAATGACG CAATTAGAGG GATGTGAAAA TGCCCTTAGG TGAAGGATGG     780

GTGGAAAATC ATTTAAAACA TGATTACAAA ATATTAATAA ATACTCAACT GCTTAATAGG     840

CATAAATATT TTGAACAAAA CTAAAATCCC ATTTAAATTG GCTGCCAGAG GTCAGGGAGG     900

TGGTTCAGCC GTGCACGGCT CAGCAGCAGG CATAGGTTCT GACGGCTGTG CCACTGGGCG     960

GTTTCACTGT GGAACATCTG AGTTCACTTA CGCAAGCCCG GCCTCCTGCA CCCCTGGGCC    1020

GTGTGCCAGA GCCTGGGGTT TATGGCTGCA GACCTGCACA GCCTGTTACT GGGCTGGGTC    1080

TTGTGGGCGG TTCTAACCTG GTGGTGGGTA TCTGTGTTAA ATACATCCAA ACACGGGAAA    1140

GGAATGGTAA AAATTGGGTA TGATAATCTT AAGGGACCAC TGTCACCTAT GCGGTGCGTC    1200

GTCCACCTGC AGCCGTCCTG CAGTCTAAGA CTGTGTACAG GTGGGTCCCT CTCGTCGGGC    1260

CCCGTCAAGC CCTACGCGTG TGACATCTGT ACTTTTCTAA ATGTTTCCAC TTCAGTGAAA    1320

AGCTGGCACC CTGTTTGTTA CAAAGGTTGA TCAGACACCG CTGTGGTGTG GCTGCAACAG    1380

ATACTCTAAC CATATGTCTG TGTCCACACC TGGTGACAG                           1419
```

(2) INFORMATION FOR SEQ ID NO: 215:

(i) SEQUENCE CHARACTERISTICS:
        (A) LENGTH: 1773 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 215:

```
GTACGAGTCC ACGGCCAGCA AGGCTTCACT GGGTGACATC TCTTCCGCCA TCTTGTAGCT      60

TTATGTGGGG CGTGCTTGGG TTATGAATGG GTCTCTTTTC CTCTTCTCTT GGCAAAGCAG     120

TCTTAGAGAC AAGATTAGGA ATTGTCTCAA TAACCACTTT AATACATAAA AGTTTAATCG     180

GGGCTGGGCG CGGTGGCTTA CACCTGTAAT CCCAGCACTT TGGGAGGCTG AGGCAGACGG     240

ATAACCTGAG GTCAGCAGTT TGAGACCAGC CTGGCCAACA CAGTGAAACC CCATCTGTAT     300

TAAAAATACA AAAATGAGCC GGGCGTGGTG GCGGGCGCTG TAATCCCAGA TACTTGGGAG     360

GCTGAGACAA GAGAATCGCT TGAACCCGGG AGCGGAGGTT GCAGGTTGCA GTGAGCCAAG     420

ATGGCGCCAC TGCCTTCCAG CCTGGCGACA GAGCGAGACT CCATCTCAAA AAAAAAAGT      480

TTAATCAGTA AGCAGATCCT CCTGGATCTA TTTTAGCTAA GTCAATTTGG TTAGATTCTG     540
```

```
TTTAAGCTAC TCAGTATCTA TTTCAGTTAA AGTATAACAG AATTTTCTCT TAATTGACCT      600

GTGCATACGT TGAATATTTC CATTTCCAAT GTCAAAAATA AATGCTTTGC ACGGAGGGAG      660

GCACGCGAGG ATCCTTGGCA AAGGCCATCC CCTGCCCGCC CCTGTCTTAG CCTGGTGCCT      720

TCTCAAAACC AGGAGGCCTT AGACTCCAAG GATGTGTGTG TCCAGATGAG AAGGATCCCG      780

AACAGTCTTC GAGAAGGCAC CCGCTCCCAC CTCTGCCTGG GTGCCCTGGA GCCTTCTCCT      840

CTCCTCTCCT CCACGCACTC ACACTGCTCT CTGGATGCCC TGGAGCCCTC TCCTCTCCTC      900

CACCCACCCC ACCTCTCCCT GGGTGCCCTG GAGCCCTCTC CTCTCCTCCA CCCACCCCAC      960

CTCTCCCTGG GTGCCCTGGA GCCCTCTCCT CTCCTCCACC CACCCCACCT CTCCCTGGGT     1020

GCCCTGGAGC CCTGTCCTCC CCTCCATGCA CGCACGCTGC TCTCTGGGTG CCCTGGAGCC     1080

CTCTCCCCTT CTCCCCTCCA CGCACACACA CTGCTCTCTG GGTGCCCCAT GCTCCTGGAC     1140

TCTCCTTTGC TGACCTAGCT CTGCCTCTAC CTGGTGTCCA AACGCACAGG GGTCCCAGGC     1200

CCCAGCCACG TCTCTCGCCT GTGGCTCTGA ACAGCATCTG TGTTGCACTT GCTGGTGGAC     1260

AGCAGCCTCC CGGCCGCACC ATGCCCGCAC CATGCCCACA CCATGCCCGC ACCATTCTGG     1320

ACTTTGTCAC CTCATCTCAG TGAAGGGCTC TGACACCCCC CACTTAGGCG GCTGACTCCC     1380

TCTTCCCTCA CACCCAGGCC TCCCATGTTT CCACTGTCAT CACTCACCAA AGCCACCCCA     1440

CAACCCCCCA CTCCGGGCCC CCTGCTCACT CCAAATCCAC TCCTTACTCA CACAGCCCCC     1500

ACCAAACCCG CGTAAGTCAG AGTGCGGGTG TCCTCAGGAC GGCTCTGCAC CCCTGCCTGG     1560

GGCTGGCCGC GCCTGGCCTT CCCCGGACAC TCCCGACCGC CAGCCCCGCG GAGAGCCTTT     1620

GTGTGCCGTT CCCTCGGCCT CCCCACCCGC TGTGGCCTCT CCCCAAGTGA AGAGTGAGCA     1680

GATGGAAGAG CAGGGCTTGC CCACAGCTGG ATGTCAAGTC CCCCTGCTTT CAGTCCGGGC     1740

TGCAGCTGAA CTCACCTTTC TGCTCTGCCC AAG                                 1773

(2) INFORMATION FOR SEQ ID NO: 216:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 216:

ATCCTGAGGA CCCAGCTGCA C                                                 21

(2) INFORMATION FOR SEQ ID NO: 217:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 217:

GTTAGCGTCC GCTCATGCGT G                                                 21

(2) INFORMATION FOR SEQ ID NO: 218:

(i) SEQUENCE CHARACTERISTICS:
        (A) LENGTH: 23 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO: 218:

GACGGGAGTT TCTCCTCGGG GTC                                           23

(2) INFORMATION FOR SEQ ID NO: 219:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 219:

GAGTCTCCGG ATCATCCACG TC                                            22

(2) INFORMATION FOR SEQ ID NO: 220:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 220:

GCTGATGAGG AGCAGGCGAG                                               20

(2) INFORMATION FOR SEQ ID NO: 221:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 221:

ATCCAAGTGT GCCTCTTAGA C                                             21

(2) INFORMATION FOR SEQ ID NO: 222:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 222:

GTTTGCTAAT GCTGCTCCCG TC                                            22

(2) INFORMATION FOR SEQ ID NO: 223:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 223:

GTGCTGGAGG CCTCTGCCGA CGGGAGCAGC                    30

(2) INFORMATION FOR SEQ ID NO: 224:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 224:

GGCCTCGGGG GCCAGTGTCT C                             21

(2) INFORMATION FOR SEQ ID NO: 225:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 225:

GCCTCTGCCG ACGGGAGCAG C                             21

(2) INFORMATION FOR SEQ ID NO: 226:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 226:

AGGCTGTCCA GGGATGCCAT C                             21

(2) INFORMATION FOR SEQ ID NO: 227:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 227:

ACCTGGCCTC TTGTTTCTTC TC                            22

(2) INFORMATION FOR SEQ ID NO: 228:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 228:

CTGTAGGATT CTTGCAACTT TTCT                          24

(2) INFORMATION FOR SEQ ID NO: 229:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 229:

CACACCAGGA AGTGCATGAT GTCAG                                      25

(2) INFORMATION FOR SEQ ID NO: 230:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 230:

CTCCCAAGCT GTCTATACCA GCCGC                                      25

(2) INFORMATION FOR SEQ ID NO: 231:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 231:

ATAGGCGGCT GGTATAGACA G                                              21

(2) INFORMATION FOR SEQ ID NO: 232:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 232:

TCTCTGAGCA TCTCTCCTGC CCTCA                                      25

(2) INFORMATION FOR SEQ ID NO: 233:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 233:

CGTCTTCATA TGCCTCCTTG                                               20

(2) INFORMATION FOR SEQ ID NO: 234:

(i) SEQUENCE CHARACTERISTICS:

(A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 234:

AAGACCCAGG CCTGGGAGTT CTTCT                                        25

(2) INFORMATION FOR SEQ ID NO: 235:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 235:

CCCCTGGTGA GCCTGGCGAG                                              20

(2) INFORMATION FOR SEQ ID NO: 236:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 236:

CTGAGTATCG TTCCCAAATG TG                                           22

(2) INFORMATION FOR SEQ ID NO: 237:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 237:

CTGGGGCCCC CCAAACCTGA CCTGC                                        25

(2) INFORMATION FOR SEQ ID NO: 238:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 238:

GGCCATTAGA ACACACTCAC TG                                           22

(2) INFORMATION FOR SEQ ID NO: 239:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 239:

CTGAACCTGG GCTTCACTGC AC                                              22

(2) INFORMATION FOR SEQ ID NO: 240:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 240:

GATGTCCACT CTCTGGCCCT TG                                              22

(2) INFORMATION FOR SEQ ID NO: 241:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 241:

CAAAGGGATG GCGGTGATGA C                                               21

(2) INFORMATION FOR SEQ ID NO: 242:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 242:

CTGTAGATCA GAGAATAATG AG                                              22

(2) INFORMATION FOR SEQ ID NO: 243:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 243:

GTAAGAGGCT GTCTGAACAT C                                               21

(2) INFORMATION FOR SEQ ID NO: 244:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 244:

```
GTCAGATGAG ATGGGAGACA GC                                              22

(2) INFORMATION FOR SEQ ID NO: 245:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 245:

GGTGAGTGTG CCCAGTTCCA G                                               21

(2) INFORMATION FOR SEQ ID NO: 246:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 246:

CGTTAAGTCC ACTGAGCACT G                                               21

(2) INFORMATION FOR SEQ ID NO: 247:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 247:

GATCCCTGAG CTCTGGAAGG GGCTC                                           25

(2) INFORMATION FOR SEQ ID NO: 248:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 248:

GAGATGGCAG CTGCAAGTCA C                                               21

(2) INFORMATION FOR SEQ ID NO: 249:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 249:

GGGCGAGGTT ATGTTGGTCT G                                               21
```

(2) INFORMATION FOR SEQ ID NO: 250:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 250:

TTTGGGGAAC AGGGAGACAT GAACC                        25

(2) INFORMATION FOR SEQ ID NO: 251:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 251:

CTGATCATTG CTCTCCTGTC CCTGT                        25

(2) INFORMATION FOR SEQ ID NO: 252:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 252:

ACCAGGCTGT CCATCAGCAC                              20

(2) INFORMATION FOR SEQ ID NO: 253:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 253:

TAAGTGTCCC CGACTCAGTG TC                           22

(2) INFORMATION FOR SEQ ID NO: 254:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 254:

AGCCAGGGCG TGACGTAGGA G                             21

(2) INFORMATION FOR SEQ ID NO: 255:

(i) SEQUENCE CHARACTERISTICS:
        (A) LENGTH: 21 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 255:

AAGTATCCTG CCAGGCTTCA G                                              21

(2) INFORMATION FOR SEQ ID NO: 256:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 256:

GAAGAGGATG AGCTGAGAGT C                                              21

(2) INFORMATION FOR SEQ ID NO: 257:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 257:

CAAGGGTAAC AGCGTGAGTA C                                              21

(2) INFORMATION FOR SEQ ID NO: 258:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 258:

TGAGGCTGGG CCTCCAGTGT C                                              21

(2) INFORMATION FOR SEQ ID NO: 259:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 259:

GGCTCTGAGG CTGGCACAGG ATG                                            23

(2) INFORMATION FOR SEQ ID NO: 260:

(i) SEQUENCE CHARACTERISTICS:
        (A) LENGTH: 21 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 260:

GGAAACCACG GCTACCAGGT C                                              21

(2) INFORMATION FOR SEQ ID NO: 261:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 261:

CCGGACCCCC TGGCGAGCGT G                                              21

(2) INFORMATION FOR SEQ ID NO: 262:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 262:

CACAGGAACA GTTAGGGTCT C                                              21

(2) INFORMATION FOR SEQ ID NO: 263:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 263:

CCCAAGGTAA CCTCTCCTTG C                                              21

(2) INFORMATION FOR SEQ ID NO: 264:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 264:

GATCCGGAAC GCCTCATCCC AAGAC                                          25

(2) INFORMATION FOR SEQ ID NO: 265:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 265:

```
GTCTTGGGAT GAGGCGTTCC GGATC                                              25
```

(2) INFORMATION FOR SEQ ID NO: 266:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 266:

```
GTCCGGGGCG ACCATCTTGA C                                                  21
```

(2) INFORMATION FOR SEQ ID NO: 267:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 267:

```
GCCCTGGCAG CCCTGGTCCT G                                                  21
```

(2) INFORMATION FOR SEQ ID NO: 268:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 268:

```
TAGGGAGGCT GAGGTCCAGA AAGTG                                              25
```

(2) INFORMATION FOR SEQ ID NO: 269:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 269:

```
AGGGCCCAGC AAGAAGCACC TGC                                                23
```

(2) INFORMATION FOR SEQ ID NO: 270:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 270:

```
GCTGAGGACC GTGGCCTCTA GC                                                 22
```

(2) INFORMATION FOR SEQ ID NO: 271:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 271:

CCTGCAGGAG GGGTGCTAGA G                                              21

(2) INFORMATION FOR SEQ ID NO: 272:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 272:

CACAGAGAGA ACACTACAGT CAC                                            23

(2) INFORMATION FOR SEQ ID NO: 273:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 273:

CTGCTGTGAG TGTCCCTGAT G                                              21

(2) INFORMATION FOR SEQ ID NO: 274:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 274:

GGAGGGAAGG TTTAGAATCT G                                              21

(2) INFORMATION FOR SEQ ID NO: 275:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 275:

GGTGAGGCCT CATGGCTGTC                                                20

(2) INFORMATION FOR SEQ ID NO: 276:

(i) SEQUENCE CHARACTERISTICS:
        (A) LENGTH: 26 base pairs
        (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO: 276:

TGGCTGTCTG ATTAGCTAGG AGGCGG                                        26

(2) INFORMATION FOR SEQ ID NO: 277:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 277:

GGGTTCCTCT CTAATCACGG CCAGAC                                        26

(2) INFORMATION FOR SEQ ID NO: 278:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 278:

AGAAGGGAAG GACAGGGCAT GTGAAG                                        26

(2) INFORMATION FOR SEQ ID NO: 279:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 279:

CCTCTGGAGC AAGAGTAAGT AG                                            22

(2) INFORMATION FOR SEQ ID NO: 280:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 280:

ACCCCACACC CTATCTCCAT G                                             21

(2) INFORMATION FOR SEQ ID NO: 281:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 281:

TTTCTCAAGG CTTGTCGTTG GCCTTG                                    26

(2) INFORMATION FOR SEQ ID NO: 282:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 282:

GATTCAAAGG AGGCAGAGAT GGGAGC                                    26

(2) INFORMATION FOR SEQ ID NO: 283:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 283:

CCTCTCAGGA AACCCAGACA CAAGCA                                    26

(2) INFORMATION FOR SEQ ID NO: 284:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 284:

GTTCCCAGGT TGACAGCTCA G                                         21

(2) INFORMATION FOR SEQ ID NO: 285:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 285:

GTCCTGCCAA ACTGAGCTGT C                                         21

(2) INFORMATION FOR SEQ ID NO: 286:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 286:

ATTGGAGAGA TGCGTCTGAC AGGAGG                                    26

(2) INFORMATION FOR SEQ ID NO: 287:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 287:

CCCTGTCTGT GCCTTCACCC CTTGC                                              25

(2) INFORMATION FOR SEQ ID NO: 288:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 288:

CTTCTCCCCT GAGGATGGCT GAC                                                23

(2) INFORMATION FOR SEQ ID NO: 289:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 289:

TGCCTCCATT ACTGCTCCTC C                                                  21

(2) INFORMATION FOR SEQ ID NO: 290:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 290:

TGTAGGAGAG CACAGACGCA TCAAGC                                             26

(2) INFORMATION FOR SEQ ID NO: 291:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 291:

TGAGTGGCTT GGCCCTCTGT G                                                  21

(2) INFORMATION FOR SEQ ID NO: 292:

```
    (i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 292:

AGAGGGAGAA CAGCCAACTC ATCCG                                              25

(2) INFORMATION FOR SEQ ID NO: 293:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 293:

GAGTATCACC CGCCTCTCTG TTGAGC                                             26

(2) INFORMATION FOR SEQ ID NO: 294:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 294:

TCAGTCAGCC CCACCATCCT TCTG                                               24

(2) INFORMATION FOR SEQ ID NO: 295:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 295:

GTGGGGGCTG CCAGAAGGAT G                                                  21

(2) INFORMATION FOR SEQ ID NO: 296:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 296:

TGAGGTGCCA GACAGCAGCA CAG                                                23

(2) INFORMATION FOR SEQ ID NO: 297:

(i) SEQUENCE CHARACTERISTICS:
        (A) LENGTH: 26 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO: 297:

AGTGCCAGCT CAGATCTCTG CAGCTC                                            26

(2) INFORMATION FOR SEQ ID NO: 298:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 298:

GTCCGCTGGA GTCATCTCTA C                                                 21

(2) INFORMATION FOR SEQ ID NO: 299:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 299:

GAGAACAGAT TTGGTAGAGA TGAC                                              24

(2) INFORMATION FOR SEQ ID NO: 300:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 300:

CAGGGGAACC TTCGGCACCA G                                                 21

(2) INFORMATION FOR SEQ ID NO: 301:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 301:

CCCATGCCAG TACCCTCAGC ATGGC                                             25

(2) INFORMATION FOR SEQ ID NO: 302:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 302:

GGGAGAGCAG GGGAATATGG GTCAG                        25

(2) INFORMATION FOR SEQ ID NO: 303:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 303:

GCAACACTCC ATGACCACAG C                            21

(2) INFORMATION FOR SEQ ID NO: 304:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 304:

CCTGCCTGGG TGAAGTCCGA C                            21

(2) INFORMATION FOR SEQ ID NO: 305:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 305:

GGAGAGAGAG ATCCAGCAGA GGGGA                        25

(2) INFORMATION FOR SEQ ID NO: 306:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 306:

GGGACAAACT GTCAGGCGGA AGTTC                        25

(2) INFORMATION FOR SEQ ID NO: 307:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 307:

CATGCCTTCA GAACTCTACA G                            21

(2) INFORMATION FOR SEQ ID NO: 308:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 308:

GGGGAAAGAA TGACTATCCA G                                          21

(2) INFORMATION FOR SEQ ID NO: 309:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 309:

GTTGCCCACA CTGCCCTTGT C                                          21

(2) INFORMATION FOR SEQ ID NO: 310:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 310:

AACCCTTCTC CAGAGAGGCA AAGGG                                      25

(2) INFORMATION FOR SEQ ID NO: 311:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 311:

CCGTGGGGCC AGAGCCAGCA G                                          21

(2) INFORMATION FOR SEQ ID NO: 312:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 312:

GCACAGAGAG GGAAGAGAGT GGGGA                                      25

(2) INFORMATION FOR SEQ ID NO: 313:

(i) SEQUENCE CHARACTERISTICS:

(A) LENGTH: 21 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO: 313:

GCTGGTCCTG TTGTATGTAG C                                                 21

(2) INFORMATION FOR SEQ ID NO: 314:

(i) SEQUENCE CHARACTERISTICS:
                (A) LENGTH: 25 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO: 314:

CCAGCACCAT ATGGTAGGGG CACAT                                             25

(2) INFORMATION FOR SEQ ID NO: 315:

(i) SEQUENCE CHARACTERISTICS:
                (A) LENGTH: 25 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO: 315:

CCAGGGTCCC CATGCCCATA TGTGC                                             25

(2) INFORMATION FOR SEQ ID NO: 316:

(i) SEQUENCE CHARACTERISTICS:
                (A) LENGTH: 25 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO: 316:

CATGTCCCTT CTGAGCACTG GGCTA                                             25

(2) INFORMATION FOR SEQ ID NO: 317:

(i) SEQUENCE CHARACTERISTICS:
                (A) LENGTH: 26 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO: 317:

GGACCCTGGA CAGGAAGGCC AGCAGG                                            26

(2) INFORMATION FOR SEQ ID NO: 318:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO: 318:

GATGGAGAGA GGGCACTATG GC                                                    22

(2) INFORMATION FOR SEQ ID NO: 319:

(i) SEQUENCE CHARACTERISTICS:
                  (A) LENGTH: 26 base pairs
                  (B) TYPE: nucleic acid
                  (C) STRANDEDNESS: single
                  (D) TOPOLOGY: linear (ii) MOLECULE TYPE: DNA (genomic)

(xi) SEQUENCE DESCRIPTION: SEQ ID NO: 319:

GGGCTTTTTG GCCAGGCCAT AGTGCC                                                26

(2) INFORMATION FOR SEQ ID NO: 320:

(i) SEQUENCE CHARACTERISTICS:
                  (A) LENGTH: 29 base pairs
                  (B) TYPE: nucleic acid
                  (C) STRANDEDNESS: single
                  (D) TOPOLOGY: linear (ii) MOLECULE TYPE: DNA (genomic)

(xi) SEQUENCE DESCRIPTION: SEQ ID NO: 320:

GAGGGGGTTC AGTTTGGGTT GCTTGTCTG                                             29

(2) INFORMATION FOR SEQ ID NO: 321:

(i) SEQUENCE CHARACTERISTICS:
                  (A) LENGTH: 23 base pairs
                  (B) TYPE: nucleic acid
                  (C) STRANDEDNESS: single
                  (D) TOPOLOGY: linear (ii) MOLECULE TYPE: DNA (genomic)

(xi) SEQUENCE DESCRIPTION: SEQ ID NO: 321:

TTTTTCCTTT GCATTCATCT CTC                                                   23

(2) INFORMATION FOR SEQ ID NO: 322:

(i) SEQUENCE CHARACTERISTICS:
                  (A) LENGTH: 22 base pairs
                  (B) TYPE: nucleic acid
                  (C) STRANDEDNESS: single
                  (D) TOPOLOGY: linear (ii) MOLECULE TYPE: DNA (genomic)

(xi) SEQUENCE DESCRIPTION: SEQ ID NO: 322:

CATTGTTTCC TGTGTCTTCT GG                                                    22

(2) INFORMATION FOR SEQ ID NO: 323:

(i) SEQUENCE CHARACTERISTICS:
                  (A) LENGTH: 21 base pairs
                  (B) TYPE: nucleic acid
                  (C) STRANDEDNESS: single
                  (D) TOPOLOGY: linear (ii) MOLECULE TYPE: DNA (genomic)

(xi) SEQUENCE DESCRIPTION: SEQ ID NO: 323:

```
AGAGACAACT TCCCAAAGCA C                                              21

(2) INFORMATION FOR SEQ ID NO: 324:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 324:

AGGCCCCTTC CCCATGTCTA C                                              21

(2) INFORMATION FOR SEQ ID NO: 325:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 325:

AAGTCCGCGT ATCCACAAAG CTGAGCAT                                       28

(2) INFORMATION FOR SEQ ID NO: 326:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 326:

GCCACGTCCC TTCCCCCATT C                                              21

(2) INFORMATION FOR SEQ ID NO: 327:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 327:

AGTTGGAGGT ACTGGCCACG ACTG                                           24

(2) INFORMATION FOR SEQ ID NO: 328:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 328:

GCGTTTTCCC ACATGCCTGA G                                              21
```

(2) INFORMATION FOR SEQ ID NO: 329:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 329:

TGCTGATCCC TGCCATACTT TTGAC                                              25

(2) INFORMATION FOR SEQ ID NO: 330:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 330:

CTCTCCCTTC CAAGAGAAGA CATC                                               24

(2) INFORMATION FOR SEQ ID NO: 331:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 331:

GTGAAGGTAT ATTTGTATAC TACAC                                              25

(2) INFORMATION FOR SEQ ID NO: 332:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 332:

TGTTATCTTA AACATCAAAG CTAC                                               24

(2) INFORMATION FOR SEQ ID NO: 333:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 333:

CATTGTAGTT ACATCAGTCT TACC                                               24

(2) INFORMATION FOR SEQ ID NO: 334:

(i) SEQUENCE CHARACTERISTICS:
        (A) LENGTH: 24 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 334:

GCTTCTTCTG CAGTGCATTA CCTG                                              24

(2) INFORMATION FOR SEQ ID NO: 335:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 335:

TCCACCCTAC TTGCACATAG AAAGG                                             25

(2) INFORMATION FOR SEQ ID NO: 336:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 336:

GACAAGGGCT CACAAAGAGA ATGGG                                             25

(2) INFORMATION FOR SEQ ID NO: 337:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 337:

TCGGCCAAGT TTTTGACGTA CAGCT                                             25

(2) INFORMATION FOR SEQ ID NO: 338:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 338:

TGGCGTGGTA AAATGTGACA TAAAA                                             25

(2) INFORMATION FOR SEQ ID NO: 339:

(i) SEQUENCE CHARACTERISTICS:
        (A) LENGTH: 24 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO: 339:

GGGAGGAATA AAAACTATGG AATC                                          24

(2) INFORMATION FOR SEQ ID NO: 340:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 340:

GACCAGCTTC ACCAGGCTCA C                                            21

(2) INFORMATION FOR SEQ ID NO: 341:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 341:

GTACTGAAAG CTTGTAATGC CTC                                        23

(2) INFORMATION FOR SEQ ID NO: 342:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 342:

GGAGACCCAT CATTTCACTA AGG                                        23

(2) INFORMATION FOR SEQ ID NO: 343:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 343:

TGAACCTGGT CAAACTGTGA GTAC                                      24

(2) INFORMATION FOR SEQ ID NO: 344:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 344:

```
TGTCAGGCAT ATTCAGCTTT TGGCA                                              25

(2) INFORMATION FOR SEQ ID NO: 345:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 345:

ACCAAGATTC CCCCATTTGT GCTGA                                              25

(2) INFORMATION FOR SEQ ID NO: 346:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 346:

GTTGCTTATG GTATGCTTGC TGTC                                               24

(2) INFORMATION FOR SEQ ID NO: 347:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 347:

TTTGTCGCTC TGTGCTTAGA GG                                                 22

(2) INFORMATION FOR SEQ ID NO: 348:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 348:

CTTCCCTTTG GCAAACTCCA GGGAT                                              25

(2) INFORMATION FOR SEQ ID NO: 349:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 349:

GCTGGGACCT GGAACACTGG ACTTC                                              25

(2) INFORMATION FOR SEQ ID NO: 350:
```

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 350:

TGGAGGTCAT GGGGAATTTC AATCA                                              25

(2) INFORMATION FOR SEQ ID NO: 351:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 351:

GAACCTGGAT ATGTGGTACT ATCTG                                              25

(2) INFORMATION FOR SEQ ID NO: 352:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 352:

GAATACAATG CTGAAGGATA CAGTG                                              25

(2) INFORMATION FOR SEQ ID NO: 353:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 353:

CTTGTACAGG TTGGAAACTG AAC                                                23

(2) INFORMATION FOR SEQ ID NO: 354:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 354:

CCACGGGCAC CCTAAGAAGA                                                    20

(2) INFORMATION FOR SEQ ID NO: 355:

(i) SEQUENCE CHARACTERISTICS:
            (A) LENGTH: 21 base pairs
            (B) TYPE: nucleic acid

```
            (C) STRANDEDNESS: single
            (D) TOPOLOGY: linear (ii) MOLECULE TYPE: DNA (genomic)

(xi) SEQUENCE DESCRIPTION: SEQ ID NO: 355:

CCGTGGGCTT CCTGGTGAGA G                                            21

(2) INFORMATION FOR SEQ ID NO: 356:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 356:

TGGTAAAGTG TCTGAAATGA TGC                                          23

(2) INFORMATION FOR SEQ ID NO: 357:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 357:

CACCCTGGAT ACCATGAATG TC                                           22

(2) INFORMATION FOR SEQ ID NO: 358:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 358:

CTGCAAACAC AGTTCCAATC TTTCA                                        25

(2) INFORMATION FOR SEQ ID NO: 359:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 359:

CAGTAGCCAA GATGGCAGAA TC                                           22

(2) INFORMATION FOR SEQ ID NO: 360:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)
```

```
    (xi) SEQUENCE DESCRIPTION: SEQ ID NO: 360:

CCAGTAAGGC CGTTTGCTCC AG                                              22

(2) INFORMATION FOR SEQ ID NO: 361:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 361:

CGTTGGACCT CCTGTAAGTA G                                               21

(2) INFORMATION FOR SEQ ID NO: 362:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 362:

AAAATGCAGT GTGGTCCATT AGG                                             23

(2) INFORMATION FOR SEQ ID NO: 363:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 363:

TAATGTGTGC TGCCTCTACA GC                                              22

(2) INFORMATION FOR SEQ ID NO: 364:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 364:

CATATAGCAG ACGGGAGTGT AC                                              22

(2) INFORMATION FOR SEQ ID NO: 365:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 365:

CTTGAGCTTC TCTTTACCTT GAC                                             23
```

(2) INFORMATION FOR SEQ ID NO: 366:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 366:

CACCACTGGG ACCAGGAGGA C                        21

(2) INFORMATION FOR SEQ ID NO: 367:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 367:

CGTAAGTAGC TCTATCATCA C                        21

(2) INFORMATION FOR SEQ ID NO: 368:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 368:

AAGGCAGATG GAAAGCAGAT G                        21

(2) INFORMATION FOR SEQ ID NO: 369:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 369:

GGGTTGGGTG AAGTGTTTTG GCTTG                    25

(2) INFORMATION FOR SEQ ID NO: 370:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 370:

GAGGATGCTA AAGCTAATGA CAC                      23

(2) INFORMATION FOR SEQ ID NO: 371:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 371:

GCTGTCTATC ACTTACTTCC TAG                                                    23

(2) INFORMATION FOR SEQ ID NO: 372:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 372:

TCAAAAATGC AACTGTCAGC AAGAC                                                  25

(2) INFORMATION FOR SEQ ID NO: 373:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 373:

AAAAAGTCGG GGGAAAAGGT GCCTT                                                  25

(2) INFORMATION FOR SEQ ID NO: 374:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 374:

TCTCCCCTGC TCTGCTTTCA GTCCT                                                  25

(2) INFORMATION FOR SEQ ID NO: 375:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 375:

TTTCATCCGT GGCAGCATCA TAAGC                                                  25

(2) INFORMATION FOR SEQ ID NO: 376:

(i) SEQUENCE CHARACTERISTICS:
            (A) LENGTH: 22 base pairs
            (B) TYPE: nucleic acid
            (C) STRANDEDNESS: single (D) TOPOLOGY: linear (ii) MOLECULE TYPE: DNA (genomic)

(xi) SEQUENCE DESCRIPTION: SEQ ID NO: 376:

CTGAGACTGG ACTGATTCGC AG                                           22

(2) INFORMATION FOR SEQ ID NO: 377:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 377:

TGGAGCTGCA TGGTGATGGA TC                                           22

(2) INFORMATION FOR SEQ ID NO: 378:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 378:

TATCAGATGG TGTAAAAAAA AAAGTGTGGT TCTTAGATG                         39

(2) INFORMATION FOR SEQ ID NO: 379:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 379:

GCTTTCGTGG GAACCCACAA TGAGT                                        25

(2) INFORMATION FOR SEQ ID NO: 380:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 380:

TAGCAACGTA TGTCACCACT G                                            21

(2) INFORMATION FOR SEQ ID NO: 381:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 381:

TGGCCATCTC CATTTTCAGT C                                          21

(2) INFORMATION FOR SEQ ID NO: 382:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 382:

TGCTTCAGTC CTGAAATCAT GT                                         22

(2) INFORMATION FOR SEQ ID NO: 383:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 383:

GAGCTGTAAA TCACCATACC GTAC                                       24

(2) INFORMATION FOR SEQ ID NO: 384:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 384:

TGGCTCATTC TCTCCATCAG CAC                                        23

(2) INFORMATION FOR SEQ ID NO: 385:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 385:

TGCACTCATG TAGATACTGC CAGGT                                      25

(2) INFORMATION FOR SEQ ID NO: 386:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 386:

GACTTGTTGC AGGGTCATCA GTGGC                                      25

(2) INFORMATION FOR SEQ ID NO: 387:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 387:

AAACCAGGGC TCGGAAGCTA CACAA                                  25

(2) INFORMATION FOR SEQ ID NO: 388:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 388:

GGTCCACTGG AATCGGATTG CTGTT                                  25

(2) INFORMATION FOR SEQ ID NO: 389:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 389:

TCTCCCTCCT TTCAATAGCC CAGCC                                  25

(2) INFORMATION FOR SEQ ID NO: 390:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 390:

GTGAAAACTT GGGCATCCTT GTGCA                                  25

(2) INFORMATION FOR SEQ ID NO: 391:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 391:

GAATGGTAAG GAATCGAGAC ATTGC                                  25

(2) INFORMATION FOR SEQ ID NO: 392:

(i) SEQUENCE CHARACTERISTICS:

(A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 392:

AATTTGGAAA ATTCTCAATT CAACATAAAA AAAAATCCAA GTACGAAG                48

(2) INFORMATION FOR SEQ ID NO: 393:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 393:

GGAGTACCCT CCTTCTGAGA GTGGC                                        25

(2) INFORMATION FOR SEQ ID NO: 394:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 394:

ATTGCTGGGG CTCTTTGGGA CTAGG                                        25

(2) INFORMATION FOR SEQ ID NO: 395:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 395:

ACTCTGTGAG ATGTGCGTCA G                                            21

(2) INFORMATION FOR SEQ ID NO: 396:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 396:

GTTGGGGCCA GCAGGACCGA C                                            21

(2) INFORMATION FOR SEQ ID NO: 397:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 397:

GAAGCCCTGT AAGTAAGAAC CTG                                               23

(2) INFORMATION FOR SEQ ID NO: 398:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 398:

GTTACAGCTC TGGTATTCCG AC                                                22

(2) INFORMATION FOR SEQ ID NO: 399:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 399:

GATTTGCTGG TCCGGCTGTG AG                                                22

(2) INFORMATION FOR SEQ ID NO: 400:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 400:

CTTCCGTTAT TTTCCATCTT CTATC                                             25

(2) INFORMATION FOR SEQ ID NO: 401:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 401:

TGCGGGAATG ATCCACTTGA AGAAA                                             25

(2) INFORMATION FOR SEQ ID NO: 402:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 402:

TCGGAATTGC TCTGAATAGA ATGAA                                              25

(2) INFORMATION FOR SEQ ID NO: 403:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 403:

GAAATTCCCA TCTTACCCAA ATTCTTG                                            27

(2) INFORMATION FOR SEQ ID NO: 404:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 404:

GAAAAGCTGA CTTCAGACCA GGAG                                               24

(2) INFORMATION FOR SEQ ID NO: 405:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 405:

CATAAAGGAA GACAGGAGTT GC                                                 22

(2) INFORMATION FOR SEQ ID NO: 406:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 406:

GTGTGTGCTG GACAGATTTC CTGGC                                              25

(2) INFORMATION FOR SEQ ID NO: 407:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 407:

CTCACAATCT TCAAGCCAAC CTGTG                                              25

(2) INFORMATION FOR SEQ ID NO: 408:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 408:

TCTGTCACAT TTGAAGTGGC AGCTT                                                      25

(2) INFORMATION FOR SEQ ID NO: 409:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 409:

GGAGGGGAAG GTTAGCATTC CATCG                                                      25

(2) INFORMATION FOR SEQ ID NO: 410:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 410:

AAAGCCCATT CTTTGGCCTA AGCAA                                                      25

(2) INFORMATION FOR SEQ ID NO: 411:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 411:

AGGGTTCGTT ACTGAGCACT G                                                            21

(2) INFORMATION FOR SEQ ID NO: 412:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 412:

CCACGGGGCC ATGAGGACCA G                                                            21

(2) INFORMATION FOR SEQ ID NO: 413:

(i) SEQUENCE CHARACTERISTICS:
        (A) LENGTH: 20 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 413:

ATGGTCAACC CGGACACAAG                                               20

(2) INFORMATION FOR SEQ ID NO: 414:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 414:

CAACTTAGCT AGGCCCAAGA TAC                                           23

(2) INFORMATION FOR SEQ ID NO: 415:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 415:

CAACCCAGAT TGATGCTAAG CTTC                                          24

(2) INFORMATION FOR SEQ ID NO: 416:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 416:

GTATCAATTC TCAGCATGGA CTG                                           23

(2) INFORMATION FOR SEQ ID NO: 417:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 417:

GCAGATTACC AGCAGAGGTG AGAGC                                         25

(2) INFORMATION FOR SEQ ID NO: 418:

(i) SEQUENCE CHARACTERISTICS:
        (A) LENGTH: 25 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 418:

TGAAAATCCT TCTGAGCTGA AGGCC                                             25

(2) INFORMATION FOR SEQ ID NO: 419:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 419:

TCCCATTGAA TTTGGAAAAA AAAAAAATAT GTCTCTTGAC                              40

(2) INFORMATION FOR SEQ ID NO: 420:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 420:

GACACCAGGT ACATGTGAGC TG                                                22

(2) INFORMATION FOR SEQ ID NO: 421:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 421:

CAAGAGAAGA CAGTTCATCT CTG                                               23

(2) INFORMATION FOR SEQ ID NO: 422:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 422:

TGGGGCTAAC TTTAATGGGT TGTC                                              24

(2) INFORMATION FOR SEQ ID NO: 423:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 423:

```
GAACATGCTT CCGTGTGAAG CTC                                               23
```

(2) INFORMATION FOR SEQ ID NO: 424:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 424:

```
AGGGAAATGA GGTTGGGTGC TGGTT                                             25
```

(2) INFORMATION FOR SEQ ID NO: 425:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 425:

```
TGTTACTTAT GAGAGTCAGT ATCTTTC                                           27
```

(2) INFORMATION FOR SEQ ID NO: 426:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 426:

```
GTCCAATCAA TCCATCTTCT AATGTG                                            26
```

(2) INFORMATION FOR SEQ ID NO: 427:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 427:

```
CCCTTTTCCT AAGCTTGGAT CTGAG                                             25
```

(2) INFORMATION FOR SEQ ID NO: 428:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 428:

```
TTAACCCCCC TTTAGACCCC CCTTG                                             25
```

(2) INFORMATION FOR SEQ ID NO: 429:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 429:

GGACAGACAT CTTCAGAATG AC                                                22

(2) INFORMATION FOR SEQ ID NO: 430:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 430:

TTGCCCACAA TTTAAGCAAG TAG                                               23

(2) INFORMATION FOR SEQ ID NO: 431:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 431:

CCTTCCATTT CTTCTGCACA TCTAC                                             25

(2) INFORMATION FOR SEQ ID NO: 432:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 432:

TGTGGATCAC ACTCATGGGA AAGTG                                             25

(2) INFORMATION FOR SEQ ID NO: 433:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 433:

GTTCATAATA CAAAGGTGCT AAT                                               23

(2) INFORMATION FOR SEQ ID NO: 434:

(i) SEQUENCE CHARACTERISTICS:
            (A) LENGTH: 22 base pairs
            (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO: 434:

GAAACAAAGC TTCTGTGGAA CC                                              22

(2) INFORMATION FOR SEQ ID NO: 435:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 435:

CCTATAGCAC CTTGCCTGGA TC                                              22

(2) INFORMATION FOR SEQ ID NO: 436:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 436:

CACTGTTACC CTAGGACTAT G                                               21

(2) INFORMATION FOR SEQ ID NO: 437:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 437:

CTGGGCTCAG AGCGCTGC                                                   18

(2) INFORMATION FOR SEQ ID NO: 438:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 438:

ACAGACCCTT GGTTCTGAGG AC                                              22

(2) INFORMATION FOR SEQ ID NO: 439:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 439:

TTGAAAATAT GGAAGTATTT TCCATCTGCG G                                      31

(2) INFORMATION FOR SEQ ID NO: 440:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 440:

TGAAGGACTA TGAATGCCTC                                                   20

(2) INFORMATION FOR SEQ ID NO: 441:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 441:

TTATTTGGGA AGTTGTGGA AAG                                                23

(2) INFORMATION FOR SEQ ID NO: 442:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 442:

ATTAAGGTAC TGAAGATAGG CAGG                                              24

(2) INFORMATION FOR SEQ ID NO: 443:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 443:

GTAGCTTTTC TATAGGTCTG GCATC                                             25

(2) INFORMATION FOR SEQ ID NO: 444:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 444:

ACTGGGAATC AAACAAGGAG GAC                                               23

(2) INFORMATION FOR SEQ ID NO: 445:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 445:

CTGGGAAGGA GCAAGTTGGC                                    20

(2) INFORMATION FOR SEQ ID NO: 446:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 446:

CATCTGGGAC ATGCTGCACT CAGC                              24

(2) INFORMATION FOR SEQ ID NO: 447:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 447:

CAGTGTGCTC AACCAGTTCA AG                                22

(2) INFORMATION FOR SEQ ID NO: 448:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 448:

GCAAAGCACA GGCTCTCTTA GCG                               23

(2) INFORMATION FOR SEQ ID NO: 449:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 449:

GACGAAGTGC CACCTATGCT AG                                22

(2) INFORMATION FOR SEQ ID NO: 450:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 450:

CCTTTCTCAC AGCTCCCTCG AC                                              22

(2) INFORMATION FOR SEQ ID NO: 451:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 451:

GACGAAGTGC CACCTATGCT AG                                              22

(2) INFORMATION FOR SEQ ID NO: 452:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 452:

CCTTTCTCAC AGCTCCCTCG AC                                              22

(2) INFORMATION FOR SEQ ID NO: 453:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 453:

CTGGAAGGTA ACTTTTACCC CAC                                             23

(2) INFORMATION FOR SEQ ID NO: 454:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 454:

GGAGCCCTGG GAAAAGAATA GG                                              22

(2) INFORMATION FOR SEQ ID NO: 455:

(i) SEQUENCE CHARACTERISTICS:
        (A) LENGTH: 21 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 455:

CCCCATCTGT GAAGTGAGCT C                                              21

(2) INFORMATION FOR SEQ ID NO: 456:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 456:

CACAAAACAC ACACTTACTC GTAC                                           24

(2) INFORMATION FOR SEQ ID NO: 457:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 457:

ATACTTATGT AACCATCCTG TAGAC                                          25

(2) INFORMATION FOR SEQ ID NO: 458:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 458:

TATGGCTGCA TAGTATTCCA CATC                                           24

(2) INFORMATION FOR SEQ ID NO: 459:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 459:

CACCATAATG GGGTGTTTTA ATGC                                           24

(2) INFORMATION FOR SEQ ID NO: 460:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 460:

ATAAAAAGAT TTCACAATGG CAG                                                    23

(2) INFORMATION FOR SEQ ID NO: 461:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 461:

CAGTGCTTTC TTTAGAATGA GCATC                                                  25

(2) INFORMATION FOR SEQ ID NO: 462:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 462:

AACACCACTG AGTAGACCGT TAG                                                    23

(2) INFORMATION FOR SEQ ID NO: 463:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 463:

GGTCAAATGA GTTATTGTGT CATTGG                                                 26

(2) INFORMATION FOR SEQ ID NO: 464:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 464:

TGCAAGTGGA AATGTACAGT TAGG                                                   24

(2) INFORMATION FOR SEQ ID NO: 465:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 465:

CTATGCATGG CTGAGCTCGG TG                                                     22

(2) INFORMATION FOR SEQ ID NO: 466:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 466:

ACTTCTTGCC CTAAACAGAA CC                                         22

(2) INFORMATION FOR SEQ ID NO: 467:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 467:

GAGAACATGC CCATGAGTCA GG                                         22

(2) INFORMATION FOR SEQ ID NO: 468:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 468:

CTGAGTAGAT GCAAGCCACT AG                                         22

(2) INFORMATION FOR SEQ ID NO: 469:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 469:

TCACAAAGCG GGAGTCCTAG                                            20

(2) INFORMATION FOR SEQ ID NO: 470:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 470:

GGACTGAATA AGCACTACTC G                                           21

(2) INFORMATION FOR SEQ ID NO: 471:

(i) SEQUENCE CHARACTERISTICS:

(A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 471:

CTGATTTAGG GAAGCAGGAT CAC                                            23

(2) INFORMATION FOR SEQ ID NO: 472:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 472:

TGATGCATCT GCTTAGAACT TATC                                           24

(2) INFORMATION FOR SEQ ID NO: 473:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 473:

GCTTCTCTGT ATTTTCTGAA TGTTC                                          25

(2) INFORMATION FOR SEQ ID NO: 474:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 474:

AGGACACCAA GTTCATGTAA TGC                                            23

(2) INFORMATION FOR SEQ ID NO: 475:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 475:

CCATCAGAAG AATTCTCCTT GGAC                                           24

(2) INFORMATION FOR SEQ ID NO: 476:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 476:

GCAACAAGAG TGAAACTCCA TC                                          22

(2) INFORMATION FOR SEQ ID NO: 477:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 477:

GATAAAAAGT TATGTTTAAA TGGC                                        24

(2) INFORMATION FOR SEQ ID NO: 478:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 478:

GGAATTCAAG CGTGGTGTGG TCGGCCTG                                    28

(2) INFORMATION FOR SEQ ID NO: 479:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 479:

GGGGATCCCT CACCACGATC ACCACTCT                                    28

(2) INFORMATION FOR SEQ ID NO: 480:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 480:

TTGGTGACGT GGATGATACT TTC                                         23

(2) INFORMATION FOR SEQ ID NO: 481:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 481:

```
GACCAGGAAT TCCTCTAGCA C                                              21

(2) INFORMATION FOR SEQ ID NO: 482:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 482:

CAGTCACTCC AAGCCTCCTG                                                20

(2) INFORMATION FOR SEQ ID NO: 483:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 483:

CCATCCACAC CTGGCAAACC                                                20

(2) INFORMATION FOR SEQ ID NO: 484:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 484:

TATGTCCTGA GCTGTAGTCA TC                                             22

(2) INFORMATION FOR SEQ ID NO: 485:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 485:

GGAAATGCCA CACTCAGTTG GC                                             22

(2) INFORMATION FOR SEQ ID NO: 486:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 486:

AGTCAGCTGT TGGGACAATC C                                              21
```

(2) INFORMATION FOR SEQ ID NO: 487:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 487:

GAACTTATCA GATTAGGTAG CATGTC                                              26

(2) INFORMATION FOR SEQ ID NO: 488:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 488:

GGGAACTAGG AAGCATCTTC CTTAC                                               25

(2) INFORMATION FOR SEQ ID NO: 489:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 489:

CAAAGTATGC TTTCTGTAGC TAGG                                                24

(2) INFORMATION FOR SEQ ID NO: 490:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 490:

CAAATGTAAG AGATCCCAGT C                                                   21

(2) INFORMATION FOR SEQ ID NO: 491:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 491:

AAGTTAACAC CTACTGATTA CAACAGGTTA GAACTTCAGG AG                            42

(2) INFORMATION FOR SEQ ID NO: 492:

(i) SEQUENCE CHARACTERISTICS:
        (A) LENGTH: 22 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 492:

TTCAGGCAAA CCGGTAAGAC AC                                              22

(2) INFORMATION FOR SEQ ID NO: 493:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 493:

GATGAATGAA TGGAAGAACA TCC                                             23

(2) INFORMATION FOR SEQ ID NO: 494:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 494:

GCACTATGTA GGATGGCCTA TG                                              22

(2) INFORMATION FOR SEQ ID NO: 495:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 495:

ATGGATGCTA CAAACCACGC AG                                              22

(2) INFORMATION FOR SEQ ID NO: 496:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 496:

GGTTGTTTCT GCCTTCCGTG C                                               21

(2) INFORMATION FOR SEQ ID NO: 497:

(i) SEQUENCE CHARACTERISTICS:
        (A) LENGTH: 25 base pairs
        (B) TYPE: nucleic acid
        (C) STRANDEDNESS: single
        (D) TOPOLOGY: linear
```

```
   (ii) MOLECULE TYPE: DNA (genomic)

(xi) SEQUENCE DESCRIPTION: SEQ ID NO: 497:

TTTGCTTCTT AATCTCAACT CTGAG                                              25

(2) INFORMATION FOR SEQ ID NO: 498:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 498:

CATTATCCGT ACTTGTGCTT ATCC                                               24

(2) INFORMATION FOR SEQ ID NO: 499:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 499:

CACTCACTAT GAACACATTG AG                                                 22

(2) INFORMATION FOR SEQ ID NO: 500:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 500:

GGAATTCCTT GGCCCTGCTG GCAAGAGT                                           28

(2) INFORMATION FOR SEQ ID NO: 501:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 501:

AAGGATCCCA GGCGGAAGTT CCATTGGC                                           28

(2) INFORMATION FOR SEQ ID NO: 502:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 502:
```

GTGCCAGAGT TAATCTGTTC ATGG                     24

(2) INFORMATION FOR SEQ ID NO: 503:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 503:

GTTACATAAT GATTTCATAA AGCAG                    25

(2) INFORMATION FOR SEQ ID NO: 504:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 504:

TTTATATGAG TATGAAGCAG GCAC                     24

(2) INFORMATION FOR SEQ ID NO: 505:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 505:

GAGAAGCTGA TGCCTAGAAC AG                       22

(2) INFORMATION FOR SEQ ID NO: 506:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 506:

CACCTGGCTC CTTGCAGAGT C                        21

(2) INFORMATION FOR SEQ ID NO: 507:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 507:

TCTTGTTTAC CCTTGTGTAT CTAC                     24

(2) INFORMATION FOR SEQ ID NO: 508:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 508:

CCAATTTTGA AGATCTGGTG ACAC                                              24

(2) INFORMATION FOR SEQ ID NO: 509:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 509:

CATCTTATCT CACTGGATAT TCAG                                              24

(2) INFORMATION FOR SEQ ID NO: 510:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 510:

CTCACTACAA TCTAGTTTAT GGC                                               23

(2) INFORMATION FOR SEQ ID NO: 511:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 511:

TCAATTCAGG CTGTGTACTT GC                                                22

(2) INFORMATION FOR SEQ ID NO: 512:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 512:

TGAGCCATGC CCTCTGCCAG                                                   20

(2) INFORMATION FOR SEQ ID NO: 513:

(i) SEQUENCE CHARACTERISTICS:
            (A) LENGTH: 20 base pairs
            (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO: 513:

GTGTTTCTCA CCCAGGCTCC                                                    20

(2) INFORMATION FOR SEQ ID NO: 514:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 514:

AGGAGCGCCG GGAGACTCTG                                                    20

(2) INFORMATION FOR SEQ ID NO: 515:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 515:

GGGCTAGGGG TGTCAGTAGG                                                    20

(2) INFORMATION FOR SEQ ID NO: 516:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 516:

CACAGTGCCT GCTATACAGA AG                                                 22

(2) INFORMATION FOR SEQ ID NO: 517:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 517:

CCACAGCGCT CACAAAGTTC TC                                                 22

(2) INFORMATION FOR SEQ ID NO: 518:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 518:

ATTGCACGGC TTAGGGGACC                                               20

(2) INFORMATION FOR SEQ ID NO: 519:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 519:

ACAGAGATGG AACAAACATG AGCC                                          24

(2) INFORMATION FOR SEQ ID NO: 520:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 520:

GGTGAGTGCT TTATCCTCTT TGGC                                          24

(2) INFORMATION FOR SEQ ID NO: 521:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 521:

CAGTGAAGAT GCCAGAGCCA GG                                            22

(2) INFORMATION FOR SEQ ID NO: 522:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 522:

TGGAGGTTCC TAGGCCTTCA TG                                            22

(2) INFORMATION FOR SEQ ID NO: 523:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 523:

TTTCCCCGGC TCCTACTTCC                                               20

(2) INFORMATION FOR SEQ ID NO: 524:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 524:

GCGTTTGGGA GTGGCTGTAG                                                      20

(2) INFORMATION FOR SEQ ID NO: 525:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 525:

GAGGTCCAGC AAAACCAGGG                                                      20

(2) INFORMATION FOR SEQ ID NO: 526:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 526:

GCCCGGGCTT CCTGGTCCTC                                                      20

(2) INFORMATION FOR SEQ ID NO: 527:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 527:

GGCTGGCCCT GGGTCTCTGG                                                      20

(2) INFORMATION FOR SEQ ID NO: 528:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 528:

GTGCCTGTCT CTACCTTTGT GC                                               22

(2) INFORMATION FOR SEQ ID NO: 529:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 529:

ACCACCCAGC TTGCCAGCTT G                                         21

(2) INFORMATION FOR SEQ ID NO: 530:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 530:

GGCACTAGGG TAAGCTGGTA AG                                        22

(2) INFORMATION FOR SEQ ID NO: 531:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 531:

CTGAGAGGAG ACATGAAGAT GG                                        22

(2) INFORMATION FOR SEQ ID NO: 532:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 532:

GACCCCCGAC ATGGCAAAGT G                                         21

(2) INFORMATION FOR SEQ ID NO: 533:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 533:

CAGACACCCC CATCTCCGTG                                           20

(2) INFORMATION FOR SEQ ID NO: 534:

(i) SEQUENCE CHARACTERISTICS:
        (A) LENGTH: 20 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO: 534:

CACGGAGATG GGGGTGTCTG                                               20

(2) INFORMATION FOR SEQ ID NO: 535:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 535:

GGAGAGAGCT CAATACGAGG TC                                            22

(2) INFORMATION FOR SEQ ID NO: 536:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 536:

CCAGTGTCCA ACCAACTGTC C                                             21

(2) INFORMATION FOR SEQ ID NO: 537:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 537:

ATGACCAGAG ACATGCCGAC CTG                                           23

(2) INFORMATION FOR SEQ ID NO: 538:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 538:

ATCTGTAACA CAGGACTGTA GG                                            22

(2) INFORMATION FOR SEQ ID NO: 539:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 539:

ACAAGCTAGA GGCCTGAGCA GG                                              22

(2) INFORMATION FOR SEQ ID NO: 540:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 540:

GGGCATCAGA CAAGGTATCA TG                                              22

(2) INFORMATION FOR SEQ ID NO: 541:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 541:

TCAGTCCTGG CTGAACTCCA G                                               21

(2) INFORMATION FOR SEQ ID NO: 542:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 542:

CTTCCAGGAG CTGCCTTCTG                                                 20

(2) INFORMATION FOR SEQ ID NO: 543:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 543:

ATCCAGGTCA CACAGGCTCA G                                               21

(2) INFORMATION FOR SEQ ID NO: 544:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 544:

CCTACAGCTA CAGCCACAGA G                                               21

(2) INFORMATION FOR SEQ ID NO: 545:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 545:

GTGCCTTGTC CTGCCCAGTA C                                        21

(2) INFORMATION FOR SEQ ID NO: 546:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 546:

CTCTGGGACC TAGAGGCCAC                                        20

(2) INFORMATION FOR SEQ ID NO: 547:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 547:

CATTTCCTGA GGTTATGGAG C                                        21

(2) INFORMATION FOR SEQ ID NO: 548:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 548:

CTGCAGCTGT CTCAGAGGAA CAG                                    23

(2) INFORMATION FOR SEQ ID NO: 549:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 549:

CCCCAGGCTC TTGGAGTCTA G                                        21

(2) INFORMATION FOR SEQ ID NO: 550:

(i) SEQUENCE CHARACTERISTICS:

(A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 550:

TGGATCTCAG TTTCCCTACC TG                                              22

(2) INFORMATION FOR SEQ ID NO: 551:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 551:

CAAGAGGTGG TGATTGAGCA AGAGC                                           25

(2) INFORMATION FOR SEQ ID NO: 552:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 552:

GTTCATCATG CCGTGGCTGG AC                                              22

(2) INFORMATION FOR SEQ ID NO: 553:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 553:

CAGGCTGAGG AGTGCATGAT GG                                              22

(2) INFORMATION FOR SEQ ID NO: 554:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 554:

GCTCATCTGG TTCCAGGCTC TG                                              22

(2) INFORMATION FOR SEQ ID NO: 555:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 555:

GAGCCAGACT AACTCGGAGC TC                                    22

(2) INFORMATION FOR SEQ ID NO: 556:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 556:

ACCATGGAAC AGGTGGTCTG G                                     21

(2) INFORMATION FOR SEQ ID NO: 557:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 557:

GCAGATGCTG TATCCAGCAG TG                                    22

(2) INFORMATION FOR SEQ ID NO: 558:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 558:

CTTTGCTGGT CTGCCAAGTG G                                     21

(2) INFORMATION FOR SEQ ID NO: 559:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 559:

CTTGTCTCCT TTGACGCCTG G                                     21

(2) INFORMATION FOR SEQ ID NO: 560:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 560:

```
GAGGTTGTGA CCTTCTCTTT CC                                            22

(2) INFORMATION FOR SEQ ID NO: 561:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 561:

GACCAGACCA GAACCCTGAG                                               20

(2) INFORMATION FOR SEQ ID NO: 562:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 562:

GGGGTGTGGC CGAAAGTTAG G                                             21

(2) INFORMATION FOR SEQ ID NO: 563:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 563:

CAAGGAGCAG CGGTCACGAA G                                             21

(2) INFORMATION FOR SEQ ID NO: 564:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 564:

CCGGAATTCC TGGCCAAGAG CTCATGCT                                      28

(2) INFORMATION FOR SEQ ID NO: 565:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 565:

AAGGATCCCC TCCTATCCCA CAGCACAG                                      28
```

(2) INFORMATION FOR SEQ ID NO: 566:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 566:

```
GGAATTCAAG CGTGGTGTGG TCGGCCTGGG GGATCCCTCA CCACGATCAC CACTCTGGAA      60
TTCCTTGGCC CTGCTGGCAA GAGTAAGGAT CCCAGGCGGA AGTTCCATTG GCCCGGAATT     120
CCTGGCCAAG AGCTCATGCT AAGGATCCCC TCCTATCCCA CAGCACAGAT GGATCCATGC     180
TGTGCTGTGG GATAGGATGA TTTCCGTTGA GTCCATCTTT GCCA                     224
```

(2) INFORMATION FOR SEQ ID NO: 567:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 567:

```
ATGATTTCCG TTGAGTCCAT CTTTGCCA                                        28
```

(2) INFORMATION FOR SEQ ID NO: 568:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 568:

```
AACACCAGAG TCTCCTCCAT G                                               21
```

(2) INFORMATION FOR SEQ ID NO: 569:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 569:

```
CAGATTTTCA GACAAGTGAA CACG                                            24
```

(2) INFORMATION FOR SEQ ID NO: 570:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 570:

```
AGGTGGTGCT TTTCTGTCTG C                                               21
```

(2) INFORMATION FOR SEQ ID NO: 571:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 571:

CCGGGGAAGG GTCTGTATGT CA                            22

(2) INFORMATION FOR SEQ ID NO: 572:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 572:

TTTAACAAGC CCTGCGTGAC C                             21

(2) INFORMATION FOR SEQ ID NO: 573:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 573:

CCACACGTCA TTAATTCCCA AGC                           23

(2) INFORMATION FOR SEQ ID NO: 574:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 574:

TCTCCTATGG TGTTTTGGCC TC                            22

(2) INFORMATION FOR SEQ ID NO: 575:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 575:

TAGGACTCCT GAGTCCCAGA C                             21

(2) INFORMATION FOR SEQ ID NO: 576:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 576:

AGGTGGGCCC GGCTGAATGG                                                    20

(2) INFORMATION FOR SEQ ID NO: 577:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 577:

GGCGCTGGCG ACTCCTCTCC                                                    20

(2) INFORMATION FOR SEQ ID NO: 578:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 578:

CCGAGGAGAG CGGCGGTCGT C                                                  21

(2) INFORMATION FOR SEQ ID NO: 579:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 579:

CTCTCCATCA GGCCGGGGAG C                                                  21

(2) INFORMATION FOR SEQ ID NO: 580:

(i) SEQUENCE CHARACTERISTICS:
           (A) LENGTH: 22 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 580:

CTGATTTGGA GGCCAGCGCT GC                                                 22

(2) INFORMATION FOR SEQ ID NO: 581:

(i) SEQUENCE CHARACTERISTICS:
           (A) LENGTH: 22 base pairs
           (B) TYPE: nucleic acid
           (C) STRANDEDNESS: single (D) TOPOLOGY: linear (ii) MOLECULE TYPE: DNA (genomic)

(xi) SEQUENCE DESCRIPTION: SEQ ID NO: 581:

CAGGCCTGCT CCAAGCCCTC TG                                              22

(2) INFORMATION FOR SEQ ID NO: 582:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 582:

TGAGCCGGGT CTGCCAGACA G                                               21

(2) INFORMATION FOR SEQ ID NO: 583:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 583:

TGAGCAGGCC CAGCTGGACA AC                                              22

(2) INFORMATION FOR SEQ ID NO: 584:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 584:

CACCAAGGGA AGGGTCCGTG C                                               21

(2) INFORMATION FOR SEQ ID NO: 585:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 585:

CTACCAGCTC CTTGGCCTTG TGG                                             23

(2) INFORMATION FOR SEQ ID NO: 586:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 586:

GACCCTGTTG TCCTGGGAGT TGG        23

(2) INFORMATION FOR SEQ ID NO: 587:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 587:

GCTCCGGAGA GGCTGCAGAT G        21

(2) INFORMATION FOR SEQ ID NO: 588:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 588:

CTCTCCGGAG CTGGTGCCTG G        21

(2) INFORMATION FOR SEQ ID NO: 589:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 589:

CAAGTATGGG GTGGTCAGAT GGC        23

(2) INFORMATION FOR SEQ ID NO: 590:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 590:

TGGGGGTGGG GCTTCTCAGG        20

(2) INFORMATION FOR SEQ ID NO: 591:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 591:

GGATCATTGG CCAGGGCTTC TACC        24

(2) INFORMATION FOR SEQ ID NO: 592:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 592:

CCAGACCCGA CCTCAGGACG C                                           21

(2) INFORMATION FOR SEQ ID NO: 593:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 593:

GGCCAAGTTA GGGTTAGGAG ATC                                         23

(2) INFORMATION FOR SEQ ID NO: 594:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 594:

GGAAGGTTGT GGTCCGTCAG AG                                          22

(2) INFORMATION FOR SEQ ID NO: 595:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 595:

CTGTCTGCTC TGAGCTCCTG TC                                          22

(2) INFORMATION FOR SEQ ID NO: 596:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 596:

GACCCCTGCG TCGACGTCC                                              19

(2) INFORMATION FOR SEQ ID NO: 597:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 597:

CTGGCCTAGC TTTCTTCCTG                                            20

(2) INFORMATION FOR SEQ ID NO: 598:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 598:

GACCCTGCAG GCCTCACTTC A                                          21

(2) INFORMATION FOR SEQ ID NO: 599:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 599:

CTCGCCCCGG CCACAGACAC AA                                         22

(2) INFORMATION FOR SEQ ID NO: 600:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 600:

GCTGCTTGGG CTTGAGTAGG GTG                                        23

(2) INFORMATION FOR SEQ ID NO: 601:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 601:

CTTGAGGTCA GCAGCCTTGG CAG                                        23

(2) INFORMATION FOR SEQ ID NO: 602:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 602:

CTGCCAAGGC TGCTGACCTC AAG                                              23

(2) INFORMATION FOR SEQ ID NO: 603:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 603:

GGCTGAGGGC TCATGGAAGA C                                                21

(2) INFORMATION FOR SEQ ID NO: 604:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 604:

GGAGACTACT AGGTGGCATC T                                                21

(2) INFORMATION FOR SEQ ID NO: 605:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 605:

CCAGGGAACA GCTCAGCCAG AG                                               22

(2) INFORMATION FOR SEQ ID NO: 606:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 606:

CCTCCAGCCA TCTCTGACCA C                                                21

(2) INFORMATION FOR SEQ ID NO: 607:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 607:

GCAGTCTCAC TCCCAAGTGT G                           21

(2) INFORMATION FOR SEQ ID NO: 608:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 608:

GCCGCTGCCC ACCATAGCTC C                           21

(2) INFORMATION FOR SEQ ID NO: 609:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 609:

CTGAATGCCA TCTCCACCTG TAC                         23

(2) INFORMATION FOR SEQ ID NO: 610:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 610:

CACCGAGGTA GCACTGGTTG CC                          22

(2) INFORMATION FOR SEQ ID NO: 611:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 611:

GCGACCAGCC TCTCCCTGTG AG                          22

(2) INFORMATION FOR SEQ ID NO: 612:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 612:

CCCGACGGGC CTTACTCAT                              19

(2) INFORMATION FOR SEQ ID NO: 613:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 613:

CCAACATGGG CCACTGAGC                                      19

(2) INFORMATION FOR SEQ ID NO: 614:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 614:

CCTCACCTCA GGTCCACAAG GC                                 22

(2) INFORMATION FOR SEQ ID NO: 615:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 615:

GTCTGGGGCG CCGCAGATAC TC                                 22

(2) INFORMATION FOR SEQ ID NO: 616:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 616:

GTATGTGGCT GCAGCGCTTT CT                                 22

(2) INFORMATION FOR SEQ ID NO: 617:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 617:

GGCCCATCAA GGCAACCAAA T                                   21

(2) INFORMATION FOR SEQ ID NO: 618:

(i) SEQUENCE CHARACTERISTICS:
        (A) LENGTH: 22 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 618:

GTATGTGGCT GCAGCGCTTT CT                                              22

(2) INFORMATION FOR SEQ ID NO: 619:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 619:

GGCCCATCAA GGCAACCAAA T                                               21

(2) INFORMATION FOR SEQ ID NO: 620:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 620:

GAACCGGCTC CTGTGTCCA                                                  19

(2) INFORMATION FOR SEQ ID NO: 621:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 621:

GGTCCTGGCT CGTCAGTGC                                                  19

(2) INFORMATION FOR SEQ ID NO: 622:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 622:

GTATGGGCAC TGACGAGCCA GGAC                                            24

(2) INFORMATION FOR SEQ ID NO: 623:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 623:

GGGGGTGGGG GACTGTGGTA                                                        20

(2) INFORMATION FOR SEQ ID NO: 624:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 624:

GCCGGTGTTC ACAGAAGCCC                                                        20

(2) INFORMATION FOR SEQ ID NO: 625:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 625:

CTGACAGACA CGGCAAGAGG AGA                                                    23

(2) INFORMATION FOR SEQ ID NO: 626:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 626:

GGCCTCGACC TTAAGATGAA C                                                      21

(2) INFORMATION FOR SEQ ID NO: 627:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 627:

GCCGATCTTC CACCGGGAGC T                                                      21

(2) INFORMATION FOR SEQ ID NO: 628:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 628:

```
CCTCAACTGG CTACTTCCCA CC                                              22

(2) INFORMATION FOR SEQ ID NO: 629:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 629:

CATCTCGGAT CTGGGCAGTG CC                                              22

(2) INFORMATION FOR SEQ ID NO: 630:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 630:

GCTCTGGTCA AGGCTGGGCA AG                                              22

(2) INFORMATION FOR SEQ ID NO: 631:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 631:

CGTCACCCCG CAAAGTAACT TCC                                             23

(2) INFORMATION FOR SEQ ID NO: 632:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 632:

GGAAGTTACT TTGCGGGGTG ACG                                             23

(2) INFORMATION FOR SEQ ID NO: 633:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 633:

CTAGTGCAGA GGACAGCAGA C                                               21

(2) INFORMATION FOR SEQ ID NO: 634:
```

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 634:

CTGGAAGACA GCACCGAGTA GA                                                    22

(2) INFORMATION FOR SEQ ID NO: 635:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 635:

GCGCCTACTA ACAAGTCAGT CTC                                                   23

(2) INFORMATION FOR SEQ ID NO: 636:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 636:

CCTACGCGTG TGACATCTGT AC                                                    22

(2) INFORMATION FOR SEQ ID NO: 637:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 637:

GACCCATTCA TAACCCAAGC AC                                                    22

(2) INFORMATION FOR SEQ ID NO: 638:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 638:

GAGCAGATGG AAGAGCAGGG CTTG                                                  24

(2) INFORMATION FOR SEQ ID NO: 639:

(i) SEQUENCE CHARACTERISTICS:
            (A) LENGTH: 22 base pairs
            (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO: 639:

GTGCTTCGGG CGTCCTTGTC AC                                         22

(2) INFORMATION FOR SEQ ID NO: 640:

(i) SEQUENCE CHARACTERISTICS:
        (A) LENGTH: 6246 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 640:

CTCCCAAAGT GCTGGGATTA CAGGCGTGAG CCACCTCGCC CAGCCCATTT AGTGAATTCT      60

TAGACAACAC TGACAAATGG ACCCTGGAAA TCCCAGAAGC TGCCCTACGT GGCCACTGTT     120

GCTGGTGGGG TGAGCAGAGC CCCTTGCAGG CGGAAAACCT AAGGCTTTGC TCTCAGCTAC     180

TCGCACGGTC GGGCTGTGTG AGGTGACCCC CTACCCTCCT GGCCTCCGCG GAGCATGCTG     240

TCTGGGCCCG GTCGGTCCCT CTGCTGTGCG GTTAGACTGT GTCAGTCTGT ATTCTGCAGC     300

TGTAACAGAA CACCGCAGCT TGGGTAGTTT ACAAGGGAAA GAGATCCATG TGGCTCCTAG     360

TTCTGGAGGC TGGGAAGCCC AAGACCGAGG GGTGCATCCA TCGAGGGCCT CCCCACTGCG     420

TCATTCCATG GTGGAAGGCA GAAGGGCCAA GAGGAGGTGC CAGAGAGAGA AAGGGGCCCA     480

ACCCATCCTT TTCATGAGGA ACCCACTGCG GAGACAACGG TGTTAGTTTA CTCCGGAGAG     540

CCGAGCTCTC AAACCTAATC ACCTCTTAAT AGCATTGCAG TGCAGTGGCC GTTCAATTGC     600

AGCATGTGTT TTGGAGGAGA CATTAACCCG GCTGACTGTG TGTTGACGCA CCTGGGGCCA     660

GTCATTCCTG AGGACCCAGC TGGAGGGGGT TCCAGGGTTT TAGGGCAGAG AGGTTCAGCC     720

CAGCATTAGG CGTGTTAGTA AGAAAAAGGA ATGGAAGCAA AGTAAGCGTG TGTAAGAGAC     780

AGCACCGTGC AGCTAACAAA GTCACTCTTC CCAGGAAAGT AAGTTTTTAA AAACTCAATC     840

AATCAGTGCA ATCACAGAAA TATAAAAAAT GTATATAGAA GAACGGAAGG AACCACTGTC     900

AATATTTGGA TGTAGTCTAA TAGCAGGTGT GTGGATGATT TGATTTATTT TATCCTCAAC     960

TGGCTACTTC CCACCCACCC AACAATACAC TTAGTTCAAA CACACAACTT TTCTCTTCAC    1020

AGGGTCCCAG CGGCCTGGTC GGACCCAAAG GAGAGGTGAG TGCCCGGCGA CTGTTCCGAT    1080

GACACCATCC ATGGGCCCTG CTGGCTTCCT GCCCACCTCT GGGCAACCAG GCACCCTGCA    1140

GGCACTGCCC AGATCCGAGA TGTAAAAAAG CTTGCTCTGG TCAAGGCTGG GCAAGACGGC    1200

TCGTGCCGGC TGGGAAAGAG CACGTCGGGG TGGCTCTGGG CTCCTGGGCT GGCCCCTGAC    1260

CCACCTTCCT CTGTTCCTCT GCAGTCTGGC AGTCGAGGGG AGCTGGGCCC CAAAGGCACC    1320

CAGGGTCCCA ACGGCACCAG CGGTGTTCAG GGTGTCCCCG GCCCCCCGG TCCTCTGGGC     1380

CTGCAGGGCG TCCCGGGTGT TCCTGGCATC ACGGGGAAGC CGGGAGTTCC GGTACGTCGC    1440

TTTTCCGGCT TTTCCAGCTT TCACAGGGTT GAGATCGTGT TTTTTCCGGA AGGAAGTTAC    1500

TTTGCGGGGT GACGGTGGGA ATGCCTCACC GAGGCTGCCG CCCCCATGCT GACGAATGTG    1560

TGGGGTGAAT TCCAGGGGAA GGAGGCCAGC GAGCAGCGCA TCAGGGAGCT GTGTGGGGGG    1620

ATGATCAGCG GTAAGTCAGC CACCTGCACC GGCTGCAGCG GGGCCCATCC CCGCCTGGGG    1680

GTCCCGTGCC TGGGGCTACA CAGAAGCCAA CGTGCCACTG CTTTCCAGCC AAAGTGAGCC    1740
```

```
CCTAGCACTC ACCCCGCCTG TTAGCCCTTG GGGGTCCACG TCCGCCTTGG GTCTGCTGTC    1800

CTCTGCACTA GAGGATGGCC CACGCTCCCG CCCCGGATTC AACCAGATTC CCAGCACGCA    1860

GCAGACGCCC TAAAGCCTGC TGAATGCAAT GGGTACAAGA ACAGCGGAGT GTGCCCCTGT    1920

GGCTGGCAGG GCAGGTCCCT AAACACCCCC AAGGGCACTT CCTTCACCTT CCCACTCAGG    1980

CTTCTCAGGC TCCAAGGGGT TGGGGGTCCT TTCTAGCTCC AGCATTCATC ACCCCAAAGC    2040

AGTTAAACCA TTTTCCATCA ATCAGAAGGA AAACTTGCTT CTGGAAGACA GCACCGAGTA    2100

GATATTTTAT GCTTTACGTA ACAATACTTC TGATGATCCT CTCTCGAGTA AACGCCTGCA    2160

CCCTTGTTTT CCCAAAGAAC AAATTGCACA GTTAGCCGCG CACCTAAGGA AGCCTTTGGC    2220

ACCCGGGTCC ATTGGTCGGC CCGGTCCAGC TGGCCCCCCT GGGCCCCCAG GACCCCCAGG    2280

CTCCATTGGT CACCCTGGCG CTCGAGGACC CCCCGGATAC CGCGGTCCCA CTGGGGAGCT    2340

GGGAGACCCC GGGCCCAGAG GTGAGTGTTT GACCCCATGA CACGGTCACC CTGCTGTAAA    2400

AATCCCTGAG ACTGACTTGT TAGTAGGCGC TGCTTCTGGT GCCTGCCATG CGCCCTCAGG    2460

GGTAACCCCT GGAACGTGGG GGCCTCTCAT GTTTTGGGGC CTAGCGCATG TTAACTCCTT    2520

GGTAATCCTG TGGGAACTGG AACATTTTTA ACATGTGATG TTTTTCTCAA ATACCATTAG    2580

AACAATATTT GGCAGGGAGG GATTGATTTA AAATGTGACG AAGGCTGGGC GCCGTGGCTC    2640

ACGCCTGTAA TCCCAACACT TTGGGGGGCT GAGGTGGGCA GATCACGAGG TCGGGAGTTC    2700

AAGACCAGCC TGACCAACAT GGTGAAACCC TGTCTCTACT AAAAATACAA AAATTAGCTG    2760

GGCATGGTGG CACACGCCTG TAATCCCAGC TACTCAGGAG GCTGAGGCAG GAGAATCTCT    2820

TGAACCCTGA AGGCAGAGGT TGCAGCGAGC TGAGATCGCA GGATTGCACT CCAGCTTGGG    2880

CGACAGAGCG AGACTCCGTC TCCATAAAAG AAAAAAAAAA TGTGAGGAAT GGCCGGGTGC    2940

GGTGGCTCAT GCCTGTAATC CCAGCACGTT GGGAGGACGA GGCAGGTGGA TTACTGGAAG    3000

TCAGGAGTTC AAGACCAGCC TGGTCAACAT GGTGAAACCC CGCCTCTACT AAAAATACAA    3060

AATTAGCCAG GCAAAACACA GATGTAAGAT TTGAATGACG CAATTAGAGG GATGTGAAAA    3120

TGCCCTTAGG TGAAGGATGG GTGGAAAATC ATTTAAAACA TGATTACAAA ATATTAATAA    3180

ATACTCAACT GCTTAATAGG CATAAATATT TTGAACAAAA CTAAAATCCC ATTTAAATTG    3240

GCTGCCAGAG GTCAGGGAGG TGGTTCAGCC GTGCACGGCT CAGCAGCAGG CATAGGTTCT    3300

GACGGCTGTG CCACTGGGCG GTTTCACTGT GGAACATCTG AGTTCACTTA CGCAAGCCCG    3360

GCCTCCTGCA CCCCTGGGCC GTGTGCCAGA GCCTGGGGTT TATGGCTGCA GACCTGCACA    3420

GCCTGTTACT GGGCTGGGTC TTGTGGGCGG TTCTAACCTG GTGGTGGGTA TCTGTGTTAA    3480

ATACATCCAA ACACGGGAAA GGAATGGTAA AAATTGGGTA TGATAATCTT AAGGGACCAC    3540

TGTCACCTAT GCGGTGCGTC GTCCACCTGC AGCCGTCCTG CAGTCTAAGA CTGTGTACAG    3600

GTGGGTCCCT CTCGTCGGGC CCCGTCAAGC CCTACGCGTG TGACATCTGT ACTTTTCTAA    3660

ATGTTTCCAC TTCAGTGAAA AGCTGGCACC CTGTTTGTTA CAAAGGTTGA TCAGACACCG    3720

CTGTGGTGTG GCTGCAACAG ATACTCTAAC CATATGTCTG TGTCCACACC TGGTGACAGG    3780

AAACCAGGGT GACAGAGGAG ACAAAGGCGC GGCAGGAGCA GGGCTGGACG GGCCTGAAGG    3840

AGACCAGGGG CCCCAAGGTA CGAGTCCACG GCCAGCAAGG CTTCACTGGG TGACATCTCT    3900

TCCGCCATCT TGTAGCTTTA TGTGGGCGT GCTTGGGTTA TGAATGGGTC TCTTTTCCTC    3960

TTCTCTTGGC AAAGCAGTCT TAGAGACAAG ATTAGGAATT GTCTCAATAA CCACTTTAAT    4020

ACATAAAAGT TTAATCGGGG CTGGGCGCGG TGGCTTACAC CTGTAATCCC AGCACTTTGG    4080
```

-continued

```
GAGGCTGAGG CAGACGGATA ACCTGAGGTC AGCAGTTTGA GACCAGCCTG GCCAACACAG    4140

TGAAACCCCA TCTGTATTAA AAATACAAAA ATGAGCCGGG CGTGGTGGCG GGCGCTGTAA    4200

TCCCAGATAC TTGGGAGGCT GAGACAAGAG AATCGCTTGA ACCCGGGAGC GGAGGTTGCA    4260

GGTTGCAGTG AGCCAAGATG GCGCCACTGC CTTCCAGCCT GGCGACAGAG CGAGACTCCA    4320

TCTCAAAAAA AAAAGTTTA ATCAGTAAGC AGATCCTCCT GGATCTATTT TAGCTAAGTC    4380

AATTTGGTTA GATTCTGTTT AAGCTACTCA GTATCTATTT CAGTTAAAGT ATAACAGAAT    4440

TTTCTCTTAA TTGACCTGTG CATACGTTGA ATATTTCCAT TTCCAATGTC AAAAATAAAT    4500

GCTTTGCACG GAGGGAGGCA CGCGAGGATC CTTGGCAAAG GCCATCCCCT GCCCGCCCCT    4560

GTCTTAGCCT GGTGCCTTCT CAAAACCAGG AGGCCTTAGA CTCCAAGGAT GTGTGTGTCC    4620

AGATGAGAAG GATCCCGAAC AGTCTTCGAG AAGGCACCCG CTCCCACCTC TGCCTGGGTG    4680

CCCTGGAGCC TTCTCCTCTC CTCTCCTCCA CGCACTCACA CTGCTCTCTG GATGCCCTGG    4740

AGCCCTCTCC TCTCCTCCAC CCACCCCACC TCTCCCTGGG TGCCCTGGAG CCCTCTCCTC    4800

TCCTCCACCC ACCCCACCTC TCCCTGGGTG CCCTGGAGCC CTCTCCTCTC CTCCACCCAC    4860

CCCACCTCTC CCTGGGTGCC CTGGAGCCCT GTCCTCCCCT CCATGCACGC ACGCTGCTCT    4920

CTGGGTGCCC TGGAGCCCTC TCCCCTTCTC CCCTCCACGC ACACACACTG CTCTCTGGGT    4980

GCCCCATGCT CCTGGACTCT CCTTTGCTGA CCTAGCTCTG CCTCTACCTG GTGTCCAAAC    5040

GCACAGGGGT CCCAGGCCCC AGCCACGTCT CTCGCCTGTG GCTCTGAACA GCATCTGTGT    5100

TGCACTTGCT GGTGGACAGC AGCCTCCCGG CCGCACCATG CCCGCACCAT GCCCACACCA    5160

TGCCCGCACC ATTCTGGACT TTGTCACCTC ATCTCAGTGA AGGGCTCTGA CACCCCCCAC    5220

TTAGGCGGCT GACTCCCTCT TCCCTCACAC CCAGGCCTCC CATGTTTCCA CTGTCATCAC    5280

TCACCAAAGC CACCCCACAA CCCCCCACTC CGGGCCCCCT GCTCACTCCA AATCCACTCC    5340

TTACTCACAC AGCCCCCACC AAACCCGCGT AAGTCAGAGT GCGGGTGTCC TCAGGACGGC    5400

TCTGCACCCC TGCCTGGGGC TGGCCGCGCC TGGCCTTCCC CGGACACTCC CGACCGCCAG    5460

CCCCGCGGAG AGCCTTTGTG TGCCGTTCCC TCGGCCTCCC CACCCGCTGT GGCCTCTCCC    5520

CAAGTGAAGA GTGAGCAGAT GGAAGAGCAG GGCTTGCCCA CAGCTGGATG TCAAGTCCCC    5580

CTGCTTTCAG TCCGGGCTGC AGCTGAACTC ACCTTTCTGC TCTGCCCAAG GACCCCAAGG    5640

CGTGCCCGGC ACCAGCAAGG ACGGCCAGGA CGGTGCTCCC GGCGAGCCTG GCCTCCCGG    5700

AGATCCTGGG CTTCCAGGTG CCATTGGGGC CCAGGGGACA CCGGGGATCT GCGACACCTC    5760

AGCCTGCCAA GGAGCCGTGT TAGGAGGGGT CGGGGAGAAA TCAGGCTCTC GAAGCTCATA    5820

AAATTCAACG TGAGGAAGCA AGTGACAAGG ACGCCCGAAG CACAGTGGAC GGTCATGAAG    5880

GAGCGGGGT GTGGCAGGCG GGTGACGTCC AGGAGAGGGA GCGCCCCTGG CTGCCCCTCG    5940

GCCGCCGACT GGACGCGTGG GCCTTGCCAG CGAGCACCCT CATTGGGCTG TCGCCTGACA    6000

GCATACCTCA AAAGGCCCTA GCTAATAAAC CTGTAAGCCC AGCATTTGAG AGAAGGTAGG    6060

GTGTGTATAT ATAAAAGGTT GTGTACAACT CCACGAGGTG AAAAATATTC AGTAACTTGT    6120

TTGCATAGCA TTTGTGTAAA GACTATGATC TCATCCCAAT AAAATGATAT ATTAAATCTT    6180

CAGATTAATG ACTGGCTACA GAGTAACAAA AAATAAACAA TTTAATGTAC AGTAAATTCT    6240

CTCCCA                                                                6246
```

(2) INFORMATION FOR SEQ ID NO: 641:

(i) SEQUENCE CHARACTERISTICS:
        (A) LENGTH: 28 base pairs

```
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 641:

ATGGATCCTC GCGGTCGCAC TGGTGATG                                              28

(2) INFORMATION FOR SEQ ID NO: 642:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 642:

ATGAATTCCA GCCTTGGTTG GGGTCAAT                                              28

(2) INFORMATION FOR SEQ ID NO: 643:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 643:

ATGGATCCAT GTCTGGTTCG GCGAGAGC                                              28

(2) INFORMATION FOR SEQ ID NO: 644:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 644:

ATGAATTCTC AATCACTGTC TTGCCCC                                               27

(2) INFORMATION FOR SEQ ID NO: 645:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 645:

CCTTTCTGCT CCTTTCTCCA                                                       20

(2) INFORMATION FOR SEQ ID NO: 646:

(i) SEQUENCE CHARACTERISTICS:
        (A) LENGTH: 20 base pairs
        (B) TYPE: nucleic acid
        (C) STRANDEDNESS: double
        (D) TOPOLOGY: linear
```

```
        (ii) MOLECULE TYPE: DNA (genomic)

(xi) SEQUENCE DESCRIPTION: SEQ ID NO: 646:

AGCAACACAG TTACACAAGG                                              20

(2) INFORMATION FOR SEQ ID NO: 647:

(i) SEQUENCE CHARACTERISTICS:
         (A) LENGTH: 21 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 647:

GTACATTTCC TAGAGAACTT G                                            21

(2) INFORMATION FOR SEQ ID NO: 648:

(i) SEQUENCE CHARACTERISTICS:
         (A) LENGTH: 24 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 648:

CTACTCTCAG CCCAGGAGGT CCTG                                         24

(2) INFORMATION FOR SEQ ID NO: 649:

(i) SEQUENCE CHARACTERISTICS:
         (A) LENGTH: 21 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 649:

CTTTCGCTAA GAGAGCCTGT G                                            21

(2) INFORMATION FOR SEQ ID NO: 650:

(i) SEQUENCE CHARACTERISTICS:
         (A) LENGTH: 20 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 650:

GGACTGAGCA CGCAGCTCTG                                              20

(2) INFORMATION FOR SEQ ID NO: 651:

(i) SEQUENCE CHARACTERISTICS:
         (A) LENGTH: 22 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO: 651:
```

```
GTTTCTGTGA GCCAGCCTCC TG                                                    22

(2) INFORMATION FOR SEQ ID NO: 652:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 652:

GGCACAGTGG CCCACGATAA GAC                                                   23

(2) INFORMATION FOR SEQ ID NO: 653:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 653:

TTTATATGAG TATGAAGCAG GCAC                                                  24

(2) INFORMATION FOR SEQ ID NO: 654:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 654:

TCTTGTTTAC CCTTGTGTAT CTAC                                                  24

(2) INFORMATION FOR SEQ ID NO: 655:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 655:

GGCAGCCCAG GTATTCGTGG                                                       20

(2) INFORMATION FOR SEQ ID NO: 656:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 656:

GCCCTGGTGG CCTGGACTTC                                                       20

(2) INFORMATION FOR SEQ ID NO: 657:
```

(i) SEQUENCE CHARACTERISTICS:
       (A) LENGTH: 45 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO: 657:

GACTGATCAG CGAATTCTAC GTCGCTTTTT TTTTTTTTTT TTTTT                      45

(2) INFORMATION FOR SEQ ID NO: 658:

(i) SEQUENCE CHARACTERISTICS:
       (A) LENGTH: 21 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO: 658:

CAGGGCTGGC AGGAATTCCT G                                                21

(2) INFORMATION FOR SEQ ID NO: 659:

(i) SEQUENCE CHARACTERISTICS:
       (A) LENGTH: 20 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO: 659:

AATTCCTGGA GTGCCTGGAC                                                  20

(2) INFORMATION FOR SEQ ID NO: 660:

(i) SEQUENCE CHARACTERISTICS:
       (A) LENGTH: 21 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO: 660:

GGAAGACAGC AGAGTCATCA G                                                21

(2) INFORMATION FOR SEQ ID NO: 661:

(i) SEQUENCE CHARACTERISTICS:
       (A) LENGTH: 21 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO: 661:

AGTTTGAACT CCAGTGGGTG C                                                21

(2) INFORMATION FOR SEQ ID NO: 662:

(i) SEQUENCE CHARACTERISTICS:
       (A) LENGTH: 21 base pairs
       (B) TYPE: nucleic acid (C) STRANDEDNESS: double
            (D) TOPOLOGY: linear (ii) MOLECULE TYPE: DNA (genomic)

(xi) SEQUENCE DESCRIPTION: SEQ ID NO: 662:

ACCTCATCAG TGGTCTGGCT G                                                 21

(2) INFORMATION FOR SEQ ID NO: 663:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 663:

CAGGAAAGCC GGGGAAACCA G                                                 21

(2) INFORMATION FOR SEQ ID NO: 664:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 664:

GTCCATCTCG TCCAGTCAGA C                                                 21

(2) INFORMATION FOR SEQ ID NO: 665:

(i) SEQUENCE CHARACTERISTICS:
            (A) LENGTH: 22 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 665:

CCTGCCAAGG AGCCGTGTTA GG                                                22

(2) INFORMATION FOR SEQ ID NO: 666:

(i) SEQUENCE CHARACTERISTICS:
            (A) LENGTH: 23 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 666:

CCTTTTGAGG TATGCTGTCA GGC                                               23
```